US008937213B2

(12) United States Patent
Hopkins et al.

(10) Patent No.: US 8,937,213 B2
(45) Date of Patent: Jan. 20, 2015

(54) TRANSGENIC BIOSENSORS

(76) Inventors: Christopher E. Hopkins, Salt Lake City, UT (US); Miluka Gunaratna, Salt Lake City, UT (US)

(*) Notice: Subject to any disclaimer, the term of this patent is extended or adjusted under 35 U.S.C. 154(b) by 0 days.

(21) Appl. No.: 13/476,790

(22) Filed: May 21, 2012

(65) Prior Publication Data

US 2012/0304320 A1 Nov. 29, 2012

Related U.S. Application Data

(60) Provisional application No. 61/488,720, filed on May 21, 2011.

(51) Int. Cl.

| | |
|---|---|
| ***A01K 67/00*** | (2006.01) |
| ***A01K 67/033*** | (2006.01) |
| ***C12N 15/85*** | (2006.01) |
| *G01N 33/00* | (2006.01) |

(52) U.S. Cl.

CPC ........ *A01K 67/0336* (2013.01); *C12N 15/8509* (2013.01); *A01K 2267/03* (2013.01); *A01K 2217/15* (2013.01); *A01K 2217/203* (2013.01); *A01K 2267/0393* (2013.01)

USPC .................................................. 800/8; 800/3

(58) Field of Classification Search

USPC ........................................................ 800/8, 3

See application file for complete search history.

(56) References Cited

U.S. PATENT DOCUMENTS

| | | | | |
|---|---|---|---|---|
| 6,461,814 | B1 | 10/2002 | Spinella | |
| 6,852,541 | B2 | 2/2005 | Obayan et al. | |
| 6,953,666 | B1 | 10/2005 | Kinkade, Jr. et al. | |
| 7,288,374 | B2 | 10/2007 | Pincemail et al. | |
| 7,306,905 | B2 | 12/2007 | Ron et al. | |
| 7,853,406 | B2 | 12/2010 | Michelson et al. | |
| 7,915,402 | B2 * | 3/2011 | Anderson et al. | 540/519 |
| 7,964,177 | B2 | 6/2011 | Soga et al. | |
| 7,993,859 | B2 | 8/2011 | Des Rosiers et al. | |
| 8,030,010 | B2 | 10/2011 | Des Rosiers et al. | |
| 2002/0192671 | A1 | 12/2002 | Castle et al. | |
| 2004/0171107 | A1 | 9/2004 | Nelson et al. | |
| 2005/0221280 | A1 | 10/2005 | Westwick et al. | |
| 2006/0040338 | A1 | 2/2006 | Westwick et al. | |
| 2006/0078921 | A1 | 4/2006 | Boess et al. | |
| 2007/0172871 | A1 | 7/2007 | Dishaw et al. | |
| 2011/0021369 | A1 | 1/2011 | Mhlanga et al. | |
| 2011/0206615 | A1 | 8/2011 | Miyawaki et al. | |
| 2011/0262025 | A1 | 10/2011 | Jarrold et al. | |
| 2011/0262570 | A1 | 10/2011 | Finlay et al. | |
| 2012/0184460 | A1 * | 7/2012 | Liang et al. | 506/12 |

OTHER PUBLICATIONS

Hong et al. J Mol Bio 344:369-381, 2004.*

Roberts et al. Development 141:715-724, 2014.*

Hasegawa, Koichi, Satsuki Miwa, Kaname Tsutsumiuchi, and Johji Miwa, "Allyl Isothiocyanate That Induces GST and UGT Expression Confers Oxidative Stress Resistance on *C. elegans*, as Demonstrated by Nematode Biosensor," PloS One 5, No. 2 (2010): e9267. doi:10.1371/journal.pone.0009267, pp. 1-8.

Roh, Ji-Yeon, Junho Lee, and Jinhee Choi. "Assessment of Stress-related Gene Expression in the Heavy Metal-exposed Nematode *Caenorhabditis elegans*: a Potential Biomarker for Metal-Induced Toxicity Monitoring and Environmental Risk Assessment," Environmental Toxicology and Chemistry / SETAC 25, No. 11 (Nov. 2006): 2946-2956.

Lagido, C, J Pettitt, A J Porter, G I Paton, and L A Glover. "Development and Application of Bioluminescent *Caenorhabditis elegans* as Multicellular Eukaryotic Biosensors," FEBS Letters 493, No. 1 (Mar. 23, 2001), 36-39.

Leung, Chi K, Andrew Deonarine, Kevin Strange, and Keith P Choe. "High-throughput Screening and Biosensing with Fluorescent <em>*C. elegans*</em> Strains." Journal of Visualized Experiments: JoVE No. 51 (2011), doi:10.3791/2745.

Lagido, Cristina, Debbie McLaggan, Aileen Flett, Jonathan Pettitt, and L Anne Glover. "Rapid Sublethal Toxicity Assessment Using Bioluminescent *Caenorhabditis elegans*, a Novel Whole-animal Metabolic Biosensor," Toxicological Sciences: An Official Journal of the Society of Toxicology 109, No. 1 (May 2009): 88-95. doi:10.1093/toxsci/kfp058.

Candido, E P, and D Jones. "Transgenic *Caenorhabditis elegans* Strains as Biosensors," Trends in Biotechnology 14, No. 4 (Apr. 1996): 125-129.

Anbalagan, Charumathi, Ivan Lafayette, Melissa Antoniou-Kourounioti, Mainul Haque, John King, Bob Johnsen, David Baillie, Carmen Gutierrez, Jose A Rodriguez Martin, and David De Pomerai. "Transgenic Nematodes as Biosensors for Metal Stress in Soil Pore Water Samples." Ecotoxicology (London, England) 21, No. 2 (Mar. 2012): 439-455. doi:10.1007/s10646-011-0804-0.

McLaggan, Debbie, Maria R Amezaga, Eleni Petra, Andrew Frost, Elizabeth I Duff, Stewart M Rhind, Paul A Fowler, L Anne Glover, and Cristina Lagido. "Impact of Sublethal Levels of Environmental Pollutants Found in Sewage Sludge on a Novel *Caenorhabditis elegans* Model Biosensor." PloS One 7, No. 10 (2012): e46503. doi:10.1371/journal.pone.0046503.

Hasegawa, Koichi, Satsuki Miwa, Tomoko Tajima, Kaname Tsutsumiuchi, Hajime Taniguchi, and Johji Miwa. "A Rapid and Inexpensive Method to Screen for Common Foods That Reduce the Action of Acrylamide, a Harmful Substance in Food." Toxicology Letters 175, No. 1-3 (Dec. 10, 2007): 82-88. doi:10.1016/j.toxlet.2007.09.013.

Hunt, Piper Reid, Nicholas Olejnik, and Robert L Sprando. "Toxicity Ranking of Heavy Metals with Screening Method Using Adult *Caenorhabditis elegans* and Propidium Iodide Replicates Toxicity Ranking in Rat." Food and Chemical Toxicology: An International Journal Published for the British Industrial Biological Research Association 50, No. 9 (Sep. 2012): 3280-3290. doi:10.1016/j.fct.2012.06.051.

(Continued)

*Primary Examiner* — Marcia S Noble

(74) *Attorney, Agent, or Firm* — Kenneth E. Horton; Kirton McConkie

(57) ABSTRACT

Systems and methods relate to transgenic organisms and their use as biosensors are described. In some embodiments, the systems and methods include a first population of transgenic organisms that includes a first constitutively expressed reporter gene, and a first transgene that includes a first inducible promoter from a response pathway gene, wherein the first inducible promoter is coupled to a first reporter gene. Other embodiments are described.

13 Claims, 7 Drawing Sheets

(56) References Cited

OTHER PUBLICATIONS

Boyd, Windy A, Marjolein V Smith, and Jonathan H Freedman. "*Caenorhabditis elegans* as a Model in Developmental Toxicology." Methods in Molecular Biology (Clifton, N.J.) 889 (2012): 15-24. doi:10.1007/978-1-61779-867-2_3.

Caito, Samuel, Stephanie Fretham, Ebany Martinez-Finley, Sudipta Chakraborty, Daina Avila, Pan Chen, and Michael Aschner. "Genome-Wide Analyses of Metal Responsive Genes in *Caenorhabditis elegans*." Frontiers in Genetics 3 (2012): 52. doi:10.3389/fgene.2012.00052.

Tsyusko, Olga V, Jason M Unrine, David Spurgeon, Eric Blalock, Daniel Starnes, Michael Tseng, Greg Joice, and Paul M Bertsch. "Toxicogenomic Responses of the Model Organism *Caenorhabditis elegans* to Gold Nanoparticles." Environmental Science & Technology 46, No. 7 (Apr. 3, 2012): 4115-4124. doi:10.1021/es2033108.

Swain, Suresh, Jodie F Wren, Stephen R Stürzenbaum, Peter Kille, A John Morgan, Tjalling Jager, Martijs J Jonker, et al. "Linking toxicant Physiological Mode of Action with Induced Gene Expression Changes in *Caenorhabditis elegans*." BMC Systems Biology 4 (2010): 32. doi:10.1186/1752-0509-4-32.

Shyu YJ, Hiatt SM, Duren HM, Ellis RE, Kerppola TK, Hu CD. "Visualization of protein interactions in living *Caenorhabditis elegans* using biomolecular fluorescence complementation analysis." Nat Protoc. 2008:3(4):588-96. doi: 10.1038/nprot.2008.16.

Eva Zeiser, Christian Frøkjær-Jensen, Erik Jorgensen, Julie Ahringer "MosSCI and Gateway Compatible Plasmid Toolkit for Constitutive and Inducible Expression of Transgenes in the *C. elegans* Germline" PLoS ONE 6(5): e20082. (May 26, 2011) doi:10.1371/journal.pone.0020082.

Christian Frøkjær-Jensen, M. Wayne Davis, Christopher E. Hopkins, Blake Newman, Jason M. Thummel, Søren-Peter Olesen, Morten Grunnet, and Erik M. Jorgensen "Single copy insertion of transgenes in *C. elegans*" Nat Genet. Nov. 2008 ; 40(11): 1375-1383. doi:10.1038/ng.248.

Jennifer I Semple, Rosa Garcia-Verdugo, Ben Lehner "Rapid selection of transgenic *C. elegans* using antibiotic resistance" Nature Methods 7(9) Sep. 2010:725-729.

Koichi Hasegawa, Johji Miwa "Genetic and Cellular Characterization of *Caenorhabditis elegans* Mutants Abnormal in the Regulation of Many Phase II Enzymes" PLos ONE 5(6): e11194. doi:10.1371/journal.pone.0011194. Jun. 17, 2010.

Koichi Hasegawa, Satsuki Miwa, Kaname Tsutsumiuchi, Johji Miwa "Allyl Isothiocyanate that Induces GST and UGT Expression Confers Oxidative Stress Resistance on *C. elegans*, as Demonstrated by Nematode Biosensor" PLoS ONE 5(2): e9267. doi:10.1371/journal.pone.0009267. Feb. 17, 2010.

Koichi Hasegawa, Satsuki Miwa, Kaname Tsutsumiuchi, Hajime Taniguchi, Johji Miwa "Extremely low dose of acrylamide decreases lifespan in *Caenorhabditis elegans*" Toxicology Letters 152 (2004) 183-189. Jun. 15, 2004.

Koichi Hasegawa, Satsuki Miwa, Kazunori Isomura, Kaname Tsutsumiuchi, Hajime Taniguchi, and Johji Miwa "Acrylamide-Responsive Genes in the Nematode *Caenorhabditis elegans*" Toxicological Sciences 101(2), 215-225 (2008) doi:10.1093/toxsci/kfm276. Advance Access publication Nov. 7, 2007.

* cited by examiner biosensor profiling plate concept

Sensitivity and selectivity of hsp-16.41 biosensor
FIGURE 3B
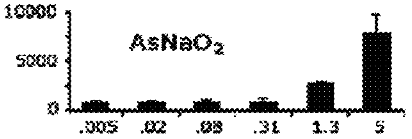
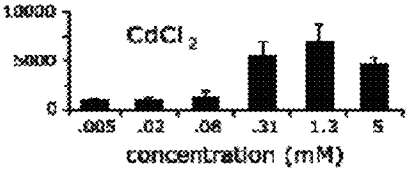
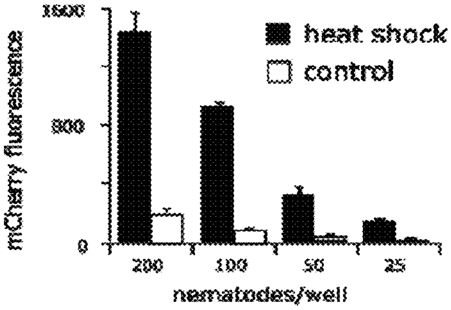
FIGURE 3A
FIGURE 3C
Chronic exposure reveals need for normalization to population change
FIGURE 4B
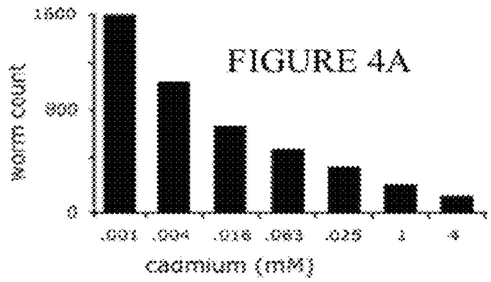
FIGURE 4A
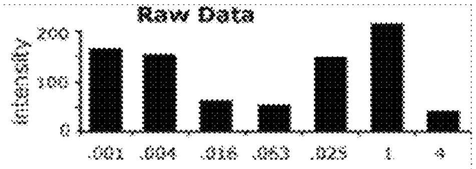
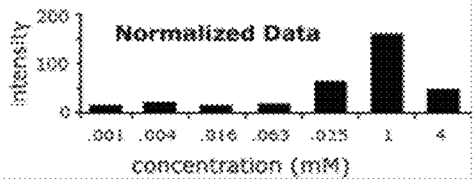
FIGURE 4C

Dual color worm normalization
FIGURE 5A
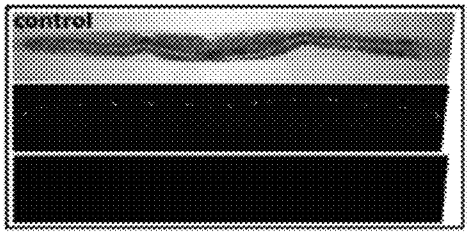
FIGURE 5B
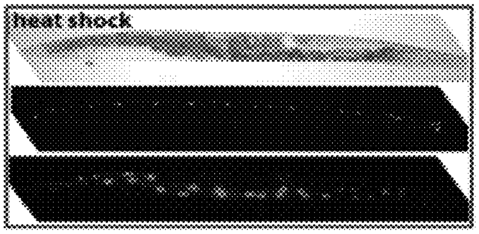
$$\text{Normalized ratio} = \frac{(R_i / G_i)}{(R_c / G_c)}$$
Copas biosort
FIGURE 6A
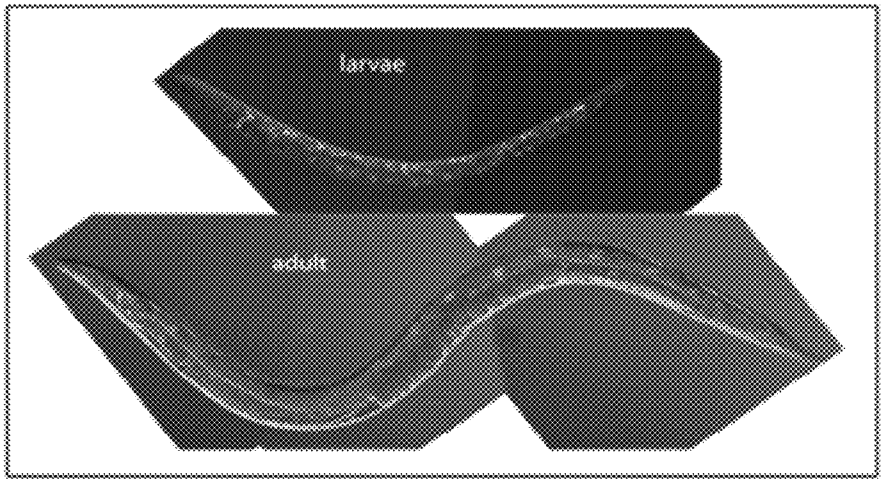
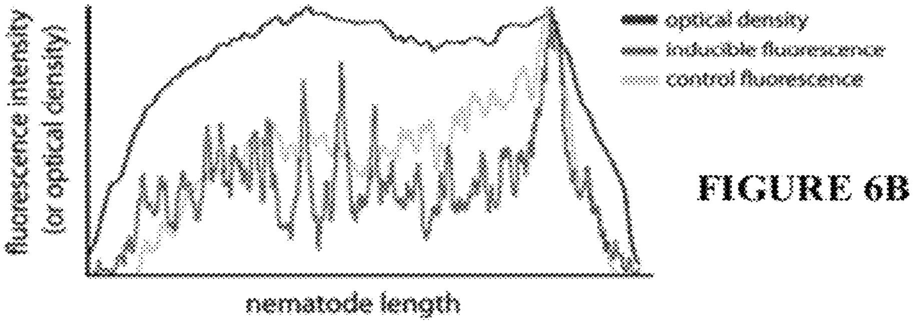
FIGURE 6B

Specific and selective biosensor response to two types of oxidative stressors

Digitized readout toxicity pathway activation

Sets of Biosensor Panels detect Different Types of Toxicity

Genotoxicity
- BER ① ② ③ ④
- NER ⑤ ⑥ ⑦ ⑧
- MMR ⑨ ⑩ ⑪ ⑫
- RCR ⑬ ⑭ ⑮ ⑯

Oxidative Stress
- Cytoplasmic ① ② ③ ④
- Mitochondrial ⑤ ⑥ ⑦ ⑧
- Endoplasmic reticulum ⑨ ⑩ ⑪ ⑫
- Peroxisome ⑬ ⑭ ⑮ ⑯

Xenobiotic Activation
- Cyp450s ① ② ③ ④
- GSTs ⑤ ⑥ ⑦ ⑧
- UGTs ⑨ ⑩ ⑪ ⑫
- ABC transporter ⑬ ⑭ ⑮ ⑯

Endocrine Activity
- NHRs ① ② ③ ④
- Insulin pathway ⑤ ⑥ ⑦ ⑧
- sterol receptors ⑨ ⑩ ⑪ ⑫
- MAP kinases ⑬ ⑭ ⑮ ⑯

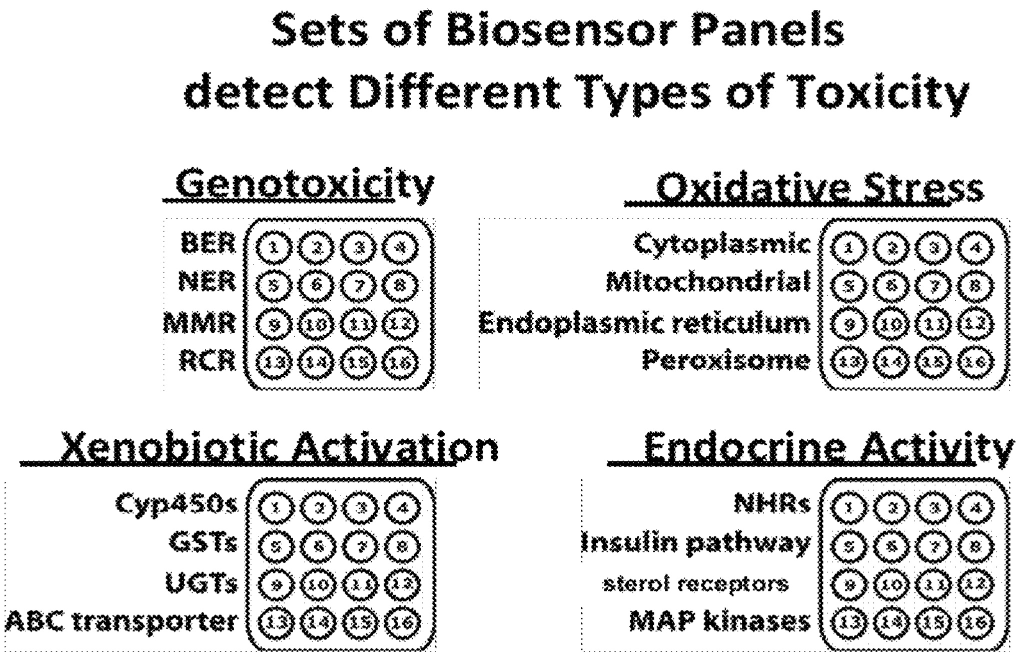

FIGURE 10

SEQUENCE LISTING

```
<160> NUMBER OF SEQ ID NOS: 162

<210> SEQ ID NO 1
<211> LENGTH: 346
```

<212> TYPE: DNA
<213> ORGANISM: Caenorhabditis elegans

<400> SEQUENCE: 1
gattatagtt tgaagatttc taatttcaca attagagcaa atgttgttcg gtatttattt 60
tcaacggtat ttatactatt ttccaccttt ttctagaaca ttcgagctgc ttgttgcaaa 120
aggagggcga ctcacattcg gtacatggaa aagtagtgta cacaataaag agacccagat 180
acattttccg tctgcgtctc tttgcaccca ccgggagtat tttcaaacga atgcatctag 240
gaccttctag aacattctgt aaggctgcag aatgcgggta tataaggaaa gcgggctcag 300
aggaagccaa cacgctttgt tctagtgcat ctaaaaaact tcgaaa 346

<210> SEQ ID NO 2
<211> LENGTH: 346
<212> TYPE: DNA
<213> ORGANISM: Caenorhabditis elegans

<400> SEQUENCE: 2
tttcgaagtt ttttagatgc actagaacaa agcgtgttgg cttcctctga gcccgctttc 60
cttatatacc cgcattctgc agccttacag aatgttctag aaggtcctag atgcattcgt 120
ttgaaaatac tcccggtggg tgcaaagaga cgcagacgga aaatgtatct gggtctcttt 180
attgtgtaca ctacttttcc atgtaccgaa tgtgagtcgc cctccttttg caacaagcag 240
ctcgaatgtt ctagaaaaag gtggaaaata gtataaatac cgttgaaaat aaataccgaa 300
caacatttgc tctaattgtg aaattagaaa tcttcaaact ataatc 346

<210> SEQ ID NO 3
<211> LENGTH: 348
<212> TYPE: DNA
<213> ORGANISM: Caenorhabditis elegans

<400> SEQUENCE: 3
tcttgaagtt tagagaatga acagtaagca cttgaacaaa gtgtattggt ttcctctgaa 60
cacgattggc ttatataccc gtatcctgca gccgtttaga atgttctaga aggtcctaga 120
tgcattcatt tcaaaataca ccccataggt gcaaagagac gcagattgaa aaagtatctg 180
ggtttcttca gtacgcacac tatttctcaa tgttctgaat gtgagtcgcc ctccttttgc 240
aagaagcagc tcgaatgttc tagaaaaagg tggaaatgag tataaataca gtgacaaaac 300
cgaaccaaac aacattcact ctaattgtga aatcttcaaa ctacaatc 348

<210> SEQ ID NO 4
<211> LENGTH: 348
<212> TYPE: DNA
<213> ORGANISM: Caenorhabditis elegans

<400> SEQUENCE: 4
tcttgaagtt tagagaatga acagtaagca cttgaacaaa gtgtattggt ttcctctgaa 60
cacgattggc ttatataccc gtatcctgca gccgtttaga atgttctaga aggtcctaga 120
tgcattcatt tcaaaataca ccccataggt gcaaagagac gcagattgaa aaagtatctg 180
ggtttcttca gtacgcacac tatttctcaa tgttctgaat gtgagtcgcc ctccttttgc 240
aagaagcagc tcgaatgttc tagaaaaagg tggaaatgag tataaataca gtgacaaaac 300
cgaaccaaac aacattcact ctaattgtga aatcttcaaa ctacaatc 348

<210> SEQ ID NO 5

<211> LENGTH: 348
<212> TYPE: DNA
<213> ORGANISM: Caenorhabditis elegans

<400> SEQUENCE: 5
gattgtagtt tgaagatttc acaattagag tgaatgttgt ttggttcggt tttgtcactg 60
tatttatact catttccacc tttttctaga acattcgagc tgcttcttgc aaaaggaggg 120
cgactcacat tcagaacatt gagaaatagt gtgcgtactg aagaaaccca gatacttttt 180
caatctgcgt ctctttgcac ctatggggtg tattttgaaa tgaatgcatc taggaccttc 240
tagaacattc taaacggctg caggatacgg gtatataagc caatcgtgtt cagaggaaac 300
caatacactt tgttcaagtg cttactgttc attctctaaa cttcaaga 348

<210> SEQ ID NO 6
<211> LENGTH: 348
<212> TYPE: DNA
<213> ORGANISM: Caenorhabditis elegans

<400> SEQUENCE: 6
gattgtagtt tgaagatttc acaattagag tgaatgttgt ttggttcggt tttgtcactg 60
tatttatact catttccacc tttttctaga acattcgagc tgcttcttgc aaaaggaggg 120
cgactcacat tcagaacatt gagaaatagt gtgcgtactg aagaaaccca gatacttttt 180
caatctgcgt ctctttgcac ctatggggtg tattttgaaa tgaatgcatc taggaccttc 240
tagaacattc taaacggctg caggatacgg gtatataagc caatcgtgtt cagaggaaac 300
caatacactt tgttcaagtg cttactgttc attctctaaa cttcaaga 348

<210> SEQ ID NO 7
<211> LENGTH: 1716
<212> TYPE: DNA
<213> ORGANISM: Caenorhabditis elegans

<400> SEQUENCE: 7
acaattcaga aggagcaata attctgtgat atttaaacta atttctcttt gtttctttgt 60
tatgagtatt tatttttagt tcttgttcat catgcttttt ttgtcacttt tccctcccca 120
atcccatatt cctctgcttt tctctcattt tcggttacgt gtattaattg aatgtatacg 180
acgacgacag tcactagttt cgaaataact attttacgag gatgaataaa cacactgatc 240
gctgagcgac gctccgagca cttttcgaga agtttctaag aagccacttg accgagagag 300
agggagaaag aaaagcttgg catagaaatg tgcttgtgtt tatttgaact gttaaaagtg 360
tttgacgggg gcgaagtcac tggggaaacc tcgagatcaa taggacacgt ggcaatttga 420
atttttggat aattggaaaa gcagtacccg actaaagatc cgaatttgat tttcagacat 480
tttactgcaa acttgattac acacggtaat tttccaaaag ttttgtgcat tgaatcccga 540
aaaacttcac aaacgcataa tattacaacc cgatctatga gcaaagtaaa tagagagaat 600
caggctgaaa gcttattgtg attaatgaac attaggaaca atgctgattt caatttgaaa 660
catttttttt tcagatcgaa aatcagtttt ttcagatcga aaatcacatt ggatcttgac 720
attttcaaga gaattattaa aatttaaatg gctatttgaa aagtattgat tttctgaaag 780
ataataacta cttaccatct atgtcgtacc tgactatgcc aattattttc aacaattgtt 840
tattttaaaa aatttttgaa gtaagcttaa aacaaaccca ggacctctga aatgtaccaa 900
gtttggaaac taattccaag tactggtaat aacaaaaatt ttgaattcga ggcggataag 960
cgccagttgg gagttttctg attataatta tattaataga attgccaaaa atcatgataa 1020
acccctccaa tcatttttg attttcgaaa aagtttcaat gtaggttttg gtgagctgcg 1080
aagttttcca aaaatgtcta aaaactaaat tcatatggtt caatttttgt caaaaacgtt 1140
cagctcatga ggagcttgaa actaaccaat aaattttggt cattaaattg gtcagttaaa 1200
ttgataattg aaattaaccg gatatgtttg gaaaaataaa tgcaaaagtt catgatcatc 1260
agatcaaaaa ccaaaaactt cccctacatt tctatttcca aattgaagat ttcttgaagc 1320
ctacaaatag tacagtttac aaatatctct ccttctttct ctcgtccctt cttgcgcatc 1380
ctcagagctc ggagctccta tccgtcaata taaacaatca ttgtttcttt tcttctcctc 1440 gtacctttt tcttcttcaa atccattttt cctccgcccc cttatcctac agtccaattc 1500
ctttcactct ccactttctg agcttcttct ccaactcgca aaagcttcaa agctcacaga 1560 gcatttacg atagtgcatt gtaatgttct ccaccctaga gtgcatctcc aacctgcgca 1620
tatgttttcg ctctttgaca ttacattttc ttccgattca cattttattc atccacccga 1680
taaatatatt ttcacacttt taattttcta gagaaa 1716

<210> SEQ ID NO 8
<211> LENGTH: 1859
<212> TYPE: DNA
<213> ORGANISM: Caenorhabditis elegans

<400> SEQUENCE: 8
tattctacgt caataggaat tgtcagaatt atcagttttg atatcaaaaa ttgccagctt 60
tagtacagta gaataactat gcgattcatg ctgcttatta tttattcaaa atttaaattt 120
taaccaactg tgagtttatt ttatagaaca tttttcgaaa taaaattcaa aaaaataaaa 180
attgttattt ttcaaaatct taatcttaat ttagcaccat taccgacagg caatgataga 240
acaccaaacc ggactgacca agtgtcgtac cagtttcgag caatcaagta ttgagagact 300
gatattcttg ctgatactat actcttaaga tatgaaacga tatctacccc tctagccccc 360
tactcgtgcg ccctcagtta cctacctacc ccgttaccta ccctacccta cctacctact 420
cagtctccta cctaccccga ccgtatcata tctttagaat atagtatcaa caagaatacc 480
aatcacccaa ccccaatcac tcgaaaccgt taggcaccag gttagccagt ctggattaat 540
cgagagtaaa ccacttgact ccagacaact acatcttata cttacttacg tctgggggac 600
aatcttggga ttctcaagat gacttccatt acgaagtctc ttgcaataac caattaccac 660
aattttggag cagaattaaa ctcacccacc agtacaggat caaagatgaa taatgaatga 720
gaggccctcc tctcattgtt gtgggcgggg tcaaggggtc aaagtttttt gaatttcgaa 780
attttgaaat tttggaattg ttaaattttt ggaaatctaa tttttgaaag aaccacattt 840
tccgtttaca atttgagttc aattccgcaa ccccgtcaaa tttaagaaga gaaagaaaaa 900
aaacacaacg tgtttgcacc tgtaaggtag tttttttttg ttgccttcgg cgttttgatt 960
cacatgaaag tttctacgga aaaactttca ttgcataacg atcttcatat cttgtttctg 1020
gaaacgaaaa tttccaacat gaaagaaacc cgacgctatt tattctcgca acacaaaaat 1080
ttcacattta aataaccgcg gtttttctcg aacagcatat ttgacgcgca ttgctcgtca 1140
agtttgatgc gtgcacacta ttttgctgtt gtttttttct tttttctcta aattttcttt 1200
acgctttcgt agtttctata gaaacgattc tccactcccg gttttcttcc gattctcaaa 1260
attaattaaa atttagttat taaaaatcct ttttcttgaa ataatcgttc aatttcgagt 1320
tttcaagagt ggagacgttg aatttgtgag ccgcttattt tttctgtgtt tttgttttgt 1380

-continued

```
ggtttttaat cagtgtcata atcatacttt ccattgtttc tttattattc aaagttgtag   1440

attcagtatt ttagatcggt gatgtttatg aatcttctca ctcaggtctc caacgcgatt   1500

tttccgcagg tcagtgctta tccgaaacat tcgtcattcg caacttgggc ctatttgatc   1560

tatggcgttg tgttgttgcc tttaccttaa ttatcatcat tttcatcaga aacccacaaa   1620

aactagagac atagctacaa aattctgcga ccgagaggcg ggtacacaca caatgttgtc   1680

tatttcatct cgctccacct tctctctctc tctctcgtgt ttaccatttc ttttttaatt   1740

ttgcatctat cgactgtgat ctgcctgttt ttttctaatt ctaaactttt tgccgtgata   1800

ttccttagag tgttccctag aaaattcgtt gaatttacag gtcgaagccg ctcaaaaag    1859
```

<210> SEQ ID NO 9
<211> LENGTH: 1703
<212> TYPE: DNA
<213> ORGANISM: Caenorhabditis elegans

<400> SEQUENCE: 9

```
aaaaacttga tccgatcgaa gaaaaaaccg aaaaaaaatt cgaattgttg tgttgttcgt     60

cagttggatg gaatgatgat gaaggaagtt gattaatgga tatgactgat gattagtggt    120

ggaatatgga ataattattt atttgattta ttctgattat tctgaattag aatgtatttt    180

catatttcag gaaaaatgat tttatttcga aacgaacttg ttctagatta aaaaaattga    240

aatttaatat ttagtgctat acaattacag taccccatgg aaatacacaa atatcataaa    300

tacaagaatt atcttcctgg aagttaaact tatattttcg atgtaagtga aaaagtttaa    360

aagagaaatg atgtttgttg atcttcctgt aagtggaaac tggagaattc ataagcttaa    420

aaattccaaa atattaaaac ttgcgtgttt tttctgaaaa tcgattaaaa cagcaatatt    480

cagcatgttt ccagagccaa aaaaacctgc aagcatggga tacttttgca gttaaaaaat    540

gtttcaggaa cttgaatgaa gttaggatgc atttgaacag agtaatgaaa ttatatgaaa    600

ttcatatgta gactctccta ctcagttgtt tgtatgtgag ttttgtatat tataacttat    660

tttgaaatta tctttaatta cttgtaatgt tttttgtatg agttaaataa taatcttttg    720

aaaattcttt ttcaaataac cattttctgt ttaaaaaaac agtgagccca atataaactt    780

gttttccatc aaaccgagct tctaccaaag ttaacttaaa ttccataatt ttcacaaacc    840

attcatagtt tgtctacgta gccttatcct tttttgaaca ttgaaaaagt gaggagaaag    900

tgcgaaaaac gagttttttt ctttctcttc ttcttggtcg tcacgtcaag acactctgaa    960

cgttggaatg ggaaaagcat cgaagatcga aaaattctga ttttttctaa agtacacaac   1020

ttatattgat attgcattgg gatttaaaaa agctctactc gaacattttg attaatttta   1080

atatctcatt tattcatctt tcgataacag atatatcaca ttgttcggta ggataaaagg   1140

gctaaaatca agttttgagg aatgttcatt tgtttggaag gtgatattat agtctgcgat   1200

aactacataa gtttggaaac cgaacacatg ttttttttggc actttgctaa aaagttgtct   1260

gaaaacgttg gaaatcaata tttggtcatt tatttaggtc attttcggac cattataagt   1320

gttttctaat acaaaactgg cgctgctccg ctatttaaaa gactgaaagt gacataaatg   1380

atctaatttc cagatctctt ataacttttt ttatagcggt tccactccta atttgatgtg   1440

tttacttgtt gcatcagatc atttttcact tcttgtaatt cttatcagtt ttctatattt   1500

tctttcttat caatttttca gcttttcaac attttccagt tagttattca atttttattc   1560

cgcacgatca ctgctgtttg aattcaaata ttggagtatt aaaattatac atttataacc   1620

attctaatgt ctaccttcta cacaaattac ccttcctagt agaaaatata tttttggctt   1680
```

gaaatttgtt ctgtactgtc caa 1703

<210> SEQ ID NO 10
<211> LENGTH: 1851
<212> TYPE: DNA
<213> ORGANISM: Caenorhabditis elegans

<400> SEQUENCE: 10
tttctaagtt cgcacattcc tcgatttcca cttgccgtta cctttcatta tctcctttta 60
ctttaatcta tcacagtttc atagatatca aacgttaatt ttttgttgcg agctagtttg 120
ttttttttcc tcttgttcgg tccattcgct ttaacttgtc acctattttt tgttttctct 180
acagtcctct tggttcatga tcctgttaat tatcaatgct cttttctgtg atattcgata 240
ttcgaatcaa caatgtgtat gattagtgtc aaagtaactt atcggatttt gaatataatt 300
caattattcg tgtaataaat aactattttt tagtttactc atgtttgcca caaactagaa 360
ggtttattta ttcataacta cttgcaattt cacatttgaa ttctaactgt atgattgctt 420
caactctctg cgattttttg cgctaaaata cggtacccgg tctcggcgcg acaaaaaatt 480
tctagatttt tagaaaattt tacagattta ttgcaacagc tgttaccttt ttcacaaaaa 540
aatcgactga atttcgcgaa gttatgatat ctcaagcggc cgcttgcggg aaaagccata 600
ttttttttca aattttcgta gctgcacaat ttttcataat tttttcattt gttaaaaata 660
aatgtatttt aaataattgt cctatttcag tttttcaata aattttttta acgaaaaact 720
ataaaaatag atgaattcta gagccacgta atttcagaat tacagtactc tttcaaggcg 780
catacccttt taacataaat tttcgcgtcg agaccgggta ccgtactttg acgcaaattt 840
tgcatctggg taattcttgt ttttgggttc ttcactttcc accacttttt tttcgaaagc 900
atcaaatttc acatattcac gtcacaatcc tagcaaagcc caatagctca ttcaagtcat 960
atttgtctct ttctttctca ttctcctgat tagcaacact gtcttatcaa ccactaggtt 1020
ccgtcttaat cgtccaaata ttgatccgct cgctcgtgtt ttctcaactt ctttatttgc 1080
tgtgtttttc tgtttctata gttctccatt ttccatctcc tcttcgcttg ttgaatggac 1140
tttattttga taagttcatt ttaatttttc taacaatctc atcactagct catgatgaca 1200
attgcaaaga aattcgtcat atagagggga aaaatgctga caaatattga aaagccttca 1260
ggagagatgt agagacgtag gagtagagac agaacataaa tttgagaagc ttgtagggag 1320
aatagacata gagttaccat gggaaaaacg ctcgcatttt ccatttaacg agattttcta 1380
gatcacaaca ttttgtgatc cgttgtgcga aaatcaagct ttttatcaaa cttttatcgt 1440
ctgttcattc tttctgacaa tctttattat cttattaaac ttgactaatt gtattgaaag 1500
tattttttta gatgcgaacg aagttccatt tttcatgact taacatctct taacgttagt 1560
gaaattttttg aattccaatt aggactacgg taggagttct gtagttgatt tcctgaacac 1620
ttgttttgta acctttctga acggatttta atatttctaa aattttaaat tgcaaatctg 1680
agtcctatta aaagatgttt catccgtaaa accaacaaac aaaatatcac tttatcatca 1740
tgagatttaa tgtttccttt tgattttctg aattgttgta ctttccttca aacgacttat 1800
tgaactgatg taactttcct tctaatgtta tcatttgtat ttttttgcag a 1851

<210> SEQ ID NO 11
<211> LENGTH: 1614
<212> TYPE: DNA
<213> ORGANISM: Caenorhabditis elegans

<400> SEQUENCE: 11
aaaccaaatt tactactttt actatatttt tagttgaaaa taaaaagaga aaaacattta 60
ttttctaaaa acagtaattt tcctttagtc agtttatttc tcattgagat attgtgaact 120
cctgttttaa aatcaaatga gaaaaattga acacaaattt taaatttaca taaatcccca 180
aaaactatca atatttccaa cctagacaca ctataattga ataagattct cgtgaccttc 240
ggacatacag tttgtcaaag acaagcactc ccacatttgc cggttaattg tgataaccct 300
atcaacttgg ctccgtcttc actctcactt gcaattgcac aacttctttc tttttggatg 360
taagtagcaa cattttatca tcactctatt gggaaatttt taaaacaaaa tttcttcaat 420
acgattgccg gtctcgccac gataaattgt aggtacatgc gaaaaaaataa tgcccattta 480 aagagtactg taatttccat ctctctttgt tgcaggattt tttgtcgatt tttttagttg 540
ttcaatacaa ataaattcat tcgaaaactg tcatgtcacg ataaacaaac aaattttggt 600
atttaacaaa aatttgtcgt gtcgagacct aagctagaat agtactataa tttttgagct 660
ttaatttttt caagtttttt acaaaatttt tttttctgtt gattaattga tgtattttta 720
tcggagatct ataaaaaaat caatgaaatt ttcgaagaag ccaaaaaaagt actgttgata 780 ctacagtaat cttcaaaggc gcacaccttt cggcatttaa caaaaatttg tcgtgttaag 840
accgggtaat ttgttaggca aatatttgaa aaaaaactgc ttaaatattt catgaaaatt 900
ctgttatctt taatcagatt tttaaaaaat tattatcaaa tttcaaaaaa ttacctaaaa 960
taatgtctga aattcttctt tactcacgcg aactgcaact tccagacatt aattgaggaa 1020
atttcaaatt aatcaataac aatgaatacg attttcagat taaacgagta ttttcctaca 1080
tttttattaa tttttttgat taatattaat ttttaaaatg aaatttttgg ataatcctac 1140
taaaataagc atgtcccgca aggccctatt tcaaaagttt agtgcctgaa aaatcaatat 1200
ttcgcaagaa cagtctacca atttttccaa tttatacttc cggcaattgc caccaattcg 1260
gtgatctaga aaatacccat ataggctcta cagtaccttc ccttatcacc cacatccaat 1320
tttgctatca gttagtcttc aatcacactt agtctttgaa caaatgaact cataactctc 1380
acaagatgtt tgcaactatc atattgatgt cattcagttc tcatatgaga aggcgggcac 1440
attgttgtat attgataaac cacccccatt ttcctcttct tccagcaaaa aaaaataaaa 1500
ttaatattgt ctcagacgct tgtgaaactg gtgctctcaa ttgaaaagca ccattgactt 1560
cgcagaaact ggcagttcat ttggctttcg gatacttaca accatacgct caca 1614

<210> SEQ ID NO 12
<211> LENGTH: 388
<212> TYPE: DNA
<213> ORGANISM: Caenorhabditis elegans

<400> SEQUENCE: 12
tctgtatata tgcaaaagga aaattaaata ttatctatcg atggaaatgt tagaaaagcg 60
aattacttgg cacggcagca ggtgccacaa agcctgcagc tgaataaagt taagatacga 120
ttgcttgctg acaaatagga cactaaattg gaaaatacac accacatttt gatttttaat 180
cagatctttt ttaattttaa ttttagtcac atctagacta ctctgactac tattctcaca 240
cgtgtggcca acaatcattc ggactacgct gtaggcagtc aggagttttc aaatgataag 300
gtgttcaaca gtgtagtctt atttgtatca ttttcacata aaacgcaatt tcaaaaactc 360
ccaattttct tcagactgcg gtaaaata 388

<210> SEQ ID NO 13
<211> LENGTH: 681
<212> TYPE: DNA
<213> ORGANISM: Caenorhabditis elegans

<400> SEQUENCE: 13

```
ccagttaccg agatctaatt tttttctatt ttctttttct acttttcatg aaatacgcat      60
ttttgaaaac gaataataaa gtatgatatg ctgtcaaaaa atttcctgca ttcttgcaaa     120
accggacgtc gaacaccaat ttgccacttt gatctacgta gatctacaaa aaatgcggga     180
gaagatcttc tcgagacgca gaattctcaa ctgatttcaa atcgttaaga acgtgctgac     240
gtcacatatt tttgggcaaa aaattcccgc atttttttgta gatcaaaccc tattgggaca    300
tcctggcatc acgtgatttg cctaaaacca aaaataatgc gcattcagag aacatgccta     360
ttgtgcctac ctatttatta actttgacag tagataggca ggcggctgct tagagcctat     420
aagctagcct acctaggcaa cccacatagc ctacctttca acttttcaaa agatcattgg     480
atcactaaca caatgtgact agttgtggtt tgttacaaat tgcctcattg tcaccctaaa     540
ctccctatta tttcccgtaa atgatgacga ttttgatctt ttgtagggtt atcttgaagt     600
gaaagatcac taagtaccca gactgcactc tagtcttttt cccctttaaa tagtctcgag     660
aatgagtttg agaaactaaa a                                               681
```

<210> SEQ ID NO 14
<211> LENGTH: 1390
<212> TYPE: DNA
<213> ORGANISM: Caenorhabditis elegans

<400> SEQUENCE: 14

```
tataattttt tttcttaatt ttcatatgtt tacattaaaa atttgagaaa ataaagtagt      60
tcaagacaaa atcaaatatg gtagagactg tggtttaagt ttgggtttac tagggaatgg     120
tcagcttagg ggtgaggtac ctagagacgc cacatatgcc aaacggaagc tgagatcatt     180
ggctacaaga atatgctttc aaattctgca acggacctct gggagtctgg aaattcttgt     240
ctgaaattat gcttttgaat gctcgaaagt ggtaagaatt tagaatttat tacagaaaaa     300
cgtttaatta ataaaattag ttttatactt gaaacaagta ttgtatgcac tgtatcaaaa     360
cacattttca tctttctagg tattcaactt cacgtttttc tgtaataaat tctaaattct     420
taccactttc gagcattcaa aagcataatt tcagacaaga atttccagac tcccagaggt     480
ccgttgcaga atttgaacgc atattcttgt agccaatgat ctcagcttcc gtttggcata     540
tgtggcgtct ctaggtacct caccccctaag ctgaccattc cctagttagg cttaggcttc    600
ggcttaggct tacgattaag cttaggatta agcctaggct taggctttgt ctgagttcaa     660
ctctccacca cgggaaaatt tttttgcaaa ttttttcgtc ccaaaaaaaa aaggaaaaaa     720
aaactttatt tttacttgat ttttttcact tttttttcga gttcaactct ccaccacggg     780
aaaatttttt tgcaaatttt ttcgtcccaa aaaaaaaagg aaaaaaaaac tttattttta     840
cttgattttt tcactttttt ttcgagctca gctcgaccgt ccctcaatga aaacaagcaa     900
cctgatgtat tccagatact cccgtaccaa aggtcatttc tcgttagtca caaaatattc     960
tgattgaaaa tggtgaaaaa taacgagaga gttgaaaatt ctacagacta tggcctaaac    1020
gcagcaggtg agacacagta gagaacaaga ggcagaagag agagcagaag gcagaggaag    1080
aactaaaggg tatataaaaa gtgttttgtt gatcagtggg atcaaatagt gtgcttttta    1140
aaagtttttt tttccataaa tgtattgata tctagaattt ttttcgagtt cactgttgtt    1200
```

-continued taacagtgtc acatggtgtc aggctgtctc aatacagttt gatctacaaa aaatgcggaa 1260
atcttaacca tgcaaaatca gttgaaaact cttcgtattt tctcccgcat tttttataga 1320
tctacgtaga tcaaaccgaa atgagatact ttgatacacc gtgcagtgtt aaaaaaaata 1380
cagttacagc 1390

<210> SEQ ID NO 15
<211> LENGTH: 395
<212> TYPE: DNA
<213> ORGANISM: Caenorhabditis elegans

<400> SEQUENCE: 15
tctcattctc ttcaagacat aacacaacgg gctgacgacc atatcatcaa cgacgatttt 60
ttaggaactg tactttatct gtgtctgacc aacacgtgtg aatgaagttt caactggaaa 120
atttgtttga aacactgcaa agaatttcga attttgatga taattttaaa tgccattatc 180
agttttaata cgccactcta gtctttgatt ctttgcacac acacacacac acacacacac 240
acacacactc acaaacacgc ctgaaatttc gcaatatgct gatttaacga gaaaacattt 300
gatgacaata aacttggcgt attaatataa aagggaaaat tcaattcaga ttctcaacgg 360
tttattttct gtcacaactc ttcctaatat tcacc 395

<210> SEQ ID NO 16
<211> LENGTH: 741
<212> TYPE: DNA
<213> ORGANISM: Caenorhabditis elegans

<400> SEQUENCE: 16
tacacagcca agtctcataa ccaaaataat attgatagta aaaacatgag tgaacacgtt 60
tcaaaacaac atgtcattga aaatcaattt taatgttcac gggaattttt ttccaaaaca 120
gttttactca aacatatttt ccatttgaaa gtttgggaaa ctatccctgg cacgttttca 180
ctgcattggt ctttccagtt gattcagcca gagttggaaa gcctgtactt ttttcccaac 240
aaccgtttct actgctcaac ttgtaacctc aaatttgcct aattgactcc gaagcttcaa 300
aacttgcttt aaagaacttt gatgaaaatc gctgcggcga aagaatcatt gcggaatttt 360
tgccccaggg atctaaattt ccaacctact ccactgaacc aaatttttc aaacttcacc 420 aattttttta ttttattttc acatgtcatt aaaacactaa gaattcaata catgtatgaa 480
aactgcaaac accaaagtac ggtttggact tgtaagcaaa acaccggtag tctctttgac 540
ttatcatgta ttgtcatcct atttcgtcag acggtcttgt aagttcacat tgacttactc 600
tgcgtctctc ataggacaca tactccgcat ctttctcaat agatcaaata tattttgtca 660
tcacctatta tttaaactgg ttggtttttc acaatgtcac aactaattga actctccact 720
tattgaactt gacttgaaat c 741

<210> SEQ ID NO 17
<211> LENGTH: 330
<212> TYPE: DNA
<213> ORGANISM: Caenorhabditis elegans

<400> SEQUENCE: 17
accgccgagt tacgacatca gattcaagcc tttgaaagtt tgaatcttta ataattaaat 60
gaataattaa ttgggagaaa catgtacata aataaaattt ccattaaaca atgttcattt 120
gtttaagctg gcacagacca caaaagctga aaccacaaag ttttttaaac cttgttcttt 180
tcttaaattt tgtagtttct tatcttatca ctcgtgtttc ttgtcctcca aataattgtg 240
aaaattgtag ttaatgtgtc aaaaaagtca catataagaa gacgaacaac ttgatttttt 300
gttgacttca tttgaaaaaa aatagaaaac 330

<210> SEQ ID NO 18
<211> LENGTH: 953
<212> TYPE: DNA
<213> ORGANISM: Caenorhabditis elegans

<400> SEQUENCE: 18
agaacccatt tttacaaatt gtgttcttgt ggtgttcgcg tattaacttt ttatagctgt 60
tttttactta taggatgatt aagaaaaaag ttccggcttt ctcaaagtaa ggtaaatatt 120
ttgaaaataa agaacttgta aaaggataca gctaactgat taaaaacaaa agacccatgt 180
tagttcacgc tcggatttgg agttcagctg gaggggaaag aattcagcgt tgaaatattt 240
cagttggaat ttcacctgat attatttaaa aaatgttata cgaaaattga aaaagcgcct 300 cttacccccct cttcgcccgc tttcctcttg cctactgtgc agtttttttgt ctttacggag 360 ttaacaagtt gataacctgt ttaaggacaa cagataaaaa cagagaaaat taaaaaccac 420
tattggcgat ttgaaatttc cgttcccatt tttcactttt caatttcaaa tatgtactta 480
acggtttccg atcattaaca cgtaatccat catttctaga caacaagtca caccaatgcc 540
aatcaaaagt gcaaacatgc tataacgaat cttttttttc aattaaactg tttacgatgg 600
aaattaggat agtgtcatag cattaatttt cattgttcaa aaacagaaag aagtcacaaa 660
atcttcacgt gaacatgttt cgtttccata aacaaattgt attttcaaag acagccggga 720
attttcagac caattcaggt gacaactatg ggctaccacc cacctaactg tttgttcgcg 780
attattctga ctcacatcat gttttcaaaa gtgactgtat aattggagtg tagcataatc 840
aacacaaact acagaatggg aaatttgtga cagtatcaat cacattaaca gatctataaa 900
agagactggg aaagttgttc agagacacaa attcgttgtc tacttatcaa atc 953

<210> SEQ ID NO 19
<211> LENGTH: 607
<212> TYPE: DNA
<213> ORGANISM: Caenorhabditis elegans

<400> SEQUENCE: 19
aattttaaag tttatggatt atttagaatt tatgaatatt ttaaatatag cttgtaatag 60
tagcattggc ttttttatta gttagaatgc agtatttata tagattgtag ttgtgtgcgt 120
gctaagatta ttggagtatt ggtgttgtca cgtcttcagt ctctctgccg tgcgctcacg 180
agaatggggc aagcgaagtt gcggctgacg cgttattgga tgctggcgcg tttcgcgacc 240
agcgttggtt ttatcgagaa ttttctctgc agtacaaagt cccaaattcg gtggtttttt 300
atcgatttga cgcgcgtttg ctcaatttct cgattttccg cgttttttat tcagttctca 360
ttaattaacg ttcgatgctt gttcacaaaa ttcagttttt gttttcactt gctcgttggt 420
gtcgttcgtt gtgtaagaaa attgatttct aaatattttg tttaaattgc taaaaaataa 480
ttcaataatt tacattattg aattattaaa agttgtattt ttcaaacatc tcgcgcattc 540
tccgtccgtt tctctcaatt tttcactgtc atgtccgcat tttaatattc attttttttc 600
aggtaat 607

<210> SEQ ID NO 20
<211> LENGTH: 1723
<212> TYPE: DNA

<213> ORGANISM: Caenorhabditis elegans

<400> SEQUENCE: 20
ttggttatag gaatatcctc ctaggataga cgttttttc tagtaatttt tgttgttttt 60
gttcgttaca ataaatctca tttttatttt ctggattaat ttgattacca atcgtttcca 120
gcgattttca catattttc cagaatttaa tacagattaa tattttcgaa aaatttaaac 180
atttcttttt cacattttaa ttcatctcta ttcattatgc aatactcttt tggttttcaa 240
gcatccgaca ttcctccgtt tcatttatgt ttgcatttct gctggcatga atgcatttca 300
ttgtgtctcg atgagaaaaa ggacaatttc atgagcttat cagttacttc gttttcaaaa 360
ttttaatgtt gaccagccat tgatgtcata ttttgtctaa gaagctcaag aactattatt 420
ttttgaagct taatttcgaa gagcaacatt ttttttcatt aaaattcagc agtcattgtt 480
ctttaaaaag ttttgattct cgtttttaaa cgatttttaa ttcagtcgag aattgaataa 540
cttcccgatt tcccggccac catcgtttaa taccttttct ttatgagact aacttccaag 600
tatgcaaatt gcaaatcgac gcaaggggaa tacactcgct cacttctcat cgaaattcga 660 aacctttcc cattttcttt catgtctttt tcgcttttct cctctctgcc catttccatt 720
tatttctcaa acaccgttca gtgaacacga aaacccttac ggaaattgtg ttgtaagaat 780
acaaaaactt ccgtagcata gcgagaaaga gtcaccattt tgtagtgttt gcccccggtg 840
gtatagtttg cacaagtttc tgaaagaaga agaagacaca tttgaggtct tatgcacata 900
aaaatcaatg ttagactatc tttttcacgt agtttctttt tgcaaagtgg aaacttctca 960
ttaaacactt tttgcttttc aattgtctga acaagttttc gattaaacag ctgtaaagct 1020
tttgcaagtt tcatggttta tgaactattt cgaatcggtt acattgctga agttttagtg 1080
tttcttgaat atgtcgtcac taccaggact ggaccaaaaa tcaaaaagaa tttaaagtga 1140
aataccaaaa aaaaaatcgt cgatttgcga tttttgaagg actgtaagtg actttttgg 1200 cttcatttag gtcccaaaaa accttttttt tctcaaaaaa tgtgactcaa aataccaaaa 1260
aagtcttaac ctgatcactt cgccttctca actcaagcca tttttgctgt ttagttcgaa 1320
tatggaacaa atcataagaa tcttgagtac ctatatgcga tacccgattc attttcctct 1380
cttctaaata acatcatttc ctctcttttt ccctctctct ctctctctgt ttttgtttgt 1440
gactcacttt gtccacaacg cgcgcggaac cggcttgttg ccacacacac actgtgatga 1500
aatatgcggg aggaaagctt ttcgcctaat agttgactta cttttcatct atattcctca 1560
attttgcaac taatagattg atttgtcatg gttttgattt cagggttttg aatattcttt 1620
gaaattggaa tttttaacaa aaatgcaaat tatgtgccaa gtcatatctc ctcctcacac 1680
tttttctatc acatgccccc aaaaaaatta atttttttca gga 1723

<210> SEQ ID NO 21
<211> LENGTH: 2546
<212> TYPE: DNA
<213> ORGANISM: Caenorhabditis elegans

<400> SEQUENCE: 21
gaatgcagga tataaatcac gattttcgtt ttcgaacaca actttaaact tcaatttttc 60
ctttgtttct ctgaaaactt tgcagtcatt ttcaagcttc cacagaactt tacaaaaaaa 120
ctagattttc tccaacgtgg cgatattccc gagtttcgag aagaatccag cttgtcaatg 180
ctgtataaaa cctttacttt tctatcgttt ccattatttc tttcactgca cctgttactg 240
ccaggtgctt tatttcgcct atcgtctatt ttgttttcct cctaccaaat ttgacaaccc 300

```
tccgcaaaca ctcattccta ttttagcccg gtgaaatttc gatatggaga aaaacaaaaa    360
caagtgtgag cttccacttc ggaataattt ccggagaatg agaattgtac aattttctcc    420
tataagacca tacaataaaa ttttatcaga aacatgaagc tttggtcatt atcatttttt    480
gttacccttg aaatttgatc acaaggcttt aatttttcat gagacgtcaa tttttctga    540
tgataaataa catagttcaa agtattgcgt aatgtttcaa ttttaacatg acacataata    600
aatcagaaac tcgaaaaacg tatttaaata tagattttgt cgggaagttt aatgtgcaac    660
tgtctcgata tctttctttg aaaacattta atttttatta tattttccaa actggattcg    720
agaattctcg tattcttaaa caaatttaca atgaaaatat aaataattaa tttaaaggaa    780
catgttctgc aatcctccct gggtcccgcc acgaaaccgc cacgcactac catgaaaggc    840
gcgttcgcat tcgttctgcc gctcgtttct gttttccaga tctttccatc attttcttca    900
ttcattcgcg ctctctcatt atcttgagtt gccggctatt ttcgctgctc tctgcttttt    960
cgtatcgctt tttcactctt tccagcattc agaaaattgc attatttcgg ttttcattta   1020
aaaaactcat agcaaagtat tttgttattg atttcgcaat actttcgaaa agtatcggaa   1080
aattttaatg tttagtctgt gcgttcctca ttccctgttc tcgttgtact cttaactgat   1140
gtttttaaat ttagttttcc ggggctctct tgaaaagacc caatagtcgt attgaacctt   1200
cgcctgatcg ccactagctc atcttttagt cttatgacgg gctcacatga ttctccccag   1260
tgtcctcccg ttttctcact gcacttgttt tgtcgttcgt tcatcagtac aaagtacaag   1320
cactttcgcg tctgtctgaa aattggttcg ggtgccgtta ggacattatt catactttcc   1380
tgctagtcgc agattataaa aaaatgtcct tgaccgtctg ctctttctta tgttctccct   1440
atatatgcgt caaacgaaca actgaccctg ttcacttttc ctattcttcg tttcatcatt   1500
ttctgtaaca aaaatggaaa caatacttta cacagacgtc actattattc aggcctatga   1560
tttctctatc gtttagttaa agatgaaaag aaactggtcg acccagttgc atgacgagaa   1620
aaaagaacac cccgttcgat tttcgttgta ttccctctgc acacattgtc cccttcttcc   1680
tcatcatttc tttccctaca cagcactcta gaatgttctt cttgtgcaga aagagtgccg   1740
tttgagtcag cgaccccccc cccccccctc ctttctcttg ctcttcctca ctggttctcg   1800
taataggcga cttcttgcta acagaaagtg agcatagcaa catttttttac tttgtggcct   1860
tcaataatac gtgcgtcgtt taattagaat gtttgagtaa agttcaacgt gtagattcaa   1920
tattcacgtt ttgggcgctc tttaatttat tactgtcaag aatcagttta ccaaacggtg   1980
agtttctttt tttttgtcta attgtaagat ttagcggggt aaaaccaaca gaaatgtcat   2040
gctttttga ataatctcaa tcagttgtta tatgaattat tttcccattt tagcaatact   2100
gcttggtagt tattttcggt cagagaaacg aggacatcag ctgaacatct gcgtctctaa   2160
caacactcgg ggaaggcgga gtcagtgtgc gcgtgcgttg ggggttttat cgatcgttga   2220
ggcgggcata cagcagtcat acaccccatt cgaccagaac gctccgctcg cgtgccacct   2280
tgtctccatt ctcatttcac ttgtctctac tcggacatta ctcctcatcg attagctctt   2340
tactaccatt ttacttttat gcctttcttt tttcgtttga cttgcctatg acgagtgggg   2400
atgaagtttg ctttgttagt cttactagtg tatcgatttt ttgggtaata tttcgcaact   2460
ttctaggact ttctttcata atcacctctt ctctcgcctc ctcattccag ttttattcgc   2520
actcattttc tattttttca gcaatc                                        2546
```

<210> SEQ ID NO 22

<211> LENGTH: 580
<212> TYPE: DNA
<213> ORGANISM: Caenorhabditis elegans

<400> SEQUENCE: 22
aatcaataaa aaaacgttcg aaaaacgttt gaaacaaaaa aataatattc gaattcttct 60 ccccttccc gtaaatcctg cagctctcta ccgtactttc gccgtctctc aatttcgcgg 120
cgagacccat caccacggca atcctccatt tgtgtcgctg ggcctaaatt ttttccgttt 180
ttttgctcga ttttcgccgt ttctctgcga aatttttcca aatttctgtt caatttaatc 240
aaaatattgt tctggacgct tgttcagcat agaaagtgga gattctgttg tattttaagc 300
ttggaaaacg aatttattat gaaatttcat ttttttgcta aataatttct ctattcttga 360
atttttacag ctttttaacg caaaatattc tttcctcttt gttctaaatg ggtagttaca 420
cacattatgc ggtctataac gtcttttgtc acctttgaaa ctagtctcta aagaaaaatc 480
aataattttt gcccctacgc tctcctccaa atgtttcgct ctcgccgtca ttttctgaca 540
attttactcg gtttcttttc aaattatata atttcagtcg 580

<210> SEQ ID NO 23
<211> LENGTH: 1037
<212> TYPE: DNA
<213> ORGANISM: Caenorhabditis elegans

<400> SEQUENCE: 23
tgtaaacatt tgttattata tttttaaact ttgtgttgtg gatgtgaata tgtggaattt 60
aataaaacat ttctcgatat aataatgatt ttgttgaatt agaaaaatta gaaaagtgga 120
cgattctaaa aacaaaagtt acaacgaaaa tcatcgaagg aaaaaacaac tgaattccaa 180
aatagttttc agaggtgatc acaaaatgtt ctcaaacgat atatattcta ccatcaataa 240
ttttattggc actatatcac agtccataat tcctgtgctt taattatact tttcagtata 300
gaacaatatg ctatattatc aagttatgcg tccaataaac acaatttatt tttcagactg 360
aatttaagcc atattgagaa tagcgaaata aaaacgtaga ggaaatttgt gatcgccatt 420
cacaattaat tcttagatcg caatgataac aaacttcgat tcaaaagtca tcatgcaaat 480
tcaccgttct cgtgtgtgtg tgtttttgga ggaaataaca caattttgtg actgattttt 540
ttacaacatg tggtttgtag catagttcaa agtcattcta gagggggctc agagggagtt 600
ctttcgctat gtcatcgttt gtttttgcac accaagaaaa atgaaaataa atgctctagg 660
atgtcatgga tcgtttccat tcttaataag tagaagctag gatttcctat acaaaaataa 720
gtaatcttcg tttctacgtc tatcaactta aatttttgta tacaatccac tttggtaata 780
ttcaaggcct tcctgtaaaa tgttttatga tcaatccgtt acaccaagaa aacaagtgca 840
atttgtcatc atgtaggctt ccgcctgtgt ttacttcctt cccccagcac aacactgact 900
atttatacca aattaataat gcagcattcc tcatgtgata actcgtttga cttttatatc 960
tttctacgtg catctttcaa gctcgaaaat taattttaaa aatttacatt gcagaacaat 1020
tgcggaacga agaagcg 1037

<210> SEQ ID NO 24
<211> LENGTH: 2502
<212> TYPE: DNA
<213> ORGANISM: Caenorhabditis elegans

<400> SEQUENCE: 24
attaatgaag aatccgaggt tcctcactaa agattctcgc tttatgatag agtcctcaag 60

-continued

```
cttgtatatt agagttttgg ggtgtttacc taaacttatg caaacggttt tatcatggtt    120
taactaaagt agtgaattgt tggaccaatt taaaataaca tcgatcgctt cctgcagatc    180
atttgtggaa ttagtttttt caaaagagca atatagtttg aggtcatcag cgtactgcat    240
atatttaaca gtttttggaa tgtttgcacc aagatcattt gcaaatatgc cgaaaagtat    300
aggtgaaagt acgctccctt gggggacacc acatggggcg ttcctaacag aagatagaga    360
attgttcact tttactttga acgtacggtt ggagaggaat gagtccaccc agcctatgag    420
catagaattg aacccggcct ttattaattt ttgcattaag agtgaatggt ttactttgtc    480
aaatgcctta ctgtaatcaa aaaatacaac atctacttga ttattgaaat taaaattttc    540
tatataggaa cttgatatac ccaatttcta ttaaaaaatt gaattcgcgc cgagcaaaat    600
gtgatgtcaa tttcagtttt ccaattttct caattttttt gaccactaac taaaattttg    660
ataccaaagg atttttgctc aaatttcgaa ataattgcgg taaaattggc tctaaacact    720
agtttttgac ctagcgaatt ttgatgtcaa tttcaattta tttacatttt atttggaaat    780
tttcttcact gcggatccct agcaaaattt gttaaacatc acttttccga gcaatttgtg    840
atgtcgattt ccgtgtcttt acacggtttt tgccttttttg cttaaatttt tcaaaaattt    900
cagtaaaccc caaccaaaat gaattttact cacaaatttc gctcttcaat tattttttta    960
gtgaaattca caaaatctga cctcacccta aattcccact gagcacattt ggatgtcgat   1020
gtttgttcaa gtttttggcc aagttttaaa caattgcagt caaattcaac caaatcacgt   1080
ggtgtcagtt tgtcccatta cggtttgatc tacaatgcgg gcattttttg cccaatcaat   1140
tgagaactct gcatcacagc taccacattt tttgtagata tacgtagatc aaacggaaat   1200
tagacactct ggcaccactt gccaaatcat atgcaaaact gctcaatggt agaatttgac   1260
aacccaaatt gctcatcaag tttttgtgtc attttccgcg caaacaggga ttcaaatttc   1320
tgccatcaaa aactcatttt ctacaaaaga actacaaata ttatttcaaa aaggcggcag   1380
tggtggtcaa agaacaaaca tctgaacata ttgaagaagg tgtctctctc tctctctctg   1440
tctttccctg ctcacacaaa tctgtgtgtc tctctccaga aaataacaac acttgaggtt   1500
cacgggagga cggggggagc tcccgcctgt gctccaactc tcttgtcatg ccactttatg   1560
ttgctccagt gtttttgtct ctctaaatct ccagctagct gttctttcat gttcccttag   1620
ccccaatacc gccgcctttc gatcttttgg ctgtttttttg ggggatataa gaagtttcga   1680
ggaggaagac tagatctatt catcctaaaa taaatttttt ttcttttttt ttaggcttta   1740
tcagactcta aaatgctcgt acgacaccaa attccagatt tcagttttct atattttcgg   1800
tcctataata ctatattcaa aaaattagcg tcttcgaagg aatctgacat ctaaaagttc   1860
tattggtctt ttttccggca aatcggcaga ttgccgaaat caaaaatttc cggcaaattg   1920
gcaaaacggc aaattgagag attgccggaa ttgaaaattt ccggcacaga ggcaaaccgg   1980
caaattgctg atttctcaga aaaactgcaa ttgccgaaaa ttttcggcta attgaggttt   2040
tgcattttat ttttggcaaa ttgcctgaat tggaaatttc tggcaaacca gcaatttgcc   2100
aaaaatgaaa atttccggca aattgccgat ttgccgaatt tgctagaaaa aaaattaatc   2160
ggcaaaattt tacgcatcta ttttgaaaag aaagcaaatt ctatgaaaat atctaaagaa   2220
aatcttttaa aaaaatgcac agttttaaat gtttcattcc tttcaaaaat ccctctaacc   2280
gcttccggca aattaatatc cggcaaaggg caaatcacca aaccggcaaa ttgccaattt   2340
gccgaacaaa aacaactgaa ttatgctatt aataattcct ggttcctgat ttccaatttt   2400
```

tgattatttc ttactcactt cagtatcgga aaacgttcac aactttggaa agaatttgat 2460
gcccgtaatt tgctgaataa atttaatttt ttcaatgtcc ag 2502

<210> SEQ ID NO 25
<211> LENGTH: 609
<212> TYPE: DNA
<213> ORGANISM: Caenorhabditis elegans

<400> SEQUENCE: 25
gttttctgca aaataatcat tgattttaac acctcgtaaa ataattttaa aaaaagaagt 60
taaaatttta attgcaaccc tatttgtaaa aagaaaactc attttcgcca aaaataaagc 120
aaaaataatt caagagaaaa acgcgccgcg tgttgcgatt ggggcgtaac tgcaatgtgt 180
gcgcacacaa tctcaacaag cgctgcgaga cccgccgcct gaccgtaatg tgaaatgggc 240
ggagacgaga agtttttttc tgtttgaaag ttgatgcaaa agcccgtgat tcttttttc 300 gagaaatttc tcgagttttt tccaacgaaa aattcattaa atttaaacct tttagctctc 360
ctttccaata ttttgcatca ttattctcct aaaacttggc atattcagtg gaaatgatgc 420
aaaatgccct gacttttgtt atcaaaaata caagaaattg tcccgtttaa cggttgaaaa 480
gcaaattttg tgtcattttg tttaggaaat gtcaaaataa gctcaaaaac cgattacaaa 540
ttatatttta ctgcttttta tcctattttc tcgcgttttc gttcatgatg caattttctt 600
tcaggcact 609

<210> SEQ ID NO 26
<211> LENGTH: 836
<212> TYPE: DNA
<213> ORGANISM: Caenorhabditis elegans

<400> SEQUENCE: 26
ttttcggctg aaaaattggt tttttgagtt ttaaaattta tttttagcgg gaaattacat 60
gaaaacaacg aaaaaacccg aagaaacccg cgaaaattca gaaaatgatc aaaaaaccaa 120
aagaagcttc gagaaaaaaa gcagaaaata aatgtgcggc gcgaaaaatc tcgtgcggca 180
aacttgcaaa tctaggcgtg tcgggccaat ggcagacacc gcgccgcaaa ttcagccaat 240
cagcgcgctc agctccacct agaaaagtgt gcgcaccttg caaaactggg cggagcgagt 300
gaaatgatgc aaaagtctat tctgatgtaa attagccatt ttacatcaaa atttgcgtca 360
ttttcgttat ttttctctca tttttcatat tttgaacgaa aaattgaggt tttttgcttc 420
tattttcatc agaaaccatt gaaaaatgct tatttttggg ccatttttcg tcgaaattag 480
gggaaaaaac tattctacag ttttcccagc tattttctca tttattcctg tatttttcag 540
tcattacctg cttcccagac gataatgcaa ggcttctcgc ttcattttca taaaaaacga 600
ttgaaaaatg cttatttata ggccatttat cgtctaaatt aggggaaata tctgttttac 660
cgttttccca gccgatttct catccattct cgttattttt cactcctttt ctgcttctca 720
gacgataatg caaggcttct cgcttcattt tcgatgagaa actctgattt tgctcgcatt 780
ttcgcctttc cgctgcagat tttcacacaa ttttcgtagt ttttcagaca caaaag 836

<210> SEQ ID NO 27
<211> LENGTH: 580
<212> TYPE: DNA
<213> ORGANISM: Caenorhabditis elegans

<400> SEQUENCE: 27
agagaataca aaaagagacg aaaatggttc agtggaacga aacaaacgtg ggatgtaacc 60
atggaagtga gaataattga tggaatagct aatgagctga agctgagtag atcagagact 120
actttattct aaaaagtaca gtagttggaa aattacatgt ttcatttcta attttcaagg 180
aaaagctagt aattaccgta atcttgtttg tacctgaaat tttatgtact gcaggtgacc 240
aagtatgttt gaggcatgac ttcacacacc taactgataa aggcctctat cacaaactag 300
agttgtgacg gaaaattcaa cttctcagaa tatagctcaa aatctatcaa attttatttt 360
caaaaatcca aataattgtg cacgcaatgt acttactgct tcataaagtt cagaagaatt 420
ggataaattt gaatgaagtt ttcaaagctt ttatcagtga ctgtacattg tgataggctt 480
gtgctgttat cagctgcctc aaataggttg tcgcttgaaa atttatataa aaggcctacc 540
agcagacatg agaatcaagc ttcaaaggct ctactcaaaa 580

<210> SEQ ID NO 28
<211> LENGTH: 584
<212> TYPE: DNA
<213> ORGANISM: Caenorhabditis elegans

<400> SEQUENCE: 28
ctgcgaggaa gagaaaaaat cgtgctgtga aggaaaaacc gagaagactg agcaaaagaa 60
ataaccaatg agcaagtgaa cttttcccac gtctactact aaattattgt cgatctataa 120
ttctttcgct tatcaatctt gtcaattgaa ataaaacaat atttttctaa ttctttttgg 180
aacgaacaca cgtgtttaaa tgaatgttgt gctaaaaacg tcacatcaat ggtacgtgaa 240
tgttgcaaac accttgtcaa taactgataa aatcagaaac tagagctgtg actgaatcgt 300
atactagaac ggagtctctc taaaaacgtt ctaaaaacaa acaaaaaatt gtgcaaagga 360
ttagagtgct caagatcaat gagcaaactc acaatcaact atctgttatt gttttgggtc 420
tcttctatat ctctattctt ttagtatcat aagtttgtac attgtgacag ggccaccctc 480
ttttatcaca tatttgaagt ggtaaacagc cagcaaaaac caaataaaaa ggcagtgaga 540
aaaagaagaa ggcagctcaa tttgactgct gaaattaaga aatc 584

<210> SEQ ID NO 29
<211> LENGTH: 1031
<212> TYPE: DNA
<213> ORGANISM: Caenorhabditis elegans

<400> SEQUENCE: 29
tctgctgatt tatttgagct tctctgtgtg accaagacga gagccgaaga gtgaagtttc 60
cactgtcaca ccatgtattt tatactagtt cagagtatct ttgaacacct gttttaaaaa 120
ggtacaatac caaaaggcgc tcttaatgca cccggttaca tttgtatttg tttgatcaga 180
tggatgtctg tctgacaaac gtcggccaaa gaatgcactt gcagacttta ctttaatttt 240
ttgtctagtt tgaaaattct tcggatttgt tagtttcaag aactttcaat gaaaccgaaa 300
gtttgttgag ttagcgagaa ttacttctga ttacctgaaa attaatttga ctcaatcttt 360
tacctactta gaaagactaa agtttctgca caaatttgtt tgaacaggtg cttcaaaatg 420
ttacagaatt ttcattttca tccacataaa aagttgattg acaaatagtg tgggcgacat 480
gatttcttga acaatttgtt tcgcttttca atttggactc agttcttcga aatttagtta 540
ttatccatat tattactgtt ttgagtttta tcgcagtagg aaatactggt gtatatacat 600
attatatttt tccgttttgt ttacccagaa agcttaaaat tcaagttggt cagaaaaata 660
aaaaaacaac ttttgcaaga aataccattt tttcatcgtg cggaaagaac aattgaaaac 720
taagtatttt ttgctaaact gcagtactgc tacaatacta atactgtacc acgatagtca 780
cccaacagta cgaactccta ctaaaaattt attaaaaaaa gttttattat tcaaattttg 840
aaaatccata agttctaaat actttgttca gtatgctata cttaacacaa atggtattct 900
gcaattgaaa cagaaactac aataatttta tcacaaaaca cagttctccc tactttctta 960
tcacattatg tcatcggggt ggcaagtata taaaggaatg ctgtaaaaag atatgtacta 1020
ctgtctcaag t 1031

<210> SEQ ID NO 30
<211> LENGTH: 1084
<212> TYPE: DNA
<213> ORGANISM: Caenorhabditis elegans

<400> SEQUENCE: 30
agaatttgca aaacgagcag gaaagtcata ttcgcagaaa aaagtcgttg caaacattcg 60
tttttatatg tttttctttg agaaagcgtg gttcattttt gaaagtgaaa aatatttgct 120
taaaacttcc aaatttaaat ctgcagtgat tcagagaggt tgagaattat tttcaaaaac 180
attcaatgtt ttcccttgga gtgactatgc aaatatgaaa atgttttcca aaaatatttg 240
gatgccctga taaaaagtag gtgaaatttc gcaggggaac atcatattaa aatgttgaat 300
ttttagaaga aatggaaatg tttgtcggtg gtatgctcga atatttgaga tattatatat 360
ttactgttaa atccgaaatt tttgacaaac ggaaaaaatt tgtgtcgaaa tactacattt 420
tcgataacac aaaggtactt ccataacact tataaaaact gtttgactat cttatttcag 480
gaaaaaaaaa tccaagaata aacattttc agaatttgaa ctttctaatg gctgattaat 540
aaaacaaagt tatacaacta ttcaaagcag ttgctcaatc tggcattttc ttgtgttttt 600
ttttgaatat ttcatcagca agatgttgat aattttgtgt taattctaat tgttttctac 660
aatttttcaa accgaaaatt gacctttgac tttgtttact ttgttctcgt gggttaactg 720
ttcactgatt tctattgctg ttgatgaggt ctttgatcaa atttgtattg tttttatact 780
gcatattgct tcaattctaa atcatctaat atattgtcaa acaacttctt gttttttttt 840
tcattcaaaa cttctgcaaa aacgttctct taacaaaggt tcacacaaca actctcctct 900
ccatctcttt ctctcaacaa caatgtgctg gccttgcatg tttgccagtg cgggttgttt 960
acgcgttttc aagatttttg gtctcctatc taacgtcccg aaatgcattt tttcctttca 1020
tttggttttt ttctgttcga gaaaagtgac cgtttgtcaa atcttctaat tttcagtgaa 1080
taaa 1084

<210> SEQ ID NO 31
<211> LENGTH: 1929
<212> TYPE: DNA
<213> ORGANISM: Caenorhabditis elegans

<400> SEQUENCE: 31
caattattat aagaaaataa atttaaagtt atccgagcaa caattatcaa taaatattac 60
ttttttaaat gaaaaccttt ttaatttcag cagaaatctt agaaatcaga tgatcaataa 120
ataaaaacgg ctgacttttt aaaggcgcat agaattttct tggtggcggg tcccgcaccg 180
aagagccgtt ttctaaataa tatacactaa tgattatttt tattaaattt tttcacggtt 240
ttcgagagta ttctttatat aaattcaatt ttaaagcatt ctcgtcgagt ttgaatccga 300
aattatcgat tttcgttttt ctctgctttc tctaccgctg ttttctctcc tccgctgtct 360
tcgcaagatt atagagctct tttgaatcaa tttgtttcat gtttccgctt ttgacgttat 420

```
tttaaacata tactgatata aataaattaa gaatagagta gaaaatctag ttcaagtaaa    480

gatgcaacat ttctttctgc aaaatttctc gaaaacacct gttttccaaa acttttcaat    540

tacacaatta gaatttcgga aaagttaaca tatataagaa catattatat atatatatat    600

atatatatat atatagatta actctcacag ttaaagaaat ctgaatagta atattgcgaa    660

atagttttgc ataagtttgt ttgattaaat taaatgtgaa gcactaacgc tattgaatcc    720

aggaaaaact cgaattattt gtttgatttt tattaaacac actttgtgaa caattttcgg    780

ttaagaggct ttgttgtagt aaaaatccta aatctacgat tatcttctta aaatttgaca    840

tacttcttac gtatgttaca ggataaatcg agttttgatg tatttcgtaa atagttttta    900

atcatgttat ctttttattt cccatctcta tgttttaatg ttgtctttac actaattcac    960

ccgtaatgtc cgtgcacaaa agaatttaac attcagatat tatggaaaca aaatcatccc   1020

aaacttcaca tccgtggctt gttctactca ttttcgccac ttttgcggtc tcaatttttg   1080

ctgtatacag caattttcct gaagtctcgg cagatgagaa ggttcatttg aaatatccca   1140

ggaatctgga agacgctaag cagctgggca gagttctctc gaagtacaag gagaacaact   1200

attcagtagt tctgtgcggt gtaattgtcg tctacgtatt tctacagtcc ttcgctatcc   1260

ctggatctat ttttctaaca attctatcag gatacctgtt tccattctat gtggcaattg   1320

tgttggtgtg ctcctgctct gcaactggag ccgccatctg ctacaccatt tctaaacttt   1380

ttggacgatc atttgttttg caaaagtttc ccgaaagaat cgcaaaatgg caggatgatc   1440

tgagcaagca tcgtgatgac tttctgaact atatgatttt ccttcgagta actccaattg   1500

ttccaaattg gctaatcaac attgccagtc ctgttctaga tgttccactg gctccattct   1560

tctggggaac atttctaggc gttgctccac caagtttcct gtatattcaa gctggctcaa   1620

cactggaaca attgagccat accagtgtag catggagttg gagttctatc gttttactta   1680

cgggttcggc gattttgtcg ctggctccta ttttgctcaa gaagaagctc aaatcggatt   1740

aattttctct cttatttcct ctttcgatct catttttttt ccattgcttt ctgtgcaaaa   1800

cttgtgatat ttagagaata tagccgataa ctcatttcta tactattttt atttattttt   1860

cgcctccttt tttgtcataa taatcatatt ttcttcacta ataaacaatt tttaggtgat   1920

gaaacaatg                                                           1929
```

<210> SEQ ID NO 32
<211> LENGTH: 1091
<212> TYPE: DNA
<213> ORGANISM: Caenorhabditis elegans

<400> SEQUENCE: 32

```
gaaactctcc tggatttttc tagattcttt tccagttaca tttcacatag aatctctaac     60

taccggtgca tttgccaatc ttcttactga aattctgtgc cttgttttgt cattaaaatt    120

ttacaccgaa taaattattt gtctttgtaa tagcttatga ctttaacaag gtcatttttt    180

ctaactggct cattcgcgct gaagtttaaa agaagtttgc ttttttgtcg gttaagccgt    240

tcatacattt tttggcaatc ttggtacaac catctactac atttatatca aaacgaaaaa    300

atgtataaat tttccctcgt cttcatctac ccgcaatcat aaaggaatct cattccgtcc    360

cactcgccct ttctttcttc aaccgaaatt ttttttcccg cggcgcaaac cctcatgtgc    420

cgtcgatagc tcagttggta gagcggagga ctgtagagtc agcaggtatc cttaggtcac    480

tggttcgaat ccggttggac ggatttcttt tttattttct gtatcaagtg taactcttca    540
```

-continued

```
gaaaatcatc gggagcagtc gtacgaaatt ttaattataa aaattaaaca ttccagcatt    600

tttctttggg aggtgaagta gagtcagcgc ggatttaccg gatttacagt tagtttgata    660

cacattcaac attcaatatt accgaatttc aaaacaaaac atttttacct aagtctttta    720

gattattgga aaattacagg taaagttttg gtgaaatgcc aaagtcataa tgcgagatgg    780

ttttttttt tgaaaaattc agatcaaaac tacgtgtttg gtttgtgata aaatattatg    840

atgaaaaaaa ctcgaagaaa tcataaccca aatgatattc agttcacaaa cataagtatc    900

atgatgcaaa atacaaagct gaatgtattt tttcaagacc gcagatcaca attaagacat    960

ggtaaacaca aactctactg cgtaccgcag tgaaatgtgg tttgtagtat gactggtaga   1020

gacacatcga cctatataaa catcaaaaaa ttgtttaaaa aaatattcca tcgagaattg   1080

cttcatttca a                                                        1091
```

<210> SEQ ID NO 33
<211> LENGTH: 1769
<212> TYPE: DNA
<213> ORGANISM: Caenorhabditis elegans

<400> SEQUENCE: 33

```
atattggaag tcaatgagaa ggaggaattc tggattgcaa acgagaattt ggaagtgagt     60

ttggagatag tagcaagcct aagcctgggc ctgagctgag tcaaagccaa agccgaagcc    120

taagcctaaa tctaagcctg agcctaagca taagcctcag tctaagatta agcctaagcc    180

tgagcctgag cctgagcctg agcctaagcc taagcctaag ccaaagccaa aacctaagct    240

taaacctaag cctgagaata agcctaagtc tatgccaaag ccaaagccaa agcctaaagc    300

taagcctatg cataaaccta agcataagcc ttaacctaag ccttaaccta aacctataag    360

cctaagccta aattttcagg cactcactac cgaaaatttt ccattaatgt tcaactcaat    420

gctgtcgacc gtcctgaaac caattgacac cctcattgaa tgtttcaaaa aagaaggacc    480

ctacggcctg gattactcgg cctattcgga ttttgaagaa atgcagcaaa aattcactaa    540

aatcgttcac gagaagcata tcattccgga tttggttcca gccattggaa acgggatcaa    600

ggagaagctg gaagctggtg ggatccgagt gttggatgtc gggtgtgggg gtggattcca    660

ttcgggcttg ctcgcggagc actatccgaa atctcagttt gttggattag atatcaccga    720

gaaagctatc aaagcagcga ggctcaagaa gaaatctgat ggcactgatt ttgaaaactt    780

ggaatttgta gtagctgacg ctgcaataat gccaagttca tggaccgact cattcgattt    840

agtcatcctg tttgggtctt gccacgatca aatgagacct gacttggtaa tttttgtatt    900

cagtttcaga gaggtatccc aatcatttac agtgccttct cgaagttcac cgtgtggtga    960

agccagatgg tttagtcgcg gtcaccgacg ttgatggatc tagcaatgtg ttcaccgatc   1020

gtgagaccta cgggaagatg gctgcgatga agtatggtgg atcgatgctt cattgtcttc   1080

cggttgggag caataggcca gatgcactat gttgcggctc aatgtgggga aggaagagag   1140

cagttgagat aatgaataag tgtggttttg ataatatcga cattattccg actgactact   1200

tccctggaac tgttttgtat ttgatgaaaa aataaataaa ctgtagctag tgttttttta   1260

taattgtaat actttttcct atttattcaa tctttttcc cgattttcac tgctttgttg   1320

tgactgtatc attatgatcc tgatgaataa atatcaataa acaaatacag ttttttttt   1380

atttgacatt gatttttgat tctgagaata taatacatat ctatgagaaa ttaattaatt   1440

aataattaat aagaattaat aaatttaata agaattaaag taaaatatag tgggaatata   1500

gtggaaaaat tgttttgtaa ttgtatgcaa tatgtttata attttcaaaa tcaaagagca   1560
```

gcacgacgga gcccaatatc aaaagttcaa gcgacacact caaaatacga ctcatacctg 1620
cgtctcctcc ctctcccaat ttcgcaacat attttcgtat tttgtggttt cttcagtcgt 1680
ctatttctcg cacatacttc cacctgatgc aatttcgagt cctcaccaaa taaatagccg 1740
gcaatgtttg ccatttctca gttttcatc 1769

<210> SEQ ID NO 34
<211> LENGTH: 1406
<212> TYPE: DNA
<213> ORGANISM: Caenorhabditis elegans

<400> SEQUENCE: 34 ttttttttt ttttggattt tcgactttaa aattagccta aatttatcct aaaattatcc 60
taaaaattaa aatttcacat ggttgacaaa tttgcagtgg agcgcatttg cagaattttt 120
tttttgaatt tttttttcat aaaaagcgta acattttcca aattaatggg atttttaaag 180
gaaaaaatta tcccaaaaat tttaattttc taattgaaaa aagtgttatt agcccaattt 240
ttaaaggttt tttttgcaat tttcatcaga aaaagcgtta aaaatatcaa tttttcgtga 300
aaagttgatg aattctctca aaaactcggc aaaaagtacc gccaaaaatt caaattctcc 360
aatttttcat ctctaccagc aaattcgcga tggagcgcat ttgcagagtt ttttcagaaa 420
aatcgtaaaa ttttccgaat taacgagttt ttttttaagt aaaagtgatc ccaaaaattc 480
aaaattttcc gatttttgaa attttttttgg tgcaaaaaaa ctaattttca aattaaaaaa 540
aagtgatttg tctaaaataa aaagcgttta aaaaaacctt ttaaaaattt tttttcccaa 600
aattcacgtg gtgccagggg ctgtcccatc gacggtttga tctacaaaaa atgcgggagt 660
ttttcgccca aaaatgttgt gacgtcagcg ctttcttaac catgcgaaat cagtccccgc 720
gcattttttg tagatcaaag tagatcaaat cgaaatgagg cattctgaca ccacgtgaaa 780
atttcaaatt ctccaatttt tcatctctac catcaaattt gcgatgaagc gcatttgcaa 840
ggcctttttt taaatttttt aaaaactcct taaagttaaa aaaaatcatt tagctttaga 900
aagcccaaaa attaaaaaaa aattttttt taatcgaata tcaaaaatgc atttgtgctc 960
caccgcacgg cggtaatttc gaaatttctt taaaattttt tttataaatt tctgtatttc 1020
acaactgtat tttttcccga attttcctcg cctaataaca ctatttgtca tgattcttac 1080
gtcattgtcg ccgccgtttc tctttttctc tcgccactct ctcatttcca tacactattt 1140
ccactctcat ttttatcatc attttcttca gtttttgctg cttttaaagc ctatgttttc 1200 ccttttata taatatcgca gaattttgtt tttgtaaatt taatatatat atatatatat 1260
tatttatttg atgataatgt gatttctaat ttttttttcc ccaatttttt tcaaattcaa 1320
attgtctcta cgcttttctt atacttcatt gcctttttttt ttcaacaaaa atttgagaaa 1380
aaacaccaaa aaatttcaga aaaacc 1406

<210> SEQ ID NO 35
<211> LENGTH: 1051
<212> TYPE: DNA
<213> ORGANISM: Caenorhabditis elegans

<400> SEQUENCE: 35
gcacgtgtat ttttttcggc acgtgaaaat tttttttcaa catgtatata tatatttttt 60
caaatttgga atgtcttatg aaaaacgtcg aaaaggagga actcatttag attaattgtt 120
atgcaaagtg cagattttta acaacgaatt tttgagatca aattgtcaca gttagctgat 180

-continued

```
gttttcgaac tctacacatg tgtgaaggtt cactcagtct gattggttca aaagtggcgg    240

tacgagtcgc tgatcggtct tgcagttctc aatttcgagg aaaatcaaac aagaagatta    300

gccaaaatta aaaatttacg tttttgaaca gtgttttcat tgttattctc atttatgtta    360

tgaaaacatt ttcaaacgtt ttttcctgga tggtaccatt cattacatca agaacttcct    420

gtcactttaa tgatcttttg ttttttgta gtttgaatta aaatgatgat atccattgaa    480

attgagtgta ggcgtatcat gatgacaatt aattaatttt gatcttttgc tacagggttt    540

tccataggtc agttagtaag tgaaatctat aaatttggat tgtaaacgtt ttttcaacct    600

tgattttgtg tttttttca gttttttatt tattttagat atttaacatt taaactattg    660

aagcttttaa aaatcatagt tttatgtaaa attgaaaatt gtggtaaatg acgttttagg    720

ccgaattagt ttttcattta agactacatt ttatttcaac atctaagaac tttttgacat    780

ttttcgagcc attgttcaaa aaacatcatt gaacactaca cggttcaaaa tgtttacact    840

agatacacaa accaatagag acactctttt aagaggcaaa tggtcagaga attagacaat    900

gagacattct tttcttctgt gaatttgtat gttatagtga ttagacagtt aggatgacat    960

atatttgtca gcacaatttc tcttataaat acaagaaaat tttcagagat tctcatatcc   1020

atttctattt cattgaaaag ttttttcaaa c                                  1051
```

<210> SEQ ID NO 36
<211> LENGTH: 1121
<212> TYPE: DNA
<213> ORGANISM: Caenorhabditis elegans

<400> SEQUENCE: 36

```
tgactaacaa tatgaaatgt gtataaagct tcatgatttc acaaaattga agtctaaaaa     60

atataagctt taattttttg ctgtatgagc ccctcaaatt ctcttatata ctttttcctg    120

ctaatggcta cttctttgat cgaagatttg gccaaccggt taagtttgcc gacaccagca    180

taaagaaatt ccgttcatcg cattcaattg agttatagga gcaaacatta aaaattgatg    240

gtataacttc ttacaataac atgtgaacaa acagcacgtg ggcataatca agaaaagaag    300

cttttgattt tgaagttgat aagggaaacg atcaaggtgt tcaagaccga aaataatatt    360

ttcagtttga gtaagttgaa aattatatta tttttgaata ctttttaaac agctaacaga    420

tattgcaata gagtgcttga agttgtatgt caatatagtt ttcgtgaata gacattaatt    480

acagtgcggc tcataataaa ttttattgtt ttttttagta ttctacaatt ccatcgagta    540

gctcctgaaa atgtgaatag cctagatagt aaccgattga gaaagtaaac gtgcgcttat    600

gagttacgtt tcgtattttc acaaaatcgc agtataattt ttagtcattt cttcaaaaac    660

caaaaatcta ctgtaccctt attgtaatca aaaatgtgac ggaatctcgc atgaaaccaa    720

agattgttta caatcccaaa aataatccaa aaattgccct gtttctctca attcactgta    780

cattttcaaa gttttccaca gatacatttt cattcatctg tgaaatcgaa tcttttagac    840

tatgtatttg tcataaaatt ttgtgattct tttttgttct gttcactctc tgtcccttat    900

cgttcgtatc tctatttctc tattctctcg ttaccatctt atctattgtt attccatttt    960

tttggtcatt tgtttattga actcccttta ctcaactgca cacaaacatt tctttttatt   1020

ttcttttgaa tatatgctcc atgctaacca gaactgacct gttgattctt tttttttccc   1080

aatatactag tccttttctt aagttttacc aatgttttta g                       1121
```

<210> SEQ ID NO 37
<211> LENGTH: 854

<212> TYPE: DNA
<213> ORGANISM: Caenorhabditis elegans

<400> SEQUENCE: 37
tcagcgatga gcacaccgtt caaagatttt ctgaagcatt gggcttacat gtgaaacaag 60
cagcactcga tattagtgaa ggaaaaatac cgaaagcaat aattgcattc aactaaatac 120
tgtatttgca cttggtatta cagaaacgca aagttctgag aatgcgtact gggtaacata 180
tttgacgcgc aaaatatctc gtagcgaaaa ctaaaataat ttaaaaaata attcgctttc 240
gattagaaat tcatttcgaa attcgagtat gtaaatcgac tacagtagtc aataaaagta 300
ttactgtagt tttcgttacg aaatattttg cgcgtcaaat atgttgccca atacgcattc 360
tcagcatgtt gtgttcccgt aacatttaac ctattttaca taatctaggt gttttaaact 420
ttttataaaa ctttctcgta atgctatctt tgcctcttag aaaacttatt cagcgacgtg 480
tatcataacc aattctaatc ggcttgttag aaagaagaaa tataatactt cggcgtctcc 540
actttgtgac tgggcacaaa atgcaattca gattctactt tcgaaatagc cataaaatca 600
taagatcaca gatctttctt cgtttctcag gcaaccaggt gcacaattgt catcactcga 660
ccagtgagac cacaatagaa cagcaaacgt tgtcatcttt ttggttagac actttctttc 720
tgcctctgcg tcttttcata aggtgtgcat actcttgttt gcccaacaac ctagccgatc 780
agaaaacgca ctatatttga cctgcgtgta cactgctata aaagtaacat tttgttcttt 840
catttcttcg aaaa 854

<210> SEQ ID NO 38
<211> LENGTH: 1616
<212> TYPE: DNA
<213> ORGANISM: Caenorhabditis elegans

<400> SEQUENCE: 38
aatgcaaaaa aataagcctt tccgaaaaaa cgggcccttg ggcctttaaa ggacacaaaa 60
acaggaaagc ataagacacc aaagagtaat tggatttcta cactttggtt cctagaatta 120
tttataaggt gttattgcgt ttttgtgaga ttgttctatt tatccagtca aaaattgcat 180
tttctttgtt tttgcttcaa aaaaatacat tttcagtgga aatttcagct gaaaagcaga 240
attttgaggt tttcgagtaa ataacgtaaa acactaaatt acaaatattg atttttgatg 300
tcttagacca aattttcgta aacatgtttg tatttttgga aaaaataggt tttttgtcga 360
ttttaactta atttttcgaa caaaaaatga ttttttctcc gatttaccaa agttttgact 420
taaaattccg attttctggg tcatttttcc cctaaaaata cgattttaat tcaaaaaatc 480
tatattttca aagaccaaag taccataacc ttcaaaaaac aaccactttc tctattgcat 540
cagcgaattg tcatcacccc tctcaaaata tacaaaacgt catcattttt ctgtgttttc 600
tctaattctc ctgaaaaatt ctataaaacc aacagttttt atcatcaaaa atgccttttg 660
accgactttt tttaaagttg aaaatcgtac agttttagca gaaattccag agtttcattt 720
tgaagtatgc tggaaataat aaaattattc taacatttat taatattttg taaaactaat 780
tctatacaat aaaaaagtaa aatttaatat taaaaaaacc ggtttttctc aaatttccat 840
tccccaatgt cctgttctat tatttgttcc gattcggcca cagaacgcgc acacacacac 900
tttttgctga ttctctgcct cctttctttg atttgaccgc attttatatt gattttcggc 960
cacaattcca ctatttgttc agtttgtcga tttgttggaa atttcaattc cggcaattcg 1020
ccgatttgcc ggaaatttaa attcagacaa tttgccggtt tgccggaaat tttcagttcc 1080
ggcaattttt taatttgccg gaagtttcca tttcggcaac ttgccaattt gccggaaatt 1140
cgccgttttg ccggaaattt tcaattccga caacttgcct atttcccgga aattacaatt 1200
ccgccgattt accaatttgc cagaaatttt taattccggc aatttgccga tttgtcggag 1260
atttcaatcc ggcattttgc cgaaaatttc aatttcggca gttcgccgat ttgtggaaaa 1320
taacaattct ggtcattcgc caatttgccg aaaatttcaa ttccggcaat tcgccgattt 1380
gccggaaatt ttcaattccg gcgattttcc tatttggcga atatttttaa ttccgccggt 1440
ttgccgcttt gccggaaatt tcaattccgg aactttgccg atttgccgat ttgccggaaa 1500
aaatcttttg ccgcccaccc ctaataaaga cttcaaaata tgcgtttttt tttgctttta 1560
acacgctaaa actctctaaa aatccccaat ttttcagctt aaaaaacccc aaaaaa 1616

<210> SEQ ID NO 39
<211> LENGTH: 726
<212> TYPE: DNA
<213> ORGANISM: Caenorhabditis elegans

<400> SEQUENCE: 39
ttttgcagac taaaaataac tactctgcca gtgtttaatt tatagatgca atttgtcact 60
attttcattt tatatcgacc aacccattca cacttcacta atcgtgttaa aactcaatta 120
gtggaaaatt tgaaattcta tgaaactttc atttgcgaca aaagattgtt gttttcttca 180
aaccaaaaat ttatcaatgg gaaaatgaga tagacaagaa ctgggaaaaa agtcgaggtt 240
aataatttaa agaaatattg aatattcggc gccataatat taacgaaaat aaccaaaata 300
tgcccaatta ttatccaaaa agattagaag ttggcaaacc ttgggcaaga atttccagag 360
attgcactaa agttgtagcc aagtttgatc caactttatc caatctttta ctaaaattat 420
ccttaagact atttaaattt tagatagaga attggcgaga gttagatccc acttggatat 480
gacttatagt tagcctaacc tgaagctatt gcttgcttga tcatttggtt tatcgctttg 540
ctacttggat aaccagctcc aatagttgtt atttttgctt ttgtcatcat ttttccacga 600
tttacactct caagtgaaac caactgttct ttgatgccag acgatgacat tacacttgat 660
aagaaaatat atataaactg gaattaaaaa caattgatac atcgattcaa ttactgaatt 720
ctaatt 726

<210> SEQ ID NO 40
<211> LENGTH: 1283
<212> TYPE: DNA
<213> ORGANISM: Caenorhabditis elegans

<400> SEQUENCE: 40
atttcatttc ttttttataa atacttcggc tctattactg aatgaataaa tgtataatga 60
tgctctccaa atcctcttat tattcgctcg aaccgcccgt tcccatagat accgtctagt 120
tttgacaggt gttcaaccat ctgccgggaa ttacgagaag agtcgaatta attgagatcc 180
tcgtctaaat aaatctgaag tttaaaataa agccagaaat acctgaaaag agagaaaaag 240
tgtgtccacg atgtctttgt ttatgaccag tggtgtgtta tcgagaaaaa ctccaatgaa 300
tcacacacca gagaagaatc gagaaaggtc gggaaattag gaatgagaaa taataaatgt 360
gaggaagtaa taaaagaatc ttcgagaact cattccactt ttagatataa aacaagcagc 420
aaacgggttt gtaggtatta tatttatcta ttttaagttt aataaactat ttttgctaaa 480
cttaaacggt tcaggtgttg aaaaagtcct aaaatttttg atattatcaa attcttttag 540
cgtggcggtt ttcttttttt tcgaaatatt gagtttttca tctgaaaaat gcactattcg 600

-continued

```
tgtccttcaa aagttcatgt gtcatcagta gccactcgaa agatcgatca gtccattttg    660
atttcgaaag taagaagaga tcattactat tcaagagacg caggcacgga gcctgttgcg    720
ccgcgaatct tccaggcatt cttggcgctc cgcccaaaaa attgcaaaaa taaaagttgc    780
ttgaatcatg ttgaatgtca cttaatcgtg tggctttcaa tgttctcttt cagaaaatgt    840
atttttttatt tgataatgtt aagaattcgc cgagttattc ttcctcaaaa tgtggtgcgc    900
gctctctctc cccttttcg tcgcgaacat tctctgcgga ggcatctctt cttttaattc    960
acaattctca acacttttct gtaggcaaaa ctctctaata ttgctccttt ttcagatttt   1020
tgttcaaact ttttttgtat ttatcttgtt caagtgtttt ccattcagca gttacagact   1080
atttaaggaa attttaggtt tttagcacat ttttctaatt ttttgacgaa attcgaattt   1140
tctagaatcc cgccacgccc agtcatctag taaatttgtt gaacttcatt tctctatttt   1200
taatcattgt tctcgacgtc ctaatttttt atctccattt gagtgactat ttcttgattt   1260
ttaaattatt ttttacagta aaa                                           1283
```

<210> SEQ ID NO 41
<211> LENGTH: 1622
<212> TYPE: DNA
<213> ORGANISM: Caenorhabditis elegans

<400> SEQUENCE: 41

```
gctctgccag aagaagcatt aaattgtttg atattcaaac ttttgtatat agaatctcgt     60
tatttataaa ctcttttttt tgtatttctt ctggtttttg atgataagaa attttatgtg    120
cacataaatc aaaaaagccg gaaattaaat agcgttttat caggcagaaa attggccacg    180
tgacgtcatc attttcctgt ttgaagaaaa tctggaaaat tttttgtttc agtcaatttt    240
taaagatgaa aacttaagtt agactgtaaa agcaattttc gcgccaaaat tacggtatcg    300
ggtctcgaaa cgacagtttt ttatctattg cgaaaatatg tgcgccttta aagagtactg    360
tagttgcaaa cttttgtcgc tgtggagttt ttatcgattt tttatatttt ttcgatgaaa    420
acaactcaaa tataacaata aaaacacaaa attaaaaaaa aaatcgataa aaaatccgcg    480
tcaacgaaag tttaaagtta cagtatttgt cgtttcgaga ccgggtaccg tagtttttgg    540
tgaaaacatt gcaaaatttg gtcaacaatt tcatcgctgc gagaccgaca caacacttta    600
ttttattttt gggtttccct tatcgcttat cataaacatg tgacgtcatc atctcttgta    660
cagagcaccg cgactgggag tataagaatc gccggaaaac atcaataatc agttcggtag    720
aagtgaaaat tgagcgtaaa atatgatcat ttttcgatgc accatatttg acgcgcaata    780
cttctacaag ccgctgtgta ctgctcgtgg acaactttgg attatttttt gtttttaaaa    840
ttcaaaatag tcaatatatt gcttatttat agcgcgcctt tttgacagta agtttgtcaa    900
atttgcgcgt aagttatggt gtttgcacat atgcaccata cagcaacacc ccgcggcccg    960
gctagtggta catccatgca aatgcgctct actgataatt tgagtttaac caggtttagg   1020
cgcaagataa gaaaaaagct ttggaccaaa aaatttagag tttatttttt tcggacattt   1080
tttatataca tcacaaaaat attgggccac tcgtttttga taaaaacgac aagcccaaaa   1140
gttcaggtat acggtagaca aattgcgtac aggtaccact tttccacgta gtgccaggtt   1200
gtcccattac gctttgatct atgaaaaatg cgggaatttt tcgtccagaa aaatgtgacg   1260
tcagcacgtt ctcaaccatg cgaaatcagt tgaaaactct gcgtctattc tcccgcattt   1320
tttgtagatc tgtagatttg tagatcaatc cattccccgt ataccctgac ccataatcaa   1380
```

tacctaccta atttttgtct ttccccctac ttttttgcct gtccaaaata agcgagacta 1440
tgccgtagtc tggtgtccaa caacatgttc cttatcagtg ataacgctac aatcttcttt 1500 ctttttctc tgtttctctt gtctctccca acccatattc cgtattacac ctcgtcgtgg 1560
tcattttttt gttcagagtt ttatttaatt ctaaatttcc taactaaaat ttcagaacca 1620
aa 1622

<210> SEQ ID NO 42
<211> LENGTH: 1555
<212> TYPE: DNA
<213> ORGANISM: Caenorhabditis elegans

<400> SEQUENCE: 42
aaactctttt ttttgtattt cttctggttt ttgatgataa gaaattttat gtgcacataa 60
atcaaaaaag ccggaaatta aatagcgttt tatcaggcag aaaattggcc acgtgacgtc 120
atcattttcc tgtttgaaga aaatctggaa aattttttgt ttcagtcaat ttttaaagat 180
gaaaacttaa gttagactgt aaaagcaatt ttcgcgccaa aattacggta tcgggtctcg 240
aaacgacagt tttttatcta ttgcgaaaat atgtgcgcct ttaaagagta ctgtagttgc 300
aaacttttgt cgctgtggag tttttatcga tttttttatat tttttcgatg aaaacaactc 360
aaatataaca ataaaaacac aaaattaaaa aaaaaatcga taaaaaatcc gcgtcaacga 420
aagtttaaag ttacagtatt tgtcgtttcg agaccgggta ccgtagtttt tggtgaaaac 480
attgcaaaat ttggtcaaca atttcatcgc tgcgagaccg acacaacact ttattttatt 540
tttgggtttc ccttatcgct tatcataaac atgtgacgtc atcatctctt gtacagagca 600
ccgcgactgg gagtataaga atcgccggaa aacatcaata atcagttcgg tagaagtgaa 660
aattgagcgt aaaatatgat catttttcga tgcaccatat ttgacgcgca atacttctac 720
aagccgctgt gtactgctcg tggacaactt tggattattt tttgttttta aaattcaaaa 780
tagtcaatat attgcttatt tatagcgcgc ctttttgaca gtaagtttgt caaatttgcg 840
cgtaagttat ggtgtttgca catatgcacc atacagcaac accccgcggc ccggctagtg 900
gtacatccat gcaaatgcgc tctactgata atttgagttt aaccaggttt aggcgcaaga 960
taagaaaaaa gctttggacc aaaaaattta gagtttattt ttttcggaca tttttttatat 1020 acatcacaaa aatattgggc cactcgtttt tgataaaaac gacaagccca aaagttcagg 1080
tatacggtag acaaattgcg tacaggtacc acttttccac gtagtgccag gttgtcccat 1140
tacgctttga tctatgaaaa atgcgggaat ttttcgtcca gaaaaatgtg acgtcagcac 1200
gttctcaacc atgcgaaatc agttgaaaac tctgcgtcta ttctcccgca ttttttgtag 1260
atctgtagat ttgtagatca atccattccc cgtataccct gacccataat caatacctac 1320
ctaatttttg tctttccccc tacttttttg cctgtccaaa ataagcgaga ctatgccgta 1380
gtctggtgtc caacaacatg ttccttatca gtgataacgc tacaatcttc tttctttttt 1440
ctctgtttct cttgtctctc ccaacccata ttccgtatta cacctcgtcg tggtcatttt 1500
tttgttcaga gttttattta attctaaatt tcctaactaa aatttcagaa ccaaa 1555

<210> SEQ ID NO 43
<211> LENGTH: 2432
<212> TYPE: DNA
<213> ORGANISM: Caenorhabditis elegans

<400> SEQUENCE: 43
ttttattctg aactatatac aaaatgtgct caatataacg agttttgtaa ttttgtgaga 60

-continued

```
aagtcgtatt gaaaattagt ttaaatgtga tttaatattt cgaaaaagta gtctaatttt    120
agctaaattc tacaattttg acaacttttc cgtgtcgcaa aacgaatttt tgtagaggag    180
tgtacctaag cgagtcggag aaacgtgcat tcttccattt ttttccccg gggagcccat    240
agccagtttc cggacgggcg gtcttgttcc aaacgttttt aaaatttaat attgcaattt    300
aattatctat tcagcatccg tagcccagcc gcattgtgga tctcagattg gcgaatgctt    360
gtgcgctcca ttggactccg gagccattcc gtctgttgat ttcctgattt ctgcggaatt    420
gtccggatcg acgagctctg taaaaaatta atttaggaaa aatcaacatt ttttcgataa    480
gcaaacctta attccttcgt cacacttcta tggaatccag ctgacggcgg cggctgaaat    540
atttttgcaa aaaaactcac ttttcgactt ttcctctttc tgcgatcggt tttcgcctcg    600
atttgcgttg attagcttaa aatagttttt atattttaac taataataaa gaaaaacaaa    660
aaaaaatgag aaaaaacaat caaaaactcg aaaaaaacat tacgaaatca gcaaagaaaa    720
tgaagaaaaa atatatacag taattttaaa ggcgcacaca caaaagtttc ggtacgcgtg    780
ccgagaccac tcagcagaag tgtgctcctt tgaatctgga gtacggtcaa tggggattta    840
tttttgaaaa tgcaaatgcc aaaatacaag aaaaataaca aattgcatta attttagtga    900
atttctgaa aatgagattt tttgtgcttt ttttggaatt gtgcaacttt tagtgcattt    960
tcatcgtcct tttttctgaa ttcttgaagt ttctggaatt tttgttcccc cccccccccc   1020
aatctaagac taaacctaag gctgagtcta ggcctacgcc taagcctaag cctaagacta   1080
agcctattgg tgtatgtgca cataaatcaa ttttttttaaa aattattatt attttttgca   1140
aaacacaaac gttttttttc agattttta tttttcaccc tttcaacctg caaaacccat   1200
ttttcttcca ccaaaacaca gctgttcttg ccaccatttg cctgatggaa aatttatata   1260
aattggctgt cctttgtgag aaaactagaa caataatgat gacattaagt actagagtat   1320
aaatatattt tttttgctg acaattcctg gcgtcccccg ttgacattga aaatgtataa   1380
aagaggcggc cagacaccat ccccgcaaat gtgtttttgt tgttcacttt tcttttttt   1440
tccactctct ctctctcagc tgtttgcatg ttgtttttat ggtgatctat ggtctctaag   1500
aatttgttta taagctaaga actgctcgct gagaaggttt tttttggttc gtagctagtt   1560
ttttttacgt ttatcgaaaa aaaattgaaa aaagtcgaaa tttccatctt aaaaaaattag   1620
tgaattttaa tatttttgtt aaataatcgc cattgtttcg tgcttttctc gctctgtaaa   1680
attgaaaatc tataaatttt gggtaatttc gagtattacg ggagcacaaa attttgagaa   1740
tgcgttttgc acaacctatt tgacgcgcaa aatatctcgt agcgaaagct acagtaattc   1800
tgtagcgctg gtgtcgattt acgggctcaa gttttcgaat taattttttt tcgaaaagtt   1860
acatcgatat ttcattttcc ttcgtgctat tttcaaaaat cgagcccgta aatcgacaca   1920
agcggtacag taatcattta aaggattact gtagttttcg ctatgagata ttttgcgcgt   1980
caaatatgtt ttgtgtcccc gtaatatttt tttaaatcaa atttcacatt ttaaccataa   2040
aaaactcttt caaaagtgta attttctacg caaaaatgcc gttcggatga aaaattactt   2100
ttgaaaaaca aactcgaaac tacggtacgc aaaaaagtac atcggtgttt gcacataagt   2160
gaaaacaatg ttgttttttt gtaattaaaa tcgattaatt tttttcccg gaaaacaaaa   2220
acgttttcag cgtggatttc tattgtttct tgcgtaaaaa aaaattattt accaatttta   2280
aacgataatt tccacgaatt ttcgccatta atctctcgat tttgttgatt cttgactccg   2340
agcaatctct ccggttttcg caaacgatta tattatttat ttgttttcct tttcagtgcc   2400
```

gattctcgga aattcaacag taaatcttca aa 2432

<210> SEQ ID NO 44
<211> LENGTH: 2150
<212> TYPE: DNA
<213> ORGANISM: Caenorhabditis elegans

<400> SEQUENCE: 44
tttgagaatt ttctcgggaa attaaacctg tgtttttcat taaatttgat gcaagcaaca 60
agtcattata caataaaatt ggtgaaaata tgattttttt gaaatatttg gggcgaggct 120
tttagttttt tgaagagctt acaaaaatta gaatttaaga aattttcgaa cacaaatttg 180
agagaacttt tgactttttt caaaaaattg ttttcaaaaa ttttaatatt ttcaaagacg 240
aaagaatttg tttttttgtc taaatttacc taatcattat ttttcaatca aataattgca 300
tctctgaaaa cctgggaact ttgaaaatga cgtcattctt ttttccctcc ttttcttttc 360
catttggtta ttgacgtttt ccaccccctc ttgcaaaaaa aactaaacaa aaaagaaacc 420
attggcaact actaacgcca attttgtgtt gcttcatcgg gtttctttta gttttttttc 480
tgagagcgct gagattattt ggaaatttgc attttctcac gttctagctc agaaagagat 540
cagctttctg aaattgaaat ttaaaaaatc gctctaaatt gaaacagctg ttttttatgt 600
cgattgtctc tgcaaatata tttttttcag aatatataag tatgtgtttg tttaagtttt 660
atttaaaatt ttcttgaatt ttatgaacga cattagagct tatgttagtc caaatatttc 720
aaaatttatt aacttgaatc ttgcgcaaaa ttatttgaaa aatcaatttc cagccaaaat 780
cttctttaaa attttatttg aattgtcaaa aacaaatgcc tcattattaa ttttatgcca 840
atattaaaaa aaaattaatt ctcgataatc ttaaaataag atttttagaa aaacaacttt 900
caaaagcttc tatgcgaaaa aaattgtttt tattcgaatt aaaaaaaatg ttttcttcaa 960
aaaaaacaaa tttcttaaat catagatccg tgttgctcaa ctgctcaatg tttcccatga 1020
caaaaagtcc atgtctctct ctatcatttc tcatctctct tttttctcta gccatcataa 1080
aaataaacac atgtttcaac aatcattcct tggtttttta tctctcgatt gctatatcat 1140
ttttattttt tttactattg ggtaaatttt gaagagggta ctgatttttt ttcaaaattt 1200
ttccaatcca aaagtctttt gaattgcgtt aaatcatgtc tattgtacca caatgaccaa 1260
atgccatagt aaaacttttc aaaaaaatgt ttgaattttt ttttgagcgt cagaaagtgg 1320
caattacaga gtttttttta gcactatgaa aattgaaaat tttcggagtt tttcaaaatg 1380
attttttgaa attggaaaaa ttacagaaaa caatttttttg ccattttttt ggaagttgcc 1440
gataaaaaaa aatttctttg gattttatgg ttttattttg ttgaaaatat taatattcaa 1500
accaggggtg tgcggcaaat ctcaaaactt gccgagctcg gcaaattcgg caaatctctt 1560
ttttcaatat ttgccgagca cggcaaattc ggcaaatttg cctagctagg caaattcggc 1620
aaattcggca aatttgccgt gcttaacaaa ctcggaaaaa tttgatactt tttgatgttt 1680
tttggagcac caaaactact gaaatcttaa cactcatctg gtttctgaat aagttccgtg 1740
tagtatgtct gcttaagcat caaaataacg caattttgtg tcattttact aaatttttgg 1800
cgaaaaaatc aatggtttta gtcaaaattg cattgtcaaa tttatgacgt gtgcggcaaa 1860
tttcgaaatt tgccgagctc ggcaaattcc gcaaatctac tgttttgaaa tttgccgtgc 1920
tcggcaaatt cggcaaattt gccgcacacc cctgattcaa acattgtaag ggtttgaaca 1980
tgttcttaaa atgtgacaaa aactcagtaa taaaacattt aaatttttttg aacactttta 2040 ccatgatatt tggtcatttt ggcacagcct taaggttaaa gctttaacaa tttccccact 2100
gacgctactc caccataatt ttgaaaatct aaaatattca gaaattcgaa 2150

<210> SEQ ID NO 45
<211> LENGTH: 1845
<212> TYPE: DNA
<213> ORGANISM: Caenorhabditis elegans

<400> SEQUENCE: 45
tttttaagaa aatgaccaaa agaatattaa aattttgaat tatggtaaag aatacaagcc 60
agcaaagaat ctagttattg ttggaaaact atgaacatca tgtcctcagt tttcaagaaa 120
acattaagat ttcaaaacta tgtattctgc atggcaatgt tgcaacaaac catttcctca 180
taaaactagc caactaacac agttattcct aataaccaca atgttctctt ttcatatgtt 240
gcctatgtaa ttctttctca gaaacattat catgaccata aaatagacaa tgtattggtt 300
tctatgtttc ttcttcctgc cagtgtcctc tcgcgttgtt tgagtactat tgttccccac 360
tctccccccc cggcgtgcgt attatcgctg aaaatgtcat attatctaat cgaacaatgc 420
ccattttttg ggatgtttaa tagcaaacat attccgattg gaattgcaaa attgagttat 480
catcttttta ttgttggtct tgtgactgtg agtttatgtt tggaatatag ttttgataag 540
tttgaaacta ttgtgaactt ggaatttttg attctccaag tttttaaaac gctatgcacc 600
taaacttggt attttttttc aatttaacaa aattctactt tcaaaaaaca ctactcttat 660
ttgcatgttc catagtatgt atttcttggc agtgtttttc aaaaatagaa ctccttccga 720
tttaaacaca taatgttgtg ctttttaagc ctagacacga cttccgatgt gatttttctt 780
cgaattctcc ctgtctgtaa gaaactcaca tgctgactgc aaagaatgtg cctattgcgg 840
acctcaatca gtgtcggcta cactttttta gtgtcgtccc gaaagttgtg gtgttctgag 900
aaaacataat ttttattgat ttttaatgca gcaaaatttc aaataactga tacccggttc 960
accctaattt tcccatggat actccaaata tgttcagaaa tgcatatttt tgtacaaaat 1020
ataacgtttt ctaaagtgtt tgctaaaatg ttattgttct aaaatctttt gaaagaacca 1080
gaaaatctca aattcttaaa acatttttca tcgaaatgtg atatttgacc agccagtggc 1140
gcctaacttc tgaactttgc ttcacgcaat ctctgctttg atttctgtcg tttctctact 1200
gatttttgtt cactttcacg taagcgttca actcgcggaa ccaaagcctc cgttcatatc 1260
atattaggct ttcatatcta ccatttttct actaatcatt gttgttacaa tcgtttttttc 1320 tctgtttcga agaggcactc tacttatgac tacaacataa aagtagtatg gaattcgcgt 1380
ccttggtgac cagaggcgtt cctatttcga atctctattc gggtggaggc attatccgaa 1440
tcccgagaaa cattcttgtt tgtgtaatct gtctaatcaa tccccccttcc tatttttctc 1500 tgttcccttc cttgtcttca acatcgccct tcgatcatct gaattcagtt cgttttcgct 1560
ccgcccatga agttgggcta cataaaaaga ggaactgaaa tgacatcagg ggaagttgga 1620
tatatatttc attaagttgt actatcattt ttttcttttt tctcttttttt tcggtttgat 1680 tctatctttt caagatggcc tcgcttattt ctacgattgt caagtcaacg gtcaaagttt 1740
ttgaattgtt gcatttttct ggttctttga ttttgttcct ttttaattcc agttgtagtt 1800
taaattattt tcaggaaaga aaaccgagaa aaaagatatt acaaa 1845

<210> SEQ ID NO 46
<211> LENGTH: 2272
<212> TYPE: DNA
<213> ORGANISM: Caenorhabditis elegans

<400> SEQUENCE: 46

```
agtttggcca atacctgtga ataaaaaata atttattatt ttaggaagtt ttataaatgc     60
aaaaaaagga gtagaggaat tgtattagaa tattattaaa tggaaatatg aaatagcaat    120
tggttgatat tatacttcga atctcagaat cactaaaatg aaaaccagaa ctgcttctgc    180
ttgattttta acatactttt atgttatttg caatgattaa aaaatatata taatacgcga    240
gaaatttgaa actggtttgg ctcgataaaa aattggtgag aaacccaaaa tatcgtgaaa    300
gaagcggtgg aattaaaatg atttgagaaa gtaaattttg ataatacgaa ttataattcg    360
aaaaaatggt ggtacttaaa atatagcaaa taaaacaggt gagaaaaagt tttgaggttt    420
ttactatatt ttaatcaaac cgtttgtttt atttattttc aggcatcgaa attttatgta    480
ctcaagctta tagtaaaaat acaaatattt gatatattaa acagagataa aacataaata    540
acgagctcta aaaaattagc atattttggg aattaagaaa accagtgaaa gccgtaaaaa    600
tgatctgaag ctatgaataa gtttggttag agactctatt tctagtagat tactttatta    660
taataatgag cagaaacaga tatttttta gcatttttc acttcatcat taaattaaaa      720
tcattacaaa aaatcgatag tccttgagaa gagagacacc aatttacaag caggcaacaa    780
acgagagaga gcgtattatc gtgtaaacgg tatatacggg agaagagtac gggagaccga    840
cggaagaaaa gcaatgggag gtgtataggg tggtggctgt gttgtgccta ggaggcagga    900
aaatataacg ttaaaaagtg cagacgcaga cacaccaatt gcccctcaga ctccaattca    960
gctgtctccg tctcttcctc gtcctcatcg cacaccctta gaccggttgc ttaaaaggag   1020
gagaagcaag tacgcaagca ttacaaacga cgacattact gacctcttat aattaaagta   1080
ataaattgtg aaaatgtaca ccgtttttta tgaattgcat aaagcgaatt tatttataaa   1140
aagttaatat atataaaagc tacatgttca ctgatctaca atttttggtt tcagattttt   1200
ttgaaatgtt gttatcaaca gtcgaacttt aaattttct tgaaaacttg atacataaat    1260
taaaaattga acgataacat ttggctaact ttttccatgt ttgcctttgt gcaaaggtta   1320
tcacttgatt atttattttt ttgaaatctg gagcaataaa aaaaaatagt aaggatagag   1380
ataaatacaa actgaagccc ttatgtttat tacaagttat gacaatttca gtgtagtttt   1440
gaaaatatca agtattgcag ttaaatttac aatgccaaaa aatctaagaa acattacgaa   1500
gttttcatga aaatacctcg aaaactatga aaatagatca aagaatatcc ttaaatatga   1560
aagaattcag acttcattgg gttttgaaaa aaaatggaag ggaaaaggaa tctgattaaa   1620
atcagttttt ggcattgtag aagtatactt caataagttt gttttcaatg atagagctta   1680
gtcagttaac attcaagtta acttgtaatt gtaacctggt aataaaaaat caaaagataa   1740
acaaaaaata ttgtggaatt atcaaataca actaatcgga aaaagttgat tttgaggcaa   1800
acatagcttc atctgctgta cattatgaaa attttattga agaggagtta atgaagtggt   1860
acaaaacacg atgaaatgat aaaacatgaa caaaatcgag ttggtcacta tacactaaac   1920
aggacacgta ataagaaaag tcaataggca cggagagaca aaaaggtcat cctacaattg   1980
cggtggctaa ctgcatctta actacgtcgt agcattaaaa aagattgata agacagtgcg   2040
tgtatgaacg cacaaaaaga aaaacctagc aggacatcat gaggttttat tttagcgttt   2100
ttttgcatat catttttat tcattttgtt tcagtaaaat aagtttagat tcattttta      2160
aagcgaaagt taatagaata atttgatctt gaagttgaaa attgttgtta atttttaaaa   2220
actttgtttt caaattgcct aatattttt tgaaaacaga acataaaata ac            2272
```

-continued

<210> SEQ ID NO 47
<211> LENGTH: 1075
<212> TYPE: DNA
<213> ORGANISM: Caenorhabditis elegans

<400> SEQUENCE: 47
cttctacgtg gaattctgga ggttgaagct tctggtctaa ccatcatcag taagaatgta 60
aagaccattt cgtgtttcat atttatgccg tcaattgtca gtacaagggg ccgccccgttt 120 tcgtttcgtt tcgtttaaat tatagggaat acattataaa atcacacctt ttgtgtatat 180
cttcgtagtt ttattggaca ttttaatagg ccttgtttat aaaagaaaat ataataatga 240
tgacattata caaaaaagta ttcaaggaat gttttatagt tacaaaacct ataggtatac 300
agaatatgtc aaaatagggg aaaaaactga atgtatgcag tcgacgaata aggttgtctt 360
gacatttttt tggttaataa tgtttttcct gccagtttcg atatctttga aattttgatc 420
cagatgacat caatcctagc tatggaataa tgggggaact ctctttaaat tcacaacttc 480
attcgagcaa aatttgtctt ttgcacacga aaaattatta ttattattgc acaatcaaat 540
atttttcccc cgtgcaagtg tgcaatgggg cgacgggtcg agccagaaac ccgtgttgtt 600
gaaaatcaaa ccaagtgcaa aatatccatt ttgcttaatt taaaacgatc taggataact 660
ccactagcaa ctagaatatc taattgaagg attgaaattt ggaaacttac aataaggtat 720
tctattttat tacgttttca atcttgctag gaaaacttgg aaaaaaaatc cataaacgtt 780
tcccggttat ttcagaaatc gatagtcgac ctccgttgtt ccttatctaa atttcatcaa 840
ttgtatcctt tttgataaga caatactatc tttttatcac tacgtctcct tcactctaaa 900
tcctaatgta gtatcaatca atttgatgaa aagactacac tggggcccac ttattttctt 960
tttcaatcaa aattcacact ttattttata tatttcttgt aaattgtatt tttcttcatt 1020
tttaattcta cttttttca acaattaact ctcgaattct tcaatttttt acaga 1075

<210> SEQ ID NO 48
<211> LENGTH: 645
<212> TYPE: DNA
<213> ORGANISM: Caenorhabditis elegans

<400> SEQUENCE: 48
aattttcagg agaatcaatc gacgagcttg aagatttcga caccggtcta ctatcttccg 60
gaggatccga ttattctttt taaaattttc ttcttttaaa aaatttcttt tgaaataaat 120
aaattctcac ctaggaattt caacaattca acttgaaaaa agttcgcgca aactacgaac 180
aaatgtgtgt cgagcgggcg gagccactga gaaagaggag caaaatgtac acaaaaccat 240
atttgagtgt aatttttcaa agtttggcgc cgattttctg tgagagatga gttttctcaa 300
tttatatttg gttattttta ttttagttct tactggtaaa tttctgggta agtcctgatg 360
actttgaaaa cgaaaaaaac tctttcattg atgctagtgc gattgctagg aaagcaactt 420
ttcagttacc aagaaaaagt ccaaggccat agggattagc tgcgtggcat aacaactcat 480
ccatcctcgc agatgcaaat ccgctctatt ggcaaataac atggaagagt ataaacattt 540
tctcttccac acggaaacct agtccccttg gggagcggta gtgcccacaa ccccgcatgt 600
ttaccaaact acacagacag cgctattgtc tgcaagtggc aaaaa 645

<210> SEQ ID NO 49
<211> LENGTH: 1825
<212> TYPE: DNA
<213> ORGANISM: Caenorhabditis elegans

<400> SEQUENCE: 49
agcgtttcgt tttagaatcg ccagtgtatt ttttgtgata gtcctatgtg ctttaaatta 60
tttattttga aaggttcaat aaattatatt ttatgaccga acacattata ttctcagttg 120
ttatcttata tatccacacc ggaatgttga atatctgacc atatatattt agaatgttgc 180
ggtaattttt ttgttgctgt ggaattttat tttattttta tttttcatag tttcaacatt 240
ttacaattta ttgaaattta tgggttttaa ttgttatatt tggcgttttt cgtttacttt 300
ttcgataaaa ataaattcag ttaaaaacta agttataaca atgaaaacac ataaatttga 360
acaaatcgta gaaaaatcac tacaaatttg acagatttta tgggttctat cgcgatttat 420
tgaaattaac gtcttttaat tgttttattt tagtttttta gataaatact gttttcaaac 480
gaaaaacttt gaaaaatcga taaatctcgc agtactcctg aaaggcacac actcgtttgt 540
acttaagaaa aattgtcgcg acgagaccaa ctgtccaact acggtagttt tcaaaatacg 600
cggttcaccg caaagtcaaa ttgcggacct gaacattttt ttatttttcc cgcaaacttt 660
ttttttcaat tttgcctaaa gcgctcgaat aaacatgaaa gtctcgtgtt tccttccatc 720
cagacctctc atttttcaat tttaaaacta aaagcacttt ttgacctact ttttgtcgca 780
accgccaaaa ctcgcttcca gaattattcc ctttttagga ttttcgacgc aacatctcca 840
accggttagt tttttcgcag attttctcgc attcgcgtag tttcacttgt ttacttcgtg 900
gcgcctcgtt tttttccgct ctctcgtctg accaccttca tatttattga tctgcgccta 960
gcggcgcccg ttgaaatact ccacattttt ttgcaatctt gtctgcgagt tcaggttatt 1020
ttcgactttt atgaaagctt gctaggaagc catagcaacc ggggaagaat acgctagcca 1080
aatgagagat agaatcgatc agctaaattt aagataaata gtgaattcga attctaagac 1140
ctgctcgacc agctgaaatt ctaaaactct gcgccaagat gtatagacag gtaataatat 1200
ttgaattttc tttaaaagtg accttgaacc ctaagatttt cgctcctcct aaacgttgta 1260
gtctgttact ccctgccgcg acaattgtca gcaaaaatcg cgtcacatga tgatgaaagt 1320
ttgtggcaat gttataaaaa gactgacctt atttcgtttc ttggaagatg caaagaaatg 1380
tttattaaaa attgcagtgt gaaatcatgt ctctcgctcc aaaggtgcat ttcttatttg 1440
ttttttaaaa atatatttgg ttacttagat attaatttaa atcacggaaa agtttaaacc 1500
cctcgatttc tgttatttaa catgatcact cacttttata acaattaatt tggtttttca 1560
aagatgttcc cagaatgttt tattagttct catttcgtcc tccgattttt tttctttcgt 1620
cgctctccaa ttttgccaat gtatttcatt cccattagat aagcaccgcc cgtcacctta 1680
ttctccttct tttcacattg caaacaaatt cgttgccgtt gggtttcaat atccttttca 1740
ttttttgtcg tattgttgtt cttgtgattg tggttgttat tttatcgcgg tattattttt 1800
ttttgttaaa ctaattaatt tttag 1825

<210> SEQ ID NO 50
<211> LENGTH: 2300
<212> TYPE: DNA
<213> ORGANISM: Caenorhabditis elegans

<400> SEQUENCE: 50
tatcaaagtt ttgttgttac ccacccaaac tttgttttag ttgcaacaag ctcacttaga 60
aggaaattga ttttcagtat ttattgaaca cagcaagaaa aatcagcaaa cgtggtactt 120
gtgtgttgca tgcgctcatt ttaataataa tgttgttgaa ttataacaaa taaaaacatg 180
tagcatattt ttgtattttc aggcttaaat aaccatttct aagcctaaag agaaaaaaaa 240

```
atgtacaaca cgttaaattt aaatggagaa agaaattaac aacatttgat tggatttaga    300
aataagggca cgtaatacac aagtaccaaa cgtgaacttt aaaaatttgc gtacctacca    360
tataatacaa aaccgtgaaa ggtggaatag ttttgaatgg caaattgttt gaattcattt    420
ctatagtgct aaactgaaca aatattagtt tcagttttaa aaaaagtgtt tgaaattctt    480
catttgcagt caagcagtgg caattactca gcttttgaca ttcaagacaa ccaagaaata    540
tgttttcaaa aagtttttcc gtattcagtc aagttctatt ttcctctgaa ctatagctaa    600
taatttataa ttgtacatat caggaaaaat tatgtggttt aagaatctct gaaatttttt    660
ggaaattggg aggtgaaaga atacagtaca cttttgtaat tttagctaat acgttcgaga    720
gttattatca ttatggcagc acacttgttg gtgatttcta ttttttgaca tgatatgttt    780
gaatatgatt ttcctcgtta tgtggaaaat tttgtagagg cagatgctaa acgacaagct    840
agacttttta gtgaattttt gaatcaatta tttataatgg catcaaacaa atcgaaagga    900
tctgtgcctt ttgatatttt tggttttgca acaatttgtc tttgttgttc aaacacgtat    960
acatcaaaaa ctattgttta tttcaacatt ttcagtgtat cttttaaaga tcacatcagg   1020
ttgttactaa aattagtttt gaattcaaaa ataaccaatt aaatgttcca aacatataaa   1080
aaatatttca aatatgtatc agcttcatga gtagtccata acaaaaccca gaagttcatc   1140
ggaggttgta tatctctgag agtgtcaacc cacttcttat ttttgcgata aaactaatta   1200
aaaactaaaa taggaacaaa acattaattt tatgcttcga gtgaaaattc gtatttattc   1260
actttttagg gagtttctca attattttaa tacatagata catagatatt actttttaaa   1320
taatatttac gttcaatcca aataagattt taaaacgatt cagtaaaagt tcttgcaaaa   1380
caatcaatta gcaactgagt ttggttttta aactgtttaa atctgaaaac atttttaaga   1440
aaatgaaatc cgtctaaatt cattatattt agcaggaaca tgttaaaatt tagtttctga   1500
aatttaccaa ttatttggaa ctaatgtgaa ataataagaa tattattatt caatcatttt   1560
cttgcagaca aagggaatta gaggcgtctg gtcagcattt gtcgtggctc aactgttccg   1620
caagatacat tcgtcgagtt gcgggtctcg tttgatattc acaaaaggag ggttcatct    1680
gcgaagttac acacttcttc tatcaaacca cattgcctca ttttcccaat aactgtctca   1740
tttttgaaga agatgcgatc aatcaccgtc taaaactgat tgcgttgcaa caaatctgtg   1800
atgatatgat atgatggaac ggacggaaag gttaaatttc gagtgaagaa aaaatataga   1860
agtaatatga atgagtagat gaaagaaaaa gacaaaagag aaattgatat gaccgcgcag   1920
cagacagggg catctggtgt gagcgtgcgg ttttttctgt tacctctaac gcagtccgta   1980
cacttgtcgg cgtttatttg tggctgtggg cccattgcgt tgatgacggt ccctctagct   2040
ggctttcatt gtgatccaat tgcaccattt ggtttttgag ttttattcta tttctatcgt   2100
cttttgtgat aaattaattg agtgaatgaa taatgtataa gagcctcatt atattctatt   2160
tactaaacaa aactcaatta tttcttttga aaagataatg aaatttccag tcatcattcc   2220
ataaatataa ttattatttt gccttcgcaa taatcctaaa gattttttat atccttcaag   2280
tttatcaaaa ttgtttaggt                                               2300
```

<210> SEQ ID NO 51
<211> LENGTH: 2931
<212> TYPE: DNA
<213> ORGANISM: Caenorhabditis elegans

<400> SEQUENCE: 51

-continued

```
attccaattt cccagccatc cggaaattcg ctgtaaaaat tggaaagtag gacaaataga     60
gaatataata caaagattaa acacttttta cgacaatgtt gacttcgtca tggtacattc    120
agaagtgtct gggaaatgtt cagcaggaaa acattgcaga agagaaaaac aactcggaat    180
gtttgctgaa aagttctgct tggaggtatt tttaaacttg gagaagatat cattgctcta    240
ctttggcggc ttctatcgcg gtagtcttta gtttgatcaa aaatttatca actggcaaaa    300
tacgtacaaa atagttatat acattttgct agttgacaaa tttctgataa agttgaaggg    360
aactgagagg ttataacctg tcaatcaagg agcattatgt ttttaggcgc acctacttac    420
ttcatgcctg cttggctact tacctgccta ttacctgcag tttatatgta ggcactgatg    480
taggcacgta gccatcaagt aggccgcctt ttgaggctca tttgacccat agaccttaaa    540
ataggccgtt ctagaaccct tcttatctga aacaacaatc tttcagacat tttcgaatgg    600
tcaacaactt aagtttttat tttgcaaaaa caaaaaacaa caagttttca atgttttttt    660
gccagtggaa attattgttg ttggataggt acagatgcta ccgggttacc gagatcgtgc    720
ctaccaggcc tacctattgc ctgcctgcca tgtgcctacc tacacttcat ttcggcaaaa    780
ggtcaggggc caatgaaaaa ggagcatgaa tagattcgca tcagaaattg atgtcggtgt    840
aaggcaggtg caggtaaaat gaaggcaggc ctgtggcagg caaaggtcag catggcaagc    900
attttgggaa taccaaccag tagttttcat cagagcacga ttgcatcgac gaaaaatttg    960
aatttttgtg tattttgaag agtgccgtga aaagtctaaa tcttttgcta ttgcctctga   1020
ttccttctcg aacctgaact ataaaactga tgtaaagaaa aaaagtttcc aacttaagag   1080
atatcttatc aatttaaact ttaccgagtg attctgtgat atctcaaatt tcagtcgaaa   1140
atcacatgtg gttttccctt ttaattccga gagagagaga gagagaaagg aatttcacct   1200
ccacaacaac ccataatcat tcaattaggt tctaaacaca tacaagaaga agacaggaaa   1260
atgttagcct tttagtcata ggtgctgctc gatcatgatg ttgatgaacc aaacatcgca   1320
ttttgtagga ggggaagagg acaggagact gtccatttga aagtgactac tttgtcggat   1380
atttagagag tgacttactt acgaaagtta taaagtttgg ttagcaggaa atctggtttt   1440
tactgagaaa actctctgag ggaaaagctc ggggtgggtc atatacccgc gagatatctg   1500
ccggtcatta tttaagaatg tacagctcta ctttggcaga tcatatctcg gttattccag   1560
tacatatcaa aaattgactg aatatgaaaa taaaggaaaa tgttcaacct gtattttacc   1620
agttgaacat tttttgataa aaccaaaaat aatcgaaatt gtgcttaacg gaaaagaagt   1680
tagattaaga ttccaggctg ggtcccgcca cgataagctg caaaattatt ttttggagct   1740
gtctgttcag aatcgtcgtt attagaaggt ggaagtgctg aaatctgaaa aaaagaactc   1800
aagaatctat agaatctctc atatatgaga gatcggctcc gtgaaaggca ctaatctgga   1860
atacttcaga aattcggcga aatcttggaa attgaaaact ttgagatttt tttcttgtag   1920
atcgaaaccc gcgagatgtc agatgcttct gaattcagat ttacaaaatg agctcttcag   1980
acactcctga aagatcagct gaccagaata tgcccaccta aggcaggcgt gacttacctg   2040
aaaggtgacc tacgcctatt ctcttgccag aactcgaaac tattttctag gaaaaacttt   2100
tttgtagatc gcattccatg ggagctatac cttccctgta ggcacgcagg cactagtttc   2160
cgtgcctacc tggaatccac ataaccggag cacggagcag caacttcacc ttcagaaatg   2220
attcagagct ttacatatag tttcctgttc ctgaaaagca tgttctacga tgccatgatt   2280
ctcatttcga tgccacttct caaccaactt ttgccgagct tctgaacttg tcgagggagt   2340
ctgaataccc cccaccgccc acactaaact tttttcctct gatccgtgag aatatcctca   2400
```

ttatctcaca atcagtaatg tccaaatcag gcgggggagg aggggtaaaa aaacacggaa 2460
acgaggaggc gaaaagcgtc tctgggttcc cgcccttcct cccacacgtc ttctctatgc 2520
gtctctctga caatctctcg ttaaagttgc cttttttggg aaaagcttct gtctctgttt 2580
ctctctgtca acgtgtttct cagcttgcgg gcgccaaacc accaccacca tcactgactg 2640
tcgattcgcg gtgtgttgtg tttcaattgc gtaaagagtg agagagagga aaagatagag 2700
agagagagag accccaaggt tatacgtctg ttatacttgt tacccatata ctcttctaca 2760
cctttacctt caacctttcc ccacattgac tccgcctctc tctctcttac ttcttggaag 2820
acactcccca ccccctctta tctatttttt cgaaattctc gacccttcac cctccccccct 2880 tacccgcacc ggtcatcatt ctgactctgc gaactactgg agaggaacac c 2931

<210> SEQ ID NO 52
<211> LENGTH: 1860
<212> TYPE: DNA
<213> ORGANISM: Caenorhabditis elegans

<400> SEQUENCE: 52
catgaaggcg accgaaaagt gtccagtgaa gattttctaa aaatctcgaa tctggaatca 60
tgatgtgaaa tatatgaata aagaatcttt ttaaaatatt ttgaaaattc tatacatctc 120
taaaaaaatg caatctcgtt attacaaaaa gcaaaatctt tcaccttaag cctagatgta 180
ggtaatgttt gatgaacagt aaattttgaa acagtaaatt tttgaattac aaattgaaat 240
ttttttaaaa tctattcaga atccctatat ccgcatgcat cagggaacgt gccaaatttg 300
aaaaatgtgt gtttctcaat ctctaatcat ttatcatatg gtcatgacaa caactggtgt 360
caaggtgtac gataacggta cactgtggca attgacactc tttttttctt tatttctcta 420
ttcaacaaga cttgtattta ttaagaaaat gcaatgagag agcgtggtga taagacgggt 480
aattccctcg cttttctcat tttttgcggt gttgtgttcg tgtcatttga gataatccat 540
gttgattcca cttttattgt tgatttgata gatgttccaa gtttttactg cttcctgaaa 600
gcataattct taaaaataat gcttcatagc agttgtggct tcatacaatt ttcaaaaaaa 660
aattcactgt ttcaaaaaaa ttgaattcaa tttcctgcat tatgacgtac gtgttaaaaa 720
aatatgttca cctaaaaatt ccgctcgaac tgtcgcgaaa tctgtgtttc agtgaaataa 780
aataaaaaca tctagacaaa atacagttct cctcaaaaat tgctgtttca aaataataat 840
ttaaaaaaaa acaccaaagt gtcgtattta aatttaaaaa aaaactatcg tttcaacaaa 900
acaggttcaa atctatttta gtattaaaat ctataacttt ataaaatttg ctatttaggt 960
tttacgaatt gttgtttttt actctgaatt gtaaaattac cgtttcaaat atattcttct 1020
aaattcaaaa atttagtata caatttttct agaaacattg aagtattacc aggaattttt 1080
ggatatttcc tataaattct attttgatca atttgtagtt gtcttatcat atattgcatt 1140
ggatgataat aggaaatgat ccgattctct ttcctgttcc aaaactaggt aaatgtacct 1200
catatatttt gttaattttg tagtcacaat aacatgttat gataataata tcgataaaaa 1260
atatcgtgat gtttaaacat taagtttcat ttttttcggt actgttctaa ttgttcaaaa 1320
caatttaaaa aatttcggtc aatttataga caataccgat tttaataatg aatgtaaaat 1380
tttcactgtt tcactaattt tataacaatt ttcattcctt ccaattcaca ttgtgttagt 1440
gtagtgatca ttacttatat attttaaaaa aatagggtgt tagttttttc cgtttgtctg 1500
tttgtttccg tgacgtcaca acgcatgaga cccattttgg cgcaaattca aatttcttca 1560

```
gaaaaatttt ggtgcaaact caaatttctt cagaaaaatt ttagcgggaa ttcaaatttc   1620

ttctgaaaat tttggtggga tttcaaattt gttcagaaaa attttggtgc aaattcaaat   1680

ttcttcagaa atattttggt ggttttttct tccgcgccgg aggcgcgatc agcagctagt   1740

tttcaaataa atttactgtt tcaaaaatac gatattttt gcctaatttt tgagaatatc    1800

actatgacgt ctaaacgtaa agcgattcca taatctactt caaaattcca ggctccccaa   1860
```

<210> SEQ ID NO 53
<211> LENGTH: 2793
<212> TYPE: DNA
<213> ORGANISM: Caenorhabditis elegans

<400> SEQUENCE: 53

```
cagtgtaggc cgtcttgctc atagagacaa ataaactttt tgagatggtt ttttaataga     60

aaatacattt tatagaaatg agaaaaataa agttttacta ttagaaaagc gtaacaaaaa    120

gcttccgtaa ttatttatat gaatgttccg atatttttag cgatgtgtgc atcgtgcact    180

cacaatacta atgttatgag cttccttgca ataaacggtg gggctggaaa ctgacaggaa    240

gtgggtttat tcgatgatta caataccaca ggactgatga cacgcgtaat caaaagttga    300

aactagaaaa cataaacacg cggctttcat ctgaatcaga gacgaatatc cataaatcac    360

ggcccccaaa tagaaaccag tttattttat gtcacttctt ttccccatta actttcctgt    420

cacaatcata caacagagtt cgatcataca ggtccaaagg ttttgggtat atcttgtgga    480

catgtatgct gtgaaatgtt gaacatttca tataaaattt taaaatcaga ctattagatc    540

gaatagttct acgaaatttg taaacagttt ccatcgaaat acctattttt tgtaacacga    600

agtcgacctc tctcccggag acgctgctac agaaaggttt gaattttgag caaagttacg    660

gtattaggtc tcgaatgaaa agtttcgaaa gtacgcaaaa ctctacaata gggttaagaa    720

tcgataattt tctagattgt ccaaaaaagt agactaattt tgccattccg ttcagtgcct    780

tcaagaagta cttgaagtct atacctcacc tacttgtctg atatggtaat ttactatcga    840

gcttattagc aattttcttc acgggaaagg agttgtaggt taacttcaag tcgcgaggta    900

ggcatatttg tgcctggcga taacaagaga cgttccacaa acatcttact cagtttctat    960

ttgaaacttg gcgaagtaga catgaagttg aaccttcgga acgtcagtcc aaaggtttga   1020

aggaggggtt ccccgaactg tcatacactt catttcatcg tcagctgtct gagatcaaac   1080

attcaataag catgaagatc tctgaacgac cgaaaagata tcgataaagt gatgataaag   1140

gtctgcagca gaatggtttt gcagacattt cttcagaagt taaaacaacg ttgtcgtacc   1200

caagtatctt atcaagggag aaaaagagtc aaaagataaa ttccgccatt tgcccctccg   1260

gtccgtaata acgagtattt cttatcacgt gtgctgatct tttttcttaa cacacataca   1320

atcaatcgat ttgtcagaca tgggaaagaa taagacgtga tggatgaatg gaataatgtg   1380

aacgatgaac gagatacgtg acagtcagaa agttcactgt gaatagagta tggtataaat   1440

ggttgagaga cgacggatta cggaaagatc gaattatcac aacgtttttg atgtatctgg   1500

accgttcaca tggaatttag taattgttac ttcttgggcg acagagaaaa ttcggccagt   1560

ctcatcaaat agagagtttt tttgaaaatc tgcattgcag ggcgaacaaa atcaatttcc   1620

acattatttt aggccggttt taaagagaaa tggagagatt ttgagaactg tgaaataagg   1680

ctggttaata aattgtgcat aaaaaatcta gagagattgg aaagccatgc ctatttcact   1740

gcagcttcac caacaatcta atcataattt tgaaaatgaa aattacatta gcatggtcct   1800

ttactcacat ttttttagga tgtcgacact tttttcattt gaggtcgcta caactgttgc   1860
```

tcaaagttgg agcatgtgcg acctatttcc actcctcctc cacagacccc gtttgattgg 1920
tgcaaaagtg ggcagagcga aaagctgatt ggtcttgcag ttttcatttt gaagggaatt 1980
aaaaaacgga gttagtaaca attgagaatt accgttttta aatgtataac ttttcaaatc 2040
ttccgtttct gaatttatta tatacatata ttatatagac tcaattacaa attatataaa 2100
tttaatttat atattatata gccttaatta ttaaactttt tattttgaga tatttttaaa 2160
tttcaaactt tttttcagta tttaagtaag cttcctattc acgctactcc acttttagtg 2220
tgtttcaaat gaatggacgt tataccaaaa ttcaattgaa atatccagct tcataaatat 2280
attggcatgg gaatgagcct cgtcacgaac attttagaaa aacatcagga caaacttata 2340
ttgtactata acttgcaaac ctgcagcagc agaactttga acacccaaat ccatttccga 2400
cggaagtatt ctacatcttg tggccgcgta tacccatgac tactgtaccc aaactgggga 2460
aaacccaaat tgctagtaaa cgcccactaa ataaactgtt agcattgaaa gtgtgaacac 2520
gtgaatcgta tgtcaagtga taggaagtgt gacgttttgt aattaatctt aacttccaag 2580
tgtttgtttc cttgaaataa gatgcctaca cacggcggcg aaatggatac tttttatgtc 2640
tgcgcttatt ctctttgtcc cccatcatca tacaatcttc aacgccttca catatcagac 2700
agtccgtcgg gcactgacca accattcagg ctgcctgtct gtcatttata ggctgtctag 2760
ttatcttcaa ttaatgtttg aaaattcaga agc 2793

<210> SEQ ID NO 54
<211> LENGTH: 2016
<212> TYPE: DNA
<213> ORGANISM: Caenorhabditis elegans

<400> SEQUENCE: 54
aattaattat tttcacattt tttcgaattt tgtcgattta taggcgaaat tttacgttaa 60
cctaacggaa atatgagttt ataatgcatt tttaatcgaa aattcggttt tttcaataaa 120
atttgctatg aaatccgcaa aaacgcctgg aaattgtctg aaaacgaaga aaaataaaaa 180
taaaaatccg aattctgtgc attgtgacgt ggcggtgttt gcgtacccga catttaattt 240
cacgacactt gtttttatgt ttttattgtt ttctcgattt ctgcaagttt tccacttaaa 300
acgtgcggaa aaaatccaga aactgtaaat aatactaaaa aaatataaat tttccacaaa 360
aaaggcatga aaactaacaa ttacctcaaa tatcgtgaaa aatgcaaaaa aataagcctt 420
tccgaaaaaa cgggcccttg ggcctttaaa ggacacaaaa acaggaaagc ataagacacc 480
aaagagtaat tggatttcta cactttggtt cctagaatta tttataaggt gttattgcgt 540
ttttgtgaga ttgttctatt tatccagtca aaaattgcat tttctttgtt tttgcttcaa 600
aaaaatacat tttcagtgga aatttcagct gaaaagcaga attttgaggt tttcgagtaa 660
ataacgtaaa acactaaatt acaaatattg atttttgatg tcttagacca aattttcgta 720
aacatgtttg tatttttgga aaaaataggt tttttgtcga ttttaactta atttttcgaa 780
caaaaaatga ttttttctcc gatttaccaa agttttgact taaaattccg attttctggg 840
tcatttttcc cctaaaaata cgattttaat tcaaaaaatc tatattttca aagaccaaag 900
taccataacc ttcaaaaaac aaccactttc tctattgcat cagcgaattg tcatcacccc 960
tctcaaaata tacaaaacgt catcattttt ctgtgttttc tctaattctc ctgaaaaatt 1020
ctataaaacc aacagttttt atcatcaaaa atgccttttg accgactttt tttaaagttg 1080
aaaatcgtac agttttagca gaaattccag agtttcattt tgaagtatgc tggaaataat 1140
aaaattattc taacatttat taatattttg taaaactaat tctatacaat aaaaaagtaa 1200
aatttaatat taaaaaaacc ggtttttctc aaatttccat tccccaatgt cctgttctat 1260
tatttgttcc gattcggcca cagaacgcgc acacacacac tttttgctga ttctctgcct 1320
cctttctttg atttgaccgc attttatatt gattttcggc cacaattcca ctatttgttc 1380
agtttgtcga tttgttggaa atttcaattc cggcaattcg ccgatttgcc ggaaatttaa 1440
attcagacaa tttgccggtt tgccggaaat tttcagttcc ggcaattttt taatttgccg 1500
gaagtttcca tttcggcaac ttgccaattt gccggaaatt cgccgttttg ccggaaattt 1560
tcaattccga caacttgcct atttcccgga aattacaatt ccgccgattt accaatttgc 1620
cagaaatttt taattccggc aatttgccga tttgtcggag atttcaatcc ggcattttgc 1680
cgaaaatttc aatttcggca gttcgccgat ttgtggaaaa taacaattct ggtcattcgc 1740
caatttgccg aaaatttcaa ttccggcaat tcgccgattt gccggaaatt ttcaattccg 1800
gcgattttcc tatttggcga atatttttaa ttccgccggt ttgccgcttt gccggaaatt 1860
tcaattccgg aactttgccg atttgccgat ttgccggaaa aaatcttttg ccgcccaccc 1920
ctaataaaga cttcaaaata tgcgtttttt tttgctttta acacgctaaa actctctaaa 1980
aatccccaat ttttcagctt aaaaaacccc aaaaaa 2016

<210> SEQ ID NO 55
<211> LENGTH: 1336
<212> TYPE: DNA
<213> ORGANISM: Caenorhabditis elegans

<400> SEQUENCE: 55
atccatttat ttatgtccag tacaagacga ccgttcatat cttcttagtc attttctttc 60
agccggtgta ctctttgttc aattttctct ttcttggtgc aacctttatt cacgtgtatc 120
ttctccgagc ttgtttgcat attttttttt tgaaatttca tgtgctaatt tattcatgtc 180
atttttgaag ttaaactctt cacatttcat aataaatatt tattgaaccc gtttgactac 240
tccaaattca cgaagttacc aaaataaaag tgatatttga ctttcagaaa taccatttca 300
aattccctaa gacgctcggg aaatattaat tactgcaatt tatattctgc ttgtattttt 360
cgaagttggg tccaactgtg tgaagtattg taagaatcat atccttctcc ttcacattct 420
acataaacaa ttcatttcta ttctgtaaat tttttctgat gatttacggt aaaaacgagc 480
gaaattcggt ccgggacaag ggtttctacg acgagtccat cgtggtgccg ctcgcttgtt 540
tgaattcccg cgtgccgcat tcctcgtgtc gagacccgat gtccaactgg ggggattacc 600
aactcggggg attggccccg cccacagaac cgtggcttgc aattttttct tgttaattct 660
cgctctattg agaaaaaaata attttaaaac cgtgcggcag tttcaaaaat gggcgtattg 720
caagccacgg ttctgtgggc ggggccaatc ccccgagttc ttcgggtctc taaggaaagg 780
attcgtacat tctggtcctt tttatttatt tttaacctct ttttattttt ttaaaccgca 840
atccattacc agttccattt tctccgtact cgtcagtgta gcgagtgacg agtgaaattg 900
accccatttc ttatcttatc gaaaacaatc taaatagttt ccgcattcgc ataaccagaa 960
aattcttcgg tagtcgttct catttgtttt tatttcatga acataaagta acgccatagt 1020
ctttttatga aacgtggcgt taagaaagct ctcgaaaagt ctcgatttct ccagcactaa 1080
tacacgtcat ctccgataag tacacgttgc ataggcggtc ctaataaaag cgaccgcgga 1140
cgttcacatt cagttctttg ttttcttttt gtcgtctgca ctccttcttt gcgacgtgta 1200
ttttgtgttc ttctctgtgt ttccacttct cgttagtatt ctcgcgcttc tactctgaaa 1260
ggtttttctt cttaaatgtt ctcatttttc agccactcag cgaacagttg aactgaccgc 1320
tcatcaagag aaaaat 1336

<210> SEQ ID NO 56
<211> LENGTH: 2797
<212> TYPE: DNA
<213> ORGANISM: Caenorhabditis elegans

<400> SEQUENCE: 56
aaatttcaac ttccggagcc cgatacctat aggccacgtg agaactttct caggagagac 60
gcagagagac acaaattgac tgacgaggag ccaggagaaa tgagcagaaa taaatcaaat 120
tgaagagttt ctgaggagtt cttttttctc tcttccactt catcctaccc gcctgagcca 180
ccgggggaac tgacaaaaga gagctgtcac gtggttccag actgtcccat tacggtttga 240
tctacaaaaa atgcgggaat ttttttccca aaaaaaatgt gacgttagca cctatcggtt 300
agccatacga aatcagttga gaagtctgcc gcatttttttg tagatctacg tagatcaagc 360
cgaaatgaga cactctgaca ccacgtgaga tgtgctcatt gtggccgcga gagtggtgtc 420
aaggaatatg agagtacata tggtaattgg tgtataccat aattagatgg gaatttgaga 480
gcttttggag gaaggagagg gtttttcggc gaaaaattag tgtccgaaat gagaaaaatt 540
gaaaaaaaat gcaagttttc actaaaaaac tacacttttt ggagaaaaat tggaaaatct 600
gccagttttc agtgaaatcg agtttgaaaa aataaaaaat tcgagaattt tttttttaa 660 tgaaagattt gtgctcgaaa tagctgtaaa atcagcttaa tttccgaaaa aaagatcgtg 720
atttctcgga aattcatttt ttttaatttg taattttgat ttttccacac aatttcaagc 780
tttaaaaatg ttaaaagtca cctaaaaagt cgattttcat aacaaaatac ctagaaaatt 840
gtcgaaaacc ggcaaatttc ggcctaaatc tacttttagg cagattttaa gttgaaaaat 900
gcacaaatat ttctaaaacc tgacaattca acgatttttt cctagaaaaa atcgtcgaaa 960
tcgacttttt cgacttttca gtatttttc agtagaaaag ttcacaaaaa tgtccgaatt 1020
cgacggaaaa ttcaaatttt ttttttccag aaaaagtgct gattttagcc gaaattgggt 1080
ggaaaaatcg aaatttcgac gaaaaaaatc caattgcaat tgaaaaacat tgattttcgt 1140
tcatcgaagt atcctctttt gttattttcc actttttcc cgcaggtatt ctctcgccat 1200
tcaccaagac atcacacgaa tcccggagac gcagacaact gaagagaccc actttttgtg 1260
tgattcaaag gggtcaacgc atatagccgg ccgattcgtg atgactcatc tctgtgttat 1320
tctataaatc tcttgatttt tttgaggatt taactctttt ttttcgaaaa aaacgtgttt 1380
ttccgaattt tgtatggtta aaagtatcgg aatcaccgtt ttttgttgat ttttttctca 1440
atttcttttt ttgtttgagt aatgattaag aaataagaac ggaaagaaga gaagaaactg 1500
tgaaaaatga gagaaaatat ttcaaaatca ggaaaaaaaa tcattttcca aattttcagg 1560
atattatgcg gattattagg gttagaacac attttaaatt ataattttaa ttattttttaa 1620 cattgaaaaa acaaaaaatc atccgaaaac tactcttctt tcacaaaaat cggtcaaaaa 1680
taaaaaattg cgaaaaaaaa acaaaacaaa ttaaatgtag caagcgcgct ccattgacaa 1740
aatgccgaaa tttttgcgag cgaagtttga atttcgttgc aacatggggc atttttcgtg 1800
aaaaacaaga tttaaaagaa tttatacttt attcttgctc aagaaaatta atttttccat 1860
aaattctatt aaaagtggca gttaaaacaa caatttctaa gatttttca cttttttttt 1920 ggcgtttgct tgtttttcag agtttggaat agttttatgt caaattttga tttcttctca 1980

```
ttactttctt cataaaaaaa aatgcaaaaa agcaaatttt atcactaaat cgttcaattt   2040
ccacctagaa aagacgaatt taacgcaatt ttccgattag agcgcatttg cattgtgcgg   2100
gaaattcaaa ttattcaaaa attctcctct agtttccagt tctagtacaa tcggtggccg   2160
agttttttttc ttttttttttc cagcggccac atagcaagag ccaacctgta tacttttgca   2220
gttcttgtgc aaatctgagc tccgccgagc acaaacaagt ttggacagtc cacttctctg   2280
cgtctctcgt gatgagtgtg ctctctcgtc taacctctaa tccttcccag atatttgcac   2340
atctacccca gttccacata gccataaaga cttgggtcat ttttatcgat tttttcggtt   2400
tgctcacaat attgtgagtt tcttaattag gtcttggtag ctttttggag cattttgtga   2460
ctttttatgc ctaaaaacca gtttaaatat actttttttaa tgcttaacta gatccaaaca   2520
cctttgaaaa ttgtccaaaa aaattatttt ttggccgaaa atttcagtcg aaaaaagcat   2580
tttttcggcc taaaaaaaat tccaaaaaaa tccctaattt tttctgtatc tccagagcca   2640
ctttttaagg tataaatcag caaaatttc cgatcaaaat tccatttccc tatatctttt   2700
ccctctctct atctcaccct atctcgtgcg ttagccgacg tttactaagt cccagtcagt   2760
ttaattctat caaattcttc acttttactt acagaaa                              2797
```

<210> SEQ ID NO 57
<211> LENGTH: 2737
<212> TYPE: DNA
<213> ORGANISM: Caenorhabditis elegans

<400> SEQUENCE: 57

```
atcacacggt tgaaaaaagt cgaaatgaat gaaaacaagg gcattttgga atttttttaa     60
aagaagaagt aaggtgagtt aaaagaatga aaagcggcgt gcttgagatc taatgaaaca    120
agggaccgcc cttgtttgtg atttgctaac aaccgctatc gtttgaaata ttccgggcgg    180
agttctagct gatttctact tggagtatca tagaattgga aacggaacga aattgccata    240
gtatgaaact tttaatttgt atatacaaat ataatcgacc catttaatag gcctactgcg    300
gattaatttc agtgctcctt ctaaaggcag acaatgaaac agttgtgtag taaaaacaat    360
gttcacaaga cctgaaacaa ttttctgaaa attgtttgat aatattgttc aataaacata    420
aaagatggtt cacaaaatta aaactaaatt aaaaattaat aagaaaacca gttgtcacaa    480
acgcattcgc aaccaaaacc gctaaacgct attccaacta aagttataat tgcatttttt    540
gcaattaact gttttaccac aaaacaaaac aaaattccag tttaacaaat tatcaaaatt    600
ccaataagat ccttttttaa attaaaaagg tgagattttt ctagagagtc cgaatagaaa    660
atggtaacca aaccgatgac gatgacaatg gtaatcggat caatgcagaa gttgttttga    720
aattatttc aaagtcgtta attttgagaa tatttgattt tttttagagt atgtactaga    780
tttgttctct acctcaaatg atcaaattct ttgactgcat taaaacaaaa ttttggcaaa    840
attatcgaaa atctcagaga aaataaacaa acagtctatc acatttcaaa tgaagaggaa    900
gccaaatttg aatatagacg gtccgatgaa gaatttttttg acaatttatt ttaactcgga    960
atggttatta aatttgattt ttttaaattt atatttccca ttattttaat tttttaattt   1020
atgaaacttt ttatgtgaaa aaaaaattta tgtgtttttg attataacag attttacgtc   1080
agaagccgaa ccatctttaa taaaaaattt gaaaaaaaaa atcacttcta caattttcat   1140
ttttcaaatt tgagccatca aagtcaatta ggaaaattaa ttctttcaat cgttgcagtt   1200
acagtgctat ttcaggatct ttgagagctc gccgtgagct tggttctgga gattcgcaga   1260
taaaaattca tgagtaaccg tttcaagaca tgggctatca aatggcatag gtctcatatg   1320
```

caagtccgat tggcatcttc tgatggttcc ctagtgagtt tattaattca caagagcatt 1380
gtatcggaat tttggcaaac tgttaaaacg gaattatatg ctttgttcag ttttgtttca 1440
gtgtgttaca cagttaattg ttttagaaac cattgcaagc aattataact ttggtgttga 1500
agtttagttg tgaatgagtt cgtgacaact ggttttctta ttagtgtgta tattaatctt 1560
gtagatcatc tcacatgctt attaggcagt ggtcatttct atttaatttt gtttgaaagg 1620
gttttaattt tttgattttt tttgttttgt tttagcgaac tcaaattgaa actaatcgcc 1680
aaattttata ataaggcctt ttcaaaacat ttgatcaaac ggaaaagttt tttcaaaaaa 1740
taaaattttg cagcggctta ggcacacgaa catccgacag gcgattcaat tgtatcaaat 1800
acttagtgct tctaggcaaa atgtagattt tagatataaa ttaagccctt tttcacagtt 1860
tgtaacgcca gggaaaacat ttttgagcaa attttgaaaa atcttatcag aaaaatgttt 1920
tgattgggtt aaaaaaacac ctagaaactc tactcctctt taatgaaagc ttgtgtttca 1980
aactcttttt gtgcttaaat aaatttttat gcaaattcat aattttacca actttttttcc 2040 cactgaaaca tttcaaacat aatgtcaagt cgtacaaaat cttataacta acgattttct 2100
aatcgtatct cctgttatcg ttatctttac aatcgaagat aaacggctga gaaattttag 2160
gtccgaggta caccactacg cacaattgcg gatttttgcac tatttggaga gttgagccaa 2220
aactgtctta ctttttatga aactgtggaa tgttgtaaac aattggtgaa tatatttatt 2280
gtaaaatttt tatttgaaaa tcatattctt ttgtatcgaa ttttggaatt ccacgtttga 2340
aaactgcaag agcgccttat gctgacgtgt gttagttaga ttgagagact cgcacggagt 2400
agacgcagac acaccacaca gcacaaacag acgtcgacgt ccgcaattct cgttggttat 2460
cgactctttt gtcccattcc accaccaaaa cttgccacga tttgatgttg ctaggacata 2520
aaggtccagt gggaaactgc aaattctttg ttttcactgg tttttttcca tttgttagtt 2580
actagcttga taatttaaaa atgaaacgtc tcaaaactag ttcacttgac ctacttcgaa 2640
caccaatttg tatcgtgcgt catattcctt gccgttgcaa tttcacgtgc acttttatga 2700
atttcataga tttttttca gataattaac cgacaaa 2737

<210> SEQ ID NO 58
<211> LENGTH: 500
<212> TYPE: DNA
<213> ORGANISM: Caenorhabditis elegans

<400> SEQUENCE: 58
ctgttgcggc gcacctcgaa gaatagctcc tgttgggaca ttttgtgatg gctgaagtag 60
gaaattatat taaatttaca ttaaaactaa agaaaaaata cgaaaaatta tgggaaatca 120
gtggtaaatg cgaaaaaatg atttaaaaaa ccgataaacg ttgaaaacgc gacggtctcc 180
aaaataatgc aagcgtgctc cactgcgaat cccctgctca tttgcgcgcg cattcaaatt 240
tagatttccc cgatttatcg tgaaaatcgc tgccatctga caccgcattg caccgaagat 300
ggccaaagat aaccaaaaaa ccaatgaatc attggtctat cgaaaataca ttatattttg 360
ttgggagcag ccccacgaaa gccacgagag cccgcaaaaa ggtaaatatt gacttaatat 420
ttgtggcggt ctcttacttg gttccactta cttttaccaa taggcagtta tttttgcgtt 480
ttgtcgaaaa aatcgatata 500

<210> SEQ ID NO 59
<211> LENGTH: 502
<212> TYPE: DNA

-continued

<213> ORGANISM: Caenorhabditis elegans

<400> SEQUENCE: 59
atcgccaacc aaggaaagta gtgatctaca agttttctct gcaaaaaaaa caatcgtaat 60
tgcataacat ctatcgaact cgagagtctc ccaaaaaatc cctccaaatc tttactgcat 120
ttgcatgtaa agattttacc tatttttcta aactgctgtg ttcctgtatt ttcactctac 180
ctgtttcgtt tatttattta tttaagcatc aagtttattg aactctaata aattctcggg 240
aaattcgtgt cttaattatt cttgccaggg aaagttacgt ttccttatcg aacacctgtt 300
gcgaaaccag aaaagggcgg gtctgactaa gtgaacaaat atttcgtaat aactttcttc 360
caacagaaat taaaacacgc aaaaaacggc caactcacta gctggaacgt ggagccatgg 420
agatggataa aataactctg attgtcgaca tagcttcaag aatatcgtat tctgcatttt 480
caaaaagtct ttttcgttca aa 502

<210> SEQ ID NO 60
<211> LENGTH: 1200
<212> TYPE: DNA
<213> ORGANISM: Caenorhabditis elegans

<400> SEQUENCE: 60
gcataaaatg tttgaacttg gcatattata atacaaaaac aaaaattgaa agagccaaga 60
aatgggcgga gcctattatt gattatcctt gtattttgca aaaattgttg acagatgatt 120
ttttttccac actaactcta ttgggagttt ttcaacaatt tgatatccaa aaaaaagagg 180
aaaatccgct aacaatgtga aaaactagca tcataatttg aattgccgcg cagtttcctg 240
gcgttccaga atgatctatt tgtatttgaa agaagacctt tgaaataggc atctcaaaat 300
ttgccgagct tggcaaattc ggcaaatttc tgtttccaat aattgccgag cacggcaaac 360
tcggcataat cggcaaattt gcctggcttc gcaaactcgg aaaaatctaa gaattttgat 420
attttttgga gcacaaaaat tactgttaca ctaagaacac gtttgcttgg ttggaaatgt 480
ccgtgtggtt caatttcatg ccagtttact agatttttgg agccgaatca agagttttag 540
taattgtttt tctgttcaac ttttggtgta cgcggcaaat cccgaaattt gccgaactcg 600
gcaaacagca aaatatgaaa cgtttatcac agaacttgtt aggggatttt tcaaatatat 660
atatattttt ttaattcttg gaaaaagctt gtctacctcg aaatacccta aaatcattca 720
aaaattttaa atattaccat tgagagcaaa tttacgggcc tctgaaatag tggaaaaatg 780
aaaaattaac tgaaagttaa tacgaaaatt ttcaagcttg taaaagattt ttggttgttc 840
cggaaatcgg ataatcggaa aacagccacc cttgtttctg actaatgagc taagaaattg 900
attggtactt ccatagttga tgaatgttat cagtaaaatg ggtttggcaa tgcttttgtt 960
attccaccgt gatataaact gaaaagcaca actgataaga tgaggcacct gagtgtctag 1020
acatggcaac ggaagtgggc gggattggaa tttttgagac gtggcttaag ttgtataaaa 1080
ctgaccggct aaattttaat ttcagtgagt ttttgagttt tccaattctc acccaaattc 1140
cacattttat gcatcgccta agtttttttt ttaattttaa tttttttttc cagatcccga 1200

<210> SEQ ID NO 61
<211> LENGTH: 1994
<212> TYPE: DNA
<213> ORGANISM: Caenorhabditis elegans

<400> SEQUENCE: 61
gcttggagag catctatggc gtcttttcgg aatatcaagt cagtcacgaa gtcttgtgcc 60

```
aattccttta ccaatcgttc gaatctggat cgaggaatga gcagttcagt agactgttgt    120
tgttttcgga tttctcgcag agcaactgta ccagaatgaa aaggatatga tcgtactggc    180
tgagtgcacg atttgcggca tactcccgaa aggttctttt tgccagccat tgtttggtag    240
atgtggtgtg aaatggagag attgtaaacc cttctatagg tgccaaaggt gagtgggcgt    300
agcttcgaag tcaactgcgg tgaagggggc gtggtttctt actattagag aaactgtatc    360
agactaactc cgataaagcc atagtcagtg aactctcaac atagttagga agagttactc    420
agattaaata aaatcgtcaa agaacaatca ggccaattct gggctaggca tagttcatag    480
gcagaacttg gtagaggaaa tcagagtaaa gtaacgatga ttttaatttt tccgtctgaa    540
aaaagatatt gaaagcattt tgccgatcga acaagacacc caaagtctca tgacgacatc    600
ccagaaagag tttcagccaa attcccaaca acagcctaaa ggaaaatctg aaaagaacaa    660
aacatttgaa cgtgctagag cgtacttgca catacttgca catactgtaa gtcaacatag    720
aactctactc ataagtgtga caaatttgtt acaccaacag tacgaagcca agatttgatt    780
aaagacaatt gttgtttaaa ctgcttgata aaaggtcaca tggttgcaaa gattgccaga    840
gcgaacgcaa aaattgctct cgctgtgaag gtggtgaaca ctgactcagc aaagtcggaa    900
aacatgatat gatttgtctt agtttattgg ttacctttat ccgaaggtgc atcaagttgc    960
ctattggcgt tatgttgaag atgactgata taatacattg taacgatttc gggaaaaata   1020
catatttaac aagataatta ttttttcga ttttccgaaa aaatggaata aaagaaaaac   1080
ggacattttc gatattttc aaaatccaat aaagatcagc attttttgt atttcaattt     1140
caaaaaaaaa atcgaaatta atttttaaa attggaactc gagttcctgc tcaatcctgg   1200
tcaatgatta aattaaatta tgctcgtaca gtaacttgtt atttctgtgt ttaattaaag   1260
gcgcattact gatgcgattt gggtctctcc acgattgcac tctgttgtgt tatttacttt   1320
tatttttaaa tattttattt gttattttaa ttcattttcc gcatcatttt ttcaaggaat   1380
ttcattgata tttatgccat tcgatttaaa tttaattttt tgtcgttatt ttacgtcgaa   1440
caatgagtca aacacctaat tctggttatg caacgtgggg ttacaccctt actatagtat   1500
atatatagaa tacttgcaaa aattgttata tttacacttc gaaaatcagt ccgaaaaaga   1560
cgtaaagcaa ctttgcctaa tgaacttttt ttaattaata atttcacaaa aattgtgaaa   1620
cttgttattt ctcttgtttt ttgcctttga attttaaata tgtcgaattt ttccaactat   1680
tcagctgttc ttgtcgattt ttgttaattt cgaaactagt tcagtaagaa gtgcgaattc   1740
agaaagaaaa acaaatcaag agtatttttt atttcgtttt tctctcaatt tctcttcact   1800
tctctcccat tttagtgcat gtattttcct cttctctctt cttgttgtct agtttagaca   1860
acgcggtcac tgttagagag tgcagacggt tagcgtaaca aacaaaaaag tagaattcat   1920
ttttggcgtt ggaaaccgca ttaaatactg tcctcacagt ttccgttcgt cttaatttca   1980
aatctttgct cttg                                                     1994
```

<210> SEQ ID NO 62
<211> LENGTH: 2995
<212> TYPE: DNA
<213> ORGANISM: Caenorhabditis elegans

<400> SEQUENCE: 62

```
ctcgttttca ttgttggctt cgattattgg attttataaa ttatggtgat gtagttttga     60
atgtagacaa taaattggaa atgaaatcga tgaaatgctc aagtttataa atagcaaaaa    120
```

-continued

```
aaaaaacatc ggtagacttt atttgatcta ctgtgaaaat gttttccggc aaatcggcaa    180
attgccagaa ttgaaaattt ccggcaaatc ggcaaaatgc cagaattgaa atttccggcg    240
aatcggcaaa atgccaaaat tgaaatttcc ggcgaatcgg caaaatgcca gatttgaaat    300
ttccgacaat tcggcaaatt accacaattg aaaatttccg gcaaatcggc aaattgtcag    360
aattgaaaat ttcggcaaat cggcaaattg ccagaattga aaatttcggc aaatcggcga    420
attgccagaa ttggaattcc cggcaaaatg ctagaattta aattttcggc aaatcggcaa    480
attaccagaa ttgaaaattt cggcaaatcg gcgaattgcc agaattgaaa tttccggcaa    540
atcgcaaaat aagcaaattc tataaaaaat atatagcgaa aaaatttcaa aaaggcactg    600
ttttaagtgt ttccgtctta taaaaaatcc cttgaaacat tttcggcaaa tctgatggca    660
aaccggcaat ttgccgaaaa tgaaaatttc cggcaaatcg gcaacatgcc gaatttgtcg    720
acaaaaaatt tgccaaaagg caattgattt aactagtttt aactaaattt gagtttttca    780
tcgatttcat ctcatttccc atcttcctga gttgtattag gcttcacatt acccccttca    840
aagtacggta gctttgaaga ccattttcat tgacacatag ctccgggtcg aataatgtat    900
cgttttccac cacctttcgt caataaatca tttacgtcat atcgtttttt gcaagcttat    960
acatatttct gtgtaggcgg caactgagac tgataaaaaa cgcattttct aaatggtttt   1020
ttgatgttgt tggactgtgg gaatggacta tggaattata acaatctgga gagaaaagag   1080
tgcccgagag aagcagagaa acaagatgaa cgtggcatac gtacacttcc acaacagcag   1140
ccgtcttgtg gcctatataa atgaccagat tcaagcggcc atttatactt ttcgatcttc   1200
ttctttttc ctttgtcttg agattgaaat ttgagagata acgaatccaa atagacaata   1260
tgcacttaat ttacttgaaa atgagcttaa aactcacaaa aaaaacaaat aatttggact   1320
tttttgcaca tttcctgcaa aatttgatgt ttatccagct tgtgatgaat aatttttgca   1380
cagcaaaatg aattttgtgg caattttaat ttcaatcttc catccattag ttttcctgga   1440
attttttgt tgaaaattct gatgacttgg agatttaata taagcttttt agtcgaattc    1500
ctccgtttta gacgtctaac tagttaaaaa tcgttcaaat ccttttaaat taattagtga   1560
gtaaaattca aaaagttcca gaaacttttt atagttcatt aaaaatgtat tttttcacac   1620
ctagttttaa tttaaaactc acgtggtgtc aggatgtctc ataagggttt gatctacaaa   1680
aaaatgcggg aattttttg gaatcagttg agatctgaac tcccgcattt tttgtagatc    1740
tacgtagata aagccgatat agcacactct gacaccacgt gaaaacctat aaattctcct   1800
aattcatttt gttaatctga tcccagtgac ctctaatctt gatcatttta tcaccacgcg   1860
tacttctatt ttgcaaagac ctatgatatc agttgtctga cggtcagaaa gtctcggaaa   1920
aaggcgttga ccgagtaatt acaataaaaa aattaacgat ataaaacgtc gaatagccaa   1980
ataggtagat agcgtcagaa aaaccaatca gtgatttgct ccgcccactt ttcaaccaat   2040
cagaagggtt tactgggcgg agctatacgt tctcaatttg gaaaaagttc aaatagtgag   2100
attttatctt ttttttttg tagattcatg aataaatttc agactaattc gtgttttcat    2160
tctcgctaat ttagctttat tacgcgaaca ctaggttctg agaatgcgta ttgcacaaca   2220
tatttgacgc gcataatatc tcgtagcgaa aactacagta ataattcgaa tgattactgt   2280
agcgtttgtc acgatttacg gggtcgatta tcgaaacgga ttaaaatcat ttagttatct   2340
ataaaattaa gcaagaaaat gaggaaataa aatggaaaat atattcattt aaataatcaa   2400
ccccgtaaat cgacacaaca gagctacagt agtcatttaa agggttactg tagttttcgc   2460
tatgagatat tttgcgcgtc aaatatgttg tgcaatactc aaaaattgtg tgactataat   2520
```

aattagctat acaattctgt ggttttttg agcaaaaccg aaaaacgaaa aaatttcgtt 2580
tttggcaaaa cactccaaaa tcggtatttt tcattcaaaa aaccatattt tttacggttt 2640
acgccctatt tcctacaaac aacagaaatt gaacgtggtg tcagagtgtc tcattttggt 2700
ttgatctacg ttgatctaca aaaaatgcgg gagaagagac gcagagttct caactgattt 2760
agcatggtta agagtgtgct gacgtcacat ttttgagcaa aaaattcccg cattttttg 2820
tagatcaaac cgtaatggga gagcctggca tcacgtggca ttagactttt tgagcaagtt 2880
tgaccaaaat ctttttttctt cgatttttcg gttttccaaa aaaataacgc caggcttagc 2940
ctccacctca atattcttat gtgattgttt ccagaacctc ttccccacta aaaca 2995

<210> SEQ ID NO 63
<211> LENGTH: 648
<212> TYPE: DNA
<213> ORGANISM: Caenorhabditis elegans

<400> SEQUENCE: 63
ttactggcat ttaaaggaaa gaactcggaa aatttatgaa gatttgaaga aaggcacttg 60
ttaattgatg ggttttcatt gtgttttatt aaatatgaag ttgtgatagt tttaatgtga 120
ttaaaataaa atttaaatca actatcgtga aaagtttaac tacaaaactg tattaaatct 180
gagaacacat actttataag ttgggaaatt gttgatcaag tctaagttga actaatatat 240
tcttgatgga atcggaccga aaaaatcaat ttatcttatt cagaaaccat cttgagaatg 300
cctacatttt ggcgcgagaa tagcggcaga agagagagct agaacggtag gcattctcat 360
gatctcatgg tttttcttat acatttttctt tttttctgcc gtttagttta ttgatctcaa 420
ttggtttgtt ggtctccccc tccccctgtc tgcggtcatt tagtccaata agtcaacgtg 480
tactaactgc acctggactt tgttcacttc ctctataaaa tgactttttg attgtcttct 540
ttcttattct atatctactt tttgaatttg taaattttat agctacaatt tcactttgaa 600
actgtttggt tttttttca gaaaccatac aattttgttt ctccaaac 648

<210> SEQ ID NO 64
<211> LENGTH: 1443
<212> TYPE: DNA
<213> ORGANISM: Caenorhabditis elegans

<400> SEQUENCE: 64
tggaatggga atgagaagat tcggatacgg gtacccaatg tggggataag ctgtgcaatc 60
actactgtgt agttatgtat aaactatgta aaattgaaga aaataaatat tttgactacc 120
tcaatccatg ttgtcacact gtaacaagaa aattaaaatc tgataagctt cagctaaaaa 180
ctcaaaacta agattctcag gaagatattt gggtatttga actaattttg accgcttttc 240
atgcacacgc aatggatttc taagtatcca agtatgatta tttcatattt cgccacttag 300
aatccagaaa tttcaggagc atatttttgt gatacaaaat aacgtatttc tgttgcatta 360
aacttctgtc taaaactgtt cggatctgaa attgaaatta gcatttaact ttttgttcca 420
actgaaataa tgtattactg gacaaaaaaa tattaccatg acatcttgct tcttttggag 480
aataataaaa taccttcagt tatagatttt aggtaacaaa taccatattt attcacacaa 540
gttgatgaaa ctcgttcgat attttaaatt aaactgcctt taaatatcta ttagccagtt 600
gttgtatggt cctatgcaca cactatcttg tatctatagt ttaatatatg cggcctatat 660
tgtgacatat attcttcccg tttgctctgt tgttctcccc ttcctgtata atgggagatt 720

```
gtaaatgaga gttgttctgg tcccaatacc tagccactga gaaccctcct cttctatcta    780

ctactcattt atattatcgt cattattttt atttttattt atacatatag tgggcttatc    840

aacatatatg agggtaaaat acttataatt aatcagcagt tcagaagaaa aaacaatgaa    900

tgataaggaa atttttagag aacggataga aaagggatct tttgatttct tcagtgacac    960

tgttatcatt ttcgaaaatt gggtatgaca atggagacgc cccacaatgg aaataacttc   1020

aaggttatcc atatatactg catacatatc cacaatatta tgaggtttct ctaggaaact   1080

gaaagaatcc tagtgtttga atgtgttgag catattaatt ttaagaagcc aagaaaccat   1140

aacttctgat aatgactgat atctaggctg tcacgagggt tgcttaaagt gttacagttg   1200

tgccagtaat attaatagct caatttctac aacatacaaa ccattatggt accctacaaa   1260

cactacaaat ggtttgaaac cttgttgttt attgttttta ctgaactctt atccacctga   1320

tacctaaaaa acgtcatgtt aagagaacaa caccgcccat tttgaatcct ttataaccac   1380

tgggagatga ccggatttcc aagtactcgt agttctaaaa acctttaaaa acccaaaaaa   1440

aag                                                                 1443
```

<210> SEQ ID NO 65
<211> LENGTH: 494
<212> TYPE: DNA
<213> ORGANISM: Caenorhabditis elegans

<400> SEQUENCE: 65

```
catgttttct ctgcaaaaaa acaatcgtaa ttgcataaca tctttcgaac tcgatagtct     60

cccaaaaaat tcctccaaat ctttactgca tttgcttgta aagattttac ctatttttct    120

aaactgctgt gttcctgtat tttcactcta cctgtttcgt ttatttattt atttaagcat    180

caagtttatt gatctctaat aaattctcgg gaaattcgtg tcttaattat taatattata    240

gttattcttg ccagggaaag ttacgtttcc ttatcaaaca cctgttgcga aaccagaaaa    300

gggcgggtct gactaagtga acaaatattt cgtaataact ttcttccaac agaaattaaa    360

acacgcaaaa aacggccaac tcactagctg gaacgtggag ccccatgata actccatgat    420

aaaataactc tgattgtcga catagcttca agaatatcgt attctgcatt ttcaaaaagt    480

atttttcgtt caaa                                                      494
```

<210> SEQ ID NO 66
<211> LENGTH: 1683
<212> TYPE: DNA
<213> ORGANISM: Caenorhabditis elegans

<400> SEQUENCE: 66

```
gcacaagccg ccgtgagact cgacgatacc acaaatttca acgatttctt cacaagcttc     60

aataatgacc tcgggctcga tcaggaatgg atggttttca tcaaagcttt ctacgcagaa    120

ctcaatctca aagtcgaata atttttattt cattgttttt ttgtttgata cctgttttga    180

ttaccatttt ttatcactat atttctgact tctttctcat ttttttaaa tttccggtcg     240

atctttcaca gacacgattg tatccgtgca gtatttgaaa ataacaaatt tttctgattt    300

ctgtgggttt cacgtgaaga tcttcttcaa gaagaggtca tcagattgcg gaagatctat    360

attaccgatc tgacgcaaga ctaccatgta tatttggaaa ggaaaaattt tctgtgcaga    420

ggttgatggt ttaaattttg atttagatat tttcttcatt taatttgaaa atttccatgc    480

ctgaaaatat cctcagtgag gattctcacc taccgtatac ttaaaggcgc acacctgtct    540

caaccggagc gttgcgagac ccgcggcatc aaactacaca ctgtgttttg atgatctttc    600
```

```
gatcgttctc gaaaaaagaa agagcagagt tcattaaaac aaatggcggc aaaatgtcta    660

taaaggcgag tcgttctctt cattatcttt tgattttcga tgtgttctcc ttattgtttt    720

gttcgttgac cccttatctg cattctcacc gctacgcaac gtatatttaa cgtcagcttt    780

ttcgcagaaa atttttctat attctcatgc aaatttactg ttctcaatgc tggacgtgtc    840

gcttgtgctt tgatctcaaa tctaacattt tcccttcaaa tattttatat ctgcaacggt    900

ggggcagaaa tttaaaagtt gacctttgtc agccaactgc tatcagttat cagttggccg    960

gagatctttc tattttcact ttcttgcaac gtattcagac atttttgat gaatcggttc    1020

acagaatttt cgtcctgatg ttggtcagtg atgcgccagc cggaaattag aaccgtatgc   1080

cgttatcaat ttttcaaagg ctaaaaagtt atgaggtgta tttattgttt taacacctga   1140

cctgctagta ggaaggaaat taattttatg tttaaattga aatgaaagag tcgagctcca   1200

cgtgtcgtct ccctagtttc tctattcctc ttcttctccg cctatctctc ggcttctctc   1260

ctttcgcgct cctctcacaa ttcctcctaa tcgtgctgtt tttggggtgg tccaacacgg   1320

caaaaaaggc agcaaaaagt gtctgccgtc tcgtgcctct ttcttattga aagggcacga   1380

gagaatagta tcaagaggct cctcgttcgg gccgttgaag atggtatctg gtgcttcggc   1440

ggagacggga ggagcggccg tttctcgggt catcacagcc cattccttct aatgtttaca   1500

ctgaacttgt cgcaatccct cctctaaatc tcattcatcc attcattcat attcgtgtta   1560

tgtgttcgct tttacataat ttccattttc accacgtttc tcctcaaatt tgcattattt   1620

aaatctctgc cttttcataa acatttataa ttttcagggt atcacctata ctaaccatcc   1680

aaa                                                                 1683
```

<210> SEQ ID NO 67
<211> LENGTH: 2110
<212> TYPE: DNA
<213> ORGANISM: Caenorhabditis elegans

<400> SEQUENCE: 67

```
aggcaaacat cacgtttccg atatcaaaag acattgaata aaagaaaacc aatagaatgt     60

aaactattaa agtgacaatt tcagtgaaat ttatcaaaat acgaaaataa taaaattaaa    120

aattagcgcc agctaactat ttagcagagc aaatacgttt tgacccaata taaaaacaat    180

aatatgaaaa aaaaaattaa aataaagttt taccaaatcg atattggcaa aacatcttgt    240

ttttgaggct ccatatctct gcaggaaaaa atcgcactaa aaagtgatca actagaaact    300

tgttaaacac aatgtaatct aaaacttttc agttgaacac tattttgtaa aaaatttcgt    360

tgccaagata tagatcttta actatttaga atattcaaaa ataatgaagc tcaaatcaat    420

tggttccaac tcggcaacga aattttttac aaaaaagtgt tcaactgaaa tgttttagat    480

cacattgtgt ttaacaagtt tctagttgat cactttttag tgcgattttt tcctgcagag    540

atatggagcc tcaaaaacaa gatgttttgc caatatcgat ttggtaaaac gtcttgataa    600

ggcatcagaa tcaatgattc ggtcattgaa aataatgaaa aataggttat ttgtgacact    660

ctaaaatatt tcatgcattt tttaaaaaat ttcaaaaaaa aatttttcga tcaaattttc    720

tcatggtgga gaaaaaagtg acaattttcg aaaaaaatta aaatttctga aaagtttcca    780

gggtaattat ggttcaatta aaaagcaaaa aaattatgta aaaccctcaa aaaaatgttc    840

taaatacttg tttcccgttc tgaaaatttt gtataaaaaa ggccaaaagt taaaccatgt    900

atgggaaccg aacccacaaa cttctgctca agaggcgaac gcgttcacca ctcgaccacc    960
```

gaaccgatgt tttcgccctt ccaccattgt ggtgagactt ctgttggcgc cagagacaaa 1020
aatccactgt taaccatagg aaatgcactg atttcagtgt agaatttcag acgtaaaaat 1080
ttcagatttc cagcccgaac gggcaaaaat ttcagtcata ttcttatagt agagaatgtc 1140
agctttccga tacaatattt ttttttgaat atcgctccat ttattctggt cattccctag 1200
tcagttgcct gcccgtggcg gaggaagaac ataataggag gatacgcaga gatgcagaaa 1260
aaaaacttcc gtttgttggt aggtagtaat ttctcctttt gatctccaaa gatgttggga 1320
aattcgcctt ttggaatgtt ttatggcgca ctttttaaca gttaaataca tagccacact 1380
ttctatagac taaacaagta ctcttgacat atgtcattca tcatgtactc tttagatttt 1440
ccagccttac caacctcctc cacagtttat ctcattgatt gtactctttg aaggaggacc 1500
attggttctg actttttga ccttatactg attcaaaatg tcatcaaaga cacgagcttc 1560
gtaatgagac ttcagaaaaa aatttctgaa catttttata gcggttcaaa aattctagga 1620
aatttagcaa attttagcta tagctatagg ctttacaaaa ccttcaattt atttttttg 1680 gtcagataca cgatctcatt tcattttgct gattaagatt catttgaagc tgagaggtaa 1740
acaaaaatcg ccggaaattg taaaaatgcc agaaccttta tacaacctgt atgaaggttc 1800
accttacaat tatatctgtg tttttcactt gtttagagga gtggtaggtg gaagacatta 1860
aagtgtcgtt ctcgtagaac tgttgtttgg actgatagct tttaaatacg actttttaa 1920 aaactttttg agattataca actaattgca ccatcattta ttttttgccg atgtgcaact 1980
ttcatattgt tttttctcct cactttctcc gttgtccttg ttcataacac aatttgcaaa 2040
tcacattgaa atttcagatt tccgattctc gaagctttac taacatctcc accactaacc 2100
aagcctcaac 2110

<210> SEQ ID NO 68
<211> LENGTH: 884
<212> TYPE: DNA
<213> ORGANISM: Caenorhabditis elegans

<400> SEQUENCE: 68
aactttttgc aattcctaaa tacttaccat tatttttgcc caatcaggtt aatgatctct 60
atcgtgtagt tttccccttt tagttccagt tctgctgtga tatttattta tttttgcgaa 120
tacatttcaa ttcctaactt ttttcggaat acaaaccagt aactcataaa atgttcgatt 180
tatactcaca tccgcgcgaa cacttcagtg ccgggtgtta taacacgtca gcgtttcgcc 240
agatgatgca attggcgttt ttccttggag aacaaatagc ctcgtagaga cgcattttat 300
ttccacactg cattggactc aattggtggt gtatttgctt tgaaggtgaa tttaaattca 360
gacttttttt tcgaaacttg cgcagaaaat tgtgaatttt tcgattttta tagtggaaaa 420
taggtttttt tcaaaatatt tttattgaaa attaaaatgt ttgctttcta tgctctatta 480
ttgccgaaga aatcaatttt aatgaaatat tcaaagaaat cgcggaaaat tttcaaaaaa 540
tttccacgat tttattttgt acgcaatcgc atctgcatac cgtacccggt ttcgaatttc 600
gaacttttcg aagcttttct tgaatttttt tctgctttcc aattagaatt aaaagtgtaa 660
tttaatcaaa ttctagtaaa tttcaaacaa atttgggatt aaatgttaaa ttttattaac 720
attttcaggc tttaaaaaaa tatttcaaag ttttgtgtca aagtctgcaa acactctcga 780
ataccgtaac cttgcatctt ttttaatttt ttgttttctt tatttttatc actcctatac 840
tttttctata atttaaagca attttataat atatttttac agaa 884

<210> SEQ ID NO 69
<211> LENGTH: 1475
<212> TYPE: DNA
<213> ORGANISM: Caenorhabditis elegans

<400> SEQUENCE: 69
tgctagcggt caccactatc gactgagcta tctgccccta agaaagttta aaaaacttac 60
cgattttgag ttccaacatc attttctcgc tatttttgat aacgttttgg ttagcattgt 120
actccggcag tattggtagg tcattctcgt tgtttggagt ctttatttca gactccacga 180
cggctggagc aacattctga attatatttt ttaattattg ttatactttt tagcaaaaaa 240
ctgacatttg aaatagatct actgttgcaa ataatgtctg gcaacggatc ccatctctca 300
cttggcctgc ctgagcctac atccaatctt gcaattgctt gctcacaatc tctcactaat 360
ttcaccaatc cgtaaaatct ggcttcccgg agcaactgat gtcgggttct gaaagtttta 420
tttaatttat aaaactttaa acttctagct taaaacatct accatttcct gaatttcagg 480
caaattcttg aagtatccat cgaactttgt tagagtcgct ttagaagtga caaattcctt 540
gccacctaca ttgagccgga gcatttactt tcagaaacaa taacagtttg agtttatctg 600
gaatttgtta gataacttta ggtagatttg aaatttttgg tagatcggtt tcatcaaatt 660
tatcaatgtc ataaataaac tttgtagcta taaattttaa aatagctttt tttacacttt 720
attcaaggaa acactgagaa atagctgcga aaacaaaaaa aaacatttga ggggagaacc 780
tagacgcagg agagaaagaa cgtagaatct actagaaaaa gtgtctgcgt ctcttcaaaa 840
aacaaattta aacttagcaa gatgaccacc acagcaaaaa tgaaaaagag gaacgcggag 900
ggacagggac agggttcagt gagaaaaaaa ttagaaattt tggaaaaatg agataatttt 960
taaacttttt gcagtattcc aaagtttttc ggaaaattga gacaaaaatt ttaatcaaac 1020
ttcccatgaa aatgacagaa aattttaaaa ttgaaattaa atgaaatttc tttattttct 1080
ggatttttag gagtttctgg aaatttctta gcataagcat aagcctaact acaaactaaa 1140
aacttcaaac taccaactga atacaattaa ttacctcatg attttgttcc cagcagccgt 1200
aacatgttaa aaactctatg ggtcctgtga gatgtcggcc gctctaactc tgcacattgc 1260
agagattttc agacagtgtg tgaccaattt taggctgaaa atctgccgac tgtactcttt 1320
ttggaaatgt tttgtttcga aatttttttac tcactctcac tataactcca actcacctgg 1380
ttgcgaaatt cagcgctttt caacgtaatc taaaatgaaa aatattcatt ccatcactcc 1440
tccaactccc catttttgtt tgaaattctc tgaaa 1475

<210> SEQ ID NO 70
<211> LENGTH: 2811
<212> TYPE: DNA
<213> ORGANISM: Caenorhabditis elegans

<400> SEQUENCE: 70
aagaacgccg acgacaacaa caaacatttt catcgggagc cctggaaaat gacgaatgta 60
tgcattacca ttgttgaaat ttggactgga agcgcaatgg atgaaaaaac cacgctattt 120
cgaagctcat ttctgatgct ggggcacaac acaaaattaa atgagacgag gagggggaga 180
agggatggag agcatgcatg ttttgttgtt cactttcgaa aaaatgtatc gattttttct 240
agcaaatgtt tgaagtaaat aacaactttc aaatgtgata attagttatc aattcagtca 300
gtttatcaaa aaaaagtacg tcattagcat aactttgccg tatttgcatg tctaggaaat 360
tttagaaact agaattgcta aaaagtggtt taaaagttgc gggacgccga aaattggctg 420

-continued

```
agaaattgtc aaaaatttcc aagtgacgga aaaccgtatg ttattgtgat tagtaagacg    480
atttcgcaat tttatatata ttttgtcaca aatctgaaat cactcgtgct attttaggtg    540
taaaagtcac atgttattgc acaaacacga gcagaaaatg aattaaaatt accttctcgg    600
tttttcagac attgtcttca actttgtcta ggtatttcga aatttcaaaa aaactccacc    660
tgacccacaa atcaatacta gtaagttagt aaacacaaca gtatgggaat tggttgatat    720
gtacgttgcg agacttgttt gtgcttatct tttcccctc tctacttaac aatcaaataa    780
cctgcaaaac actatggatt tttctcttca gtttggggca attcttccag aaaaccacca    840
aaaaagaccg caattttgct aacggtcttg ttcacactgg tagataagat aacattgcgt    900
aggtcgatcc taccgatcaa acgggagata tatgggggga gtaggagaga aattacggga    960
agaaggctat cgagcggcct tgacacggtg cttgactttt tggcgaaacg tatcagttga   1020
cctctattat ttgggctata cagagatgag gtatgatgga cagaaacaga aaaacacaca   1080
caaagggtat tgatgagaat catagacggt gacaacgcca attcaatgag cagtagatgt   1140
gcaggagacg tgtctcgttc agttggaaac gaaggcgaga cgtgaaaaga gtgcgtggtt   1200
gcgagagacg cagtgataga gacaaactgg ataggttatg agaacgagaa ccactcggac   1260
tgaggccatt cgtagaatga agaatggaag ttgtatctgt cttttaatag actcaaatga   1320
aactgaagaa aaaaagtaca aaacataaga cactatatat ttttttcat attgaaaaag   1380
agtttgcaaa ttttcttgaa attcaaaaat tctgtttttc gtgacaacac tttttgctta   1440
ctcattttgt aaaattttaa cgtgggctat tgtttttgtg tttaaatatt tatactacat   1500
ttttgaaaat tattattttc acattgccac gtgaactcaa aatttattca tgcaaattta   1560
gaataaaatc tgttcaacta agcctatacg cctcgtgcag aagtccaaat ttgaaaggta   1620
aacctaaacc taaatttgat catgaacact gagcctgaaa gcctgtaaac cataggcaaa   1680
gcctaaaaac agcttacaaa cctttctctg aaattatgtc tgaatacgta agtttattat   1740
atgaactaag ctttacagct aaatctatgt ttgcaggctc agttttgaac gttaataact   1800
ttcgaatcca catggaaatt tagatataat tgaataaaaa agtcctcgtt aatatttgaa   1860
aaaaaatgtt gtcaatttac gaatcctttt ttttcgccta aaaaggagaa tgtcaaaagt   1920
actaaataaa aaaacaaaac attcaagagc aactaagcag tttttccgaa attttttcca   1980
aagttccaaa gtcaacctta accttaagct gcagaatttc tgatgtttac cagctactac   2040
gaaacaaaaa cgattctcat agatgatttc ccattttcgc acacaaaatg ttggcatcac   2100
aaacaaagtg agcacaagta tggagagaga tttgagagca cagacatcaa agaataaact   2160
atgttctttg ttctttttaa actactttga aaaaaaacaa atgaatttac atatttaaaa   2220
tgttgcaatt gcaatttcat gatggaaata ttggaaaatg tctataaaat aacgcagaca   2280
gtgccaatca aaagcttttc tcatctaccc agtcggttga gtgaatgaaa ggaaacatat   2340
aatatcaaag ctggcgtgcc aattcctttt tgtgctcggc tgcattattt acactgccgg   2400
tgtttccgcg ctccttctca tcgacataat ttccctcatt tcctctcagt cttccgcgca   2460
gttccatcca tcgcaatccg ccttcttgcc taaatttgtc tgacccaata ctctaactaa   2520
ctttcattta tgtccaatgc attattctct ctgtaggtga cccagtgtcc ttcctttttt   2580
ctctctcaag atgtgagacc ccccccccct tttctcctca acggcgaggg gctacgtgag   2640
tttccgctgt gtgcgacgcg tccttgcccg ctcttcccaa actgcacggc caatggggtg   2700
ccgggaggcg gggtaggggc gggccaatcg acgcgttcca cgactaagta agcgtggaca   2760
ccccatcgtc tgcagaagag gacactctcg atccattcgc tattcatcgt g            2811
```

<210> SEQ ID NO 71
<211> LENGTH: 1113
<212> TYPE: DNA
<213> ORGANISM: Caenorhabditis elegans

<400> SEQUENCE: 71
gaacacgttg catcgataaa tcgagaatat tctcgaagcg caaaaagaaa tttcgcaact 60
atttcagacc gaataatgta ataatgtaat gggtctcttc gatagaaaat aaacgaagat 120
aaacgaagac acaattcttc ctgacgcgcg agcttcaata tgcacgtgat gactaatttg 180
gtttccatgg tgatcttttt gttcctttta tcgattcaaa tttacaataa aaataagaaa 240
ttaaagttct aaatggcgct ccaatcaatt tgccttccaa tttaacgtcg attccttcta 300
tatcaggtca taaaatgaat aaaaaacaat gatcaataaa atgatgcggt agttgcgtaa 360
atcgacacat gatggtcgcc tcttccgtgc gagacccatt gggcggagtt ctcacaagaa 420
tgaggccaat cggcacacaa cacgcgtgcg acaggcagtg aacgacgtgt ttttggctca 480
gttcctacca atccctggtg tacacacgag cgccacgtgg accttaacaa ttcgggtcta 540
tttttatgct tctgctctgc attttctgga ttattagtaa taatatcatt aaaagtgata 600
taacgctccc cgagtctata taaaatttct cctccataca acacatgttt tttggctttc 660
ttcttctaag cttaaaattt atagttattt actaactgta ttttccactt attaaagata 720
atttttgaaa agtgtttgta aatacttaaa attgaacccg aaacaatctg tatttgtcca 780
ttcacatgtg attcacagaa aagaatgaaa ataaatgcga aaaaaaaata aataaagtaa 840
aggcgcattg attttaccgc tcgcggtatc tcgccacgaa aacacgtttc gcgtcaagcg 900
gctcacgttt tcgatgcgat cgcggtttgt taattgcgaa aacaccttcc cttctcttca 960
atcgttcgct caatttctag aaaatatttc tgaataatct gaaaacctct aatcttgttt 1020
cttagttttt aactttttgt cggtgttccc gataatctct cgccctctaa actcactcga 1080
tcgattgtcg tttataggta aagtttttag gta 1113

<210> SEQ ID NO 72
<211> LENGTH: 2263
<212> TYPE: DNA
<213> ORGANISM: Caenorhabditis elegans

<400> SEQUENCE: 72
aataaaagat gtgatggtca atttaggata gtaaaagatg acaggtggat tgagggaaaa 60
gagacaggtt acttctgttg agtggacaca ttgcaacccc cggccaccac cgccacggac 120
acgccgccca cttttgcggt gtgaggtgcg aaactgtctt ccgacagatt tgtaaatatt 180
acgaggaagt tgatgtaata cggaagaggt ccactggatt tatgtgaatg aagaatcaaa 240
agattgtaaa atgtttagat atgatgagct acagggtcaa aggtgatttg atacacgatt 300
ttcgagcaga aatgctgact tttcgaaatc tcattgttgt ttaatcaatc acgggatgta 360
cgaaagggat cttggttttg gatttttgaa aatcaaaata ttacaggaaa atataatgca 420
aaactagtac agactgtgaa aatgtttcta accttgattt ctgctccgtc caactgtgaa 480
attacattgt gtgtcaattt caaaaacggt acgtgatttt ttagttctgg tttttaagtg 540
aactttatgt atatgagctc tgaaaacagg aaaataaggg aaaattaata aggtagtcag 600
aatgaaatat tgcaattcga acataagcat ttagtttgaa acaacccgta tttcccttat 660
tagttttgta gcttctagtt tgtcatgcac tgattttccg acagaccggc tatactctgt 720

-continued

```
gggaatttcc gcaaaaatta aatttaaaat taatagatga gatgtggtat gtagttttaa    780

aaaagtcgat ggattcagaa aatgctcaga aaaatccgcg cattaatttc caaaactatc    840

acatttcaga aaagtatcaa acatcatatt tttggagtcc aatactactt cttcatttct    900

ttttttttt tcttttccac tagttttaca ataaaatata ttgttttgtc ctaatgaagc    960

acatttcatt ttgtaatgtt ttttaacttt ctactgtagg atattctatt ccgtaatcgt   1020

acaaatcttc tttctctccc aaatttaggc tgcgccctgt ttcaaagctc tgctaatagt   1080

acgcaaaaca aatgtattcg ctaactcttt cgctcatttc ggtataagtg tcacttggag   1140

atctcttcgt ctctcgcaac ccgtatttgt attgtttatc ttccaaaatg gtagtcgact   1200

gctcatatga attgaattac tagcgggata tgaaagagac atgagattta taaaaagtaa   1260

ctgaatattt caacttttga aattgaactt gtatcatttt cgaaactaaa atggaaaaac   1320

aggaacgata ttacttcatt tttccactta aagatggagt agcaaaattt gggtgattgt   1380

ttttagaatc aaaattgatc ctaaatacct attgagacaa cttgaaaatg tctcaaaaat   1440

tattgtatta ggttagtcat tctctaaaag aaaacgggca acccttcaag tattaaatca   1500

ttttgagctt gaaaagagag aacattgttc attaaaattc atgtttgggc tcctaaatct   1560

acaaaaaata tcacatttat attttcggca attctgattt cctgtaatcg acaatttcag   1620

cgattgccga aatcgtcgaa aagtcgatta ccgaacggca attgctgcat gctatgtatc   1680

acaccgtttc agcgttgtgt atcgtatttg ttcaaagata attttcttgt aaatctcgat   1740

gttattgact actgcagcta atacatttga attcccatta attcctttaa tttgataagt   1800

gtgacttggt tcccgttgcc caccatcttt tgttcctttc ctcctatctt caaatcaaac   1860

gcatctggaa tctatttttt tcattgttgt ctgtctaccg atgccaacga tctgaccttt   1920

cttaattggt attcgcgctc attttgacat tgtgtcaact tcaactattt gcgcgggttt   1980

acctgcaaaa aagtaaacaa gaaaaatgga gatgaaatga aagaatttcc aatagaaatt   2040

tgttgttgaa aactctctga accatgagac cgtccaagac gttaacatca aatcttttca   2100

attcagaaac gtttcctctt tttctccttt tgtgacacgt ttcctccgtt cttttttgga   2160

gagtcactat atttttaata cgattttgct ttacaatttc ttttttaaac ttttattgat   2220

tttgtgcttc ttattttcca tttttcataa aaagtattcc aga                     2263
```

<210> SEQ ID NO 73
<211> LENGTH: 850
<212> TYPE: DNA
<213> ORGANISM: Caenorhabditis elegans

<400> SEQUENCE: 73

```
gtcgcgaaag gtttgaattc ccaactggaa aaactgagat taagaaatgg aggtatattg     60

cctgattgag atgagaaacc ggtttatgag acggataaac aagtaagttt gctgagtaac    120

gatcacaaat ttcacaaatt ctcaagacaa gtgagatgat taatttctat aaggattaat    180

ttagatgatc cgaacattac ttgagtgact gttataatag aaagactgaa aaatcgtctt    240

ttaaattaac atattccata ttgctggatc cggcaaacaa aaacaatgtt ccaggacact    300

cactccacgt gttctgagct gtcgtctcgg tcgttgattg gctgattccg cctctgtttg    360

caactagtaa cgcgccgcag tttgcagttt tcagtgaagg acaacgtgtt tgcaagagac    420

gcagacactg tgcggcactt gcaaattggg gcgggacttt tagggacacg tcgagaaggg    480

gtgagccccg gcgaaagaaa gcaaacaagc ggagagaaaa ggggagtaat tgaccgttgg    540

aaagacacct cattccattt attctcggtc gttaggaaga gacggcgatg agattccttt    600
```

tggtgggctt cgtcgccctt ctggctgttt caggtatgtc tttttattga ttttcagagc 660
ttagtgagct ttaaatagaa aaccgtagtt ttgaaattgt aaaaaaaatt tttaagctta 720
aatgtacgct gaaaatatta aaactgtgtt cacagaataa aaacattagg ctttattttt 780
tcattctgtg catacacgcc acgcagtttt tgaattcacg tttttattcc caacaatcat 840
cacttttcag 850

<210> SEQ ID NO 74
<211> LENGTH: 2171
<212> TYPE: DNA
<213> ORGANISM: Caenorhabditis elegans

<400> SEQUENCE: 74
tctgcggttc tgaaaatatt aaaaccaatg atggaaaaga atttattcgg gataaggatt 60
tttgacaaac ggacatatgg catatcctaa tgtgagcaga ggagctgtgg tcggagcaac 120
cgaccgcacc ggctcacttc tgctgtgatt cggctcggcg ccacgaaaag agtaagagag 180
acgtgacgac ggcaatagat gaatcgaaat ctatggatgc aagaaacctc ttttcaaatc 240
attcgaacgg ttagaattgt gcaaacacgg cgacgcacaa acgcacatat cgtggggaca 300
cgtgaacgat ggccgacttg agaagaggaa gaataacaga cggcgggaga gacgaggaaa 360
gggcacaaaa ctgagatgat ggtggtcgca ggcgctgagc gtgatctctt ctgttctatt 420
tcagacacca cgggattgta ttcaacaaca ttttgttgtt tctactgatc ggatgggatg 480
attgtaatta accactattt atgtttctca cgaattgtga cactaaatgt gaaaaccaat 540
agaaaacata atcgtatttc ttcaaatctg atattaaacg ggtagttcta attatgaaaa 600
tattgcccca cgacgaagaa ttaatattaa taatatttct tatttttcac ctgcacagac 660
actatagtta tcgatgatcc cagttttatt tggtctaaaa ataaaatttg aacttctgag 720
ggattgttga gcgacattga tatggaagaa gcgctatcga taaaaatttc tatcgttcca 780
tgacaaccaa tcacatgttc aaatgactga atgccaaaga aaacctcgaa agcgaaccgg 840
tttttcttcc ggtgaccgtt tagattttta taaaatcttt tagttagctg aaaatgaaat 900
ttattgcagc tccgtgagaa aaataatcag atatacgcag aaatgactga gggacgatac 960
gaaaatgcga agaatctgcc ttgcaagagg acagatgtcg gtactcaaca cgtacccaac 1020
acagtctcct ataggattga caatttatct tcagagcaga ccggaataat attaacaaca 1080
aaaagctaaa cttaaaaacc gaaacgaaag caattcaaac ttaaaatgaa aactaaaata 1140
aaaagcaaaa accgaatgct gaaaaaaaaa ttgtctaccg tacacctaca gtaagattct 1200
gcatatttgc gtgacagtgt ttgcacatgt ttattcgaaa aatgtcattg ttttttttc 1260 gtttttactt ttttcgccaa tcatttagct ttaccctaga ttttcattct tattttgttt 1320
tccaaatcaa tcaataaaca ataaattttg tgaaaattta cctgcaaacc tccattaaaa 1380
tttgcaaacc cggcaaactg tcacagagag aatgaaaaat tgattgaaaa taataaaact 1440
gcttggccag tttgaaccga ttttaacaat taagcttaat ttttttgaag tatttgcata 1500
cacaccatgc agtttttttt taaagtttta ccgtaaatcc ctactgagct aataaattaa 1560
aaaatttcga ttaaaacaag catttatcac gagttctaaa ctgatatgag acatatttaa 1620
tttattccga ttcacttcaa ctgatgaaaa cttttgttca aattctcaaa tatatttcaa 1680
tcgtatcaca tttttttcg gcagctgcag cgaatttttc ctttcatgag ccatgggcaa 1740
cggcttaatt acaccaacag ccgttgtcgg tgtttggatg tattgcccta aatgaccgcc 1800

-continued cgtacgttgt cctctccatg caacgacgct gaatattctt ctgctctcac actcgtatac 1860
tagttgtggt tgaggcgcct cgatggacag catgagagag agtgtatcct ataataagac 1920
gtagacagac gcgctctagc aaattcttta ccgcagcact ccacagcgtt cgtcagtccg 1980
ccttgtttca cgttgtcgat tgcagacaca atgcccctca ttttctattc acttctcatt 2040
gtattctatc tgtatgtgca tagtaacttg ttttacagcg agtaatctca aaaatcgata 2100
tatttttcct tttcataata ttgttctgtt accttggtac cctcattatt atttttttgaa 2160 tttaggtaac c 2171

<210> SEQ ID NO 75
<211> LENGTH: 4107
<212> TYPE: DNA
<213> ORGANISM: Caenorhabditis elegans

<400> SEQUENCE: 75
aagtgatgtt ttggcaattg gaaaagctag actaggaatg aggataaatt atgacatcat 60
taggacttgt aatttagaaa ttacacggag gcaaaccgta atgcgttttt ttaaaataat 120 atttcttaa tttttccctt ttaatttctg ctcaagtttg tttgttggca aaataaatta 180
tttaaaactt ctcaaaacta tttaaatagg ttttttgaaa ggatgtgaaa ttccttatgg 240
aattttagat gatcttcaat ttgaaaactg ttggcagagt atcgccagtg aaaaattttt 300
ctaaacaaaa taactcaaaa aaaatcagat ctttcaaagt tgtcagtaga agtttttggt 360
aaattgccaa atgttccaaa aatgtggacg ttttgaaaat gttgagcatt tcagatttaa 420
gctactgcaa tcttcaaata aaaatatttg aaacatagct agaatatatg aatcgcaaaa 480
agagttttgg taaattggta tatttttcac aactgtggta ttggtctcat tcagttatac 540
atctttattc ttaactttga tataccgtac tctaaataaa ctttcctatt acaaccacac 600
ttttaaattt catatgtttt cactcttcag aggtcaaaaa ttggaagaaa ttattaacga 660
aaaaaataaa aaattagaaa ttaattatta tgtttttatg ttcaatttac gtttcaattt 720
ttcgtatttg aaacttggca atttaccaaa gctttcacta taaatttttt tactttttct 780
acaaaatttt agtgtgtttt actacgttat cctgtcattt tagactataa taagtgagta 840
cagtattgtt ttcatttagt tcatatttct atgttctatt ataattgtct gtatctgata 900
ttcgattttt ttgaatgaac atgagtttta aagtatatca aagttaaaat acggatgtat 960
agctaaagga ggcagtaaca catatttgaa aactttgatt tcatgttctc ttccttcttt 1020
tcccacggcg ttatgtttga ccacagaagc atctattttt ggaatcaata taattttttt 1080
cggtgctttt agcaaataat ataaagtttg ggaactacct ctaatgttca ttttcatttt 1140
tgatattctc ccttgacata tcaaaatatt tcgagcagta tgcatttcct tatcattttt 1200
caactgtatt tcctgatttt agcttttcat attaatcaag taggttcatg gtttcaataa 1260
attgtgggtt aattatagat ctgcctaatc ttcaagccaa tgccttctac ggagtattgc 1320
cagtgtggat ttagtttgaa aagtattcta ataaaatact ccaaaatttt aagttagttt 1380
tggcaaattg ccaacatttg gactttttga gctatttcca gcattgccac aggaactgtc 1440
agaatgtttg aatacaaaca gttgaaaata taaaaattgt agaaaattgt tttaggtcta 1500
ctttcaaaat ttttataggt tttattataa ctaaaattat tatgactaat ttttcaccat 1560
aaaaaattaa ttgcaaataa aaaatttcaa aaatgttttg aaacgtttta ctattttatt 1620
tggacattta agcactaacg tgttcaaagc tgaaatttca aaacgtcata actttgctga 1680
aacttgactt gggcagctaa atttttcgga gagatcataa ctaacagtct tctatcggat 1740
attcaacatg agaaccccaa acctacgggc cccttcaaag atttcccttg tgaatgggca 1800
attttaaata atctctccat ttacgatatt tcaccttcaa ataaacaatg aattattcta 1860
gattacttgt tgtcattcag tcaagatatt ctcaagtatt ccaagttctc cattgtttaa 1920
tgattttgct ccaattctat ccaatttccc tttgttcgct gctttagtcc cgccaccacc 1980
ccctgtgcaa agagataacg tgtgagtgaa tctaatagcc agaatctgga aatatatata 2040
tgtttagaat cacaaaagga aaatgtgcag gcggggagat caaaatcgaa actgtatttg 2100
tgtggaacaa tgcaactatt gagagaaaca tgaagcatat ggactacgag ttgagtaggc 2160
ttcaaaagta ttcaggaatc tcaaccaacg agttttgccc agaaattacc aagaaaccag 2220
tgtaagtttc attttatttt ttggatttag ttagattttt taaataatca aaaaccgatt 2280
tcttgccgat gtcatactgt agacactgtg agaagtagga ctacctcaat attgataagt 2340
gcctacctat gtgcctagaa ggcaggtgtg gcttgcattg aacttaacag tagacgtagg 2400
tctcttgaag ttttgcttcc aggcaggcag gtaggcattt gaataattta aagctatagt 2460
aaggagtacg gtaaattaca atatcatttc gtgataaatt tcaggcaaga tcgaaatcat 2520
tttgcaatgc tctacacctt tccttatatt acgtcaactt gtgatcgtgt cagacttttt 2580
gttcgaaatg cagtttcctg gagttcagag gtctaaaaat attcctgaaa aaattataat 2640
tctagatgtt caggtgaacc gagcccgagt agcatgcgaa tgtgaaaaaa ttgtggaaat 2700
gacgcgtggc taacgaggta cttctcgtcg ccgatctttc tcttgaccag gaccgaataa 2760
atatttgaaa atgcacttat tgtttgttct caatgccgaa ttgtttacaa tgtacctttt 2820
ggtaaagagg aactcgtttg tactggccag ctaataaaat attcacatta ttcttcatac 2880
tatgttttca tatagaattt atcaatttta taatttagat gataacgagt gctgtactcc 2940
tggagtccac caggacttga taagagaatt gaagcaccac ttttataatg agcagtacta 3000
atttcgaatc tggaaatgat atttcagaaa caatccagga aacaccagaa aaatatcacc 3060
actttgaaaa atatgtgcat ttattcaatt atgctcaaat ttcagctttg gctcacgagt 3120
gatacggtca accacaattt tctccagagt acgcaattta cgcaaacacc aaacgatggc 3180
gccaaagcgc cattcaaatt ttattcatcc gtttcagcct ttttcagtct tcttgtctct 3240
cattttcgcc attttcattg ttttatttac acaaacggtc gtttaaaatg tagtttccat 3300
ctttttccga tggttcatca tttttgtcat gcgtcttttg tgaaactggt tttgcaaaac 3360
gaagcaaaaa atggataact gtgtcaaggg cgatttttcg attcgtcatg tccacataaa 3420
cgcgataatg tgtttttatc gttggtttca ttcagaaatt ggttgataaa tacattctac 3480
tacattctgg ctgtgtgatc caatttttaa atccgaaagt ctagaaattt agtgcaaaat 3540
aagcatggaa agttctaaac cccttaaaga atactgatct cagctgtttc tgttcttttc 3600
aatcagattc ccaattgcga taatatcaaa aagccctctg ctggactgct gtccacccgc 3660
aagggcatta tttccttatc ccaaaatgct ctccgtctgc atctcttcaa ctcactcact 3720
ctctcgctct cttcgcagtg cgaggccgac acgcaacgtg gcctctcatc agacacgctc 3780
cgcctattct caatgtgtgg cgaccgccga ttggccagtc gctgacgtgg accaatagat 3840
acgcggcacc tcgagccgtg tcagccacgc aagacacacg tcgacttact ccattgtcgt 3900
agcagacgag ctcagttcaa catcatcagt ttcagttttg ctcttgttcg gtttcatttc 3960
tagtctttct tctctgaaat tctcgaattt tattctttgg tatattctca ttcaatttat 4020
ctcttctttt tccgattcat atgtttaatt gttatattta atttttaatt tcagattcaa 4080
cttggtgtcg ttttatcgaa aaacgaa 4107

<210> SEQ ID NO 76
<211> LENGTH: 1524
<212> TYPE: DNA
<213> ORGANISM: Caenorhabditis elegans

<400> SEQUENCE: 76
ttcactcctt gtctgcaaca aacgaataat agaatcaata gatggcaaaa atttgaaaac 60
agcgtacagt caagataagg gtaatgtatg tttttgtcgt caacctctaa acgtcaaact 120
gaaaacttaa agggcggcgg ttggttaaat ggcgggcgtg tagtactaaa aacaaaggtt 180
tgagtaagtg cgccccattg ataacaagga tctgaagaag tcttcttcgg ataatggagg 240
tcagttctga tgggaaaatc gagaaatcga gtttttttta tttgattgca agctaatcac 300
atttaaaacg cttacatggg aaagttggcg tttgaaaatc gaatgtaata tacatttttt 360
tgattttctg attacttttg agctagcatt ttaccattta tatgaaaaat aaaaaactaa 420
gttgcgattt ggatgtggtc aattacccat ttataaaact gaaaagtatg tttatttcag 480
ttcaaaaaca ttagaatttt agaacccttc tagctaattc gacccttctc caagccatgc 540
aataaccttt gatgaatctt atctcaacca attcacattg cagagattct tatctccagc 600
ataacgtatc tccaatcgct ttctccccca tcgtccaaca cagccgctat tatcggccaa 660
agtactacgt gtctcgagtc cgatcctgac ctacttttta tgtgtacttt agttcaattg 720
cgtctggttg gatttgaatt tgttgattcc caaataggag agattctgga taatttcttc 780
gaaagcgtta caaaatgcgc agaattttgt gtatttttaa aacagttgat tttagttttt 840
tggtttaaat atctagtgta tctgctttta gcaacaaaaa atgattctaa aactcgtttc 900
tttctaaatc atgtcaccac ttatacactt ggccttttcc gatttttctt tctctctttc 960
tatagctctt tcttactctc acctgccgtt tccataacag tgctctctaa atttggtata 1020
aaacacgcag cgcaaccgca acgcaaccta gtaactgacg tgtcccacgg acaccctcca 1080
ctcacgacac tctcgcacac aaacgcgcac acagggccac acgcggcgct cgccgattgg 1140
ccgaatgact ctgcgtctct gcgcgctgca cacggtgagc cttcgctgtg ctgacgttgc 1200
cttgtcctat cgtcctaggc cacgtcgacg attcggcagt tcgttccttc gctctctccc 1260
tctcgatgcg ctcgtcgatc cgtcagtttg ctctcccttc accactccca tcggttgacg 1320
gtaccatttc ggcctacagt cgaccttgag cattcgggcg gtctatcggg agagacgacc 1380
tacaaacaga agcagtccta ggttttcctg cattccattt ctctcaccga ctggccttgt 1440
ttcggttctt tctttatctc tttcttctca gcaattcaac aagtcgtttc atattttagg 1500
cctaataata atttttattt ttac 1524

<210> SEQ ID NO 77
<211> LENGTH: 1560
<212> TYPE: DNA
<213> ORGANISM: Caenorhabditis elegans

<400> SEQUENCE: 77
gccatttggt ttgacaccac acttcacaaa accaaagtca caaatcatag aagttgaggg 60
aaatctttct attcgatggc tttcagatct agtcttaaat agcgacaata tttgttcaaa 120
aagaaacaga atcgttcgaa attctgatat ttatcttaaa tcaaagcgtt atttggcttt 180
tttttttaaa gatctctatt aacagaaaca ccacgatgac gcgtgagttt ataacttaca 240
attggcaaca agaatagtga ataaaactga caaggctaca cttgacgggc agaccatctc 300

-continued

```
ggaagacgac gaaacggaca gaatgatcta gaagagtctc gtctgcggga tttcgactca    360
gcgtcgtcat cccttccgga acctccatat caaatagcac cgtttctcgc ttctccgcct    420
ccccaggcac tattatgagc tgttgtgtgt gtgcaagctc acatcataca agaaatctcg    480
aattcccact aataatagac aatgagactg atgttttgat tgagttgaga tcgtttgatt    540
agtcagaata gacggaaatt ggatggacca acagaaaaag agaggaacgc gaatcgaaaa    600
atataactgt ggaaatcggc aaaaaaaaag aatgataaca aaagggaaaa gcgcgtggca    660
tattcttcca acaaaatatg tgttttttg gcgaccgact gtgcaactct ctcatcattt    720
atattctaca caaaaataat tcggaatatc caaaaacatg cataaagtcg cggaaatgtt    780
acgaatgtca atccgaaaac agaattgtga gtttacatga atatatactc aaatctactt    840
gaataatgct gaaatgtgta ttccaataca ctttttaat ctcacaaaat tcagtaaata    900
atctcacact ggagagtcaa agagttctac agctaaattt ctcatttacg aatcaaatta    960
gagttttaaa gcgttccttc gtattaatat cagtgtaaaa aaataattaa gacaaaaaat   1020
atttcaaaaa accagaaaaa gcgaaaaaat gaaaaaaaaa aaagaatgac aaaaacaaag   1080
cgaaactttt ttctcagact acggtagatc ttgttgtgtg cagcgtgttt gcacagattg   1140
tcgaccgtac ccggaacttt tttatttgaa atattttcaa aaaaatatat tttctctttc   1200
caaattattc acatttttcg atattttaat cgtttcttca tggttttgct gtttggaaaa   1260
agacgttcat cacagggtaa gatttataat tgtttaattc tcagcaatta atttccatga   1320
gcagcgaacg actaattgtc aaaattgagc gtgttttata ttgattctgt ctctgtgcta   1380
ttccatcttt cctgcctaaa atgtatggct tttctcgtta catttctcca atactttcca   1440
aagagacgca gacataaacg aatgtttgcc ctattgcgaa agaagtaaat gaatcaccct   1500
tccttttccc tttttccac tattttttat tttttatttt ttgaagcaac atcggcgacc   1560
```

<210> SEQ ID NO 78
<211> LENGTH: 784
<212> TYPE: DNA
<213> ORGANISM: Caenorhabditis elegans

<400> SEQUENCE: 78

```
tccattaatc tatttgttta atttattcta attctcgatc gggaataaat aatttggaaa     60
ttattcaact tattaaattc atagatctgg gaaactatca agaatcaaaa tcttaagact    120
attctcctct cgtctcgttt cacatctctt cgttctccgt ctatcgatcg ggtgatgctg    180
caaatcattt ttatcgatct acaaagtgct gcatttacta acggcatatc gtttcgagac    240
ccaaacgctg atgtgcgtta ttgcaaataa cagttatttt tccaaaccag cattacatta    300
cagtccactt tttttccttt tcatattttc atcctggacc cagctacata cattaccgca    360
aacgtgcaaa cggtagattt tatttactag ttccttttt ccgaaaaatt tcaaaaaatt    420
gtaaactgcg tttccgtttt caaagaactt ttttgaagtt tcaacgcttt tcatcgcaaa    480
tatttacaaa tacgtctcgt tatttagaaa ttttaaaatt ttttgaacag tgaaaatcct    540
tttcaaactt cgcgctaaaa ttataaagca accgcgccct aacgtcagaa tcaccaaaca    600
ctttttgcgt acacttgttg aaaacacgct tctatatgcg tggatgatga caattttcaa    660
atctgtgtcg tttttagaaa taatttcgtg aactttttta aaatctcaat tttcttttat    720
agtttcgttc ccactatcat tttggacact cattcttctt attttaggtc ttaaattgta    780
cata                                                                  784
```

<210> SEQ ID NO 79
<211> LENGTH: 1487
<212> TYPE: DNA
<213> ORGANISM: Caenorhabditis elegans

<400> SEQUENCE: 79

```
atattcaatt cattccaaaa acgatttttt taaagttttt ttcaccagac acactttatt      60
tctctcaatt ttcaacagac acgatagttc tgtccaacct ccattcgatt tgtgtagtcc     120
ttttccggca ttcgtacttc aagctcatac aacgtgtcgt ctgtttcatt tcgatgagcc     180
atcataaacg cacgtctgta aatgtgttca ttatttcatg tcataaatta tttgcaatat     240
ataccgttcg tttctttgtt gaaccgatcg tttgatatac tccaaatctt ctggagtcaa     300
ttgatgacga acatttggtc ctgaatggat tccaattctt atttctatta ttaatttatt     360
atctcaccat tgataactgg cttttcattc tgatctttct ttctcttctt ttcatcagta     420
ttatcaactt ttcttgccgg ttttgctttt tctggtgatt tttgtttttc tccaattgtg     480
ggcattgggt agtaagtaga tgtggcgaac tgtttttgtt ggtaagtagg tgcaatagct     540
gtatgaggat ctgatcccat tctttcaata ggaatttcag atgcttgtct gaaatattca     600
aataattatt ttgttagttc ggatgtttcg ataagatatt attcagatgc aaaattttta     660
ttctgcccga aaactacggt actgtactat aattttctcg cgaaaatcac aaaatattgc     720
atccaaataa catccaatac gccttcaaat ttatgaaaaa ttacggtagc ttatgagtag     780
gttttggcac atgtacattc gtgtgaacga ctgtggttgt ttcatgcttt ttgacttctt     840
gcttgacttc tgaaataaaa aaaaactttc ataagatgct ttgttcattc aacaaaagcc     900
gtttaccttg cttcttgata cttttctctg gaacgtgtgc actagtcttc tgatgagttg     960
gctccacagt atcgttgagc aaagttttcg agtaatgctt cacatttagt tcttctgatt    1020
caacacttgt cgattgactt gttggctgac tgaatcatag aataattgat aatctgaata    1080
tattaaaaag ttaactcacg tttcgtcgaa atgtgcaact cgattgtgat gaatcgatcg    1140
ttccaatgga tgctctttct tcagtatcgc tgatttggac tttgagtttt tgtttttact    1200
atgactacag cccattcttg aatctttctc tcttattgca cacgatacga tttcctggta    1260
ttttgtcggc ggaagaatat atgagtaaaa tcagaaatga atcttttttt atctaaagtt    1320
ttttattcga agaaagaatc ttcgcgaaac atgtttctgt cacagtttat ctgaactaca    1380
aatcttaggt tcacgaactt acttacttgc ttcgttaatt aaaaaaaaat tatattcttt    1440
tgctttcgtt tgcatgcaat ttccaaaact ataactccta ttttcag                  1487
```

<210> SEQ ID NO 80
<211> LENGTH: 1659
<212> TYPE: DNA
<213> ORGANISM: Caenorhabditis elegans

<400> SEQUENCE: 80

```
gcaaatgtga atggaaccaa gaagagaacg agcaaaaatg ccaccgggaa actcattata      60
tcattctgga aacaattata cttcaaaaaa tggaagcaaa atataaaaca ggagttgtga     120
atagagaaaa cgacgcttta tatcatcagt tttggcattg aaatgaatca ataacataaa     180
ttgagcgaga aaaagagaaa cagcaaaata gtgaaaaacg aatgattgac cgagagaacg     240
ggggaaggtt ggaatttttg taaacaaacg agggaaacat catgttgaaa acatatatat     300
acacattttt tatttaatgc gtcggaatat tcagaaaatc gttcagatca tcgataattt     360
ttattgataa aagaccaaaa atccagttta catgaggaaa acaatacact gtgaatttta     420
```

```
aagaaaatta aatattccaa aaaaatttaa tttaatttgt aatttgggaa actgaaacaa    480
taaaacacta tcgaaaactt aaaaaaaaac atggattgaa gctcaaaaaa actgttttaa    540
tgtttcgttt tgtagaactt tagatttttg taaagcggga gacaccacga atccgcaaga    600
agtttcttcc agaagcagat tcgctgaaaa aaaatgaagt tgtcttaaac ctgatgcttt    660
tttttgataa tttttataca ttatgtggtt tcctggttgg ccattttgtt aaaatcatta    720
tttcctgtaa taaaagtcag gcgttctcag ttatttccag atatcggatt cctaaaatag    780
ctgaactcca aaaaacggtc aagtctctga acaccaaacg cgctccttcg aacaaaaaaa    840
gcagcgcgta cgtttaacga acagtttttt cttctagaaa ttgttttctc attgcgcaat    900
gcattgctca ttataaataa ttatgtttta aacagttgct gggaggtttt cgctatctca    960
gtcgttgtta aacaattacc agagtgtgtt atcgtattta tctttgccgt ataatatctt   1020
ttccatattt atgcgattgc ggaaatttac cactgactct gcggaaactg cggaaattta   1080
ccactgaaat atcactcata tcgtacgttt ctttgaattc gtctccttgt tattcaaatt   1140
atgtcttcgt ttttgaacga gatatttacc tctagctttc tagatcgtca catcacttag   1200
gttcgccttg aacttctgtt ccgctaaaga cggctggttc acatatattt ttaacaatgt   1260
aattattact tatgacccga ataaaacggt agaacgcttt gtgaaattat tcgaaagcaa   1320
atgcgcccca aggagagagt gtgaatgaga ggctgcgttt tgtcatcatg tagaggcagc   1380
attggggtgt tctgtagaga acttagtcta cgtgtctcat cttccatatt tcttaatttt   1440
gttctattgg ctctttttgc atctcttctt tgattcgatt ctttaactga attagatcag   1500
aaattatact tgaagtttta tcttgaaaac ctactgtaga aaagtttgtc cgtgttctac   1560
tttcttatta gactttcgcg tttcggcctt tcctatgttc tacccccatc ttccgttctt   1620
ttttattatt ccaagatttt acagagaagt cgtttaacc                          1659
```

<210> SEQ ID NO 81
<211> LENGTH: 747
<212> TYPE: DNA
<213> ORGANISM: Caenorhabditis elegans

<400> SEQUENCE: 81

```
ccgggctcga acaagacatg gacgagccat tcgatatgtg atcatctgtt atcacaaaaa     60
tgatcaattt tcttcataat ttatcaaagt ttctgttttc cttccatttc atctgatgaa    120
ttcctacttt cttgttcctt ttcactaact ttattattat aattataatt attcataatg    180
ttctttcttt cccatcatca tatccatcct tctatacatt ttgtttccat ttgttgttga    240
aattttatat gctatttcat tttttgtcgt cctttttttc cgttcttcat tttattgact    300
tctcttcatg atttctggca ttcagctcga taattcattt ataccctgtt ctttctagtg    360
ttttttcgcg ttgtttgtga cggttaaatt cttccctcta catctttgcg cgtttccaca    420
caaaaatctg tacacgacat tcggttttct cgttgttcca tttctttttt gttcaacgga    480
gcgcgtttgt cgttgcagga atcggtttta atatcatcat ccattcacgc attctctttt    540
tcatgttgtt cattgtgttt ttcttcaatt tttgtcaagt ttccttcaca cgtgcatttt    600
agtaatttct ttctataata aattgcagtt tgttaaatat ttaaatgatc aatgagctct    660
cttttcttgg ttggctcatc ctctttgtat tttttgaatt atagttgaag aaaacgttaa    720
taacttttca gaaaaccaaa aataaaa                                         747
```

<210> SEQ ID NO 82

-continued

<211> LENGTH: 2141
<212> TYPE: DNA
<213> ORGANISM: Caenorhabditis elegans

<400> SEQUENCE: 82
atatagaaaa acggtctctt aatttcaaaa aaactaaatc aaataatgtg atagactctc 60
tcaattgaaa tagataaaat tgagagagac cgtggctatt acatttgtaa attaattttc 120
ttaaactcta cttctatctc cagtgagcca tactcgtgaa ttgatcgcat tgaattcttc 180
tcttcaatat caccttgtcc aataattaca tcgtctcgtg agcacatctt ctattaaaca 240
aaattagcac taggctagtt ctcttctaaa gtgagaaatg agaagaaatg tgagttgtag 300
agacgtgtat aataaaatcc ataaaaatta aaaatattgt gagttcttct gagattacgt 360
gaaggccgaa taagaggtga cggtgataat cacaagaatt taaaaataat ttttccatag 420
aacgaatata taattgcgta aatggtcgtg gttgctcaga atctcgagag actgtggcaa 480
attgtcgaag ttttggcatt ttgccaaaat ttggtaaatt gccaaatcat cgaaaatgta 540
tattttcaaa gtgatttcga gcagttttgg aaactttttac tataatattt gagcacttga 600
gaaaccgatt tcaactattt ccataccgtg gaaaaattat gttttaagtt ttggcattct 660
gccaaagttt tgacattttg ccaaaatttg gtaaattgcc aattagttca aggtgtgtac 720
ttttaaagtg attttgaaca gttttggaaa ctattactgt gatattttag cactttagga 780
actgatttta actatttcaa tactgtataa taattctttc gacaacattc tcatcgggcc 840
acatgcgatc acggaagaat ctgaaattaa aagataaata gaaaacaatt tgagattatt 900
aaatattacc tctcggtgag atctggaaaa gcttgatcgt agagagtcaa aatttccggc 960
acattttgtt cgtcaaccat gcgggaaaag tagaccaggt agtcggcgac ctcatttgga 1020
actccatcct catcggctga agctgttaaa aattaagaaa tgagataagt ttgtgttgtt 1080
aacaagcacc taaataacta ccataaatat gtttatagaa ttactctatt gattgattat 1140
caatttttct tttgaaaaga tttcacaatg cacgatcatt gatcctctga tactcaactt 1200
ctctctcggg cttttaaatg attaacttct tatgaactct tatgaacacc ttttcattta 1260
ttatttcttt caaatgaata aagctgtgat tcatttaatc tgagatttga ggatattcga 1320
caccgaaaaa cactgaaaat gacaaaagta gtcattttca tatacaatga gggagttctg 1380
agaattggca ttgattcttc actgtaacag tatttggaaa atttggtttt tctgaatttt 1440
atgtattttg ctcatggaat gttaatctgc agtttttatg caaaattatt tcagaccaaa 1500
ttctccaaat gtctgtttgc cgaattaaaa taaatcggtt aatcaaaaaa ggaccgagtc 1560
ttcagtcttt tcgaactgtt tcaaatttta acatttttca actcatttta ctcttattca 1620
tcaattctga aaaatagcat tctgtgaact tacaagaaaa ggtgttggtg cgacgacgat 1680
cagagtgatc ttcagtggat aaatcgaatt ccacgcgtcg agacattact gaaagaaggt 1740
ttttatattg atattattta aatgtcaaac taaattcgaa aaggtacgct aaaattaaga 1800
gaaaacattt ttttaattgt aaaatttgat gaaaggaatt ggaaaatgtg atggaaaaaa 1860
gaaaattgca agcgttgcat gggatttcgc aagagtgccg cacggttttt tgtgtacgca 1920
tttgctcgtc attcatgttg tctaggcagt tttgatgaca ttttttattc taaaaacaaa 1980
atgttttatt tcatttgctg tttaatgttt gaatatgtat ggaaactaat ttgataccct 2040
ttccgctgca ttatttttgc aaaatctcaa aattatatat cttcaattca ctacctagaa 2100
ggcatatctt cctgcattta aaaatctatt ttatttcaga t 2141

<210> SEQ ID NO 83
<211> LENGTH: 1463
<212> TYPE: DNA
<213> ORGANISM: Caenorhabditis elegans

<400> SEQUENCE: 83
agatcaatgg cactgaaaac gctcatttaa atgcaaaaga tcgtgtcccg taaaaatttt 60
ctgtataatt ccgtgattat tttcactcgg gaatcgctcg cccactatgg gggagtctac 120
gcaaggacaa cgcaaggaca aggacaacat tctaatggaa tggaaacgat tgcccgactg 180
caccaattct agttcaagtg aacaatgata acttttgtat tctgtattcc ttcacgtctc 240
ccagcgagcg taataaatta ttattattat tataaaagga gagttttgat cagataaatt 300
tattatcgtt gaatatccac tttctctgtt tctcgtttca ttctctaaac gacgtatgga 360
taatacatat gatgaaggtc taaaaacttc aaagaaatgt ctcctagttt tgcaaatttc 420
caccgaaaaa aaatttggtc ggttctcgga ccatttatgt attgtatttt atttggctta 480
tgttttactc aggaaagtaa ataacttttg ctaaatgtac ataaaatcag caatgttttc 540
aaaaatgttt tgaggtaatc cggcttctat gtgatatatt aattcaatcc taactgataa 600
gataattata aatttaaaac ttactgctac ctccaacttc tggaacagca taagaattgg 660
ttggtggaat ggtaacatat cttggctgcc catatccatg acgtggtggt aatttgattc 720
tatagactgc ccgtttttct ctaattgatt cagttatcaa attccacgca tcatcggaat 780
atttctacaa aacattgaat taaaaacttg aaaaattaat tatggaccaa cttcaaatgt 840
tttcagatct tcaagggaag taatttcaaa gttttcaatt tcattaaaaa ccgaaaaaat 900
tgaagcgaga atcgtaagaa ctgcaaaaac aatgagcaga atagtagcga atagaaaatt 960
tgtgtgcttc atttttgttt tcagtttcag acaggtgtct atattttata cttttcaaca 1020
caatagatat taattatttt agagagaaaa aaacaggaaa cagctacata gtgtgaagtg 1080
aaaatagaaa tatgaaaaat gaaataacaa tgactttgac gaatttatcc ctcttaccct 1140
aaattttcaa taaaatcaaa atacaacaaa agctccaaac tctaaaatta ctaaattgta 1200
tttttgtacc aaaactagct tcccgacatt gataagtaac gcactggcac aaactctaat 1260
tttttagtga acacaaaaac agtaatctgc aaaactttct ttctcgtatt ctctgtttct 1320
ctacataccg tacttaatat ttcactatct tatctctctg tgtctcttgc cgaccaaaaa 1380
actaatggtg gatcgctata taaagaaatg ttaggtaagg agttgaatgt cagttatttc 1440
tgtaaaaact agaagtttct aaa 1463

<210> SEQ ID NO 84
<211> LENGTH: 628
<212> TYPE: DNA
<213> ORGANISM: Caenorhabditis elegans

<400> SEQUENCE: 84
attattatgt tcctatttct tttatcaaat aaatgcagtt ttaaaatttt ggacttttct 60
gagaacgtac agcaataaat aaaaatctaa aaccaatcac attcaaaagg tcggagcaag 120
ttcggagctc cgggattcaa ggtcacaata atgaaattgt ttttttattg cttgacattg 180
atcgaaatta atttgttatt ttttgcaaaa tcgaaaatga atatttttga attagaaatg 240
tttttacaaa attttgaacc gccataaaaa atgttgaaaa gttaaagttt tattacgaaa 300
ttcgtacatt tgaaaacctt ttgggtctac atgttcaaaa tcgcccgaac cgttagtctt 360
cctttaaagt cagttatgac tgtgttctgt gtctcctcga ctctgttttc tgaattgtca 420

```
tcacaccaaa agaccaatct ttagatcttt gtatttcttt tcattacttg ctatcaaatt    480

agccatgaaa aacatatgtc atcatattac tcactcaaaa tactacaaac tacactgacg    540

aggttaccgt ttgatcttat catctcttaa attagtcggg gtatataaga agaacaaatc    600

gagtacattg tttcaagaaa aattccca                                       628
```

<210> SEQ ID NO 85
<211> LENGTH: 1441
<212> TYPE: DNA
<213> ORGANISM: Caenorhabditis elegans

<400> SEQUENCE: 85

```
gattattttc ttatgctaaa ctggcagaca gcagatcttt ttatatctgc acaaggggcg     60

gtgggattta tagaaactta agtttactac gcctgccgcc taatccgtga aaccttattt    120

ttatattttt ccgcctcccg aaacagttga tacgtgaaaa agcacggaag agaaaaaagc    180

ttcttttgga cttgattaat ctgttggtca tgagaaagcg tgacacaagg taggttacgg    240

tagcaattgc gtaattaatc ggatcagtct atgcgcattt ctgaaacatt ggggatttca    300

aatctagttt atcaaacaga tacaaatcac attgacatct cgtggaaaca gtctgtaaag    360

taccgcaaat tttacaattt ttgatattat tgtcgttaaa caagttccat ttcaaatttt    420

ttattgaata cggtaaaaaa acaagagagg cagctggttg aagtgagtca ctcttgttga    480

gttttcgtta ctggaaacct gaatgaagat agtttttaac tttagcatta cgcctcatta    540

ttttcctatt tcctttttac tattttactt gtatttttaa actttgttta gcacattgag    600

cacataaaac caaatgttat aaatatcctt atcatcaacc catcggtttc tttttaactt    660

ttttctttct cgaatttcaa tgacccggaa aaccaccaca tcatatgaaa atcgaatcta    720

aaaatttgca gatacgcatc tgtcctgctg cgctcttttt ttatttttga atgttttttt    780

ttctgcaaac gttgggaaca gtcatccaat ccttcaaccg ttcgtctcgt tttgaatgac    840

aaacgttctc tttccgtcct ctgtttgagt atatttacat tgctaattca aaaaaaaata    900

gtatagaata taatgatact tagagatagt tctggcataa agtttaaact tgaatgaaat    960

catcaatgcc attaataact gtgtcactgc attagtttat cagcaagtgt gccagcaaaa   1020

aaaacgtttc gagacgattc gatacattcc tgaaaaactt cgataaaagg gaagtatcca   1080

aacaaccaca cccaactttc atcattgact cgctgttttg ctttttattt ttgttaatct   1140

tccttacaat tagttttaaa gtttaaaaca aatattacat gttagaaaga actgtatttt   1200

ggtcagtttg ttcgaataat ttcgaaatct aaaacctttt ctttttgatg attcgtcgga   1260

gtagatgttt ctcgaaggag gtaaaaaaaa ccgtgggcga ttcttgtttg cattgaggat   1320

aatagagcag tagtagaaaa gcagggagtg tcaactcagt tttgtcttct tcttccccta   1380

tttctgtctt actttcgttt tgtttctttg aaataattag attttcagaa actattataa   1440

a                                                                   1441
```

<210> SEQ ID NO 86
<211> LENGTH: 537
<212> TYPE: DNA
<213> ORGANISM: Caenorhabditis elegans

<400> SEQUENCE: 86

```
aggaaattta tccaaatgat tttactattt gagaatgtat tatgcggtaa ctttttttgaa     60

ataaactaat cgtgacactc aaaaacttag aatctatttt aaaagaatag ataattccag    120

tttttgatat ccgggaattt atgatttttt ggaagaacgc aagaaatcga tacatttggg    180
```

tacgcataat aggtactctt gcacttggat caaattccta gagaacgatt agatgcttta 240
gacgcagaaa caaaaaaatg tgaccgatac aaaatcgacc acaatctcaa gaaaaataag 300
tgcgcaacac aatccgaggt caatctagac atttatgctc ttcctgcgag acaaaaatgc 360
attgtatttt ttcattcaga ttcattcagg tgtcttgaag agatatcaaa tcacatgtga 420
caaaattttg atcgaaaaat aagttgcatc ataataaaat catcttatga tcttcctata 480
taatctttct tcaatttcgg aaactacgat tcgaatatat gttttatttt aggcgaa 537

<210> SEQ ID NO 87
<211> LENGTH: 2201
<212> TYPE: DNA
<213> ORGANISM: Caenorhabditis elegans

<400> SEQUENCE: 87
aaccttaggg taaagtttat tttatttttt tttctttacg atagggttat ccaggctttc 60
taagccgtaa ataaacttcc attttaaatt ttaaaatatt ttaaagctca agcttatagt 120
atagggaaca aagctttctg atagtttaga actaacaaag agcttatgtt ctacaaaaac 180
agggacgttt ttatttatag ggggggaggt gtaaggattc taaccgtctc tacacttctc 240
ccacttccct tttccccagt gatagaaggc taagagtgta tagggattaa tgcttttatt 300
tacaggatca ccggccagaa agtcagtcac gccatggatc aacccttcgc tcttctccga 360
atacagctct gcaattgatc catccgtgca cagtgccaaa cgctccttac gcgttcgatc 420
cctgagataa ttgcaataat tcccacacac tcgatttatt ccaagcctct aaacttcctg 480
gctaccgtaa ccctgtgtgt gtgtgcgcac acttgtgtgc gcgcaccttg tttacgtctt 540
ctggaccttt ctgcggagga atccagggct ccgccctgcc accgcagagg ggtatataag 600
acgtggattc tatcactcca gatcttctct tacttttctg ttccccttta cttgttccct 660
ttgtctcatt tcttacttgt acccattcca ttggggttat taattcataa taaatctatt 720
ccttagcaca taccttgttc tgttgtagta tgggatgcaa caacttcggt tgtcataatg 780
ataattgagg ggaacactta aacaattacc ggtatacgct taaacattta ctatatgttc 840
attcaatcaa tcacatatcg acacaacaat taacacaatc cacaagtttt tgcgcaatac 900
tccttcttct gttcctttgt gattcgtgga tccgcacaga agccacgtcc tgcccagaga 960
tggcagctgt aatttttatg aatttttatt atcaaattcg aattccccgt catttttttgt 1020 tcataatcct atattttcaa agatctagct caaaattgcg tgaaattcca tgtttgcgga 1080
cttttggcgc tacagtaacc cggattattt ttgaaaatcg agatggagct ctgaaaatat 1140
gggagaaaag gtagaaaatc atggaaaact cgaatttggc attgaatttt ttaaagaaaa 1200
aataaaatct gaaatttaaa aaattgaaaa tttcacccaa agtttcaagc aaaattatcg 1260
aacaaaaata tcgattttta tccgttttgt aatatcaaat tcgaattccc cttcattttt 1320
tgcccccaac cagagatcta gctaaaaatc gcgtgagatt cggtgtttgc gtacttttgg 1380
cgctacagta atccggtaat ttctgaaaa ttaagctatt tagagctcta aaattttcgg 1440
tttcgggcaa aaaatggcag ggaactcgaa aatttttaat aaatttttaa aataaagtgc 1500
aggaaaaaag ttacgaacgc cccaaaactt actcaatatt atcgtgacat gacggagtgg 1560
tctgagcact ttcaaattca ttcgggtgga aatttggaat actcatggca aaattggtgc 1620
cgaagagcac ataaagagca gtaataatca gaaagaatcg cattctggaa gcttctgacc 1680
tgaaaatgct ccagtgggga gattttatac tggaaaattt ttaagtattt agataattaa 1740

```
ttgttcgtat ttcggaactg tgttttatca aaaagcactg tgttttgtgc tcttaattct   1800

gtaatagtag attttttttcc ctaaaaatta gagtttttca ttatcaaact ttgatttttt   1860

catgattttt ttctaaacat gcggttcaac aattccatga actcaaaaca agccgaaatt   1920

tgaagtaaat tctgtgaaaa atgatatttt ttctaatatt attcaataaa tctattttct   1980

tgtcctatat ttggagcatt tcaattgaag tttgctccat tttctgcccg cggcctagaa   2040

acctccgtgg ccgaacaaca agcgcgctct actgcactct ttttattttc gtattttcaa   2100

tttaatttca ataattttta tcggttttct tcgatttttt cgcacttccc cccagtattt   2160

tttcaatttt tccgataaaa atacaaattt tccagctaac a                       2201
```

<210> SEQ ID NO 88
<211> LENGTH: 942
<212> TYPE: DNA
<213> ORGANISM: Caenorhabditis elegans

<400> SEQUENCE: 88

```
ttttatacga aaaatacttt aaaatcagag gaaaatactt tgggaccggt gaaaaagcat     60

ggaggttcgc acaaacttgt ttaggaaaac agaaatatgt ctccgtggca ggaccatact    120

gtgcgccgtt gatgtccctt tgatacagta ctcttcgcat tatttatttt ttttcggcgc    180

gcctaggggt tttcgagcgc agagttcagg aggccttctg gattatggat agaggcttga    240

tttttaaaat tgtttaattc aatacagttt tattaaagtt ttttctaaaa atcttttcta    300

aaaataatat ctgattgctg tttatacacg agaacaaaac taatttcatg gaaacaattt    360

tttctcttta ttttctcttc gaataattta aattttaaca attcaggttt taaataatca    420

atttttaaat aagcaagtga attttaagca taacttttct tcctagtgta cgtaaatcat    480

tctttccaac aaacatattt tttcgtgacg aaacttcgcc ttccagaata ttcttttttc    540

agaaaataaa taccaaaaag cacaatttct tatctcttgc tcattctttt ctttgtatcg    600

tgctcatgct tttattcatt cctcattttt atcttgcgaa accaatgtat tttcaataaa    660

aaaaacgagt gatgcatgtg cgctccaccg gccgacggaa gatcgaacat gcactgcgct    720

tcgcgagtaa atagaacgct ctggaaagtt ccgcactctt ctctctcatg attcggcgca    780

ctctctcttc catttctccg tgtttcctct tctgatgttg acccatattt attctgccgg    840

gtgtattctt tttatctatc tgttgcttca tttattccgt taacctgtta ctggttaata    900

tttcaaaaat tcatatgatt tcttttcaga ttactttcca ca                       942
```

<210> SEQ ID NO 89
<211> LENGTH: 1311
<212> TYPE: DNA
<213> ORGANISM: Caenorhabditis elegans

<400> SEQUENCE: 89

```
aactaaacat tgaaatttct gcacttcttt attgtaatga tgcttctgtg tctgacttgg     60

cattttcaaa aataatggaa tggtggagaa ttgacagcgc agaccattgt taagactatg    120

actgtgcagt ttatttgcac agcactgtct ggcacactct cttcatatca catggactct    180

ctcttgctca ccctttgaca cggattaggt tagaggcata ccagtgggag tcagagtgct    240

cagaaaagta gttgccatcg tggtaagagt tctgaaaagc atcgaaggtt ttttagggac    300

caaggaaata tgaatggagc atgtaaaaat acttgtaaaa ctgtaaaaaa taactcagcc    360

caaaactgag ggaaccgtac tttctgaaag aaatatgtat gaataccgat gtttttaggt    420

tcaatcaaac aatttattcg gatttttcac gaaatattac agagagtgtg acgttacata    480
```

-continued

```
ataatgttca ctgtttgacg cagtcacgag cttccaaaca attttatatt atcgagacgc    540

aaagattcac aattttcgcg ccagaatagc acaacctggt ctcgacatga caagttttag    600

ttaaatgcga aaagatgtgc gcctttaaag agtactgtaa cttcgaattt ttcttgttgc    660

ggaatttgtg aattttcatc gctttctcat tgtatttcga atgaaaaatt ggctttttttg   720

acaaacttag acacaaaaat aatgctcatt aaattttaac aaatcgagga aaaaaaatat    780

tgtgaaatgt gaaaaattcc gcagaaatga gacgctttcc ggtggcaact ttcccacaat    840

ttttcactga tagaatgtaa atttttgaat taatatcact ttcagaagtt tttatacatt    900

attttctcct tataaagttt gtgtgaatca catttcggc cgaaaaaacc ggttttccat     960

ggaatgcatg cttccgatgc ttttcgcttt tattggcgga tggttacgca acctcaccga   1020

ttttatctct attttccgca cttttcttct ctatttccaa aattttcagc ctagtttatt   1080

tttgaaattt cagcaaaata attaatttcc tcacaaaact ggcgaaaggg cttttcgttt   1140

ctctgccgtc tctcttttcg cacgctctat aagcaagtgt ccgtgaagcg cacttgcacc   1200

cgtttatttt cacaacacgt tttcagataa ttttagctat ttttcattga ttttcagtag   1260

tttttacagc tattataatg gtatttttta gtaatttcca gtataaatcc g            1311
```

<210> SEQ ID NO 90
<211> LENGTH: 550
<212> TYPE: DNA
<213> ORGANISM: Caenorhabditis elegans

<400> SEQUENCE: 90

```
tttctctgca aaaaattgga gatttttttca gtctctttca actaatgtaa atacgctctc    60

ttgtgactaa gcgcgcgcgt ttgaaccaga ggacaatttt tttcctcagc gctagtagcc    120

cctgaaagag ttattcatac ttgaaaaaag aaacttttct atagatttct gcatgaaaaa    180

tcaatcctca gcgcttcttc tcttgctttt cctgattgta atgaaatttt agagttttta    240

aattgtaaaa aaaaaactaa acaagttctt tttgaaggga aaattcgttt ttaaatgctt    300

aaaatgcttc aaaaaaaaaa caaataaaaa aaattgtttc tgtgcataca ccgtcacgac    360

aaaatgcaga cttgccattg gtctcgccgc gaaaaaacat gtttcttttg aaagattgtc    420

ttaatttttt gatttcaatc atgatttcaa tcagaatttt gcgatctttc agcattttta    480

tctattttaa agctttataa attaaaaatt aaatttttaa aaatcttcca gattgtcata    540

cgggtcccgg                                                           550
```

<210> SEQ ID NO 91
<211> LENGTH: 836
<212> TYPE: DNA
<213> ORGANISM: Caenorhabditis elegans

<400> SEQUENCE: 91

```
aaattattat ataattttca aaattactgg ttgatgaggt tagattagtg ataccttgga    60

agtggtctat gtaataacaa tttttgcaca aaaggagatg agatttgata tggaagattg    120

gcaacacaaa cgtcaaagaa tggccattcc attttcatta catctcctcc attaacttgt    180

aatttgtttt gtagaggtct gaaatatatt tattttaaat tcgaaaatat ttttcaaaaa    240

atacgtacgt tcccataact cttttcttga cttcagcaat cattctagga tcgatttcac    300

atgcaattac agtttttgcc acctccagca ttttaaccgt caagtttcct gttcctggtc    360

cgacttcaag cactgtatcg gtggctttaa gagctgattt ctcaacgatt gcattcacaa    420
```

ctccaggatt tttgagaata tgttgtcctt tgtcggtgtt aaatggaagt gctataaaat 480
caatgttatg aatagaaatt ttgcaaaaat aacatacatt gaacatttcc agttgatgat 540
cctgctttcg tctttttaac tttactcgtt tttcccattt tgagtttttt taaatctgaa 600
aatgaacgaa aaataatagt atttctgaaa ataggaaaat aatgaaaaga aataaaggta 660
gaatgatttg tccacgtgaa gtacaaaacg tgggactaaa aaacaattct agtccgcgcg 720
tcgtgtactc ctctcagaca aacagaagtt gcacaatttt ttgaaatcga tcccttttaa 780
tcactttttc ctattcttct agcgtttaat tattttctat tgattttatt tacaca 836

<210> SEQ ID NO 92
<211> LENGTH: 2115
<212> TYPE: DNA
<213> ORGANISM: Caenorhabditis elegans

<400> SEQUENCE: 92
aaaaaaaccg gctggtttgc tgaacggcaa ttgctgttca tccctatacc tgcctaccta 60
ccgccaattc agataatgtg gtgaaaaatt tcacgaaaaa aagagcaaaa agaaactata 120
attttaaaac cggagtttga aaccgtcatc gtcgttgtca ttaataccat tatcattatt 180
gacatcagga atcacgccat tttgctccgt tatcatacac atcgtcatca tcatcatcgt 240
cgtcaacacc catcaaaaaa aatgtataaa aggtttcact caaaaagagg gttttatcat 300
tttatcaaga cttaaaaatg tcctcgtagt ttgactatga tatcattttt ccattatcac 360
catgtttgcg ttttcctttt tccaaacatt tcttttgcac ggcgatgatg cttggcattt 420
tgcactcgtg aaagtttcag cttgccagtg cgccgccgcg ttgtccatgg caatgcggca 480
tttgtattca acggcagaaa attgagagat ttgtttctct cgcgtacctc gcatgttttg 540
atttttcgac ctcggtttgt ccctcaaaca aagagaatcg tttgtcgccc tcaccgcgca 600
cgcatatacg gaaaaatgct acaatttcaa ggcgtgatag agatcagctc tcccgctgat 660
ttctatcgat tccaatagag atttattcac ctcatacggc ggcattagtt tgggcggtgt 720
tttttggtgt ttgttgtgtc caaaatacga aaacggaaaa ccttcatttc agcttagttt 780
ctaaaattga ttttctttta tataattttt ttcaataatg ctgaatgcac gtgctcgccg 840
gctgcccttt tgcaatgaga ctatgcaaac gcgcccgaat gcaaacgctg ctggtggacc 900
cctctcggac ataaaattat atttcttatt ttttcgaatc tgtttttctt tcatattttc 960
gaaaaaaaat gacaatatta tttgatgaaa aaactacgaa aattggcaaa accaaaaaca 1020
aaaccaagga aggatttctg gcttccctca taaattgaaa taaaagagtt taccgaacta 1080
ggccattttg gctcggccat atctggggta gatttacggc gcgttgcttg tcgcgtcgcg 1140
gctcgagttt agttgtaaaa ctaaatgtat ttgtccgtgt ggagtataca actttgccac 1200
gcgttgtcca gcaggagatt tgcaatagag caagaaaaat tcaatgagga aggccggacc 1260
ccgtgaaaat tcgcagaaaa gtaatgaaat cgaaacagaa aactccgaga ggactacacg 1320
gccgaggatt tttcctcgtc cgctcttttg ttaggccatt ttttgaattg gtaaacggag 1380
ttttctagtc cccgaaaata taatttagac caaccagcga gcacgtgctg ccattgtcgg 1440
accaaaaaaa aaacgccaaa aaaccgtgta tttttttttc gttttttgat ccaaatgctc 1500
atttcgtcaa aactgatgcc tactttggct gcctacctac gcctacctac ctacgtgcct 1560
acatatcgcc tattctttgc attttggcgt ccagtacttc actttccaca gaatagataa 1620
aaaagtgtat tttgacaaaa aaatttattt gacctcggcg catttgatct cgagaaaacg 1680
tggcgatttt tgtttttacc agttccaaac tacatgtaac tttgccacgt ctgccagatt 1740
tgcgttccaa catgtcaaaa tttggaaaaa aaaaccgttg tttaccgaat gacacacaaa 1800
cacttttccc catctcattg ccctcttaat ctttgcaagg tttcacaaca ttttgagaat 1860
tctgctaaac cgtctgcgtc tctcattcct ccaccctatt gtcacggttt tgctatctgt 1920
ttctctcgtt ttttcgtggt tttttctctt tttatgacct tgcgtgtatt tgccaactat 1980
tttttgtttg tgggcatttt ttttggggaa aaagtttgat ttctggatga tttgaatatt 2040
cgtgtatttt ataagctttt tcctaacttt tctactttcg ttcatttctg ttgtttcagc 2100
cgtaatccga acagc 2115

<210> SEQ ID NO 93
<211> LENGTH: 1106
<212> TYPE: DNA
<213> ORGANISM: Caenorhabditis elegans

<400> SEQUENCE: 93
tatttcttgt gattcgcttc gattttctga aaaaagattt aattgaatat taaaactaca 60
aagaggttaa aaatgatttc cgattttctc gattcaaatt tagagaattc cagattttag 120
ctcaattgtt gtgaaaacaa tttttagctt ttgagaatta actttttctg ccaaaaaaat 180
tacctggagg agccaattac aattagctcc aagtgtttca atacagtatt tgagagctcc 240
atttggtcca agtccaagtc gatccattac atcattcaca gtgatcattt cctaaacttt 300
agtattttaa atgaaaaata tgaccttaag tattaaaata acattgatag atgatctgta 360
ccacgtttca taattattgt cctatattca ttggaataaa atacttacag tgatatttac 420
atcaggtgcg tatgccattg tgtcattagc aggatcaaga ttgatagtga gaaatggtcg 480
tttggtttgt gagaaaatgt ccgttaatcc tgcacaaaat gtagattttc cagctccagg 540
agctccaatt acaagaactc cgtacatagt ccaatgagta ctgaaatttt ctagttgaat 600
cttaattttc tacggattgt tttgatagga aaacatttaa gaagaacaaa aatatataaa 660
tacaatttaa tttaatttaa aacaaacaaa aaagcaggat aaacgggcct ggcacagggc 720
caagtacgca tttacaccgt acatgacgac atattgcgga ccattgcatt ttgccgcgtt 780
aattttttat ttaaacggct tgcatttctc cttactatcc agctgacaat ttttagtttc 840
tttagaatta tttgcaatca aaactcgttt tttgtaaaca tatttactca ggtaatgtgt 900
tgatttctca cttttttttg aaatcaaagc agaattagtc ctatttttat tctacataaa 960
tatctaaatg tattcaatta aaaattgggc cattgaactt ctaattaatt caatttataa 1020
atttatcgtg atgttttctt ttagttaatt tgtccttaat cgtgccgtct attttatttc 1080
ttcataaaaa acttttcagt tccgac 1106

<210> SEQ ID NO 94
<211> LENGTH: 2241
<212> TYPE: DNA
<213> ORGANISM: Caenorhabditis elegans

<400> SEQUENCE: 94
caccagcatc aggagccaac atcagtgccg acaccatcgt cgcgaaacat gcaaagctgt 60
ggagtcgaaa gcactcaaca gccggaccgt aaacaggtga gcatacagta ctcggaggaa 120
gaaggctccg aatattttac cgatgagctt gacgatgttg atgatgagat tgatgatgct 180
gctgctgcag cccgtgcggc tgagaatatt cgtattccgg cgtgtctatt acagacggct 240
gctcaaaaat ctgaggaaga ggatgagtac gatgtaagac actcattggg ttacccattt 300

```
ttctttggtt ggccggagaa aaattattta ctatgctccg atatttgttg atcgaaattt    360
tccaaaaaaa gagctgtagg aaattgagat tgataaaatt aatttttatg catttttcgc    420
caccacctga tgtcatggtt tacaaaaaac caaacagtta aaatttaatt agatacaatt    480
tttgaaaaaa aaaagtgttt tgtacattta gaactaatcc ataagcgacg tgcatttcaa    540
tgaaattgtt tatttttatt tggcgtattt ctacgatttt ggacaaactt gtttgaaaca    600
agacaacaat tttcgaaata tcgtagcatc gtttgaactt atcatattta tttttaaaaa    660
atttctttcc gccaagaaaa atgggtaacc agcgtcgtcg aaaggctatg atcattaatt    720
tttataggtc atggagacgt atctttaatt aatactctat atactggtac gacgggtaag    780
atacattaag ttgtacaaaa attacagttt tcctccttta ttttctccaa aaaacctttt    840
gtctagaaac atctcaacat tatttagtta attttttttt agtttttcaa agtttataat    900
ttcaaaaaat tatttttctg ctttttcggt ttttcttcat gttcaaaact tcttcctctc    960
tcgtcatttt tgtataatgc atcgcggcga tataaatttg cattttatct ggttatggct   1020
tcatcatttt tttttcaaac gaattttggg aaaaaagaat gctatagtca ttttaattac   1080
atccctcata tttgtggcgt actgtttcct ttccctgcta tcccgattga tgtttttaaa   1140
ggcacaccga cgagaatttt cgattaaaat tgtaaattag agtaaaatct atgacttgtc   1200
aatcgaaaat cttgtcggcg ctctttagga actccataaa aattgaaaca aaaattattt   1260
taaaaattac caatttttc caggtggccg ctgcgtggtc gacaaaaatc gacgtggaca    1320
cgcgcctcga acaagatcaa atggagggtg tcgatgaggc ggaatgggac aaataggcgc   1380
tactggacca tttcatatta ttttcagtca agtagtgtac aatgaacaca atttctcac    1440
ggttctgtaa aaatgttttt tctattgaaa tgtttgattt ttcgccccca tcaccaatcc   1500
atcaccacct ctccctctct cgctttttat ttgtctcatg ctttattcat catttttat    1560
gattattatt atgagtatta ttactattgt atagtctcca atttcgtgat ttttggtttt   1620
ctagaaaatt gcgcccgctc gcccgccccc acgacttacc acctccccct gaattttttt   1680
gtgctcccat cgcctagtcg aatttattct tttgtatttt tgtgtgtcca ctttctctct   1740
cggtcgatgt gttttaacat ccatattttc tgccccgcct cgtccccccct ctcaatcgcc  1800
cgctccccgc cccgccttta cactgtgttt cgatgaaata aacagtagag aattgtaaaa   1860
ctatgtgcgt gagaatttgg aaaattttag ttttttgtga tatcggaagc ttttttaggg   1920
gaatttgaat ttatttttaa aaattgttca aagataaatt agctccgaaa ttggaaatcg   1980
tagtggaaca tttgaatttc cgccagccag acatgtggca ttgcggttac cgtacccgca   2040
attgtgatga attttcaaaa atcggtgatc ttctggattt tcgctgtcaa gcttgagttt   2100
aagggtctcc tcactgatct atgtccattt tgcggcagga attcttttttt ttttagtttc  2160
attcggatat ctctaaaata tcaagaaaaa tcgataattt cacttttcct gaaaactttc   2220
atattttcag aattttcact a                                              2241
```

<210> SEQ ID NO 95
<211> LENGTH: 661
<212> TYPE: DNA
<213> ORGANISM: Caenorhabditis elegans

<400> SEQUENCE: 95

```
tttcatagat tttttaataa tcagtctgct cactgataaa cacgtcgatt gccgcagtat     60
cttggagaag agaactgaac ttcattgttt gaaacctaga aaatagtgaa aattagttag    120
aaagagaagg agacggagaa tgaaaaaggg aaaatcgcgc gcgatggaag aaatttgaaa    180
```

```
aaagacttta cttttgatat ttttcgaaat tttttaaaat aattatgttt agagttaaaa    240
ttgcaaggaa aaatgaaaca aaaattagtt taaaaataaa aaccaccgta tctctttccc    300
tgcgaaacca attcaccgta ttattgtatg tgcctttaat ctttaacagt aagcataaca    360
tgtgattttc gccttctttt tattaaaatc taaattatta cagaactttt aaataatttg    420
attatattct ttgtttaatt tttaatcatt taaattcaat ttagaaatgc taaaaatccc    480
aaaacaatga gacactattt ccctgcagga ccattttaca gaaatactgt atgcaccttt    540
aatttctttt caaaagtaag cggcctttct gtcgaatcat ttttcgttga tgaactcttt    600
tttcttcact tttactctat attatcacaa aaattcgaat ttttcagcga aaaaatcgaa    660
a                                                                    661
```

<210> SEQ ID NO 96
<211> LENGTH: 1207
<212> TYPE: DNA
<213> ORGANISM: Caenorhabditis elegans

<400> SEQUENCE: 96

```
agaatgtctg gtctccgaat cgtcaactcc cttgcatatt ctttagctcc aggacagctc     60
ggtgtagctg caatttgcaa cggaggagga gaagccacag cagtgctcat caaaaaactg    120
taatatgaac ctcttgccta aatgttttct ggtcttctat tcatcattcc ttgattcact    180
tttacaacaa atttcgatta cgtatttata aatagttaag gttcttgtca cataaatgtt    240
tattctcaaa tggtgcatac gtgttattga ttgggaaatg aattaaggtt aatatgtaca    300
ttatcaggaa tggttttgag ccatctcaaa agagatatac tggaaaaatc ggaaaagcat    360
ttttcttttg agatatatca ttcattcacg tcttcaaggc aaaacatata aggggagatc    420
gtatacaaat aatcacaggg aagaattggt ggatgataaa atgatcccat aaaccattat    480
tagtttgaga gatcaagttg ggggaatgag aatattaagg ggggaagaat ttaaccggga    540
agcaaacata gagcgattta atttttccgg gatttgcttt gctaggcggt tccaggtggc    600
gaggttggct ctgaggaatc ctttgtttgt ttcgccaaca gatctgagca tgtaggggta    660
tcttggagtt acagctttct tcaccgacga tgacacattt gggtagtgga agtttccagt    720
tatgatgttg tggtaggtgc gaaggatctg caagacccgc ctatattgca ctgacttcaa    780
attggcttgg gccaaacgat cctcgtatga agaatacttt atgttgcagc gttggaagac    840
gagcctggtg aagaaatgag atgaatcaat aaaggctatg aacgggtaac tcaataaagt    900
atcttcctgg actgggatga ttccgagaaa acaatcacaa acgatacggt aatgaatagg    960
aatccattga tttcatttta tctgtaattt cagtgtctga caagagatcg tcgtttcgga   1020
attattacag gcccaaatat ggctggaaag tcaacatatc tgaaacaagc tgcccaacta   1080
gcaatcatgg cataggtagg atgcttcatt ccagcaaact atgcttcgtt gccaagtaac   1140
ctaaaagttt tgatttgcta ttttctatcg tcgaattaat ttcagttttt aatcgtatct   1200
tctccag                                                             1207
```

<210> SEQ ID NO 97
<211> LENGTH: 475
<212> TYPE: DNA
<213> ORGANISM: Caenorhabditis elegans

<400> SEQUENCE: 97

```
gatggtactg agaagaagac cgatttcgat gctccaacaa cacttgctta attattcacg     60
```

gagatgtcat aattacagct ttggttttca ttatttgttt ggttattatt tatatcacaa 120
atttcgctaa tcggcgagac ccctctattg cttttctctc ctatctcgtt tttgttaacc 180
cagtttcttt tgaatgaacc cttgttatga cgattttatg gttttccaac ggtaattcaa 240
taaatgatat tatatgtgga aatcttgaat ctgatttgat cgatttagtc tcgaaacgtt 300
catgaaggca acaaacaaac aaccgttgat taaattagtt ttttgaattt cgcgcaccta 360
atattccaga ggagcgggct tgcattatct tttttacacg aatttcttat ttacagtatg 420
cactattctt tctcctctcc cattaatttc ttgtcaatcc catccctttt tgtag 475

<210> SEQ ID NO 98
<211> LENGTH: 1109
<212> TYPE: DNA
<213> ORGANISM: Caenorhabditis elegans

<400> SEQUENCE: 98
gcgagccgtt tttttgagac cctgaaattc ggaatttctt tttattttat atttttaaat 60
tcatttaaat ataaaaatag agcacaaacc tcatcaaatg tgctcactag aaaattacac 120
gtcctgcatt tttcgttttt gatggtgact tctttttgtg acgtggcacc aattaataca 180
gcaagcagga gcagtatccg gctcattttc accctgaaaa atggaaaaaa ttggattttt 240
atgtagcttt aagacacgac aaaccgttat tttagagaaa ttacacgcag aataagcgaa 300
tgagcgcggc cgaatgcact gcaaattgtc tacgttgtcc agtttctcgg ccctgtgagc 360
ggagaaaaga gagggagaaa agaaaaatga acaaatattg gctttgaccg ggattactag 420
caaaagaggt gactgatgga agagggaaca attaaatatt agaaaaattc gaaaaagtta 480
attattttcg ctggaaatca ccttaatttg gggagtttcg aaagaaattt tgataaaaat 540
agaattatcc actttttatt tcgtgaaaaa aacaacaatt tcgactgaaa atccagcttt 600
aattcgagaa ataacaaata tttatttatt taattaaatt aaattaaatt aaagaaaata 660
attgaattac tgtagtgatc gttgcgggac ccgatgaacc gaaatcggta tgcgccttgt 720
agttacggta agaaaaacgg gcggtgtcga gaatttaatt taaattgcat ttccaaaaca 780
attttcctcg tttgaaaata aattttacga gtttttggtt agtttaaatg ctaaaaactt 840
gatttaattt aataaaacgt acctaaaaat tcagtttcgt agcagaaaac acgaaaattt 900
cagtttttag taaaatttc ggaatttcta ttttcaagtc ttgtttatag ttacttttta 960
tggtgttcaa tcaacttttt gaagtttaaa atgtttaaaa cgtttaaaat tactttacaa 1020
gaaccgaaaa aaaccgaaaa tatttcaatt tttagttttt cagcaacctt ttcttaaatc 1080
agaaataatt ttatgaaatt ttggttcaa 1109

<210> SEQ ID NO 99
<211> LENGTH: 1049
<212> TYPE: DNA
<213> ORGANISM: Caenorhabditis elegans

<400> SEQUENCE: 99
cgagaaacat caaccatcga agagcagctt ccttggccag agtgtcgtct gataggtcga 60
tgtagtcgag caggcacacg actgctctgc acagttctcc gttgtaaaag tagaaaaagc 120
agagtttcgc gggaatactc gcgaaaatct ctcgatcttt gctccgacac tccatcgcct 180
cctttcgtag agtttgccac gtgatgaaca ttttgcatgc ggttcgttga tacttcgcaa 240
gtccttgaaa gtattcggac gaggcgtagt atgaggtgat tcgagccaat ttgctcagcg 300
agttcatgtc aatcggtcca ttgacgccga attcggcgat aaaaagctcg gaaatctcct 360

```
gttgcaactc ggcagtttgt tcggcaaacc cgatcaccgt gcagctcaca tttttgcgta    420

gctcatctag tttttcgatg tgctgcttgt caactgactt gtttgtgatc ttcatgaaag    480

tttatctaga aaaattaaaa ttaaactgtt ttaatggaat taacattatt acatacataa    540

aaagcaagtt ttttgattga ttttcattaa aaatcgagga aaaattgaaa atgaaagggt    600

ttcaacgcac gttatcttct aaaaaattta aaaaattttc ttctagatga tacgcttcac    660

atacgcgacg cgtaacattg gagcaacgtt gtcacttttt cttaaaaatc tcttataaga    720

gttggcacgg tgccagatcc ggaattccac cagatcttga attaaaataa gtttttttgc    780

aagttttagc aagttgaagc aagttttttt attgattttc accggaaatc gaggaaaatt    840

gaaaatgaaa cgattttcga ggcaaaaata aaaaatttcc ctccgatttt gaagtccgtg    900

aatgcgcgtg cggtgcaact gcgtacaaaa caccaaactt tacgacagtg cggtaaattc    960

tacttttcaa agtttgagcc ccaaaattcg tttaattttt gtttaaaact tttcttgttt   1020

attgaattat ttacattttt tcagtcgac                                     1049
```

```
<210> SEQ ID NO 100
<211> LENGTH: 282
<212> TYPE: DNA
<213> ORGANISM: Caenorhabditis elegans

<400> SEQUENCE: 100

ttgaccaaga tactttgaaa tcatccgcgg atcatacaca attagtacaa cgtttgacat     60

ttctcctgaa aaatggaatt tcagttctaa aaacacaaaa ataaagttag aaattgttaa    120

aaacaaaaaa gtttatttga attcgccgaa gagcgcgcca aaacatgtga catttctcgg    180

ccgtgaaaac taggccaccg cggccacaaa caaattttag ttttcttcgc tgaaaaaaac    240

atgtttttca gtctgaaatc agagttttta gtatgaaaca ag                       282
```

```
<210> SEQ ID NO 101
<211> LENGTH: 1275
<212> TYPE: DNA
<213> ORGANISM: Caenorhabditis elegans

<400> SEQUENCE: 101

ccctaaatat attcacaata tctcatattt ctagatatgc agtttcttct tctggaacta     60

cacatcgttg gccattatgc ttcgcccatt tggtaatgat ttggatactt gcgttgcacc    120

ttgggtcttc tatctaactc atccggtttt tcggaagaaa gttgttcaga gaatatttat    180

ttttaggcct gactcatgat aataaagttt cgatttattt tctataagtc cgcagagatt    240

gaaaagtggc aaatttgatt ttgcttattc cataaaagtt atctctactt aattaatttt    300

atcatgtttt atgcaatttt caaagtaatg ttggtgcgcc aaaaaattct acttaagctt    360

gaaaatttga gatgaaactc taaattgtat gcagttattt tggtaataca gctttcaaaa    420

cacagaactt gcatcttttg atcatttcta acaatgtagc cttcacctaa ttttagttcc    480

cagaagttaa ctcagacgga taatgagcgt tttaaatttt tgaatttctg gttttgccgc    540

caatacttaa caagagcaca cgctatcttg aggaaaacaa ctacctgaaa aggggcgtag    600

tcatttagtt cacacttctc tgtgcgtttt tttaaataat gttagtttcc aaaaattttt    660

agagacccga agaactcggg ggatgtccaa ttggggggat taccaactcg ggggacacgg    720

ttttaaaatt atttttcttt gttaattctc gctctattga gaaaaataca gttttaaaac    780

cgtgcggcag ttgcagaaat gggcgtattg caagccacgg ttctgtgggc ggggccaatc    840
```

```
ccccgagttg gtaatccccc caattgggca tcccccgagt tcttcgggtc tcaattttta    900

gaattgttta aaaataataa tgccaaccca aagcacaaaa tccctgcctc ttaagtgaca    960

gtcttcattc tccgagtttt gaattccagg cgtgtgtgac gactcattca aattattgtt   1020

tttgtttttt tttcagattc tcactcaatt ttgaaatttt ctgcgtttca aaaggttttt   1080

tcggaatatt ttttaattct aaagcttcaa aaactgaatt aaaagaattt tctcctaaaa   1140

agtcgccgaa gaaacgcaga gaaaatcggc aaaaggcggc aaacatttta ttttcaaatt   1200

ttatccgctt tcccttgtgt ttatctttat tttccctcaa tttgcttaac cgaaacgtct   1260

gttttcagaa tataa                                                    1275
```

<210> SEQ ID NO 102
<211> LENGTH: 1549
<212> TYPE: DNA
<213> ORGANISM: Caenorhabditis elegans

<400> SEQUENCE: 102

```
ggacgtgcgg cgaattgcac caattggtgc atgttcaaaa aggaacggag aagagccacc     60

ctgtgaccac tcgagcacta atttgaatga atcaacctcc ccaagtagta acatactaac    120

cgagaatagt ttgaagttct gggggtataa acaagaatgg agatagcaaa actaacgccc    180

gagagtaagt aaatacttat atggtgagcc taagtctcgc gtcgatttat tgttttctgt    240

tcagaacaca acgtgcatat ctagaaattt tcgatgattc atgcaaaaat gttttcaaat    300

aatttttcaa aaactgaaga aagtttgaga aataatataa atttaggctt tccttcagat    360

aaatttaaat ataaaaaatc atatatattt tcaagatgcg agaaaaaatat ggaagcggcc    420

agcagagata cgctatagcg ctaaacaatg tgtgcgattc acaagagctt ctgaaagata    480

aaaattgtga ctacgattca ataattgatt caaagtttga taagtcaatc gatttcaagt    540

gaaaagaaag agcttgagaa catgatgagt agcaggtgta gaaaacgcat cgacgcgatt    600

ttttgttttg tttggcgcca ctaaacacac agacattcgg tcatacactc ttccaaatat    660

agtcaatata cagtgtgttc gagtgagaga gaatggaaca tgtcgaaata tagtgtctga    720

agacgagaca ctggattatt ttgacgggaa agcgtgttcc ttccggttgc aggatgctgg    780

tgcagcaaag tgtcaaaatc gatgggaaca gggaaggacc ccaaggataa ttgaaagatg    840

agcgaggaga aagagagcga ctgaatgagt tattacgagc ggcagatagc cggaatagct    900

ggcctatttt acattgcggt cgtcgctttt tgcggaacgg gtcgaacggt tttcaatgca    960

attagacgat tcgtcatctt tttgacattt tttagataca aaaaatactt atcaataaaa   1020

aagtttttta gaaaaactta aaatatcgaa tttatcttta gaaaatgaat taaagaagat   1080

gaaaaataaa atgaaaatct aaaacagatt ccataccgta gtttcacaca aagggacatt   1140

tatagttctc aaatttgtgt cccgccgcga aatcaaaaca aaagaaagtt agtccgtgta   1200

ctccactcgg acaacattgt ttcgcaacac ttttttctgc gaacattaaa aaatataaat   1260

ttgttcaact tccatttttt aatgttatca aatgtttcaa tttttcttaa tttttatgat   1320

attttcagct gaaattttttg tttcgattag atcacaaact ttttttttgat gtttaattga   1380

aattttagag atgtattaga aagtttttta atcttcaaac aaaaaacatt tttgtcaaat   1440

cgagacctca aaataattta tcttttcaat acaatttagt ttccttgctt ttaacgttca   1500

aatcttgatc atttcttttt ttttgtttat aaacgattgt ttcagataa               1549
```

<210> SEQ ID NO 103
<211> LENGTH: 2228

<212> TYPE: DNA
<213> ORGANISM: Caenorhabditis elegans

<400> SEQUENCE: 103
actgggtcga cgagaagttt tggaagtgag aatttactaa aaaaaagaat taaaattaga 60
ataattctgt agacatccac aaatcacctg tttttcagtc gatgaaaact tgaaagttta 120
taatcgtcta ctttatcctc cttcttttca aagtcaatta gaacaccatc agctcctgaa 180
catcgatttt ttatatatcg atcactggga aagaatctga aatcactgat ataatagaga 240
cattgcattg ttgacatacc ttgtcagtcg aactcgaatc aacgatctga tcttcatttt 300
ttgtgttagt tggttagtcg ttagtagatt ataaattcgg taataaattt atagtggtag 360
aaattaatga gaattatatc cacgaatccg cgtgtactgc ggaaatattc attttatatt 420
tataaaaaat gttacaagtg agatcaaatt ttttttaat gtatcataga agagaagcgc 480
caaatcaata gaatgctgca cattttaccg catccaatcg ttccattttc tgaatttgaa 540
ataattattc atagctccat aacggttgag taacgtgaat gataattctg ttttaaatta 600
ttaagactaa ttcccctatt tgaattccct ccaaaataag aactgcaaga ctagcgattt 660
gatttgagca atttgcatcg cctactttcc aaccaatcaa attaagtgtg cgaagttcga 720
agtcgcctac ctaccatata cttcccatcg ggtctcttaa caatcattgg cttgaacgaa 780
acttctctac aaactctcgt tggtggcgac agaaaccgtc ttgtcatttt gccacgtagc 840
aatagatccg ccaatgcttc aggaatctga tttgatttca gtgcttctga tggaatactt 900
ccaaagcatc gatgaaatgc ctgtgggact ccatcaatgt cttcgaattg gaacttccat 960
agacaacatg gttgttctct gaattttaaa aaaatgatta tgattaatga ttgagtataa 1020
gttcctgagc cagttgggca acctacattc caagagaagg atcgcactcc tttccaaatg 1080
tgatccttgg aagtatggac tttgtgtcaa ggattgctcg agcatccaga ttccgtggta 1140
gaagatatcg attgttccaa aaatcatcga gaaccactag aatctctctg atcctagacc 1200
tctcattata tgaatttacg atagaagttg tccgaaatct ggcattttct ccccaatcca 1260
tcggttttgt ttcaattggg tgaattttta gaaacgtctc acctgaatca agaggatgtg 1320
atgaagatct taaatctctg cagttcacct tcataacata cgtacatcag tggagaccta 1380
cttccagggt ctctgaacca tcgatcagga atatgaattg ttaaactgaa cacgtgggtt 1440
actgtagtta tatttatatt tctcacttaa caacaggaat cggtatctgt ttgatagggt 1500
tgaagtgtat tccatctcga aaatgaatcg gaacatggaa gaattgtttc ctggctagag 1560
atccacaaaa gttcgagacg ttgtcaccgg taatccgatc tccgagaaga acaatctgta 1620
agaggtctca tctgggagaa gcttatttca gtagttacct tctgttcaga ctctgcgatt 1680
ccttgactat aatagtcgat cccttcaaga ttctgatgaa ttgcatccga aaatgcttct 1740
ttaacaactt cgtgcaaatg aaaacgtaat tcgttttgat catcatactg aaacttcgga 1800
aagattttaa gtattacccc gatccaaatg tttcgaatta aagttataaa tacggtaccc 1860
ggtttcgaca cgatttttgt caaactcgag gaaactacag tagtccttaa aggcgcatac 1920
taatagcgca aaatctcaac cttcgcttac caacttaccc gcacaccttc ctttctctgc 1980
gaatcaataa taaaattcga aatcggcgtc atcattctat aaccagtaca atgaataatc 2040
aaactaaata gaaaggcagc ttgaaacatt tctttaatct tctcgcaacg aaatgtgctc 2100
cggctctcca ggcttatcag tgttagaaga gaagagaagg ataaaacaac aataaaaaca 2160
gttttcattt gtctcgtttc ttgcttcttc ccccacgatc tgctgatctg aaaatgcatt 2220
ctttcagt 2228

<210> SEQ ID NO 104
<211> LENGTH: 1895
<212> TYPE: DNA
<213> ORGANISM: Caenorhabditis elegans

<400> SEQUENCE: 104
caagtggtat gccaactcat ttgagagatc taaacatcga agcccatcct ctacttcgac 60
agcccgtaga agttgtgtag cacattttga acatgtgagc ctgtacaaaa gccataatac 120
ttctcaacta ctatcatcgt catctctccg tcaccaatga tctctactca aaacggttat 180
ggacggtttt tttgcataag gattcaacta gccctacacg attgctttga tctctgtaca 240
tttttgcgtt taatatggat atttgctttt taatggattt tcgatcttct acttttattg 300
ttgatttttc tggttttgtg ggggttgtgt acaaattttg tttatttgtt gtcggtaacc 360
acgggtacca tattatgtga atcgtttatc atcgtattaa atcatgtata catgcattgt 420
acagagtttt tgaatataat aaatgaacat gacgtcattt gcacctactt tgtgcttttg 480
aactttcact gtttcagata ttttttattt atgaaaaaag gtatctatga acaagctttt 540
caatacatta taactttgtt gtatctggtc tgatcctcaa tatttttgag tcttcaaaag 600
aaacaattat aaattgcaat acatctcaac actgttttat ggcgtctcaa attttgaaaa 660
aaaaaattat tttataaaaa ttgatttgca gcagacatgt tgaaaacggt gcttttcttt 720
taaattattt ttgttgtgat aatgtaatta actacaactt tacataaatt gaactgaata 780
tacgggtcat tcatttttac aaaccttatc tattctatca ataccatgac ttttttcgcg 840
aaaagtcagc cgacatgaca tgactcttat ctcttttttt tttgttaatt cttttttttgt 900 tgcgacaaat tagtgtcaaa aaacgtgaac ccattcgatc acataacatt ttgaacttca 960
agaaaatcac acaatcgata aatgatgaag tatggtaagt caaaattttc taatattcca 1020
actgattaat agttagtgtg tttgagtttt actttttcaa attaatgttt acattaaaac 1080
aactataaca atcctcaatt gaaatattgt acacgaaata aaaatcaaaa catatgtatg 1140
aacatatttc tcttatcttt ttgtattctg tcaaaggggt ctaatttttt tgaccatttt 1200
tttgtcagtt agaaccaaat aaaatcatgc cgcatgtctg tgaaaaatca ccttattctt 1260
tctctttgag attgataaaa acgttctgta ggttttccaa aatgttaact aaaaaatcaa 1320
atttaagccg tcggtatagt attacaggct aggtatagga tgctcggata atattaattt 1380
taaaaattcg aaaatgcatc atacataaaa ctttttaata caaaatatag atgttttctt 1440
tttatttatt tattaatata acgtatctat ataattttca attaagcaat aaatattttt 1500
gaagatttga ggataaaact aagcaaattc taaaactgca atgttcaatg aaattgcgtt 1560
attcagtgtt acctataaag atttttcaaa acgttactct cttattcttc tcccattcac 1620
gtgttgcact ttctgccagc cgccttctcg gagaaactag gaaatatctg tgactttctc 1680
tagccactct ctactctctc gtcagtgcaa atagagcgcg aatgctttaa aatgacgcat 1740
caatcactct gtcggtcatt tgattttaca cttttcactg atagcttaaa gctcggaagc 1800
ggaactatag tgaaacattt tataaattac gatttagatt tttttgaatt ctgtatcatg 1860
ctgcctaatt tttaataatt tgaatatttt taggc 1895

<210> SEQ ID NO 105
<211> LENGTH: 1302
<212> TYPE: DNA
<213> ORGANISM: Caenorhabditis elegans

<400> SEQUENCE: 105
tgcccagaga gccgtcgacc aattcaacgg agtcgatttc aacggaagag ctctacgcgt 60
caacttggct caaaacagaa acaactaatt ttcatatcgg tactttgtta cttgtttgat 120
ctttaatgat ctcaataata ataaacccat gaaatcgtta tcataaatat atatgctcta 180
tttttttatt tcgaatcttc atttggggtc aatctgatgg caagcgttga ggctagaagc 240
ttgaaggaac ggcttcggtt cgagcaagtt ttgaatcctg ggctatgcgc agcccaatgt 300
gagcttacaa ctgaaaattc aagtttcaac actcttcgcg gtcttatttt ggactaattc 360
ctcatatttt cagcttgaaa tggaaaaaat ctgtcgaaat cgatgctatt cgaggggcgg 420
ggccaaaacg caaccctggc acggttttta cgcaactgcc gcacgttttc tccaaggcag 480
ggtgagcgga aaaattaaac cgtcataaat tttctgctac ggcctaaaat cgtcatgtct 540
ggaatcttct ctgtttacgg ttagtttttt aataatttat tttaagtatt aaacaatcgg 600
aaactggtta aaatagccaa taaaactcga tattgtcctg aaattttggg atttttcgga 660
aaaatcgaat tcgcgaagtt ttccctaata ttttcatttg aaaaggcaat tttaagtgtt 720
tagattcaaa tttggttgcg aaatatttaa atcaattaaa attttccttt tttttagttg 780
gaaacgctcc attccagacc accgaggagg agcttggaaa cttcttcagc agcatcggac 840
aaatcaacaa cgtcaggtaa ctctcccagc cagcccgagc ttcatgattt ctaacgcaat 900
atctctttca gaatcgtctg tgatcgcgaa accggacgtc cacgtggatt cgccttcatc 960
gagttcgccg aggaaggatc cgcacagaga gccgtcgagc agatgaatgg agccgagttc 1020
aatggaagac cactccgcgt caacctcgcc aacaaataag ttgatcttca tatcgggttt 1080
ttgttacttt tttgctcttc actgatctca ttattaataa caatccaatg aaactatcga 1140
tttaattatt taattcaatt tcaactattc tctaactaat ctgttcaaca ttcggggaag 1200
tttctctatt tgtcatcctt ccatccgccg acctgattca actttcttct tccccagctg 1260
ctccgttcaa gagcctactc gactactaac ctgttgctga aa 1302

<210> SEQ ID NO 106
<211> LENGTH: 2410
<212> TYPE: DNA
<213> ORGANISM: Caenorhabditis elegans

<400> SEQUENCE: 106
tccggcaaat cggcacattt ccggaattga aaatttccgg cgaatcggca aattgccgga 60
attgaaaatt ttctgcgaat cggaaaatag tgggaaattg aaaatttccg gcgaatcggc 120
aagtttgccg gagtcgtaaa tttctggcaa ctcagcaaat tggaggaata aaacatttgc 180
agaccggaaa ttgtcgccca cccctgtttt gcactacgct ttgacaagtg tgaatttatt 240
cgcttttttt atttgcctga attttgccga taaagaagat ttccggcaaa gtggaaaatt 300
gccggaattt aaaaatttcc ggcaaatcgg caaaatgccc aatttgccgc ccacgcctgc 360
ttcacaaatt gattaattgc agcctcttcc gtagctgaac ctctggaaga agccactaca 420
acgagtgtgc cagagccaac agagtttcaa ttgtcacggg acatttatag cactgtaaag 480
ccgactgatg aggctcatag cccgccgatt caagcccaac cgaagaaaaa agccacgcca 540
agacggaaga aagcagatga cgtggaaact gtagtagctg acggaacagc gacgatcccg 600
aagccgaaga gaaaaaggcc gccgaggaag aagcctgagc cgaagccgaa tatcgttttt 660
gaaacaacgc cgaatcctcc gacagaaagc ttcgcagcca acaacaattt ccagcagttc 720

```
cagtttcaaa atcagcctgg tagttggacc tacaacaatg gattcggcaa tggatatggg    780

tacggcggtg gaaccactgg atacatggat aatcttgttg gcagagggtt tgacacggtt    840

tctcagcagc ctggatttca gaatcaaggt acatttttta aaaggaattg agaaaaatgt    900

gccaaaaaat tttaaaggtg gactacgctt tgtggggaaa ttgctttaaa atacgcctat    960

ggtaccacaa tgaccgaata tcatgattaa aaaattcaaa aatttttttct aaattttata   1020

tgattttttg aaaattggaa aaatcacagt tttcccctaa ttcctatttg aattaccgcc   1080

aattgaattt gttcgatggg gcgcgcttgc acgtttttaa atttatttat tttatttttt   1140

gttattttcc accgattttt aatgttttcg gtgtattttt gctcgaattt tagagaaaaa   1200

gtcaaaataa atgcaaattt tcgattaaaa agtgcgctta caggcgtaaa tcagtgaaat   1260

taattaattc aggttcgaaa tcgtttaaaa gcgttacttt ttcattttta cgcctgtaag   1320

cgtgcttttt aatcgaaaat ttgcatttat gttgattttt tctctaaaat tcgagcaaaa   1380

atacaccgaa aacattaaaa atcggtggaa aataacaaaa aataaaaataa ataaatttaa   1440

aaacgtgcaa gcgcgcccca tcgaacaaat tcaattggcg gtaattcaaa taggaattag   1500

gggaaaactg tgattttttc aattttcaaa aaatcatata aaatttataa attttttttt   1560

gaatttttta tcatgaaatt cggtcattgt ggtaccatag gcatgtttta aagcaatttc   1620

cccactagcg ctaccccacc tttaaaggaa ttgtgaaaat tgtgaaaaaa aaaatcaaaa   1680

tttcgaaaaa aaaagcgcta attttaacta aaatctctaa ttttggccac ttttccgtgc   1740

tgcagcgtcc gaaagtgcac tttttttgaa ttattattct tattattata cattaaaaac   1800

ccccgtactc ctccaataac gccaatatta tcgaccatct ggacgtgacc gcgtgcaacc   1860

acggcctagc tgccgccacc ccattcaaac gagacatttc ggcgggagag tccttttttt   1920

cgataattcg gatttttttg tctgtttcaa gtaattttcg ccataaaaat taccattttc   1980

ttcttcggtg ccatttctaa tgattttcca gtgcgttttg agtctgaaag tttgaaaata   2040

agagtttttg cacaaaaatg tgtgagaaaa gttcaagaaa atcgtcgaaa aattcaataa   2100

attaatttta aaatttaaaa aaaaattaat tttttttaaa aatcaattct gtgcatacac   2160

cgccacgcaa aagtgcacac aattacctac cgtagtcaat gcgaaattaa atgattttta   2220

tcgattttct tcattttcag gttacgaatt caccggtttg cctgcaaata actcgaataa   2280

tttcccattt ttgtgattta atttttcaaa tatccttatc tatgccctca ggtttatttt   2340

atctcatttc cactcgtgtt ttttgaataa aaattctttt tttttcttct agatttccgt   2400

ttatttcaga                                                          2410
```

<210> SEQ ID NO 107
<211> LENGTH: 2249
<212> TYPE: DNA
<213> ORGANISM: Caenorhabditis elegans

<400> SEQUENCE: 107

```
atttttcgaa tattttgtct gaaagtttca cgtgatgtca gagtgtctca tttcggcttg     60

atctacgtag atctacgaaa atgcgggagt tgagacgcag agttttcaac tgatttcgca    120

tggttaagaa cgtgctgacg tcacattttg ttgggcaaaa aatgcccgcg tttttgtaga    180

tcaaaccgta atgggacagc ctggcaccac gtgaaattcc agaaaaaatg tctgaaccta    240

ctgtagttca caatttaaag gcgcatacca aaaaattata gcgggaatta aatttttatt    300

taataatttt ttcagttaca gagcaattaa aaaattcaat ttcatcaaaa ttttatagac    360

caattttctc gctttatagc tgagctccgc gagccaaaat aggaagggga gcacgaaaaa    420
```

aaaacagaaa aatgagctcg acagagccca tagcctcaag cgctaacgaa ccaaaaaatg 480
cacacacaca caggaggcgg agtcgtggaa atttcgaaaa aaaaaacaag attttcttct 540
ctctcggctc aaatttgaat gcggagcaag aatattacgg gaacaaaaaa ttctgagaat 600
gcgtactgca caacatattt gacgcgcaaa atatctcgtt gcgaaaagca aactacagtg 660
attctttaaa tgacatttgt agtgtcgatt tacgggatct cgattttcga aatgaattca 720
tttatcattg atcgagcccg taaatcgaca cacgcactac agtagtaatt taaagggtta 780
ctgtagtttt gttttcgcta cgagatattt tgtgcgtcaa atatgttgcc caatacgcat 840
tctcaggatt ttttgttagc gtaataaaat aacagaaaac acagaaaaag gcatgaaatt 900
taatttgaaa taccgcgctg agttttctag gccacgtgtc gtgtactccc cgtggacaag 960
cggtttttgc cttatttttc tgaagtacaa attctcaagt acaagtaaaa aagtacaaat 1020
tttaccaaat ttgaggaaaa gaactagcat gacaaaaata gaattagaaa aattctagag 1080
aaaaactacg gatttctggc ttccctcata aaatgaaatg gaagagtttg ccgaactagg 1140
ccattttggc tcagccatat ctggagtaga tttacggcgc gttccgtgtc gcggctcgat 1200
tttagttgta aaactaaatg aatttgtccg tgtggagtac acgactttac cacgcgttgt 1260
ccggcaggcg attgtcaatg gagcgcgaaa aattcaatgc accagatttg acgcgcaaaa 1320
tttgaatttt caagttgtaa atccctttttt tcttcccatt gtcccatcaa atatccttct 1380
tcaaaaaaac ccctgcgtct ctcaggccat atctgcggta gatttacggc gcgttgcgtg 1440
tcgcgtcgcg gctcgatttt agttgtctgg cgggcgatta tcaatgaagc gcgaataaat 1500
caatgaggaa ggccagaacc ccgtgaagat ccaagaaaag ttttctaggc cacgttccgt 1560
gtactccacg tggaaaatgt cctttccggc aggagattgt caatggagcg cgaaaaattc 1620
aatgcaccag atttgaccac gcgtcgtgta ctccacgtgg aaaatgtgga cactagggat 1680
ctactaaatg cctggaaaat cgtaaaaatc tcgaaacttc ctaaagaaaa aaaaagcaaa 1740
tacacaaaaa cgcattgatg tatgaacaaa ttgccctccc cgtctcccac caaaaactcc 1800
caaaaattgc tcttttttca tgtttatatg ggggaccgcg ggatttcata atagctccgt 1860
ggtccgctca gctcatccgg agccaaaaag agcacacaca cacacgcaca cataaaagtt 1920
gtaaactagt ttcgagcaaa aatgatacga cggatgagtg tgtcacgcaa tcagtgagct 1980
tctctcgctt tcgaaagaaa aatctttttc gcaaaaagaa aaagtacttt acactggcca 2040
cagtgtaaaa taagggtgaa aagatcgaaa atcggaggtt tcaaatttga atttccgcgc 2100
aaatgagagg gacgaggtgc gatggcctac aaaactccgc aggtgtactc ctctcggaaa 2160
acggtgcgag aattaatttt ttaatttata tttaattttc agcgattttt ctcagttttc 2220
cggttaaaat ttaaattttt tcaggaaaa 2249

<210> SEQ ID NO 108
<211> LENGTH: 1234
<212> TYPE: DNA
<213> ORGANISM: Caenorhabditis elegans

<400> SEQUENCE: 108
aaactgcaat ttcgtaaacg attgaaaatt gagaaagatc aggtatctga acaaaaactt 60
gtacatttga aatctcaact tcatttattc caggatacct acaaatatga atcctatgtg 120
cttcaatgaa ttctacagga aaatattcaa taaatgacca aatcgaaaaa ctttatttat 180
gatcccaatt atgttttctt tgattatgct acaaattcaa gaatcggcaa ataatgggaa 240
aatacgattt ttttttcaca atcaatatat actgcttgat ctctctgtta gaatttcctc 300
caaaatctga actgtatgac caaaaatcaa tttttttgaa aatgcatttg tcccaatatt 360
tcctttctac cattctgctt tgatcttttt taacctttttt attcgaataa aaatatattc 420
cgaattaaat acaattaatg tgtttccacc aactttacac ataaaaattc attttctgat 480
gtaaagattt tttctaacat acatgcatta acttatttct ggagaaatat ttctctggtt 540
taaaaaaaaa aacttctatt tagttatgat ttttcctttt cacaacgtga aaagttgcaa 600
aacttctgcg aacgacgcca cttctccacg gtgttgtttc tccggaacat ttttccccag 660
tgggacgcca cgcgcaactg cgctctactg ccaattttca aaaacggaat tctttcgctg 720
aaattttctt taattttctt tcgtttttca acgtttttca ttctctaaac ttaaataatc 780
gaaatatttc gaaatgatta atgaagaaag gtaggcgtta taatatttat aatcaaaatt 840
tctcaatatc atgttagata ttcatttttg gcgaatattc aacaattgaa aatcaaaata 900
ccattattta tcgactggcg ttatttttat tgtttcagaa aagctgaaat aaagcgaatg 960
ttggaaaaat gccgtaaaac ggaaaaccga cagaaatttt ggcgatggtt gcccaatttt 1020
cagttgaaca gctggcagac tcctgttgtc attggtgttg cagctgtttc tgctgcaatt 1080
atctatcact atttttccta attaccctta ttcctattgt tcaatttttc ttcatcctga 1140
ttttgtgatc tacctcatgt aataattttc tcttcttctt tattattttc tgcgctctgt 1200
actttcttaa aactgtataa attaaaattg caga 1234

<210> SEQ ID NO 109
<211> LENGTH: 435
<212> TYPE: DNA
<213> ORGANISM: Caenorhabditis elegans

<400> SEQUENCE: 109
cccacacagc cagaagattt ttatgggcgg cagacatttt cttaaatcca ataatgtttt 60
aatttgataa aatcgaagat aaaagttcac gataaacaca agtgaagtta aaaaataaaa 120
ataaaacatt caaaaaagaa ataaacgcat tctccgtaaa tcgacacaat gacaattctg 180
gcaggtctcg ccacgaagag tgttcaaatc atgtgcgcct ttaagacgcc aagccatttt 240
ctcttctgtt ttttaccact tattttgttc ttcaaaatgg tttttttgtt ttgttctttt 300
attaataatc aaatgtttgt ttattttata catatatact gcttgttttg cattaatatc 360
aatctgttat cgatatttat ttctttttct ttcaatacat gactctattc gtaacatttc 420
acaatttttt gcagg 435

<210> SEQ ID NO 110
<211> LENGTH: 1559
<212> TYPE: DNA
<213> ORGANISM: Caenorhabditis elegans

<400> SEQUENCE: 110
gaacgtccga catgatgaga tgcaataacc tgaaaatgag gcactttatg ataagaaaat 60
gcggtaaaac atgcgaaata tggcaccata aaccgtgagc aggacaaaga acaaacactt 120
ggaaaagaaa agaaaataga aagaaaaaaa ggaaaactgg agaaaacaaa ctcaataaca 180
caacgcgaga aatacaattt cgtttcgttt tttcttctat ttattagatt tctcacaatt 240
tgttaccagt aaagtcacgt tctatatttc aaactactcc taaaattcgg tttgaacagt 300
tctctgataa acgaatttcg aagaacgatc agaaaacaaa tctacggttg tgtgtgatca 360
atggggtcaa acggtggacg aaaggggacg gcggagagag gaaaaagtga gagaaaataa 420
ataaaattga ccttcgagtg cagagttttg ctggtatttt ggtcagaatt gattatgaaa 480
atctgaaaat taccgccggg aaagttgaaa atttgacgtg gaaacgttta aaaaaataag 540
atgagaaagt tagtactgta gatgtcgtcg gatcaagtgc acagtacgca agcaccgtta 600
cgaaaaattg cactaattgc tcaattaaat ttttttaaaa aattaatttt tatagtgtgt 660
tttgtgtttt ttttctgctt ttttaatgat ttttaaaggc ttgattatgt ttttttctca 720
aaatttgaat aatcaataac attaattaat tactttatta aaaaaccaca tttggcattt 780
taataaagca agttatcgcg acaaacggca aaaatgtctc tttttataaa aattgttttt 840
ttttgagtta agagaagatg tggagttttt tgaactacat tagttttcta aaaattttat 900
catctagatt ttgaggaaaa aagcagatta tatatcttta atcttggttt taaaattttt 960
ttaaaaagca gaatattaaa gtaaaatatt ataaaaagaa aaattcgtgt ttgcaaaatt 1020
tgtttgaacg gaaccttgca aaaatgatat ttagcagcta aactaactga aaactactgc 1080
ataaagcttt cccaaaaaga gctaccatcc agaaaatgtt tttttttttca aagccgaaaa 1140 agaagaaaaa aagatagaaa accgaaaaag cagcatcgtt ttcgcgcact ctttcttctt 1200
tttttctttc tttttctaaa aaaaaatatt ctccgtagct tgaagtctca ggatttccaa 1260
agggaatttc cttgatagaa tatggaaaaa caagagagtc atcagagaag ggagaggaaa 1320
agcggggatg ctggcgaaga ccgggggcac cgactgaaat ataggcaccg gcggggaggc 1380
ggggcgctct ctcctctccg ctttactccg ccccgattgt cagtggagca ggtttgcaat 1440
gagtgttctc tgatgccccc tcagcgcggg agttttgaaa tcaaatattt tgtattttaa 1500
cctactttat tgatttttca attaaaatga aatgttattt gtttaaaatt taatttcag 1559

<210> SEQ ID NO 111
<211> LENGTH: 1476
<212> TYPE: DNA
<213> ORGANISM: Caenorhabditis elegans

<400> SEQUENCE: 111
tgtaggtcta aaaatatttg tttgagaata aatattcgaa atcaatctaa cgtttttcca 60
atctacaggt ggcacgacac gctcacaacc aataagtttc ttgccacgct cgtcgatttt 120
ttgtagaatt cccatttctg agagtgtttc ttcgctttct gcttgctctg gaacttctga 180
aataactttc ccgcgattat ttggatttct atatattttc aaactactta cctattttcg 240
ttttccaaag tctcgaattg tgtacttgtc gacgttggtt ccagatttga gcattatgaa 300
gaattccaat tttaaaatca caaactggct caaaatctat acgctcgaat agagaattgt 360
gtgatgtaag agcctgaaaa ttatatttga ttttctttcc atcttttttt attttcggga 420
ataataaaac attcaaaaag ggctgagatc tatctatttt tcacatgcga cccatttcta 480
tttcacgtga agcacatgat tctgaagggc aatggaaatg aaaacccgga aaaacaaaat 540
ctttcagttt aaattgtatc aaaacaagtt tttctagatt acaaatgtac ctgaatagtg 600
atccatgaat tgggacagac cacatcgaaa taacatttca cacgtggcaa tggagccatt 660
ttgaagtttg gctgaaatta aatttatgtc gagaaattaa aaaaaatcag agcgtcatca 720
tgagaaaata ggaaaggttt agactgtaaa atcaggtttt catggcggga atgacattaa 780
aatggtgata aggtgattat tttatcaaaa gaattttttg aatgattgca cctaaaatcg 840
agtgcttttt ctttaatttg attatcaaaa gaaaataccc aagaaatgga aaatgaaaat 900
ttaagagatg aaaggaaaaa gcgacccgga aaaacatcaa gctgggaaga aatctcaact 960
agttagacca aagcttcgaa ctctgcgagc atgtattttt tttcctcact ttctcctttt 1020
cttctctatt tctctagatc tttattactg cgggggcaaa aagagtaaga gatagaaaag 1080
aatgacgcaa aaaatacacg gatttaatat ttgctttgct tttttattca gagaggaaag 1140
gtcaattggg ggtttcccct cgttttatga atgaaaaccg cacataaata taattatttc 1200
cacagtttta aacggcagaa acggttcgtg ttataatttg tgagataatt gattttgcat 1260
tacgaaatta gaagaaaagg cggaaataaa taaattagtg tcgcaatttt tttctcaaaa 1320
aggaaataat gcaattacgc tccaccggac agtaaaattc tcagtttatt tgaaaaacaa 1380
aaatttaatt ttttcccttt ttttcaattg aaatctcaaa tttctgaact caaaatgaaa 1440
ttttcagact ttaccagaat attgtgacat cgaccg 1476

<210> SEQ ID NO 112
<211> LENGTH: 1697
<212> TYPE: DNA
<213> ORGANISM: Caenorhabditis elegans

<400> SEQUENCE: 112
atcgcagaaa tgtgaaatca taaaatccat agtgagattg agttgtttat tattttatga 60
aatgagataa tcagttggat aactactgct cacgccgtat tcgatctatc attcgattct 120
ccgattctgg aacatcaaat tttaatcata gggagagagg ttcgggtact tgagaaaaaa 180
atgtcgtgtt tcgagaggtt ttgaaaagtc agttgttaac tggttcggtc aacatgtaga 240
gattgtagag aaatatgaga acttagagaa ttgacgtatg aagagaaaaa agtgggaaag 300
gggagccgct gttgttttcg aaagaagaaa ataagacaga aaaaatcgga gaggaacata 360
acaacaagtt aagttgactt ttgaactgga aatttgtcaa tattgaaaaa aggaacagtg 420
agaaatatcg atttccacgt cgctcgattc tatgaaaaga aattatgcac acacaagctt 480
cacagtgagc atgctgaatg attgagcaaa tacatgagag aataagagag gaatgagatg 540
aaaagaagcg ttcaaatcaa aagaaaccag acaaaatggc gattttttac gggaatatga 600
acctactgat tggcagtgga cagctggaag aataagaaga tactgaagga aggttgaagt 660
tgaagcttgg aagacagatg atgagagaga ggaaaacctg tttctttttg attacgatcg 720
gacggaaatg agaaggaagt aagtgttttc acacgtaggt gggcattgag atctttgaag 780
gtgcattcga caggttaata atcattctaa ataccaggtg acaatggagg atacttttaa 840
acagtaaata tattggaata aaacataaaa gttagtctta ctcagaattt ctaaaatttc 900
agccttctgg aacgaaaggt aaaatcataa taataataca agtggggctg ttagtagccc 960
taaatacaag taaaatgacc gaacacagcc gttaaagaat gttgcagaaa attgcgaaat 1020
atttccttac tcttaagaac aacattcgat gtgacgcaat atgatgcatt tccttagaca 1080
aaaacgttca gttcaaaata aacaacaata aaaccgtttg tacgatttct agaatacgag 1140
tttatcagtt gttcggaaaa tatcttatca atcgtttgac tgatgttttt taaccatgtg 1200
agaatttgaa aaaaaatttc atgattgcca aaaattaaaa taaacaggaa gcttttaccg 1260
agttttcgtg attttcagaa tgaagaaatt aatatgaagc tcaaaatcaa aagcagaggg 1320
aaaagaaaaa atcgaaatct tctttcggtt aaacaacacg cgcttgcgga acttcggagc 1380
atcgtatttt gtttttgcgc tctatttttg aatcggaaac tgttttttttg tcagttttcg 1440 aaattgtttt ttttctgttt ttttacttca tgcaagagtt taactttacg caaaaattaa 1500
ttaaaaatac gcagaaggcc cactttacac aggaattaat tgaaaatact caggaatttc 1560
actttactta gtccttttttc cagagtttcc aacggaatca atatattaat ttaatttcgc 1620
aacatttttc tttgaataaa cctatttgca aatgagaatg tttcagatat ttgcttatcg 1680
aagcctggga attgctt 1697

<210> SEQ ID NO 113
<211> LENGTH: 849
<212> TYPE: DNA
<213> ORGANISM: Caenorhabditis elegans

<400> SEQUENCE: 113
gcgtaaattg gtttctataa attcttgaca aactcattcc gaacggctga aaatattgat 60
tgaactgaat tcacattatt cattaaaaaa aataggttag cctgttatgt agagaaattt 120
agtgaataaa aaactgaata tgtatttatt taatagattt ctcggcacac aggaattagg 180
aataactccc aaaaaataga tatttggcag gagggccgaa cagctgtgtt ttccgtgacg 240
tcatacaggt caatggacac aggatgtagt catattacgg gaacacacaa ttctgagaat 300
gcgcactggg gcatttgatt tgacgcgcaa tatctcttag cgaaaactat ttacagtaag 360
aatttaaatt ctaccgtagc gggctcaatt ttcgaaaata tattttctta tcgaattttg 420
agagcagttt ttcagttttc catgcttgat tttattattt tatctttaaa taaatttttt 480
tcattgaaaa aacgggaaaa acaccgggag aaattgatct ggtgagaaaa ttataatatt 540
tctgctgttt tcctgttgac aactttagaa atgtcaatta aacaactata ttttaaaata 600
atcatttatt tttttaatta cgtcaactag aaaacattaa ctttttgcga aaattcactt 660
ctaccacact catcatcccg aaaacagcga ggtctcatga aattgcaagc gcgctctact 720
gcaaggaaag gcagcgcgcg aagcaaattt tcaaacaatt ttttgaacgt tttaccgcat 780
tttctcactt tctcgcttaa ttttgctatg ttttttgcga tttttttgta atttttcttc 840
gtttttcag 849

<210> SEQ ID NO 114
<211> LENGTH: 828
<212> TYPE: DNA
<213> ORGANISM: Caenorhabditis elegans

<400> SEQUENCE: 114
tcactaaaca aaaaacatat atttgtaaaa taccattttt cttttcatca acagcttcaa 60
aactatctga agtgctggat tttcgttcag ctccgtcgat cagctcgaag tcttgctcct 120
gttctggagt atcgctcatt ctggaaagat ttaaatacaa ccgaggaacc agaagagcgc 180
atgaaaatat agagcgtgta atttaacgtc agttattgac agagaaaata gaattacgaa 240
agaccaaatc gggcaacgag gaaaacgttt aacacaaaca caacactgaa aataagcaag 300
aaaaggagga agttatcgga aaaccgaaga actttcaact tcggaaagaa ccgtttaatt 360
tatgtttaaa atcaaacaaa aaattcccga aacatccctt ttaaactttg attttcacga 420
aaaacaacga atgaccgaaa aatgtgatca atctctgaga gtgtgcactt ttgcgtgacg 480
gtgaactgtc cgcgtgcacc agattcgacg cgcaaaataa tcggcgcgag gttcgaacga 540
acgttcgtga atttgtggga gcggttttta atgtttaaaa atcagttttg gtttatttta 600
tttgaaaaaa aaaacgataa aagctatatt ccagcagtat ctaaaatgat cttcttttaa 660
tattctaatt ttaatgtttt aaaattcatt tttcgctgca gcaaaaagtt ggtgtttgcg 720
tacaaaaccc gcgccagtct tgaaaaacgc acgcattatt tattcacatg tttcgcaata 780
tttccatatg aacttctcaa catcaccaat ttaaattaag ttacagga 828

<210> SEQ ID NO 115
<211> LENGTH: 222
<212> TYPE: DNA
<213> ORGANISM: Caenorhabditis elegans

<400> SEQUENCE: 115
cttgtttcat actaaaaact ctgatttcag actgaaaaac atgttttttt cagcgaagaa 60
aactaaaatt tgtttgtggc cgcggtggcc tagttttcac ggccgagaaa tgtcacatgt 120
tttggcgcgc tcttcggcga attcaaataa actttttttgt ttttaacaat ttctaacttt 180
atttttgtgt ttttagaact gaaattccat ttttcaggag aa 222

<210> SEQ ID NO 116
<211> LENGTH: 222
<212> TYPE: DNA
<213> ORGANISM: Caenorhabditis elegans

<400> SEQUENCE: 116
ttctcctgaa aaatggaatt tcagttctaa aaacacaaaa ataaagttag aaattgttaa 60
aaacaaaaaa gtttatttga attcgccgaa gagcgcgcca aaacatgtga catttctcgg 120
ccgtgaaaac taggccaccg cggccacaaa caaattttag ttttcttcgc tgaaaaaaac 180
atgtttttca gtctgaaatc agagttttta gtatgaaaca ag 222

<210> SEQ ID NO 117
<211> LENGTH: 633
<212> TYPE: DNA
<213> ORGANISM: Caenorhabditis elegans

<400> SEQUENCE: 117
ctcttctttt actaatccat caagcgactt ttcacggagt aatctgaatt aataatattt 60
atcagtgcat atctctgaaa actaacttga cgacaaatgc ttcgacatca aaatccggct 120
ttgtgacgtc caaaacacta gacattttac attcaatact gaaaaattaa agaaaattca 180
ggaaaactcg agaatgaaaa aaaacagatt tgagacacca tcaatacaaa gggaacgaaa 240
tttgggggaa atgctggttg ccgaaaaaat aagtagaagg taagatgtgt tcaactggaa 300
catacatttt ctgaattgca aactcgattt ctctcacatt cacaattttt aatcacattt 360
aatgcttcag ttttagaaag ttctgaagta tcctcttctt cctattcagt ttctcaaaat 420
cgatggtgtc tccaggacgt gcacaaatgc gctctattgc gaattgtgga acatcattgc 480
gcgcgcgact agaaaaaaat gagcgcgttc ttgaaaatta ttttgctttc tctaatttta 540
aacgatttcg attacatttt atctgaactt tcttgggttt aatcgaataa aaaacacaaa 600
aatattcttc agactggtaa aaacttcttc aat 633

<210> SEQ ID NO 118
<211> LENGTH: 898
<212> TYPE: DNA
<213> ORGANISM: Caenorhabditis elegans

<400> SEQUENCE: 118
gtctagtttc aaaaaaaatt aaattaaatt aaattgtgta atatgtggca ttatttatat 60 actttttttgt cgatcatctg ttaagttagt ttttagtctt atcttcttgt cgcacaaaac 120
attatggttt gtgtttaata gaacaagaaa gtgggtgaca agaatcgtat gatttggaga 180
aacccagcaa tcaagaagat tttgtttcaa aattcgtagt ctggatactt tagaatgtat 240
tctcaatttt cgaataaagt ttagaggatg ttttttcaaa cttttatcaa tttttgaaaa 300

```
ctatctgatg gttttataat tattacagtc acatatttgt agcttgtgaa tctaaaccta    360

ttatgtatat tctcgtttta aaaaaattaa ttgccgaaaa aaagcaaaaa attttaatct    420

tacgaaaaaa agtttttttt ttggatttat cagcttcagt gctcattttc atccctaact    480

ttctttcaag aaattttaga tatgaagaac aattttaaaa ttctagatca accaaatctc    540

tgaaacaaaa ctagttttct attgtttcta catattgata ttttttttaa actccattat    600

catttttaat tttttaaaaa gttttctaac taccatctgc tctccatcac ctctttatgt    660

tttttgcatt tgagcagtga aaagtttgaa gaatattggt acaactttta taccttccaa    720

aaagtgcttg ccccattctc tatgttctct tatcagtaca ctatatctca acagtcgaca    780

catttgtgtg gaaaagtgtt gtttgtgtct gactgttgtt tctaccaccg atactattta    840

taaggtggtc taccgaaaaa catcaatacg tttctttttt attcctgaaa ataaaaac      898
```

<210> SEQ ID NO 119
<211> LENGTH: 898
<212> TYPE: DNA
<213> ORGANISM: Caenorhabditis elegans

<400> SEQUENCE: 119

```
gtttttattt tcaggaataa aaaagaaacg tattgatgtt tttcggtaga ccaccttata     60

aatagtatcg gtggtagaaa caacagtcag acacaaacaa cacttttcca cacaaatgtg    120

tcgactgttg agatatagtg tactgataag agaacataga gaatggggca agcacttttt    180

ggaaggtata aaagttgtac caatattctt caaacttttc actgctcaaa tgcaaaaaac    240

ataaagaggt gatggagagc agatggtagt tagaaaactt tttaaaaaat taaaaatgat    300

aatggagttt aaaaaaaata tcaatatgta gaaacaatag aaaactagtt ttgtttcaga    360

gatttggttg atctagaatt ttaaaattgt tcttcatatc taaaatttct tgaaagaaag    420

ttagggatga aaatgagcac tgaagctgat aaatccaaaa aaaaaacttt ttttcgtaag    480

attaaaattt tttgcttttt ttcggcaatt aattttttta aaacgagaat atacataata    540

ggtttagatt cacaagctac aaatatgtga ctgtaataat tataaaacca tcagatagtt    600

ttcaaaaatt gataaaagtt tgaaaaaaca tcctctaaac tttattcgaa aattgagaat    660

acattctaaa gtatccagac tacgaatttt gaaacaaaat cttcttgatt gctgggtttc    720

tccaaatcat acgattcttg tcacccactt tcttgttcta ttaaacacaa accataatgt    780

tttgtgcgac aagaagataa gactaaaaac taacttaaca gatgatcgac aaaaaagtat    840

ataaataatg ccacatatta cacaatttaa tttaatttaa tttttttga aactagac      898
```

<210> SEQ ID NO 120
<211> LENGTH: 890
<212> TYPE: DNA
<213> ORGANISM: Caenorhabditis elegans

<400> SEQUENCE: 120

```
gaatcttcga tgttcattgt gaattttgta tcactgcctt gcctttattc acttcaggaa     60

ttttatgttt tacttgtaat ctcaataaaa atgaactttc aaattaataa taacaaacta    120

attttctagt tttacatcag atatctgctg agcttctgct cctcttccgt caaaattaaa    180

tcaaattggc tgagcagcgg cccagtcaac tagcgaagtt aggacatagg ttttcttttt    240

tttttttgtt gaaatgggca aattgccgga attgaaattt ctggcaaatt ggcaaattgc    300

cggaattgaa catttgccca aatctgcaaa ttgccggaat tgaaatttct ggcaaatggg    360
```

caaatcgcca gaattgaaat ttccgccaaa ttgtgatttt gcactttttt ctggaaattt 420
cagaatttca atttcaatcg gcaaatttgt acgcatccta ttttgaaaag taagcaaatt 480
ctatgaaaat atctaaagaa aacgggaaaa aaactcaaaa agacactgtt tttagtgttt 540
ccgttttata aaaaatgcct ctaaacattt ccgacaaatt tgatgatccg gcaaacgaca 600
caccggcaat ttgccgacga aaaaagttgc caaacggcaa ttgttactgg atcttatagt 660
gatcaaattt tggaaaactc aagtacagtc agaaaagcag tcagaaccca gggtctatta 720
aaacatcttt tacacattga aaagttacat atacttgaaa aaaggagaca tagagaaaaa 780
ctcagatact gtctctgaca atttttctgc tttgtgccac tgaatggtaa acaagctgaa 840
aggtataaaa actattgcaa tttttgacag aatggtattt gaaatcaagg 890

<210> SEQ ID NO 121
<211> LENGTH: 1116
<212> TYPE: DNA
<213> ORGANISM: Caenorhabditis elegans

<400> SEQUENCE: 121
atgtaacccc aataattttt ttttgttgca ttttactact tatatccgtt tccatttttt 60
aattttatgt tgtcacgttt tgtctaaata gtgtaatctt cttgtactaa ttattccaat 120
tattttaacc cgtaagcgat aaatgaaaca acactttttg gtttttattt gctaatttta 180
aataaattgt catcaattct gaaaaataat aaattttaaa aaaataccga agaggcaaac 240
aagacatttt ggaaattctg atccggataa atattccgtt agatttttat tagactcgaa 300
attgcctgaa acccccgatt ttataacgaa acctcttgaa aacttctcaa aaaagagaag 360
ttaccaaact ttaccaaatt tggtctccca tcgaccttca atgtacctaa ctctagttga 420
atacgcaaga taattaattg ctacaaccaa aattaaacgg cggtttcaaa aaaatattgt 480
tttcagccgc tgcaacattg acaagtggga aaaatttcaa attttaacta attttaggtc 540
attttttgag ccgccataac ttttttttgag aagttttcaa gatattttat tttgaagttc 600
ggagttttca gacaacttcg agtcaaataa aaatattttt taagtcgacg acaccacctc 660
ggagataatc tttaaaaaaa tcttttcaga aatgcaaaaa ttccaataag tgtcaaaact 720
cccgagtagc gcttaagcag tggcacgtct gtatttatgt atttttgttt ttttttttta 780
ctttattatt ttgtgcttta ttactgtttt ttttttaaat ttattttgtt tcatgaaatt 840
ttaggactaa cgtgaaactc aacataaaaa agctagaaaa gtttcgcgta ctgtattcta 900
tttttctttg attttattaa tgtaatacat cacttttata tcttgagtga ctaaactctt 960
gttaagtgtg tttcaataat gttttgattt tttgacttta cttatacgtg ctttgtagtt 1020
ttagtgacat tagtgaccga aagtgagacg ataacaaatt gggagcggta tataagtgaa 1080
ctacgaaact tctaaaaaaa caaaggctgt ttcaca 1116

<210> SEQ ID NO 122
<211> LENGTH: 1807
<212> TYPE: DNA
<213> ORGANISM: Caenorhabditis elegans

<400> SEQUENCE: 122
tgtgggaaaa gttggaggtt tttgcacatt ttaggtgagc gaatatcccg ttgaaattat 60
agaaattacc gattgccgga cagttttgga aattgtcaaa tccatctatt tttcgaaaaa 120
ttaatagaaa actacattgg ttttcagtat ttgataagtc tacgagacaa aaatgtctac 180
gagacaaatg tacacaaatt atcaaattta cacttccggc aattctgatt ttcggaaatt 240

```
gtccattccg gcaattttgc aaaatttgaa attttataaa aataattctc tacctgcctg    300
cctacaggca tgccgcaact aaccttgaaa actttaaaag aaactccgaa tttcttaaaa    360
ttttaagtcg gctggaaact tagaaatctc ttgccaagat aaaaaacatc gagaacatcg    420
taatcaattt tatttgattt gatacgttca caaagtgaaa ttccaatatt gaaaatcaaa    480
ttcaattaat caattaagag ttcagtgagt cgtccttgaa atgtaccaat ttcacttgag    540
cgctcagaat ttcgttcaaa atcatcaatt tctcgtccaa aaatcgatga aattttgcga    600
gtaggtacaa gtttgtgctg gaaattaatt tattggttgt atggatattt ttttttaatt    660
taagaattaa aaatttacca tgaaaataaa gtatgaaata ttacaactat cagggtaaac    720
caagcaacgc gagatccagt caaactgtac acgactaaac tttaaatagc aatactaatc    780
taaaaagcaa atatttttct ttaagtagaa gcaaggcaga agtttgacat tttttccgac    840
cagttgaatt gtgattctat atacatctgg ttcactcgaa tttcagacaa acaactccac    900
attcctcaat ttctgtgata gaacaataac ttattttctt cacatttctc tttcaattat    960
gcattttcat tctttaagtg tcttttttta aaatttgaca ccatttgccc gcgactcgtt   1020
gtccggaggt ttcctcttac ctcggagaaa ttccgctaaa tctaccatgc atgagtctca   1080
ccacgtggac aacgagttac tgtaacttgt gtcaatttac gggccgctat cctttttttta  1140
aatgatatgt accaattgat acaaagaaat acttgttttg ttatcaaaat agagtataaa   1200
atataaatga aataattcaa aaattattct caattgggcc agatacaata ggatagtggg   1260
gaagttcaag gatgatattg tgtcagacaa ggagcaaaaa tgcattaggc cagtttttac   1320
agaattcatt ccaagtacag aatttttcaa acattccatt aggaaatggt gaagaaaacc   1380
aatacatttc aacttccaaa tttttgaaat ggatttaaag cttccctata aaatttgttt   1440
atgaaaataa ttttaacgat ttcatttaca atcaccacat tttttagaat tctcagcaca   1500
ggttgaattg ttcagtacct tttttcaaca tctagttcac ctacatatga gttcttaatt   1560
taattacgtt ttttgaaaag taaatatgtt atttggcaag tccattcaaa caaaagacgt   1620
cgaccactta taatcaaaaa gtacacttgc ggcagacatc tcgatacttg ttttctctgc   1680
ctgttgtcac tgatcttatc gatatgtaat attgtgaaat gttgcgcagt gttgaaaaat   1740
aagatataaa attaggaaag aattgtataa aaatcagaca aaactattct gtccaacaaa   1800
gatcatt                                                             1807
```

```
<210> SEQ ID NO 123
<211> LENGTH: 1546
<212> TYPE: DNA
<213> ORGANISM: Caenorhabditis elegans

<400> SEQUENCE: 123

gatgagatgc aataacctga aaatgaggca ctttatgata agaaaatgcg gtaaaacatg     60
cgaaatatgg caccataaac cgtgagcagg acaaagaaca aacacttgga aaagaaaaga    120
aaatagaaag aaaaaaagga aaactggaga aaacaaactc aataacacaa cgcgagaaat    180
acaatttcgt ttcgtttttt cttctattta ttagatttct cacaatttgt taccagtaaa    240
gtcacgttct atatttcaaa ctactcctaa aattcggttt gaacagttct ctgataaacg    300
aatttcgaag aacgatcaga aaacaaatct acggttgtgt gtgatcaatg gggtcaaacg    360
gtggacgaaa ggggacggcg gagagaggaa aaagtgagag aaaataaata aaattgacct    420
tcgagtgcag agttttgctg gtattttggt cagaattgat tatgaaaatc tgaaaattac    480
```

```
cgccgggaaa gttgaaaatt tgacgtggaa acgtttaaaa aaataagatg agaaagttag    540
tactgtagat gtcgtcggat caagtgcaca gtacgcaagc accgttacga aaaattgcac    600
taattgctca attaaatttt tttaaaaaat taatttttat agtgtgtttt gtgttttttt    660
tctgcttttt taatgatttt taaaggcttg attatgtttt tttctcaaaa tttgaataat    720
caataacatt aattaattac tttattaaaa aaccacattt ggcattttaa taaagcaagt    780
tatcgcgaca aacggcaaaa atgtctcttt ttataaaaat tgtttttttt tgagttaaga    840
gaagatgtgg agtttttga actacattag ttttctaaaa attttatcat ctagattttg    900
aggaaaaaag cagattatat atctttaatc ttggttttaa aattttttta aaaagcagaa    960
tattaaagta aaatattata aaaagaaaaa ttcgtgtttg caaaatttgt ttgaacggaa   1020
ccttgcaaaa atgatattta gcagctaaac taactgaaaa ctactgcata aagctttccc   1080
aaaaagagct accatccaga aaatgttttt tttttcaaag ccgaaaaaga agaaaaaaag   1140
atagaaaacc gaaaaagcag catcgttttc gcgcactctt tcttcttttt ttctttcttt   1200
ttctaaaaaa aaatattctc cgtagcttga agtctcagga tttccaaagg gaatttcctt   1260
gatagaatat ggaaaaacaa gagagtcatc agagaaggga gaggaaaagc ggggatgctg   1320
gcgaagaccg ggggcaccga ctgaaatata ggcaccggcg gggaggcggg gcgctctctc   1380
ctctccgctt tactccgccc cgattgtcag tggagcaggt ttgcaatgag tgttctctga   1440
tgccccctca gcgcgggagt tttgaaatca aatattttgt attttaacct actttattga   1500
tttttcaatt aaaatgaaat gttatttgtt taaaatttaa tttcag                  1546
```

<210> SEQ ID NO 124
<211> LENGTH: 1375
<212> TYPE: DNA
<213> ORGANISM: Caenorhabditis elegans

<400> SEQUENCE: 124

```
accatgtacc caatttctcc agatgtctca aaaagtcctt cttcttgtta atatagctcg     60
cctcctcaaa ttttgatctt ccaattcctc tccgcccaat atattctagt ccgtgtctta    120
ccccttgaca aaaatgagct tttctcagat tccgactaat tccaaaaaaa ttccctacgt    180
tttgaataat tgtcgctttg tatttttttt tctcgttttc atacgggtgt tcatcattca    240
ttttactttt ttaaaaaattt tcctctcgtt tcttttgaac gtcccatttt tattgcaatc    300
gttcattgtc tagggtctat ccttctaatc attcttcttc tcagaaatat cacaaaccgt    360
ctgtgttgca ttcaaatttt taagtaaaaa taataaacta aagaaccaca atgaaggtct    420
aagttggcaa aattgaaaag ccgaaagctt ttcccggaat aatagtaatt actggagtgc    480
atcccgaact gtctaaaagt agagaaaaga ttaagtggat atatattttt tatatttttt    540
aatatagtaa tctgtttgaa ctgttataca aaccgaaatc gtgttagttt ggacaaagtt    600
ttgcatcaaa tttttttga gttttagatc gaactattgt gtttttaatg taccagtcaa    660
tatttggcat tcacaagcgg tatagccaaa tgtacccaga gttgatcaga tagcgttttt    720
cttcactgtg ttccgttgtt atcaaataaa ttatgcaaaa actgcgaaaa tttgagttca    780
aacattaaaa aaaatcatat ttttctaggt tattgcgagt ttttagcaag aacaactaat    840
gttttcatgt ttaaacaaaa aaactgagtg agtgagaaaa aatctcatgt atgccatggg    900
atcaagccat atattttcca tagactaaaa ttatttagag atggaaaatt gaaaacagga    960
gacgggttac tgtaggaaga tttttttaag actattgcaa atacataaat cttttgaata   1020
tattttactt cttcgaccgc cgctttgaaa cagtgcgtta ctgtgaacgt tgaaaaccaa   1080
```

acatttgaac tcttcacctc acttgtccat tttgttaatt gtctagccaa ctgtagccac 1140
ctttgatcag gtagaccttt tccaatctgc gtctctcatt ctctcaaatt cacttagcca 1200
tgttttgtac ggacatcatt tctgatacat taactacgat aatagttgtg cacgctgtgg 1260
tcatttgatt aacttttttt cctgttgcag cagttcgcga gtatataacc tgtctttaac 1320
tgataaatcg tttgcattgg tcgtttgaag gaaacaacaa tacgctttcc aaaaa 1375

<210> SEQ ID NO 125
<211> LENGTH: 1350
<212> TYPE: DNA
<213> ORGANISM: Caenorhabditis elegans

<400> SEQUENCE: 125
tacagttaca attgaaataa atggaaatct ctcttatttt tacattgaaa tttcttgctg 60
gtcacttctt ccaatccacc gtagttaacc gactgggtgg tctactaccc gtttctggtt 120
ttctctgcac tctcttcgga gagagtgcag acaaaattct ccgcgttcgc agtcctggtt 180
ctgtttcgag acgttgacgt cgcccgacac cactcctaca actgttcgga cagcgtctgc 240
aattttcgat tagtaatata gttttggttg tgaatataat ataaattgtg aaaaattgca 300
ttgagaatta ggaaaagagc atgtgagaag aggaggggaa tttttagaat aactgagaat 360
ataatttaga gaaacacgat tacttcgcat caattcagaa tatcttttaa aatctgagaa 420
attttggtta aaaaataaca cagggcgctt agtttgtggt tttctcaatt ctgtttaatt 480
tttaaaacag taattcttat ttcgataaac taaaatgaat atgaaatttt cttacgatta 540
aaaaatgcat gaaaccagat ataacaaatt gaaggaaaac tgaaaaactt cagaaagtgt 600
ttttttctga aaataaaagc agaaaaattc gaagctcgcg caaagaacgt aaacgcgctc 660
cattgctaac tcatttgaac attagttttt ttcattgggc tttcaatctt gtaagtgatg 720
tttaggcatc taaaagtttt ataaattgac aaaatccagc ttaaaagatg ctatcaaaaa 780
ctaacttttc agaatattta tttggctaat gtttgaccca tacgtttttt gccgaaaaga 840
atttcaaaaa tgaaaagtat cttgaaatgc atcaaaatcc gggaatattg ccgatggtca 900
gtttttcagc atttctaaat tgagagactg aaatgggaat ttatttattt ttattcatct 960 gctttttttat ttcatgaata tccgcatctg aaatcagctt ttttttcag gaaaattgat 1020 tgaaagaaga caataacagc tcgttgttca acatctcgat tcttccatat gaatcgatga 1080
atggaaaaac cgtggcattt ggtaaagttt tggctggaac cgaagttgtc tcccgcatcg 1140
ccttcaataa atcaaacacg aagggttcca aggcttgcgt catcaccgac tgtggagaag 1200
ttatctgaaa ggttttatca tagattttca aattttttgg tttattatta tttctttctt 1260
tttgttccga taagtccata tatgaaattt gtccagtttt tatgaaaata aacatttatt 1320
ttatttaata tttttttatt catcatatgc 1350

<210> SEQ ID NO 126
<211> LENGTH: 632
<212> TYPE: DNA
<213> ORGANISM: Caenorhabditis elegans

<400> SEQUENCE: 126
tctgaaaaac gttgatttaa aattttataa aaaatttgaa gcaaaaatga aagagaaaac 60
taaaaaaaaa gtaaatgtac tgaagtgatt ggcagattaa taataattta tcgataaaac 120
cattttttaa aaaacttcat cagtttttgt gagtgtcagc aaagaagaag aagattcacg 180
atcaaaaatt cgttgagcct atatgaaata gttgcgctgg tttttcgacg gggggatcaa 240
atacgtcaaa taggtcaaat agacgaagca ttcataaaaa gtacaatatt cattgaaaaa 300
tagttttgga tttgtttttt tgttttcttc atttttttgt tgaaaaaata atggtaatta 360
aaagttttta ataattattt aaatcaagat tgaaatatca gaaaacgaca aaaattcgtt 420
cgagaacttt ctcaagacta ccgtactctt taaagacgca tgacgatttt cacatgggtc 480
tcaccacgac ttgtctgaaa tttgaatgtt cgttcaaaaa cttttttttt tgcgattttc 540
aaaaccaaag cttaacaaac aattttcctc aagttttcaa cgctttttgc tcgttttttt 600
cgctcaaata aattatttca gaaggttttg ca 632

<210> SEQ ID NO 127
<211> LENGTH: 1057
<212> TYPE: DNA
<213> ORGANISM: Caenorhabditis elegans

<400> SEQUENCE: 127
tatattcaaa aaaatatatt ttttgtaaat gttcttgaca aggtgtcagg aaatcagaat 60
aaacattcaa caggtgttta tgtttttttt gtatcattct aaaaatccta acccgtgcct 120
gattttcata aaactaaaac actaaatgtt gtcaatctgt gaccctggag cctagaataa 180
gttttccaaa atctgattat taaaaacaca acaacagatt ttaaatagat ttgagcacaa 240
gtcatgcatt gagcataagc cacaaatgaa ataacgagag tgaattttta gagtctaatt 300
gaattgcatt agcttttcta aaaacttttt ttcggctcaa aatcatttcc acaaaaaaaa 360
cagttttaaa ataataagag ttggccttca gagcggtttt gtgtttaaca aattataatt 420
cttattgtca gctcgattac gttttttttt cagtatcttt cgttttgctt tttgttttta 480
gttactcgcc acgagagagg gtttccctcc aaatttcgca aaaactagca caaattatat 540
gtatgtaccg gaactaacct ataatacttc cgggttcatg ccaaattcta atttctaaat 600
ccccagacag acacgctctc aacttcctcc ctctttttgt ttatgaatga atttagtttg 660
tgacaatcag ctaaaagtcg tgatttgaaa agttcaagaa atcgtcaagc tcgtgaccac 720
gaaaaagttc tagtcacaat acatcataga ctagaaagca tttctcgatc aactagttga 780 cagcttttttg tgaataaaga ttgagaattc gagttgtttt cgaaccatga ttacatggct 840
taacaataat acatgcagct cattgagtct atacaaacac aaaatacggg tctgcgtcta 900
attatttcct acaatatttt tgttattatt cacaaaaaac gggagatagt cgacagctct 960
caaccggttg aagagttgtg tcgtgaagaa acaatataaa aacattgaaa agtaataact 1020
gataacaaca gttctcaaac aatattatag tgatcaa 1057

<210> SEQ ID NO 128
<211> LENGTH: 509
<212> TYPE: DNA
<213> ORGANISM: Caenorhabditis elegans

<400> SEQUENCE: 128
agcaaataaa ataattttat ggtttttcat ttgaaaaaaa agttattaac cttccggcgc 60
aaatgaataa aataataaaa atgattaagt tattgcacgg cccaattcat cgttgctata 120
cttattgact acagaatatt tttacttcta tcaacaatgc aagtttgaaa atttccataa 180
ataagatttt tcttatcact accttttttgc ttattttcat tttaatttcg tggtctctgc 240
tctccctttt ctgacctgct gacagtttga atcgtcttca aactaaatac tcggtatgtt 300
tgcctaaatc tcttgtaaga gagtagtctc tcattcagag aatttcactc ttgttgttag 360
aacaaacttc actggcgtgt attttgggaa aatagattat atatatttaa gagattaata 420
cgatttctaa ttttagttgt ccatcaaatt gaattttttt gtgtcgtttt tctgaataaa 480
catctgaaat tgattcacca tttttcaga 509

<210> SEQ ID NO 129
<211> LENGTH: 570
<212> TYPE: DNA
<213> ORGANISM: Caenorhabditis elegans

<400> SEQUENCE: 129
ttattaatat tattgtattt ctgaatgtac cgtattgtat ttctacatat tgaatcaata 60
aattgttttg tacaataatt ctttggctga gactggtcgg acaaattcaa tgcaagcctg 120
caaacttatt agactctaat agaaaatttt ctcaaattgg aacaattatt ctataattcc 180
ttgccggttt tgcagaaaaa atgttttttt aagaattaaa aattttaatt atgttccaat 240
taaacctaca tcaatgctct agaattctcc aaaacatcaa aaaaatttgt tgacaagatt 300
ggaaaatctg aaatattttt aatttttaa tatcaaaccc ccttcaaatg ctacacaact 360
taaaaataaa aacaaaaagt gtggtcaaca actttcaaag cgtagaacac gcattttgtg 420
ttgtgtgtct tatttctttt ctacctctta tctatcgtct cattcgcgcg cttttcaatt 480
ttgggggtag gctgagttag tataagaaaa gttaataaaa aatattagtt tctaattttc 540
gagtttctaa tctagcagta ttttaaaata 570

<210> SEQ ID NO 130
<211> LENGTH: 287
<212> TYPE: DNA
<213> ORGANISM: Caenorhabditis elegans

<400> SEQUENCE: 130
atctttaata attaaatgaa taattaattg ggagaaacat gtacataaat aaaatttcca 60
ttaaacaatg ttcatttgtt taagctggca cagaccacaa aagctgaaac cacaaagttt 120
tttaaacctt gttcttttct taaattttgt agtttcttat cttatcactc gtgtttcttg 180
tcctccaaat aattgtgaaa attgtagtta atgtgtcaaa aaagtcacat ataagaagac 240
gaacaacttg attttttgtt gacttcattt gaaaaaaaat agaaaac 287

<210> SEQ ID NO 131
<211> LENGTH: 1670
<212> TYPE: DNA
<213> ORGANISM: Caenorhabditis elegans

<400> SEQUENCE: 131
tactgaattt tgcaaaaatg aggagtatag gaaaactcgc tcagaaaatc gaaaaaaaat 60
tagttccgtt ttgtaacact cagactttac aactaccaat tagaaaaaat aataatacac 120
taaaagagaa gaatagaaat cagaagaagt cagtatcatg ggagctcatg agttaattgc 180
ctgaaatgcg tattcccaga aataaaaatg cggtttctta gctctgagat ctgaagtgta 240
agactgccaa tagattccat gagattcgtt gtgacaaggg gttctgaaaa aaggaatcgc 300
gcaaatttat ttattgcaca gttgtagatg ataaagtttc tttcagattt gaataatttt 360
taaaagcttc taaaaattat cttgcagcta attgtccaaa aattattaaa catttgaata 420
tttttctttg cttccaacag gttttatgga aattattaac aactgtaaaa cgttaacgta 480
gaataaagta aatcgatctt gaaaacccaa aagaaccggc cctatatttt tggcaggtgg 540
aaattttgaa tgaaatttaa taatatagct cctgaacttt taaacgatga tattagatgt 600
tgaatgatca atttccttgt agtcataacc atacggtttt tgaaacatca taattttatc 660
gaaatcactt gtaaatcccc cgggtacagc tataaccaac cctattcgac aatttcaatt 720
tcggatattg taaaaaaaaa ttttaaaggt ggtgtagtcg aatttttttt attgctttat 780
taggttcaaa attgtctgaa aaaaaccgaa tttcataatg aaacttcttg aaaacttctc 840
aaaaaaagtt atgacggctc aaaaaatgac ctaaaattag ttaaaatttg aaatttgacc 900
gacttgtcaa tgacgcagct gctggaaaca attttttttt gaaattaccg tccaatttgg 960
gtatttaagt taattatctc gcgttttcaa cttcattata aagcttataa acagcgagaa 1020
ttttaaattt tttttaccaa atctcgccgt ccatcgaatt caaaatacat aaatggtgtt 1080
gaaaacgcaa aatacataat tacatgctat actcacaatt tgacggtgat ttcaaaaaaa 1140
aattgtttcc agccgctgcg acattgacaa gtcggtcaaa tttcaaattt aaacgaattt 1200
tagaccattt tttgagccgt cataactttt ttttgttgag aagttttcaa gaaatttcat 1260
tatgaaattc ggctttttca gacacttttt agtctaataa agcaatcaaa aaattcgact 1320
tcaccacctt taacttagca attgccaaaa ttttttattg cagtacatat aaaattagaa 1380
acacacaatg tctcaaacct ggaattacta ggaattttta agaaaatgac tgaaaaaaca 1440
aactatgcca aggacaaatt taatgttttt ttcaaagtat agcatgtcga aaatactgtt 1500
tttgataatt aaactgttta atactactaa tttttcacat tctcatacga ctatgaaaat 1560
aagtgtagga aatgtaacct gtgtgatgaa cattctactt tgccttatca aattggaaaa 1620
acctcgtata aaatggtcaa caaaaaatga aactgattta acttctgatc 1670

<210> SEQ ID NO 132
<211> LENGTH: 648
<212> TYPE: DNA
<213> ORGANISM: Caenorhabditis elegans

<400> SEQUENCE: 132
aagttcacaa tttattcatt catccatgta aactgtatat tttgaatttg tgttgtaaag 60
aatttatctt cgaataaaat gtttttaaag gtttttaaat tgtattctgg tgagattgct 120
taaatagagt ccttcggcga taaaaatgct aaaaattata tgaaaaaaac tatacaaaga 180
atatgtctcg aagtgtttca ttccagatca aagtcgaaaa ttagcttaga aaaaggatct 240
tcgtcaaaac ccctgattta acaccaagac gaataggaaa aataaagtaa tttaaaataa 300
aataaattac aagtgcgctc cattgtaaaa acgctagaat ttgcaaaaac tgaacaatat 360
ttgattttcg actggaaaaa aaacttgttg gtaaattgca tgaacagttt taaaatgtca 420
ttaagaaaac tgatgccaat ttttggttgt tttctctcgt ttaggaaatt aaaattccct 480
cttatttttt tagcatgaac cgtcaacgat ttctggtcag ataaattatg gttattatag 540
tgtgtagttt tttgagttta aaccaatgtt tcgaaatttt tatcagtaaa cagaaactac 600
ggtttgctgt atataagtta attccgatag caaaagtaga aatccaaa 648

<210> SEQ ID NO 133
<211> LENGTH: 1081
<212> TYPE: DNA
<213> ORGANISM: Caenorhabditis elegans

<400> SEQUENCE: 133
cttctgtaat aaaaaaaaat tgaaatgttt agtgaggaga gtgatagaaa ataaaaaaag 60
ccgagactaa acattttccc tgtgctgccc tgtttataaa cgtttcaaag gaaaattctg 120

-continued aaccctgtaa caactgtcgt cgaccttcga atagctcaaa aacatttggt ctgcttgtgg 180
atcgcacgtt tgtttcacaa aattcattgt gatttgtcgt ttgagatata tcccttctat 240
caatcaacat gttgatgccg gaacttttaa tcccaagaaa tctgttacac aaagatcgga 300
aaataccttt aattgcttac aacttttatt aatagtcgat agatacactt gcttttgact 360
tgccagaaat ttaagtatga tgcttatcaa ataattacat tgattacaat tattaaataa 420
ttgaataatt gctaactaca actaaaaaat tattcgaaac ttttttgtaa aactaagaat 480
cagtccgcgg atgaatggta atattgttca aattcgtcta gaaaaaaaac caaaaaaata 540
attaaaaaat gagaaactgc gcaaaatata tatatttaaa atgaaacaca acgaggcggc 600
tctcgttaac cagcattgtg caaataaccc aaaaactctg ttcacgccaa agtgctgaaa 660
agagaaaaga ggctggcgtg aagccgacag gtataggtcc tgaaaccgcg ccccactggt 720
tactcgaatt tgcgaatcat tcttcttttt ttttttcaa agcaacttcc ctttattaat 780
ttcagattat tgaacattca attttttttt gttgtaaaaa tcaattgttt ttctccgaat 840
agttaagaaa aatgtatgtt ttgaaaatta tctgttcttg ggaaataata gagttctgca 900
aacaaactta ctatcagtcg attcgcctaa ttcgaccctt ctatcaaaaa cgttgtgctg 960
aatgtataaa ttgtgaattt ttgagtgaaa ataactgata agagcttttt tatcagtcaa 1020
ctgacagtgt gcatgttttg tataaaaaca gtccactgat ttcgaaaaat caaatcagaa 1080
t 1081

<210> SEQ ID NO 134
<211> LENGTH: 2047
<212> TYPE: DNA
<213> ORGANISM: Caenorhabditis elegans

<400> SEQUENCE: 134
ctttgtaaat tattttcaat taatttattt gcacatgtga actattagaa aagaaaaagt 60
ttacttttat atttggtgct atattggtga taaatctatg caattggtaa taaatcggaa 120
atacgtttat tttctgcaat tgaatataat aaaaggtaaa taaatgatga gtgcgagaaa 180
tttgagttcc ataattgtac aagccaggga gttttgaaaa ataacagaac cggtacctat 240
ttctcttttt ataacatata acatctgaaa ccgacatgtt aaataaaaaa ttttgagaaa 300
gaaagttgtt aattctcgtt aatttgcgat atgtctataa taaacctcgt agcatttcta 360
tcgactaaaa atttgttata atcagaaaaa accatcgaag ttttcaagtc aaatttcaaa 420
atactcttca catcaaaact tgcaaaatta aactcacaga ctggaaaagg aaattcgaaa 480
atgtctgaag aataacggtt ttggaaaccg agctgtactt ttttccagga agatcgttca 540
caaacaaaat caaatagcca taaattgaaa tacttgcaca acttaaaaaa tacgagaaca 600
ttgaagaaat atcgatgttc ttcaatacac ataaaatgtt gttgtcatat tgtttccatg 660
agcaaatggc tgaaatctgg gcaataataa tatttgataa atgtccatta ctcacttggt 720
atagcaactt tatgaactaa agaaattata aaagaattga taattataaa tgcaagacat 780
cggggtcgaa acctaacgaa tgatcgaaaa tttggaaatt tcaatgatat gactttttgt 840
attgctagta gaaacatgga aacagcgaaa atattcggga aaacggtatt ttgagaatgt 900
gctattagag ccataatgga ctgaacgata gcccaatttg taattagaat cttacgattt 960
acatttctga aaatttatag atattaactt taaaacatat atgaatggat cttacaatcc 1020
attaattaca atcaatacaa taacattgtt catattaatt aaaaataaag taatgctcat 1080

-continued

```
taataaagac atcaaatgat taatttttaa aatgtgacat gatttatgtc tcaaataatg   1140
tgtcttgttg tgattccatg aacggcagta aaatataaaa acgatactat ttgtagaagc   1200
aaaaaccatc aataaagtta tttcaaagtc aatatgactt gttgctaagt tctgaaaagt   1260
ctgaaatact tgcatagctt aaaagcgtaa aagtgaatta ctatgcataa gtctgtgggc   1320
gaaatgcatg tgacaacatt tgcacctgtt tggtttttaa tagcctccaa atttaagact   1380
atgaaaattc attctgcggt ccttcctgaa caatggcacg tccaaacgtc tacaacattt   1440
gaatatttat atttaataca aaagtagacc ataaaaatag aattaacatt tttttgatcg   1500
acaatttcca aaaaaataac aaaaactgag attgttccaa atttttttc caaaagttat   1560
ataaaatttt aaaaaaattt caaaactttt actatgatat atttacagcc cccccccccc   1620
acaaaaataa cggatttcat cgctttgaat ttttaataaa ttttcaatga aaatttatgg   1680
aatagacacg ggaccaggcg gaagtcttga tactttttgg tactgtgtac caaccaaaaa   1740
ttgcagatac aaaaagaata aaaacatttt ttttaaattt ttttattcaa ttttccgtat   1800
ttttgaacca cacttaaata aactctattt gaagcacagt cttatttccg tgttttcatc   1860
agagaccaca gttccttatc cttgcgttat caattttcat tacatcttta catcaaatct   1920
tttgtggcaa atgtacaaaa tgtacatttt gaagtaaata tacccgataa gaattagtta   1980
tcggtcaaga gactgtttga ttgctttata taaaatcaga tatttcaatt ttaattctca   2040
aatcgaa                                                             2047
```

<210> SEQ ID NO 135
<211> LENGTH: 2212
<212> TYPE: DNA
<213> ORGANISM: Caenorhabditis elegans

<400> SEQUENCE: 135

```
ttgtcttata ttttattaaa atcggggcga agccctgatt ttaaatccat attgtttttt     60
ttgtcttcca ctatccctac aaataggaaa gagaatgtgt tctttctgat gaagtaaaaa    120
cggcgcagcc agccgacagc cgaaattttc acgattttcg gctggtagcg ccagccgaaa    180
aattaaaaga agtcggctgg cggcgccagc cgacagccga accagctttt tgtcggctgg    240
tagctttaaa tttttttcca gtttttaca gaaaattcgt ccagttctta cagaaaattc     300
gcgtttctat gttttaaatt tgataacatt tgcagtaacg gagactgctg acccggcgtt    360
tcccatgaga aaagagagag agagagagag ggggagacag tgagatatac ggcagagaca    420
tagacagggg agacaccatt agagatcgtc tcctatagag tgctgccggc agggggcgtt    480
gtggacctgt gggaagaagg ggggagacaa ccgcacactg tgcggttgta aatgcggaat    540
aatccattta aaactaagga aaatagtggt ctaatgctta acagtgagcc gcctagataa    600
aacaaaaaaa agtcggctgg ctgcgccagc cgacagccga aattttcact attttcggct    660
ggtgccacca gccgacagcc gaaaaattga agtcaatcgg ctgtcggcgc cagccgacag    720
ccgaaaaaat cagccagccg ctcagccctg gtggggtggc gatgtgttgg cagccaaccc    780
ttcaacgaac tgtatctccc gcctgtatct cccttcaaag tgagatcctg taacagtaat    840
tagagaccat atttacagcc agcctacatg catcactgga gactctgtgg agagggagga    900
ggcaagagaa aggggaggca agagggggcg ggcgggcact gctgaacctt gaaagcgccg    960
tagctccgct cacaattgga attgaaaaat gaaaagtata tatttgaagt caacgttaaa   1020
aggagaatat gatagcattt gaaattttgg aaattggtga agaatgaaaa aaaaagcctc   1080
tggagcaagg cttgaagctc acaacttcag gaacggggct cgaggaactc atggccaaaa   1140
```

```
acttttttatt tgtctcgctt ctcatagcaa aaataataag atttaaaaca taaaattgat   1200
tatccaacaa aaaactggtc caggaaaaga gggaaactga aaattcgagg tcaaaaatta   1260
aataaactaa aattgtgaaa aatggtcgta gagagctgtg ctttcagctg gcattcggaa   1320
tttatgcact tattacgaat ttaacataaa atcccatttg atagtggaaa aattttcatt   1380
tttccagcaa aaacgtcatt tttttgagaa aatgcagcaa tttgcgattt ctgaagttat   1440
ttttaacttt tttgaaaaaa aaaaatattt ttgaagagaa aatttcctga aaaatacgtt   1500
tttcaaaaaa tttacctcaa aaagtgccaa actgaccgac ttatggacga aaaaccatca   1560
aaaatcgcta atttgcacac caaaaaaaag gggggggggg ggaaatgcaa ttttcgattt   1620
cacactaaag agcccacttc tatagcaatt tttgagtttc actcaaaata tctcggctca   1680
atgagctcca atctttctga aaacaagaat acagaggtgg ggcaagcttt ttgaagagac   1740
agcaaaaaac tgcatcaaaa tccatccacc caccgtcaag ttacacgcgc gttttcattt   1800
accacttttg tcggattttg aagcttaata tctcggctcc tgtaaatcga aatcggctga   1860
aaattcacaa gaaaacttac ttcactacga tcctcctgtc attaaatttt cgtgagctta   1920
gaccgaaaac tgacaaaacg ccaaactttg ctaacgctcg ccactgacgc caagccttca   1980
gacacgcttt cactaaatac agtctatttt tccgtgtttt catcagagac cacagtttta   2040
aaataatgcg ttttcaattt atttgatgtg atttatacat tttcccatca gaaatgctgt   2100
gctaaatgta ttcaatgtgt ctttttgagt gaaaccactc ttaatttatc agtcaacaga   2160
taatgttgct ttgtataaaa aggattcatc gaatttgaaa ttttcaatca aa           2212
```

```
<210> SEQ ID NO 136
<211> LENGTH: 1481
<212> TYPE: DNA
<213> ORGANISM: Caenorhabditis elegans

<400> SEQUENCE: 136

ggccaaaaat agtaaaactt gatcgttttc tgccattgaa aactgcgtta ctatcatgct     60
tggtttttgg gggcgctggt atagaatatg tgctcaagga agtgccggat atcagaaaac    120
tgatagtttt gatcaaaaag ttgtgtatgc ctgtctttct gtctgtctgt tgacactccc    180
tccgagaggc agccagagcc tcagagtgac aaatgcgaac ggcagacgga atggaggaaa    240
aggatgagcg gtgctaataa cagtacacag tttgacgaaa atccaagttt attgagcagg    300
gcagctttaa gctgggaata aacaaggcaa aaacgtagag aatatttagg gaattgggca    360
cgaagatcag caacgagcag ccatggcgtt gggagaacga agaaaagaag tgaagaatgg    420
ctacatttta ggccagaatt aatatgagca agggaataaa cagcgcgcgc tacgacactc    480
cgatgtgtac aatggcgcgc gcttgcatcc ttggcggcaa attcaaatga gaattattta    540
atttaattaa tttaaatggt ggaatgatta ttaaagaacg aacaaacgga attgtgtgag    600
taaattaccg gcggatgatt atcgctggat tgtgggcaat tcttgccgat aattataatc    660
cgcaaagttg gggcggagga cctctactga ggccaagtca caacactgtc taccgtctgt    720
ctattctata tctagaagat gtcaacattc agtggttatt ttttagtaat aaaagtgtaa    780
aacaaaacaa ttcagatctg caaagctgaa aagtgatgaa aattgatatc ttcaattata    840
atttatagta cttttttaat aattactcta attacacccc actgctttac tttgaaatct    900
catatctcgc tccattctga agtagtcaac tagaaacggt aaaaaatcca tagaaaattg    960
tttttccagg tgacaatttt taaataaaaa tggggtgcaa tagtaataga gcaattatgc   1020
```

```
taattttgtg aaactgtagt ttcaatactt taaactctat ctgtacgttg ttctctattg   1080

aaaaatacat accagatcag ttatcaattt catttctcat atgtcaatcg ctattaattt   1140

tactgataag aacacgctgt gtcagttgtg tcagttgtag ttgcaacgag aaatacaatt   1200

tctttttggg tttcttctta agtttctcgg cttgaataat gggaaaacta attaacagtt   1260

gactaaatta tttaatttta ttatcccgcc cttaaaaagt tacccaaaaa gatttagtga   1320

agttatgtcg ttctaatata atacttcgaa caacttgtgt cagttgtagt cagttgttaa   1380

aatctaaatt tggtgataag atagtcgtat cactagttct gcaacgttat tatttaaata   1440

gccggagatt gacaaaaata ttcattcata atttttaaaa a                       1481
```

<210> SEQ ID NO 137
<211> LENGTH: 895
<212> TYPE: DNA
<213> ORGANISM: Caenorhabditis elegans

<400> SEQUENCE: 137

```
tctttaatga taatttatgg gatctgtatt tctctttctg tcaataaaaa ttgaaaatga     60

tttttacatt ctcaatattt tctaaatcat gtttcgtgaa gctgaagagt aaaattcgac    120

atttagaagg tttcgttaga aaaatgaaaa gtgtagtgcc agaggggact ttatctaaaa    180

caggcctgaa ggttcgaccc gcgttacagt tccagtctaa agtaataaca ctaattcaaa    240

ataatatata cgaaaaaaaa acacttgaat attatttgat ttttaaagat tttcaatttt    300

gaaattatca aatttccttg aatttgggaa tttttgaaga agtttcagat gcaggtttga    360

aatcctagaa tgtgcaagta tgaaaactga aacaaaatgt atttatacga ctttttttggt   420

cactgccaaa cttataatcg gtcaaaacta tgtttgcaca aatttctaac attaaaaata    480

aacgatttta attttttttt gaaaattatg cctgtataca tttcagcatt ataagagcgt    540

ttttaagcga ttccctactg atgatactgt agcattctaa aattattgta gcttaatagc    600

tatctaattt gtaaaattaa atttaaaaaa ataaatttga agtggatcta ttagaacctt    660

catacaatat ttcctactct tttaaatttg aaatttttcg agtcagtgct agtgatagat    720

agaatacatc cattccgtag ttatctacgc tttcctcttg gaatcaacac atcaaaactc    780

aaagtacgcc tttattaaag aaccgtgctt tgtagtttta aattacttgc ttccattgtt    840

tgtagccttt ccttataaaa gatagcaggt tctgtttaac tatctcaatt tcaaa         895
```

<210> SEQ ID NO 138
<211> LENGTH: 1036
<212> TYPE: DNA
<213> ORGANISM: Caenorhabditis elegans

<400> SEQUENCE: 138

```
atttttgaac taaataatat ttcaaattgc acccgcaaat atcgtcactt ttataccgat     60

aaacaaataa agtttagtga tgacttatga taagaacctc tttgagtcta tatgtacgtg    120

aaacaaacgt taaagaataa cggctttacg tgttagtcat tcataaaatt tcataagttg    180

atctggaaat ttgtgttatg gacgttacgc cattatttct cgtcactcaa cgtctcgtca    240

atggtaattg tttttcagag acggtgaatc atgtttcagt tgatgatttt aggaaacgca    300

tgccatgttg agacaccata ataatttaaa tttttgtggg taccttttat tgggattttc    360

taacatttca gtcagaactt ttagtagaat ttttttatag atcttttttt ttcagcttaa    420

aattagtgtt ctaattactg tttaaaaaat gaaaactgaa acgtttgatg attttgtttt    480

taaaaaattt tcaatttttt tcgatatgtt tttattgatt gtaagatcaa ctcttttaaa    540
```

gtttactttt catttttgt taataaataa gaaaatttta ccgacttttt agaaatttaa 600
tttattgaaa aactgataaa cgtcttgttt tgatcaattt tccaataaag aatactttta 660
gcgttagtca caacatatac tcaaaatgtg tcaaaaaaca atgtttcgaa cagttttatt 720
gtttttttta gcttcatccc gaacaactaa aaattgactt tcccgataac ttaagacgaa 780
taagtttaaa atttgaaatc tagttatttt tcacgatttt gacttttgtt ctgtccgcgc 840
cgaatctgaa acttgaacac taattcaatg tacacataag aatagacaag tagtgaatat 900
gcccattatc acacagacta catactttga ctgttccaag cgtcgcaagc gtcgcaagtg 960
tagcattttg agtcagtgat aacaatgtaa gaaagtatat aaagaacatg catttgttca 1020
tttctattgc aaaaca 1036

<210> SEQ ID NO 139
<211> LENGTH: 1435
<212> TYPE: DNA
<213> ORGANISM: Caenorhabditis elegans

<400> SEQUENCE: 139
tgattccaaa tgataattgg ctagtcttaa aacattttat attttaggga attcgaaatc 60
aaaactatgc acgtcatatc aaaatcaatt tttgttcaat attaatgtta tttattcatt 120
tgacagctat caataattat atttattaaa atagctgata gaactattta gggcattcac 180
aaacatttca gaatgtttcc gaaagttcgc aacagcggat tcgccacaat gcttcctcat 240
aacccatttg taacaccatt tttcaattgt aaacatgctt gtcaaaaatg cagtatcatt 300
gggttgcaaa acataactcg ggcatttgta tttaaatata ttgaagttag aagaacggag 360
ctttgacaaa caggcaatga atggagtttg tttcaaataa atgaaatcac atccaacaaa 420
aaccaactct gtgtatcaat cgcctcttgg caaacattta tcggagaaac tctgaaacgg 480
gtactatttc tagtttagtt ttggtatatt tcacaactga acaccttcac actgtttact 540
tatttccact atatcagcat tatttctcga gttccgataa tcgtccaaca ttctatgagc 600
tttatctcca aactggctat atcgtaaatg cttgaaaaaa taaaaaggat catagcaatc 660
cgactcatta gcaggtgttg tgggaatatt atcaagaaat gcgttgtaat tctccgtagt 720
attttctgtt tttagctttt cacaaatgtt tcttatagta tccgaaaagc atgtctttcc 780
atcttctaat tgatcactga tatcatcaat ctgaaaatat tagattgatt ttttgctgag 840
aagaacctca aaaccaacta tgaaaaaatc atttagtttg atgcagccgt cacggtagtt 900
taacaaatgt gtacaagcaa cttggacaca aggacgaggg tcattgatgt agtaagattg 960
caaaaaagga actcagaaca gtaagaaagc caaagttaaa agcattgttg tcctgaaaaa 1020
tccttattag tgtgtgataa aaataaattt cacaagttgg acagttatta tttcacaaaa 1080
taaaatatta ttttgttgtg tgtactttac aattgacgaa aagatcaaac cgacgcaaaa 1140
atgatcaata taatccgttc atatttgttt ggtaaagcat ttttctgcta atcaaaaact 1200
gttggtgcaa aataatcgca cgttttttcg tttttttttt aattttttgg tctcaaaatt 1260
acataaattt tcggaaacat ttctaacgct gaaaaaaaca tttaattgtg tgaagtgtag 1320
ccgtgaaaat gtgttaggtg ttgctaccct cttatcttca atcttatcat gtttttgtct 1380
cctttataaa gaattgccgg tgaacttgaa gttcagatgt ataactgttt ctatc 1435

<210> SEQ ID NO 140
<211> LENGTH: 1043
<212> TYPE: DNA

<213> ORGANISM: Caenorhabditis elegans

<400> SEQUENCE: 140
tcccttgtta tttgattttt aagatttgcc cttatgtcag tgtcttctgc atgagtacat 60
gcatatttgc atattattag aatgttatgt ataaaaagaa aaagagagcc acctcttaac 120
gataatccaa tttcttgtta cgcagaaacg cctcgttttc ctgtggactt tcgatatctt 180
caacatgctg ctattatcac tcccatgacc cgtttcctat ctgtttttat ttcgattact 240
acacatctgc tagaaacaca cgtcacgtgt gatttgtact caccgttttc tcctttcata 300
ctttttagcc tacaaaccac gaattgcttt gtgacttgac tcaattttct cccgaaactt 360
tttttcgtcc tcaattccca ctacccattt tcttgcttct ccctgttgca atattttcaa 420
tttcccatcc aaaaacggcc cgagcacggg ttttcttttc ctttttgtag gttcacttct 480
tctttttctt cttcgtttct attttttttac acaatcattg ttcacctttg ggcaccccag 540
tgaaacattt gtttgataaa aattgtgtgt tccacggcac taaccacaaa atctttgcta 600
caaatactac tcgtattgtt tgtgatgact gtggtgaaag taagaagaat cgagagacat 660
taggggacaa atataaaata gaaacgataa ggcgacgaaa acgcacattc ttctcgattt 720
ccgaccgtca atcgctgagt gaataattgt tgacggcaac tgggaaaatc tgtgagaaaa 780
taatgtacca tgttttcgaa tttctaaaat tagagataat ttcttccgtt ttctctttta 840
catcttgttt tcttcatttt acaacaaatc cttcttcttt ctcttaccgc tttgtgcact 900
tgcactgtaa atgacggcaa cttacggacc tagcgttcga cgaacacagt caaggacgct 960
cacacatcgt cgacgggttc acctgctctg ttgcagtgat ttttgatgtt tttattggtg 1020
actagttttt gactttttac aaa 1043

<210> SEQ ID NO 141
<211> LENGTH: 1364
<212> TYPE: DNA
<213> ORGANISM: Caenorhabditis elegans

<400> SEQUENCE: 141
atttgaggac tgggatgtca ttaggactga aattattcta aattagataa tatattttaa 60
ggtaaaacgt ctgtttaaat tatttgtata agcaacaaaa aataaacgaa aactaaaatt 120
ctacctgaag ttcaggtcct gaacaataac ataaaaaatt tgggaaaaca cgaaaaaata 180
aacttaaaaa attaattaaa aaattaaaga ttaaaattaa agattaaata atctctagaa 240
catagatctc taaaacactt cccgtagcgg ttcatttttg ttcgagtctg actggcgttt 300
tctatgggaa acagaaaaca acacgctgtt tgctcagttt cgagaatttt ggaattcaca 360
gacttatttt gttttgccgt atatgatctt aatcatagac atataatatt tatgacaatg 420
ctttgctata attctgtgtg gtgagcgttc gcagaaggtt ctgcacaatt ctttcaatga 480
aaaaaaaaag aaaattataa gaacttatta gaaaattata agatgtagaa agttattcat 540
aaaagttagt attcccaaga aaaatcataa agaaaggttt tttttcaagg ttttttttcag 600 atttttggcg ttgttcaact tgtattgcaa tcattattat tgcgatcatt agtaatttaa 660
tataatttgc tccagagcat ttgtaagcaa tgaaatccaa ttttccctct gtggtgtttg 720
gtttagaaac ttttgcaatt tcgtcttgat gtgccgcggc atgccgcaaa aatcataggg 780
gatttgattt cccagtagtt gaagttggca gagttaacta taaggatgac ctaaaacaag 840
ttttaggcta cttgttatag acatggactt cgatttctaa tttggacagc atccgctaca 900
gtgaaagtct gcggattgat ttcaaactct ctaaaatcga acgagttttc aattttttt 960 tcaattttga tgcctaattt agtgaacacg gtaattatag tttcttgtat ataaaacccg 1020
tttaactcct taaattactg tttacgtttc gtgttgtaat aaacgatctc ttgatcttca 1080
ttcaactatg ctggcacaaa aatagacaca attcgaagag gcgcagaggg agtaacagac 1140
acaaaaaatg ttaggacgtc tgcgatctcg ccggtaagaa acactgaaaa tactctctgc 1200
gtagtcacga aagctacaaa ctttaatgta ttcaaccaaa taatgttaac tgtataaaaa 1260
gaaacaaaga aaaaaaagta taaaaagaaa ctttaaacca aaactaatca tcagattcaa 1320
tatcttctat ctgtttgaca ttctatttct gtaagctcga aaat 1364

<210> SEQ ID NO 142
<211> LENGTH: 625
<212> TYPE: DNA
<213> ORGANISM: Caenorhabditis elegans

<400> SEQUENCE: 142
agtagagtca atatcttgaa atgtttagaa ttctcgcgta tctcacatgt tgaggtgaga 60
tatttgtaat gaatagtttc atagtctttg gccaaaatat gattatacgt taaagcaaat 120
tttgatgtta cgccgtttga agaaatgttt ttagcatgtt taacagagat tcagactaaa 180
tttattctac acagtttctg aagggatatt ttttgccaga gtcaattttc ttgtaaacca 240
gtgagcctta ggtacataga aaattttgaa aaatatccaa gaataaaatt ttttctgcat 300
gccttattct gggcttattt tttgcggttt tcaattcaat tttatcgtat ttcaaaaaat 360
taaattagaa caaatgcata ttcattttta catccttttc taattggtaa ttataatttc 420
aaaaatcttc tttgcttatc atttgtaaca acaactacaa aaactgtact cgtagtttta 480
tctaaccgta ttctttgacc gcatcctccc ttttgaccat tcaagtaaaa agatgacaat 540
cgccgtctac atattgccac gtgacgcaaa ttacttataa aaccattcgt ataaatattt 600
cattgatttc ttgaattcaa aaagc 625

<210> SEQ ID NO 143
<211> LENGTH: 2328
<212> TYPE: DNA
<213> ORGANISM: Caenorhabditis elegans

<400> SEQUENCE: 143
cccgaatttt tttatcgcag aaaaccaaga tggaataaat aaatggataa tctaattaaa 60
aattgtaatt tactatttgg aatcaaaaat aaataaacaa atcttataat atgtcagcaa 120
taaaaataat aaaagaacaa ttgaaagttc aatgtgttgt caagaaatcc attaaagtat 180
cgtcatcaac ggggtcatca atttccatgt tgttgttatt gtcttccata acatctattt 240
ccatgaagtc ttagagtact gacaatagtt tatttagtaa attaattttt gagaaagttt 300
cttgacacat tgctttgaga ctttgattaa atcacaaatg actcactatt atcataattt 360
tctatccaaa atgttgattt catttcaatt tccattgaat cagctattcc attacatcca 420
tcagttggtt tacaaaatgg gaccagtggc ctcaatatct gtattttctt cctttttttgt 480 gaaaatcgta cttttgaaaa tactaatgga ttctcgttct gatcgaaatg aggaaactgt 540
gctgttttct aagaacactt gagacgtgga ttttctttgt tgttcttaaa tacgaaaatc 600
aaatttactg acaaaatatc taaaacttac aatcacttcg ttgctgtagg gataatcaca 660
aaaatttgac atgattttct ggttttcatt ctgaaaaact gggagcattt taatttgaaa 720
aaaacgaacc gtagtctgcc ccaattgatt tgttggtaaa ggaagtgaat taaagcgaca 780
aggaatacat ttatctgttg aaagtgaatg catttttctg gaaagacgga ataaattgaa 840
attaaaacaa tattcagtta aagggaaact gaattatccc aaacccgggt tatttcaaaa 900
cggaatctac atcttacttt aattctgatt gtcagcccta taacaactat ttcatctatt 960
caaaaagata caaaaataaa ccaattaaca ttacttcgta gatacctcat cacatgacca 1020
ccctctcaag ttgatataat taactttcta aattgaccaa aagtgtttgc taatgtgtat 1080
agggtatagt aaataggaag gagttcggaa gttcgatgag agtaaatatc ttttgtgaaa 1140
tatctattgg aaattagcgg aaaaaagata aattttctcc tgaagtgcac aactaataac 1200
gaatatctta atgtggaaat aaatcaaatc aaatcaatat acatcccaat catgacatcc 1260
aagaacccca caaaaatatg ttcctaaaaa ctaactgata attaatttga atgtttccaa 1320
cagaaccttg ctcgcttttt gcacattttt ccactttgtt tcgctctaca cgcttgtatt 1380
tttttaatta attatatttt ttcggcctca ataaaaatta aaattccaga ttgaacacat 1440
ttaatgtcag aatataatta cagtaccttt ttatgacaaa acatatttcg gtataatctc 1500
agatttccac ttcttgtttc atggcccaag tttttctcaa tgctcacttg taacggaaaa 1560
tggagtcagt gaagctgttc aattctagat aatatgatgc tatcaaaggt cttaaaattt 1620
agataaaatg atgaaaatga cgacattaaa gtgtagcctt actgaaaaaa ccaattattg 1680
aactttaaga aaaaaaacat tttggaaaat aaaggtaatt catttttcgt acacctaaaa 1740
tttgaaaaac cgaaatttca gtgagaacgt cttcaactgc atcaaaaaaa ttgtgaagaa 1800
aatcgaattg aaaagagagg ctaaattggc ttcatatctt taatttagcc gattatacac 1860
gtcgggccag tcttttttaa atgactgtca tggaggactt gatttcaaga ttggaagtga 1920
tgaactacaa aaaatatcaa acaattttta actgcataaa aacggttttt ctccgggatc 1980
aaagatgttt tcggtatcaa gtcacattca tggttcatta aaacatacta tttttctagt 2040
cttaaaatgt aatctgtata attttatgtt gttgattgaa ctcataatat gacaggattt 2100
tttttgtgat ttctgtaatg aagtacagtc ttacacgaaa actagagtaa tacaagtcat 2160
aaattttatt cgtctttttt cccgtagtcc tttcaataat gtatgaaaag catttacaaa 2220
ctacaactct ttcaaaaact agagttctta tcatacaaac cacacatttt ttgcagctct 2280
atataaacca actgataatg aggttttgtc tactctcatt actcaatt 2328

<210> SEQ ID NO 144
<211> LENGTH: 948
<212> TYPE: DNA
<213> ORGANISM: Caenorhabditis elegans

<400> SEQUENCE: 144
gtgaatacca caactgaatg tctcgaatat ggagccaatg attcggaaat ctatgaggaa 60
atggcatcga tttgcaagta tattgtacgg gattcgagag ctcacgggga ctcggttcca 120
gagtgatttt tgttgttcgc caattttatg attgtttctt gttgttaagt tttctaaaaa 180
ataaattctt tgattttaat aaatttcgaa aattcaaata ttatggggac gccgagggaa 240
tcagggtgca aaggcgctct aacgccaaat gacaaccgag cattgggtct cgttaggaaa 300
tggcggcaaa cgagacattt aaattttttta ttacgggaac acaaaattct aataatgcgt 360
attgcacaat atatcttacg cgctaagtat ctcgtagcga aaactacagt aattttttaa 420
tgactacgct tgtgtcgatt tacgagctcg attttagaga tgaatttatt ttcgaatagt 480
gtcagcgata tttcgcttta atttcgaatc gagcccgtaa atcgacacaa acgctacagt 540
agtcatttaa agaaattact gtagttttcg ctacgagata ttttgtgcgt caaatatgat 600
gcgcaatacg cagtctcaga actttgtgtt cccataataa aaagtgagag ttttcatgcg 660
cccttggagc gctactgcac ctcaatttca aaaaacgcat ttttctgcgt ccccataata 720
caccgggatt ttcttttctc ttcgtctgaa aaacaatcaa tcatcattaa aatcatcatc 780
tatcaccaat acagaatcca tagatcaaac agatcaaaaa accaacttga acgcttgcag 840
gcaactacga taaaaatata ttttgtagtg tagtcatcat atcaatcatc tagctataat 900
aatgcctgcc gtataaatac aaaacacgat gatgatcttt ttgcgaaa 948

<210> SEQ ID NO 145
<211> LENGTH: 1233
<212> TYPE: DNA
<213> ORGANISM: Caenorhabditis elegans

<400> SEQUENCE: 145
attagagaac ttttcgagaa gtctaccgtt gtagttttcg aaatagtaat ttatttagtg 60
acgtttataa aggtttacat gatttggttt ggaaattttt taggagttta ttcataaaaa 120
caaagtaacc atggacattc cagaagtcta tagtacacgc gatcctaccg tacccttcag 180
tatttctatc agattgatag ctttcggtag tcaggtacag cctaaaaaat tcctgcttgc 240
ctttttgcct acatgtctgc ctaccttcag tcataatgcc tacataatga tttttttccaa 300 ttgaaacttg cagacagaaa ttcaaatggc aaaaagaaac aaacaccgaa acattaatca 360
catttctttt catatcagtt ttcctgtcaa agcacatttc tggagtctgt gtgtattttt 420
ttgtgtcttt atgtgatcgg tgttgtgaaa tttgtagttg atgttgataa catacttttt 480
tttgaaacaa aaagtgattg attaggcttg aattcagaga tatgttcgtg atactttgcg 540
attctcgagc caaaaacacg gtatccggtc tcgacacgac aactttttcg caaaatacaa 600
gctgatgtgc gccttgaaag agtactgtaa tttcaacctt tcgttgttgc ggaattttca 660
tagtttctcg ttcaaaatat atgtatttat taaacaaaaa actaaaacaa aacaattgag 720
aacacataaa ttgtgaaaaa tcaatgagac cacagcaaaa aattttgtat ctacagtact 780
ctttaaaggc gcacatccgt tcttattttc agcaaaaatg tcgcttcgag accgggtacc 840
gtattttttt ttgtgcaaaa ctttaggtct aggtaatatt aaaaaaaaat tccacaaaac 900
tagaatctag agctttccat taaatttttt gatgacattt gaaaattcat gatgattttt 960
ttccaacaat ttcgaaatat ccctcttttc acctggtcca ctgaattctc tttccgaaag 1020
accaccacaa tttcagggct ccgcccattt cgtggtttgt agccttcccg accctacgtt 1080
tttgatgaca attgtgagag aagtgagagg ttcagacaca aaaagcgacg tggtcgaatg 1140
agtataaata gagagtgaag tttccaattt ccctcacaat tgtttgtttg caatccactt 1200
tccaaaaaaa cacaacttca atcaaaaatc att 1233

<210> SEQ ID NO 146
<211> LENGTH: 656
<212> TYPE: DNA
<213> ORGANISM: Caenorhabditis elegans

<400> SEQUENCE: 146
gctaaacttt cgtattcgac tgataatgag aacgtggagg agtatcgtga ggttctcact 60
gaaaaagctg aacgtctcat ggaagactta aagcgatggc acttgtacag taaagatgtg 120
acaaaggatt tagaaacggc ggaaaagttg actttatgat aagaataccg ataaaattat 180
gaaatttctc gaaacttttg aattgtgaag caacttctta ataaagtaac tcattgactt 240

```
taatttttaa accacggctt agagaaaatt aaaaatcaaa cactgcagct tttttgatgc    300

gaaaattcat tgatatggaa caaacctcaa atttgataaa taatacaata atttgtcaag    360

aaatcacaaa aacgttcttt tgaaatgcaa gttataagac atacgcaaga tgttatgtcg    420

gtggctggtt ttaactataa aatacgaaac aattgacctc ctgacacaaa atttccgagc    480

ttgatttgtc tgatatcatt tgtgctttgg aattattgtt tcatgtgcat aaaatctaca    540

ctgtgttcat tcacgataag aagaatttca gacagaaacc acaggaggtt catcgatata    600

aaatgctaat catttgattt aaagaaccat actcttttta ctctcgtcgt taagaa        656


<210> SEQ ID NO 147
<211> LENGTH: 1275
<212> TYPE: DNA
<213> ORGANISM: Caenorhabditis elegans

<400> SEQUENCE: 147

cagctatccc gaattctcga gcgacatccg tcatctgaaa gagatactaa tgtcatgtga     60

agtggtatta aaaatatagt aagcacggta gaaacattaa cttataaaat tgagatttct    120

gataaataaa atttttccgg gagttctgta aaacttctta cggttttaac ttgataattc    180

catagggttt aaaatttcct tttgtttctt gagtttcttc tcggaatttg aacaaaaata    240

acgcgtttaa tctcgaatca gtacaatgat ggactacacg gcagttttaa aaaaccaatt    300

aataataata atcctaaaaa atgagaagaa tatttaagaa aatgtaaaag ttttccgcgg    360

aattccgcta aaattcgaaa attgaaagtg ttcaaattgc aagcgattgt gcattcagac    420

gtgacagtgt ctggggtgta ttgcgtactc gacattttaa ctgacgacac ttgtactttt    480

gcgccatact tccggagctc cagctccgcg gagccctgag caattatttt tttacttttt    540

atgaaaagct ttctatagat atcttttaag aagttacact ataattgtgc aaatcaaact    600

ggctccggac aacacaaatt tcgtctatac ctttatgatc tttttttgtt aaacaagtga    660

aacaattatt tccttttcaa actgctcttg tttcttctct ttattaatca attttttttt    720

ttttgctttg tgtaaattaa ttgtttgtcg cggatgagct aattctgagg tttgaccagc    780

agaaatctgt tttctgaaaa atcaataact cgccgcttaa ttttggtttt attcaagtga    840

tatgcaatta gaaggttcta atcatttata tctcgctgaa agatctcaga tttcaagcct    900

tttgctaagg atttaattcc taaaactttt tttgacctat catttttttgt gtgatctacc    960

gctgtaaata cttgttgttt tgcggctaaa ctctttcaat gtttccaaca agtgagccaa   1020

tatcaagtaa aaaaagaaaa atcgttttct attcaaccat tttattctgt aaataatatt   1080

aaattcatct tcacggtaca atcttcttct cccatctaat aaagtccacg cacactccgt   1140

tccgtcgttt ccctattcgt tatcattcat catcttgcca ttttcttctc cgccaaatcc   1200

cattgtctta tactaaattt catcctctcg tctgtagaag tgtatattat tgaaaaatta   1260

aagtatattt tcagg                                                     1275


<210> SEQ ID NO 148
<211> LENGTH: 358
<212> TYPE: DNA
<213> ORGANISM: Caenorhabditis elegans

<400> SEQUENCE: 148

cgcttcattt tccaacaaac caagtactgg agccatttac tataagaact aaattaaata     60

ttaaatatat cgtttcaaga attcattgga atgaggcaaa agtaaatact taggattaaa    120

aaatccagct ttatattaaa aactttaaag gcgcatatga gatgttattc gggtcccgca    180
```

gcgctcatgc ggggtacgat agtacttcaa agaattacgc gggaatttct tttatgcggg 240
aaaacggttt tttcttgttt actagttcct ttctttcgtc taattttgat atcttgtgtt 300
tttttccaat tataaaatgt ttgtctcttc ttaaatttga aattttgaaa tttttcag 358

<210> SEQ ID NO 149
<211> LENGTH: 2636
<212> TYPE: DNA
<213> ORGANISM: Caenorhabditis elegans

<400> SEQUENCE: 149
ctctccttct ttcatattct gtgtccactt ctcactcatt gaatcataca tctctatgtt 60
ttctcatagt catcatatat tgtcagctgc agaaatctca tcatttttcc aaacgaaaag 120
ctcttaagag aaatgcttgt tttctgtggg gtacagcgaa tggcttctgt gggaatgcag 180
tttgtgaatg taaatagatt gttatgcagt cttgcaaatg tgtcggaggc caaaagtaga 240
gtagacatat ttgaaattta tagctttgag tgtccttagt ctattttgat atttcatttc 300
tgctttcctc agtctctcat tccagctgca aaaaataaaa ataagaaaaa acacgaatcc 360
cgtccattcg ccattcaaca tagatcatat tcctcagatt ttttgcagaa tatgtaattt 420
ttgctgaatg ctcgctctat tgtccttcat tggttatcaa tctttttgca ttaatagctt 480
taatttttga tgttttcgaa agattaggga aaaatttttt aatgtgtctt ttgtgacttg 540
agattatatg ctacactgaa aaaattggtc gcataacatt tcagagttca aagtgttttt 600
tctttcgatt gtgtaagcgg caaaattcta ctttatcatg catttttgtt tcaatcaaaa 660
atttgatgtg atttgtacat ggcgtcggtt tggtactagt tgtccacttc ctcagccatg 720
aaaagtgtga gtaagtgata acgtttatta tctttttttga attcattcta tgtttaagct 780
acacgtattt aactagctga ctcatttcca ccaaatatgc caaaagacct ccgagatttt 840
tttttgaaga taatttcgat ttcgcagaaa aaaaaacata taagtgatgt gggggtgtgt 900
cgccttcttc agctttccat agtgaaagtt tcgtaaaaac aagcttgcta tttcattttt 960
ccccgttcta ataccttgtc gcccagaaaa aatatttata tgatcttttt caactctttt 1020
tttgtaaaaa tggccaaaga ttagctaata tttgtatacc atcaaagttc tgccaaaatc 1080
tcgttgaaac atccatcgta gaacactcat tgggttccat caatacattt tttgtgtaac 1140
atcagtcgat tgttatcatt cgtatatgca tggtcatctc aaccgccctt acgacgtctt 1200
caaccatttt ctcttctaac tctctttctc tcaatttcac ttctcactac tctagtctat 1260
tcaattcttt gaaaaggcaa aaaaaaatgc ataaaaagat gaagaagaca ttcaacagac 1320
gggtgtcttc cttattttta ttcaaatcaa aacaaatggc gaccttctta ttcttctctt 1380
ttgcccgatg attcattttc tttttccatt aattttgtta tctattgctg aataacccgc 1440
tttactgaat gtgtggactg gcatttgcca cgttgcattt tggaaaagag ccgatgtagt 1500
tcttccgggt atatgtattc acagaacgat tcataagatc agacatatag acataaaatt 1560
cagcgcattc tgccttgtgg tttgtcaact acttccgtct tttttctgca tattcatttc 1620
ccgcttctgc tgtcttgttc atgaactctt gaactttgca ctttgccctc tttttaagtt 1680
tctctcgatt gatgcagcag cagcagactg tcattcatat ttgtctagtg atttcgtagg 1740
ttcaaacaac ttattaagcg gtttcaccta aaatttcgca tcccaaaata aaagttcaat 1800
tgcgaactag aagtacccag aagcgaaatt tttttgcttc aaaaatacgg tacccggttt 1860
tcaacaaaat cgttttcaag tgacatgagc gattttcctt tttatggaaa atttctaatt 1920
caaaaataaa tatttgaaat accttttta gattattata tttattcttg gtattttctc 1980
tattcccact aaaatagact gatacgagaa cagttcttgt ttgcgcaaac tcacattttc 2040
tctctctatc tctccgtctc ttcttccgta tctctctgac ggtcccatac tctctcactc 2100
atcgtcagac accaccactt atcgatctat tttcgacgag tgagcggctg ttcgtcgcat 2160 gttttttat aacttgattc gatcaatttc atcatatctt cttcacttat ttgaatttcc 2220
gttttgaaca tcatttttcc gtcggaaagt tgaagcattt gtttgatttt ctcggtggaa 2280
gattagattt caaaactttc gaaatttaac aatagaaaaa gagaaaaaag tgtagttatt 2340
aggaaatatt ttagacaatt ttgttggcaa ttaattgaaa ttaatttctt ctttctacat 2400
attttaaaaa tgtatctttt tttctattta tatttccttt ccggggatga gcgacaatta 2460
ttttcggcag ctctacaaaa tgactgcttg agataaaatt tctacttaaa atttattgtc 2520
gaaagataga aaaatgttgc ctcaaactgt aattttgtcg agttgcccaa aataattgtc 2580
gcacacctca gattttttt tctattattt tttaaataat taaaattaca gtggaa 2636

<210> SEQ ID NO 150
<211> LENGTH: 2645
<212> TYPE: DNA
<213> ORGANISM: Caenorhabditis elegans

<400> SEQUENCE: 150
tattttgact tttgaatttt ggaggttttc aagaataggc aaacgttttg gcatcttttt 60
gaaaaaatct gattttttgg tagattctat ccactttcta aaaattctac atgctctgaa 120
caaagtggaa aatacactga aaatttcaga tcgaagtttc aggtgtttga atttgtgtaa 180
tagtctgaaa aatctgaata taagctttca aatgagacat ctcgaagaaa atgaatttgt 240
gaaaaaatcc aatttttttc taattcgagc acaaaatgat gtcggtctat cacacctcct 300
tgttgttagg tgaataattg ttaaattctt aatctttatg atataacaaa gataggcttc 360
taactacgtc acgcctacat attcaatgaa attttgtagt gctactacta tttgtgcaag 420
ccggaatatg aatgtccttt cattttttt cgtcccaaaa gtatataaaa tatctcacga 480
tatactcaga gattgggcaa caaagttcag gagaactttt gatgcacacc ggaaataaaa 540
gggcttcact gctttttttg ttgaattcat attggttttg gcgggaaata ttgaatcatt 600
attgatactt ttgaaacagg aatagacagt atttttcgta cggaaattcg ataatttccg 660
aaaatgttcg gttgcctccc tcgcccccttt tgaaattaca ggagactaaa attcgaagaa 720
tgcgtattac gaaacgtata cgcgcaaaat atctcatagc gaaaactaca gtaatttttt 780
aaattactac tgtagcgctt gtgtcgattt atgggctcga ttaaaattga gcaaaaaatt 840
tagaaaatac tatgcaggcg cggaggaaaa taaaatatcg atatcactat tcggaaacaa 900
attcatttca aaaatcgagc acgtaaatcg acacaagcgc tacagtagca atttttaaaa 960
aaattactgt agttttcgct acgagatatt ttgcgcgtca aatttgctgc gcaatacgca 1020
ttctcagaat tttgcgttac cgtaatatac acggtgaaga acacgagcca ccaggagtac 1080
ggtagccctg actttaattg caaaaaaaga gaaaacagtg aaaaaaatct gtatataatt 1140
gctattattt ttaaatttcg caaaaaaaat tagaaatgac cacattaatt ttgaattcct 1200
gcgcgaatga attctatttt ttgcgtattc ctgcaatatt tattggattt tctcttagcc 1260
taaagcctaa aacgcagaaa tttcgaaata ataaattgac catttttgaa ttattggtgc 1320
aaaattgaga aaaattgtga aaaattatac cattttttga acaattacgc tcagcttact 1380
aattgtaaga ttactcagat ttatggcaaa acacgatttt tacgccttca aaaaatccta 1440

-continued

```
gcttttggca aaacttacag gaaattaaaa aattcagaat aaaaagtaat aagatccagg   1500

aagccatgac tcgaatcatt gtagttgaac tgtatgaatg atttgatccc agcttcttcc   1560

gccaccctaa acaccccata atttccgttt tccgcttgaa taggaaatgt tgtatatttc   1620

tgtactcctt cctgaagtat taaaactcgt tttcgtttat taaactgttt ctttttttcag  1680

atcactcaac ttcctcttct caacgtcaac ttcgactcgg ctaattataa ttttatttat   1740

ttttctgatt tttttaaaat tcttgttttt tctcaaattt ccaatttcaa catcatctta   1800

ttttcaaata aaaatattta ttttgcgact ttctattaat ttgaaacagc gaatattgtt   1860

aatttattaa gtaaatttaa tcattttaga tcgttttcaa ccgattttcg agggctttcc   1920

acaaattttg tacttttaaa taaatttaaa gtttattcta ccgaaaacac tatttatttt   1980

tccacgtgga caccgccaat ttctctgaa aattctaaaa ttctggttga aaattaattt   2040

ttaaagcttc ctcacgagaa aagcgccaac gcacgaggag cgcgccagca aacccgcatt   2100

gacgcagtct cggtgcactt ctgaactcca aaacacactg ttcccgttcg atttttctcg   2160

catttttcat agtttttttc gaaattgaag cttttaaagg tgttttagac ttgattcgaa   2220

gtgaaatatt gattgattga gccggaaaat aggcaaaaag ttctggaaaa acgcgcgaaa   2280

ttaaaattcc agtgactttc gagataatga tattgatttt tccgagtaat taagttgata   2340

tccagctatt tatttttgcg tgacattcta attaccggat tttcaaagtt ttttcgaaaa   2400

aaaaacaaag caaaatcgat ttatttcgaa ttactcgcga cttctcaact ttgaagctga   2460

aaatagttag ttttgttttt tctgttatca gtgcgcgctt tttctgcaat aataacattc   2520

cgcagtacga ttttttcaaa ttttttgctt ttcgagaacg gaaaatcaag tttatttcag   2580

tgtgcacgaa aaacgagcga gattctgact tgaccagttc gttcggaatc gactcatttt   2640

tggag                                                               2645
```

<210> SEQ ID NO 151
<211> LENGTH: 1848
<212> TYPE: DNA
<213> ORGANISM: Caenorhabditis elegans

<400> SEQUENCE: 151

```
gatctgttct ttccgaaaag aagtagttaa caggtgcggc ttcactgggt ggtctcattt     60

ttcattttaa cctgttaatt tattccggct tcacctctaa tccttaatga cattaacatc    120

ttcctaatgt gtctaagctt ttcccacgga aagctaattt cctctctctt atttttctca    180

ttaccgttct ggttgagctt catcttatac cgtgaatggt ttcataatta cgtgctacat    240

aatttgttat gctggtcgag gctcaacgtt tcgaacatct ggctcttttc cttcagctaa    300

ccacaccact cttcgttaca atcccttctg cgcacacata tcctatctac cagccggaca    360

gatgctcgtt tctcggtgca aaacgttgag agttgagatc gagcagccgg ttggtagttc    420

ttaatgacaa attgccaaga ctttttctga attattttag gatttaaaac ttttctaaag    480

tattacgata gttcataatt tctttctttt ttaaaaattg gctctttttt gtaatgtatg    540

gtatctaact aaaactaggc ctcatttcca taactattct ttaaattgag ttgagctcaa    600

agagttagac agaactggtg tgaatcatag aacccacctg tgtttttact ttctttgaaa    660

aatgtcggtc acttagtcgt ctctctgtct gttccttttc ctaatcacaa gtaacaacac    720

acagtcttct ttcacatata ttatttgttg accaatcgta gggtcaacta tctagtactc    780

gagaccgcct atttgaacag agctcctcac tgtcaccaaa tgtaccgtat tgctttccgg    840
```

-continued

```
ctgttattgt tgttatcact gcttcttctt cctatcatgt tacccatcca actatacacc    900

ttagactagt catcttattg atatacattc ctcccatcca acacaacggt attctattta    960

tttatccaat tagtcatagt cgtaccacca tccagcacga aggtgcctct ttagtaaaga   1020

gtagaaagaa gaaccggatg ggaaatgttt ttgttacaaa aatgacacat attgtagtgg   1080

acagaaggag tgagacagac atgagcaagc caatttgttt ataatttctc ttctagaaaa   1140

aaatacattt ttccatactt cactagtcaa aacctttcac ctttctaata catctcgtaa   1200

accataatct tgatagttct gagcatttca atacgaaagc ttctcactgt ctagatctct   1260

gactgagtgc cctcatcaaa agtgcaatct gtcatctgtt tcctcataat cacggagcac   1320

taatttttct ctctgcgtct ctataatcag atatctctcg tcactaagaa ctttccgaaa   1380

tgtttatgct tctcatctga ccacttcggt tccgcacaaa aaagtacggc attccaaaag   1440

aaatctgatc cccctccgtt cattcgtggt ccgagtcggt gccaccagtc gttgcgcatt   1500

gaatatttgt ttggtccgtt ccccttcttc tccgactgct gacctcgggc actttgatga   1560

ccgggccacc acctcagtac ccctctatta caccctcttt gcctccgcgc atatgactcc   1620

accccttctc gtggaaggcg tgtatctccc ctcttttccg ctattccctc gatggatata   1680

tattcaaatg tatgtgtgtt cctgacggga gggcgtctcg cttgagagca tcgtcacatc   1740

ttttacaatt ttacttatga ttttacttca tcttcttctt cttactgcga ttttgatatg   1800

cattcttatg taaactatta ttattccagg tttcctcact cttttcaa                1848
```

```
<210> SEQ ID NO 152
<211> LENGTH: 1957
<212> TYPE: DNA
<213> ORGANISM: Caenorhabditis elegans

<400> SEQUENCE: 152
```

```
taggttaaca ctgataaatc ttgcagaact gttttatttt attaaatgag acattaccga     60

tctaaataaa tttacaatcc catcaaactt tctcctttat cctccagaat cccatcattt    120

tcatcggcac ttcttcaaaa gtttaaatgt gagtgaccgc ccgtctcgct ctactaatcg    180

tatatgcaaa ttttctttga tatcatagaa cctgtcatac ttctccaagt atatgaaaga    240

caattaaaac tactgagaga aagaagtagt tcgcgataaa aaagtacata taatacacct    300

tttcacctag aagagatgct ttcaacttct acttttctgg tcatatgtaa atagttgggt    360

tttttgacag tttgacaggt ttacggcagt caagacgaca aaaatggtta tcaaaaggag    420

ctggcataca gccaatacca ccagttctga tctttttacg attatcaaat tgtacatggg    480

gggttaagtt gaattttagt ttcatttttt caaaagttta aactcgaaaa ataactgaat    540

tgaaatatag tgaagttggc aatataccaa gggtagaaaa tcagacgagt gattttattt    600

ctagacaatc ttaaattgct caaattgtgg tctttctat atttgaactt ttaaatgcag    660

caatttgtga aacatacaat tgaaacaaat ttcctcaaaa actgccacca gctgaggtat    720

catgaagcct tctgttcaca catgttgcca cctaatcggt cacttatcct aattaacatt    780

cttccactaa attgtcccct agtcaccccc acttgaacga tatacacacc aactgttctc    840

gttcactaat acacttcttc cggagggatt caactggtta tattctgcag ttgtcggcag    900

gtgtgtggta gacggtgacg taatattgca cagggtgtcg gggaatgatt atgaagtcga    960

gatgcgcaac agctggtaat tgaagccacg agagaaaatg gaaaagacta tgatgagggc   1020

acaaggatag aaaaattgac tgggagtgac caaacaggcg aggtcacaat gaaattggtg   1080

aaaatggaaa ccctaaaagt aactttagat tttagaaaat agttggacga tttttcgttt   1140
```

tcaaagttca aagcatgcat tattatcatc tgaagatgca cgatttgact tgtgtgactg 1200
atatctcgtc gcgatcttac cgtaacctac agtacttcca tattaactaa agttggttcg 1260
cttcgagaca tcgggaacgt gagttatgta tttggcatta ttcgtcattt tatattctag 1320
aaagatttac attctgtcaa gttggaatat tttttcttag ccgtgcaata gaacttttgt 1380
tgaatttctc agagtacaat ttttatgacc gccgatttcc tctcgataag cattacgtta 1440
tttacctatg gttttcaact atttaatgag atttatcagg acctcccgta gttttatctt 1500
ctatttttac tcaaattttg agctcaaaaa taacaggaaa gatttaatcg aaaaaaacat 1560
atttctgaaa tccaagagca atcgcgcgct attgataatc tggtttgccg catttctcgc 1620
ggcaacaaca aagagtttga atcgaaacgc ctttttattt gaaaaaaaac ctttttttgtt 1680 ttaaaattta gtctatacgt gaatctaaca cacacaaact gttcactaat ttctctttgt 1740
tcgtcttttt accatttcat ttcgaaactc gctgtcgtct cgtttctctc accactcttc 1800
acacttttgc cgcctaatcg atcgatcttg ccgcggcgca ctcacatttt tctcttattt 1860
tcttaccggc aaaaaatgta cgttttaccg cacttttcgc ttacattact atttcaaatt 1920
ctcttatcaa aattatttca gaaacgaagt aacacaa 1957

<210> SEQ ID NO 153
<211> LENGTH: 791
<212> TYPE: DNA
<213> ORGANISM: Caenorhabditis elegans

<400> SEQUENCE: 153
catgaagaaa cagtggccgt attgggaaaa atgaacgatt tttcggcggg aataatttat 60 tttttatgt ttttctatgc gttttcgggt gttttcgggt tgctaagcga ttggttgcct 120
ttttgaatca ctagtcttgg tttttgttgt ttctgtgaat gaataattgg tttttcgagg 180
tttttttgtc aaacatgcct aaaaaataaa ttatgacgtt ttagttgatt tgtttgttct 240
ttaaacgtct gaaaataagg tttaaatcta atttattaat tataaaattc gtcaaaataa 300
gttgcgcgtc aaattatatg tattgtacgc agtgtcaaac tccaggcctc agttttcatg 360
aatttaccag cgatttttgt tataaatttt tttattgaaa tttaaaattt ttatttttca 420
accaatttgc ctcgaaaatt cgttatttcc ccattaaaaa ccgcttttct aaagtgttgc 480
gcgtcaaata aaatgcctgg tacgcaatgc acggagaatg cgcaaaggac gactgctggc 540
gcactttttg aatgcggtaa attgaggcgc gaagtttcat tcgaaaacgc gcgcgaaact 600
tcattcatcg cactttctcc gttcatttcg tcctattttt ttgtggtttt tcgcgatttt 660
ttcgcttttc tgagtgaaaa aataattttc cttcgttttt tcaatgaaaa tccgcggaaa 720
acccattttt tcccgtgaaa atccgcattt ttcgctgtat ttcataattt ttattcagat 780
ctcccgtcaa a 791

<210> SEQ ID NO 154
<211> LENGTH: 1005
<212> TYPE: DNA
<213> ORGANISM: Caenorhabditis elegans

<400> SEQUENCE: 154
ttgctgttct taattgattt cataaatatg tataaagcat taaatttgaa tatattttta 60
ataaagaaaa atcgatattc acattagagc gcgcttgcaa tttcacgatg agacctgacg 120
ataccgcgcg aattaaatcg atcgcttttt ggcctaaaat gctcattaac aattgttttt 180

```
gtagtttttta gcttaaaatt atattttaaa atccagtttg ccttgttaca tattggaaaa    240

cggtattttt agagtttttc ctcaaaaacc aagcgaaaac cttgaatttt gttccgaaaa    300

cttgttcaaa acattttttt cgttgaaaac tcaaataatt caccaattta tctattttag    360

gccgaaatct cttatttttt cagtccaaaa agcaccaaat ttggtcaaaa acctgtccaa    420

aatctaccgt accctcgtgt tgctcgtgaa atgcggtgca ttgtgtgcaa acaccgcggc    480

gtgaacatgc acactctgca acgcgggaaa tcatttcgaa aaggttttta ggcgcgtatt    540

gcccgatttt tcggctcatt tcgtgtgttt tcatttattt ttgccttctt tctccggtcg    600

cgatgcgttt aattaagttt tgcttctaaa tttcgtcaat ttcgctgaaa aaccacgtag    660

aaaacttgat aggaactgga tatcctaaaa aaaaggattt ccttgagaaa aatgggtttt    720

ttttctgaat ttcgcagtga tattcttgaa attctcagcg cagcgctccc cagacaatcg    780

atattcctaa tttttcaagc atcttgtggc tcagccagct gttctgtaat tatcgatttt    840

atttgttaca gcgtctatat aaataccta gaaagtcatc attctgcact cttaatacct    900

ttcactcgtg tgagttgcat tctccatagc aactctacct ctctccttct atctcttttt    960

ctcttttcaa atctaatttc gtttcagaga ctcccgctat aaacg                   1005
```

<210> SEQ ID NO 155
<211> LENGTH: 727
<212> TYPE: DNA
<213> ORGANISM: Caenorhabditis elegans

<400> SEQUENCE: 155

```
ttcgctttaa ctcctccaga agttgacggt ccgccagtgc ctccactagt cgtcgggagt     60

ttatggttca gtttcgcctt tttcatgtcc tccggcttca taatcgtatc atttaggcgt    120

ttgtgttttt tacgttccat tatttataag attctaaacg agaaactctt aagattttcc    180

ggaaaataat gataaaaacg gttgtgaaat tgaatgagaa taaaaaaacg aaacaagcac    240

gagtgaggca ggtgcgctcc aatgcgaatt tctttgcgcg gatgtttaaa tggttatttt    300

tttatgggaa tcgacaagtc acatgctacg ctagagagag ttttacattt tacagtcttt    360

ttggaattta ataatatata tattatcata aaatcgaata aaaattgttt cgaataatga    420

atagctttgt tttttcgtct tgacttctga aataatttta aatttgagaa aaatttgtgt    480

cgcaatatat aattattaat attattaata atgtaatttt tttataataa actgatttat    540

attttaaaaa caaaaaagga atgacaattc agtttagttt tatgaaaaac tttgaaaaga    600

caaaaataat tacagtaaac gcgctccgct agactcccca aatttgtttt tgttttccag    660

gcttgtgtcc aggcaaattc cagctttctt tttgtttcag aatttctagg tatttatctc    720

cgtgaaa                                                              727
```

<210> SEQ ID NO 156
<211> LENGTH: 2600
<212> TYPE: DNA
<213> ORGANISM: Caenorhabditis elegans

<400> SEQUENCE: 156

```
gaaaacttcg attcttatgg ttaaaacgag ccttgttagt aaaaattatt gagtgaataa     60

ataaattaga tcaagtattt tcacttctgc caaaattcaa ctaaatagaa atggttggaa    120

ttaagttaca agctaccagt ttacaaaaca ataattgaca ggtaatcgga gtgaagacag    180

tttttgcct ttgataattt tacattcaca tttaatttta cattcacata aaaaaagaat    240

cacacatttt tttcaattga caagtttttg ataaagtgga agacatcgga gatatgaccc    300
```

```
gtcaaagttg ctcagcaggg tgcaaaacta aaagaggaaa tactgtgaaa cattttgaca    360
atttagagaa atacacagcg aaagaatgaa atctaaaaaa gcgtattaac tttaactaga    420
taaacatact aacttattga ggtaaatctg agcagatcct cttcctattc ccaatattta    480
cccaattagt cttctgattg cgcacctgca tatcttaagt actcaaatac aacacacatc    540
ttgagaaatg atgactccac actcagaatg caattcacac tattagaagc catgtgcaat    600
atgaaaacaa gcttatcctg aagctgcaaa cccatttacc tcatcaatta tttgcgatgt    660
gccgacctgt tgcatggctt ccgacactgt aaggggataa tctgtttgtc ggcacgcttc    720
aaccgattaa ttggcgtgtg aaacgatact aatccagtcg attctcgact aactgtaaac    780
actttgatgc taaccgacgt gccggctaat atactctctg tgttacgtca gaatccttta    840
aatatgcaaa tatggataag gtggaatgat ctcaagaggt gtgattgggt caaattggat    900
tacgtaattc ttaagtgggc taaaggtata ctgtaactgg ggtgcaattt atgtgggaag    960
tgcggcgaag ttatattggg gttttataga ttctataact tgttacattg attttgaata   1020
gatttcaatt ttcagaaaag tgggaaaact gtatttacat tttgaaagaa atttaatgca   1080
acagaaaata gtgattggct ggaaaagtgc ccctatgtta taaacttttt gttgaagctt   1140
tgaaattttt cacaaattat tcaactgaag tctcacacgt cgaaaaatgg ccaaacaaat   1200
ttttaaaaaa tagaggcctg atcatagttt ctgccatttc atggccgtct gtgacgtcac   1260
atgaggtttt tcgactattt ggcttccagg gttttacctg tttttaattt caaaattata   1320
tattcttcag taaatctctg aaagtcacag tcgtttcagc gaactttcaa ggccgcgtgt   1380
gacgtcacac tcttgcaaag aaagctgcac gtggtgtcag gttgtcccat aacggtttgc   1440
tctacgaaaa atgcgggaat tttttcatca aaaaatgtga cgtcagcacg ttcttaacca   1500
tgcgaaatca gttgagaagt ctgcgtctaa gttcccgcgt tttttgtaga tcacaacgga   1560
atgggacatt ctgacaccat gtgaagctgg ccttgagata gttttgtaga ttcaaaatat   1620
ttttaatgtc caatatttgt tttcaaaaca ttcgttaaaa tgtgcagaat atgttaaact   1680
gaaggttcct aggtttaaaa cttcaagcta aagctttccg gctcagttct caggttcagg   1740
tctgtaatct ttctgtaagc ttgtaatctt gttagttcct cagacagact tagctgctaa   1800
atttatttca tgtctaatat tacacttcaa gagctatgag tttgtcttca taaaagtttt   1860
ggctcccata taggaacttt ggaacatcat ttgatccccg tttcgaaaac gttcgaaaat   1920
tgttttgttt ctttatttaa acccgacagt tcaaattctt tatcttgatc aaaccctttt   1980
ttttcatctg tccattcctc ggccttaacc taatttatac agtttcgcaa taacctcccc   2040
cgtgcttgct ccagtaccag ctgttgcgtc acgacttctt attttcaaaa ctcaaatctt   2100
gcatcacacc tcatcaatta atcatcctca tcaagcctgc aaacttatac ccccttctct   2160
agacccctct cctgacattt gacactcctg tggtagaggg gtgtggcctt gcctgggcgg   2220
ggcgtgcaat gagaagctgt gcacgcacac cattcattca cacccaaaac attcacaccg   2280
attagtcgta ttctaacttc tcttttcaat tcagttgata tgctggtaag tctagaaatt   2340
atttattttt gatctacata cctgtccaat attgttcgtc tccccctccc cctcctgaga   2400
aacaaatttt tgtttttgtc tgctcgcctc accctcaacc tctctctctc tggatgtgtt   2460
cgtggtgtag aaacaaaaac agatttttgt ttttttgttt tttgtttctt gttttagaac   2520
ttgtatccta gtaattgtta gacatctccc tactatcttt cccctatata aaccccccttc   2580
aaaaccttac taatttccag                                                2600
```

<210> SEQ ID NO 157
<211> LENGTH: 394
<212> TYPE: DNA
<213> ORGANISM: Caenorhabditis elegans

<400> SEQUENCE: 157
aacagaactc acccgtttct agaacaacgt ttgctatcaa ctccaccccg aaagaatcca 60
ggtggttcgt ctgacattat gctgcaattt tatgagaata ttcagacgca acaacaacgt 120
gacaaacgac gagataaaaa tctatcaagg ctgaaacaat gacaaaaaag aaatcccgac 180
aaatgaaaat ggcgcctaaa acaaactttt ttaaaggacg tcgggtttca ttcacagatg 240
ggtctcggaa cgaaatcatg gagtacggta tcacacactt gaatttgaaa gtgaacttct 300
ttatttgttt ctcttgcaag tttaaactta agtttttaat tttttctgct tgtttctcaa 360
taaaataaaa atattacttg atttgtagcg caga 394

<210> SEQ ID NO 158
<211> LENGTH: 2557
<212> TYPE: DNA
<213> ORGANISM: Caenorhabditis elegans

<400> SEQUENCE: 158
ttctgcgtga aatgtgatgt ttctacagta acccgtacaa ccaaggcatc gaacttcacg 60
acatttacga attcaaattt gaattgcaaa ctttttaatt ttatcgattt tctttctttt 120
tgagctttat caatagctct aagcgattat tcaacagaat ttcacttttt tacgcctaaa 180
tgattgaaaa tttgataaaa tatcaataat ttacggttat cctcttcgta atcttcgctt 240
tcttcccaga gtagtgaaaa tatcgacttt ttgatagaaa ctggattttt taacttccct 300
gttcgaaaaa ctatttttcc ttaaatgaga tctgaaataa ggtgataaat taataaatta 360
agtgtatttc tgaggaaatt tgactgtttt agcacaatta atcttgtttc agaaaaaaag 420
tccagttttc tagatttttc cgtcttattg tcgaattaat atccctatta tcactttttc 480
atgctcatcc tcgagcggca gcgtctcaaa gaattgtgag agcaaacgcg ctccattgac 540
ctccacactc agccgccaaa aacaaacgtt cgaacattcg tgtgttgtgc ctccttttcc 600
gttatcttgc agtcatcttt tgtcgttttt ttctttgttc tttttgttga acgtgttgct 660
aagcaattat tacatcaatt gaagaaaagg ctcgccgatt tattgttgcc agaaagattc 720
tgagattctc gaagtcgatt ttataatatt taaccttggt ttttgcattg tttcgtttaa 780
aaaaaccact gtttatgtga aaaacgatta gtttactaat aaaactactt ttaaaccttt 840
acctttacct caccgctccg tgttcatggc tcatagattt tcgatactca aatccaaaaa 900
taaatttacg agggcaatta atgtgaaaca aaaacaatcc taagatttcc acatgtttga 960
cctctccggc accttcttcc ttagccccac cactccatca cctctttggc ggtgttcttc 1020
gaaacccact taggaaagca gtgtgtatct catttggtat gctcttttcg attttatagc 1080
tctttgtcgc aatttcaatg ctttaaacaa tccaaatcgc attatatttg tgcatggagg 1140
caaatgacgg ggttggaatc ttagatgaga tcaggagctt tcagggtaaa cgcccggttc 1200
attttgtacc acatttcatc attttcctgt cgtccttggt atcctcaact tgtcccggtt 1260
ttgttttcgg tacactcttc cgtgatgcca cctgctccgt ctcaattatc gtttagaaat 1320
gtgaactgtc cagatgggtg actcatattg ctgctgctac aatccacttt cttttctcat 1380
cggcatgctt acgagcccat cataaacttt tttttccgcg aaatttgcaa taaaccggcc 1440
aaaaactttc tccaaattgt tacgcaatat atacaatcca taagaatatc ttctcaatgt 1500
ttatgatttc ttcgcagcac tttctcttcg tgtgctaaca tcttattttt ataatatttc 1560
cgctaaaatt ccgatttttg agtattaatt tatcgtaaaa ttatcataat agcaccgaaa 1620
actacaaaaa atggtaaagt cttttaaatc ggctcgacat tatcgtatta aggaatcaca 1680
aaattctgag aatgcgtact gcgcaacata tttgacgcgc aaaatatctc gtagcgaaaa 1740
ctacagtaat tctttaaatg actactgtag cgcttgtgtc gatttacggg ctcaattttt 1800
gaaaataatt tttttttcg aattttgaca acccgtaaat cgtcacaagc gctacggtag 1860
tcatttaaag gattactgta gttctagcta cgagatattt tgcgcgccaa atatgatgcg 1920
taatacgcat tctctgaatt ttgtgtttcc gtaataattt cacaagattt tggcattcct 1980
ctttaaaggc gcacggattt attccaatgg gtctcggcac gcaaaaagtt tgatagactt 2040
ttaaattctc cttgcatttt taattcaatt actaaaattt tcgtgaattt ttctgttaaa 2100
atttttaaaa tcagttttct aatattttcc aggctgacaa acagaaacaa aaacacaaca 2160
aacattttaa aaatcagttt tcaaattaaa aataacgatt tctcattgaa aattgtgttt 2220
tatgtttgcg aaaataaaag agaactgatt caaaacaatt ttaacaaaaa aaaaccccaa 2280
aattcgccag aaatcaagat aaaaaattca agagggtcaa aattttccga ttttactgac 2340
tttcaccttt tttttcgtag ttcagtgcag ttgttggagt ttttgacgaa aactaggaaa 2400
aaaatcgata aaaattactc aaatcgagct gaattttgag gacaatgttt aaaaaaaaac 2460
actatttttc caataatttc actcatttc agactaaatc gaaaatcaaa tcgtactctg 2520
actacgggtc agtagagagg tcaaccatca gccgaag 2557

<210> SEQ ID NO 159
<211> LENGTH: 284
<212> TYPE: DNA
<213> ORGANISM: Caenorhabditis elegans

<400> SEQUENCE: 159
aaattcgagg aattttagat ttcatcttga aatttgcaat ggaaaaaata attattcaaa 60
gaaaatcaca gaaaatgcaa caaaaaaaac aaaaaaagaa caaaaaacaa gtcgaaaagt 120
gcgcccgggt cgtttgctga cgcatctctt caaacgagac gcgctgctgg cgcacttctc 180
gtgccctgtg cgtgcatttc cgcaacaaaa ttcaacactt gttttgaaac gcaccgccct 240
gtttcttttt tcaattttga taagaaaatc agcattgttt cagg 284

<210> SEQ ID NO 160
<211> LENGTH: 405
<212> TYPE: DNA
<213> ORGANISM: Caenorhabditis elegans

<400> SEQUENCE: 160
tagaaacatg tttcccgtaa gtgacctatc cagtgaaaca aaaacatgtt tctgtccgcc 60
ttccttccat cggtggaggt gcatgctaga ttgcctccta aactctaata cctaaaattt 120
taataattta ttgacaacat acagtttcac cgataaccga cactcttatt ttttctgatc 180
ctgactattc tgttcattat ttcagctcct atcatagaac gatctttcca gatcttggac 240
aagtcacagt tacaggtaat tttttcaaca ggtgtttgta taatgtctta gtttctgtaa 300
aattgtttta tcatgtaaaa tatttcagat tattcgaggg cagaaaaacg tgatattact 360
attggagagg aattgacaaa gttgtgtgat aaatttaatt ttgag 405

<210> SEQ ID NO 161

<211> LENGTH: 899
<212> TYPE: DNA
<213> ORGANISM: Caenorhabditis elegans

<400> SEQUENCE: 161

```
cgagtttctt gtgagaacca aaaactattc ctctgcaaga aaaaatttat taatccggca     60
taaaatactt tttattacaa taggaacttc acagtcgctt cctccgacgc tttgagcggt    120
acatcgatgc ttatcaccat gctgattgtt acctttctta cccgtttgac tttctgcaat    180
ttttaactgc aaagatgttt aatgcagata ctcgaaagaa acgaaaaaat gataaaaaag    240
tgaaaaaccc caaaaataaa tttgaaaact ccgcgtaagc ttgctcgatc gctgcgagac    300
cattgcatac cgtactactt ctttaaaggc gcacacatca aatctagctg tttcgtgaca    360
ggacccagca atgttcagcc gcgaagtttt gaatcgccat tttttttaa tttctagaat    420
gtttatagtt ttgctttcga tgagattttt aagcattatg aggaacaaat ttttttaaaa    480
actttagaag ttttaaaatt taattttgcg attatgcttt gctttcgcgt gtcctttccg    540
ttgttcctcg ctccaaatat atcacagtaa ttaaccacta cttatgtagt tatcacgttt    600
ctaaaaatat aaattcattt ttatttctct attgattcgg tttgttgctc ttcttgtctc    660
aatcttgtgc tactgccgaa taccctgcta atttttcgtt ttcagtcatt cgattcactt    720
gggttgttgt ttaaaatggt aagatttttg caggttactt tctttcccat gaggtaaatg    780
catttattgc gggtgcgctc tatcgcacga cgccgcgaat cattgtattt caaattgatt    840
ttcctgttgc acttttatta gttacaattt ttattagtta tttttagttg gattcgaca     899
```

<210> SEQ ID NO 162
<211> LENGTH: 1290
<212> TYPE: DNA
<213> ORGANISM: Caenorhabditis elegans

<400> SEQUENCE: 162

```
gaaaacctaa aatgaacaaa attttttgtc attaaataac aacgcttcgg ttaacgcttg     60
aaattgatat tcggaaaata aaaagcctga tttttgttcg atttctgaaa tatatttcat    120
gctttacccg tttttaattg cgaacaattc taaatttgaa atataatttt caatcaacga    180
aaaacaattt tcaagataaa aaattattat ataaatttaa gctaagtatt aataaattaa    240
taagtaatag tattcaaaaa tcatagaatc ttgcaagaaa aaatgtttta aagatttaat    300
agttcgagtg attgaaaaac gaatagtact ttaaaaaata atgctttaag gcagaaaagt    360
gatataaaaa ttaagctcaa aagggcaaaa gataaggtta atgtccagtt ttggttttaa    420
aatggttcgg acacaatgta catagtagac atttgggtgt cctcttcctt ctcttttccc    480
cattgcgtcc actgaccctc cttgctgtat gtctgcgcat cgtctttttc tacacttttt    540
ccttttccct ggcccgttcc tatcggtgcc tttcacacac gcgagcggca gtggacgaga    600
cgggagggcg aggtgttgaa caagagtaca gcaagtgcgc gccatcgaaa aagcggaaaa    660
aaaaatttca aatggcgcta ctttgaaaat tgagaattct gtatttactg ccagttttac    720
ttgcatttaa atttccatgt tttctattct aaaacgaaaa tctatctaag aaaaccctta    780
ataaaaacct ataaatcata aattgtgatt cttaaattcg aaaatatgtt cgttcaactt    840
gacgcctaga aatatgtgga cttaatcctg ttataaatca gtagttgacg acaaaaaatag    900
tagagcagca aaagcagttc taacttgtga aaaacatgaa agttcttgtt ttcgtcaagc    960
gaacgggggc tcgaggaagg acttggcacg tgtctctagg ccatgttttt ctcaattttt   1020
gttgctctag agaaagcttt tgctattgat tatgggacaa tcttggggat atgaaggtaa   1080
```

-continued

```
cattttaaaa ataagtttag gtaaatgtgt agcataattt ttgaaaaaaa aagctccact   1140

gttaaaaatg ccgattttag ggattgcgaa acgttcacta tgtacacata aatggctata   1200

taatttgaat ttgcattcaa taaatctttt ccttccaatt gtatgtttta acttaaaaat   1260

aattaattaa aattatctca ggagtcaaaa                                    1290
```

TRANSGENIC BIOSENSORS

CROSS-REFERENCE TO RELATED APPLICATIONS

The application claims priority to U.S. provisional patent application No. 61/488,720, filed May 21, 2011 which is hereby incorporated by reference in its entirely.

BACKGROUND

One of the most difficult problems in drug discovery and toxicology is the ability to extrapolate results from early studies at the biochemical and cell-based level to effects in humans. The resulting inefficiencies in this extrapolation result in a high attrition rate in drug development and are an enormous drain of resources, effectively passing the buck on to consumers in one manner or another.

From the pollutants in the air we breathe to side-effects from drugs necessary for our health, we are surrounded by chemicals in our environment. It is important to determine which of these chemicals pose health risks and which are relatively harmless. Over 50,000 chemicals are in need of accurate toxicology assessment (Whittenberger J. Toxicity testing: strategies to determine needs and priorities. Washington D.C.: National Academy Press; 1984; and Kreweski D. Toxicity Testing in the 21st Century: A Vision and a Strategy. 500 Fifth Street, NW Washington, D.C. 20001: National Academy Press; 2007). Understanding the mechanism of action is becoming recognized as a critical parameter for accurate toxicology assessment (Lock et al. Toxicol. Lett. 2003 April; 140-141:317-322.). However, there are limited choices in the marketplace for comprehensive tests to report toxicology pathway activation. The currently available methods are tedious in application or removed from a whole-organism format. As a result, toxicology researchers are in need of fast and efficient high-throughput methods to detect toxicology pathway activation.

Methods using intact cells or whole organisms are challenging to apply in high-throughput formats. Whole organism approaches are the most reliable in capturing accurate correlative toxicity data because the tests are performed in a native-context platform. Yet these approaches are costly for high-throughput implementation with classical models such as the mouse. Tissue must be harvested and either RNA extracted for transcription analysis (microarrays (Shioda J. Environ. Pathol. Toxicol. Oncol 2004; 23 (1):13-31), RNA-seq (Kamb Res. Toxicol. 2011 August; 24 (8):1163-1168.), rtPCR (Walker J. Biochem. Mol. Toxicol. 2001; 15 (3):121-127.)) or metabolic analysis by specific biochemical assay (P450 (Guengerich Chem. Res. Toxicol. 2008 January; 21 (1):70-83) and MDR (Sarkadi Physiol. Rev. 2006 October; 86 (4):1179-1236.) transporter activity). Furthermore, tissue specific toxicity mandates careful dissection to allow accurate capture of toxicology data (such as sedimented-tissue lysates of liver, brain, and other tissues). As a result, intact organism toxicity approaches are difficult to implement in cost effective high-throughput strategies. In vitro analysis on cell culture systems is a method more amenable to high-throughput analysis. The common approach is to transfect primary cultures with reporter plasmids and detect gene activation as increased expression of reporter genes. These platforms are expensive, time consuming to maintain, and can be plagued with reproducibility problems. An additional drawback of cell culture transfection methods is the lack of native context. Frequently cell culture responses can give hypersensitive results and these results disappear upon whole organism analysis. Creation of transgenic immortalized lines can solve some reproducibility issues (Youdim et al. Drug Metab. Dispos. 2007 February; 35 (2):275-282), but these lines are even further removed from native context and can give misleading results. Better methods are needed both in the research setting and in the market place.

Other public health related areas are also in need of improved methods for predicting effects in humans and animals including air quality, cosmetics, apparel, infant food, drinking water, environmental toxicology, food additives, nutraceuticals, manufacturing, organic foods, plastics, pesticides, industrial toxicity, toys, and waste water. Just about any area where exposure of potential toxins to humans or animals occurs is an area where improved method for detecting toxicological liabilities would be a benefit.

BRIEF SUMMARY

The described systems and methods relate to transgenic organisms and their use as biosensors. In some implementations, the described systems and methods include a first population of transgenic organisms that includes a first constitutively expressed reporter gene, and a first transgene that includes a first inducible promoter from a response pathway gene, wherein the first inducible promoter is operably coupled to a first reporter gene.

In other implementations, the population of transgenic organisms further includes a second population of transgenic organisms having a second transgene that includes a second inducible promoter that is operably coupled to a second reporter gene, wherein the second population of transgenic organisms further includes a second constitutively expressed reporter gene, and wherein the first inducible promoter and the second inducible promoter each include a promoter that is derived from a different gene.

In still other implementations, the described systems and methods comprise an object that includes a transgene, a transgenic organism, or a construct, wherein the object includes a promoter region having a promoter, a fragment of the promoter, or a homolog of either the promoter or the fragment of the promoter, wherein the homolog includes at least about a 95% identity to the promoter or the fragment of the promoter, wherein the promoter region is operably coupled to a reporter gene, wherein the reporter gene encodes a protein selected from a fluorescent protein and a luminescent protein, and wherein the promoter region includes a promoter region for a gene selected from: *C. elegans* genes cdr-1, gcs-1, ugt-1, gst-38, hsp-60, hsp-16.41, mtl-2, hsp-16.2, gst-4, ugt-13, hsp-3, hsp-6, hsp-4, hsp-1, skn-1, dnj-13, daf-21, Hsp-17, cyp-13A7, cyp-14A3, cyp-35A2, zyg-12, ZK742.4, ZK742.3, fkb-1, fkb-2, fkb-3, fkb-4, fkb-5, fkb-6, fkb-7, fkb-8, fmo-1, fmo-2, fmo-3, fmo-4, fmo-5, ftn-1, ftn-2, fzy-1, gen-1, glp-1, gsr-1, gst-1, gst-23, gst-25, gst-41, H01G02.2, haf-6, syp-2, T05A12.4, T05G5.3, T06E6.2, T07F12.4, Hsp-12.2, T05E11.3, Cnx-1, Crt-1, cyp-35A1, cyp-35C1, cyp-35A3, pqe-1, cyp-37B1, cyp-35B2, cyp-35B1, cyp-22A1 (daf-9), cyp-14A5, cyp-35B3, cyp-34A6, daf-16, exo-3, nth-1, pme-1, ung-1, xpa-1, mrt-2, ercc-1, ZK697.8, ZK287.5, haf-7, hda-1, hda-10, hda-11, hda-2, hda-3, hda-4, hda-5, hda-6, hdac-1, hif-1, him-1, him-14, him-3, him-4, him-6, hmg-3, hmg-4, hmg-5, hpr-17, hpr-9, hrdl-1, hsf-1, hsp-1, hsp-16.48, tbb-4, tnc-2, top-3, tor-2, trx-2, xpf-1, xpg-1, rad-23, mlh-1, msh-2, msh-4, msh-5, msh-6, brc-1, brc-2, rad-50, cku-70, lin-35, mei-1, cki-1, cki-2, cep-1, ced-3, ced-9, ced-13, vem-1, dhs-23, sodh-2, dnj-19, Xbp-1, hsp-16.49, hsp-2, htp-1, htp-3, hus-1, imb-3, ire-1, irk-1, K07C5.2, K07C5.4, K08F4.1, K11G12.5, kin-18, lagr-1, let-2, let-92, lig-1, lig-4, lim-4, lin-12, lin-44, lin-49, lrk-1, lst-3, M18.5, vps-41, W01A11.1, W02C12.1, W03G1.5, W06H8.2, Hipr-1, cdc-48.1, cdc-48.3, Ubq-1, Ubq-2, Gst-10, Gst-13, f25d1.5, fil-1, k10h10.6, hsp-70, f44e5.4, f44e5.5, hsp-16.11, hsp-16.1, nurf-1, aip-1, y43f8b.2, Dod-17, Dod-24, C55A6.7, F56D5.3, cyp-13A11, cyp-13A6, cyp-25A4, mac-1, mboa-2, mdf-1, mdf-2, mec-14, med-1, mel-28, misc-1, mnat-1, mre-11, mrp-1, mrp-2, mrp-3, mrp-4, mrp-5, mrp-6, mrp-7, mrp-8, mspn-1, mus-1, mut-2, mxl-1, mxl-2, mxl-3, ndx-1, Y55B1AL.2, Y56A3A.33, Y66D12A.15, Y66D12A.15, Y73C8C.10, cyp-29A2, cyp-31A1, cyp-31A3, cyp-33B1, cyp-33E1, cyp-34A10, cyp-34A9, cyp-35A4, cyp-35D1, abl-1, abu-1, acr-14, acr-22, agt-1, ahr-1, air-2, ama-1, apa-2, apn-1, apn-1, aps-2, arf-1, asp-5, atf-5, atgr-7, ndx-4, nft-1, nhr-6, nol-5, npl-4.2, nuc-1, odc-1, paa-1, pas-4, pat-10, pcn-1, pdi-1, pdi-2, pdi-3, pdr-1, pek-1, pgp-1, pgp-10, pgp-2, phi-37, phi-44, phi-9, pink-1, pme-2, pme-3, T08D2.4, T08D2.7, T08H10.1, T10B5.8, T13A10.2, atl-1, atm-1, B0222.9, B0432.2, B0495.2, B0563.7, brd-1, C01G5.5, C06A1.6, C06H2.3, C07D8.6, C08H9.3, C09D4.3, C11E4.2, C25A1.5, C30G7.5, C35C5.2, C35D10.2, C35D10.6, C37A2.4, C37C3.6a, C44H4.4, C56G3.2, catp-6, cbn-1, F17A9.5, F18A1.5, F19G12.2, F23C8.9, F36A4.15, F43D2.1, F43G6.5, F44B9.8, F45E12.3, F49E12.6, F52B5.2, F52C12.1, F53C11.5, F53F1.2, F53F1.3, F53F10.2, F55B11.1, F57B10.5, F57B10.6, F58F9.1, F59A2.3, F59F4.1, fan-1, fdps-1, figl-1, trxr-1, tut-1, uba-1, ubc-1, ubc-20, ccch-1, cct-1, cct-2, cct-3, cct-4, cct-5, cct-6, cct-7, cct-8, cdc-14, cdc-48.2, cdk-7, ced-4, cel-1, cft-1, chk-1, chk-2, chn-1, cku-80, cle-1, clk-2, clpp-1, cmd-1, cnb-1, col-135, pme-4, pme-5, pmrt-5, pms-2, png-1, polh-1, polk-1, prx-6, ptl-1, R02D3.3, R03D7.2, R05D11.6, R05F9.10, R09H10.3, R10E4.9, R13D11.4, R151.6, rab-1, rab-7, srp-2, ssc-1, sti-1, sulp-7, sut-1, sut-2, wrn-1, xpc-1, Y110A7A.4, Y38F1A.5, Y38H8A.3, cps-6, crb-1, crn-1, crn-2, crn-3, crn-4, crn-5, crn-6, crp-1, csb-1, ctl-2, ctl-3, cul-1, cul-2, cul-4, cul-5, cyh-1, cyn-1, cyn-10, cyn-11, cyn-12, cyn-13, cyn-14, cyn-15, cyn-16, rad-51, rad-54, rbx-1, rbx-2, rcf-3, rcq-5, rec-8, rev-1, rfc-1, rfc-4, rfl-1, rme-8, rnf-121, rnh-1.0, rpa-1, rpa-2, rpn-10, rps-19, rps-26, T23G5.6, T26A5.5, T27E9.1, tag-353, tars-1, tbb-2, Y73F8A.24, ymel-1, ZC168.4, ZC395.10, ZC443.1, cyn-17, cyn-2, cyn-3, cyn-4, cyn-5, cyn-6, cyn-7, cyn-8, cyn-9, cyp-13A12, cyp-13A4, cyp-14A2, cyp-33C1, cyp-33C2, cyp-33C9, cyp-33E2, cyp-42A1, cyp14A2, cyp33C9, cyp34A6, D1081.8, D2023.4, daf-1, daf-14, daf-3, rpt-3, rpt-4, rpt-5, rpt-6, rtel-1, san-1, scav-1, scav-2, scav-3, scav-4, scav-5, scc-3, sdz-8, sec-22, sep-1, set-25, set-26, set-8, set-9, unc-11, unc-26, unc-57, uri-1, usp-14, vps-4, T15B7.2, T16H12.4, ugt-62, Y39G8B.1, Y39G8B.2, daf-5, daf-7, daf-8, dbl-1, ddb-1, dhs-22, djr-1.1, dna-2, dog-1, drh-3, drp-1, dut-1, E01A2.1, eft-2, egl-1, eif-2, emb-9, epg-2, eps-8, exo-1, F09E5.2, F14F9.5, F15E6.6, F16A11.2, F17A9.4, sft-4, sgg-1, sin-3, sir-2.1, sir-2.2, sir-2.3, sir-2.4, skr-15, slt-1, slx-1, smf-1, smk-1, sod-1, sod-2, sod-3, sod-4, sod-5, spas-1, ugt-61, Y43E12A.1, Y43F8C.13, Y48G1BL.2, Y50D7A.1, Y50D7A.2, Y54E10A.3, ufd-1, ugt-22, ugt-52, ZK1128.4, ZK1290.5, and Y39H10A.7; ABCE-1, ABCF-1, ABCF-2, ABCF-3, ABT-1, ABT-2, ABT-4, ABT-5, ABTM-1, acr-14, acr-22, ahr-1, akt-1, akt-2, apa-2, ape-1, apn-1, aps-2, ard-1, arf-1, arf-1.1, arl-7, asp-5, atf-5, atgr-7, B0222.9, B0432.2, B0495.2, B0563.7, bec-1, bmk-1, C01B10.7, C01G12.5, C01G5.5, C01H6.4, C03A7.12, C03A7.13, C04F12.1, C05C9.1, C06A1.6, C06E4.3, C06E4.4, C06E4.6, C06G1.1, C06H2.3, C07A9.13, C07D8.6, C08H9.3, C09D4.3, C11E4.2, C16C8.14, C23G10.6, C25A1.5, C25A1.6, C27D8.4, C28H8.11, C30G12.2, C30G7.5, C31H1.1, C32D5.12, C33E10.10, C35B1.5, C35C5.2, C35D10.2, C35D10.6, C37A2.4, C37C3.6a, C41A3.1, C44H4.4, C46H11.2, C55A6.3, C55A6.4, C55A6.6, C55C3.1, C55H1.1, C56G3.2, cah-5, car-1, catp-6, cbn-1, ccch-1, cct-2, cct-3, cct-4, cct-5, cct-6, cct-7, cct-8, cdc-14, cdr-5, ced-1, ced-10, ced-12, ced-13, ced-2, ced-5, ced-6, CED-7, ceh-20, ceh-30, ces-1, ces-2, cgh-1, chn-1, cit-1.2, ckb-2, cle-1, clec-149, clpp-1, cmd-1, cnb-1, Cnx-1, cnx-1, col-135, coq-6, cpb-3, crb-1, crp-1, Crt-1, crt-1, csp-1, csp-2, csp-3, ctl-1, cul-1, cul-2, cul-3, cul-5, cyn-1, cyn-10, cyn-11, cyn-12, cyn-14, cyn-15, cyn-16, cyn-17, cyn-2, cyn-3, cyn-4, cyn-5, cyn-6, cyn-7, cyn-8, cyn-9, CYP-13A1, CYP-13A10, CYP-13A2, CYP-13A3, CYP-13A5, CYP-13A8, CYP-13B1, CYP-13B2, CYP-14A1, CYP-14A4, CYP-23A1, CYP-25A1, CYP-25A2, CYP-25A3, CYP-25A5, CYP-25A6, CYP-29A3, CYP-29A4, CYP-31A2, CYP-32A1, CYP-32B1, CYP-33A1, CYP-33C11, CYP-33C3, CYP-33C4, CYP-33C5, CYP-33C6, CYP-33C7, CYP-33C8, CYP-33D1, CYP-33D3, CYP-33E3, CYP-34A1, CYP-34A2, CYP-34A4, CYP-34A5, CYP-34A7, CYP-34A8, CYP-35A5, CYP-36A1, CYP-37A1, CYP-43A1, CYP-44A1, cyp14A2, cyp14A5, cyp33C9, D1007.16, D1054.8, D1081.8, D2023.4, dad-1, daf-1, daf-14, daf-21, daf-3, daf-5, daf-7, daf-8, DAF-9, dbl-1, DC2.5, dhs-1, dhs-10, dhs-11, dhs-12, dhs-13, dhs-14, dhs-15, dhs-16, dhs-18, dhs-19, dhs-2, dhs-20, dhs-21, dhs-24, dhs-25, dhs-26, dhs-28, dhs-29, dhs-3, dhs-30, dhs-31, dhs-4, dhs-5, dhs-6, dhs-8, dhs-9, djr-1.1, dnj-11, dnj-25, dnj-27, dnj-7, Dod-17, Dod-24, dop-1, dop-1, dop-3, dop-3, dpl-1, dpr-1, drh-3, duox-2, dut-1, E01A2.1, E04F6.15, eat-3, efl-1, efl-2, eft-2, egg-1, egg-2, egl-38, emb-9, eor-1, eor-2, epg-2, eps-8, exos-3, F02C12.2, F07A11.2, F09E5.2, F10D11.6, F10D2.12, F10D2.8, F10D7.3, F12E12.11, F14D12.1b, F14F9.5, F15E6.6, F16A11.2, F17A9.5, F18A1.5, F19G12.2, F20G2.1, F20G2.2, F22D6.15, F22E5.6, F23C8.9, F26D2.15, F28A10.1, F28H7.2, F30B5.4, F32A5.8, F36A4.15, F43G6.5, F44B9.8, f44e5.4, f44e5.5, F45E12.3, F46H5.2a, F49E12.6, F52B5.2, F52C12.1, F53C11.5, F53F1.2, F53F1.3, F53F10.2, F54C1.1, F54F3.4, F55A11.6, F55B11.1, F55E10.6, F56A4.4, F57B10.5, F57B10.6, F58F9.1, F59A2.3, F59E11.2, F59F4.1, fan-1, fasn-1, fdps-1, fil-1, fipr-24, fis-1, fkb-1, fkb-2, fkb-3, fkb-4, fkb-5, fkb-6, fkb-7, fkb-8, fnta-1, ftn-1, ftn-2, gab-1, gad-3, gale-1, gdi-1, ggtb-1, gla-3, gld-1, glp-1, glrx-10, gsr-1, gst-11, gst-12, gst-14, gst-15, gst-16, gst-18, gst-19, gst-2, gst-20, gst-21, gst-22, gst-24, gst-26, gst-28, gst-29, gst-3, gst-30, gst-31, gst-32, gst-33, gst-34, gst-35, gst-36, gst-39, gst-40, gst-42, gst-43, gst-44, gst-5, gst-6, gst-8, gst-9, gstk-1, gstk-2, gsto-1, gsto-2, gsto-3, H01G02.2, H04M03.3, H06H21.9, H10D18.6, H23N18.4, HAF-1, HAF-2, HAF-3, HAF-4, HAF-8, HAF-9, hda-10, hda-11, hda-5, hi-14, hif-1, him-10, him-4, hke-4.1, hlh-2, hlh-3, HMT-1, hpo-15, hps-1, hps-60, hsd-1, hsd-2, hsd-3, hsf-1, hsp-1, hsp-16.1, hsp-16.1, hsp-2, hsp-60, icd-1, ikb-1, imb-3, ing-3, irk-1, irp-1, irp-2, itr-1, jkk-1, jnk-1, K02E11.3, K02E11.4, K02E11.5, K02E11.6, K02E11.7, K02E11.9, K04A8.10, K07C5.2, K07C5.4, K08F4.1, K10F12.4, K11D12.6, K11G12.5, kin-18, kin-4, lagr-1, lbp-1, lbp-2, lbp-3, lbp-4, lbp-5, lbp-6, lbp-7, lbp-8, lbp-9, let-2, let-23, let-60, let-92, lim-4, fin-1, lin-12, lin-3, lin-31, lin-44, fin-49, lip-1, lips-11, lrk-1, lst-3, M18.5, M57.2, mab-5, maoc-1, mca-2, mec-14, med-1, mei-2, mek-1, mek-2, mel-26, mev-1, misc-1, mlt-7, mpk-1, mtl-1, mus-1, mut-2, mxl-1, mxl-2, mxl-3, nas-39, ncs-3, ndx-4, nhr-181, nhr-6, nhr-64, nol-5, npl-4, npl-4.2, nrf-5, nsy-1, nurf-1, odc-1, paa-1, pag-3, pah-1, pas-4, pat-10, pax-2, pdi-1, pdr-1, pek-1, PGP-11, PGP-12, PGP-13, PGP-14, PGP-15, PGP-3, PGP-4, PGP-5, PGP-6, PGP-7, PGP-8, PGP-9, phi-37, phi-44, phi-9, pink-1, pkc-2, pmk-1, pmk-2, pmk-3, PMP-1, PMP-2, PMP-3, PMP-4, PMP-5, pmrt-5, png-1, polq-1, pqe-1, pqn-60, prdx-2, prx-1, prx-5, psr-1, ptl-1, ptp-3, ptp-3, pxn-2, qdpr-1, R03D7.2, R05D11.6, R05D8.7, R05D8.9, R05F9.10, R07B7.4, R07B7.5, R09H10.3, R10E4.9, R119.3, R11A8.5, R13D11.4, R151.6, rab-1, rab-5, rae-1, rcf-3, rcq-5, rfc-1, rfl-1, rfp-1, rgef-1, rgs-2, rgs-2, rme-8, rnf-1, rnf-121, rnh-1.0, rnp-2, rpa-2, rps-19, rps-26, rtel-1, scav-1, scav-2, scav-3, scav-4, scav-5, sdz-8, sdz-8, sec-22, sek-1, sel-10, sel-8, sem-5, ser-3, set-25, set-26, set-8, set-9, sex-1, sft-4, sgg-1, skr-15, slt-1, smf-1, smk-1, smo-1, sod-2, sod-4, sod-5, srp-2, srp-7, sti-1, sulp-7, sup-9, sup-9, sut-1, sut-2, syp-2, T01G6.1, T01G6.10, T05A12.4, T05G5.3, T06E6.2, T07F12.4, T08D2.4, T08D2.7, T08H10.1, T10B5.10, T10B5.8, T13A10.2, T15B7.2, T16G1.6, T19B4.1, T19C3.5, T19H12.3, T21B4.4, T23G5.6, T25G12.2, T26A5.5, T27E9.1, tag-124, tag-353, tag-63, tars-1, tbb-2, tbb-4, tbh-1, tnc-2, tor-2, tra-1, trx-2, trxr-1, tut-1, uba-1, ubc-14, ubc-20, ubxn-4, ugt-10, ugt-11, ugt-12, ugt-14, ugt-15, ugt-16, ugt-17, ugt-18, ugt-19, ugt-2, ugt-20, ugt-21, ugt-23, ugt-24, ugt-25, ugt-26, ugt-27, ugt-28, ugt-29, ugt-3, ugt-30, ugt-31, ugt-32, ugt-33, ugt-34, ugt-35, ugt-36, ugt-37, ugt-38, ugt-39, ugt-4, ugt-40, ugt-41, ugt-42, ugt-43, ugt-44, ugt-45, ugt-46, ugt-47, ugt-48, ugt-49, ugt-5, ugt-50, ugt-51, ugt-53, ugt-54, ugt-55, ugt-56, ugt-57, ugt-58, ugt-59, ugt-6, ugt-60, ugt-63, ugt-64, ugt-65, ugt-7, ugt-8, ugt-9, unc-11, unc-2, unc-26, unc-36, unc-36, unc-43, unc-43, unc-57, unc-73, uri-1, usp-14, vit-1, vit-2, vit-3, vit-4, vit-5, vit-6, vps-11, vps-16, vps-18, vps-33, vps-39, W01A11.1, W01B11.6, W02C12.1, W03F9.9, W03G1.5, W10C8.4, wah-1, WHT-1, WHT-2, WHT-3, WHT-4, WHT-5, WHT-6, WHT-7, WHT-8, WHT-9, Y110A7A.4, Y23H5A.2, Y38F1A.5, Y38H6C.17, Y38H8A.3, Y39G8B.1, Y39G8B.2, Y39H10A.7, Y41C4A.11, Y43D4A.2, Y43E12A.1, y43f8b.2, Y43F8C.13, Y45G12C.3, Y47D3A.22, Y47D3A.29, Y47G6A.21, Y47G6A.22, Y48G1BL.2, Y50D7A.1, Y53G8B.1, Y54E10A.3, Y56A3A.33, Y66D12A.15, Y71G12B.4, Y73B6A.3, Y73C8C.10, ymel-1, ZC168.4, ZC395.10, ZC443.1, ZC513.1, ZC513.2, ZK1290.5, ZK287.5, ZK550.6, ZK616.8, ZK697.14, ZK697.8, ZK742.3, ZK742.4, ZK829.1, and zyg-12; and homologous genes from an organism selected from *Danio rerio* (zebrafish), *Drosophila melanogaster, Daphnia* spp., and *Xenopus laevis*.

In yet other implementations, the described systems and methods include an object selected from a transgene, a transgenic organism, and a construct, wherein the object comprises a promoter region that includes a promoter, a fragment of the promoter, or a homolog of either the promoter or the fragment of the promoter, wherein the homolog has at least about a 95% identity to the promoter or the fragment of the promoter, wherein the promoter region is operably coupled to a reporter gene of an inducible reporter, wherein the reporter gene encodes a protein selected from a fluorescent protein and a luminescent protein, and wherein the promoter region includes a sequence selected from those found in SEQ ID NO:1 to SEQ ID NO:162.

BRIEF DESCRIPTION OF THE DRAWINGS

FIG. 1A comprises (1) toxicity profiling data analyzed for genes involved in response pathways (e.g., qPCR, microarray, RNA seq, and/or RNAi screens from literature), (2) promoter discovery (e.g., bioinformatic scan using ModENCODE ChIP-seq data and bioinformatics scan with MultiZ alignment for 5' conserved elements), and (3) promoter isolation (e.g., design primers for region of interest and amplify from wild-type DNA).

FIG. 2A shows the initial plate layout before addition of a selected agent.

FIGS. 3A, B, and C show the fluorescence plate-reader sensitivity and toxin response. FIG. 3 A shows 2-fold dilutions starting with 200 worms per well, assayed in duplicate, were exposed to heat shock (34° C. for 1 hour) and allowed to recover for 16 hr 15 C. FIG. 3B shows Arsenic and FIG. 3C shows cadmium responses: 24 hr exposure, ~600 worms per well, assayed in triplicate.

FIGS. 4A, B, and C show the population effects of chronic toxin exposure.

FIG. 4A shows chronic exposure was assayed for effect on population size during 72 hr exposure to cadmium at various concentrations. FIG. 4B shows raw data profiles show bimodal response in fluorescence intensity over the titration range tested. FIG. 4C shows population-normalized response curves show single-mode effect of cadmium on fluorescence intensity.

FIGS. 5 and B shows the results of the dual reporter configuration for population normalization. FIG. 5A shows uninduced vs. FIG. 5B which shows induced (30° C., 1 hr) nematodes (hsp-16::hRFP, unc-47::GFP) were imaged in green and red channels. FIG. 5A is the control worms (top panel is a photograph of the worm, the middle panel is the GFP expression, and the bottom panel is the RFP expression). FIG. 5B is the heat shock treated animal (top panel is a photograph of the worm, the middle panel is the GFP expression, and the bottom panel is the RFP expression). Expression of fluorescent protein shows up as lighter shaded areas in the images. The images show significant induction of RFP in the heat shock treated animals. The equation used for normalization using values in the control animals where $R_i$ is the value measured for RFP fluorescence in the induced animal, $G_i$ is the value from GFP fluorescence in the induced animal, $R_c$ is the value for RFP fluorescence in the control animal and $G_c$ is the value of GFP fluorescence in the control animal.

FIGS. 6A and B shows the NIEHS findings with hsp-16::hRFP induction in unc-47::GFP background. FIG. 6A shows confirmation of heat shock responsiveness in the larvae and adults nematodes. FIG. 6B shows representative COPAS biosorting profile showing nematode size-dependent effects on observe fluorescence. The lighter shaded areas in the images indicated fluorescence of GFP or RFP.

FIG. 10 shows sets/formats of arrays or panels for different types of stress response biosensors and specific sub-groups.

DETAILED DESCRIPTION

Figures 1A, 1B, 1C:
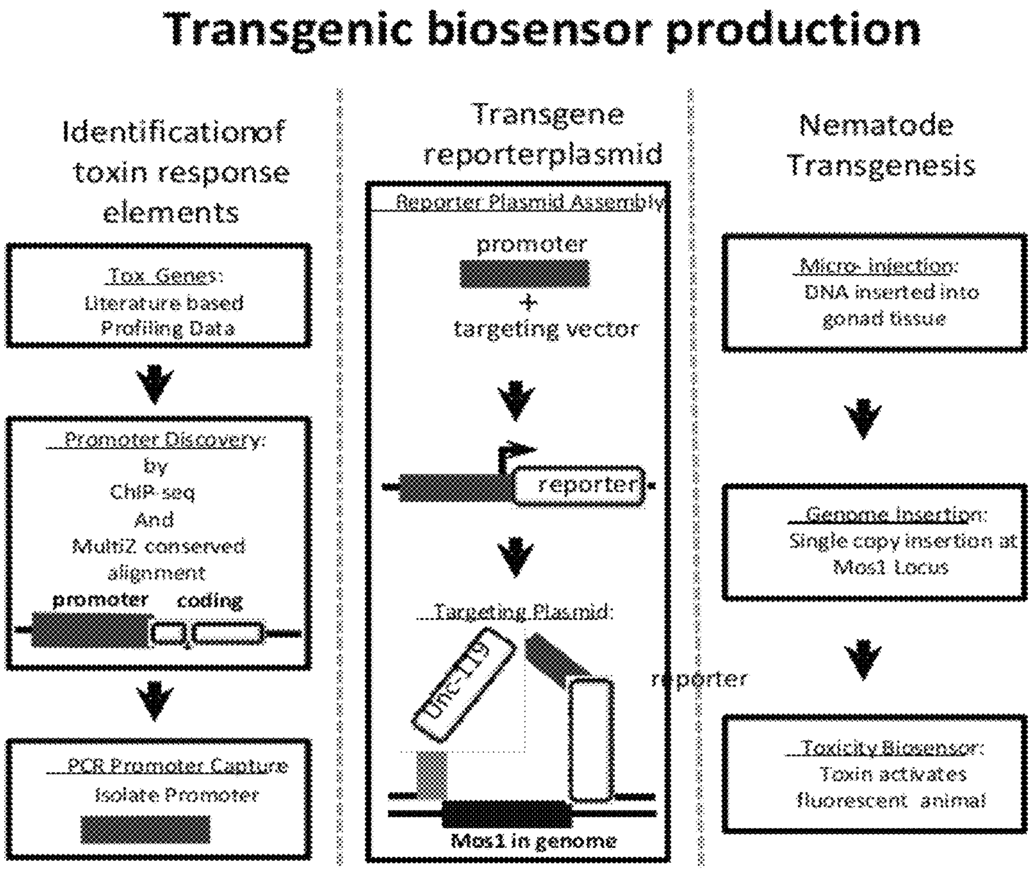
FIGS. 1A, B, and C show a schematic representation of a transgenesis algorithm for generating transgenic organisms for use in the invention. The transgenesis algorithm involves, as shown in FIG. 1A, identifying a promoter response element, as shown in FIG. 1B, operably linking or fusing the promoter response element to a reporter gene to create a functional transgene and, as shown in FIG. 1C, inserting the functional transgene into the host organism's genome (e.g., *C. elegans*).
FIG. 1B comprises (1) reporter plasmid assembly (e.g., insert promoter into targeting vector/construct by standard molecular biology techniques) and (2) targeting plasmid assembly (e.g, having a positive selection marker (e.g., unc-119 rescue) and a homology arm for transposition (e.g., sequence flanking Mos1 site to yield transgene of interest—toxin sensitive promoter driving reporter gene).
FIG. 1C comprises (1) microinjection of targeting plasmid into worm (e.g., insert targeting plasmid mix into gonad tissue of selectable background animals (e.g., unc-119 mutants)) and (2) genome insertion (e.g., array formation, Mos1 transposon insertion, homologous gene repair, transgene insertion, and array loss) to give the desired transgenic worm.

The invention described herein is a remarkable new paradigm useful for probing the effects of exposure to a stimuli (e.g., a chemical agent or heat shock), on gene expression at the organismal level in a rapid and efficient manner. The inventors have created biosensor organisms that are easily useable and provide robust reproducible results in an out-of-the-box format for testing the effects of exposure to various stimuli on gene expression levels as measured by reporter genes. Importantly, the compositions and methods described herein are unexpectedly useful for identifying gene expression responses to stimuli at the whole organism level.

In a specific implementation of the invention, the inventors have used nematodes (e.g., *C. elegans*) as model organisms. Other organisms can be used as model systems, especially those that are translucent or partially translucent. A panel for oxidative stress response transgenic biosensor organisms was created based on the promoters of 7 genes induced by oxidative stress. Seven unique nematodes lines each corresponding to a different oxidative stress gene were created by genetic engineering technology (each line "representative" of a particular oxidative stress gene). More specifically, promoter regions for each oxidative stress response gene were identified and fused, or operably linked, to the coding region of a fluorescent protein gene to create a transgene promoter reporter construct using standard molecular biology methodology. Importantly, the promoter regions were identified/chosen to contain transcription factor response elements (e.g, transcription factor binding elements) that recruit transcription factors to help modulate transcription of genes under control of the promoter. Each transgene then was inserted into the nematode genome as a single copy (e.g., using single copy transgenesis procedures) to yield seven unique lines (also referred to as representative transgenic organisms e.g., seven representative transgenic organisms). Each line also has a constitutively expressed transgene encoding another fluorescent protein for normalization purposes which was introduced using standard techniques.

The seven different promoters used to create the lines were obtained from genes involved in oxidative stress response. Two genes used were alpha cystallins which respond to cytoplasmic heat shock (hsp-16.2 and hsp-16.41) (David et al. Environ. Toxicol. Chem 2003 January; 22(1):111-118; Hong et al. J. Mol. Biol 2004 November; 344(2):369-381; Candido EPM. Prog. Mol. Subcell. Biol 2002; 28:61-78; Dengg et al. J Pharmacol Toxicol Methods 2004 December; 50(3):209-214; and Strayer et al. FASEB J 2003 December; 17(15): 2305-2307). A metallothionein gene was used to detect oxidative metal toxicity (mtl-2) (Sukaina Zeitoun-Ghandour et al. Aquatic Toxicology 2010 October; 100(2):140-150; Cui et al. Genome Biol 2007; 8 (6):R122; Roh et al. Environ. Toxicol. Chem 2006 November; 25(11):2946-2956; Liao et al. J. Biol. Chem 2002 November; 277(44):42049-42059; and Dong et al. J. Mol. Biol 2008 February; 376(3):621-633) as well as a uridine diphosphate-glucuronosyl/glucosyl transferases gene (ugt-1) (Cui et al. Genome Biol 2007; 8 (6): R122). The remaining 3 genes were chosen for unfolded protein response (UPR) oxidative stress in the mitochondria (hsp-6 and hsp-60) (Yoneda et al. J. Cell. Sci 2004 August; 117 (Pt 18):4055-4066.) and endoplasmic reticulum (hsp-4) (Vadim Kapulkin et al. FEBS Letters 2005 June; 579(14): 3063-3068; and Urano et al. J. Cell Biol 2002). Promoters for these genes were selected to contain all clearly identified transcription factor binding sites and were cloned into expression vectors containing hsRFP, which is mCherry red fluorescent protein fused to the his-57 histone gene. The resulting hsRFP reporter construct expresses red fluorescence in cell nuclei. The reporter is injected into GFP expressing nematodes (unc-47::GFP) using the MosSCI method (Frokjaer-Jensen et al. Nat Genet 2008; 40(11):1375-83), which creates single copy insertions of the transcriptional reporter genes at Mos1 loci. The result is a two-color fluorescent nematode (FIG. 5), where each strain contains both a ubiquitously-expressed GFP and hsRFP whose expression is driven by an oxidative-stress gene promoter.

Figure 7:
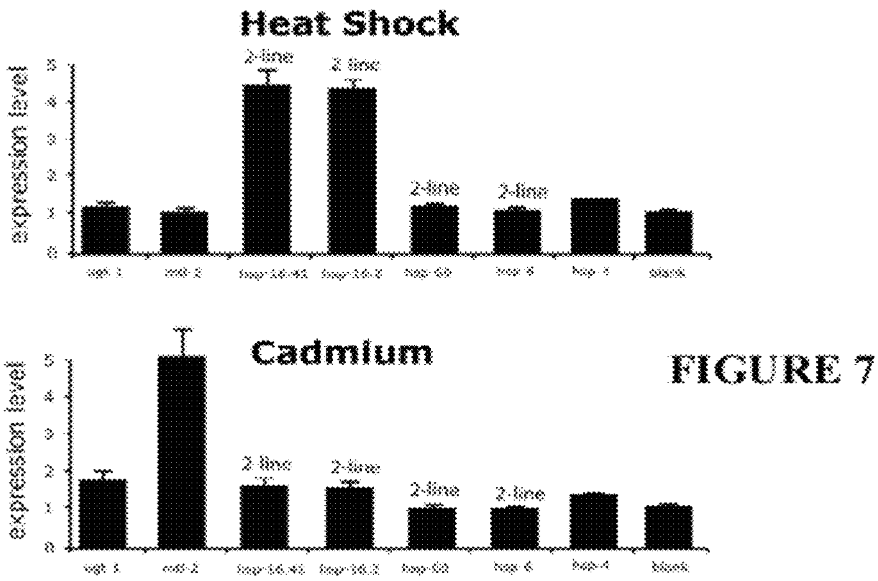
FIG. 7 shows expression response profiles using two-color nematode biosensors. The upper graph shows biosensors exposed to 34° C. for 1.5 hrs on seeded NGM plates followed by 4 hrs recovery at 20° C. The lower graph shows biosensors exposed to cadmium (1 mM, NGM plates) for 15 hrs. Responses are population-normalized changes relative to unexposed control. Error bars indicate average of 2 to 6 independent measurements. The label "2 line" indicates data derived from combining responses of two independently-derived MosSCI lines for the same reporter.

Changes in expression were quantified with a plate reader assay. The 7-member oxidative stress response biosensor panel was heat shock exposed. Significant increased expression was observed in the hsp-16.41 and hsp-16.2 reporters (FIG. 7A), in contrast to the low to non-existent expression induction of the remaining genes. Exposure to metal toxicity elicited a different response in the panel. Cadmium primarily induced metallothionein gene expression (FIG. 7B) and only mildly induced expression from ugt-1, hsp-16's, and hsp-4. Thus, the simple 7-promoter panel was capable of distinguishing different types of responses. In particular, the panel differentiated between two types of oxidative stress responses: heavy metal ion induced oxidative stress and heat shock induced oxidative stress.

In addition, these results show the inventive methods and composition have 4 remarkable features. First, the system shows induction at significant levels over background. For example, the oxidative stress response panel has strong responses occurring at greater than 4-fold over background.

Second, the system shows important levels of fidelity. The panel responses are highly reproducible, where less than 10% error occurs in the assays of 2 to 6 measures done on different days and/or different populations. Third, the method of MosSCI transgenesis creates independently derived strains with similar responses as indicated. Fourth, the arrangement of reports in a plate-reader panel provides an easy-to-use format that quickly reveals which genes are important for toxicity pathway response and can identify different types of response like one response pathway versus another response pathway.

In conclusion, the oxidative response panel demonstrated the system is feasible for sensitive and selective detection of changes in gene expression at the whole organism level when the organism is exposed to external stimuli. This system has advantages over cell culture methods because it is easier to use and amazingly less costly to implement. The inventive system is a whole organism approach, which detects cellular response in a native context. The ease of assay implementation makes the system ideal for high-throughput applications. In general, application of this technology in toxicogenomics is expected to be extremely valuable in the drug discovery sector (Yang et al. Chem Biol Interact 2004 November; 150 (1):71-85). With this inventive system, pharmaceutical companies will decrease their financial exposure because better toxicology capture at the front end of drug development translates to lower frequency of drugs failing in clinical trials due to unwanted side-effect toxicity. Additionally, this technology has clear utility in a variety of other sectors, including screening potential pharmaceutical effects for wanted or on-target effects, or differentiating between types of on-target effects.

Definitions

As used herein, "operably linked" and "operably fused" may refer to the association of two or more nucleic acid elements in a recombinant DNA construct, e.g. as when a promoter is operably linked with DNA that is transcribed to RNA for expressing a protein. Additionally, the term "operably coupled" may be used herein to comprise the terms "operably linked" and "operably fused."

As used herein, "percent identity" means the extent to which two optimally aligned DNA or protein segments are invariant throughout a window of alignment of components, for example nucleotide sequence or amino acid sequence. An "identity fraction" for aligned segments of a test sequence and a reference sequence is the number of identical components that are shared by sequences of the two aligned segments divided by the total number of sequence components in the reference segment over a window of alignment which is the smaller of the full test sequence or the full reference sequence. "Percent identity" ("% identity") is the identity fraction times 100. Such optimal alignment is understood to be deemed as local alignment of DNA sequences. For protein alignment, a local alignment of protein sequences should allow introduction of gaps to achieve optimal alignment. Percent identity is calculated over the aligned length not including the gaps introduced by the alignment per se.

As used herein, the term "promoter" refers to a region of DNA which lies upstream of the transcriptional initiation site of a gene to which RNA polymerase binds to initiate transcription of RNA. An "inducible promoter" is a promoter that increases expression of its cognate gene or reporter when exposed to an inducing agent.

As used herein, the term "fluorescent protein" refers to proteins that fluoresce in response to excitation at a particular wavelength or range of wavelengths of light. As used herein, "RFP" refers to a class of proteins called red fluorescent proteins which are fluorescent proteins that fluoresce in the red region of the spectrum, generally in emitting light having a wavelength in the range of 600 to 650 nanometers. As used herein, "GFP" refers to a class of proteins called green fluorescent proteins which are fluorescent proteins that fluoresce in the green region of the spectrum, generally in emitting light having a wavelength in the range of 500 to 50 nanometers. The terms "RFP" and "GFP" are not intended to be construed based on the amino acid sequence of the underlying protein but are intended to be construed based on the wavelength of light they emit. For example, a RFP has been constructed by site-directed mutagenesis of a protein that was originally a GFP. As the term is used herein, this new protein is a RFP.

As used herein "detectably different" refers to measurements or observations that can be meaningfully distinguished from one another. In the context of "detectably different fluorescent proteins" this refers to proteins that fluorescent at different wavelengths of light such that they level of amount of the two proteins can be meaningfully determined. Detectably different can refer to no greater than 50%, 40%, 30%, 20%, or 10% of emissions.

As used herein, the term "transgene" refers to a gene in an organism that has been introduced, or is to be introduced, that is non-native. Typically transgenes according to the invention are created by genetic engineering technology and inserted into an organism to create a transgenic organism.

Figure 2A:
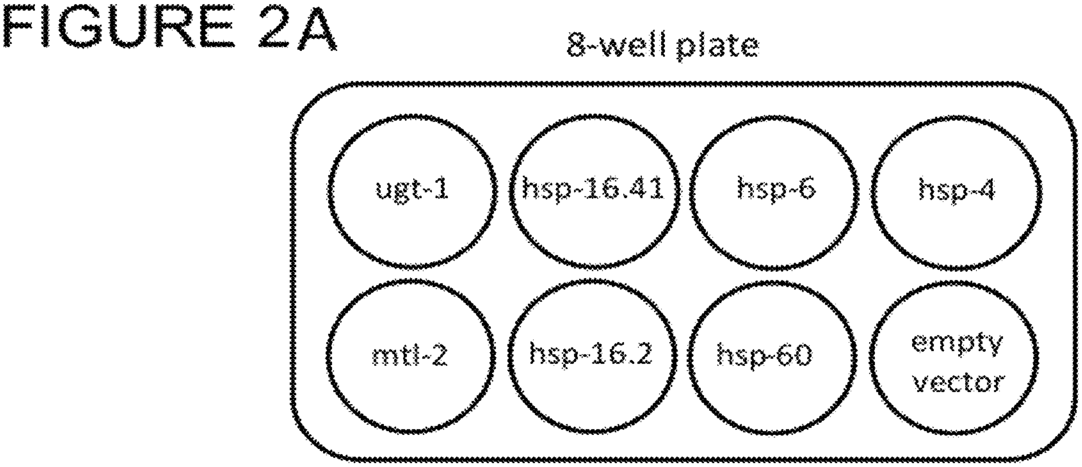
FIGS. 2A and B show a schematic representation of a plurality of representative populations of transgenic organism within the context of a multiwell plate. Each well has a population of worms from the indicated strain (as indicated by the abbreviation in the well which signifies the promoter region of the indicated gene that is fused, or operably linked, to a reporter gene).
Figure 2B:
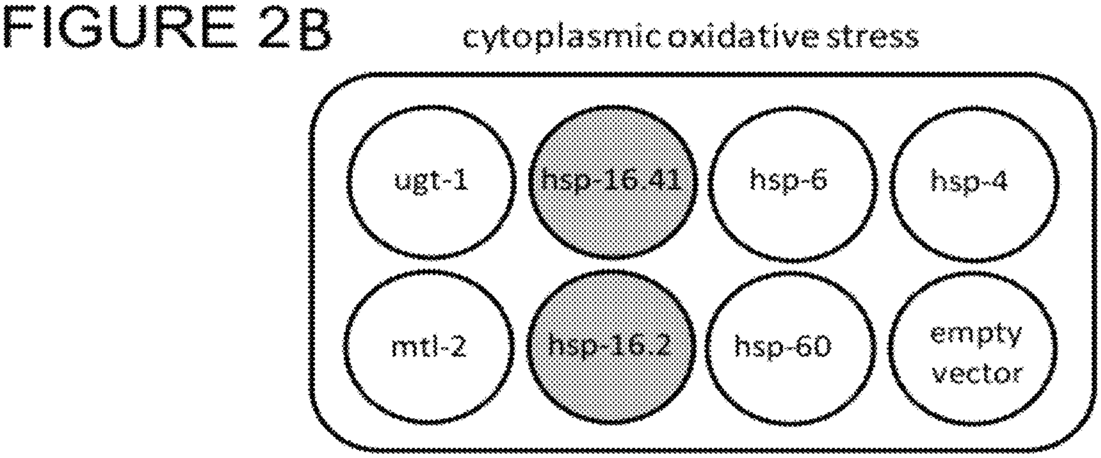
FIG. 2B shows wells highlighted in grey when the selected agent is one that selective induces cytoplasmic oxidative stress (e.g., induces promoter driven expression of reporter gene).

Thus, in one embodiment, the invention is one or more (a) representative transgenic organisms or (b) populations of representative transgenic organisms as biosensors for detecting an alteration in gene expression in response to exposure to a selected agent. Each representative transgenic organism or population of representative transgenic organisms has a transgene which is an inducible promoter of a gene operably linked, or fused, to a reporter gene. Thus, a representative transgenic organism is a biosensor having a transgene which is an inducible promoter of a gene of interest operably linked, or fused, to a reporter gene. In a specific aspect, the transgenic organisms have a second reporter transgene that is a constitutive reporter that is used to normalize the expression level of the reporter driven by the inducible promoter. A population of transgenic organisms is 1 or more transgenic organisms each organism having as a transgene the same inducible promoter operably linked or fused to a reporter gene. In one aspect, the invention is a plurality of representative transgenic organisms or population of representative transgenic organisms where each representative transgenic organism or population of representative transgenic organisms has a distinct transgene that is a distinct inducible promoter of a gene operably linked, or fused, to a reporter gene. In a specific aspect, each population of representative transgenic organisms has 10 or more, 30 or more, 50 or more, 100 or more, 150 or more, 200 or more, or 300 or more transgenic organisms. A plurality of representative populations of transgenic organisms can be envisaged in the format of e.g., microwell plate with (a) each individual well having 2 or more transgenic organisms having as a transgene the same inducible promoter operably linked or fused to a reporter gene and (b) at least 2 wells differing from one another in the identity of the inducible promoter of the transgene (e.g., the inducible promoters in the transgenic organism in the first well and the inducible promoter for the transgenic organism in the second well are different i.e., from different genes). This concept is exemplified in FIG. 2. According to a method of this embodiment, the plurality of representative transgenic organisms or population of representative transgenic organisms is contacted with or exposed to a selected agent, incubated for a time sufficient for induction of the gene driven by the inducible promoter, and expression of reporter gene is determined. In a specific aspect, the reporter gene driven by the inducible promoter encodes a fluorescent or luminescent protein. In a specific aspect, the constitutive reporter encodes a fluorescent or luminescent protein. In a specific aspect, each transgenic organism has an inducible promoter operably linked or fused to a reporter gene encoding a first fluorescent protein and a constitutive reporter encoding a second fluorescent protein wherein the first and second fluorescent protein fluoresce at detectably different wavelengths. Non-limiting examples of fluorescent proteins that fluoresce at detectably different wavelengths are GFP and RFP. Preferably, the inducible reporter expresses at least 2-fold greater, 3-fold great, or 4-fold greater than background levels (e.g., untreated organisms).

In a specific aspect of the embodiment described in the paragraph above, the invention is two or more (a) representative transgenic organisms or (b) populations of representative transgenic organisms as biosensors for detecting an alteration in gene expression as a response to exposure to a selected agent. In another specific aspect, the invention is three or more (a) representative transgenic organisms or (b) populations of representative transgenic organisms as biosensors for detecting an alteration in gene expression as a response to exposure to a selected agent. In yet another specific aspect, the invention is four or more (a) representative transgenic organisms or (b) populations of representative transgenic organisms as biosensors for detecting an alteration in gene expression as a response to exposure to a selected agent. In another specific aspect, the invention is five or more (a) representative transgenic organisms or (b) populations of representative transgenic organisms as biosensors for detecting an alteration in gene expression as a response to exposure to a selected agent. In another specific aspect, the invention is seven or more (a) representative transgenic organisms or (b) populations of representative transgenic organisms as biosensors for detecting an alteration in gene expression as a response to exposure to a selected agent. In another specific aspect, the invention is ten or more (a) representative transgenic organisms or (b) populations of representative transgenic organisms as biosensors for detecting an alteration in gene expression as a response to exposure to a selected agent. In another specific aspect, the invention is fifteen or more (a) representative transgenic organisms or (b) populations of representative transgenic organisms as biosensors for detecting an alteration in gene expression as a response to exposure to a selected agent. In another specific aspect, the invention is twenty or more (a) representative transgenic organisms or (b) populations of representative transgenic organisms as biosensors for detecting an alteration in gene expression as a response to exposure to a selected agent. Preferably, the inducible reporter is capable of expressing at least 2-fold greater, 3-fold greater, or 4-fold greater than its background expression level (e.g., untreated organisms).

The invention is a plurality of transgenic organisms for use as biosensors. The plurality of transgenic organisms includes at least two (a) representative transgenic organisms or (b) populations of representative transgenic organisms wherein the representative transgenic organisms or populations of representative transgenic organisms are distinct from one another in having transgenes comprising different inducible promoters operably linked or fused to a reporter gene (e.g., different strains) wherein the inducible promoter or promoters are chosen from SEQ ID NO:1 through SEQ ID NO:162, or a fragment thereof having 50, 100, 200, 300, 400, or 500 or more nucleotides of said promoter. For example, transgenic organism (1) has a transgene which is the inducible promoter of gene (1) operably linked or fused to a reporter gene and transgenic organism (2) has a transgene which is the inducible promoter region of gene (2) operably linked or fused to a reporter gene. The reporter genes used in the transgenic organism can be the same or different reporter genes. In a specific aspect, the reporter gene is the same gene in each transgenic organism. Typically, the inducible promoter is selected from a response pathway gene. Response pathway genes are genes from pathways that modulate an organism's response to an agent or stimuli at the gene expression level. In one specific aspect, the response pathway gene is a toxicity response pathway gene. In another specific aspect, the toxicity pathway response gene is a heavy metal, oxidative stress, endocrine disruption, xenobiotic, carcinogenic, genotoxic, neurotoxic, hepatatoxic, nephratoxic, or immunotoxic response pathway gene. In another aspect, the response pathway gene is an oxidative stress response gene, a carcinogen response pathway gene, an apoptosis pathway gene, an endocrine pathway gene, a genotoxin pathway gene, or a xenobiotic metabolism pathway. In one aspect, the response pathway gene is an oxidative stress response gene. In one aspect, the response pathway gene is a genotoxin response gene. In one aspect, the response pathway gene is a xenobiotic metabolism pathway gene. In one aspect, the plurality of (a) representative transgenic organisms or (b) populations of representative transgenic organisms comprise 2 or more, 3 or more, 4 or more, or 5 or more (a) representative transgenic organisms or (b) population of representative transgenic organisms having transgenes whose promoters are chosen from distinct oxidative stress response genes. In one aspect, the plurality of (a) representative transgenic organisms or (b) populations of representative transgenic organisms comprise 2 or more, 3 or more, 4 or more, or 5 or more (a) representative transgenic organisms or (b) population of representative transgenic organisms having representative transgenes whose promoters are chosen from distinct genotoxin stress response genes. In one aspect, the plurality of representative transgenic organisms or populations of representative transgenic organisms comprise 2 or more, 3 or more, 4 or more, or 5 or more (a) representative transgenic organisms or (b) population of representative transgenic organisms having representative transgenes whose promoters are chosen from distinct xenobiotic metabolism pathway genes. Preferably, the inducible reporter is capable of expressing at least 2-fold greater, 3-fold greater, or 4-fold greater than its background expression level (e.g., untreated transgenic organism or identical transgenic organism except for not having the inducible promoter reporter construct).

The invention is a transgenic organism, or a transgene, nucleic acid, or construct, comprising an inducible promoter operably linked, or fused, to a reporter gene to provide a biosensor functionality. In one specific aspect, the transgenic organism has the inducible promoter reporter transgene inserted into its genome by a single copy site specific insertion technology. In another specific aspect, the transgenic organism has a second reporter in its genome wherein said second reporter is expressed at a constitutive level. In one aspect, the constitutive reporter is inserted into the organism's genome as a single copy or using a single site insertion technology. The second reporter (constitutive) is used e.g., for normalization of the signal generated from the first reporter (inducible reporter). In one specific aspect, the transgene comprising the inducible promoter operably linked, or fused, to the reporter gene is inserted into the organism's genome in multiple copies, for example, 2 or more copies, 3 or more copies, 5 or more copies, 7 or more copies, or 10 or more copies. In one aspect, the reporter gene driven by the inducible promoter encodes a fluorescent or luminescent protein. In one aspect, the second reporter gene expressed at a constitutive level encodes a fluorescent protein or luminescent protein. In one aspect, the reporter gene driven by the inducible promoter encodes a fluorescent protein. In one aspect, the second reporter gene expressed at a constitutive level encodes a fluorescent protein. In one aspect, the reporter gene driven by the inducible promoter encodes a fluorescent protein which fluoresces at a wavelength that is detectably different than the wavelength that the fluorescent protein encoded by the constitutive reporter fluoresces. In one specific aspect, the reporter driven by the inducible promoter encodes a protein comprising a RFP and the reporter driven by the constitutive reporter encodes a protein comprising a GFP. Preferably, the inducible reporter is capable of expressing at least 2-fold greater, 3-fold greater, or 4-fold greater than its background expression level (e.g., untreated transgenic organism or identical transgenic organism except for not having the inducible promoter reporter construct).

In one embodiment, the invention is a method for detecting expression of a reporter gene operably linked, or fused, to an inducible promoter in a transgenic organism. According to this method, a plurality or array of representative transgenic organisms, or populations thereof, is provided wherein each representative transgenic organism, or population thereof, has an inducible promoter reporter construct integrated into its genome. A representative transgenic organism is one that has one type of inducible promoter reporter construct as a transgene e.g., a promoter from a specific gene. For example, a plurality of representative transgenic organisms can refer to e.g., a representative transgenic organism or population thereof (a) which has a transgene which is inducible promoter (a) operably linked or fused to a reporter; and representative transgenic organism or a population thereof (b) which has a transgene which is inducible promoter (b) operably linked or fused to a reporter. According to the method, each representative organism, or population thereof, is characterized by the identity of its inducible promoter (the organism "represents" a specific type of response characterized by the identity inducible promoter). Thus, each representative organism, or population thereof, has a distinct inducible promoter which is derived or obtained from a distinct gene. Each different representative transgenic organism can be present as multiple organisms to give a population of representative transgenic organisms (e.g., 3, 5, 10, 50, 100, 200 or 300 or more organisms) or as a single organism. The representative transgenic organism or population of transgenic organisms are exposed to or contacted with a selected agent and incubated with reagent and time sufficient to allow expression of the reporter gene. The reporter gene is detected or quantified. Optionally, the quantity of reporter can be normalized against the value for a second reporter gene, e.g., the constitutive reporter gene. Preferably, the reporter or reporters are fluorescents proteins. In one aspect, the inducible reporter encodes a protein comprising a RFP. In one aspect, the constitutive reporter encodes a protein comprising a GFP. Preferably, the inducible reporter is capable of expressing at least 2-fold greater, 3-fold greater, or 4-fold greater than its background expression level (e.g., untreated transgenic organism or identical transgenic organism except for not having the inducible promoter reporter construct).

In one embodiment, the invention is a method for detecting expression in a transgenic organism a first reporter gene operably linked or fused to an inducible promoter and a second reporter expressed at constitutive levels. According to this method, a plurality or array of representative transgenic organisms, or populations thereof, is provided wherein each representative transgenic organism, or population thereof, has an inducible promoter reporter construct and a constitutively expressed reporter integrated into its genome wherein the inducible promoter or promoters are chosen from SEQ ID NO:1 through SEQ ID NO:162, or a fragment thereof having 50, 100, 200, 300, 400, or 500 or more nucleotides of said promoter. A representative transgenic organism is one that has one type of inducible promoter reporter construct as a transgene. For example, a plurality of representative transgenic organisms can refer to e.g., a representative transgenic organism (a) which has a transgene which is inducible promoter (a) operably linked or fused to a reporter; and representative transgenic organism (b) which has a transgene which is inducible promoter (b) operably linked or fused to a reporter. According to the method, each representative organism, or population thereof, is characterized by the identity of its inducible promoter (the organism "represents" a specific type of response characterized by the identity inducible promoter). Thus, each representative organism, or population thereof, has a distinct inducible promoter which is derived or obtained from a distinct gene. The representative transgenic organism or population of transgenic organisms are exposed to or contacted with a selected agent and incubated with reagents and time sufficient to allow expression of the reporter genes. The level of the reporter gene is then detected or quantified. The quantity or level of the inducible reporter can be normalized against the quantity or level of a second reporter gene, e.g., the constitutive reporter gene. Preferably, the reporter or reporters encode a fluorescent proteins or proteins. In one aspect, the inducible reporter encodes a protein comprising a RFP. In one aspect, the constitutive reporter encodes a protein comprising a GFP. Preferably, the inducible reporter is capable of expressing at least 2-fold greater, 3-fold greater, or 4-fold greater than background its level (e.g., untreated transgenic organism or identical transgenic organism except for not having the inducible promoter reporter construct).

The combination of use of single site insertion technology for the inducible promoter reporter transgene and the use of second constitutive reporter for normalization in the invention has produced remarkable unprecedented results for whole organism biosensors. In one aspect, the transgene is inserted into a single site of the host organisms's genome using single site insertion technology and is present as one copy. In one aspect, the transgene is inserted into multiple sites in the host organism's genome using a site-specific insertion technology and is present in from 2 to 50 copies, more preferably 2 to 20 copies and even more preferably from 2 to 10 copies.

In an alternative aspect, the transgene is inserted into the organism's genome as multiple copies. For example, ballistic genes guns can be used to insert the transgene into the organism's genome in the range of 1 copy to about 50 copies. In another aspect, the transgene is inserted into the extra-chromosomal array of a *C. elegans* host organism. In this aspect, the host organism typically has from about 100 to about 1000 copies of the transgene.

According to one aspect of the invention, the transgenic organism is translucent or at least partially translucent. More specifically, the transgenic organism of this aspect is translucent or at least partially translucent to allow for spectrophotometric detection of one or more reporter genes in a medium or high-throughput fashion. In one specific aspect, medium or high throughput format refers to the ability detect the expression level of the reporter gene in a multi-well plate format using a plate reader that is capable of detecting and quantitating the level of fluorescence or bioluminescence of the respective reporter. In another specific aspect, the transgenic organism is a nematode, *Danio rerio* (zebrafish), *Drosophila melanogaster, Daphnia* spp., or *Xenopus laevis*. In one specific aspect, the organism is a nematode. In another specific aspect, the organism is *C. elegans*. The ordinary skilled artisan is capable of identify promoters in organisms such *Danio rerio, Drosophila melanogaster, Daphnia* spp., or *Xenopus laevis* to create the transgenic organisms in a manner similar to that described herein for *C. elegans.*

In one embodiment, the invention involves transgenesis of DNA into the worm genome (e.g., *C. elegans*). This DNA is a transgene that contains an inducible promoter operably linked or fused to a gene encoding a reporter protein. The inserted DNA then allows reporter protein expression in the transgenic organism upon exposure to a selected agent or toxin that activates or induces its expression. The genetically engineered animal serves as a biosensor (e.g., for toxicity). According to one aspect of this embodiment, the transgene is inserted into the genome using MosSCI technology. The method involves (a) providing a strain of an organism having an insertion element site and a marker for positive selection (b) injecting the organisms with a vector having a transgene comprising (1) an inducible promoter reporter construct, (2) a marker for selection, and (3) sequence elements (e.g., homology arms) sufficient for effectuating insertion into the insertion element site or sites of the strain, a vector for producing a transposase compatible with the transposon and insertion element site, and one or more plasmids acting as markers for tracking the presence of extrachromosal arrays. Injected animals are transferred to plates, allowed to grow or incubate for a time sufficient to allow for transformation and recovery, and are then screened for insertion events by use of the selection markers in the strain, the transgene, and the markers for tracking the presence of extrachromosomal markers.

Inducible Promoters

Figure 8:
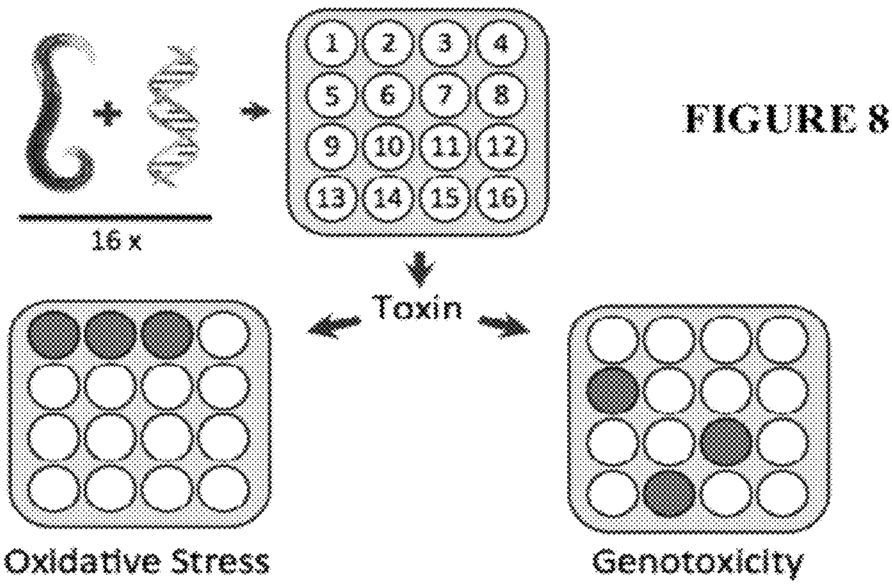
FIG. 8 shows a predicted set of results related to a panel or array of biosensors involved in oxidative stress and genotoxic stress. A 16 well microwell plate having populations of representative transgenic organisms for both oxidative stress and genotoxin stress are seeded into the wells of the plates. Exposure of organisms in the wells of the plates to a selected agent that induces oxidative stress or genotoxic stress gives digitized read-outs indicative of which toxicity pathway is being activated by the selected agent. The lower left plate shows activation of an oxidative stress pathway whereas the lower right plate shows activation of a genotoxin pathway.
Figure 9:
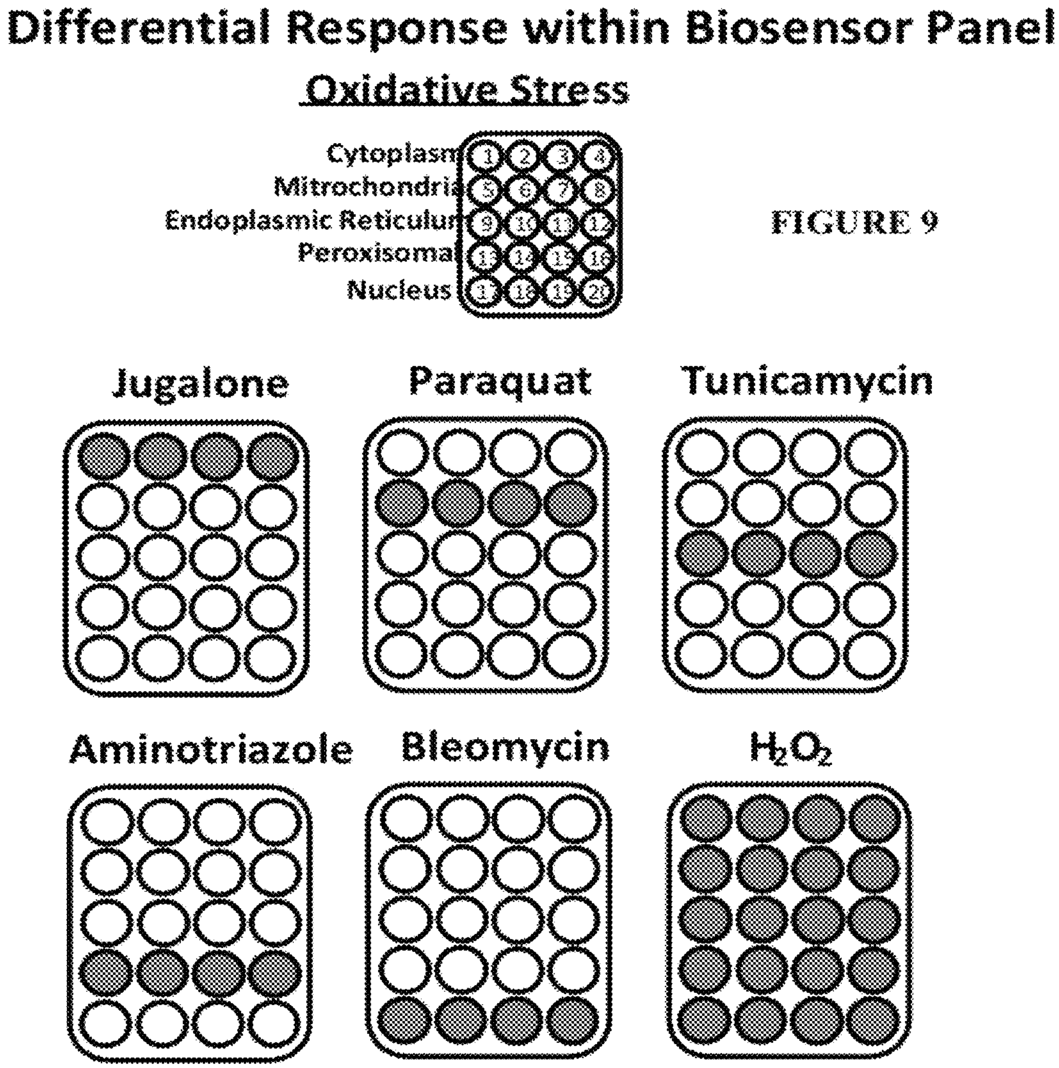
FIG. 9 shows a predicted set of results related to a panel or array of biosensors involved in oxidative stress. A 16 well microwell plate having populations of representative transgenic organisms for both oxidative stress are seeded into the wells of the plates. Exposure of the wells in the plate with a selected agent that induces oxidative stress give digitized read-outs indicative of which oxidative stress toxicity pathway is being activated by the selected agent. The plates show activation of the indicated oxidative stress pathway by induction of the reporters in the highlighted rows.

A variety of inducible promoters are used to make different transgenic biosensors organisms of the invention. Inducible promoters are chosen from different genes that are selected for being activated or modulated in response to stimuli or conditions, e.g., like toxins or a drug or drug candidate. The promoters are chosen to include transcription factor response elements which are DNA sequences that enhance or drive transcription of a gene involved in a response pathway by serving as a template for the transcriptional machinery (transcription factors) associated with the response pathway. In one embodiment of the invention, the resulting transgenic biosensor organisms are arranged into a panel. A test compound (selected agent) is exposed to members of the panel and specific types of response (e.g., toxicities) are detected (see e.g., FIG. 8 or FIG. 9). In an alternative embodiment, the same representative transgenic strain, or population thereof, is duplicated in all wells of the panel and a population of molecules, like a library, are screened for one type of toxicity. In one specific example, a library of molecules designed to inhibit or modulate a specific target or that inhibited or modulated a specific target are counter-screened against one or more representative transgenic organisms, or populations thereof, to identify a molecule or molecules that have the least toxicology liabilities or have a desirable toxicity profile.

The inducible promoters used in the invention can be any promoter element or region that is involved in regulating gene expression. Promoter regions typically lie upstream of a gene, anywhere from about 1 to 10,000 or more base pairs (bp) upstream of the start site. In general, regions ranging from 1 to 4,000 bp upstream of start codon are chosen for promoter selection. In one aspect, the region ranges from about 1 to 2500 bp upstream from the start site. In one aspect, the region ranges from about 1 to 2000 bp upstream from the start site. In one aspect, the region ranges from about 1 to 1000 bp upstream from the start site. In one aspect, the promoter is within about 500 bp upstream of the transcription start site. See e.g., Gerstein et al. Science. 2010 Dec. 24; 330(6012): 1775-87.

The genes chosen for the exemplary oxidative stress response panel are the following oxidative response genes (hsp-16.41, hsp16.2, hsp-6 and hsp-60, hsp-4, mlt-2, and ugt-1). To choose the oxidative-response gene promoters and any other promoters for use in the invention, a combination of modENCODE's TF-GFP ChIP-seq data (Niu et al. Genome Res. 2011 February; 21 (2):245-254) and multi-z 6-species alignment (Niu et al. Genome Research 2004; 14(4):708-715.) can be used to find the extent of conserved genomic regions containing TF (transcription factor) sites in front of the oxidative-response gene's start codon (or other response pathway genes). Promoter-reporter fusion constructs can be designed for Gibson (Gibson et al. Nat. Methods 2009 May; 6(5):343-345) reaction cloning using APE plasmid editor (biologylabs.utah.edu/jorgensen/wayned/ape). In general, regions ranging from 300 to 4,000 bp upstream of start codon were chosen for promoter selection. Other techniques for identifying, selecting and cloning inducible promoter regions for use in the compositions and methods of the invention are known to the skilled artisan.

Reporter Genes

Reporter genes for use in the invention include any reporter that can be expressed and quantified. Preferably, the reporter gene encodes a protein that can be detected spectrophotometrically. Some examples include fluorescent proteins (e.g., green fluorescent protein (GFP), cyan fluorescent protein (CFP), red fluorescent protein (RFP), mCherry, Tag-RFP, etc.), luciferase which is a luminescent reporter (Ranella, Firefly, etc.), chomogenic (beta-Gal, etc.), etc. See e.g., Pollock et al., Trends in Cell Biology 9:57 (1999). Useful fluorescent proteins also include mutants and spectral variants of these proteins which retain the ability to fluoresce. See e.g., Shaner et al., Nat. Biotech. 22:1567 (2004), Tag-RFP (Shaner, N. C. et al., 2008 Nature Methods, 5 (6), 545-551), fluorescent proteins fused to e.g., his-GFP or his-RFP which is histone H2B fused to the indicated fluorescent protein Essex et al. Mol. Biol. Cell 2009 February; 20 (4):1252-1267). Other fluorescent proteins that can be used in the invention include, but are not limited to, AcGFP, AcGFP1, AmCyan, AmCyan1, AQ143, AsRed2, Azami Green, Azurite, BFP, Cerulean, CFP, CGFP, Citrine, copGFP, CyPet, dKeima-Tandem, DsRed, dsRed-Express, DsRed-Monomer, DsRed2, dTomato, dTomato-Tandem, EBFP, EBFP2, ECFP, EGFP, Emerald, EosFP, EYFP, GFP, HcRed-Tandem, HcRed1, JRed, Katuska, Kusabira Orange, Kusabira Orange2, mApple, mBanana, mCerulean, mCFP, mCherry, mCitrine, mECFP, mEmerald, mGrape1, mGrape2, mHoneydew, Midori-Ishi Cyan, mKeima, mKO, mOrange, mOrange2, mPlum, mRaspberry, mRFP1, mRuby, mStrawberry, mTagBFP, mTangerine, mTeal, mTomato, mTurquoise, mWasabi, PhiYFP, ReAsH, Sapphire, Superfolder GFP, T-Sapphire, TagCFP, TagGFP, TagRFP, TagRFP-T, TagYFP, tdTomato, Topaz, TurboGFP, Venus, YFP, YPet, ZsGreen, and ZsYellow1 which are described in the literature or otherwise commercially available. hRFP and hsRFP are RFP's fused to e.g., a histone protein like H2B from *C. elegans.*

Isolated Nucleic Acids, Transgenes, Constructs, Transgenic Organisms and Transgenic *C. elegans* Organisms The invention is nucleic acids and constructs and transgenic organisms comprising those nucleic acids as described herein.

In one embodiment, the invention provides a transgene, a transgenic organism, or a construct which comprises a promoter, a fragment of a promoter having 50, 100, 200, 300, 400, or 500 or more nucleotides of the promoter, or a homolog thereof having at least 95%, 96%, 97%, 98%, or 99% identity thereto operably linked, or fused, to a reporter gene wherein said reporter gene encodes a fluorescent or luminescent protein and wherein the promoter is for the *C. elegans* gene cdr-1, gcs-1, ugt-1, gst-38, hsp-60, hsp-16.41, mtl-2, hsp-16.2, gst-4, ugt-13, hsp-3, hsp-6, hsp-4, hsp-1, skn-1, dnj-13, daf-21, Hsp-17, cyp-13A7, cyp-14A3, cyp-35A2, zyg-12, ZK742.4, ZK742.3, fkb-1, fkb-2, fkb-3, fkb-4, fkb-5, fkb-6, fkb-7, fkb-8, fmo-1, fmo-2, fmo-3, fmo-4, fmo-5, ftn-1, ftn-2, fzy-1, gen-1, glp-1, gsr-1, gst-1, gst-23, gst-25, gst-41, H01G02.2, haf-6, syp-2, T05A12.4, T05G5.3, T06E6.2, T07F12.4, Hsp-12.2, T05E11.3, Cnx-1, Crt-1, cyp-35A1, cyp-35C1, cyp-35A3, pqe-1, cyp-37B1, cyp-35B2, cyp-35B1, cyp-22A1 (daf-9), cyp-14A5, cyp-35B3, cyp-34A6, daf-16, exo-3, nth-1, pme-1, ung-1, xpa-1, mrt-2, ercc-1, ZK697.8, ZK287.5, haf-7, hda-1, hda-10, hda-11, hda-2, hda-3, hda-4, hda-5, hda-6, hdac-1, hif-1, him-1, him-14, him-3, him-4, him-6, hmg-3, hmg-4, hmg-5, hpr-17, hpr-9, hrdl-1, hsf-1, hsp-1, hsp-16.48, tbb-4, tnc-2, top-3, tor-2, trx-2, xpf-1, xpg-1, rad-23, mlh-1, msh-2, msh-4, msh-5, msh-6, brc-1, brc-2, rad-50, cku-70, lin-35, mei-1, cki-1, cki-2, cep-1, ced-3, ced-9, ced-13, vem-1, dhs-23, sodh-2, dnj-19, Xbp-1, hsp-16.49, hsp-2, htp-1, htp-3, hus-1, imb-3, ire-1, irk-1, K07C5.2, K07C5.4, K08F4.1, K11G12.5, kin-18, lagr-1, let-2, let-92, lig-1, lig-4, lim-4, lin-12, lin-44, lin-49, lrk-1, lst-3, M18.5, vps-41, W01A11.1, W02C12.1, W03G1.5, W06H8.2, Hipr-1, cdc-48.1, cdc-48.3, Ubq-1, Ubq-2, Gst-10, Gst-13, f25d1.5, fil-1, k10h10.6, hsp-70, f44e5.4, f44e5.5, hsp-16.11, hsp-16.1, nurf-1, aip-1, y43f8b.2, Dod-17, Dod-24, C55A6.7, F56D5.3, cyp-13A11, cyp-13A6, cyp-25A4, mac-1, mboa-2, mdf-1, mdf-2, mec-14, med-1, mel-28, misc-1, mnat-1, mre-11, mrp-1, mrp-2, mrp-3, mrp-4, mrp-5, mrp-6, mrp-7, mrp-8, mspn-1, mus-1, mut-2, mxl-1, mxl-2, mxl-3, ndx-1, Y55B1AL.2, Y56A3A.33, Y66D12A.15, Y66D12A.15, Y73C8C.10, cyp-29A2, cyp-31A1, cyp-31A3, cyp-33B1, cyp-33E1, cyp-34A10, cyp-34A9, cyp-35A4, cyp-35D1, abl-1, abu-1, acr-14, acr-22, agt-1, ahr-1, air-2, ama-1, apa-2, apn-1, apn-1, aps-2, arf-1, asp-5, atf-5, atgr-7, ndx-4, nft-1, nhr-6, nol-5, npl-4.2, nuc-1, odc-1, paa-1, pas-4, pat-10, pcn-1, pdi-1, pdi-2, pdi-3, pdr-1, pek-1, pgp-1, pgp-10, pgp-2, phi-37, phi-44, phi-9, pink-1, pme-2, pme-3, T08D2.4, T08D2.7, T08H10.1, T10B5.8, T13A10.2, atl-1, atm-1, B0222.9, B0432.2, B0495.2, B0563.7, brd-1, C01G5.5, C06A1.6, C06H2.3, C07D8.6, C08H9.3, C09D4.3, C11E4.2, C25A1.5, C30G7.5, C35C5.2, C35D10.2, C35D10.6, C37A2.4, C37C3.6a, C44H4.4, C56G3.2, catp-6, cbn-1, F17A9.5, F18A1.5, F19G12.2, F23C8.9, F36A4.15, F43D2.1, F43G6.5, F44B9.8, F45E12.3, F49E12.6, F52B5.2, F52C12.1, F53C11.5, F53F1.2, F53F1.3, F53F10.2, F55B11.1, F57B10.5, F57B10.6, F58F9.1, F59A2.3, F59F4.1, fan-1, fdps-1, figl-1, trxr-1, tut-1, uba-1, ubc-1, ubc-20, ccch-1, cct-1, cct-2, cct-3, cct-4, cct-5, cct-6, cct-7, cct-8, cdc-14, cdc-48.2, cdk-7, ced-4, cel-1, cft-1, chk-1, chk-2, chn-1, cku-80, cle-1, clk-2, clpp-1, cmd-1, cnb-1, col-135, pme-4, pme-5, pmrt-5, pms-2, png-1, polh-1, polk-1, prx-6, ptl-1, R02D3.3, R03D7.2, R05D11.6, R05F9.10, R09H10.3, R10E4.9, R13D11.4, R151.6, rab-1, rab-7, srp-2, ssc-1, sti-1, sulp-7, sut-1, sut-2, wrn-1, xpc-1, Y110A7A.4, Y38F1A.5, Y38H8A.3, cps-6, crb-1, crn-1, crn-2, crn-3, crn-4, crn-5, crn-6, crp-1, csb-1, ctl-2, ctl-3, cul-1, cul-2, cul-4, cul-5, cyh-1, cyn-1, cyn-10, cyn-11, cyn-12, cyn-13, cyn-14, cyn-15, cyn-16, rad-51, rad-54, rbx-1, rbx-2, rcf-3, rcq-5, rec-8, rev-1, rfc-1, rfc-4, rfl-1, rme-8, rnf-121, rnh-1.0, rpa-1, rpa-2, rpn-10, rps-19, rps-26, T23G5.6, T26A5.5, T27E9.1, tag-353, tars-1, tbb-2, Y73F8A.24, ymel-1, ZC168.4, ZC395.10, ZC443.1, cyn-17, cyn-2, cyn-3, cyn-4, cyn-5, cyn-6, cyn-7, cyn-8, cyn-9, cyp-13A12, cyp-13A4, cyp-14A2, cyp-33C1, cyp-33C2, cyp-33C9, cyp-33E2, cyp-42A1, cyp14A2, cyp33C9, cyp34A6, D1081.8, D2023.4, daf-1, daf-14, daf-3, rpt-3, rpt-4, rpt-5, rpt-6, rtel-1, san-1, scav-1, scav-2, scav-3, scav-4, scav-5, scc-3, sdz-8, sec-22, sep-1, set-25, set-26, set-8, set-9, unc-11, unc-26, unc-57, uri-1, usp-14, vps-4, T15B7.2, T16H12.4, ugt-62, Y39G8B.1, Y39G8B.2, daf-5, daf-7, daf-8, dbl-1, ddb-1, dhs-22, djr-1.1, dna-2, dog-1, drh-3, drp-1, dut-1, E01A2.1, eft-2, egl-1, eif-2, emb-9, epg-2, eps-8, exo-1, F09E5.2, F14F9.5, F15E6.6, F16A11.2, F17A9.4, sft-4, sgg-1, sin-3, sir-2.1, sir-2.2, sir-2.3, sir-2.4, skr-15, slt-1, slx-1, smf-1, smk-1, sod-1, sod-2, sod-3, sod-4, sod-5, spas-1, ugt-61, Y43E12A.1, Y43F8C.13, Y48G1BL.2, Y50D7A.1, Y50D7A.2, Y54E10A.3, ufd-1, ugt-22, ugt-52, ZK1128.4, ZK1290.5, or Y39H10A.7. The transgene, transgenic organism, or construct is used for the gene expression biosensors as described herein. According to the invention, an inducible promoter or fragment thereof, or a homolog having at least 95%, 96%, 97%, 98%, or 99% identity thereto, of one or more of the genes listed above and is operably linked, or fused, to a reporter gene using standard molecular biology techniques as described herein and elsewhere. The resulting construct can be transformed into an organism to a yield a transgenic biosensor organism as described herein. In a specific aspect, the construct further comprises one or more of the following: a selectable marker, sequence elements sufficient for site-specific integration into the host organism's genome. In one aspect, the transgene is introduced into the organism with a technique that yields a site specific single copy stable insertion. In a specific aspect, the transgenic biosensor organisms are arranged into an array or panel. The panels can be arranged into kits useful for detecting a wide variety of toxicities or gene expression responses. In one specific aspect, the transgenic organism is a nematode. In another specific aspect, the transgenic organism is *C. elegans*.

In one embodiment, the invention provides a transgene, a transgenic organism, or a construct comprising a promoter, a fragment of a promoter having 50, 100, 200, 300, 400, or 500 or more nucleotides of the promoter, or a homolog thereof having at least 95%, 96%, 97%, 98%, or 99% identity thereto, operably linked, or fused, to a reporter gene wherein said reporter gene encodes a fluorescent or luminescent protein and wherein the promoter is from an organism chosen from *Danio rerio* (zebrafish), *Drosophila melanogaster, Daphnia* spp., or *Xenopus laevis* and the promoter is for gene that organism that is homologous to the gene in *C. elegans* corresponding to cdr-1, gcs-1, ugt-1, gst-38, hsp-60, hsp-16.41, mtl-2, hsp-16.2, gst-4, ugt-13, hsp-3, hsp-6, hsp-4, hsp-1, skn-1, dnj-13, daf-21, Hsp-17, cyp-13A7, cyp-14A3, cyp-35A2, zyg-12, ZK742.4, ZK742.3, fkb-1, fkb-2, fkb-3, fkb-4, fkb-5, fkb-6, fkb-7, fkb-8, fmo-1, fmo-2, fmo-3, fmo-4, fmo-5, ftn-1, ftn-2, fzy-1, gen-1, glp-1, gsr-1, gst-1, gst-23, gst-25, gst-41, H01G02.2, haf-6, syp-2, T05A12.4, T05G5.3, T06E6.2, T07F12.4, Hsp-12.2, T05E11.3, Cnx-1, Crt-1, cyp-35A1, cyp-35C1, cyp-35A3, pqe-1, cyp-37B1, cyp-35B2, cyp-35B1, cyp-22A1 (daf-9), cyp-14A5, cyp-35B3, cyp-34A6, daf-16, exo-3, nth-1, pme-1, ung-1, xpa-1, mrt-2, ercc-1, ZK697.8, ZK287.5, haf-7, hda-1, hda-10, hda-11, hda-2, hda-3, hda-4, hda-5, hda-6, hdac-1, hif-1, him-1, him-14, him-3, him-4, him-6, hmg-3, hmg-4, hmg-5, hpr-17, hpr-9, hrdl-1, hsf-1, hsp-1, hsp-16.48, tbb-4, tnc-2, top-3, tor-2, trx-2, xpf-1, xpg-1, rad-23, mlh-1, msh-2, msh-4, msh-5, msh-6, brc-1, brc-2, rad-50, cku-70, lin-35, mei-1, cki-1, cki-2, cep-1, ced-3, ced-9, ced-13, vem-1, dhs-23, sodh-2, dnj-19, Xbp-1, hsp-16.49, hsp-2, htp-1, htp-3, hus-1, imb-3, ire-1, irk-1, K07C5.2, K07C5.4, K08F4.1, K11G12.5, kin-18, lagr-1, let-2, let-92, lig-1, lig-4, lim-4, lin-12, lin-44, lin-49, lrk-1, lst-3, M18.5, vps-41, W01A11.1, W02C12.1, W03G1.5, W06H8.2, Hipr-1, cdc-48.1, cdc-48.3, Ubq-1, Ubq-2, Gst-10, Gst-13, f25d1.5, fil-1, k10h10.6, hsp-70, f44e5.4, f44e5.5, hsp-16.11, hsp-16.1, nurf-1, aip-1, y43f8b.2, Dod-17, Dod-24, C55A6.7, F56D5.3, cyp-13A11, cyp-13A6, cyp-25A4, mac-1, mboa-2, mdf-1, mdf-2, mec-14, med-1, mel-28, misc-1, mnat-1, mre-11, mrp-1, mrp-2, mrp-3, mrp-4, mrp-5, mrp-6, mrp-7, mrp-8, mspn-1, mus-1, mut-2, mxl-1, mxl-2, mxl-3, ndx-1, Y55B1AL.2, Y56A3A.33, Y66D12A.15, Y66D12A.15, Y73C8C.10, cyp-29A2, cyp-31A1, cyp-31A3, cyp-33B1, cyp-33E1, cyp-34A10, cyp-34A9, cyp-35A4, cyp-35D1, abl-1, abu-1, acr-14, acr-22, agt-1, ahr-1, air-2, ama-1, apa-2, apn-1, apn-1, aps-2, arf-1, asp-5, atf-5, atgr-7, ndx-4, nft-1, nhr-6, nol-5, npl-4.2, nuc-1, odc-1, paa-1, pas-4, pat-10, pcn-1, pdi-1, pdi-2, pdi-3, pdr-1, pek-1, pgp-1, pgp-10, pgp-2, phi-37, phi-44, phi-9, pink-1, pme-2, pme-3, T08D2.4, T08D2.7, T08H10.1, T10B5.8, T13A10.2, atl-1, atm-1, B0222.9, B0432.2, B0495.2, B0563.7, brd-1, C01G5.5, C06A1.6, C06H2.3, C07D8.6, C08H9.3, C09D4.3, C11E4.2, C25A1.5, C30G7.5, C35C5.2, C35D10.2, C35D10.6, C37A2.4, C37C3.6a, C44H4.4, C56G3.2, catp-6, cbn-1, F17A9.5, F18A1.5, F19G12.2, F23C8.9, F36A4.15, F43D2.1, F43G6.5, F44B9.8, F45E12.3, F49E12.6, F52B5.2, F52C12.1, F53C11.5, F53F1.2, F53F1.3, F53F10.2, F55B11.1, F57B10.5, F57B10.6, F58F9.1, F59A2.3, F59F4.1, fan-1, fdps-1, figl-1, trxr-1, tut-1, uba-1, ubc-1, ubc-20, ccch-1, cct-1, cct-2, cct-3, cct-4, cct-5, cct-6, cct-7, cct-8, cdc-14, cdc-48.2, cdk-7, ced-4, cel-1, cft-1, chk-1, chk-2, chn-1, cku-80, cle-1, clk-2, clpp-1, cmd-1, cnb-1, col-135, pme-4, pme-5, pmrt-5, pms-2, png-1, polh-1, polk-1, prx-6, ptl-1, R02D3.3, R03D7.2, R05D11.6, R05F9.10, R09H10.3, R10E4.9, R13D11.4, R151.6, rab-1, rab-7, srp-2, ssc-1, sti-1, sulp-7, sut-1, sut-2, wrn-1, xpc-1, Y110A7A.4, Y38F1A.5, Y38H8A.3, cps-6, crb-1, crn-1, crn-2, crn-3, crn-4, crn-5, crn-6, crp-1, csb-1, ctl-2, ctl-3, cul-1, cul-2, cul-4, cul-5, cyh-1, cyn-1, cyn-10, cyn-11, cyn-12, cyn-13, cyn-14, cyn-15, cyn-16, rad-51, rad-54, rbx-1, rbx-2, rcf-3, rcq-5, rec-8, rev-1, rfc-1, rfc-4, rfl-1, rme-8, rnf-121, rnh-1.0, rpa-1, rpa-2, rpn-10, rps-19, rps-26, T23G5.6, T26A5.5, T27E9.1, tag-353, tars-1, tbb-2, Y73F8A.24, ymel-1, ZC168.4, ZC395.10, ZC443.1, cyn-17, cyn-2, cyn-3, cyn-4, cyn-5, cyn-6, cyn-7, cyn-8, cyn-9, cyp-13A12, cyp-13A4, cyp-14A2, cyp-33C1, cyp-33C2, cyp-33C9, cyp-33E2, cyp-42A1, cyp14A2, cyp33C9, cyp34A6, D1081.8, D2023.4, daf-1, daf-14, daf-3, rpt-3, rpt-4, rpt-5, rpt-6, rtel-1, san-1, scav-1, scav-2, scav-3, scav-4, scav-5, scc-3, sdz-8, sec-22, sep-1, set-25, set-26, set-8, set-9, unc-11, unc-26, unc-57, uri-1, usp-14, vps-4, T15B7.2, T16H12.4, ugt-62, Y39G8B.1, Y39G8B.2, daf-5, daf-7, daf-8, dbl-1, ddb-1, dhs-22, djr-1.1, dna-2, dog-1, drh-3, drp-1, dut-1, E01A2.1, eft-2, egl-1, eif-2, emb-9, epg-2, eps-8, exo-1, F09E5.2, F14F9.5, F15E6.6, F16A11.2, F17A9.4, sft-4, sgg-1, sin-3, sir-2.1, sir-2.2, sir-2.3, sir-2.4, skr-15, slt-1, slx-1, smf-1, smk-1, sod-1, sod-2, sod-3, sod-4, sod-5, spas-1, ugt-61, Y43E12A.1, Y43F8C.13, Y48G1BL.2, Y50D7A.1, Y50D7A.2, Y54E10A.3, ufd-1, ugt-22, ugt-52, ZK1128.4, ZK1290.5, or Y39H10A.7. The transgene, transgenic organism, or construct is used for the gene expression biosensors as described herein. According to the invention, an inducible promoter or fragment thereof, or a homolog having at least 95%, 96%, 97%, 98%, or 99% identity thereto, of one or more of the genes listed above and is operably linked, or fused, to a reporter gene using standard molecular biology techniques as described herein and elsewhere. The resulting construct can be transformed into an organism to a yield a transgenic biosensor organism as described herein. In one aspect, the transgene is introduced into the organism with a technique that yields a site specific single copy stable insertion. In a specific aspect, the transgenic biosensor organisms are arranged into an array or panel. The panels can be arranged into kits useful for detecting a wide variety of toxicities or gene expression responses. In one specific aspect, the transgenic organism is a nematode. In another specific aspect, the transgenic organism is *C. elegans*.

In one embodiment, the invention provides a transgene, a transgenic organism, or a construct which comprises a promoter, a fragment of a promoter having 50, 100, 200, 300, 400, or 500 or more nucleotides of the promoter, or a homolog thereof having at least 95%, 96%, 97%, 98%, or 99% identity thereto operably linked, or fused, to a reporter gene wherein said reporter gene encodes a fluorescent or luminescent protein and wherein the promoter is for the *C. elegans* gene ABCE-1, ABCF-1, ABCF-2, ABCF-3, ABT-1, ABT-2, ABT-4, ABT-5, ABTM-1, acr-14, acr-22, ahr-1, akt-1, akt-2, apa-2, ape-1, apn-1, aps-2, ard-1, arf-1, arf-1.1, arl-7, asp-5, atf-5, atgr-7, B0222.9, B0432.2, B0495.2, B0563.7, bec-1, bmk-1, C01B10.7, C01G12.5, C01G5.5, C01H6.4, C03A7.12, C03A7.13, C04F12.1, C05C9.1, C06A1.6, C06E4.3, C06E4.4, C06E4.6, C06G1.1, C06H2.3, C07A9.13, C07D8.6, C08H9.3, C09D4.3, C11E4.2, C16C8.14, C23G10.6, C25A1.5, C25A1.6, C27D8.4, C28H8.11, C30G12.2, C30G7.5, C31H1.1, C32D5.12, C33E10.10, C35B1.5, C35C5.2, C35D10.2, C35D10.6, C37A2.4, C37C3.6a, C41A3.1, C44H4.4, C46H11.2, C55A6.3, C55A6.4, C55A6.6, C55C3.1, C55H1.1, C56G3.2, cah-5, car-1, catp-6, cbn-1, ccch-1, cct-2, cct-3, cct-4, cct-5, cct-6, cct-7, cct-8, cdc-14, cdr-5, ced-1, ced-10, ced-12, ced-13, ced-2, ced-5, ced-6, CED-7, ceh-20, ceh-30, ces-1, ces-2, cgh-1, chn-1, cit-1.2, ckb-2, cle-1, clec-149, clpp-1, cmd-1, cnb-1, Cnx-1, cnx-1, col-135, coq-6, cpb-3, crb-1, crp-1, Crt-1, crt-1, csp-1, csp-2, csp-3, ctl-1, cul-1, cul-2, cul-3, cul-5, cyn-1, cyn-10, cyn-11, cyn-12, cyn-14, cyn-15, cyn-16, cyn-17, cyn-2, cyn-3, cyn-4, cyn-5, cyn-6, cyn-7, cyn-8, cyn-9, CYP-13A1, CYP-13A10, CYP-13A2, CYP-13A3, CYP-13A5, CYP-13A8, CYP-13B1, CYP-13B2, CYP-14A1, CYP-14A4, CYP-23A1, CYP-25A1, CYP-25A2, CYP-25A3, CYP-25A5, CYP-25A6, CYP-29A3, CYP-29A4, CYP-31A2, CYP-32A1, CYP-32B1, CYP-33A1, CYP-33C11, CYP-33C3, CYP-33C4, CYP-33C5, CYP-33C6, CYP-33C7, CYP-33C8, CYP-33D1, CYP-33D3, CYP-33E3, CYP-34A1, CYP-34A2, CYP-34A4, CYP-34A5, CYP-34A7, CYP-34A8, CYP-35A5, CYP-36A1, CYP-37A1, CYP-43A1, CYP-44A1, cyp14A2, cyp14A5, cyp33C9, D1007.16, D1054.8, D1081.8, D2023.4, dad-1, daf-1, daf-14, daf-21, daf-3, daf-5, daf-7, daf-8, DAF-9, dbl-1, DC2.5, dhs-1, dhs-10, dhs-11, dhs-12, dhs-13, dhs-14, dhs-15, dhs-16, dhs-18, dhs-19, dhs-2, dhs-20, dhs-21, dhs-24, dhs-25, dhs-26, dhs-28, dhs-29, dhs-3, dhs-30, dhs-31, dhs-4, dhs-5, dhs-6, dhs-8, dhs-9, djr-1.1, dnj-11, dnj-25, dnj-27, dnj-7, Dod-17, Dod-24, dop-1, dop-1, dop-3, dop-3, dpl-1, dpr-1, drh-3, duox-2, dut-1, E01A2.1, E04F6.15, eat-3, efl-1, efl-2, eft-2, egg-1, egg-2, egl-38, emb-9, eor-1, eor-2, epg-2, eps-8, exos-3, F02C12.2, F07A11.2, F09E5.2, F10D11.6, F10D2.12, F10D2.8, F10D7.3, F12E12.11, F14D12.1b, F14F9.5, F15E6.6, F16A11.2, F17A9.5, F18A1.5, F19G12.2, F20G2.1, F20G2.2, F22D6.15, F22E5.6, F23C8.9, F26D2.15, F28A10.1, F28H7.2, F30B5.4, F32A5.8, F36A4.15, F43G6.5, F44B9.8, f44e5.4, f44e5.5, F45E12.3, F46H5.2a, F49E12.6, F52B5.2, F52C12.1, F53C11.5, F53F1.2, F53F1.3, F53F10.2, F54C1.1, F54F3.4, F55A11.6, F55B11.1, F55E10.6, F56A4.4, F57B10.5, F57B10.6, F58F9.1, F59A2.3, F59E11.2, F59F4.1, fan-1, fasn-1, fdps-1, fil-1, fipr-24, fis-1, fkb-1, fkb-2, fkb-3, fkb-4, fkb-5, fkb-6, fkb-7, fkb-8, fnta-1, ftn-1, ftn-2, gab-1, gad-3, gale-1, gdi-1, ggtb-1, gla-3, gld-1, glp-1, glrx-10, gsr-1, gst-11, gst-12, gst-14, gst-15, gst-16, gst-18, gst-19, gst-2, gst-20, gst-21, gst-22, gst-24, gst-26, gst-28, gst-29, gst-3, gst-30, gst-31, gst-32, gst-33, gst-34, gst-35, gst-36, gst-39, gst-40, gst-42, gst-43, gst-44, gst-5, gst-6, gst-8, gst-9, gstk-1, gstk-2, gsto-1, gsto-2, gsto-3, H01G02.2, H04M03.3, H06H21.9, H10D18.6, H23N18.4, HAF-1, HAF-2, HAF-3, HAF-4, HAF-8, HAF-9, hda-10, hda-11, hda-5, hi-14, hif-1, him-10, him-4, hke-4.1, hlh-2, hlh-3, HMT-1, hpo-15, hps-1, hps-60, hsd-1, hsd-2, hsd-3, hsf-1, hsp-1, hsp-16.1, hsp-16.1, hsp-2, hsp-60, icd-1, ikb-1, imb-3, ing-3, irk-1, irp-1, irp-2, itr-1, jkk-1, jnk-1, K02E11.3, K02E11.4, K02E11.5, K02E11.6, K02E11.7, K02E11.9, K04A8.10, K07C5.2, K07C5.4, K08F4.1, K10F12.4, K11D12.6, K11G12.5, kin-18, kin-4, lagr-1, lbp-1, lbp-2, lbp-3, lbp-4, lbp-5, lbp-6, lbp-7, lbp-8, lbp-9, let-2, let-23, let-60, let-92, lim-4, lin-1, lin-12, lin-3, lin-31, lin-44, lin-49, lip-1, lips-11, lrk-1, lst-3, M18.5, M57.2, mab-5, maoc-1, mca-2, mec-14, med-1, mei-2, mek-1, mek-2, mel-26, mev-1, misc-1, mlt-7, mpk-1, mtl-1, mus-1, mut-2, mxl-1, mxl-2, mxl-3, nas-39, ncs-3, ndx-4, nhr-181, nhr-6, nhr-64, nol-5, npl-4, npl-4.2, nrf-5, nsy-1, nurf-1, odc-1, paa-1, pag-3, pah-1, pas-4, pat-10, pax-2, pdi-1, pdr-1, pek-1, PGP-11, PGP-12, PGP-13, PGP-14, PGP-15, PGP-3, PGP-4, PGP-5, PGP-6, PGP-7, PGP-8, PGP-9, phi-37, phi-44, phi-9, pink-1, pkc-2, pmk-1, pmk-2, pmk-3, PMP-1, PMP-2, PMP-3, PMP-4, PMP-5, pmrt-5, png-1, polq-1, pqe-1, pqn-60, prdx-2, prx-1, prx-5, psr-1, ptl-1, ptp-3, ptp-3, pxn-2, qdpr-1, R03D7.2, R05D11.6, R05D8.7, R05D8.9, R05F9.10, R07B7.4, R07B7.5, R09H10.3, R10E4.9, R119.3, R11A8.5, R13D11.4, R151.6, rab-1, rab-5, rae-1, rcf-3, rcq-5, rfc-1, rfl-1, rfp-1, rgef-1, rgs-2, rgs-2, rme-8, rnf-1, rnf-121, rnh-1.0, rnp-2, rpa-2, rps-19, rps-26, rtel-1, scav-1, scav-2, scav-3, scav-4, scav-5, sdz-8, sdz-8, sec-22, sek-1, sel-10, sel-8, sem-5, ser-3, set-25, set-26, set-8, set-9, sex-1, sft-4, sgg-1, skr-15, slt-1, smf-1, smk-1, smo-1, sod-2, sod-4, sod-5, srp-2, srp-7, sti-1, sulp-7, sup-9, sup-9, sut-1, sut-2, syp-2, T01G6.1, T01G6.10, T05A12.4, T05G5.3, T06E6.2, T07F12.4, T08D2.4, T08D2.7, T08H10.1, T10B5.10, T10B5.8, T13A10.2, T15B7.2, T16G1.6, T19B4.1, T19C3.5, T19H12.3, T21B4.4, T23G5.6, T25G12.2, T26A5.5, T27E9.1, tag-124, tag-353, tag-63, tars-1, tbb-2, tbb-4, tbh-1, tnc-2, tor-2, tra-1, trx-2, trxr-1, tut-1, uba-1, ubc-14, ubc-20, ubxn-4, ugt-10, ugt-11, ugt-12, ugt-14, ugt-15, ugt-16, ugt-17, ugt-18, ugt-19, ugt-2, ugt-20, ugt-21, ugt-23, ugt-24, ugt-25, ugt-26, ugt-27, ugt-28, ugt-29, ugt-3, ugt-30, ugt-31, ugt-32, ugt-33, ugt-34, ugt-35, ugt-36, ugt-37, ugt-38, ugt-39, ugt-4, ugt-40, ugt-41, ugt-42, ugt-43, ugt-44, ugt-45, ugt-46, ugt-47, ugt-48, ugt-49, ugt-5, ugt-50, ugt-51, ugt-53, ugt-54, ugt-55, ugt-56, ugt-57, ugt-58, ugt-59, ugt-6, ugt-60, ugt-63, ugt-64, ugt-65, ugt-7, ugt-8, ugt-9, unc-11, unc-2, unc-26, unc-36, unc-36, unc-43, unc-43, unc-57, unc-73, uri-1, usp-14, vit-1, vit-2, vit-3, vit-4, vit-5, vit-6, vps-11, vps-16, vps-18, vps-33, vps-39, W01A11.1, W01B11.6, W02C12.1, W03F9.9, W03G1.5, W10C8.4, wah-1, WHT-1, WHT-2, WHT-3, WHT-4, WHT-5, WHT-6, WHT-7, WHT-8, WHT-9, Y110A7A.4, Y23H5A.2, Y38F1A.5, Y38H6C.17, Y38H8A.3, Y39G8B.1, Y39G8B.2, Y39H10A.7, Y41C4A.11, Y43D4A.2, Y43E12A.1, y43f8b.2, Y43F8C.13, Y45G12C.3, Y47D3A.22, Y47D3A.29, Y47G6A.21, Y47G6A.22, Y48G1BL.2, Y50D7A.1, Y53G8B.1, Y54E10A.3, Y56A3A.33, Y66D12A.15, Y71G12B.4, Y73B6A.3, Y73C8C.10, ymel-1, ZC168.4, ZC395.10, ZC443.1, ZC513.1, ZC513.2, ZK1290.5, ZK287.5, ZK550.6, ZK616.8, ZK697.14, ZK697.8, ZK742.3, ZK742.4, ZK829.1, or zyg-12. The transgene, transgenic organism, or construct is used for the gene expression biosensors as described herein. According to the invention, an inducible promoter or fragment thereof, or a homolog having at least 95%, 96%, 97%, 98%, or 99% identity thereto, of one or more of the genes listed above and is operably linked, or fused, to a reporter gene using standard molecular biology techniques as described herein and elsewhere. The resulting construct can be transformed into an organism to a yield a transgenic biosensor organism as described herein. In a specific aspect, the construct further comprises one or more of the following: a selectable marker, sequence elements sufficient for site-specific integration into the host organism's genome. In one aspect, the transgene is introduced into the organism with a technique that yields a site specific single copy stable insertion. In a specific aspect, the transgenic biosensor organisms are arranged into an array or panel. The panels can be arranged into kits useful for detecting a wide variety of toxicities or gene expression responses. In one specific aspect, the transgenic organism is a nematode. In another specific aspect, the transgenic organism is *C. elegans*.

In one embodiment, the invention provides a transgene, a transgenic organism, or a construct comprising a promoter, a fragment of a promoter having 50, 100, 200, 300, 400, or 500 or more nucleotides of the promoter, or a homolog thereof having at least 95%, 96%, 97%, 98%, or 99% identity thereto, operably linked, or fused, to a reporter gene wherein said reporter gene encodes a fluorescent or luminescent protein and wherein the promoter is from an organism chosen from *Danio rerio, Drosophila melanogaster, Daphnia* spp., or *Xenopus laevis* and the promoter is for gene that organism that is homologous to the gene in *C. elegans corresponding to ABCE*-1, ABCF-1, ABCF-2, ABCF-3, ABT-1, ABT-2, ABT-4, ABT-5, ABTM-1, acr-14, acr-22, ahr-1, akt-1, akt-2, apa-2, ape-1, apn-1, aps-2, ard-1, arf-1, arf-1.1, arl-7, asp-5, atf-5, atgr-7, B0222.9, B0432.2, B0495.2, B0563.7, bec-1, bmk-1, C01B10.7, C01G12.5, C01G5.5, C01H6.4, C03A7.12, C03A7.13, C04F12.1, C05C9.1, C06A1.6, C06E4.3, C06E4.4, C06E4.6, C06G1.1, C06H2.3, C07A9.13, C07D8.6, C08H9.3, C09D4.3, C11E4.2, C16C8.14, C23G10.6, C25A1.5, C25A1.6, C27D8.4, C28H8.11, C30G12.2, C30G7.5, C31H1.1, C32D5.12, C33E10.10, C35B1.5, C35C5.2, C35D10.2, C35D10.6, C37A2.4, C37C3.6a, C41A3.1, C44H4.4, C46H11.2, C55A6.3, C55A6.4, C55A6.6, C55C3.1, C55H1.1, C56G3.2, cah-5, car-1, catp-6, cbn-1, ccch-1, cct-2, cct-3, cct-4, cct-5, cct-6, cct-7, cct-8, cdc-14, cdr-5, ced-1, ced-10, ced-12, ced-13, ced-2, ced-5, ced-6, CED-7, ceh-20, ceh-30, ces-1, ces-2, cgh-1, chn-1, cit-1.2, ckb-2, cle-1, clec-149, clpp-1, cmd-1, cnb-1, Cnx-1, cnx-1, col-135, coq-6, cpb-3, crb-1, crp-1, Crt-1, crt-1, csp-1, csp-2, csp-3, ctl-1, cul-1, cul-2, cul-3, cul-5, cyn-1, cyn-10, cyn-11, cyn-12, cyn-14, cyn-15, cyn-16, cyn-17, cyn-2, cyn-3, cyn-4, cyn-5, cyn-6, cyn-7, cyn-8, cyn-9, CYP-13A1, CYP-13A10, CYP-13A2, CYP-13A3, CYP-13A5, CYP-13A8, CYP-13B1, CYP-13B2, CYP-14A1, CYP-14A4, CYP-23A1, CYP-25A1, CYP-25A2, CYP-25A3, CYP-25A5, CYP-25A6, CYP-29A3, CYP-29A4, CYP-31A2, CYP-32A1, CYP-32B1, CYP-33A1, CYP-33C11, CYP-33C3, CYP-33C4, CYP-33C5, CYP-33C6, CYP-33C7, CYP-33C8, CYP-33D1, CYP-33D3, CYP-33E3, CYP-34A1, CYP-34A2, CYP-34A4, CYP-34A5, CYP-34A7, CYP-34A8, CYP-35A5, CYP-36A1, CYP-37A1, CYP-43A1, CYP-44A1, cyp14A2, cyp14A5, cyp33C9, D1007.16, D1054.8, D1081.8, D2023.4, dad-1, daf-1, daf-14, daf-21, daf-3, daf-5, daf-7, daf-8, DAF-9, dbl-1, DC2.5, dhs-1, dhs-10, dhs-11, dhs-12, dhs-13, dhs-14, dhs-15, dhs-16, dhs-18, dhs-19, dhs-2, dhs-20, dhs-21, dhs-24, dhs-25, dhs-26, dhs-28, dhs-29, dhs-3, dhs-30, dhs-31, dhs-4, dhs-5, dhs-6, dhs-8, dhs-9, djr-1.1, dnj-11, dnj-25, dnj-27, dnj-7, Dod-17, Dod-24, dop-1, dop-1, dop-3, dop-3, dpl-1, dpr-1, drh-3, duox-2, dut-1, E01A2.1, E04F6.15, eat-3, efl-1, efl-2, eft-2, egg-1, egg-2, egl-38, emb-9, eor-1, eor-2, epg-2, eps-8, exos-3, F02C12.2, F07A11.2, F09E5.2, F10D11.6, F10D2.12, F10D2.8, F10D7.3, F12E12.11, F14D12.1b, F14F9.5, F15E6.6, F16A11.2, F17A9.5, F18A1.5, F19G12.2, F20G2.1, F20G2.2, F22D6.15, F22E5.6, F23C8.9, F26D2.15, F28A10.1, F28H7.2, F30B5.4, F32A5.8, F36A4.15, F43G6.5, F44B9.8, f44e5.4, f44e5.5, F45E12.3, F46H5.2a, F49E12.6, F52B5.2, F52C12.1, F53C11.5, F53F1.2, F53F1.3, F53F10.2, F54C1.1, F54F3.4, F55A11.6, F55B11.1, F55E10.6, F56A4.4, F57B10.5, F57B10.6, F58F9.1, F59A2.3, F59E11.2, F59F4.1, fan-1, fasn-1, fdps-1, fil-1, fipr-24, fis-1, fkb-1, fkb-2, fkb-3, fkb-4, fkb-5, fkb-6, fkb-7, fkb-8, fnta-1, ftn-1, ftn-2, gab-1, gad-3, gale-1, gdi-1, ggtb-1, gla-3, gld-1, glp-1, glrx-10, gsr-1, gst-11, gst-12, gst-14, gst-15, gst-16, gst-18, gst-19, gst-2, gst-20, gst-21, gst-22, gst-24, gst-26, gst-28, gst-29, gst-3, gst-30, gst-31, gst-32, gst-33, gst-34, gst-35, gst-36, gst-39, gst-40, gst-42, gst-43, gst-44, gst-5, gst-6, gst-8, gst-9, gstk-1, gstk-2, gsto-1, gsto-2, gsto-3, H01G02.2, H04M03.3, H06H21.9, H10D18.6, H23N18.4, HAF-1, HAF-2, HAF-3, HAF-4, HAF-8, HAF-9, hda-10, hda-11, hda-5, hi-14, hif-1, him-10, him-4, hke-4.1, hlh-2, hlh-3, HMT-1, hpo-15, hps-1, hps-60, hsd-1, hsd-2, hsd-3, hsf-1, hsp-1, hsp-16.1, hsp-16.1, hsp-2, hsp-60, icd-1, ikb-1, imb-3, ing-3, irk-1, irp-1, irp-2, itr-1, jkk-1, jnk-1, K02E11.3, K02E11.4, K02E11.5, K02E11.6, K02E11.7, K02E11.9, K04A8.10, K07C5.2, K07C5.4, K08F4.1, K10F12.4, K11D12.6, K11G12.5, kin-18, kin-4, lagr-1, lbp-1, lbp-2, lbp-3, lbp-4, lbp-5, lbp-6, lbp-7, lbp-8, lbp-9, let-2, let-23, let-60, let-92, lim-4, fin-1, lin-12, lin-3, lin-31, lin-44, lin-49, lip-1, lips-11, lrk-1, lst-3, M18.5, M57.2, mab-5, maoc-1, mca-2, mec-14, med-1, mei-2, mek-1, mek-2, mel-26, mev-1, misc-1, mlt-7, mpk-1, mtl-1, mus-1, mut-2, mxl-1, mxl-2, mxl-3, nas-39, ncs-3, ndx-4, nhr-181, nhr-6, nhr-64, nol-5, npl-4, npl-4.2, nrf-5, nsy-1, nurf-1, odc-1, paa-1, pag-3, pah-1, pas-4, pat-10, pax-2, pdi-1, pdr-1, pek-1, PGP-11, PGP-12, PGP-13, PGP-14, PGP-15, PGP-3, PGP-4, PGP-5, PGP-6, PGP-7, PGP-8, PGP-9, phi-37, phi-44, phi-9, pink-1, pkc-2, pmk-1, pmk-2, pmk-3, PMP-1, PMP-2, PMP-3, PMP-4, PMP-5, pmrt-5, png-1, polq-1, pqe-1, pqn-60, prdx-2, prx-1, prx-5, psr-1, ptl-1, ptp-3, ptp-3, pxn-2, qdpr-1, R03D7.2, R05D11.6, R05D8.7, R05D8.9, R05F9.10, R07B7.4, R07B7.5, R09H10.3, R10E4.9, R119.3, R11A8.5, R13D11.4, R151.6, rab-1, rab-5, rae-1, rcf-3, rcq-5, rfc-1, rfl-1, rfp-1, rgef-1, rgs-2, rgs-2, rme-8, rnf-1, rnf-121, rnh-1.0, rnp-2, rpa-2, rps-19, rps-26, rtel-1, scav-1, scav-2, scav-3, scav-4, scav-5, sdz-8, sdz-8, sec-22, sek-1, sel-10, sel-8, sem-5, ser-3, set-25, set-26, set-8, set-9, sex-1, sft-4, sgg-1, skr-15, slt-1, smf-1, smk-1, smo-1, sod-2, sod-4, sod-5, srp-2, srp-7, sti-1, sulp-7, sup-9, sup-9, sut-1, sut-2, syp-2, T01G6.1, T01G6.10, T05A12.4, T05G5.3, T06E6.2, T07F12.4, T08D2.4, T08D2.7, T08H10.1, T10B5.10, T10B5.8, T13A10.2, T15B7.2, T16G1.6, T19B4.1, T19C3.5, T19H12.3, T21B4.4, T23G5.6, T25G12.2, T26A5.5, T27E9.1, tag-124, tag-353, tag-63, tars-1, tbb-2, tbb-4, tbh-1, tnc-2, tor-2, tra-1, trx-2, trxr-1, tut-1, uba-1, ubc-14, ubc-20, ubxn-4, ugt-10, ugt-11, ugt-12, ugt-14, ugt-15, ugt-16, ugt-17, ugt-18, ugt-19, ugt-2, ugt-20, ugt-21, ugt-23, ugt-24, ugt-25, ugt-26, ugt-27, ugt-28, ugt-29, ugt-3, ugt-30, ugt-31, ugt-32, ugt-33, ugt-34, ugt-35, ugt-36, ugt-37, ugt-38, ugt-39, ugt-4, ugt-40, ugt-41, ugt-42, ugt-43, ugt-44, ugt-45, ugt-46, ugt-47, ugt-48, ugt-49, ugt-5, ugt-50, ugt-51, ugt-53, ugt-54, ugt-55, ugt-56, ugt-57, ugt-58, ugt-59, ugt-6, ugt-60, ugt-63, ugt-64, ugt-65, ugt-7, ugt-8, ugt-9, unc-11, unc-2, unc-26, unc-36, unc-36, unc-43, unc-43, unc-57, unc-73, uri-1, usp-14, vit-1, vit-2, vit-3, vit-4, vit-5, vit-6, vps-11, vps-16, vps-18, vps-33, vps-39, W01A11.1, W01B11.6, W02C12.1, W03F9.9, W03G1.5, W10C8.4, wah-1, WHT-1, WHT-2, WHT-3, WHT-4, WHT-5, WHT-6, WHT-7, WHT-8, WHT-9, Y110A7A.4, Y23H5A.2, Y38F1A.5, Y38H6C.17, Y38H8A.3, Y39G8B.1, Y39G8B.2, Y39H10A.7, Y41C4A.11, Y43D4A.2, Y43E12A.1, y43f8b.2, Y43F8C.13, Y45G12C.3, Y47D3A.22, Y47D3A.29, Y47G6A.21, Y47G6A.22, Y48G1BL.2, Y50D7A.1, Y53G8B.1, Y54E10A.3, Y56A3A.33, Y66D12A.15, Y71G12B.4, Y73B6A.3, Y73C8C.10, ymel-1, ZC168.4, ZC395.10, ZC443.1, ZC513.1, ZC513.2, ZK1290.5, ZK287.5, ZK550.6, ZK616.8, ZK697.14, ZK697.8, ZK742.3, ZK742.4, ZK829.1, or zyg-12. The transgene, transgenic organism, or construct is used for the gene expression biosensors as described herein. According to the invention, an inducible promoter or fragment thereof, or a homolog having at least 95%, 96%, 97%, 98%, or 99% identity thereto, of one or more of the genes listed above and is operably linked, or fused, to a reporter gene using standard molecular biology techniques as described herein and elsewhere. The resulting construct can be transformed into an organism to a yield a transgenic biosensor organism as described herein. In one aspect, the transgene is introduced into the organism with a technique that yields a site specific single copy stable insertion. In a specific aspect, the transgenic biosensor organisms are arranged into an array or panel. The panels can be arranged into kits useful for detecting a wide variety of toxicities or gene expression responses. In one specific aspect, the transgenic organism is a nematode. In another specific aspect, the transgenic organism is *C. elegans*.

Examples of preferred nucleic acids corresponding to promoters that are used in the compositions and methods of the invention are given below in reference to the pathways and gene abbreviations in SEQ ID NO:1 through SEQ ID NO:XX.

Cytoplasmic Oxidative Stress Toxicity hsp-16.41

SEQ ID NO: 1

```
gattatagtttgaagatttctaatttcacaattagagcaaatgttgttcggtatttattttcaacggtatttatactattttccaccttttttctagaacatt

cgagctgcttgttgcaaaaggagggcgactcacattcggtacatggaaaagtagtgtacacaataaagagacccagatacattttccgtctg

cgtctctttgcacccaccgggagtattttcaaacgaatgcatctaggaccttctagaacattctgtaaggctgcagaatgcgggtatataagg

aaagcgggctcagaggaagccaacacgctttgttctagtgcatctaaaaaacttcgaaa
```

-continued hsp-16.2

SEQ ID NO: 2 tttcgaagtttttagatgcactagaacaaagcgtgttggcttcctctgagcccgctttccttatatacccgcattctgcagccttacagaatgttc tagaaggtcctagatgcattcgtttgaaaatactcccggtgggtgcaaagagacgcagacggaaaatgtatctgggtctctttattgtgtaca ctacttttccatgtaccgaatgtgagtcgccctccttttgcaacaagcagctcgaatgttctagaaaaaggtggaaaatagtataaataccgtt gaaaataaataccgaacaacatttgctctaattgtgaaattagaaatcttcaaactataatc hsp-16.1

SEQ ID NO: 3 tcttgaagtttagagaatgaacagtaagcacttgaacaaagtgtattggtttcctctgaacacgattggcttatatacccgtatcctgcagccgt ttagaatgttctagaaggtcctagatgcattcatttcaaaatacaccccataggtgcaaagagacgcagattgaaaaagtatctgggtttcttc agtacgcacactatttctcaatgttctgaatgtgagtcgccctccttttgcaagaagcagctcgaatgttctagaaaaaggtggaaatgagtat aaatacagtgacaaaaccgaaccaaacaacattcactctaattgtgaaatcttcaaactacaatc hsp-16.11

SEQ ID NO: 4 tcttgaagtttagagaatgaacagtaagcacttgaacaaagtgtattggtttcctctgaacacgattggcttatatacccgtatcctgcagccgt ttagaatgttctagaaggtcctagatgcattcatttcaaaatacaccccataggtgcaaagagacgcagattgaaaaagtatctgggtttcttc agtacgcacactatttctcaatgttctgaatgtgagtcgccctccttttgcaagaagcagctcgaatgttctagaaaaaggtggaaatgagtat aaatacagtgacaaaaccgaaccaaacaacattcactctaattgtgaaatcttcaaactacaatc hsp-16.48

SEQ ID NO: 5 gattgtagtttgaagatttcacaattagagtgaatgttgtttggttcggttttgtcactgtatttatactcatttccacctttttctagaacattcgagct gcttcttgcaaaaggagggcgactcacattcagaacattgagaaatagtgtgcgtactgaagaaacccagatactttttcaatctgcgtctctt tgcacctatggggtgtattttgaaatgaatgcatctaggaccttctagaacattctaaacggctgcaggatacgggtatataagccaatcgtgt tcagaggaaaccaatacactttgttcaagtgcttactgttcattctctaaacttcaaga hsp-16.49

SEQ ID NO: 6 gattgtagtttgaagatttcacaattagagtgaatgttgtttggttcggttttgtcactgtatttatactcatttccacctttttctagaacattcgagct gcttcttgcaaaaggagggcgactcacattcagaacattgagaaatagtgtgcgtactgaagaaacccagatactttttcaatctgcgtctctt tgcacctatggggtgtattttgaaatgaatgcatctaggaccttctagaacattctaaacggctgcaggatacgggtatataagccaatcgtgt tcagaggaaaccaatacactttgttcaagtgcttactgttcattctctaaacttcaaga hsp-12.2

SEQ ID NO: 7 acaattcagaaggagcaataattctgtgatatttaaactaatttctctttgtttctttgttatgagtatttatttttagttcttgttcatcatgctttttt tgtcacttttccctccccaatcccatattcctctgcttttctctcattttcggttacgtgtattaattgaatgtatacgacgacgacagtcactagtttcgaa ataactattttacgaggatgaataaacacactgatcgctgagcgacgctccgagcacttttcgagaagtttctaagaagccacttgaccgag agagagggagaaagaaaagcttggcatagaaatgtgcttgtgtttatttgaactgttaaaagtgtttgacgggggcgaagtcactggggaa acctcgagatcaataggacacgtggcaatttgaattttggataattggaaaagcagtacccgactaaagatccgaatttgattttcagacattt tactgcaaacttgattacacacggtaattttccaaaagttttgtgcattgaatcccgaaaaacttcacaaacgcataatattacaacccgatctat gagcaaagtaaatagagagaatcaggctgaaagcttattgtgattaatgaacattaggaacaatgctgatttcaatttgaaacatttttttttcag atcgaaaatcagtttttttcagatcgaaaatcacattggatcttgacattttcaagagaattattaaaatttaaatggctatttgaaaagtattgatttt ctgaaagataataactacttaccatctatgtcgtacctgactatgccaattattttcaacaattgtttattttaaaaaattttgaagtaagcttaaaa caaacccaggacctctgaaatgtaccaagtttggaaactaattccaagtactggtaataacaaaaattttgaattcgaggcggataagcgcc agttgggagttttctgattataattatattaatagaattgccaaaaatcatgataaacccctccaatcatttttttgattttcgaaaaagtttcaatgta ggttttggtgagctgcgaagttttccaaaaatgtctaaaaactaaattcatatggttcaatttttgtcaaaaacgttcagctcatgaggagcttga aactaaccaataaattttggtcattaaattggtcagttaaattgataattgaaattaaccggatatgtttggaaaaataaatgcaaaagttcatgat catcagatcaaaaaccaaaaacttcccctacatttctatttccaaattgaagatttcttgaagcctacaaatagtacagtttacaaatatctctcct -continued tctttctctcgtcccttcttgcgcatcctcagagctcggagctcctatccgtcaatataaacaatcattgtttcttttcttctcctcgtaccttttttctt cttcaaatccattttcctccgccccttatcctacagtccaattcctttcactctccactttctgagcttcttctccaactcgcaaaagcttcaaag ctcacagagcattttacgatagtgcattgtaatgttctccaccctagagtgcatctccaacctgcgcatatgttttcgctctttgacattacattttc ttccgattcacattttattcatccacccgataaatatattttcacacttttaattttctagagaaa sod-1

SEQ ID NO: 8 tattctacgtcaataggaattgtcagaattatcagttttgatatcaaaaattgccagctttagtacagtagaataactatgcgattcatgctgcttat tatttattcaaaatttaaattttaaccaactgtgagtttattttatagaacattttcgaaataaaattcaaaaaaataaaaattgttatttttcaaaatct taatcttaatttagcaccattaccgacaggcaatgatagaacaccaaaccggactgaccaagtgtcgtaccagtttcgagcaatcaagtattg agagactgatattcttgctgatactatactcttaagatatgaaacgatatctacccctctagcccccctactcgtgcgccctcagttacctacctac cccgttacctaccctaccctacctacctactcagtctcctacctaccccgaccgtatcatatctttagaatatagtatcaacaagaataccaatc acccaaccccaatcactcgaaaccgttaggcaccaggttagccagtctggattaatcgagagtaaaccacttgactccagacaactacatct tatacttacttacgtctgggggacaatcttgggattctcaagatgacttccattacgaagtctcttgcaataaccaattaccacaattttggagca gaattaaactcacccaccagtacaggatcaaagatgaataatgaatgagaggccctcctctcattgttgtgggcggggtcaaggggtcaaa gtttttgaatttcgaaatttgaaattttggaattgttaaattttggaaatctaattttgaaagaaccacatttccgtttacaatttgagttcaattcc gcaaccccgtcaaatttaagaagagaaagaaaaaaaacacaacgtgtttgcacctgtaaggtagttttttttgttgccttcggcgttttgattca catgaaagtttctacggaaaaactttcattgcataacgatcttcatatcttgtttctggaaacgaaaatttccaacatgaaagaaacccgacgct atttattctcgcaacacaaaaatttcacatttaaataaccgcggtttttctcgaacagcatatttgacgcgcattgctcgtcaagtttgatgcgtgc acactattttgctgttgtttttttctttttctctaaatttctttacgctttcgtagtttctatagaaacgattctccactcccggttttcttccgattc tcaaaattaattaaaatttagttattaaaaatcctttttcttgaaataatcgttcaatttcgagttttcaagagtggagacgttgaatttgtgagccgc ttatttttctgtgtttttgttttgtggtttttaatcagtgtcataatcatactttccattgtttctttattattcaaagttgtagattcagtattttag atcggtgatgtttatgaatcttctcactcaggtctccaacgcgatttttccgcaggtcagtgcttatccgaaacattcgtcattcgcaacttgggccta tttgatctatggcgttgtgttgttgcctttaccttaattatcatcattttcatcagaaacccacaaaaactagagacatagctacaaaattctgcgacc gagaggcgggtacacacacaatgttgtctatttcatctcgctccaccttctctctctctctcgtgtttaccatttctttttaattttgcatctatcga ctgtgatctgcctgtttttttctaattctaaacttttgccgtgatattccttagagtgttccctagaaaattcgttgaatttacaggtcgaagccgct caaaaag sto-1

SEQ ID NO: 9 aaaaacttgatccgatcgaagaaaaaaccgaaaaaaaattcgaattgttgtgttgttcgtcagttggatggaatgatgatgaaggaagttgatt aatggatatgactgatgattagtggtggaatatggaataattatttatttgatttattctgattattctgaattagaatgtattttcatatttcaggaaa aatgattttatttcgaaacgaacttgttctagattaaaaaaattgaaatttaatatttagtgctatacaattacagtaccccatggaaatacacaaat atcataaatacaagaattatcttcctggaagttaaacttatattttcgatgtaagtgaaaaagtttaaaagagaaatgatgtttgttgatcttcctgt aagtggaaactggagaattcataagcttaaaaattccaaaatattaaaacttgcgtgtttttttctgaaaatcgattaaaacagcaatattcagcat gtttccagagccaaaaaaacctgcaagcatgggatacttttgcagttaaaaaatgtttcaggaacttgaatgaagttaggatgcatttgaaca gagtaatgaaattatatgaaattcatatgtagactctcctactcagttgtttgtatgtgagttttgtatattataacttattttgaaattatctttaattact tgtaatgtttttgtatgagttaaataataatctttgaaaattctttttcaaataaccattttctgtttaaaaaaacagtgagcccaatataaacttgttt tccatcaaaccgagcttctaccaaagttaacttaaattccataattttcacaaaccattcatagtttgtctacgtagccttatcctttttttgaacattg aaaaagtgaggagaaagtgcgaaaaacgagtttttttctttctcttcttcttggtcgtcacgtcaagacactctgaacgttggaatgggaaaag catcgaagatcgaaaaattctgatttttttctaaagtacacaacttatattgatattgcattgggatttaaaaaagctctactcgaacattttgattaat tttaatatctcatttattcatctttcgataacagatatatcacattgttcggtaggataaaagggctaaaatcaagttttgaggaatgttcatttgtttg gaaggtgatattatagtctgcgataactacataagtttggaaaccgaacacatgtttttttggcactttgctaaaaagttgtctgaaaacgttgga aatcaatatttggtcatttatttaggtcattttcggaccattataagtgttttctaatacaaaactggcgctgctccgctatttaaaagactgaaagt gacataaatgatctaatttccagatctcttataactttttttatagcggttccactcctaatttgatgtgtttacttgttgcatcagatcattttcacttc -continued ttgtaattcttatcagttttctatattttctttcttatcaatttttcagcttttcaacattttccagttagttattcaatttttattccgcacgatcactgc tgtttgaattcaaatattggagtattaaaattatacatttataaccattctaatgtctaccttctacacaaattacccttcctagtagaaaatatat ttttggcttgaaatttgttctgtactgtccaa gcs-1

SEQ ID NO: 10 tttctaagttcgcacattcctcgatttccacttgccgttacctttcattatctccttttactttaatctatcacagtttcatagatatcaaacgttaatttt tgttgcgagctagtttgttttttttcctcttgttcggtccattcgctttaacttgtcacctatttttttgttttctctacagtcctcttggttcatgatcctg ttaattatcaatgctcttttctgtgatattcgatattcgaatcaacaatgtgtatgattagtgtcaaagtaacttatcggattttgaatataattcaattatt cgtgtaataaataactatttttttagtttactcatgtttgccacaaactagaaggtttatttattcataactacttgcaatttcacatttgaattctaactg tatgattgcttcaactctctgcgatttttttgcgctaaaatacggtacccggtctcggcgcgacaaaaaatttctagatttttagaaaattttacaga tttattgcaacagctgttacctttttcacaaaaaaatcgactgaatttcgcgaagttatgatatctcaagcggccgcttgcgggaaaagccatat tttttttcaaattttcgtagctgcacaatttttcataatttttttcatttgttaaaaataaatgtattttaaataattgtcctatttcagtttttcaataaat ttttttaacgaaaaactataaaaatagatgaattctagagccacgtaatttcagaattacagtactctttcaaggcgcatacccttttaacataaattttcg cgtcgagaccgggtaccgtactttgacgcaaattttgcatctgggtaattcttgtttttgggttcttcactttccaccactttttttttcgaaagcatca aatttcacatattcacgtcacaatcctagcaaagcccaatagctcattcaagtcatatttgtctctttctttctcattctcctgattagcaacactgtc ttatcaaccactaggttccgtcttaatcgtccaaatattgatccgctcgctcgtgttttctcaacttctttatttgctgtgtttttctgtttctatagttctc cattttccatctcctcttcgcttgttgaatggactttatttgataagttcattttaatttttctaacaatctcatcactagctcatgatgacaattgcaa agaaattcgtcatatagaggggaaaaatgctgacaaatattgaaaagccttcaggagagatgtagagacgtaggagtagagacagaacat aaatttgagaagcttgtagggagaatagacatagagttaccatgggaaaaacgctcgcattttccatttaacgagattttctagatcacaacat tttgtgatccgttgtgcgaaaatcaagctttttatcaaacttttatcgtctgttcattctttctgacaatctttattatcttattaaacttgactaattgta ttgaaagtattttttttagatgcgaacgaagttccattttttcatgacttaacatctcttaacgttagtgaaatttttgaattccaattaggactacggtag gagttctgtagttgatttcctgaacacttgttttgtaacctttctgaacggattttaatatttctaaaattttaaattgcaaatctgagtcctattaaaag atgtttcatccgtaaaaccaacaaacaaaatatcactttatcatcatgagatttaatgtttccttttgattttctgaattgttgtactttccttcaaacg acttattgaactgatgtaactttccttctaatgttatcatttgtatttttttgcaga hpo-15

SEQ ID NO: 11 aaaccaaatttactacttttactatattttttagttgaaaataaaaagagaaaaacatttattttctaaaaacagtaattttcctttagtcagtttatttctc attgagatattgtgaactcctgttttaaaatcaaatgagaaaaattgaacacaaattttaaatttacataaatccccaaaaactatcaatatttcca acctagacacactataattgaataagattctcgtgaccttcggacatacagtttgtcaaagacaagcactcccacatttgccggttaattgtgat aaccctatcaacttggctccgtcttcactctcacttgcaattgcacaacttctttctttttggatgtaagtagcaacattttatcatcactctattggg aaatttttaaaacaaaatttcttcaatacgattgccggtctcgccacgataaattgtaggtacatgcgaaaaaataatgcccatttaaagagtac tgtaatttccatctctctttgttgcaggatttttttgtcgatttttttagttgttcaatacaaataaattcattcgaaaactgtcatgtcacgataaacaaa caaattttggtatttaacaaaaatttgtcgtgtcgagacctaagctagaatagtactataattttttgagctttaatttttttcaagtttttttacaaaatttttt ttttctgttgattaattgatgtatttttatcggagatctataaaaaaatcaatgaaattttcgaagaagccaaaaaagtactgttgatactacagtaa tcttcaaaggcgcacacctttcggcatttaacaaaaatttgtcgtgttaagaccgggtaatttgttaggcaaatatttgaaaaaaaactgcttaa atatttcatgaaaattctgttatctttaatcagatttttaaaaaattattatcaaatttcaaaaaattacctaaaataatgtctgaaattcttctttactca cgcgaactgcaacttccagacattaattgaggaaatttcaaattaatcaataacaatgaatacgattttcagattaaacgagtattttcctacattt ttattaattttttttgattaatattaattttttaaaatgaaatttttggataatcctactaaaataagcatgtcccgcaaggccctatttcaaaagtttagtg cctgaaaaatcaatatttcgcaagaacagtctaccaatttttccaatttatacttccggcaattgccaccaattcggtgatctagaaaatacccat ataggctctacagtaccttcccttatcacccacatccaattttgctatcagttagtcttcaatcacacttagtctttgaacaaatgaactcataactc tcacaagatgtttgcaactatcatattgatgtcattcagttctcatatgagaaggcgggcacattgttgtatattgataaaccacccccattttcct cttcttccagcaaaaaaaaaataaaattaatattgtctcagacgcttgtgaaactggtgctctcaattgaaaagcaccattgacttcgcagaaact -continued ggcagttcatttggctttcggatacttacaaccatacgctcaca dhs-18

SEQ ID NO: 12 tctgtatatatgcaaaaggaaaattaaatattatctatcgatggaaatgttagaaaagcgaattacttggcacggcagcaggtgccacaaagc ctgcagctgaataaagttaagatacgattgcttgctgacaaataggacactaaattggaaaatacacaccacattttgatttttaatcagatcttt tttaattttaattttagtcacatctagactactctgactactattctcacacgtgtggccaacaatcattcggactacgctgtaggcagtcaggagt tttcaaatgataaggtgttcaacagtgtagtcttatttgtatcattttcacataaaacgcaatttcaaaaactcccaattttcttcagactgcggtaa aata gst-14

SEQ ID NO: 13 ccagttaccgagatctaatttttttctattttctttttctacttttcatgaaatacgcattttgaaaacgaataataaagtatgatatgctgtcaaaaaa tttcctgcattcttgcaaaaccggacgtcgaacaccaatttgccactttgatctacgtagatctacaaaaaatgcgggagaagatcttctcgag acgcagaattctcaactgatttcaaatcgttaagaacgtgctgacgtcacatatttttgggcaaaaaattcccgcatttttttgtagatcaaaccct attgggacatcctggcatcacgtgatttgcctaaaaccaaaaataatgcgcattcagagaacatgcctattgtgcctacctatttattaactttga cagtagataggcaggcggctgcttagagcctataagctagcctacctaggcaacccacatagcctacctttcaacttttcaaaagatcattgg atcactaacacaatgtgactagttgtggtttgttacaaattgcctcattgtcaccctaaactccctattatttcccgtaaatgatgacgattttgatc ttttgtagggttatcttgaagtgaaagatcactaagtacccagactgcactctagtctttttcccctttaaatagtctcgagaatgagtttgagaaa ctaaaa gst-32

SEQ ID NO: 14 tataattttttttcttaattttcatatgtttacattaaaaatttgagaaaataaagtagttcaagacaaaatcaaatatggtagagactgtggtttaagt ttgggtttactagggaatggtcagcttaggggtgaggtacctagagacgccacatatgccaaacggaagctgagatcattggctacaagaa tatgctttcaaattctgcaacggacctctgggagtctggaaattcttgtctgaaattatgcttttgaatgctcgaaagtggtaagaatttagaattt attacagaaaaacgtttaattaataaaattagttttatacttgaaacaagtattgtatgcactgtatcaaaacacattttcatctttctaggtattcaa cttcacgtttttctgtaataaattctaaattcttaccactttcgagcattcaaaagcataatttcagacaagaatttccagactcccagaggtccgtt gcagaatttgaacgcatattcttgtagccaatgatctcagcttccgtttggcatatgtggcgtctctaggtacctcacccctaagctgaccattc cctagttaggcttaggcttcggcttaggcttacgattaagcttaggattaagcctaggcttaggctttgtctgagttcaactctccaccacggga aaatttttttgcaaatttttttcgtcccaaaaaaaaaaggaaaaaaaaactttatttttacttgatttttttcacttttttttcgagttcaactctccaccac gggaaaatttttttgcaaatttttttcgtcccaaaaaaaaaaggaaaaaaaaactttatttttacttgatttttttcacttttttttcgagctcagctcgac cgtccctcaatgaaaacaagcaacctgatgtattccagatactcccgtaccaaaggtcatttctcgttagtcacaaaatattctgattgaaaatg gtgaaaaataacgagagagttgaaaattctacagactatggcctaaacgcagcaggtgagacacagtagagaacaagaggcagaagag agagcagaaggcagaggaagaactaaagggtatataaaaagtgttttgttgatcagtgggatcaaatagtgtgcttttttaaaagtttttttttcc ataaatgtattgatatctagaatttttttcgagttcactgttgtttaacagtgtcacatggtgtcaggctgtctcaatacagtttgatctacaaaaaat gcggaaatcttaaccatgcaaaatcagttgaaaactcttcgtattttctcccgcatttttttatagatctacgtagatcaaaccgaaatgagatactt tgatacaccgtgcagtgttaaaaaaaaatacagttacagc gst-38

SEQ ID NO: 15 tctcattctcttcaagacataacacaacgggctgacgaccatatcatcaacgacgatttttttaggaactgtactttatctgtgtctgaccaacac gtgtgaatgaagtttcaactggaaaatttgtttgaaacactgcaaagaatttcgaattttgatgataattttaaatgccattatcagttttaatacgc cactctagtctttgattctttgcacacacacacacacacacacacacacacacactcacaaacacgcctgaaatttcgcaatatgctgatttaa cgagaaaacatttgatgacaataaacttggcgtattaatataaaagggaaaattcaattcagattctcaacggtttattttctgtcacaactcttcc taatattcacc

W06H8.2

SEQ ID NO: 16

Tacacagccaagtctcataaccaaaataatattgatagtaaaaacatgagtgaacacgtttcaaaacaacatgtcattgaaaatcaattttaat gttcacgggaatttttttccaaaacagttttactcaaacatattttccatttgaaagtttgggaaactatccctggcacgttttcactgcattggtctt -continued tccagttgattcagccagagttggaaagcctgtactttttttcccaacaaccgtttctactgctcaacttgtaacctcaaatttgcctaattgactcc gaagcttcaaaacttgctttaaagaactttgatgaaaatcgctgcggcgaaagaatcattgcggaatttttgccccagggatctaaatttccaa cctactccactgaaccaaatttttttcaaacttcaccaattttttttattttattttcacatgtcattaaaacactaagaattcaatacatgtatgaaaact gcaaacaccaaagtacggtttggacttgtaagcaaaacaccggtagtctctttgacttatcatgtattgtcatcctatttcgtcagacggtcttgt aagttcacattgacttactctgcgtctctcataggacacatactccgcatctttctcaatagatcaaatatattttgtcatcacctattatttaaactg gttggtttttcacaatgtcacaactaattgaactctccacttattgaacttgacttgaaatc cyp-34A9

SEQ ID NO: 17 accgccgagttacgacatcagattcaagcctttgaaagtttgaatctttaataattaaatgaataattaattgggagaaacatgtacataaataa aatttccattaaacaatgttcatttgtttaagctggcacagaccacaaaagctgaaaccacaaagtttttaaaccttgttcttttcttaaattttgta gtttcttatcttatcactcgtgtttcttgtcctccaaataattgtgaaaattgtagttaatgtgtcaaaaaagtcacatataagaagacgaacaactt gattttttgttgacttcatttgaaaaaaaaatagaaaac ugt-41

SEQ ID NO: 18 agaacccatttttacaaattgtgttcttgtggtgttcgcgtattaactttttatagctgtttttttacttataggatgattaagaaaaaagttccggcttt ctcaaagtaaggtaaatatttgaaaataaagaacttgtaaaaggatacagctaactgattaaaaacaaaagacccatgttagttcacgctcg gatttggagttcagctggaggggaaagaattcagcgttgaaatatttcagttggaatttcacctgatattatttaaaaaatgttatacgaaaattg aaaaagcgcctcttaccccctcttcgcccgctttcctcttgcctactgtgcagttttttgtctttacggagttaacaagttgataacctgtttaagg acaacagataaaaacagagaaaattaaaaaccactattggcgatttgaaatttccgttcccatttttcacttttcaatttcaaatatgtacttaacg gtttccgatcattaacacgtaatccatcatttctagacaacaagtcacaccaatgccaatcaaaagtgcaaacatgctataacgaatcttttttttt caattaaactgtttacgatggaaattaggatagtgtcatagcattaattttcattgttcaaaaacagaaagaagtcacaaaatcttcacgtgaac atgtttcgtttccataaacaaattgtattttcaaagacagccgggaattttcagaccaattcaggtgacaactatgggctaccacccacctaact gtttgttcgcgattattctgactcacatcatgttttcaaaagtgactgtataattggagtgtagcataatcaacacaaactacagaatgggaaatt tgtgacagtatcaatcacattaacagatctataaaagagactgggaaagttgttcagagacacaaattcgttgtctacttatcaaatc dnj-19

SEQ ID NO: 19 aattttaaagtttatggattatttagaatttatgaatattttaaatatagcttgtaatagtagcattggctttttttattagttagaatgcagtatttatatag attgtagttgtgtgcgtgctaagattattggagtattggtgttgtcacgtcttcagtctctctgccgtgcgctcacgagaatggggcaagcgaa gttgcggctgacgcgttattggatgctggcgcgtttcgcgaccagcgttggttttatcgagaattttctctgcagtacaaagtcccaaattcgg tggtttttttatcgatttgacgcgcgtttgctcaatttctcgattttccgcgtttttttattcagttctcattaattaacgttcgatgcttgttcacaaaattc agtttttgttttcacttgctcgttggtgtcgttcgttgtgtaagaaaattgatttctaaatattttgtttaaattgctaaaaaataattcaataatttacatt attgaattattaaaagttgtatttttcaaacatctcgcgcattctccgtccgtttctctcaattttttcactgtcatgtccgcattttaatattcattttttt tcaggtaat hipr-1

SEQ ID NO: 20 ttggttataggaatatcctcctaggatagacgtttttttctagtaatttttgttgtttttgttcgttacaataaatctcatttttattttctggattaatt tgattaccaatcgtttccagcgattttcacatatttttccagaatttaatacagattaatattttcgaaaaatttaaacattttcttttcacattttaatt catctctattcattatgcaatactcttttggttttcaagcatccgacattcctccgtttcatttatgtttgcatttctgctggcatgaatgcatttcattg tgtctcgatgagaaaaaggacaatttcatgagcttatcagttacttcgttttcaaaattttaatgttgaccagccattgatgtcatattttgtctaag aagctcaagaactattatttttttgaagcttaatttcgaagagcaacattttttttcattaaaattcagcagtcattgttctttaaaaagttttgattctcgt ttttaaacgatttttaattcagtcgagaattgaataacttcccgatttcccggccaccatcgtttaatacctttttctttatgagactaacttccaagtat gcaaattgcaaatcgacgcaaggggaatacactcgctcacttctcatcgaaattcgaaacctttttcccatttttctttcatgtctttttttcgcttttctcc tctctgcccatttccatttatttctcaaacaccgttcagtgaacacgaaaacccttacggaaattgtgttgtaagaatacaaaaacttccgtagcatag cgagaaagagtcaccattttgtagtgtttgcccccggtggtatagtttgcacaagtttctgaaagaagaagaagacacatttgaggtcttatgc -continued acataaaaatcaatgttagactatctttttcacgtagttttcttttgcaaagtggaaacttctcattaaacacttttttgcttttcaattgtctgaacaagt tttcgattaaacagctgtaaagcttttgcaagtttcatggtttatgaactatttcgaatcggttacattgctgaagttttagtgtttcttgaatatgtcg tcactaccaggactggaccaaaaatcaaaaagaatttaaagtgaaataccaaaaaaaaaatcgtcgatttgcgatttttgaaggactgtaagt gactttttggcttcatttaggtcccaaaaaaccttttttttctcaaaaaatgtgactcaaaataccaaaaaagtcttaacctgatcacttcgccttct caactcaagccattttttgctgtttagttcgaatatggaacaaatcataagaatcttgagtacctatatgcgatacccgattcattttcctctcttcta aataacatcatttcctctctttttccctctctctctctctctgtttttgtttgtgactcactttgtccacaacgcgcgcggaaccggcttgttgccaca cacacactgtgatgaaatatgcgggaggaaagcttttcgcctaatagttgacttacttttcatctatattcctcaattttgcaactaatagattgatt tgtcatggttttgatttcagggttttgaatattctttgaaattggaatttttaacaaaaatgcaaattatgtgccaagtcatatctcctcctcacactttt tctatcacatgcccccaaaaaaattaatttttttcagga Ubq-1

SEQ ID NO: 21 gaatgcaggatataaatcacgattttcgttttcgaacacaactttaaacttcaatttttcctttgtttctctgaaaactttgcagtcattttcaagcttc cacagaactttacaaaaaaactagattttctccaacgtggcgatattcccgagtttcgagaagaatccagcttgtcaatgctgtataaaaccttt acttttctatcgtttccattatttctttcactgcacctgttactgccaggtgctttatttcgcctatcgtctattttgttttcctcctaccaaatttgacaac cctccgcaaacactcattcctatttttagcccggtgaaatttcgatatggagaaaaacaaaaacaagtgtgagcttccacttcggaataatttcc ggagaatgagaattgtacaattttctcctataagaccatacaataaaattttatcagaaacatgaagctttggtcattatcatttttttgttacccttg aaatttgatcacaaggctttaatttttcatgagacgtcaatttttttctgatgataaataacatagttcaaagtattgcgtaatgtttcaattttaacatg acacataataaatcagaaactcgaaaaacgtatttaaatatagattttgtcgggaagtttaatgtgcaactgtctcgatatctttctttgaaaacat ttaatttttattatattttccaaactggattcgagaattctcgtattcttaaacaaatttacaatgaaaatataaataattaatttaaaggaacatgttct gcaatcctccctgggtcccgccacgaaaccgccacgcactaccatgaaaggcgcgttcgcattcgttctgccgctcgtttctgttttccagat ctttccatcatttttcttcattcattcgcgctctctcattatcttgagttgccggctatttttcgctgctctctgctttttcgtatcgctttttcactctttcca gcattcagaaaattgcattatttcggttttcatttaaaaaactcatagcaaagtattttgttattgatttcgcaatactttcgaaaagtatcggaaaat tttaatgtttagtctgtgcgttcctcattccctgttctcgttgtactcttaactgatgtttttaaatttagttttccggggctctcttgaaaagacccaat agtcgtattgaaccttcgcctgatcgccactagctcatcttttagtcttatgacgggctcacatgattctccccagtgtcctcccgttttctcactg cacttgttttgtcgttcgttcatcagtacaaagtacaagcactttcgcgtctgtctgaaaattggttcgggtgccgttaggacattattcatactttc ctgctagtcgcagattataaaaaaatgtccttgaccgtctgctctttcttatgttctccctatatatgcgtcaaacgaacaactgaccctgttcact tttcctattcttcgtttcatcattttctgtaacaaaaatggaaacaatactttacacagacgtcactattattcaggcctatgatttctctatcgtttagt taaagatgaaaagaaactggtcgacccagttgcatgacgagaaaaaagaacaccccgttcgattttcgttgtattccctctgcacacattgtc cccttcttcctcatcatttctttccctacacagcactctagaatgttcttcttgtgcagaaagagtgccgtttgagtcagcgaccccccccccc ccctcctttctcttgctcttcctcactggttctcgtaataggcgacttcttgctaacagaaagtgagcatagcaacatttttttactttgtggccttca ataatacgtgcgtcgtttaattagaatgtttgagtaaagttcaacgtgtagattcaatattcacgttttgggcgctctttaatttattactgtcaagaa tcagtttaccaaacggtgagtttcttttttttttgtctaattgtaagatttagcggggtaaaaccaacagaaatgtcatgctttttttgaataatctcaat cagttgttatatgaattattttcccattttagcaatactgcttggtagttattttcggtcagagaaacgaggacatcagctgaacatctgcgtctct aacaacactcggggaaggcggagtcagtgtgcgcgtgcgttgggggttttatcgatcgttgaggcgggcatacagcagtcatacacccca ttcgaccagaacgctccgctcgcgtgccaccttgtctccattctcatttcacttgtctctactcggacattactcctcatcgattagctctttacta ccatttttacttttatgcctttctttttttcgtttgacttgcctatgacgagtggggatgaagtttgctttgttagtcttactagtgtatcgatttttttgggta atatttcgcaactttctaggactttctttcataatcacctcttctctcgcctcctcattccagttttattcgcactcattttctatttttttcagcaatc Ubq-2

SEQ ID NO: 22 aatcaataaaaaaacgttcgaaaaacgtttgaaacaaaaaaataatattcgaattcttctccccccttcccgtaaatcctgcagctctctaccgta ctttcgccgtctctcaatttcgcggcgagacccatcaccacggcaatcctccatttgtgtcgctgggcctaaatttttttccgtttttttgctcgattt tcgccgtttctctgcgaaatttttccaaatttctgttcaatttaatcaaaatattgttctggacgcttgttcagcatagaaagtggagattctgttgta ttttaagcttggaaaacgaatttattatgaaatttcatttttttgctaaataatttctctattcttgaatttttacagctttttaacgcaaaatattctttc -continued ctctttgttctaaatgggtagttacacacattatgcggtctataacgtcttttgtcacctttgaaactagtctctaaagaaaaatcaataatttttgccc ctacgctctcctccaaatgtttcgctctcgccgtcattttctgacaattttactcggtttcttttcaaattatataatttcagtcg sto-2

SEQ ID NO: 23 tgtaaacatttgttattatatttttaaactttgtgttgtggatgtgaatatgtggaatttaataaaacatttctcgatataataatgattttgttgaattag aaaaattagaaaagtggacgattctaaaaacaaaagttacaacgaaaatcatcgaaggaaaaaacaactgaattccaaaatagttttcagag gtgatcacaaaatgttctcaaacgatatatattctaccatcaataattttattggcactatatcacagtccataattcctgtgctttaattatacttttc agtatagaacaatatgctatattatcaagttatgcgtccaataaacacaatttatttttcagactgaatttaagccatattgagaatagcgaaataa aaacgtagaggaaatttgtgatcgccattcacaattaattcttagatcgcaatgataacaaacttcgattcaaaagtcatcatgcaaattcaccg ttctcgtgtgtgtgtgtttttggaggaaataacacaattttgtgactgatttttttacaacatgtggtttgtagcatagttcaaagtcattctagaggg ggctcagagggagttctttcgctatgtcatcgtttgtttttgcacaccaagaaaaatgaaaataaatgctctaggatgtcatggatcgtttccatt cttaataagtagaagctaggatttcctatacaaaaataagtaatcttcgtttctacgtctatcaacttaaatttttgtatacaatccactttggtaatat tcaaggccttcctgtaaaatgttttatgatcaatccgttacaccaagaaaacaagtgcaatttgtcatcatgtaggcttccgcctgtgtttacttcc ttcccccagcacaacactgactatttataccaaattaataatgcagcattcctcatgtgataactcgtttgacttttatatctttctacgtgcatcttt caagctcgaaaattaattttaaaaatttacattgcagaacaattgcggaacgaagaagcg sto-3

SEQ ID NO: 24 attaatgaagaatccgaggttcctcactaaagattctcgctttatgatagagtcctcaagcttgtatattagagttttggggtgtttacctaaactt atgcaaacggttttatcatggtttaactaaagtagtgaattgttggaccaatttaaaataacatcgatcgcttcctgcagatcatttgtggaattag tttttcaaaagagcaatatagtttgaggtcatcagcgtactgcatatatttaacagtttttggaatgtttgcaccaagatcatttgcaaatatgccg aaaagtataggtgaaagtacgctcccttggggacaccacatggggcgttcctaacagaagatagagaattgttcacttttactttgaacgta cggttggagaggaatgagtccacccagcctatgagcatagaattgaacccggcctttattaatttttgcattaagagtgaatggtttactttgtc aaatgccttactgtaatcaaaaaatacaacatctacttgattattgaaattaaaattttctatataggaacttgatatacccaatttctattaaaaat tgaattcgcgccgagcaaaatgtgatgtcaatttcagttttccaattttctcaatttttttgaccactaactaaaatttgataccaaaggatttttgct caaatttcgaaataattgcggtaaaattggctctaaacactagtttttgacctagcgaattttgatgtcaatttcaatttatttacattttatttggaaa ttttcttcactgcggatccctagcaaaatttgttaaacatcacttttccgagcaatttgtgatgtcgatttccgtgtctttacacggtttttgcctttttg cttaaatttttcaaaaatttcagtaaaccccaaccaaaatgaattttactcacaaatttcgctcttcaattatttttttagtgaaattcacaaaatctga cctcaccctaaattcccactgagcacatttggatgtcgatgtttgttcaagtttttggccaagttttaaacaattgcagtcaaattcaaccaaatca cgtggtgtcagtttgtcccattacggtttgatctacaatgcgggcatttttttgcccaatcaattgagaactctgcatcacagctaccacatttttttg tagatatacgtagatcaaacggaaattagacactctggcaccacttgccaaatcatatgcaaaactgctcaatggtagaatttgacaacccaa attgctcatcaagttttttgtgtcattttccgcgcaaacagggattcaaatttctgccatcaaaaactcattttctacaaaagaactacaaatattatt tcaaaaaggcggcagtggtggtcaaagaacaaacatctgaacatattgaagaaggtgtctctctctctctctctgtctttccctgctcacacaa atctgtgtgtctctctccagaaaataacaacacttgaggttcacgggaggacgggggagctcccgcctgtgctccaactctcttgtcatgc cactttatgttgctccagtgtttttgtctctctaaatctccagctagctgttctttcatgttcccttagccccaataccgccgcctttcgatcttttggc tgtttttggggggatataagaagtttcgaggaggaagactagatctattcatcctaaaataaatttttttctttttttttaggctttatcagactctaa aatgctcgtacgacaccaaattccagatttcagttttctatattttcggtcctataatactatattcaaaaaattagcgtcttcgaaggaatctgac atctaaaagttctattggtctttttttccggcaaatcggcagattgccgaaatcaaaaatttccggcaaattggcaaaacggcaaattgagagat tgccggaattgaaaatttccggcacagaggcaaaccggcaaattgctgatttctcagaaaaactgcaattgccgaaaattttcggctaattga ggttttgcattttatttttggcaaattgcctgaattggaaatttctggcaaaccagcaatttgccaaaaatgaaaatttccggcaaattgccgattt gccgaatttgctagaaaaaaaattaatcggcaaaattttacgcatctattttgaaaagaaagcaaattctatgaaaatatctaaagaaaatctttt aaaaaaatgcacagttttaaatgtttcattcctttcaaaaatccctctaaccgcttccggcaaattaatatccggcaaagggcaaatcaccaaa -continued ccggcaaattgccaatttgccgaacaaaaacaactgaattatgctattaataattcctggttcctgatttccaattttgattatttcttactcacttc agtatcggaaaacgttcacaactttggaaagaatttgatgcccgtaatttgctgaataaatttaatttttcaatgtccag Mitochondrial Oxidative Stress Toxicity hsp-6

SEQ ID NO: 25 gttttctgcaaaataatcattgattttaacacctcgtaaaataattttaaaaaaagaagttaaaattttaattgcaaccctatttgtaaaaagaaaac tcattttcgccaaaaataaagcaaaaataattcaagagaaaaacgcgccgcgtgttgcgattggggcgtaactgcaatgtgtgcgcacaca atctcaacaagcgctgcgagacccgccgcctgaccgtaatgtgaaatgggcggagacgagaagtttttttctgtttgaaagttgatgcaaaa gcccgtgattctttttttcgagaaatttctcgagtttttttccaacgaaaaattcattaaatttaaacctttagctctcctttccaatattttgcatcatta ttctcctaaaacttggcatattcagtggaaatgatgcaaaatgccctgacttttgttatcaaaaatacaagaaattgtcccgtttaacggttgaaa agcaaattttgtgtcattttgtttaggaaatgtcaaaataagctcaaaaaccgattacaaattatatttactgcttttttatcctattttctcgcgttttc gttcatgatgcaattttctttcaggcact hps-60

SEQ ID NO: 26 ttttcggctgaaaaattggtttttttgagttttaaaatttatttttagcgggaaattacatgaaaacaacgaaaaaacccgaagaaacccgcgaaa attcagaaaatgatcaaaaaaccaaaagaagcttcgagaaaaaaagcagaaaataaatgtgcggcgcgaaaaatctcgtgcggcaaactt gcaaatctaggcgtgtcgggccaatggcagacaccgcgccgcaaattcagccaatcagcgcgctcagctccacctagaaaagtgtgcgc accttgcaaaactgggcggagcgagtgaaatgatgcaaaagtctattctgatgtaaattagccattttacatcaaaatttgcgtcattttcgttat ttttctctcatttttcatattttgaacgaaaaattgaggtttttttgcttctattttcatcagaaaccattgaaaaatgcttatttttgggccatttttcgtcg aaattaggggaaaaaactattctacagttttcccagctattttctcatttattcctgtatttttcagtcattacctgcttcccagacgataatgcaag gcttctcgcttcattttcataaaaaacgattgaaaaatgcttatttataggccatttatcgtctaaattaggggaaatatctgttttaccgttttccca gccgatttctcatccattctcgttatttttcactccttttctgcttctcagacgataatgcaaggcttctcgcttcattttcgatgagaaactctgatttt gctcgcattttcgcctttccgctgcagattttcacacaattttcgtagtttttcagacacaaaag mtl-2

SEQ ID NO: 27 agagaatacaaaaagagacgaaaatggttcagtggaacgaaacaaacgtgggatgtaaccatggaagtgagaataattgatggaatagct aatgagctgaagctgagtagatcagagactactttattctaaaaagtacagtagttggaaaattacatgtttcatttctaattttcaaggaaaagc tagtaattaccgtaatcttgtttgtacctgaaattttatgtactgcaggtgaccaagtatgtttgaggcatgacttcacacacctaactgataaag gcctctatcacaaactagagttgtgacggaaaattcaacttctcagaatatagctcaaaatctatcaaattttattttcaaaaatccaaataattgt gcacgcaatgtacttactgcttcataaagttcagaagaattggataaatttgaatgaagttttcaaagcttttatcagtgactgtacattgtgatag gcttgtgctgttatcagctgcctcaaataggttgtcgcttgaaaatttatataaaaggcctaccagcagacatgagaatcaagcttcaaaggct ctactcaaaa mtl-1

SEQ ID NO: 28 ctgcgaggaagagaaaaaatcgtgctgtgaaggaaaaaccgagaagactgagcaaaagaaataaccaatgagcaagtgaacttttccca cgtctactactaaattattgtcgatctataattctttcgcttatcaatcttgtcaattgaaataaaacaatatttttctaattctttttggaacgaacaca cgtgtttaaatgaatgttgtgctaaaaacgtcacatcaatggtacgtgaatgttgcaaacaccttgtcaataactgataaaatcagaaactaga gctgtgactgaatcgtatactagaacggagtctctctaaaaacgttctaaaaacaaacaaaaaattgtgcaaaggattagagtgctcaagatc aatgagcaaactcacaatcaactatctgttattgttttgggtctcttctatatctctattcttttagtatcataagtttgtacattgtgacagggccac cctcttttatcacatatttgaagtggtaaacagccagcaaaaaccaaataaaaaggcagtgagaaaaagaagaaggcagctcaatttgactg ctgaaattaagaaatc -continued cdr-1

SEQ ID NO: 29 tctgctgatttatttgagcttctctgtgtgaccaagacgagagccgaagagtgaagtttccactgtcacaccatgtattttatactagttcagagt atctttgaacacctgttttaaaaaggtacaataccaaaaggcgctcttaatgcacccggttacatttgtatttgtttgatcagatggatgtctgtct gacaaacgtcggccaaagaatgcacttgcagactttactttaatttttttgtctagtttgaaaattcttcggatttgttagtttcaagaactttcaatg aaaccgaaagtttgttgagttagcgagaattacttctgattacctgaaaattaatttgactcaatcttttacctacttagaaagactaaagtttctgc acaaatttgtttgaacaggtgcttcaaaatgttacagaattttcattttcatccacataaaaagttgattgacaaatagtgtgggcgacatgatttc ttgaacaatttgtttcgcttttcaatttggactcagttcttcgaaatttagttattatccatattattactgttttgagttttatcgcagtaggaaatactg gtgtatatacatattatatttttccgttttgtttacccagaaagcttaaaattcaagttggtcagaaaaataaaaaaacaacttttgcaagaaatacc attttttcatcgtgcggaaagaacaattgaaaactaagtatttttttgctaaactgcagtactgctacaatactaatactgtaccacgatagtcacc caacagtacgaactcctactaaaaatttattaaaaaaagttttattattcaaattttgaaaatccataagttctaaatactttgttcagtatgctatact taacacaaatggtattctgcaattgaaacagaaactacaataattttatcacaaaacacagttctccctactttcttatcacattatgtcatcgggg tggcaagtatataaaggaatgctgtaaaaagatatgtactactgtctcaagt sod-3

SEQ ID NO: 30 agaatttgcaaaacgagcaggaaagtcatattcgcagaaaaaaagtcgttgcaaacattcgtttttatatgtttttctttgagaaagcgtggttcat ttttgaaagtgaaaaatatttgcttaaaacttccaaatttaaatctgcagtgattcagagaggttgagaattattttcaaaaacattcaatgttttcc cttggagtgactatgcaaatatgaaaatgttttccaaaaatatttggatgccctgataaaaagtaggtgaaatttcgcaggggaacatcatatta aaatgttgaatttttagaagaaatggaaatgtttgtcggtggtatgctcgaatatttgagatattatatatttactgttaaatccgaaatttttgacaa acggaaaaaaatttgtgtcgaaatactacattttcgataacacaaaggtacttccataacacttataaaaactgtttgactatcttatttcaggaaa aaaaaatccaagaataaacatttttcagaatttgaactttctaatggctgattaataaaacaaagttatacaactattcaaagcagttgctcaatct ggcattttcttgtgtttttttttgaatatttcatcagcaagatgttgataattttgtgttaattctaattgttttctacaattttttcaaaccgaaaattgac ctttgactttgtttactttgttctcgtgggttaactgttcactgatttctattgctgttgatgaggtctttgatcaaatttgtattgtttttatactgcata ttgcttcaattctaaatcatctaatatattgtcaaacaacttcttgttttttttttcattcaaaacttctgcaaaaacgttctcttaacaaaggttcac acaacaactctcctctccatctctttctctcaacaacaatgtgctggccttgcatgtttgccagtgcgggttgtttacgcgttttcaagatttttgg tctcctatctaacgtcccgaaatgcatttttttcctttcatttggttttttttctgttcgagaaaagtgaccgtttgtcaaatcttctaattttcagtgaataaa eat-3

SEQ ID NO: 31 caattattataagaaaataaatttaaagttatccgagcaacaattatcaataaatattactttttttaaatgaaaaccttttttaatttcagcagaaatctt agaaatcagatgatcaataaataaaaacggctgactttttaaaggcgcatagaattttcttggtggcgggtcccgcaccgaagagccgttttc taaataatatacactaatgattatttttattaaatttttttcacggttttcgagagtattctttatataaattcaattttaaagcattctcgtcgagtttgaat ccgaaattatcgatttttcgtttttctctgctttctctaccgctgttttctctcctccgctgtcttcgcaagattatagagctcttttgaatcaatttgtttc atgtttccgcttttgacgttattttaaacatatactgatataaataaattaagaatagagtagaaaatctagttcaagtaaagatgcaacatttctttc tgcaaaatttctcgaaaacacctgttttccaaaactttttcaattacacaattagaatttcggaaaagttaacatatataagaacatattatatatata tatatatatatatatatagattaactctcacagttaaagaaatctgaatagtaatattgcgaaatagttttgcataagtttgtttgattaaattaaat gtgaagcactaacgctattgaatccaggaaaaactcgaattatttgtttgattttttattaaacacactttgtgaacaattttcggttaagaggctttg ttgtagtaaaaatcctaaatctacgattatcttcttaaaatttgacatacttcttacgtatgttacaggataaatcgagttttgatgtatttcgtaaata gtttttaatcatgttatctttttatttcccatctctatgttttaatgttgtctttacactaattcacccgtaatgtccgtgcacaaaagaatttaacattca gatattatggaaacaaaatcatcccaaacttcacatccgtggcttgttctactcattttcgccacttttgcggtctcaattttttgctgtatacagcaa ttttcctgaagtctcggcagatgagaaggttcatttgaaatatcccaggaatctggaagacgctaagcagctgggcagagttctctcgaagta caaggagaacaactattcagtagttctgtgcggtgtaattgtcgtctacgtatttctacagtccttcgctatccctggatctatttttctaacaattc tatcaggatacctgtttccattctatgtggcaattgtgttggtgtgctcctgctctgcaactggagccgccatctgctacaccatttctaaactttttt ggacgatcatttgttttgcaaaagtttcccgaaagaatcgcaaaatggcaggatgatctgagcaagcatcgtgatgactttctgaactatatga -continued ttttccttcgagtaactccaattgttccaaattggctaatcaacattgccagtcctgttctagatgttccactggctccattcttctggggaacattt ctaggcgttgctccaccaagtttcctgtatattcaagctggctcaacactggaacaattgagccataccagtgtagcatggagttggagttcta tcgttttacttacgggttcggcgattttgtcgctggctcctatttgctcaagaagaagctcaaatcggattaattttctctcttatttcctctttcgat ctcatttttttccattgctttctgtgcaaaacttgtgatatttagagaatatagccgataactcatttctatactatttttatttatttttcgcctcc ttttttgtcataataatcatatttcttcactaataaacaatttttaggtgatgaaacaatg cyp-14A4

SEQ ID NO: 32 gaaactctcctggatttttctagattcttttccagttacatttcacatagaatctctaactaccggtgcatttgccaatcttcttactgaaattctgtgc cttgttttgtcattaaaatttacaccgaataaattatttgtctttgtaatagcttatgactttaacaaggtcatttttttctaactggctcattcgcgctg aagtttaaaagaagtttgctttttttgtcggttaagccgttcatacatttttggcaatcttggtacaaccatctactacatttatatcaaaacgaaaa aatgtataaatttttccctcgtcttcatctacccgcaatcataaaggaatctcattccgtcccactcgccctttctttcttcaaccgaaatttttttttccc gcggcgcaaaccctcatgtgccgtcgatagctcagttggtagagcggaggactgtagagtcagcaggtatccttaggtcactggttcgaat ccggttggacggatttcttttttattttctgtatcaagtgtaactcttcagaaaatcatcgggagcagtcgtacgaaattttaattataaaaattaaa cattccagcatttttctttgggaggtgaagtagagtcagcgcggatttaccggatttacagttagtttgatacacattcaacattcaatattaccg aatttcaaaacaaaacatttttacctaagtcttttagattattggaaaattacaggtaaagttttggtgaaatgccaaagtcataatgcgagatggt ttttttttttgaaaaattcagatcaaaactacgtgtttggtttgtgataaaatattatgatgaaaaaaaactcgaagaaatcataacccaaatgatatt cagttcacaaacataagtatcatgatgcaaaatacaaagctgaatgtatttttttcaagaccgcagatcacaattaagacatggtaaacacaaa ctctactgcgtaccgcagtgaaatgtggtttgtagtatgactggtagagacacatcgacctatataaacatcaaaaaaattgtttaaaaaaaatatt ccatcgagaattgcttcatttcaa cyp-33C8

SEQ ID NO: 33 atattggaagtcaatgagaaggaggaattctggattgcaaacgagaatttggaagtgagtttggagatagtagcaagcctaagcctgggcc tgagctgagtcaaagccaaagccgaagcctaagcctaaatctaagcctgagcctaagcataagcctcagtctaagattaagcctaagcctg agcctgagcctgagcctgagcctaagcctaagcctaagccaaagccaaaacctaagcttaaacctaagcctgagaataagcctaagtctat gccaaagccaaagccaaagcctaaagctaagcctatgcataaacctaagcataagccttaacctaagccttaacctaaacctataagccta agcctaaattttcaggcactcactaccgaaaattttccattaatgttcaactcaatgctgtcgaccgtcctgaaaccaattgacaccctcattga atgtttcaaaaaagaaggaccctacggcctggattactcggcctattcggattttgaagaaatgcagcaaaaaattcactaaaatcgttcacga gaagcatatcattccggatttggttccagccattggaaacgggatcaaggagaagctggaagctggtgggatccgagtgttggatgtcgg gtgtgggggtggattccattcgggcttgctcgcggagcactatccgaaatctcagtttgttggattagatatcaccgagaaagctatcaaagc agcgaggctcaagaagaaatctgatggcactgattttgaaaacttggaatttgtagtagctgacgctgcaataatgccaagttcatggaccg actcattcgatttagtcatcctgtttgggtcttgccacgatcaaatgagacctgacttggtaatttttgtattcagtttcagagaggtatcccaatc atttacagtgccttctcgaagttcaccgtgtggtgaagccagatggtttagtcgcggtcaccgacgttgatggatctagcaatgtgttcaccga tcgtgagacctacgggaagatggctgcgatgaagtatggtggatcgatgcttcattgtcttccggttgggagcaataggccagatgcactat gttgcggctcaatgtggggaaggaagagagcagttgagataatgaataagtgtggttttgataatatcgacattattccgactgactacttccc tggaactgttttgtatttgatgaaaaaaataaataaactgtagctagtgtttttttataattgtaatactttttttctatttattcaatctttttttcccgatt ttcactgctttgttgtgactgtatcattatgatcctgatgaataaatatcaataaacaaatacagttttttttttatttgacattgatttttgattctga gaatataatacatatctatgagaaattaattaattaataattaataagaattaataaatttaataagaattaaagtaaaatatagtgggaatatag tggaaaaattgttttgtaattgtatgcaatatgtttataattttcaaaatcaaagagcagcacgacggagcccaatatcaaaagttcaagcgaca cactcaaaatacgactcatacctgcgtctcctccctctcccaatttcgcaacatattttcgtattttgtggtttcttcagtcgtctatttctcgcacatactt ccacctgatgcaatttcgagtcctcaccaaataaatagccggcaatgtttgccatttctcagttttcatc glrx-10

SEQ ID NO: 34 ttttttttttttttggattttcgactttaaaattagcctaaatttatcctaaaattatcctaaaaattaaaatttcacatggttgacaaatttgcagtggag cgcatttgcagaattttttttttgaatttttttttcataaaaagcgtaacattttccaaattaatgggatttttaaaggaaaaaattatcccaaaaatttt -continued aattttctaattgaaaaaagtgttattagcccaatttttaaaggtttttttgcaattttcatcagaaaaagcgttaaaaatatcaatttttcgtgaaaa gttgatgaattctctcaaaaactcggcaaaaagtaccgccaaaaattcaaattctccaatttttcatctctaccagcaaattcgcgatggagcg catttgcagagtttttcagaaaaatcgtaaaattttccgaattaacgagtttttttttaagtaaaagtgatcccaaaaattcaaaattttccgattttt gaaatttttttggtgcaaaaaaactaattttcaaattaaaaaaaagtgatttgtctaaaataaaaagcgtttaaaaaaaccttttaaaaatttttttc ccaaaattcacgtggtgccaggggctgtcccatcgacggtttgatctacaaaaaatgcgggagtttttcgcccaaaaatgttgtgacgtcag cgctttcttaaccatgcgaaatcagtccccgcgcatttttttgtagatcaaagtagatcaaatcgaaatgaggcattctgacaccacgtgaaaat ttcaaattctccaatttttcatctctaccatcaaatttgcgatgaagcgcatttgcaaggcctttttttaaatttttttaaaaactccttaaagttaaaaa aaatcatttagctttagaaagcccaaaaattaaaaaaaaatttttttttaatcgaatatcaaaaatgcatttgtgctccaccgcacggcggtaattt cgaaatttctttaaaattttttttataaatttctgtatttcacaactgtatttttttcccgaattttcctcgcctaataacactatttgtcatgattcttacg tcattgtcgccgccgtttctctttttctctcgccactctctcatttccatacactatttccactctcatttttatcatcattttcttcagtttttgctgctt ttaaagcctatgttttccctttttatataatatcgcagaattttgtttttgtaaatttaatatatatatatatatattatttatttgatgataatgtgattt ctaatttttttttccccaatttttttcaaattcaaattgtctctacgctttcttatacttcattgcctttttttttcaacaaaaatttgagaaaaaacacc aaaaaatttcagaaaaacc

F56D5.3

SEQ ID NO: 35

Gcacgtgtatttttttcggcacgtgaaaatttttttcaacatgtatatatatatttttttcaaatttggaatgtcttatgaaaaacgtcgaaaaggagg aactcatttagattaattgttatgcaaagtgcagatttttaacaacgaatttttgagatcaaattgtcacagttagctgatgttttcgaactctacac atgtgtgaaggttcactcagtctgattggttcaaaagtggcggtacgagtcgctgatcggtcttgcagttctcaatttcgaggaaaatcaaaca agaagattagccaaaattaaaaatttacgtttttgaacagtgttttcattgttattctcatttatgttatgaaaacattttcaaacgtttttttcctggatg gtaccattcattacatcaagaacttcctgtcactttaatgatcttttgttttttttgtagtttgaattaaaatgatgatatccattgaaattgagtgtagg cgtatcatgatgacaattaattaattttgatcttttgctacagggttttccataggtcagttagtaagtgaaatctataaatttggattgtaaacgtttt ttcaaccttgatttgtgtttttttttcagtttttatttattttagatatttaacatttaaactattgaagcttttaaaaatcatagttttatgtaaaattg aaaattgtggtaaatgacgttttaggccgaattagtttttcatttaagactacattttatttcaacatctaagaactttttgacatttttcgagccattgttc aaaaaacatcattgaacactacacggttcaaaatgtttacactagatacacaaaccaatagagacactcttttaagaggcaaatggtcagagaat tagacaatgagacattcttttcttctgtgaatttgtatgttatagtgattagacagttaggatgacatatatttgtcagcacaatttctcttataaatac aagaaaattttcagagattctcatatccatttctatttcattgaaaagtttttttcaaac gad-3

SEQ ID NO: 36 tgactaacaatatgaaatgtgtataaagcttcatgatttcacaaaattgaagtctaaaaaatataagctttaatttttttgctgtatgagcccctcaa attctcttatatactttttcctgctaatggctacttctttgatcgaagatttggccaaccggttaagtttgccgacaccagcataaagaaattccgtt catcgcattcaattgagttataggagcaaacattaaaaattgatggtataacttcttacaataacatgtgaacaaacagcacgtgggcataatc aagaaaagaagcttttgattttgaagttgataagggaaacgatcaaggtgttcaagaccgaaaataatattttcagtttgagtaagttgaaaatt atattattttttgaatactttttaaacagctaacagatattgcaatagagtgcttgaagttgtatgtcaatatagttttcgtgaatagacattaattaca gtgcggctcataataaattttattgtttttttttagtattctacaattccatcgagtagctcctgaaaatgtgaatagcctagatagtaaccgattgag aaagtaaacgtgcgcttatgagttacgtttcgtattttcacaaaatcgcagtataatttttagtcatttcttcaaaaaccaaaaatctactgtaccct tattgtaatcaaaaaatgtgacggaatctcgcatgaaaccaaagattgtttacaatcccaaaaaataatccaaaaaattgccctgtttctctcaattca ctgtacattttcaaagttttccacagatacattttcattcatctgtgaaatcgaatcttttagactatgtatttgtcataaaattttgtgattcttttttgt tctgttcactctctgtcccttatcgttcgtatctctatttctctattctctcgttaccatcttatctattgttattccattttttttggtcatttgtttattg aactccctttactcaactgcacacaaacatttctttttattttcttttgaatatatgctccatgctaaccagaactgacctgttgattcttttttttttccc aatatactagtccttttcttaagttttaccaatgtttttag

F17A9.4

SEQ ID NO: 37

Tcagcgatgagcacaccgttcaaagattttctgaagcattgggcttacatgtgaaacaagcagcactcgatattagtgaaggaaaaatacc -continued gaaagcaataattgcattcaactaaatactgtatttgcacttggtattacagaaacgcaaagttctgagaatgcgtactgggtaacatatttgac gcgcaaaatatctcgtagcgaaaactaaaataatttaaaaaataattcgctttcgattagaaattcatttcgaaattcgagtatgtaaatcgacta cagtagtcaataaaagtattactgtagttttcgttacgaaatattttgcgcgtcaaatatgttgcccaatacgcattctcagcatgttgtgttcccgt aacatttaacctattttacataatctaggtgttttaaactttttataaaactttctcgtaatgctatctttgcctcttagaaaacttattcagcgacgtgt atcataaccaattctaatcggcttgttagaaagaagaaatataatacttcggcgtctccactttgtgactgggcacaaaatgcaattcagattct actttcgaaatagccataaaatcataagatcacagatctttcttcgtttctcaggcaaccaggtgcacaattgtcatcactcgaccagtgagac cacaatagaacagcaaacgttgtcatctttttggttagacactttctttctgcctctgcgtcttttcataaggtgtgcatactcttgtttgcccaaca acctagccgatcagaaaacgcactatatttgacctgcgtgtacactgctataaaagtaacattttgttctttcatttcttcgaaaa

C35B1.5

SEQ ID NO: 38 aatgcaaaaaaataagcctttccgaaaaaacgggcccttgggcctttaaaggacacaaaaacaggaaagcataagacaccaaagagtaa ttggatttctacactttggttcctagaattatttataaggtgttattgcgtttttgtgagattgttctatttatccagtcaaaaattgcattttctttgttt ttgcttcaaaaaaatacattttcagtggaaatttcagctgaaaagcagaattttgaggttttcgagtaaataacgtaaaacactaaattacaaatatt gatttttgatgtcttagaccaaatttcgtaaacatgtttgtatttttggaaaaaataggtttttgtcgattttaacttaatttttcgaacaaaaaatgat tttttctccgatttaccaaagttttgacttaaaattccgattttctgggtcatttttcccctaaaaatacgattttaattcaaaaaatctatattttcaaag accaaagtaccataaccttcaaaaaacaaccactttctctattgcatcagcgaattgtcatcacccctctcaaaatatacaaaacgtcatcatttt tctgtgttttctctaattctcctgaaaaattctataaaaccaacagtttttatcatcaaaaatgccttttgaccgactttttttaaagttgaaaatcgta cagttttagcagaaattccagagtttcattttgaagtatgctggaaataataaaattattctaacatttattaatattttgtaaaactaattctatacaa taaaaaagtaaaatttaatattaaaaaaaccggtttttctcaaatttccattccccaatgtcctgttctattatttgttccgattcggccacagaacg cgcacacacacactttttgctgattctctgcctcctttctttgatttgaccgcattttatattgattttcggccacaattccactatttgttcagtttgtc gatttgttggaaatttcaattccggcaattcgccgatttgccggaaatttaaattcagacaatttgccggtttgccggaaattttcagttccggca atttttaatttgccggaagtttccatttcggcaacttgccaatttgccggaaattcgccgttttgccggaaattttcaattccgacaacttgcctat ttcccggaaattacaattccgccgatttaccaatttgccagaaatttttaattccggcaatttgccgatttgtcggagatttcaatccggcattttg ccgaaaatttcaatttcggcagttcgccgatttgtggaaaataacaattctggtcattcgccaatttgccgaaaatttcaattccggcaattcgc cgatttgccggaaattttcaattccggcgattttcctatttggcgaatatttttaattccgccggtttgccgctttgccggaaatttcaattccggaa ctttgccgatttgccgatttgccggaaaaaatcttttgccgcccacccctaataaagacttcaaaatatgcgttttttttgcttttaacacgctaaa actctctaaaaatccccaattttcagcttaaaaaaccccaaaaaa gst-4

SEQ ID NO: 39 ttttgcagactaaaaataactactctgccagtgtttaatttatagatgcaatttgtcactattttcattttatatcgaccaacccattcacacttcacta atcgtgttaaaactcaattagtggaaaatttgaaattctatgaaactttcatttgcgacaaaagattgttgttttcttcaaaccaaaaatttatcaatg ggaaaatgagatagacaagaactgggaaaaaagtcgaggttaataatttaaagaaatattgaatattcggcgccataatattaacgaaaata accaaaatatgcccaattattatccaaaaagattagaagttggcaaaccttgggcaagaatttccagagattgcactaaagttgtagccaagtt tgatccaactttatccaatcttttactaaaattatccttaagactatttaaattttagatagagaattggcgagagttagatcccacttggatatgac ttatagttagcctaacctgaagctattgcttgcttgatcatttggtttatcgctttgctacttggataaccagctccaatagttgttatttttgcttttgt catcatttttccacgatttacactctcaagtgaaaccaactgttctttgatgccagacgatgacattacacttgataagaaaatatatataaactg gaattaaaaacaattgatacatcgattcaattactgaattctaatt Peroxisomal Oxidative Stress Toxicity hps-1

SEQ ID NO: 40 atttcatttctttttttataaatacttcggctctattactgaatgaataaatgtataatgatgctctccaaatcctcttattattcgctcgaaccgcccgtt cccatagataccgtctagttttgacaggtgttcaaccatctgccgggaattacgagaagagtcgaattaattgagatcctcgtctaaataaatc tgaagtttaaaataaagccagaaatacctgaaaagagagaaaaagtgtgtccacgatgtctttgtttatgaccagtggtgtgttatcgagaaa -continued aactccaatgaatcacacaccagagaagaatcgagaaaggtcgggaaattaggaatgagaaataataaatgtgaggaagtaataaaaga atcttcgagaactcattccacttttagatataaaacaagcagcaaacgggtttgtaggtattatatttatctattttaagtttaataaactatttttgct aaacttaaacggttcaggtgttgaaaaagtcctaaaatttttgatattatcaaattcttttagcgtggcggttttctttttttttcgaaatattgagttttt catctgaaaaatgcactattcgtgtccttcaaaagttcatgtgtcatcagtagccactcgaaagatcgatcagtccattttgatttcgaaagtaa gaagagatcattactattcaagagacgcaggcacggagcctgttgcgccgcgaatcttccaggcattcttggcgctccgcccaaaaaattg caaaaataaaagttgcttgaatcatgttgaatgtcacttaatcgtgtggctttcaatgttctctttcagaaaatgtatttttttatttgataatgttaaga attcgccgagttattcttcctcaaaatgtggtgcgcgctctctctcccccttttcgtcgcgaacattctctgcggaggcatctcttcttttaattcac aattctcaacacttttctgtaggcaaaactctctaatattgctccttttttcagattttgttcaaactttttttgtatttatcttgttcaagtgttttcca ttcagcagttacagactatttaaggaaattttaggtttttagcacatttttctaatttttttgacgaaattcgaatttctagaatcccgccacgcccagtcat ctagtaaatttgttgaacttcatttctctattttttaatcattgttctcgacgtcctaatttttttatctccatttgagtgactatttcttgatttttaaatt atttttttacagtaaaa ctl-1

SEQ ID NO: 41 gctctgccagaagaagcattaaattgtttgatattcaaacttttgtatatagaatctcgttatttataaactctttttttttgtatttcttctggtttttgatg ataagaaattttatgtgcacataaatcaaaaaagccggaaattaaatagcgttttatcaggcagaaaattggccacgtgacgtcatcattttcct gtttgaagaaaatctggaaaatttttttgtttcagtcaatttttaaagatgaaaacttaagttagactgtaaaagcaattttcgcgccaaaattacgg tatcgggtctcgaaacgacagtttttttatctattgcgaaaatatgtgcgcctttaaagagtactgtagttgcaaacttttgtcgctgtggagtttttta tcgatttttttatatttttttcgatgaaaacaactcaaatataacaataaaaacacaaaattaaaaaaaaaatcgataaaaaatccgcgtcaacgaa agtttaaagttacagtatttgtcgtttcgagaccgggtaccgtagtttttggtgaaaacattgcaaaatttggtcaacaatttcatcgctgcgaga ccgacacaacactttattttatttttgggtttcccttatcgcttatcataaacatgtgacgtcatcatctcttgtacagagcaccgcgactgggagt ataagaatcgccggaaaacatcaataatcagttcggtagaagtgaaaattgagcgtaaaatatgatcatttttcgatgcaccatatttgacgcg caatacttctacaagccgctgtgtactgctcgtggacaactttggattattttttgtttttaaaattcaaaatagtcaatatattgcttatttatagcgc gcctttttgacagtaagtttgtcaaatttgcgcgtaagttatggtgtttgcacatatgcaccatacagcaacaccccgcggcccggctagtggt acatccatgcaaatgcgctctactgataatttgagtttaaccaggtttaggcgcaagataagaaaaaaagctttggaccaaaaaatttagagttt atttttttcggacatttttttatatacatcacaaaaatattgggccactcgtttttgataaaaacgacaagcccaaaagttcaggtatacggtagac aaattgcgtacaggtaccacttttccacgtagtgccaggttgtcccattacgctttgatctatgaaaaatgcgggaatttttcgtccagaaaaat gtgacgtcagcacgttctcaaccatgcgaaatcagttgaaaactctgcgtctattctcccgcatttttttgtagatctgtagatttgtagatcaatc cattccccgtataccctgacccataatcaatacctacctaattttgtctttccccctactttttttgcctgtccaaaataagcgagactatgccgta gtctggtgtccaacaacatgttccttatcagtgataacgctacaatcttctttctttttttctctgtttctcttgtctctcccaacccatattccgtattac acctcgtcgtggtcatttttttgttcagagttttatttaattctaaatttcctaactaaaatttcagaaccaaa ctl-2

SEQ ID NO: 42 aaactctttttttttgtatttcttctggtttttgatgataagaaattttatgtgcacataaatcaaaaaagccggaaattaaatagcgttttatcaggca gaaaattggccacgtgacgtcatcattttcctgtttgaagaaaatctggaaaatttttttgtttcagtcaatttttaaagatgaaaacttaagttagac tgtaaaagcaattttcgcgccaaaattacggtatcgggtctcgaaacgacagtttttttatctattgcgaaaatatgtgcgcctttaaagagtact gtagttgcaaacttttgtcgctgtggagtttttatcgatttttttatatttttttcgatgaaaacaactcaaatataacaataaaaacacaaaattaaaaa aaaaatcgataaaaaatccgcgtcaacgaaagtttaaagttacagtatttgtcgtttcgagaccgggtaccgtagtttttggtgaaaacattgc aaaatttggtcaacaatttcatcgctgcgagaccgacacaacactttattttatttttgggtttcccttatcgcttatcataaacatgtgacgtcatc atctcttgtacagagcaccgcgactgggagtataagaatcgccggaaaacatcaataatcagttcggtagaagtgaaaattgagcgtaaaa tatgatcatttttcgatgcaccatatttgacgcgcaatacttctacaagccgctgtgtactgctcgtggacaactttggattattttttgtttttaaaat tcaaaatagtcaatatattgcttatttatagcgcgcctttttgacagtaagtttgtcaaatttgcgcgtaagttatggtgtttgcacatatgcaccat acagcaacaccccgcggcccggctagtggtacatccatgcaaatgcgctctactgataatttgagtttaaccaggtttaggcgcaagataa -continued gaaaaaagctttggaccaaaaaatttagagtttattttttttcggacatttttatatacatcacaaaaatattgggccactcgtttttgataaaaacg acaagcccaaaagttcaggtatacggtagacaaattgcgtacaggtaccacttttccacgtagtgccaggttgtcccattacgctttgatctat gaaaaatgcgggaatttttcgtccagaaaaatgtgacgtcagcacgttctcaaccatgcgaaatcagttgaaaactctgcgtctattctcccg catttttgtagatctgtagatttgtagatcaatccattccccgtataccctgacccataatcaatacctacctaattttgtctttccccctacttttt gcctgtccaaaataagcgagactatgccgtagtctggtgtccaacaacatgttccttatcagtgataacgctacaatcttctttctttttctctgtt tctcttgtctctcccaacccatattccgtattacacctcgtcgtggtcatttttttgttcagagttttatttaattctaaatttcctaactaaaatttcaga accaaa ctl-3

SEQ ID NO: 43 ttttattctgaactatatacaaaatgtgctcaatataacgagttttgtaattttgtgagaaagtcgtattgaaaattagtttaaatgtgatttaatatttc gaaaaagtagtctaatttagctaaattctacaattttgacaacttttccgtgtcgcaaaacgaatttttgtagaggagtgtacctaagcgagtcg gagaaacgtgcattcttccatttttttcccccggggagcccatagccagtttccggacgggcggtcttgttccaaacgtttttaaaatttaatatt gcaatttaattatctattcagcatccgtagcccagccgcattgtggatctcagattggcgaatgcttgtgcgctccattggactccggagccat tccgtctgttgatttcctgatttctgcggaattgtccggatcgacgagctctgtaaaaaattaatttaggaaaaatcaacatttttttcgataagcaa accttaattccttcgtcacacttctatggaatccagctgacggcggcggctgaaatatttttgcaaaaaaactcacttttcgacttttcctctttctg cgatcggttttcgcctcgatttgcgttgattagcttaaaatagtttttatatttaactaataataaagaaaaacaaaaaaaaatgagaaaaaaca atcaaaaactcgaaaaaaacattacgaaatcagcaaagaaaatgaagaaaaaatatatacagtaattttaaaggcgcacacacaaaagtttc ggtacgcgtgccgagaccactcagcagaagtgtgctcctttgaatctggagtacggtcaatggggatttatttttgaaaatgcaaatgccaaa atacaagaaaaataacaaattgcattaattttagtgaattttctgaaaatgagatttttgtgctttttttggaattgtgcaacttttagtgcattttcat cgtcctttttctgaattcttgaagtttctggaattttgttcccccccccccccaatctaagactaaacctaaggctgagtctaggcctacgcct aagcctaagcctaagactaagcctattggtgtatgtgcacataaatcaatttttttaaaaattattattatttttgcaaaacacaaacgtttttttca gatttttatttttcaccctttcaacctgcaaaacccatttttcttccaccaaaacacagctgttcttgccaccatttgcctgatggaaaatttatata aattggctgtcctttgtgagaaaactagaacaataatgatgacattaagtactagagtataaatatatttttttttgctgacaattcctggcgtccc ccgttgacattgaaaatgtataaaagaggcggccagacaccatccccgcaaatgtgtttttgttgttcacttttcttttttttttccactctctctctct cagctgtttgcatgttgtttttatggtgatctatggtctctaagaatttgtttataagctaagaactgctcgctgagaaggtttttttggttcgtagct agtttttttttacgtttatcgaaaaaaaaattgaaaaaagtcgaaatttccatcttaaaaaattagtgaattttaatattttttgttaaataatcgccattgtt tcgtgcttttctcgctctgtaaaattgaaaatctataaattttgggtaatttcgagtattacgggagcacaaaatttttgagaatgcgttttgcacaa cctatttgacgcgcaaaatatctcgtagcgaaagctacagtaattctgtagcgctggtgtcgatttacgggctcaagttttcgaattaattttttttt cgaaaagttacatcgatatttcattttccttcgtgctattttcaaaaatcgagcccgtaaatcgacacaagcggtacagtaatcatttaaaggatt actgtagttttcgctatgagatattttgcgcgtcaaatatgttttgtgtccccgtaatattttttttaaatcaaatttcacattttaaccataaaaaactct ttcaaaagtgtaattttctacgcaaaaatgccgttcggatgaaaaattactttgaaaaacaaactcgaaactacggtacgcaaaaaagtacat cggtgtttgcacataagtgaaaacaatgttgtttttttgtaattaaaatcgattaatttttttttcccggaaaacaaaaacgttttcagcgtggatttct attgtttcttgcgtaaaaaaaaattatttaccaattttaaacgataatttccacgaattttcgccattaatctctcgattttgttgattcttgactccgag caatctctccggttttcgcaaacgattatattatttatttgttttccttttcagtgccgattctcggaaattcaacagtaaatcttcaaa

W01B11.6

SEQ ID NO: 44 tttgagaattttctcgggaaattaaacctgtgtttttcattaaatttgatgcaagcaacaagtcattatacaataaaattggtgaaaatatgattttttt gaaatatttggggcgaggcttttagtttttttgaagagcttacaaaaattagaatttaagaaattttcgaacacaaatttgagagaacttttgactttt ttcaaaaaaattgttttcaaaaattttaatattttcaaagacgaaagaatttgtttttttgtctaaatttacctaatcattatttttcaatcaaataattgcat ctctgaaaacctgggaactttgaaaatgacgtcattctttttttccctccttttcttttccatttggttattgacgttttccacccccctcttgcaaaaaaa actaaacaaaaaagaaaccattggcaactactaacgccaattttgtgttgcttcatcgggtttcttttagtttttttttctgagagcgctgagattatt tggaaatttgcattttctcacgttctagctcagaaagagatcagctttctgaaattgaaatttaaaaaatcgctctaaattgaaacagctgtttttta tgtcgattgtctctgcaaatatattttttttcagaatatataagtatgtgtttgtttaagttttattttaaattttcttgaattttatgaacgacattagagc -continued ttatgttagtccaaatatttcaaaatttattaacttgaatcttgcgcaaaattatttgaaaaatcaatttccagccaaaatcttctttaaaattttatttgaa ttgtcaaaaacaaatgcctcattattaattttatgccaatattaaaaaaaaattaattctcgataatcttaaaataagatttttagaaaaacaactttc aaaagcttctatgcgaaaaaaattgtttttattcgaattaaaaaaaatgttttcttcaaaaaaaacaaatttcttaaatcatagatccgtgttgctca actgctcaatgtttcccatgacaaaaagtccatgtctctctctatcatttctcatctctctttttttctctagccatcataaaaataaacacatgtttcaa caatcattccttggtttttttatctctcgattgctatatcatttttattttttttactattgggtaaattttgaagagggtactgatttttttttcaaaatttt tccaatccaaaagtcttttgaattgcgttaaatcatgtctattgtaccacaatgaccaaatgccatagtaaaacttttcaaaaaaaatgtttgaattttttttt gagcgtcagaaagtggcaattacagagtttttttagcactatgaaaattgaaaattttcggagtttttcaaaatgatttttttgaaattggaaaaatt acagaaaacaatttttttgccatttttttggaagttgccgataaaaaaaaatttctttggattttatggttttattttgttgaaaatattaatattcaaacc aggggtgtgcggcaaatctcaaaacttgccgagctcggcaaattcggcaaatctctttttttcaatatttgccgagcacggcaaattcggcaaa tttgcctagctaggcaaattcggcaaattcggcaaatttgccgtgcttaacaaactcggaaaaaatttgatactttttgatgtttttttggagcacca aaactactgaaatcttaacactcatctggtttctgaataagttccgtgtagtatgtctgcttaagcatcaaaataacgcaattttgtgtcattttact aaatttttggcgaaaaaatcaatggttttagtcaaaattgcattgtcaaatttatgacgtgtgcggcaaatttcgaaatttgccgagctcggcaa attccgcaaatctactgttttgaaatttgccgtgctcggcaaattcggcaaatttgccgcacacccctgattcaaacattgtaagggtttgaaca tgttcttaaaatgtgacaaaaactcagtaataaaacatttaaatttttttgaacacttttaccatgatatttggtcattttggcacagccttaaggttaa agctttaacaatttccccactgacgctactccaccataattttgaaaatctaaaatattcagaaattcgaa

F10D7.3

SEQ ID NO: 45 ttttggaaatggtatcagaattgtttaaatatcttatctgaagtttatttaagtttgttacttaaaagtttgtcggtttcgcacaaaactttatttaagtta ggggcacgaaaaaaagtaaaatcacaaattatcaataattttaaaatcaaaccatcaaccagaaaccagaaaactaaaccttgtattttgaaat gtgcccgtttgaagatctatgcaataaaaaaaattacatttgaactgctatcaatttttttaaaaccggcaattttgacatttgccggtttagtacattt ttgaccgatctagataaattaaaaagctgataaatttgttaagtattcaacttttgagattcaaaattttaagaagcttttcggcattttgaaaacat atgtgacgtatgtcaagtttgtttttgccgttcaaccgatgagcctgtatgaacatttgactaatgtttttttttcaatatcagatcattttaattgttta aatttgataaacgaaattgaaaattttcgaaaatatatgtttcgaagttgtatacatttttaagagttttcactttgtggcagatttttctcttttcaattt gaaagtgtcacgtaccttgaaatagtttgtttttttttaagaaaatgaccaaaagaatattaaaattttgaattatggtaaagaatacaagccagca aagaatctagttattgttggaaaactatgaacatcatgtcctcagttttcaagaaaacattaagatttcaaaactatgtattctgcatggcaatgtt gcaacaaaccatttcctcataaaactagccaactaacacagttattcctaataaccacaatgttctcttttcatatgttgcctatgtaattctttctca gaaacattatcatgaccataaaatagacaatgtattggtttctatgtttcttcttcctgccagtgtcctctcgcgttgtttgagtactattgttcccca ctctcccccccccggcgtgcgtattatcgctgaaaatgtcatattatctaatcgaacaatgcccatttttttgggatgtttaatagcaaacatattcc gattggaattgcaaaattgagttatcatctttttattgttggtcttgtgactgtgagtttatgtttggaatatagttttgataagtttgaaactattgtga acttggaattttttgattctccaagtttttaaaacgctatgcacctaaacttggtattttttttcaatttaacaaaattctactttcaaaaaacactactct tatttgcatgttccatagtatgtatttcttggcagtgtttttcaaaaatagaactccttccgatttaaacacataatgttgtgctttttaagcctagaca cgacttccgatgtgattttttcttcgaattctccctgtctgtaagaaactcacatgctgactgcaaagaatgtgcctattgcggacctcaatcagtg tcggctacactttttttagtgtcgtcccgaaagttgtggtgttctgagaaaacataatttttattgatttttaatgcagcaaaatttcaaataactgata cccggttcaccctaatttcccatggatactccaaatatgttcagaaatgcatatttttgtacaaaatataacgttttctaaagtgtttgctaaaatgt tattgttctaaaatcttttgaaagaaccagaaaatctcaaattcttaaaacatttttcatcgaaatgtgatatttgaccagccagtggcgcctaact tctgaactttgcttcacgcaatctctgctttgatttctgtcgtttctctactgatttttgttcactttcacgtaagcgttcaactcgcggaaccaaagc ctccgttcatatcatattaggctttcatatctaccatttttctactaatcattgttgttacaatcgtttttttctctgtttcgaagaggcactctacttatga ctacaacataaaagtagtatggaattcgcgtccttggtgaccagaggcgttcctatttcgaatctctattcgggtggaggcattatccgaatcc cgagaaacattcttgtttgtgtaatctgtctaatcaatccccccttcctatttttctctgttcccttccttgtcttcaacatcgcccttcgatcatctgaat tcagttcgttttcgctccgcccatgaagttgggctacataaaaagaggaactgaaatgacatcaggggaagttggatatatatttcattaagtt gtactatcatttttttctttttttctcttttttttcggtttgattctatcttttcaagatggcctcgcttatttctacgattgtcaagtcaacggtcaaagtt -continued tttgaattgttgcatttttctggttctttgattttgttccttttaattccagttgtagtttaaattattttcaggaaagaaaaccgagaaaaaagata ttacaaa prx-1

SEQ ID NO: 46 agtttggccaatacctgtgaataaaaaataatttattattttaggaagttttataaatgcaaaaaaaggagtagaggaattgtattagaatattatt aaatggaaatatgaaatagcaattggttgatattatacttcgaatctcagaatcactaaaatgaaaaccagaactgcttctgcttgatttttaacat acttttatgttatttgcaatgattaaaaaatatatataatacgcgagaaatttgaaactggtttggctcgataaaaaattggtgagaaacccaaaa tatcgtgaaagaagcggtggaattaaaatgatttgagaaagtaaattttgataatacgaattataattcgaaaaaatggtggtacttaaaatata gcaaataaaacaggtgagaaaaagttttgaggtttttactatattttaatcaaaccgtttgttttatttattttcaggcatcgaaattttatgtactcaa gcttatagtaaaaatacaaatatttgatatattaaacagagataaaacataaataacgagctctaaaaaattagcatattttgggaattaagaaa accagtgaaagccgtaaaaatgatctgaagctatgaataagtttggttagagactctatttctagtagattactttattataataatgagcagaaa cagatattttttagcatttttcacttcatcattaaattaaaatcattacaaaaaatcgatagtccttgagaagagagacaccaatttacaagcag gcaacaaacgagagagagcgtattatcgtgtaaacggtatatacgggagaagagtacgggagaccgacggaagaaaagcaatgggag gtgtatagggtggtggctgtgttgtgcctaggaggcaggaaaatataacgttaaaaagtgcagacgcagacacaccaattgcccctcaga ctccaattcagctgtctccgtctcttcctcgtcctcatcgcacacccttagaccggttgcttaaaaggaggagaagcaagtacgcaagcatta caaacgacgacattactgacctcttataattaaagtaataaattgtgaaaatgtacaccgtttttttatgaattgcataaagcgaatttatttataaaa agttaatatatataaaagctacatgttcactgatctacaattttttggtttcagatttttttgaaatgttgttatcaacagtcgaactttaaatttttcttga aaacttgatacataaattaaaaattgaacgataacatttggctaacttttttccatgtttgcctttgtgcaaaggttatcacttgattatttatttttttga aatctggagcaataaaaaaaaatagtaaggatagagataaatacaaactgaagcccttatgtttattacaagttatgacaatttcagtgtagtttt gaaaatatcaagtattgcagttaaatttacaatgccaaaaaatctaagaaacattacgaagttttcatgaaaatacctcgaaaactatgaaaata gatcaaagaatatccttaaatatgaaagaattcagacttcattgggttttgaaaaaaaaatggaagggaaaaggaatctgattaaaatcagttttt ggcattgtagaagtatacttcaataagtttgttttcaatgatagagcttagtcagttaacattcaagttaacttgtaattgtaacctggtaataaaaa atcaaaagataaacaaaaaatattgtggaattatcaaatacaactaatcggaaaaagttgattttgaggcaaacatagcttcatctgctgtacat tatgaaaattttattgaagaggagttaatgaagtggtacaaaacacgatgaaatgataaaacatgaacaaaatcgagttggtcactatacact aaacaggacacgtaataagaaaagtcaataggcacggagagacaaaaaggtcatcctacaattgcggtggctaactgcatcttaactacgt cgtagcattaaaaaagattgataagacagtgcgtgtatgaacgcacaaaaagaaaaacctagcaggacatcatgaggttttattttagcgtttt tttgcatatcatttttttattcattttgtttcagtaaaataagtttagattcatttttttaaagcgaaagttaatagaataatttgatcttgaagttgaaaattg ttgttaatttttaaaaactttgttttcaaattgcctaatatttttttgaaaacagaacataaaataac prx-5

SEQ ID NO: 47 cttctacgtggaattctggaggttgaagcttctggtctaaccatcatcagtaagaatgtaaagaccatttcgtgtttcatatttatgccgtcaattg tcagtacaaggggccgcccgttttcgtttcgtttcgtttaaattatagggaatacattataaaatcacaccttttgtgtatatcttcgtagttttattg gacattttaatagg ccttgtttataaaagaaaatataataatgatgacattatacaaaaaagtattcaaggaatgttttatagttacaaaacctata ggtatacagaatatgtcaaaataggggaaaaaactgaatgtatgcagtcgacgaataaggttgtcttgacattttttggttaataatgtttttcct gccagtttcgatatctttgaaattttgatccagatgacatcaatcctagctatggaataatgggggaactctctttaaattcacaacttcattcgag caaaatttgtcttttgcacacgaaaaaattattattattattgcacaatcaaatatttttcccccgtgcaagtgtgcaatggggcgacgggtcgagc cagaaacccgtgttgttgaaaatcaaaccaagtgcaaaatatccattttgcttaatttaaaacgatctaggataactccactagcaactagaat atctaattgaaggattgaaatttggaaacttacaataaggtattctattttattacgttttcaatcttgctaggaaaacttggaaaaaaaaatccataa acgtttcccggttatttcagaaatcgatagtcgacctccgttgttccttatctaaatttcatcaattgtatccttttttgataagacaatactatctttttta tcactacgtctccttcactctaaatcctaatgtagtatcaatcaatttgatgaaaagactacactggggcccacttattttctttttcaatcaaaattc acactttattttatatatttcttgtaaattgtatttttcttcatttttaattctacttttttttcaacaattaactctcgaattcttcaatttttttacaga duox-2

SEQ ID NO: 48 aattttcaggagaatcaatcgacgagcttgaagatttcgacaccggtctactatcttccggaggatccgattattctttttaaaattttcttcttttaa -continued aaaatttcttttgaaataaataaattctcacctaggaatttcaacaattcaacttgaaaaaagttcgcgcaaactacgaacaaatgtgtgtcgag cgggcggagccactgagaaagaggagcaaaatgtacacaaaaccatatttgagtgtaatttttcaaagtttggcgccgattttctgtgagag atgagttttctcaatttatatttggttatttttattttagttcttactggtaaatttctgggtaagtcctgatgactttgaaaacgaaaaaaactctttcat tgatgctagtgcgattgctaggaaagcaacttttcagttaccaagaaaaagtccaaggccatagggattagctgcgtggcataacaactcat ccatcctcgcagatgcaaatccgctctattggcaaataacatggaagagtataaacattttctcttccacacggaaacctagtccccttgggg agcggtagtgcccacaaccccgcatgtttaccaaactacacagacagcgctattgtctgcaagtggcaaaaa prdx-2

SEQ ID NO: 49 agcgtttcgttttagaatcgccagtgtatttttttgtgatagtcctatgtgctttaaattatttattttgaaaggttcaataaattatattttatgaccgaa cacattatattctcagttgttatcttatatatccacaccggaatgttgaatatctgaccatatatatttagaatgttgcggtaatttttttgttgctgtgg aattttattttattttattttcatagtttcaacattttacaatttattgaaatttatgggttttaattgttatatttggcgtttttcgtttactttttcg ataaaaataaattcagttaaaaactaagttataacaatgaaaacacataaatttgaacaaatcgtagaaaaatcactacaaatttgacagattttatgggtt ctatcgcgatttattgaaattaacgtcttttaattgttttattttagtttttttagataaatactgttttcaaacgaaaaactttgaaaaatcgataaatctc gcagtactcctgaaaggcacacactcgtttgtacttaagaaaaattgtcgcgacgagaccaactgtccaactacggtagttttcaaaatacgc ggttcaccgcaaagtcaaattgcggacctgaacatttttttattttcccgcaaactttttttttcaatttgcctaaagcgctcgaataaacatgaa agtctcgtgtttccttccatccagacctctcattttcaattttaaaactaaaagcactttttgacctactttttgtcgcaaccgccaaaactcgcttc cagaattattcccttttttaggattttcgacgcaacatctccaaccggttagtttttttcgcagattttctcgcattcgcgtagtttcacttgtttacttcg tggcgcctcgtttttttccgctctctcgtctgaccaccttcatatttattgatctgcgcctagcggcgcccgttgaaatactccacatttttttgcaa tcttgtctgcgagttcaggttattttcgacttttatgaaagcttgctaggaagccatagcaaccggggaagaatacgctagccaaatgagaga tagaatcgatcagctaaatttaagataaatagtgaattcgaattctaagacctgctcgaccagctgaaattctaaaactctgcgccaagatgta tagacaggtaataatatttgaattttctttaaaagtgaccttgaaccctaagattttcgctcctcctaaacgttgtagtctgttactccctgccgcg acaattgtcagcaaaaatcgcgtcacatgatgatgaaagtttgtggcaatgttataaaaagactgaccttatttcgtttcttggaagatgcaaag aaatgtttattaaaaattgcagtgtgaaatcatgtctctcgctccaaaggtgcatttcttatttgtttttttaaaaatatatttggttacttagatattaatt taaatcacggaaaagtttaaacccctcgatttctgttatttaacatgatcactcacttttataacaattaatttggtttttcaaagatgttcccagaat gttttattagttctcatttcgtcctccgatttttttttctttcgtcgctctccaatttgccaatgtatttcattcccattagataagcaccgcccgtcacct tattctccttcttttcacattgcaaacaaattcgttgccgttgggtttcaatatccttttcatttttttgtcgtattgttgttcttgtgattgtggttgtta ttttatcgcggtattatttttttttgttaaactaattaatttttag pxn-2

SEQ ID NO: 50 tatcaaagttttgttgttacccacccaaactttgttttagttgcaacaagctcacttagaaggaaattgattttcagtatttattgaacacagcaaga aaaatcagcaaacgtggtacttgtgtgttgcatgcgctcattttaataataatgttgttgaattataacaaataaaaacatgtagcatatttttgtatt ttcaggcttaaataaccatttctaagcctaaagagaaaaaaaaatgtacaacacgttaaatttaaatggagaaagaaattaacaacatttgatt ggatttagaaataagggcacgtaatacacaagtaccaaacgtgaactttaaaaatttgcgtacctaccatataatacaaaaccgtgaaaggt ggaatagttttgaatggcaaattgtttgaattcatttctatagtgctaaactgaacaaatattagtttcagttttaaaaaaagtgtttgaaattcttcat ttgcagtcaagcagtggcaattactcagcttttgacattcaagacaaccaagaaatatgttttcaaaaagtttttccgtattcagtcaagttctattt tcctctgaactatagctaataatttataattgtacatatcaggaaaaattatgtggtttaagaatctctgaaatttttttggaaattgggaggtgaaa gaatacagtacacttttgtaattttagctaatacgttcgagagttattatcattatggcagcacacttgttggtgatttctatttttttgacatgatatgt ttgaatatgattttcctcgttatgtggaaaattttgtagaggcagatgctaaacgacaagctagactttttagtgaatttttgaatcaattatttataa tggcatcaaacaaatcgaaaggatctgtgccttttgatatttttggttttgcaacaatttgtctttgttgttcaaacacgtatacatcaaaaactattg tttatttcaacattttcagtgtatcttttaaagatcacatcaggttgttactaaaattagttttgaattcaaaaataaccaattaaatgttccaaacatat aaaaaatatttcaaatatgtatcagcttcatgagtagtccataacaaaacccagaagttcatcggaggttgtatatctctgagagtgtcaaccc acttcttatttttgcgataaaactaattaaaaactaaaataggaacaaaacattaattttatgcttcgagtgaaaattcgtatttattcactttttagg -continued gagtttctcaattattttaatacatagatacatagatattacttttaaataatatttacgttcaatccaaataagattttaaaacgattcagtaaaagtt
cttgcaaaacaatcaattagcaactgagtttggtttttaaactgtttaaatctgaaaacatttttaagaaaatgaaatccgtctaaattcattatattt
agcaggaacatgttaaaatttagtttctgaaatttaccaattatttggaactaatgtgaaataataagaatattattattcaatcattttcttgcagac
aaagggaattagaggcgtctggtcagcatttgtcgtggctcaactgttccgcaagatacattcgtcgagttgcgggtctcgtttgatattcaca
aaaggaggggttcatctgcgaagttacacacttcttctatcaaaccacattgcctcattttcccaataactgtctcatttttgaagaagatgcgat
caatcaccgtctaaaactgattgcgttgcaacaaatctgtgatgatatgatatgatggaacggacggaaaggttaaatttcgagtgaagaaaa
aatatagaagtaatatgaatgagtagatgaaagaaaaagacaaaagagaaattgatatgaccgcgcagcagacaggggcatctggtgtga
gcgtgcggtttttttctgttacctctaacgcagtccgtacacttgtcggcgtttatttgtggctgtgggcccattgcgttgatgacggtccctctag
ctggctttcattgtgatccaattgcaccatttggtttttgagttttattctatttctatcgtcttttgtgataaattaattgagtgaatgaataatgtataa
gagcctcattatattctatttactaaacaaaactcaattatttcttttgaaaagataatgaaatttccagtcatcattccataaatataattattattttg
ccttcgcaataatcctaaagatttttttatatccttcaagtttatcaaaattgtttaggt mlt-7

SEQ ID NO: 51 attccaatttcccagccatccggaaattcgctgtaaaaattggaaagtaggacaaatagagaatataatacaaagattaaacactttttacgac
aatgttgacttcgtcatggtacattcagaagtgtctgggaaatgttcagcaggaaaacattgcagaagagaaaaacaactcggaatgtttgct
gaaaagttctgcttggaggtatttttaaacttggagaagatatcattgctctactttggcggcttctatcgcggtagtctttagtttgatcaaaaatt
tatcaactggcaaaatacgtacaaaatagttatatacattttgctagttgacaaatttctgataaagttgaagggaactgagaggttataacctgt
caatcaaggagcattatgtttttaggcgcacctacttacttcatgcctgcttggctacttacctgcctattacctgcagtttatatgtaggcactga
tgtaggcacgtagccatcaagtaggccgccttttgaggctcatttgacccatagaccttaaaataggccgttctagaacccttcttatctgaaa
caacaatctttcagacattttcgaatggtcaacaacttaagttttatttgcaaaaacaaaaaacaacaagttttcaatgtttttttgccagtggaa
attattgttgttggataggtacagatgctaccgggttaccgagatcgtgcctaccaggcctacctattgcctgcctgccatgtgcctacctaca
cttcatttcggcaaaaggtcaggggccaatgaaaaaggagcatgaatagattcgcatcagaaattgatgtcggtgtaaggcaggtgcaggt
aaaatgaaggcaggcctgtggcaggcaaaggtcagcatggcaagcattttgggaataccaaccagtagttttcatcagagcacgattgcat
cgacgaaaaatttgaatttttgtgtattttgaagagtgccgtgaaaagtctaaatcttttgctattgcctctgattccttctcgaacctgaactataa
aactgatgtaaagaaaaaaagtttccaacttaagagatatcttatcaatttaaactttaccgagtgattctgtgatatctcaaatttcagtcgaaaa
tcacatgtggttttccccttttaattccgagagagagagagagagagaaaggaatttcacctccacaacaacccataatcattcaattaggttctaa
acacatacaagaagaagacaggaaaatgttagccttttagtcataggtgctgctcgatcatgatgttgatgaaccaaacatcgcattttgtag
gaggggaagaggacaggagactgtccatttgaaagtgactactttgtcggatatttagagagtgacttacttacgaaagttataaagtttggtt
agcaggaaatctggtttttactgagaaaactctctgagggaaaagctcggggtgggtcatatacccgcgagatatctgccggtcattatttaa
gaatgtacagctctactttggcagatcatatctcggttattccagtacatatcaaaaattgactgaatatgaaaataaaggaaaatgttcaacct
gtattttaccagttgaacatttttttgataaaaccaaaaataatcgaaattgtgcttaacggaaaagaagttagattaagattccaggctgggtcc
cgccacgataagctgcaaaattatttttttggagctgtctgttcagaatcgtcgttattagaaggtggaagtgctgaaatctgaaaaaaagaact
caagaatctatagaatctctcatatatgagagatcggctccgtgaaaggcactaatctggaatacttcagaaattcggcgaaatcttggaaatt
gaaaactttgagatttttttcttgtagatcgaaacccgcgagatgtcagatgcttctgaattcagatttacaaaatgagctcttcagacactcctg
aaagatcagctgaccagaatatgcccacctaaggcaggcgtgacttacctgaaaggtgacctacgcctattctcttgccagaactcgaaac
tattttctaggaaaaactttttttgtagatcgcattccatgggagctataccttccctgtaggcacgcaggcactagtttccgtgcctacctggaat
ccacataaccggagcacggagcagcaacttcaccttcagaaatgattcagagctttacatatagtttcctgttcctgaaaagcatgttctacga
tgccatgattctcatttcgatgccacttctcaaccaacttttgccgagcttctgaacttgtcgagggagtctgaatacccccccaccgcccacac
taaactttttttcctctgatccgtgagaatatcctcattatctcacaatcagtaatgtccaaatcaggcgggggaggaggggtaaaaaaacacg
gaaacgaggaggcgaaaagcgtctctgggttcccgcccttcctcccacacgtcttctctatgcgtctctctgacaatctctcgttaaagttgcc
ttttttgggaaaagcttctgtctctgtttctctctgtcaacgtgtttctcagcttgcgggcgccaaaccaccaccaccatcactgactgtcgattc
gcggtgtgttgtgtttcaattgcgtaaagagtgagagagaggaaaagatagagagagagagagaccccaaggttatacgtctgttatactt -continued gttacccatatactcttctacacctttaccttcaacctttccccacattgactccgcctctctctctcttacttcttggaagacactccccacccccct cttatctatttttttcgaaattctcgacccttcaccctcccccttacccgcaccggtcatcattctgactctgcgaactactggagaggaacacc

ZK550.6

SEQ ID NO: 52 catgaaggcgaccgaaaagtgtccagtgaagattttctaaaaatctcgaatctggaatcatgatgtgaaatatatgaataaagaatctttttaaa atattttgaaaattctatacatctctaaaaaaatgcaatctcgttattacaaaaagcaaaatctttcaccttaagcctagatgtaggtaatgtttgat gaacagtaaattttgaaacagtaaatttttgaattacaaattgaaatttttttaaaatctattcagaatccctatatccgcatgcatcagggaacgt gccaaatttgaaaaatgtgtgtttctcaatctctaatcatttatcatatggtcatgacaacaactggtgtcaaggtgtacgataacggtacactgt ggcaattgacactcttttttttctttatttctctattcaacaagacttgtatttattaagaaaatgcaatgagagagcgtggtgataagacgggtaatt ccctcgcttttctcatttttttgcggtgttgtgttcgtgtcatttgagataatccatgttgattccacttttattgttgatttgatagatgttccaagtttttta ctgcttcctgaaagcataattcttaaaaataatgcttcatagcagttgtggcttcatacaattttcaaaaaaaaaattcactgtttcaaaaaaaattga attcaatttcctgcattatgacgtacgtgttaaaaaaaatatgttcacctaaaaattccgctcgaactgtcgcgaaatctgtgtttcagtgaaataa aataaaaacatctagacaaaatacagttctcctcaaaaattgctgtttcaaaataataatttaaaaaaaaacaccaaagtgtcgtatttaaattta aaaaaaaactatcgtttcaacaaaacaggttcaaatctattttagtattaaaatctataactttataaaatttgctatttaggttttacgaattgttgttt tttactctgaattgtaaaattaccgtttcaaatatattcttctaaattcaaaaatttagtatacaatttttctagaaacattgaagtattaccaggaattt ttggatatttcctataaattctattttgatcaatttgtagttgtcttatcatatattgcattggatgataataggaaatgatccgattctctttcctgttcc aaaactaggtaaatgtacctcatatattttgttaattttgtagtcacaataacatgttatgataataatatcgataaaaaatatcgtgatgtttaaaca ttaagtttcatttttttcggtactgttctaattgttcaaaacaatttaaaaaaatttcggtcaatttatagacaataccgattttaataatgaatgtaaaat tttcactgtttcactaattttataacaattttcattccttccaattcacattgtgttagtgtagtgatcattacttatatattttaaaaaaaatagggtgtta gttttttccgtttgtctgtttgtttccgtgacgtcacaacgcatgagacccattttggcgcaaattcaaatttcttcagaaaaattttggtgcaaact caaatttcttcagaaaaattttagcgggaattcaaatttcttctgaaaattttggtgggatttcaaatttgttcagaaaaattttggtgcaaattcaaa tttcttcagaaatattttggtggtttttttcttccgcgccggaggcgcgatcagcagctagttttcaaataaatttactgtttcaaaaatacgatatttt ttgcctaatttttgagaatatcactatgacgtctaaacgtaaagcgattccataatctacttcaaaattccaggctccccaa

C28H8.11

SEQ ID NO: 53 cagtgtaggccgtcttgctcatagagacaaataaactttttgagatggtttttaatagaaaatacattttatagaaatgagaaaaaataaagtttta ctattagaaaagcgtaacaaaaagcttccgtaattatttatatgaatgttccgatatttttagcgatgtgtgcatcgtgcactcacaatactaatgt tatgagcttccttgcaataaacggtggggctggaaactgacaggaagtgggtttattcgatgattacaataccacaggactgatgacacgcg taatcaaaagttgaaactagaaaacataaacacgcggctttcatctgaatcagagacgaatatccataaatcacggcccccaaatagaaac cagtttattttatgtcacttcttttccccattaactttcctgtcacaatcatacaacagagttcgatcatacaggtccaaaggttttgggtatatcttgt ggacatgtatgctgtgaaatgttgaacatttcatataaaattttaaaatcagactattagatcgaatagttctacgaaatttgtaaacagtttccatc gaaatacctatttttttgtaacacgaagtcgacctctctcccggagacgctgctacagaaaggtttgaattttgagcaaagttacggtattaggtc tcgaatgaaaagtttcgaaagtacgcaaaactctacaatagggttaagaatcgataattttctagattgtccaaaaaaagtagactaattttgcca ttccgttcagtgccttcaagaagtacttgaagtctatacctcacctacttgtctgatatggtaatttactatcgagcttattagcaattttcttcacgg gaaaggagttgtaggttaacttcaagtcgcgaggtaggcatatttgtgcctggcgataacaagagacgttccacaaacatcttactcagtttct atttgaaacttggcgaagtagacatgaagttgaaccttcggaacgtcagtccaaaggtttgaaggaggggttccccgaactgtcatacactt catttcatcgtcagctgtctgagatcaaacattcaataagcatgaagatctctgaacgaccgaaaagatatcgataaagtgatgataaaggtc tgcagcagaatggttttgcagacatttcttcagaagttaaaacaacgttgtcgtacccaagtatcttatcaagggagaaaaagagtcaaaaga taaattccgccatttgcccctccggtccgtaataacgagtatttcttatcacgtgtgctgatctttttttcttaacacacatacaatcaatcgatttgtc agacatgggaaagaataagacgtgatggatgaatggaataatgtgaacgatgaacgagatacgtgacagtcagaaagttcactgtgaata gagtatggtataaatggttgagagacgacggattacggaaagatcgaattatcacaacgtttttgatgtatctggaccgttcacatggaattta gtaattgttacttcttgggcgacagagaaaattcggccagtctcatcaaatagagagtttttttgaaaatctgcattgcagggcgaacaaaatc -continued aatttccacattattttaggccggttttaaagagaaatggagagattttgagaactgtgaaataaggctggttaataaattgtgcataaaaaatct agagagattggaaagccatgcctatttcactgcagcttcaccaacaatctaatcataattttgaaaatgaaaattacattagcatggtcctttact cacatttttttaggatgtcgacactttttcatttgaggtcgctacaactgttgctcaaagttggagcatgtgcgacctatttccactcctcctccac agaccccgtttgattggtgcaaaagtgggcagagcgaaaagctgattggtcttgcagttttcattttgaagggaattaaaaaacggagttagt aacaattgagaattaccgtttttaaatgtataacttttcaaatcttccgtttctgaatttattatatacatatattatatagactcaattacaaattatata aatttaatttatatattatatagccttaattattaaactttttatttgagatatttttaaatttcaaactttttttcagtatttaagtaagcttcctattc acgctactccacttttagtgtgtttcaaatgaatggacgttataccaaaattcaattgaaatatccagcttcataaatatattggcatgggaatgagcctc gtcacgaacattttagaaaaacatcaggacaaacttatattgtactataacttgcaaacctgcagcagcagaactttgaacacccaaatccatt tccgacggaagtattctacatcttgtggccgcgtatacccatgactactgtacccaaactggggaaaacccaaattgctagtaaacgcccac taaataaactgttagcattgaaagtgtgaacacgtgaatcgtatgtcaagtgataggaagtgtgacgttttgtaattaatcttaacttccaagtgt ttgtttccttgaaataagatgcctacacacggcggcgaaatggatactttttatgtctgcgcttattctctttgtcccccatcatcatacaatcttca acgccttcacatatcagacagtccgtcgggcactgaccaaccattcaggctgcctgtctgtcatttataggctgtctagttatcttcaattaatgt ttgaaaattcagaagc

C35B1.5

SEQ ID NO: 54 aattaattattttcacatttttttcgaattttgtcgatttataggcgaaattttacgttaacctaacggaaatatgagtttataatgcatttttaatcgaaa attcggtttttttcaataaaatttgctatgaaatccgcaaaaacgcctggaaattgtctgaaaacgaagaaaaataaaaataaaaatccgaattct gtgcattgtgacgtggcggtgtttgcgtacccgacatttaatttcacgacacttgtttttatgtttttattgttttctcgatttctgcaagttttccactt aaaacgtgcggaaaaaatccagaaactgtaaataatactaaaaaaatataaatttccacaaaaaaggcatgaaaactaacaattacctcaa atatcgtgaaaaatgcaaaaaaataagcctttccgaaaaaacgggcccttgggcctttaaaggacacaaaaacaggaaagcataagacac caaagagtaattggatttctacactttggttcctagaattatttataaggtgttattgcgtttttgtgagattgttctatttatccagtcaaaaattgca ttttctttgtttttgcttcaaaaaaatacattttcagtggaaatttcagctgaaaagcagaattttgaggttttcgagtaaataacgtaaaacactaa attacaaatattgatttttgatgtcttagaccaaatttcgtaaacatgtttgtatttttggaaaaaataggttttttgtcgatttttaacttaatttttcgaa caaaaaatgatttttttctccgatttaccaaagttttgacttaaaattccgattttctgggtcatttttcccctaaaaatacgattttaattcaaaaaatct atattttcaaagaccaaagtaccataaccttcaaaaaacaaccactttctctattgcatcagcgaattgtcatcacccctctcaaaatatacaaa acgtcatcatttttctgtgttttctctaattctcctgaaaaattctataaaaccaacagttttatcatcaaaaatgcctttttgaccgactttttttaaagt tgaaaatcgtacagttttagcagaaattccagagtttcattttgaagtatgctggaaataataaaattattctaacatttattaatattttgtaaaact aattctatacaataaaaaagtaaaatttaatattaaaaaaaccggtttttctcaaatttccattccccaatgtcctgttctattatttgttccgattcgg ccacagaacgcgcacacacacactttttgctgattctctgcctcctttctttgatttgaccgcattttatattgattttcggccacaattccactattt gttcagtttgtcgatttgttggaaatttcaattccggcaattcgccgatttgccggaaatttaaattcagacaattgccggtttgccggaaattttc agttccggcaatttttttaatttgccggaagtttccatttcggcaacttgccaatttgccggaaattcgccgttttgccggaaattttcaattccgac aacttgcctatttcccggaaattacaattccgccgatttaccaatttgccagaaatttttaattccggcaatttgccgatttgtcggagatttcaatc cggcattttgccgaaaatttcaatttcggcagttcgccgatttgtggaaaataacaattctggtcattcgccaatttgccgaaaatttcaattccg gcaattcgccgatttgccggaaattttcaattccggcgattttcctatttggcgaatatttttaattccgccggtttgccgctttgccggaaatttca attccggaactttgccgatttgccgatttgccggaaaaaatctttttgccgcccacccctaataaagacttcaaaatatgcgttttttttttgcttttaa cacgctaaaactctctaaaaatccccaatttttcagcttaaaaaaccccaaaaaaa Endoplasmic Reticulum Oxidative Stress Toxicity hsp-4

SEQ ID NO: 55 atccatttatttatgtccagtacaagacgaccgttcatatcttcttagtcattttctttcagccggtgtgtactctttgttcaattttctctttcttggtgcaa cctttattcacgtgtatcttctccgagcttgtttgcatattttttttttgaaatttcatgtgctaatttattcatgtcatttttgaagttaaactcttcaca tttcataataaatatttattgaacccgtttgactactccaaattcacgaagttaccaaaataaaagtgatatttgactttcagaaataccatttcaaattc -continued cctaagacgctcgggaaatattaattactgcaatttatattctgcttgtatttttcgaagttgggtccaactgtgtgaagtattgtaagaatcatatc cttctccttcacattctacataaacaattcatttctattctgtaaatttttttctgatgatttacggtaaaaacgagcgaaattcggtccgggacaagg gtttctacgacgagtccatcgtggtgccgctcgcttgtttgaattcccgcgtgccgcattcctcgtgtcgagacccgatgtccaactgggggg attaccaactcgggggattggccccgcccacagaaccgtggcttgcaatttttttcttgttaattctcgctctattgagaaaaaataattttaaaac cgtgcggcagtttcaaaaatgggcgtattgcaagccacggttctgtgggcggggccaatcccccgagttcttcgggtctctaaggaaagg attcgtacattctggtcctttttatttatttttaacctcttttatttttttaaaccgcaatccattaccagttccatttttctccgtactcgtcagtgtagcg agtgacgagtgaaattgaccccatttcttatcttatcgaaaacaatctaaatagtttccgcattcgcataaccagaaaattcttcggtagtcgttc tcatttgtttttatttcatgaacataaagtaacgccatagtctttttatgaaacgtggcgttaagaaagctctcgaaaagtctcgatttctccagca ctaatacacgtcatctccgataagtacacgttgcataggcggtcctaataaaagcgaccgcggacgttcacattcagttctttgttttctttttgt cgtctgcactccttctttgcgacgtgtattttgtgttcttctctgtgtttccacttctcgttagtattctcgcgcttctactctgaaaggtttttcttctta aatgttctcattttcagccactcagcgaacagttgaactgaccgctcatcaagagaaaaat dnj-27

SEQ ID NO: 56 aaatttcaacttccggagcccgatacctataggccacgtgagaactttctcaggagagacgcagagagacacaaattgactgacgaggag ccaggagaaatgagcagaaataaatcaaattgaagagtttctgaggagttcttttttctctcttccacttcatcctacccgcctgagccaccgg gggaactgacaaaagagagctgtcacgtggttccagactgtcccattacggtttgatctacaaaaaatgcgggaatttttttcccaaaaaaaa tgtgacgttagcacctatcggttagccatacgaaatcagttgagaagtctgccgcatttttttgtagatctacgtagatcaagccgaaatgagac actctgacaccacgtgagatgtgctcattgtggccgcgagagtggtgtcaaggaatatgagagtacatatggtaattggtgtataccataatt agatgggaatttgagagcttttggaggaaggagagggtttttcggcgaaaaattagtgtccgaaatgagaaaaattgaaaaaaaatgcaag ttttcactaaaaaactacacttttttggagaaaaaattggaaaatctgccagttttcagtgaaatcgagtttgaaaaaaataaaaaattcgagaatttttt tttttaatgaaagatttgtgctcgaaatagctgtaaaatcagcttaatttccgaaaaaaagatcgtgattttctcgaaattcatttttttaatttgtaa ttttgatttttccacacaatttcaagctttaaaaatgttaaaagtcacctaaaaagtcgattttcataacaaaatacctagaaaattgtcgaaaacc ggcaaatttcggcctaaatctacttttaggcagattttaagttgaaaaatgcacaaatatttctaaaacctgacaattcaacgatttttttcctagaa aaaatcgtcgaaatcgactttttcgacttttcagtatttttttcagtagaaaagttcacaaaaatgtccgaattcgacggaaaattcaaattttttttt ccagaaaaagtgctgattttagccgaaattgggtggaaaaatcgaaatttcgacgaaaaaaatccaattgcaattgaaaaacattgattttcgt tcatcgaagtatcctcttttgttattttccactttttcccgcaggtattctctcgccattcaccaagacatcacacgaatcccggagacgcagac aactgaagagacccacttttgtgtgattcaaaggggtcaacgcatatagccggccgattcgtgatgactcatctctgtgttattctataaatctct tgatttttttgaggatttaactcttttttttcgaaaaaaaacgtgtttttccgaattttgtatggttaaaagtatcggaatcaccgtttttttgttgattttttt tctcaattttcttttttgtttgagtaatgattaagaaataagaacggaaagaagagaagaaactgtgaaaaatgagagaaaatatttcaaaatca ggaaaaaaaatcattttccaaattttcaggatattatgcggattattagggttagaacacattttaaattataattttaattatttttaacattgaaaaa acaaaaaaatcatccgaaaactactcttctttcacaaaaatcggtcaaaaataaaaaattgcgaaaaaaaaacaaaacaaattaaatgtagcaa gcgcgctccattgacaaaatgccgaaatttttgcgagcgaagtttgaatttcgttgcaacatggggcattttcgtgaaaaacaagatttaaaa gaatttatactttattcttgctcaagaaaattaatttttccataaattctattaaaagtggcagttaaaacaacaatttctaagatttttttcactttttttt ggcgtttgcttgtttttcagagtttggaatagttttatgtcaaatttgatttcttctcattactttcttcataaaaaaaaatgcaaaaaagcaaattttta tcactaaatcgttcaatttccacctagaaaagacgaatttaacgcaattttccgattagagcgcatttgcattgtgcgggaaattcaaattattca aaaattctcctctagtttccagttctagtacaatcggtggccgagtttttttcttttttttttccagcggccacatagcaagagccaacctgtatacttt tgcagttcttgtgcaaatctgagctccgccgagcacaaacaagtttggacagtccacttctctgcgtctctcgtgatgagtgtgctctctcgtct aacctctaatccttcccagatatttgcacatctaccccagttccacatagccataaagacttgggtcatttttatcgatttttttcggtttgctcacaa tattgtgagtttcttaattaggtcttggtagctttttggagcattttgtgactttttatgcctaaaaaccagtttaaatatactttttttaatgcttaactag atccaaacacctttgaaaattgtccaaaaaaaattatttttttggccgaaaatttcagtcgaaaaaagcatttttttcggcctaaaaaaaaattccaaaa aaatccctaatttttttctgtatctccagagccactttttaaggtataaatcagcaaaattttccgatcaaaattccatttccctatatcttttccctctct -continued ctatctcaccctatctcgtgcgttagccgacgtttactaagtcccagtcagtttaattctatcaaattcttcacttttacttacagaaa dnj-7

SEQ ID NO: 57 atcacacggttgaaaaaagtcgaaatgaatgaaaacaagggcattttggaattttttaaaagaagaagtaaggtgagttaaaagaatgaaa agcggcgtgcttgagatctaatgaaacaagggaccgcccttgtttgtgatttgctaacaaccgctatcgtttgaaatattccgggcggagttct agctgatttctacttggagtatcatagaattggaaacggaacgaaattgccatagtatgaaacttttaatttgtatatacaaatataatcgaccca tttaataggcctactgcggattaatttcagtgctccttctaaaggcagacaatgaaacagttgtgtagtaaaaacaatgttcacaagacctgaa acaattttctgaaaattgtttgataatattgttcaataaacataaaagatggttcacaaaattaaaactaaattaaaaattaataagaaaaccagtt gtcacaaacgcattcgcaaccaaaaccgctaaacgctattccaactaaagttataattgcatttttttgcaattaactgttttaccacaaaacaaa acaaaattccagtttaacaaattatcaaaattccaataagatcctttttaaattaaaaaggtgagatttttctagagagtccgaatagaaaatggt aaccaaaccgatgacgatgacaatggtaatcggatcaatgcagaagttgttttgaaattattttcaaagtcgttaattttgagaatatttgattttt ttagagtatgtactagatttgttctctacctcaaatgatcaaattctttgactgcattaaaacaaaattttggcaaaattatcgaaaatctcagaga aaataaacaaacagtctatcacatttcaaatgaagaggaagccaaatttgaatatagacggtccgatgaagaatttttttgacaatttattttaactcggaa tggttattaaatttgatttttttaaatttatatttcccattatttttaattttttaatttatgaaactttttatgtgaaaaaaaaaatttatgtgtttttgatt ataacagattttacgtcagaagccgaaccatctttaataaaaaaatttgaaaaaaaaaatcacttctacaattttcatttttcaaatttgagccatca aagtcaattaggaaaattaattctttcaatcgttgcagttacagtgctatttcaggatctttgagagctcgccgtgagcttggttctggagattcg cagataaaaattcatgagtaaccgtttcaagacatgggctatcaaatggcataggtctcatatgcaagtccgattggcatcttctgatggttcc ctagtgagtttattaattcacaagagcattgtatcggaattttggcaaactgttaaaacggaattatatgctttgttcagttttgtttcagtgtgttac acagttaattgttttagaaaccattgcaagcaattataactttggtgttgaagtttagttgtgaatgagttcgtgacaactggttttcttattagtgtgtat attaatcttgtagatcatctcacatgcttattaggcagtggtcatttctatttaattttgtttgaaagggttttaatttttttgatttttttttgttttgtttt agcgaactcaaattgaaactaatcgccaaattttataataaggccttttcaaaacatttgatcaaacggaaaagtttttttcaaaaaaataaaattttgc agcggcttaggcacacgaacatccgacaggcgattcaattgtatcaaatacttagtgcttctaggcaaaatgtagattttagatataaattaag cccttttttcacagtttgtaacgccagggaaaacattttttgagcaaattttgaaaaatcttatcagaaaaatgttttgattgggttaaaaaaacacct agaaactctactcctctttaatgaaagcttgtgtttcaaactctttttgtgcttaaataaatttttatgcaaattcataattttaccaactttttcccact gaaacatttcaaacataatgtcaagtcgtacaaaatcttataactaacgatttctaatcgtatctcctgttatcgttatctttacaatcgaagataa acggctgagaaattttaggtccgaggtacaccactacgcacaattgcggattttgcactatttggagagttgagccaaaactgtcttacttttta tgaaactgtggaatgttgtaaacaattggtgaatatatttattgtaaaatttttatttgaaaatcatattcttttgtatcgaattttggaattccacgttt gaaaactgcaagagcgccttatgctgacgtgtgttagttagattgagagactcgcacggagtagacgcagacacaccacacagcacaaa cagacgtcgacgtccgcaattctcgttggttatcgactcttttgtcccattccaccaccaaaacttgccacgatttgatgttgctaggacataaa ggtccagtgggaaactgcaaattctttgttttcactggttttttttccatttgttagttactagcttgataatttaaaaatgaaacgtctcaaaactagtt cacttgacctacttcgaacaccaatttgtatcgtgcgtcatattccttgccgttgcaatttcacgtgcacttttatgaatttcatagatttttttttcaga taattaaccgacaaa

Y41C4A.11

SEQ ID NO: 58

Ctgttgcggcgcacctcgaagaatagctcctgttgggacattttgtgatggctgaagtaggaaattatattaaatttacattaaaactaaagaa aaaatacgaaaaattatgggaaatcagtggtaaatgcgaaaaaatgatttaaaaaaccgataaacgttgaaaacgcgacggtctccaaaat aatgcaagcgtgctccactgcgaatcccctgctcatttgcgcgcgcattcaaatttagatttccccgatttatcgtgaaaatcgctgccatctga caccgcattgcaccgaagatggccaaagataaccaaaaaaccaatgaatcattggtctatcgaaaatacattatattttgttgggagcagcc ccacgaaagccacgagagcccgcaaaaaggtaaatattgacttaatatttgtggcggtctcttacttggttccacttacttttaccaataggca gttatttttgcgttttgtcgaaaaaaatcgatata arf-1.1

SEQ ID NO: 59 atcgccaaccaaggaaagtagtgatctacaagttttctctgcaaaaaaaaacaatcgtaattgcataacatctatcgaactcgagagtctccca aaaaatccctccaaatctttactgcatttgcatgtaaagatttacctatttttctaaactgctgtgttcctgtattttcactctacctgtttcgtttattta -continued tttatttaagcatcaagtttattgaactctaataaattctcgggaaattcgtgtcttaattattcttgccagggaaagttacgtttccttatcgaacac ctgttgcgaaaccagaaaagggcgggtctgactaagtgaacaaatatttcgtaataactttcttccaacagaaattaaaacacgcaaaaaac ggccaactcactagctggaacgtggagccatggagatggataaaataactctgattgtcgacatagcttcaagaatatcgtattctgcattttc aaaaagtctttttcgttcaaa lips-11

SEQ ID NO: 60 gcataaaatgtttgaacttggcatattataatacaaaaacaaaaattgaaagagccaagaaatgggcggagcctattattgattatccttgtatt ttgcaaaaattgttgacagatgatttttttccacactaactctattgggagttttcaacaatttgatatccaaaaaaaagaggaaaatccgctaa caatgtgaaaaactagcatcataatttgaattgccgcgcagtttcctggcgttccagaatgatctatttgtatttgaaagaagacctttgaaatag gcatctcaaaatttgccgagcttggcaaattcggcaaatttctgtttccaataattgccgagcacggcaaactcggcataatcggcaaatttgc ctggcttcgcaaactcggaaaaatctaagaattttgatatttttggagcacaaaaattactgttacactaagaacacgtttgcttggttggaaat gtccgtgtggttcaatttcatgccagtttactagattttggagccgaatcaagagttttagtaattgtttttctgttcaacttttggtgtacgcggca aatcccgaaatttgccgaactcggcaaacagcaaaatatgaaacgtttatcacagaacttgttaggggattttcaaatatatatatattttttaa ttcttggaaaaagcttgtctacctcgaaataccctaaaatcattcaaaaatttaaatattaccattgagagcaaatttacgggcctctgaaatag tggaaaaatgaaaaattaactgaaagttaatacgaaaattttcaagcttgtaaaagattttggttgttccggaaatcggataatcggaaaaca gccacccttgtttctgactaatgagctaagaaattgattggtacttccatagttgatgaatgttatcagtaaaatgggtttggcaatgcttttgttat tccaccgtgatataaactgaaaagcacaactgataagatgaggcacctgagtgtctagacatggcaacggaagtgggcgggattggaattt ttgagacgtggcttaagttgtataaaactgaccggctaaattttaatttcagtgagtttttgagttttccaattctcacccaaattccacattttatgc atcgcctaagttttttttttaattttaattttttttttccagatcccga srp-7

SEQ ID NO: 61 gcttggagagcatctatggcgtcttttcggaatatcaagtcagtcacgaagtcttgtgccaattcctttaccaatcgttcgaatctggatcgagg aatgagcagttcagtagactgttgttgttttcggatttctcgcagagcaactgtaccagaatgaaaaggatatgatcgtactggctgagtgcac gatttgcggcatactcccgaaaggttctttttgccagccattgtttggtagatgtggtgtgaaatggagagattgtaaacccttctataggtgcc aaaggtgagtgggcgtagcttcgaagtcaactgcggtgaaggggcgtggtttcttactattagagaaactgtatcagactaactccgataa agccatagtcagtgaactctcaacatagttaggaagagttactcagattaaataaaatcgtcaaagaacaatcaggccaattctgggctagg catagttcataggcagaacttggtagaggaaatcagagtaaagtaacgatgattttaatttttccgtctgaaaaaagatattgaaagcattttgc cgatcgaacaagacacccaaagtctcatgacgacatcccagaaagagtttcagccaaattcccaacaacagcctaaaggaaaatctgaaa agaacaaaacatttgaacgtgctagagcgtacttgcacatacttgcacatactgtaagtcaacatagaactctactcataagtgtgacaaattt gttacaccaacagtacgaagccaagatttgattaaagacaattgttgtttaaactgcttgataaaaggtcacatggttgcaaagattgccagag cgaacgcaaaaattgctctcgctgtgaaggtggtgaacactgactcagcaaagtcggaaaacatgatatgatttgtcttagtttattggttacc tttatccgaaggtgcatcaagttgcctattggcgttatgttgaagatgactgatataatacattgtaacgatttcgggaaaaatacatatttaaca agataattatttttttcgattttccgaaaaaatggaataaaagaaaaacggacattttcgatatttttcaaaatccaataaagatcagcatttttttgt atttcaatttcaaaaaaaaaatcgaaattaatttttaaaattggaactcgagttcctgctcaatcctggtcaatgattaaattaaattatgctcgta cagtaacttgttatttctgtgtttaattaaaggcgcattactgatgcgatttgggtctctccacgattgcactctgttgtgttatttacttttatttttaaa tattttatttgttattttaattcattttccgcatcatttttttcaaggaatttcattgatatttatgccattcgatttaaatttaatttttttgtcgttatttt acgtcgaacaatgagtcaaacacctaattctggttatgcaacgtggggttacacccttactatagtatatatatagaatacttgcaaaaattgttatattta cacttcgaaaatcagtccgaaaaagacgtaaagcaactttgcctaatgaactttttttaattaataatttcacaaaaattgtgaaacttgttatttct cttgtttttttgcctttgaattttaaatatgtcgaatttttccaactattcagctgttcttgtcgattttttgttaatttcgaaactagttcagtaagaagtgc gaattcagaaagaaaaacaaatcaagagtatttttttatttcgtttttctctcaatttctcttcacttctctcccattttagtgcatgtattttcctcttctct cttcttgttgtctagtttagacaacgcggtcactgttagagagtgcagacggttagcgtaacaaacaaaaaagtagaattcatttttggcgttgg aaaccgcattaaatactgtcctcacagtttccgttcgtcttaatttcaaatctttgctcttg -continued ale-1

SEQ ID NO: 62 ctcgttttcattgttggcttcgattattggattttataaattatggtgatgtagttttgaatgtagacaataaattggaaatgaaatcgatgaaatgct caagtttataaatagcaaaaaaaaaaacatcggtagactttatttgatctactgtgaaaatgttttccggcaaatcggcaaattgccagaattga aaatttccggcaaatcggcaaaatgccagaattgaaatttccggcgaatcggcaaaatgccaaaattgaaatttccggcgaatcggcaaaa tgccagatttgaaatttccgacaattcggcaaattaccacaattgaaaatttccggcaaatcggcaaattgtcagaattgaaaatttcggcaaa tcggcaaattgccagaattgaaaatttcggcaaatcggcgaattgccagaattggaattcccggcaaaatgctagaatttaaattttcggcaa atcggcaaattaccagaattgaaaatttcggcaaatcggcgaattgccagaattgaaatttccggcaaatcgcaaaataagcaaattctataa aaaatatatagcgaaaaaatttcaaaaaggcactgttttaagtgtttccgtcttataaaaaatcccttgaaacattttcggcaaatctgatggcaa accggcaatttgccgaaaatgaaaatttccggcaaatcggcaacatgccgaatttgtcgacaaaaaatttgccaaaaggcaattgatttaact agttttaactaaatttgagtttttcatcgatttcatctcatttcccatcttcctgagttgtattaggcttcacattaccccccttcaaagtacggtagcttt gaagaccattttcattgacacatagctccgggtcgaataatgtatcgttttccaccacctttcgtcaataaatcatttacgtcatatcgtttttttgca agcttatacatatttctgtgtaggcggcaactgagactgataaaaaacgcattttctaaatggtttttgatgttgttggactgtgggaatggact atggaattataacaatctggagagaaaagagtgcccgagagaagcagagaaacaagatgaacgtggcatacgtacacttccacaacagc agccgtcttgtggcctatataaatgaccagattcaagcggccatttatacttttcgatcttcttcttttttcctttgtcttgagattgaaatttgagag ataacgaatccaaatagacaatatgcacttaatttacttgaaaatgagcttaaaactcacaaaaaaaacaaataatttggactttttttgcacattt cctgcaaaatttgatgtttatccagcttgtgatgaataatttttgcacagcaaaatgaattttgtggcaattttaatttcaatcttccatccattagtttt cctggaatttttttgttgaaaattctgatgacttggagatttaatataagctttttagtcgaattcctccgttttagacgtctaactagttaaaaatcgt tcaaatccttttaaattaattagtgagtaaaattcaaaaagttccagaaactttttatagttcattaaaaatgtatttttttcacacctagttttaattaa aactcacgtggtgtcaggatgtctcataagggtttgatctacaaaaaaatgcgggaatttttttggaatcagttgagatctgaactcccgcatttt ttgtagatctacgtagataaagccgatatagcacactctgacaccacgtgaaaacctataaattctcctaattcattttgttaatctgatcccagt gacctctaatcttgatcattttatcaccacgcgtacttctattttgcaaagacctatgatatcagttgtctgacggtcagaaagtctcggaaaaag gcgttgaccgagtaattacaataaaaaaattaacgatataaaacgtcgaatagccaaataggtagatagcgtcagaaaaaccaatcagtgat ttgctccgcccacttttcaaccaatcagaagggtttactgggcggagctatacgttctcaatttggaaaaagttcaaatagtgagattttatctttt tttttttgtagattcatgaataaatttcagactaattcgtgttttcattctcgctaatttagctttattacgcgaacactaggttctgagaatgcgtattg cacaacatatttgacgcgcataatatctcgtagcgaaaactacagtaataattcgaatgattactgtagcgtttgtcacgatttacggggtcgat tatcgaaacggattaaaatcatttagttatctataaaattaagcaagaaaatgaggaaataaaatggaaaatatattcatttaaataatcaaccc cgtaaatcgacacaacagagctacagtagtcatttaaagggttactgtagttttcgctatgagatattttgcgcgtcaaatatgttgtgcaatact caaaaattgtgtgactataataattagctatacaattctgtggtttttttgagcaaaaccgaaaaacgaaaaaaatttcgtttttggcaaaacactcc aaaatcggtatttttcattcaaaaaaccatatttttttacggtttacgccctatttcctacaaacaacagaaattgaacgtggtgtcagagtgtctca ttttggtttgatctacgttgatctacaaaaaatgcgggagaagagacgcagagttctcaactgatttagcatggttaagagtgtgctgacgtca catttttgagcaaaaaaattcccgcatttttttgtagatcaaaccgtaatgggagagcctggcatcacgtggcattagacttttttgagcaagtttga ccaaaatctttttttcttcgatttttcggttttccaaaaaaataacgccaggcttagcctccacctcaatattcttatgtgattgtttccagaacctcttc cccactaaaaca ckb-2

SEQ ID NO: 63 ttactggcatttaaaggaaagaactcggaaaatttatgaagatttgaagaaaggcacttgttaattgatgggttttcattgtgttttattaaatatga agttgtgatagttttaatgtgattaaaataaaatttaaatcaactatcgtgaaaagtttaactacaaaactgtattaaatctgagaacacatacttta taagttgggaaattgttgatcaagtctaagttgaactaatatattcttgatggaatcggaccgaaaaaatcaatttatcttattcagaaaccatctt gagaatgcctacattttggcgcgagaatagcggcagaagagagagctagaacggtaggcattctcatgatctcatggtttttcttatacatttt ctttttttctgccgtttagtttattgatctcaattggtttgttggtctccccctcccccctgtctgcggtcatttagtccaataagtcaacgtgtactaac tgcacctggactttgttcacttcctctataaaatgactttttgattgtcttctttcttattctatatctactttttgaatttgtaaattttatagctacaat ttcactttgaaactgtttggtttttttttcagaaaccatacaattttgtttctccaaac -continued fipr-24

SEQ ID NO: 64 tggaatgggaatgagaagattcggatacgggtacccaatgtggggataagctgtgcaatcactactgtgtagttatgtataaactatgtaaaa ttgaagaaaataaatatttgactacctcaatccatgttgtcacactgtaacaagaaaattaaaatctgataagcttcagctaaaaactcaaaact aagattctcaggaagatatttgggtatttgaactaattttgaccgcttttcatgcacacgcaatggatttctaagtatccaagtatgattatttcata tttcgccacttagaatccagaaatttcaggagcatatttttgtgatacaaaataacgtatttctgttgcattaaacttctgtctaaaactgttcggat ctgaaattgaaattagcatttaactttttgttccaactgaaataatgtattactggacaaaaaaatattaccatgacatcttgcttcttttggagaata ataaaataccttcagttatagatttaggtaacaaataccatatttattcacacaagttgatgaaactcgttcgatattttaaattaaactgcctttaa atatctattagccagttgttgtatggtcctatgcacacactatcttgtatctatagtttaatatatgcggcctatattgtgacatatattcttcccgttt gctctgttgttctccccttcctgtataatgggagattgtaaatgagagttgttctggtcccaatacctagccactgagaaccctcctcttctatcta ctactcatttatattatcgtcattatttttatttttatttatacatatagtgggcttatcaacatatatgagggtaaaatacttataattaatcagcagttc agaagaaaaaacaatgaatgataaggaaatttttagagaacggatagaaaagggatcttttgatttcttcagtgacactgttatcattttcgaaa attgggtatgacaatggagacgccccacaatggaaataacttcaaggttatccatatatactgcatacatatccacaatattatgaggtttctct aggaaactgaaagaatcctagtgtttgaatgtgttgagcatattaattttaagaagccaagaaaccataacttctgataatgactgatatctagg ctgtcacgagggttgcttaaagtgttacagttgtgccagtaatattaatagctcaatttctacaacatacaaaccattatggtaccctacaaaca ctacaaatggtttgaaaccttgttgtttattgtttttactgaactcttatccacctgatacctaaaaaacgtcatgttaagagaacaacaccgccca ttttgaatcctttataaccactgggagatgaccggatttccaagtactcgtagttctaaaaacctttaaaaacccaaaaaaaag arl-7

SEQ ID NO: 65 catgttttctctgcaaaaaaacaatcgtaattgcataacatctttcgaactcgatagtctcccaaaaaattcctccaaatctttactgcatttgcttg taaagatttacctatttttctaaactgctgtgttcctgtattttcactctacctgtttcgtttatttatttatttaagcatcaagtttattgatctctaat aaattctcgggaaattcgtgtcttaattattaatattatagttattcttgccagggaaagttacgtttccttatcaaacacctgttgcgaaaccagaaaa gggcgggtctgactaagtgaacaaatatttcgtaataactttcttccaacagaaattaaaacacgcaaaaaacggccaactcactagctgga acgtggagccccatgataactccatgataaaataactctgattgtcgacatagcttcaagaatatcgtattctgcattttcaaaaagtatttttcgt tcaaa

F07A11.2

SEQ ID NO: 66 gcacaagccgccgtgagactcgacgataccacaaatttcaacgatttcttcacaagcttcaataatgacctcgggctcgatcaggaatggatgg ttttcatcaaagctttctacgcagaactcaatctcaaagtcgaataatttttatttcattgtttttttgtttgatacctgttttgattaccatttttttatca ctatatttctgacttctttctcatttttttttaaatttccggtcgatctttcacagacacgattgtatccgtgcagtatttgaaaataacaaatttttctgat ttctgtgggtttcacgtgaagatcttcttcaagaagaggtcatcagattgcggaagatctatattaccgatctgacgcaagactaccatgtatat ttggaaaggaaaaattttctgtgcagaggttgatggtttaaattttgatttagatattttcttcatttaatttgaaaatttccatgcctgaaaatatcct cagtgaggattctcacctaccgtatacttaaaggcgcacacctgtctcaaccggagcgttgcgagacccgcggcatcaaactacacactgt gttttgatgatctttcgatcgttctcgaaaaaagaaagagcagagttcattaaaacaaatggcggcaaaatgtctataaaggcgagtcgttctc ttcattatcttttgattttcgatgtgttctccttattgttttgttcgttgaccccttatctgcattctcaccgctacgcaacgtatatttaacgtcagctttt tcgcagaaaattttttctatattctcatgcaaatttactgttctcaatgctggacgtgtcgcttgtgctttgatctcaaatctaacattttcccttcaaat attttatatctgcaacggtggggcagaaatttaaaagttgacctttgtcagccaactgctatcagttatcagttggccggagatctttctattttca ctttcttgcaacgtattcagacatttttttgatgaatcggttcacagaattttcgtcctgatgttggtcagtgatgcgccagccggaaattagaacc gtatgccgttatcaatttttcaaaggctaaaaagttatgaggtgtatttattgttttaacacctgacctgctagtaggaaggaaattaattttatgttt aaattgaaatgaaagagtcgagctccacgtgtcgtctccctagtttctctattcctcttcttctccgcctatctctcggcttctctcctttcgcgctc ctctcacaattcctcctaatcgtgctgtttttggggtggtccaacacggcaaaaaaaggcagcaaaaagtgtctgccgtctcgtgcctctttctta ttgaaagggcacgagagaatagtatcaagaggctcctcgttcgggccgttgaagatggtatctggtgcttcggcggagacgggaggagc ggccgtttctcgggtcatcacagcccattccttctaatgtttacactgaacttgtcgcaatccctcctctaaatctcattcatccattcattcatatt -continued cgtgttatgtgttcgcttttacataatttccattttcaccacgtttctcctcaaatttgcattatttaaatctctgccttttcataaacatttataattttc agggtatcacctatactaaccatccaaa

C04F12.1

SEQ ID NO: 67 aggcaaacatcacgtttccgatatcaaaagacattgaataaaagaaaaccaatagaatgtaaactattaaagtgacaatttcagtgaaatttat caaaatacgaaaataataaaattaaaaattagcgccagctaactatttagcagagcaaatacgttttgacccaatataaaaacaataatatgaa aaaaaaaattaaaataaagttttaccaaatcgatattggcaaaacatcttgtttttgaggctccatatctctgcaggaaaaaatcgcactaaaaa gtgatcaactagaaacttgttaaacacaatgtaatctaaaacttttcagttgaacactattttgtaaaaaatttcgttgccaagatatagatctttaa ctatttagaatattcaaaaataatgaagctcaaatcaattggttccaactcggcaacgaaatttttttacaaaaaagtgttcaactgaaatgttttag atcacattgtgtttaacaagtttctagttgatcactttttagtgcgatttttttcctgcagagatatggagcctcaaaaacaagatgttttgccaatat cgatttggtaaaacgtcttgataaggcatcagaatcaatgattcggtcattgaaaataatgaaaaataggttatttgtgacactctaaaatatttc atgcatttttttaaaaaatttcaaaaaaaaaatttttcgatcaaatttttctcatggtggagaaaaaagtgacaattttcgaaaaaaaattaaaatttctga aaagtttccagggtaattatggttcaattaaaaagcaaaaaaaattatgtaaaaccctcaaaaaaaatgttctaaatacttgtttcccgttctgaaaa ttttgtataaaaaaggccaaaagttaaaccatgtatgggaaccgaacccacaaacttctgctcaagaggcgaacgcgttcaccactcgacc accgaaccgatgttttcgcccttccaccattgtggtgagacttctgttggcgccagagacaaaaatccactgttaaccataggaaatgcactg atttcagtgtagaatttcagacgtaaaaatttcagatttccagcccgaacgggcaaaaatttcagtcatattcttatagtagagaatgtcagcttt ccgatacaatatttttttttgaatatcgctccatttattctggtcattccctagtcagttgcctgcccgtggcggaggaagaacataataggagga tacgcagagatgcagaaaaaaaaacttccgtttgttggtaggtagtaatttctcctttttgatctccaaagatgttgggaaattcgccttttggaatg ttttatggcgcactttttaacagttaaatacatagccacactttctatagactaaacaagtactcttgacatatgtcattcatcatgtactctttagatt ttccagccttaccaacctcctccacagtttatctcattgattgtactctttgaaggaggaccattggttctgactttttttgaccttatactgattcaaa atgtcatcaaagacacgagcttcgtaatgagacttcagaaaaaaaatttctgaacatttttatagcggttcaaaaattctaggaaatttagcaaatt ttagctatagctataggctttacaaaaccttcaatttattttttttggtcagatacacgatctcatttcattttgctgattaagattcatttgaagctgag aggtaaacaaaaatcgccggaaattgtaaaaatgccagaacctttatacaacctgtatgaaggttcaccttacaattatatctgtgtttttcactt gtttagaggagtggtaggtggaagacattaaagtgtcgttctcgtagaactgttgtttggactgatagcttttaaatacgactttttttaaaaacttt ttgagattatacaactaattgcaccatcatttattttttgccgatgtgcaactttcatattgtttttttctcctcactttctccgttgtccttgttcataacac aatttgcaaatcacattgaaatttcagatttccgattctcgaagctttactaacatctccaccactaaccaagcctcaac hke-4.1

SEQ ID NO: 68 aactttttgcaattcctaaatacttaccattattttttgcccaatcaggttaatgatctctatcgtgtagtttttccccttttagttccagttctgctgtgata tttatttatttttgcgaatacatttcaattcctaactttttttcggaatacaaaccagtaactcataaaatgttcgatttatactcacatccgcgcgaac acttcagtgccgggtgttataacacgtcagcgtttcgccagatgatgcaattggcgtttttccttggagaacaaatagcctcgtagagacgca ttttatttccacactgcattggactcaattggtggtgtatttgctttgaaggtgaatttaaattcagactttttttttcgaaacttgcgcagaaaattgt gaatttttcgatttttatagtggaaaataggttttttttcaaaatatttttattgaaaattaaaatgtttgctttctatgctctattattgccgaagaaatca attttaatgaaatattcaaagaaatcgcggaaaattttcaaaaaatttccacgattttattttgtacgcaatcgcatctgcataccgtacccggttt cgaatttcgaacttttcgaagcttttcttgaatttttttctgctttccaattagaattaaaagtgtaatttaatcaaattctagtaaatttcaaacaaattt gggattaaatgttaaattttattaacattttcaggctttaaaaaaaatatttcaaagttttgtgtcaaagtctgcaaacactctcgaataccgtaacctt gcatctttttttaatttttttgttttctttatttttatcactcctatacttttttctataatttaaagcaattttataatatatttttacagaa

F22E5.6

SEQ ID NO: 69 tgctagcggtcaccactatcgactgagctatctgcccctaagaaagtttaaaaaacttaccgattttgagttccaacatcattttctcgctattttt gataacgttttggttagcattgtactccggcagtattggtaggtcattctcgttgtttggagtctttatttcagactccacgacggctggagcaac attctgaattatatttttttaattattgttatactttttagcaaaaaactgacatttgaaatagatctactgttgcaaataatgtctggcaacggatccca tctctcacttggcctgcctgagcctacatccaatcttgcaattgcttgctcacaatctctcactaatttcaccaatccgtaaaatctggcttcccg gagcaactgatgtcgggttctgaaagttttatttaatttataaaactttaaacttctagcttaaaacatctaccatttcctgaatttcaggcaaattct -continued tgaagtatccatcgaactttgttagagtcgctttagaagtgacaaattccttgccacctacattgagccggagcatttactttcagaaacaataa cagtttgagtttatctggaatttgttagataactttaggtagatttgaaattttggtagatcggtttcatcaaatttatcaatgtcataaataaacttt gtagctataaattttaaaatagctttttttacactttattcaaggaaacactgagaaatagctgcgaaaacaaaaaaaaacatttgaggggaga acctagacgcaggagagaaagaacgtagaatctactagaaaaagtgtctgcgtctcttcaaaaaacaaatttaaacttagcaagatgacca ccacagcaaaaatgaaaaagaggaacgcggagggacagggacagggttcagtgagaaaaaaattagaaattttggaaaaatgagataa tttttaaactttttgcagtattccaaagtttttcggaaaattgagacaaaaattttaatcaaacttcccatgaaaatgacagaaaattttaaaattga aattaaatgaaatttctttattttctggattttaggagtttctggaaatttcttagcataagcataagcctaactacaaactaaaaacttcaaactac caactgaatacaattaattacctcatgatttgttcccagcagccgtaacatgttaaaaactctatgggtcctgtgagatgtcggccgctctaac tctgcacattgcagagattttcagacagtgtgtgaccaattttaggctgaaaatctgccgactgtactctttttggaaatgttttgtttcgaaattttt tactcactctcactataactccaactcacctggttgcgaaattcagcgcttttcaacgtaatctaaaatgaaaaatattcattccatcactcctcca actccccatttttgtttgaaattctctgaaa pdi-2

SEQ ID NO: 70 aagaacgccgacgacaacaacaaacattttcatcgggagccctggaaaatgacgaatgtatgcattaccattgttgaaatttggactggaag cgcaatggatgaaaaaaccacgctatttcgaagctcatttctgatgctggggcacaacacaaaattaaatgagacgaggagggggagaag ggatggagagcatgcatgttttgttgttcactttcgaaaaaatgtatcgatttttttctagcaaatgtttgaagtaaataacaactttcaaatgtgata attagttatcaattcagtcagtttatcaaaaaaaagtacgtcattagcataactttgccgtatttgcatgtctaggaaattttagaaactagaattgc taaaaagtggtttaaaagttgcgggacgccgaaaattggctgagaaattgtcaaaaatttccaagtgacggaaaaccgtatgttattgtgatta gtaagacgatttcgcaattttatatatattttgtcacaaatctgaaatcactcgtgctattttaggtgtaaaagtcacatgttattgcacaaacacga gcagaaaatgaattaaaattaccttctcggtttttcagacattgtcttcaactttgtctaggtatttcgaaatttcaaaaaaactccacctgaccca caaatcaatactagtaagttagtaaacacaacagtatgggaattggttgatatgtacgttgcgagacttgtttgtgcttatctttttcccctctctac ttaacaatcaaataacctgcaaaacactatggatttttctcttcagtttggggcaattcttccagaaaaccaccaaaaaagaccgcaattttgct aacggtcttgttcacactggtagataagataacattgcgtaggtcgatcctaccgatcaaacgggagatatatgggggggagtaggagagaa attacgggaagaaggctatcgagcggccttgacacggtgcttgactttttggcgaaacgtatcagttgacctctattatttgggctatacagag atgaggtatgatggacagaaacagaaaaacacacacaaagggtattgatgagaatcatagacggtgacaacgccaattcaatgagcagta gatgtgcaggagacgtgtctcgttcagttggaaacgaaggcgagacgtgaaaagagtgcgtggttgcgagagacgcagtgatagagac aaactggataggttatgagaacgagaaccactcggactgaggccattcgtagaatgaagaatggaagttgtatctgtcttttaatagactcaa atgaaactgaagaaaaaaagtacaaaacataagacactatatattttttttcatattgaaaaagagtttgcaaatttcttgaaattcaaaaattct gtttttcgtgacaacactttttgcttactcatttgtaaaattttaacgtgggctattgtttttgtgtttaaatatttatactacattttttgaaaattatta ttttcacattgccacgtgaactcaaaatttattcatgcaaatttagaataaaatctgttcaactaagcctatacgcctcgtgcagaagtccaaatttga aaggtaaacctaaacctaaatttgatcatgaacactgagcctgaaagcctgtaaaccataggcaaagcctaaaaacagcttacaaacctttct ctgaaattatgtctgaatacgtaagtttattatatgaactaagctttacagctaaatctatgtttgcaggctcagttttgaacgttaataactttcgaa tccacatggaaatttagatataattgaataaaaaagtcctcgttaatatttgaaaaaaaatgttgtcaatttacgaatcctttttttttcgcctaaaaa ggagaatgtcaaaagtactaaataaaaaaacaaaacattcaagagcaactaagcagtttttccgaaatttttttccaaagttccaaagtcaacct taaccttaagctgcagaatttctgatgtttaccagctactacgaaacaaaaacgattctcatagatgatttcccattttcgcacacaaaatgttgg catcacaaacaaagtgagcacaagtatggagagagatttgagagcacagacatcaaagaataaactatgttctttgttctttttaaactactttg aaaaaaaacaaatgaatttacatatttaaaatgttgcaattgcaatttcatgatggaaatattggaaaatgtctataaaataacgcagacagtgc caatcaaaagcttttctcatctacccagtcggttgagtgaatgaaaggaaacatataatatcaaagctggcgtgccaattcctttttgtgctcgg ctgcattatttacactgccggtgtttccgcgctccttctcatcgacataatttccctcatttcctctcagtcttccgcgcagttccatccatcgcaat ccgccttcttgcctaaatttgtctgacccaatactctaactaactttcatttatgtccaatgcattattctctctgtaggtgacccagtgtccttccttt tttctctctcaagatgtgagacccccccccccttttctcctcaacggcgaggggctacgtgagtttccgctgtgtgcgacgcgtccttgcccg -continued ctcttcccaaactgcacggccaatggggtgccgggaggcggggtaggggcgggccaatcgacgcgttccacgactaagtaagcgtgg acaccccatcgtctgcagaagaggacactctcgatccattcgctattcatcgtg pdi-3

SEQ ID NO: 71 gaacacgttgcatcgataaatcgagaatattctcgaagcgcaaaaagaaatttcgcaactatttcagaccgaataatgtaataatgtaatggg tctcttcgatagaaaataaacgaagataaacgaagacacaattcttcctgacgcgcgagcttcaatatgcacgtgatgactaatttggtttcca tggtgatctttttgttccttttatcgattcaaatttacaataaaaataagaaattaaagttctaaatggcgctccaatcaatttgccttccaatttaac gtcgattccttctatatcaggtcataaaatgaataaaaaacaatgatcaataaaatgatgcggtagttgcgtaaatcgacacatgatggtcgcc tcttccgtgcgagacccattgggcggagttctcacaagaatgaggccaatcggcacacaacacgcgtgcgacaggcagtgaacgacgtg tttttggctcagttcctaccaatccctggtgtacacacgagcgccacgtggaccttaacaattcgggtctatttttatgcttctgctctgcattttct ggattattagtaataatatcattaaaagtgatataacgctccccgagtctatataaaatttctcctccatacaacacatgtttttggctttcttcttct aagcttaaaatttatagttatttactaactgtattttccacttattaaagataatttttgaaaagtgtttgtaaatacttaaaattgaacccgaaacaat ctgtatttgtccattcacatgtgattcacagaaaagaatgaaaataaatgcgaaaaaaaaataaataaagtaaaggcgcattgattttaccgct cgcggtatctcgccacgaaaacacgtttcgcgtcaagcggctcacgttttcgatgcgatcgcggtttgttaattgcgaaaacaccttcccttct cttcaatcgttcgctcaatttctagaaaatatttctgaataatctgaaaacctctaatcttgtttcttagtttttaactttttgtcggtgttcccgataatc tctcgccctctaaactcactcgatcgattgtcgtttataggtaaagtttttaggta itr-1

SEQ ID NO: 72 aataaaagatgtgatggtcaatttaggatagtaaaagatgacaggtggattgagggaaaagagacaggttacttctgttgagtggacacatt gcaacccccggccaccaccgccacggacacgccgcccacttttgcggtgtgaggtgcgaaactgtcttccgacagatttgtaaatattacg aggaagttgatgtaatacggaagaggtccactggatttatgtgaatgaagaatcaaaagattgtaaaatgtttagatatgatgagctacaggg tcaaaggtgatttgatacacgattttcgagcagaaatgctgacttttcgaaatctcattgttgtttaatcaatcacgggatgtacgaaagggatct tggttttggatttttgaaaatcaaaatattacaggaaaatataatgcaaaactagtacagactgtgaaaatgtttctaaccttgatttctgctccgt ccaactgtgaaattacattgtgtgtcaatttcaaaaacggtacgtgattttttagttctggtttttaagtgaactttatgtatatgagctctgaaaaca ggaaaataagggaaaattaataaggtagtcagaatgaaatattgcaattcgaacataagcatttagtttgaaacaacccgtatttccccttattag ttttgtagcttctagtttgtcatgcactgattttccgacagaccggctatactctgtgggaatttccgcaaaaattaaatttaaaattaatagatgag atgtggtatgtagttttaaaaaagtcgatggattcagaaaatgctcagaaaaatccgcgcattaatttccaaaactatcacatttcagaaaagtatca aacatcatatttttggagtccaatactacttcttcatttctttttttttttttcttttccactagttttacaataaaatatattgttttgtcctaatgaagca catttcattttgtaatgtttttaactttctactgtaggatattctattccgtaatcgtacaaatcttctttctctcccaaatttaggctgcgccctgtttc aaagctctgctaatagtacgcaaaacaaatgtattcgctaactctttcgctcatttcggtataagtgtcacttggagatctcttcgtctctcgcaa cccgtatttgtattgtttatcttccaaaatggtagtcgactgctcatatgaattgaattactagcgggatatgaaagagacatgagatttataaaa agtaactgaatatttcaacttttgaaattgaacttgtatcattttcgaaactaaaatggaaaaacaggaacgatattacttcatttttccacttaaag atggagtagcaaaatttgggtgattgtttttagaatcaaaattgatcctaaatacctattgagacaacttgaaaatgtctcaaaaattattgtatta ggttagtcattctctaaaagaaaacgggcaacccttcaagtattaaatcatttttgagcttgaaaagagagaacattgttcattaaaattcatgttt gggctcctaaatctacaaaaaaatatcacatttatattttcggcaattctgatttcctgtaatcgacaatttcagcgattgccgaaatcgtcgaaaa gtcgattaccgaacggcaattgctgcatgctatgtatcacaccgtttcagcgttgtgtatcgtatttgttcaaagataattttcttgtaaatctcgat gttattgactactgcagctaatacatttgaattcccattaattcctttaatttgataagtgtgacttggttcccgttgcccaccatcttttgttcctttcc tcctatcttcaaatcaaacgcatctggaatctatttttttcattgttgtctgtctaccgatgccaacgatctgacctttcttaattggtattcgcgctca ttttgacattgtgtcaacttcaactatttgcgcgggtttacctgcaaaaaagtaaacaagaaaaatggagatgaaatgaaagaatttccaatag aaatttgttgttgaaaactctctgaaccatgagaccgtccaagacgttaacatcaaatcttttcaattcagaaacgtttcctctttttctccttttgtg acacgtttcctccgttctttttttggagagtcactatatttttaatacgattttgctttacaatttctttttttaaacttttattgattttgtgcttcttattt tccatttttcataaaaagtattccaga -continued

T05E11.3

SEQ ID NO: 73 gtcgcgaaaggtttgaattcccaactggaaaaactgagattaagaaatggaggtatattgcctgattgagatgagaaaccggtttatgagac ggataaacaagtaagtttgctgagtaacgatcacaaatttcacaaattctcaagacaagtgagatgattaatttctataaggattaatttagatg atccgaacattacttgagtgactgttataatagaaagactgaaaaatcgtcttttaaattaacatattccatattgctggatccggcaaacaaaa acaatgttccaggacactcactccacgtgttctgagctgtcgtctcggtcgttgattggctgattccgcctctgtttgcaactagtaacgcgcc gcagtttgcagttttcagtgaaggacaacgtgtttgcaagagacgcagacactgtgcggcacttgcaaattggggcgggacttttagggac acgtcgagaaggggtgagccccggcgaaagaaagcaaacaagcggagagaaaaggggagtaattgaccgttggaaagacacctcatt ccatttattctcggtcgttaggaagagacggcgatgagattccttttggtgggcttcgtcgcccttctggctgtttcaggtatgtctttttattgatt ttcagagcttagtgagctttaaatagaaaaccgtagttttgaaattgtaaaaaaaatttttaagcttaaatgtacgctgaaaatattaaaactgtgt tcacagaataaaaacattaggctttatttttttcattctgtgcatacacgccacgcagtttttgaattcacgtttttattcccaacaatcatcacttttcag ZK632.6 (cnx-1)

SEQ ID NO: 74 tctgcggttctgaaaatattaaaaccaatgatggaaaagaatttattcgggataaggattttttgacaaacggacatatggcatatcctaatgtga gcagaggagctgtggtcggagcaaccgaccgcaccggctcacttctgctgtgattcggctcggcgccacgaaaagagtaagagagacg tgacgacggcaatagatgaatcgaaatctatggatgcaagaaacctcttttcaaatcattcgaacggttagaattgtgcaaacacggcgacg cacaaacgcacatatcgtggggacacgtgaacgatggccgacttgagaagaggaagaataacagacggcgggagagacgaggaaag ggcacaaaactgagatgatggtggtcgcaggcgctgagcgtgatctcttctgttctatttcagacacccacgggattgtattcaacaacattttg ttgtttctactgatcggatgggatgattgtaattaaccactatttatgtttctcacgaattgtgacactaaatgtgaaaaccaatagaaaacataat cgtatttcttcaaatctgatattaaacgggtagttctaattatgaaaatattgccccacgacgaagaattaatattaataatatttcttatttttcacct gcacagacactatagttatcgatgatcccagttttatttggtctaaaaataaaatttgaacttctgagggattgttgagcgacattgatatggaag aagcgctatcgataaaaatttctatcgttccatgacaaccaatcacatgttcaaatgactgaatgccaaagaaaacctcgaaagcgaaccgg tttttcttccggtgaccgtttagattttataaaatcttttagttagctgaaaatgaaatttattgcagctccgtgagaaaaataatcagatatacgca gaaatgactgagggacgatacgaaaatgcgaagaatctgccttgcaagaggacagatgtcggtactcaacacgtacccaacacagtctcc tataggattgacaatttatcttcagagcagaccggaataatattaacaacaaaaagctaaacttaaaaaccgaaacgaaagcaattcaaactt aaaatgaaaactaaaataaaaagcaaaaaccgaatgctgaaaaaaaaattgtctaccgtacacctacagtaagattctgcatatttgcgtgacagtgt ttgcacatgtttattcgaaaaatgtcattgttttttttttcgtttttactttttttcgccaatcatttagctttaccctagattttcattcttattttgttttc caaatcaatcaataaacaataaatttttgtgaaaatttacctgcaaacctccattaaaatttgcaaacccggcaaactgtcacagagagaatgaa aaattgattgaaaataataaaactgcttggccagtttgaaccgattttaacaattaagcttaattttttttgaagtatttgcatacacaccatgcagtt ttttttaaagttttaccgtaaatccctactgagctaataaattaaaaaaatttcgattaaaacaagcatttatcacgagttctaaactgatatgagac atatttaatttattccgattcacttcaactgatgaaaacttttgttcaaattctcaaatatatttcaatcgtatcacattttttttcggcagctgcagcga atttttcctttcatgagccatgggcaacggcttaattacaccaacagccgttgtcggtgtttggatgtattgccctaaatgaccgcccgtacgtt gtcctctccatgcaacgacgctgaatattcttctgctctcacactcgtatactagttgtggttgaggcgcctcgatggacagcatgagagaga gtgtatcctataataagacgtagacagacgcgctctagcaaattctttaccgcagcactccacagcgttcgtcagtccgccttgtttcacgttg tcgattgcagacacaatgcccctcattttctattcacttctcattgtattctatctgtatgtgcatagtaacttgttttacagcgagtaatctcaaaaa tcgatatatttttccttttcataatattgttctgttaccttggtaccctcattattatttttttgaatttaggtaacc Y38A10A.5 (crt-1)

SEQ ID NO: 75 aagtgatgttttggcaattggaaaaagctagactaggaatgaggataaattatgacatcattaggacttgtaatttagaaattacacggaggcaaac cgtaatgcgtttttttaaaataatattttcttaatttttttccttttaatttctgctcaagtttgtttgttggcaaaataaattatttaaaacttctcaaaac tatttaaataggtttttttgaaaggatgtgaaattccttatggaattttagatgatcttcaatttgaaaactgttggcagagtatcgccagtgaaaaat ttttctaaacaaaataactcaaaaaaaatcagatctttcaaagttgtcagtagaagtttttggtaaattgccaaatgttccaaaaatgtggacgttt tgaaaatgttgagcatttcagatttaagctactgcaatcttcaaataaaaatatttgaaacatagctagaatatatgaatcgcaaaaagagttttg -continued gtaaattggtatatttttcacaactgtggtattggtctcattcagttatacatctttattcttaactttgatataccgtactctaaataaactttcctatta caaccacacttttaaatttcatatgttttcactcttcagaggtcaaaaattggaagaaattattaacgaaaaaaataaaaaaattagaaattaattatt atgtttttatgttcaatttacgtttcaattttcgtatttgaaacttggcaatttaccaaagctttcactataaattttttacttttttctacaaaattta gtgtgttttactacgttatcctgtcattttagactataataagtgagtacagtattgttttcatttagttcatatttctatgttctattataattgtctgta tctgatattcgatttttttgaatgaacatgagttttaaagtatatcaaagttaaaatacggatgtatagctaaaggaggcagtaacacatatttgaaaactt tgatttcatgttctcttccttcttttcccacggcgttatgtttgaccacagaagcatctattttttggaatcaatataatttttttcggtgcttttagcaaat aatataaagtttgggaactacctctaatgttcattttcatttttgatattctcccttgacatatcaaaatatttcgagcagtatgcatttccttatcatttt tcaactgtatttcctgattttagcttttcatattaatcaagtaggttcatggtttcaataaattgtgggttaattatagatctgcctaatcttcaagcca atgccttctacggagtattgccagtgtggatttagtttgaaaagtattctaataaaatactccaaaattttaagttagttttggcaaattgccaacat ttggacttttttgagctatttccagcattgccacaggaactgtcagaatgtttgaatacaaacagttgaaaatataaaaattgtagaaaattgtttta ggtctactttcaaaattttatagggttttattataactaaaattattatgactaatttttcaccataaaaaattaattgcaaataaaaaaatttcaaaaatg ttttgaaacgttttactatttatttggacatttaagcactaacgtgttcaaagctgaaatttcaaaacgtcataactttgctgaaacttgacttgggc agctaaatttttcggagagatcataactaacagtcttctatcggatattcaacatgagaaccccaaacctacgggccccttcaaagatttccctt gtgaatgggcaattttaaataatctctccatttacgatatttcaccttcaaataaacaatgaattattctagattacttgttgtcattcagtcaagata ttctcaagtattccaagttctccattgtttaatgatttgctccaattctatccaatttccctttgttcgctgctttagtcccgccaccaccccctgtgc aaagagataacgtgtgagtgaatctaatagccagaatctggaaatatatatatgtttagaatcacaaaaggaaaatgtgcaggcggggagat caaaatcgaaactgtatttgtgtggaacaatgcaactattgagagaaacatgaagcatatggactacgagttgagtaggcttcaaaagtattc aggaatctcaaccaacgagttttgcccagaaattaccaagaaaccagtgtaagtttcattttatttttttggatttagttagatttttttaaataatcaa aaaccgatttcttgccgatgtcatactgtagacactgtgagaagtaggactacctcaatattgataagtgcctacctatgtgcctagaaggca ggtgtggcttgcattgaacttaacagtagacgtaggtctcttgaagttttgcttccaggcaggcaggtaggcatttgaataatttaaagctatag taaggagtacggtaaattacaatatcatttcgtgataaatttcaggcaagatcgaaatcattttgcaatgctctacacctttccttatattacgtca acttgtgatcgtgtcagactttttgttcgaaatgcagtttcctggagttcagaggtctaaaaatattcctgaaaaaattataattctagatgttcag gtgaaccgagcccgagtagcatgcgaatgtgaaaaaaattgtggaaatgacgcgtggctaacgaggtacttctcgtcgccgatctttctcttg accaggaccgaataaatatttgaaaatgcacttattgtttgttctcaatgccgaattgtttacaatgtaccttttggtaaagaggaactcgtttgta ctggccagctaataaaatattcacattattcttcatactatgttttcatatagaatttatcaattttataatttagatgataacgagtgctgtactcctg gagtccaccaggacttgataagagaattgaagcaccacttttataatgagcagtactaatttcgaatctggaaatgatatttcagaaacaatcc aggaaacaccagaaaaaatatcaccactttgaaaaatatgtgcatttattcaattatgctcaaatttcagctttggctcacgagtgatacggtcaa ccacaattttctccagagtacgcaatttacgcaaacaccaaacgatggcgccaaagcgccattcaaattttattcatccgtttcagcctttttca gtcttcttgtctctcattttcgccattttcattgttttatttacacaaacggtcgtttaaaatgtagtttccatctttttccgatggttcatcatttttgtc atgcgtcttttgtgaaactggttttgcaaaacgaagcaaaaaaatggataactgtgtcaagggcgatttttcgattcgtcatgtccacataaacgcg ataatgtgtttttatcgttggtttcattcagaaattggttgataaatacattctactacattctggctgtgtgatccaattttttaaatccgaaagtctag aaatttagtgcaaaataagcatggaaagttctaaaccccttaaagaatactgatctcagctgttttctgttcttttcaatcagattcccaattgcgat aatatcaaaaagccctctgctggactgctgtccacccgcaagggcattatttccttatcccaaaatgctctccgtctgcatctcttcaactcact cactctctcgctctcttcgcagtgcgaggccgacacgcaacgtggcctctcatcagacacgctccgcctattctcaatgtgtggcgaccgcc gattggccagtcgctgacgtggaccaatagatacgcggcacctcgagccgtgtcagccacgcaagacacacgtcgacttactccattgtc gtagcagacgagctcagttcaacatcatcagtttcagttttgctcttgttcggtttcatttctagtctttcttctctgaaattctcgaattttattctttg gtatattctcattcaatttatctcttctttttccgattcatatgtttaattgttatatttactttttaatttcagattcaacttggtgtcgttttatcgaaa aacgaa hsp-3

SEQ ID NO: 76 ttcactccttgtctgcaacaaacgaataatagaatcaatagatggcaaaaatttgaaaacagcgtacagtcaagataagggtaatgtatgttttt gtcgtcaacctctaaacgtcaaactgaaaacttaaagggcggcggttggttaaatggcgggcgtgtagtactaaaaacaaaggtttgagta -continued agtgcgccccattgataacaaggatctgaagaagtcttcttcggataatggaggtcagttctgatgggaaaatcgagaaatcgagttttttttat ttgattgcaagctaatcacatttaaaacgcttacatgggaaagttggcgtttgaaaatcgaatgtaatatacattttttgattttctgattacttttga gctagcattttaccatttatatgaaaaataaaaaactaagttgcgatttggatgtggtcaattacccatttataaaactgaaaagtatgtttatttca gttcaaaaacattagaattttagaacccttctagctaattcgacccttctccaagccatgcaataacctttgatgaatcttatctcaaccaattcac attgcagagattcttatctccagcataacgtatctccaatcgctttctcccccatcgtccaacacagccgctattatcggccaaagtactacgtg tctcgagtccgatcctgacctactttttatgtgtactttagttcaattgcgtctggttggatttgaatttgttgattcccaaataggagagattctgg ataatttcttcgaaagcgttacaaaatgcgcagaattttgtgtatttttaaaacagttgattttagtttttggtttaaatatctagtgtatctgcttttag caacaaaaaatgattctaaaactcgtttctttctaaatcatgtcaccacttatacacttggccttttccgatttttctttctctctttctatagctctttctt actctcacctgccgtttccataacagtgctctctaaatttggtataaaacacgcagcgcaaccgcaacgcaacctagtaactgacgtgtccca cggacaccctccactcacgacactctcgcacacaaacgcgcacacagggccacacgcggcgctcgccgattggccgaatgactctgcg tctctgcgcgctgcacacggtgagccttcgctgtgctgacgttgccttgtcctatcgtcctaggccacgtcgacgattcggcagttcgttcctt cgctctctccctctcgatgcgctcgtcgatccgtcagtttgctctcccttcaccactcccatcggttgacggtaccatttcggcctacagtcgac cttgagcattcgggcggtctatcgggagagacgacctacaaacagaagcagtcctaggttttcctgcattccatttctctcaccgactggcct tgtttcggttctttctttatctctttcttctcagcaattcaacaagtcgtttcatattttaggcctaataataattttatttttacaggaaaataaatcaaa cacaaagt xbp-1

SEQ ID NO: 77 gccatttggtttgacaccacacttcacaaaaccaaagtcacaaatcatagaagttgagggaaatctttctattcgatggctttcagatctagtctt aaatagcgacaatatttgttcaaaaagaaacagaatcgttcgaaattctgatatttatcttaaatcaaagcgttatttggcttttttttttaaagatct ctattaacagaaacaccacgatgacgcgtgagtttataacttacaattggcaacaagaatagtgaataaaactgacaaggctacacttgacg ggcagaccatctcggaagacgacgaaacggacagaatgatctagaagagtctcgtctgcgggatttcgactcagcgtcgtcatcccttcc ggaacctccatatcaaatagcaccgtttctcgcttctccgcctccccaggcactattatgagctgttgtgtgtgtgcaagctcacatcatacaa gaaatctcgaattcccactaataatagacaatgagactgatgttttgattgagttgagatcgtttgattagtcagaatagacggaaattggatgg accaacagaaaaagagaggaacgcgaatcgaaaaatataactgtggaaatcggcaaaaaaaaagaatgataacaaaagggaaaagcg cgtggcatattcttccaacaaaatatgtgtttttttggcgaccgactgtgcaactctctcatcatttatattctacacaaaaataattcggaatatcc aaaaacatgcataaagtcgcggaaatgttacgaatgtcaatccgaaaacagaattgtgagtttacatgaatatatactcaaatctacttgaata atgctgaaatgtgtattccaatacactttttaatctcacaaaattcagtaaataatctcacactggagagtcaaagagttctacagctaaatttct catttacgaatcaaattagagttttaaagcgttccttcgtattaatatcagtgtaaaaaaataattaagacaaaaaatatttcaaaaaaccagaaa aagcgaaaaaatgaaaaaaaaaaaagaatgacaaaaacaaagcgaaactttttctcagactacggtagatcttgttgtgtgcagcgtgtttg cacagattgtcgaccgtacccggaactttttatttgaaatattttcaaaaaaatatattttctctttccaaattattcacatttttcgatattttaatcgt ttcttcatggttttgctgtttggaaaaagacgttcatcacagggtaagatttataattgtttaattctcagcaattaatttccatgagcagcgaacg actaattgtcaaaattgagcgtgttttatattgattctgtctctgtgctattccatctttcctgcctaaaatgtatggcttttctcgttacatttctccaat actttccaaagagacgcagacataaacgaatgtttgccctattgcgaaagaagtaaatgaatcacccttccttttccctttttccactatttttat tttttatttttgaagcaacatcggcgacc cdc-48.1

SEQ ID NO: 78 tccattaatctatttgtttaatttattctaattctcgatcgggaataaataatttggaaattattcaacttattaaattcatagatctgggaaactatcaa gaatcaaaatcttaagactattctcctctcgtctcgtttcacatctcttcgttctccgtctatcgatcgggtgatgctgcaaatcatttttatcgatct acaaagtgctgcatttactaacggcatatcgtttcgagacccaaacgctgatgtgcgttattgcaaataacagttatttttccaaaccagcatta cattacagtccactttttttccttttcatattttcatcctggacccagctacatacattaccgcaaacgtgcaaacggtagattttatttactagttcct tttttccgaaaaatttcaaaaaattgtaaactgcgtttccgttttcaaagaactttttttgaagtttcaacgcttttcatcgcaaatatttacaaatacgt ctcgttatttagaaattttaaaatttttgaacagtgaaaatccttttcaaacttcgcgctaaaattataaagcaaccgcgccctaacgtcagaatc -continued accaaacactttttgcgtacacttgttgaaaacacgcttctatatgcgtggatgatgacaattttcaaatctgtgtcgtttttagaaataatttcgtg aactttttaaaatctcaattttcttttatagtttcgttcccactatcattttggacactcattcttcttattttaggtcttaaattgtacata cdc-48.3

SEQ ID NO: 79 atattcaattcattccaaaaacgatttttttaaagttttttcaccagacacactttatttctctcaattttcaacagacacgatagttctgtccaacct ccattcgatttgtgtagtccttttccggcattcgtacttcaagctcatacaacgtgtcgtctgtttcatttcgatgagccatcataaacgcacgtct gtaaatgtgttcattatttcatgtcataaattatttgcaatatataccgttcgtttctttgttgaaccgatcgtttgatatactccaaatcttctggagtc aattgatgacgaacatttggtcctgaatggattccaattcttatttctattattaatttattatctcaccattgataactggcttttcattctgatctttctt tctcttcttttcatcagtattatcaacttttcttgccggttttgctttttctggtgattttttgtttttctccaattgtgggcattgggtagtaagtagatgtg gcgaactgtttttgttggtaagtaggtgcaatagctgtatgaggatctgatcccattctttcaataggaatttcagatgcttgtctgaaatattcaa ataattattttgttagttcggatgtttcgataagatattattcagatgcaaaatttttattctgcccgaaaactacggtactgtactataatttttctcgc gaaaatcacaaaatattgcatccaaataacatccaatacgccttcaaatttatgaaaaaattacggtagcttatgagtaggttttggcacatgtac attcgtgtgaacgactgtggttgtttcatgctttttgacttcttgcttgacttctgaaataaaaaaaaactttcataagatgctttgttcattcaacaa aagccgtttaccttgcttcttgatacttttctctggaacgtgtgcactagtcttctgatgagttggctccacagtatcgttgagcaaagttttcgag taatgcttcacatttagttcttctgattcaacacttgtcgattgacttgttggctgactgaatcatagaataattgataatctgaatatattaaaaagt taactcacgtttcgtcgaaatgtgcaactcgattgtgatgaatcgatcgttccaatggatgctctttcttcagtatcgctgatttggactttgagttt ttgtttttactatgactacagcccattcttgaatctttctctcttattgcacacgatacgatttcctggtattttgtcggcggaagaatatatgagtaa aatcagaaatgaatcttttttttatctaaagtttttttattcgaagaaagaatcttcgcgaaacatgtttctgtcacagtttatctgaactacaaatctta ggttcacgaacttacttacttgcttcgttaattaaaaaaaaaattatattcttttgctttcgtttgcatgcaatttccaaaactataactcctattttcag cdc-48.2

SEQ ID NO: 80 gcaaatgtgaatggaaccaagaagagaacgagcaaaaatgccaccgggaaactcattatatcattctggaaacaattatacttcaaaaaat ggaagcaaaatataaaacaggagttgtgaatagagaaaacgacgctttatatcatcagttttggcattgaaatgaatcaataacataaattga gcgagaaaaagagaaacagcaaaatagtgaaaaacgaatgattgaccgagagaacgggggaaggttggaatttttgtaaacaaacgag ggaaacatcatgttgaaaacatatatatacacatttttttatttaatgcgtcggaatattcagaaaatcgttcagatcatcgataattttttattgataaa agaccaaaaaatccagtttacatgaggaaaacaatacactgtgaattttaaagaaaattaaatattccaaaaaaatttaatttaatttgtaatttgg gaaactgaaacaataaaacactatcgaaaacttaaaaaaaaacatggattgaagctcaaaaaaaactgttttaatgtttcgttttgtagaacttta gatttttgtaaagcgggagacaccacgaatccgcaagaagtttcttccagaagcagattcgctgaaaaaaaatgaagttgtcttaaacctgat gctttttttgataatttttatacattatgtggtttcctggttggccattttgttaaaatcattatttcctgtaataaaagtcaggcgttctcagttatttcc agatatcggattcctaaaatagctgaactccaaaaaacggtcaagtctctgaacaccaaacgcgctccttcgaacaaaaaaagcagcgcgt acgtttaacgaacagtttttcttctagaaattgttttctcattgcgcaatgcattgctcattataaataattatgttttaaacagttgctgggaggtttt cgctatctcagtcgttgttaaacaattaccagagtgtgttatcgtatttatctttgccgtataatatcttttccatatttatgcgattgcggaaatttac cactgactctgcggaaactgcggaaatttaccactgaaatatcactcatatcgtacgtttctttgaattcgtctccttgttattcaaattatgtcttc gtttttgaacgagatatttacctctagctttctagatcgtcacatcacttaggttcgccttgaacttctgttccgctaaagacggctggttcacatat atttttaacaatgtaattattacttatgacccgaataaaacggtagaacgctttgtgaaattattcgaaagcaaatgcgccccaaggagagagt gtgaatgagaggctgcgttttgtcatcatgtagaggcagcattggggtgttctgtagagaacttagtctacgtgtctcatcttccatatttcttaat tttgttctattggctctttttgcatctcttctttgattcgattctttaactgaattagatcagaaattatacttgaagttttatcttgaaaacctactgtaga aaagtttgtccgtgttctactttcttattagactttcgcgtttcggcctttcctatgttctaccccccatcttccgttctttttttattattccaagatttttaca gagaagtcgtttaacc ufd-1

SEQ ID NO: 81 ccgggctcgaacaagacatggacgagccattcgatatgtgatcatctgttatcacaaaaatgatcaattttcttcataatttatcaaagtttctgttttcct tccatttcatctgatgaattcctactttcttgttccttttcactaactttattattataattataattattcataatgttctttctttcccatcatcatat ccatccttctatacattttgtttccattgttgttgaaattttatatgctatttcatttttttgtcgtcctttttttccgttcttcattttattgacttctct -continued gcgcgttcatgatttctggcattcagctcgataattcatttataccctgttctttctagtgtttttcgcgttgtttgtgacggttaaattcttccctctac atctttttccacacaaaaatctgtacacgacattcggttttctcgttgttccatttctttttgttcaacggagcgcgtttgtcgttgcaggaatc ggttttaatatcatcatccattcacgcattctctttttcatgttgttcattgtgtttttcttcaatttttgtcaagtttccttcacacgtgcattttagta atttctttctataataaattgcagtttgttaaatatttaaatgatcaatgagctctcttttcttggttggctcatcctctttgtatttttgaattatagt tgaagaaaacgttaataacttttcagaaaaccaaaaataaaa npl-4

SEQ ID NO: 82 atatagaaaaacggtctcttaatttcaaaaaaactaaatcaaataatgtgatagactctctcaattgaaatagataaaattgagagagaccgtg gctattacatttgtaaattaattttcttaaactctacttctatctccagtgagccatactcgtgaattgatcgcattgaattcttctcttcaatatcacct tgtccaataattacatcgtctcgtgagcacatcttctattaaacaaaattagcactaggctagttctcttctaaagtgagaaatgagaagaaatgt gagttgtagagacgtgtataataaaatccataaaaattaaaaatattgtgagttcttctgagattacgtgaaggccgaataagaggtgacggt gataatcacaagaatttaaaaataatttttccatagaacgaatatataattgcgtaaatggtcgtggttgctcagaatctcgagagactgtggca aattgtcgaagttttggcattttgccaaaatttggtaaattgccaaatcatcgaaaatgtatatttcaaagtgatttcgagcagttttggaaactttt actataatatttgagcacttgagaaaccgatttcaactatttccataccgtggaaaaattatgttttaagttttggcattctgccaaagttttgacatt ttgccaaaatttggtaaattgccaattagttcaaggtgtgtacttttaaagtgattttgaacagttttggaaactattactgtgatattttagcacttta ggaactgattttaactatttcaatactgtataataattctttcgacaacattctcatcgggccacatgcgatcacggaagaatctgaaattaaaag ataaatagaaaacaatttgagattattaaatattacctctcggtgagatctggaaaagcttgatcgtagagagtcaaaatttccggcacattttgt tcgtcaaccatgcgggaaaagtagaccaggtagtcggcgacctcatttggaactccatcctcatcggctgaagctgttaaaaattaagaaat gagataagtttgtgttgttaacaagcacctaaataactaccataaatatgtttatagaattactctattgattgattatcaatttttcttttgaaaagat ttcacaatgcacgatcattgatcctctgatactcaacttctctctcgggcttttaaatgattaacttcttatgaactcttatgaacaccttttcatttatt atttctttcaaatgaataaagctgtgattcatttaatctgagatttgaggatattcgacaccgaaaaacactgaaaatgacaaaagtagtcatttt catatacaatgagggagttctgagaattggcattgattcttcactgtaacagtatttggaaaattggtttttctgaattttatgtattttgctcatgg aatgttaatctgcagtttttatgcaaaattatttcagaccaaattctccaaatgtctgtttgccgaattaaaataaatcggttaatcaaaaaaggac cgagtcttcagtcttttcgaactgtttcaaattttaacatttttcaactcattttactcttattcatcaattctgaaaaatagcattctgtgaacttacaa gaaaaggtgttggtgcgacgacgatcagagtgatcttcagtggataaatcgaattccacgcgtcgagacattactgaaagaaggtttttatat tgatattatttaaatgtcaaactaaattcgaaaaggtacgctaaaattaagagaaaacatttttttaattgtaaaatttgatgaaaggaattggaaa atgtgatggaaaaaagaaaattgcaagcgttgcatgggatttcgcaagagtgccgcacggtttttttgtgtacgcatttgctcgtcattcatgttg tctaggcagttttgatgacatttttttattctaaaaacaaaatgttttatttcatttgctgtttaatgtttgaatatgtatggaaactaatttgatacccctttc cgctgcattatttttgcaaaatctcaaaattatatatcttcaattcactacctagaaggcatatcttcctgcatttaaaaatctattttatttcagat Nuclear Oxidative Stress Toxicity ugt-1

SEQ ID NO: 83 agatcaatggcactgaaaacgctcatttaaatgcaaaagatcgtgtcccgtaaaaattttctgtataattccgtgattattttcactcgggaatcg ctcgcccactatgggggagtctacgcaaggacaacgcaaggacaaggacaacattctaatggaatggaaacgattgcccgactgcacca attctagttcaagtgaacaatgataacttttgtattctgtattccttcacgtctcccagcgagcgtaataaattattattattattataaaaggagagt tttgatcagataaatttattatcgttgaatatccactttctctgtttctcgtttcattctctaaacgacgtatggataatacatatgatgaaggtctaaa aacttcaaagaaatgtctcctagttttgcaaatttccaccgaaaaaaaaatttggtcggttctcggaccatttatgtattgtattttatttggcttatgtt ttactcaggaaagtaaataacttttgctaaatgtacataaaatcagcaatgttttcaaaaatgttttgaggtaatccggcttctatgtgatatattaa ttcaatcctaactgataagataattataaatttaaaacttactgctacctccaacttctggaacagcataagaattggttggtggaatggtaacat atcttggctgcccatatccatgacgtggtggtaatttgattctatagactgcccgtttttctctaattgattcagttatcaaattccacgcatcatcg gaatatttctacaaaacattgaattaaaaacttgaaaaattaattatggaccaacttcaaatgttttcagatcttcaagggaagtaatttcaaagttt -continued tcaatttcattaaaaaccgaaaaaaattgaagcgagaatcgtaagaactgcaaaaacaatgagcagaatagtagcgaatagaaaatttgtgtg cttcatttttgttttcagtttcagacaggtgtctatatttttatacttttcaacacaatagatattaattattttagagagaaaaaaacaggaaacagct acatagtgtgaagtgaaaatagaaatatgaaaaatgaaataacaatgactttgacgaatttatccctcttaccctaaattttcaataaaatcaaa atacaacaaaagctccaaactctaaaattactaaattgtatttttgtaccaaaactagcttcccgacattgataagtaacgcactggcacaaact ctaatttttttagtgaacacaaaaacagtaatctgcaaaactttctttctcgtattctctgtttctctacataccgtacttaatatttcactatcttatctct ctgtgtctcttgccgaccaaaaaactaatggtggatcgctatataaagaaatgttaggtaaggagttgaatgtcagttatttctgtaaaaactag aagtttctaaa ugt-13

SEQ ID NO: 84 attattatgttcctatttcttttatcaaataaatgcagttttaaaattttggacttttctgagaacgtacagcaataaataaaaatctaaaaccaatca cattcaaaaggtcggagcaagttcggagctccgggattcaaggtcacaataatgaaattgttttttttattgcttgacattgatcgaaattaatttg ttattttttgcaaaatcgaaaatgaatattttttgaattagaaatgtttttacaaaattttgaaccgccataaaaaatgttgaaaagttaaagttttatta cgaaattcgtacatttgaaaaccttttgggtctacatgttcaaaatcgcccgaaccgttagtcttcctttaaagtcagttatgactgtgttctgtgtc tcctcgactctgttttctgaattgtcatcacaccaaaagaccaatctttagatctttgtatttcttttcattacttgctatcaaattagccatgaaaaac atatgtcatcatattactcactcaaaatactacaaactacactgacgaggttaccgtttgatcttatcatctcttaaattagtcggggtatataaga agaacaaatcgagtacattgtttcaagaaaaaattccca hsp-17

SEQ ID NO: 85 gattattttcttatgctaaactggcagacagcagatctttttatatctgcacaaggggcggtgggatttatagaaacttaagtttactacgcctgc cgcctaatccgtgaaaccttatttttatatttttccgcctcccgaaacagttgatacgtgaaaaagcacggaagagaaaaaagcttcttttggac ttgattaatctgttggtcatgagaaagcgtgacacaaggtaggttacggtagcaattgcgtaattaatcggatcagtctatgcgcatttctgaaa cattggggatttcaaatctagtttatcaaacagatacaaatcacattgacatctcgtggaaacagtctgtaaagtaccgcaaattttacaattttt gatattattgtcgttaaacaagttccatttcaaatttttttattgaatacggtaaaaaaacaagagaggcagctggttgaagtgagtcactcttgttgag ttttcgttactggaaacctgaatgaagatagtttttaactttagcattacgcctcattattttcctatttcctttttactatttacttgtatttttaaact ttgtttagcacattgagcacataaaaccaaatgttataaatatccttatcatcaacccatcggtttcttttttaactttttttctttctcgaatttcaatgac ccggaaaaccaccacatcatatgaaaatcgaatctaaaaatttgcagatacgcatctgtcctgctgcgctcttttttttattttgaatgtttttttttct gcaaacgttgggaacagtcatccaatccttcaaccgttcgtctcgttttgaatgacaaacgttctctttccgtcctctgtttgagtatatttacattg ctaattcaaaaaaaaaatagtatagaatataatgatacttagagatagttctggcataaagtttaaacttgaatgaaatcatcaatgccattaataa ctgtgtcactgcattagtttatcagcaagtgtgccagcaaaaaaaaacgtttcgagacgattcgatacattcctgaaaaacttcgataaaaggg aagtatccaaacaaccacacccaactttcatcattgactcgctgttttgctttttatttttgttaatcttccttacaattagttttaaagtttaaaacaaa tattacatgttagaaagaactgtattttggtcagtttgttcgaataatttcgaaatctaaaacctttttctttttgatgattcgtcggagtagatgtttct cgaaggaggtaaaaaaaaaccgtgggcgattcttgtttgcattgaggataatagagcagtagtagaaaagcagggagtgtcaactcagtttt gtcttcttcttcccctatttctgtcttactttcgttttgtttctttgaaataattagattttcagaaactattataaa cdr-5

SEQ ID NO: 86 aggaaatttatccaaatgattttactatttgagaatgtattatgcggtaactttttttgaaataaactaatcgtgacactcaaaaacttagaatctattt taaaagaatagataattccagtttttgatatccgggaatttatgattttttggaagaacgcaagaaatcgatacatttgggtacgcataataggta ctcttgcacttggatcaaattcctagagaacgattagatgctttagacgcagaaacaaaaaaaatgtgaccgatacaaaatcgaccacaatctc aagaaaaataagtgcgcaacacaatccgaggtcaatctagacatttatgctcttcctgcgagacaaaaatgcattgtattttttcattcagattc attcaggtgtcttgaagagatatcaaatcacatgtgacaaaattttgatcgaaaaataagttgcatcataataaaatcatcttatgatcttcctata taatctttcttcaatttcggaaactacgattcgaatatatgttttattttaggcgaa rnp-2

SEQ ID NO: 87 aaccttagggtaaagtttattttatttttttttctttacgatagggttatccaggctttctaagccgtaaataaacttccattttaaattttaaaatatttta aagctcaagcttatagtatagggaacaaagctttctgatagtttagaactaacaaagagcttatgttctacaaaaacagggacgtttttatttata -continued ggggggggaggtgtaaggattctaaccgtctctacacttctcccacttcccttttccccagtgatagaaggctaagagtgtatagggattaatg cttttatttacaggatcaccggccagaaagtcagtcacgccatggatcaacccttcgctcttctccgaatacagctctgcaattgatccatccg tgcacagtgccaaacgctccttacgcgttcgatccctgagataattgcaataattcccacacactcgatttattccaagcctctaaacttcctgg ctaccgtaaccctgtgtgtgtgtgcgcacacttgtgtgcgcgcaccttgtttacgtcttctggacctttctgcggaggaatccagggctccgcc ctgccaccgcagaggggtatataagacgtggattctatcactccagatcttctcttacttttctgttcccctttacttgttccctttgtctcatttctta cttgtacccattccattggggttattaattcataataaatctattccttagcacataccttgttctgttgtagtatgggatgcaacaacttcggttgtc ataatgataattgaggggaacacttaaacaattaccggtatacgcttaaacatttactatatgttcattcaatcaatcacatatcgacacaacaat taacacaatccacaagtttttgcgcaatactccttcttctgttcctttgtgattcgtggatccgcacagaagccacgtcctgcccagagatggca gctgtaattttatgaattttattatcaaattcgaattccccgtcatttttttgttcataatcctatattttcaaagatctagctcaaaattgcgtgaaatt ccatgtttgcggacttttggcgctacagtaacccggattatttttgaaaatcgagatggagctctgaaaatatgggagaaaaggtagaaaatc atggaaaactcgaatttggcattgaattttttaaagaaaaaataaaatctgaaatttaaaaaattgaaaatttcacccaaagtttcaagcaaaatt atcgaacaaaaatatcgatttttatccgttttgtaatatcaaattcgaattccccttcatttttttgcccccaaccagagatctagctaaaaatcgcgt gagattcggtgtttgcgtacttttggcgctacagtaatccggtaattttctgaaaattaagctatttagagctctaaaattttcggtttcgggcaaa aaatggcagggaactcgaaaatttttaataaatttttaaaataaagtgcaggaaaaaagttacgaacgccccaaaacttactcaatattatcgt gacatgacggagtggtctgagcactttcaaattcattcgggtggaaatttggaatactcatggcaaaattggtgccgaagagcacataaaga gcagtaataatcagaaagaatcgcattctggaagcttctgacctgaaaatgctccagtggggagattttatactggaaaatttttaagtatttag ataattaattgttcgtatttcggaactgtgtttttatcaaaaagcactgtgttttgtgctcttaattctgtaatagtagatttttttccctaaaaattagag tttttcattatcaaactttgatttttttcatgatttttttctaaacatgcggttcaacaattccatgaactcaaaacaagccgaaatttgaagtaaattct gtgaaaaaatgatattttttctaatattattcaataaatctattttcttgtcctatatttggagcatttcaattgaagtttgctccattttctgcccgcggc ctagaaacctccgtggccgaacaacaagcgcgctctactgcactctttttattttcgtattttcaatttaatttcaataatttttatcggttttcttcga ttttttcgcacttccccccagtatttttttcaatttttccgataaaaaatacaaattttccagctaaca dnj-13

SEQ ID NO: 88 ttttatacgaaaaatactttaaaatcagaggaaaatactttgggaccggtgaaaaagcatggaggttcgcacaaacttgtttaggaaaacaga aatatgtctccgtggcaggaccatactgtgcgccgttgatgtccctttgatacagtactcttcgcattatttatttttttttcggcgcgcctaggggt tttcgagcgcagagttcaggaggccttctggattatggatagaggcttgatttttaaaattgtttaattcaatacagttttattaaagtttttttctaaa aatcttttctaaaaataatatctgattgctgtttatacacgagaacaaaactaatttcatggaaacaatttttttctctttattttctcttcgaataatttaa attttaacaattcaggttttaaataatcaatttttaaataagcaagtgaattttaagcataacttttcttcctagtgtacgtaaatcattctttccaacaa acatatttttttcgtgacgaaacttcgccttccagaatattcttttttcagaaaataaataccaaaaagcacaatttcttatctcttgctcattcttttctt tgtatcgtgctcatgcttttattcattcctcattttttatcttgcgaaaccaatgtattttcaataaaaaaaacgagtgatgcatgtgcgctccaccgg ccgacggaagatcgaacatgcactgcgcttcgcgagtaaatagaacgctctggaaagttccgcactcttctctctcatgattcggcgcactc tctcttccatttctccgtgtttcctcttctgatgttgacccatatttattctgccgggtgtattctttttatctatctgttgcttcatttattccgttaacc tgttactggttaatatttcaaaaattcatatgatttcttttcagattactttccaca dnj-25

SEQ ID NO: 89 aactaaacattgaaatttctgcacttctttattgtaatgatgcttctgtgtctgacttggcattttcaaaaataatggaatggtggagaattgacag cgcagaccattgttaagactatgactgtgcagtttatttgcacagcactgtctggcacactctcttcatatcacatggactctctcttgctcaccc tttgacacggattaggttagaggcataccagtgggagtcagagtgctcagaaaagtagttgccatcgtggtaagagttctgaaaagcatcg aaggttttttagggaccaaggaaatatgaatggagcatgtaaaaatacttgtaaaactgtaaaaaataactcagcccaaaactgagggaacc gtactttctgaaagaaatatgtatgaataccgatgtttttaggttcaatcaaacaatttattcggatttttcacgaaatattacagagagtgtgacgt tacataataatgttcactgtttgacgcagtcacgagcttccaaacaattttatattatcgagacgcaaagattcacaattttcgcgccagaatag cacaacctggtctcgacatgacaagttttagttaaatgcgaaaagatgtgcgcctttaaagagtactgtaacttcgaatttttcttgttgcggaat -continued ttgtgaattttcatcgctttctcattgtatttcgaatgaaaaattggctttttgacaaacttagacacaaaaataatgctcattaaattttaacaaatc gaggaaaaaaaatattgtgaaatgtgaaaaattccgcagaaatgagacgctttccggtggcaactttcccacaattttcactgatagaatgta aatttttgaattaatatcactttcagaagttttatacattattttctccttataaagtttgtgtgaatcacattttcggccgaaaaaaccggttttccat ggaatgcatgcttccgatgcttttcgcttttattggcggatggttacgcaacctcaccgattttatctctattttccgcactttttcttctctatttccaa aattttcagcctagtttatttttgaaatttcagcaaaataattaatttcctcacaaaactggcgaaagggcttttcgtttctctgccgtctctcttttcg cacgctctataagcaagtgtccgtgaagcgcacttgcacccgtttattttcacaacacgttttcagataattttagctatttttcattgattttcagta gtttttacagctattataatggtatttttttagtaatttccagtataaatccg pme-1

SEQ ID NO: 90 tttctctgcaaaaaattggagatttttttcagtctctttcaactaatgtaaatacgctctcttgtgactaagcgcgcgcgtttgaaccagaggacaa ttttttttcctcagcgctagtagcccctgaaagagttattcatacttgaaaaaagaaacttttctatagatttctgcatgaaaaatcaatcctcagcg cttcttctcttgcttttcctgattgtaatgaaattttagagtttttaaattgtaaaaaaaaaactaaacaagttctttttgaagggaaaattcgtttttaa atgcttaaaatgcttcaaaaaaaaaacaaataaaaaaaaattgtttctgtgcatacaccgtcacgacaaaatgcagacttgccattggtctcgcc gcgaaaaaacatgtttcttttgaaagattgtcttaatttttttgatttcaatcatgatttcaatcagaattttgcgatctttcagcatttttatctattttaaa gctttataaattaaaaattaaatttttaaaaatcttccagattgtcatacgggtcccgg tag-124

SEQ ID NO: 91 aaattattatataattttcaaaattactggttgatgaggttagattagtgataccttggaagtggtctatgtaataacaatttttgcacaaaaggag atgagatttgatatggaagattggcaacacaaacgtcaaagaatggccattccattttcattacatctcctccattaacttgtaatttgttttgtag aggtctgaaatatatttatttaaattcgaaaatatttttcaaaaaatacgtacgttcccataactcttttcttgacttcagcaatcattctaggatcga tttcacatgcaattacagttttgccacctccagcattttaaccgtcaagtttcctgttcctggtccgacttcaagcactgtatcggtggctttaag agctgatttctcaacgattgcattcacaactccaggattttgagaatatgttgtcctttgtcggtgttaaatggaagtgctataaaatcaatgttat gaatagaaattttgcaaaaataacatacattgaacatttccagttgatgatcctgctttcgtctttttaactttactcgtttttcccattttgagttttttt aaatctgaaaatgaacgaaaaataatagtatttctgaaaataggaaaataatgaaaagaaataaaggtagaatgatttgtccacgtgaagtac aaaacgtgggactaaaaaacaattctagtccgcgcgtcgtgtactcctctcagacaaacagaagttgcacaatttttttgaaatcgatcccttttt aatcactttttcctattcttctagcgtttaattattttctattgattttatttacaca pme-5

SEQ ID NO: 92 aaaaaaaccggctggtttgctgaacggcaattgctgttcatccctatacctgcctacctaccgccaattcagataatgtggtgaaaaatttcac gaaaaaaagagcaaaaagaaactataattttaaaaccggagtttgaaaccgtcatcgtcgttgtcattaataccattatcattattgacatcagg aatcacgccattttgctccgttatcatacacatcgtcatcatcatcatcgtcgtcaacacccatcaaaaaaaatgtataaaaggtttcactcaaa aagagggttttatcattttatcaagacttaaaaatgtcctcgtagtttgactatgatatcatttttccattatcaccatgtttgcgttttcctttttccaaa catttcttttgcacggcgatgatgcttggcattttgcactcgtgaaagtttcagcttgccagtgcgccgccgcgttgtccatggcaatgcggca tttgtattcaacggcagaaaattgagagatttgtttctctcgcgtacctcgcatgttttgatttttcgacctcggtttgtccctcaaacaaagagaa tcgtttgtcgccctcaccgcgcacgcatatacggaaaaatgctacaatttcaaggcgtgatagagatcagctctcccgctgatttctatcgatt ccaatagagatttattcacctcatacggcggcattagtttgggcggtgtttttttggtgtttgttgtgtccaaaatacgaaaacggaaaaccttcat ttcagcttagtttctaaaattgattttcttttatataatttttttcaataatgctgaatgcacgtgctcgccggctgcccttttgcaatgagactatgca aacgcgcccgaatgcaaacgctgctggtggacccctctcggacataaaattatatttcttatttttttcgaatctgtttttctttcatattttcgaaaa aaaatgacaatattatttgatgaaaaaactacgaaaattggcaaaaccaaaaacaaaaccaaggaaggatttctggcttccctcataaattga aataaaagagtttaccgaactaggccattttggctcggccatatctggggtagatttacggcgcgttgcttgtcgcgtcgcggctcgagttta gttgtaaaactaaatgtatttgtccgtgtggagtatacaactttgccacgcgttgtccagcaggagatttgcaatagagcaagaaaaattcaat gaggaaggccggaccccgtgaaaattcgcagaaaagtaatgaaatcgaaacagaaaactccgagaggactacacggccgaggatttttc ctcgtccgctcttttgttaggccatttttttgaattggtaaacggagttttctagtccccgaaaatataatttagaccaaccagcgagcacgtgctg ccattgtcggaccaaaaaaaaaacgccaaaaaaccgtgtattttttttttcgtttttttgatccaaatgctcatttcgtcaaaactgatgcctactttg -continued gctgcctacctacgcctacctacctacgtgcctacatatcgcctattctttgcattttggcgtccagtacttcactttccacagaatagataaaaa agtgtattttgacaaaaaaatttatttgacctcggcgcatttgatctcgagaaaacgtggcgatttttgtttttaccagttccaaactacatgtaact ttgccacgtctgccagatttgcgttccaacatgtcaaaatttggaaaaaaaaaccgttgtttaccgaatgacacacaaacacttttccccatctc attgccctcttaatctttgcaaggtttcacaacattttgagaattctgctaaaccgtctgcgtctctcattcctccaccctattgtcacggttttgcta tctgtttctctcgtttttcgtggtttttctctttttatgaccttgcgtgtatttgccaactatttttgtttgtgggcatttttttggggaaaaagttt gatttctggatgatttgaatattcgtgtattttataagctttttcctaactttctactttcgttcatttctgttgtttcagccgtaatccgaacagc air-2

SEQ ID NO: 93 tatttcttgtgattcgcttcgattttctgaaaaaagatttaattgaatattaaaactacaaagaggttaaaaatgatttccgattttctcgattcaaatt tagagaattccagattttagctcaattgttgtgaaaacaatttttagcttttgagaattaactttttctgccaaaaaaattacctggaggagccaatt acaattagctccaagtgtttcaatacagtatttgagagctccatttggtccaagtccaagtcgatccattacatcattcacagtgatcatttcctaa actttagtattttaaatgaaaaatatgaccttaagtattaaaataacattgatagatgatctgtaccacgtttcataattattgtcctatattcattgga ataaaatacttacagtgatatttacatcaggtgcgtatgccattgtgtcattagcaggatcaagattgatagtgagaaatggtcgtttggtttgtg agaaaatgtccgttaatcctgcacaaaatgtagattttccagctccaggagctccaattacaagaactccgtacatagtccaatgagtactga aattttctagttgaatcttaattttctacggattgttttgataggaaaacatttaagaagaacaaaaatatataaatacaatttaatttaatttaaaaca aacaaaaaaagcaggataaacgggcctggcacagggccaagtacgcatttacaccgtacatgacgacatattgcggaccattgcattttgc cgcgttaatttttttatttaaacggcttgcatttctccttactatccagctgacaatttttagtttctttagaattatttgcaatcaaaactcgttttttgtaa acatatttactcaggtaatgtgttgatttctcactttttttttgaaatcaaagcagaattagtcctatttttattctacataaatatctaaatgtattcaatt aaaaattgggccattgaacttctaattaattcaatttataaatttatcgtgatgttttcttttagttaatttgtccttaatcgtgccgtctattttatttct tcataaaaaaacttttcagttccgac mlh-1

SEQ ID NO: 94 caccagcatcaggagccaacatcagtgccgacaccatcgtcgcgaaacatgcaaagctgtggagtcgaaagcactcaacagccggacc gtaaacaggtgagcatacagtactcggaggaagaaggctccgaatattttaccgatgagcttgacgatgttgatgatgagattgatgatgct gctgctgcagcccgtgcggctgagaatattcgtattccggcgtgtctattacagacggctgctcaaaaatctgaggaagaggatgagtacg atgtaagacactcattgggttacccatttttctttggttggccggagaaaaattatttactatgctccgatatttgttgatcgaaattttccaaaaaa agagctgtaggaaattgagattgataaaattaatttttatgcatttttcgccaccacctgatgtcatggtttacaaaaaaaccaaacagttaaaattt aattagatacaatttttgaaaaaaaaaagtgttttgtacatttagaactaatccataagcgacgtgcatttcaatgaaattgtttatttttatttggcg tatttctacgattttggacaaacttgtttgaaacaagacaacaattttcgaaatatcgtagcatcgtttgaacttatcatatttatttttaaaaaatttct ttccgccaagaaaaatgggtaaccagcgtcgtcgaaaggctatgatcattaatttttataggtcatggagacgtatctttaattaatactctatat actggtacgacgggtaagatacattaagttgtacaaaaattacagttttcctcctttatttctccaaaaaacctttttgtctagaaacatctcaacattatt tagttaattttttttttagtttttcaaagtttataatttcaaaaaattatttttctgctttttcggtttttcttcatgttcaaaacttcttcctctctcgtca tttttgtataatgcatcgcggcgatataaatttgcattttatctggttatggcttcatcatttttttttcaaacgaattttgggaaaaaagaatgctatagt cattttaattacatccctcatatttgtggcgtactgtttcctttccctgctatcccgattgatgtttttaaaggcacaccgacgagaattttcgattaa aattgtaaattagagtaaaatctatgacttgtcaatcgaaaatcttgtcggcgctctttaggaactccataaaaattgaaacaaaaattattttaaa aattaccaatttttttccaggtggccgctgcgtggtcgacaaaaatcgacgtggacacgcgcctcgaacaagatcaaatggagggtgtcgat gaggcggaatgggacaaataggcgctactggaccatttcatattattttcagtcaagtagtgtacaatgaacacaattttctcacggttctgtaa aaatgtttttttctattgaaatgtttgatttttcgccccccatcaccaatccatcaccacctctccctctctcgctttttatttgtctcatgctttattcatcat tttttatgattattattatgagtattattactattgtatagtctccaatttcgtgatttttggttttctagaaaattgcgcccgctcgcccgcccccacg acttaccacctccccctgaatttttttgtgctcccatcgcctagtcgaatttattcttttgtatttttgtgtgtccactttctctctcggtcgatgtgtttt aacatccatattttctgccccgcctcgtccccccctctcaatcgcccgctccccgccccgcctttacactgtgtttcgatgaaataaacagtaga gaattgtaaaactatgtgcgtgagaatttggaaaatttttagtttttttgtgatatcggaagctttttttaggggaatttgaatttattttttaaaaattgttc -continued aaagataaattagctccgaaattggaaatcgtagtggaacatttgaatttccgccagccagacatgtggcattgcggttaccgtacccgcaat tgtgatgaattttcaaaaatcggtgatcttctggattttcgctgtcaagcttgagtttaagggtctcctcactgatctatgtccattttgcggcagg aattctttttttttagtttcattcggatatctctaaaatatcaagaaaaatcgataatttcacttttcctgaaaactttcatattttcagaattttcacta msh-2

SEQ ID NO: 95 tttcatagatttttaataatcagtctgctcactgataaacacgtcgattgccgcagtatcttggagaagagaactgaacttcattgtttgaaacct agaaaatagtgaaaattagttagaaagagaaggagacggagaatgaaaaagggaaaatcgcgcgcgatggaagaaatttgaaaaaaga ctttacttttgatatttttcgaaatttttaaaataattatgtttagagttaaaattgcaaggaaaaatgaaacaaaaattagtttaaaaataaaaacc accgtatctctttccctgcgaaaccaattcaccgtattattgtatgtgcctttaatctttaacagtaagcataacatgtgattttcgccttctttttatta aaatctaaattattacagaacttttaaataatttgattatattctttgtttaatttttaatcatttaaattcaatttagaaatgctaaaaatcccaaaacaa tgagacactatttccctgcaggaccattttacagaaatactgtatgcacctttaatttcttttcaaaagtaagcggcctttctgtcgaatcatttttc gttgatgaactctttttcttcacttttactctatattatcacaaaaattcgaatttttcagcgaaaaaatcgaaa msh-4

SEQ ID NO: 96 agaatgtctggtctccgaatcgtcaactcccttgcatattctttagctccaggacagctcggtgtagctgcaatttgcaacggaggaggagaa gccacagcagtgctcatcaaaaaactgtaatatgaacctcttgcctaaatgttttctggtcttctattcatcattccttgattcacttttacaacaaa tttcgattacgtatttataaatagttaaggttcttgtcacataaatgtttattctcaaatggtgcatacgtgttattgattgggaaatgaattaaggtta atatgtacattatcaggaatggttttgagccatctcaaaagagatatactggaaaaatcggaaaagcatttttcttttgagatatatcattcattca cgtcttcaaggcaaaacatataaggggagatcgtatacaaataatcacagggaagaattggtggatgataaaatgatcccataaaccattatt agtttgagagatcaagttgggggaatgagaatattaaggggggaagaatttaaccgggaagcaaacatagagcgatttaatttttccgggat ttgctttgctaggcggttccaggtggcgaggttggctctgaggaatcctttgtttgtttcgccaacagatctgagcatgtaggggtatcttgga gttacagctttcttcaccgacgatgacacatttgggtagtggaagtttccagttatgatgttgtggtaggtgcgaaggatctgcaagacccgc ctatattgcactgacttcaaattggcttgggccaaacgatcctcgtatgaagaatactttatgttgcagcgttggaagacgagcctggtgaag aaatgagatgaatcaataaaggctatgaacgggtaactcaataaagtatcttcctggactgggatgattccgagaaaacaatcacaaacgat acggtaatgaataggaatccattgatttcattttatctgtaatttcagtgtctgacaagagatcgtcgtttcggaattattacaggcccaaatatgg ctggaaagtcaacatatctgaaacaagctgcccaactagcaatcatggcataggtaggatgcttcattccagcaaactatgcttcgttgccaa gtaacctaaaagttttgatttgctattttctatcgtcgaattaatttcagttttaatcgtatcttctccag ahi-14

SEQ ID NO: 97 gatggtactgagaagaagaccgatttcgatgctccaacaacacttgcttaattattcacggagatgtcataattacagctttggttttcattatttg tttggttattatttatatcacaaatttcgctaatcggcgagacccctctattgcttttctctcctatctcgtttttgttaacccagtttcttttgaatgaac ccttgttatgacgattttatggttttccaacggtaattcaataaatgatattatatgtggaaatcttgaatctgatttgatcgatttagtctcgaaacg ttcatgaaggcaacaaacaaacaaccgttgattaaattagtttttgaatttcgcgcacctaatattccagaggagcgggcttgcattatcttttttt acacgaatttcttatttacagtatgcactattctttctcctctcccattaatttcttgtcaatcccatcccttttttgtag msh-5

SEQ ID NO: 98 gcgagccgtttttttgagaccctgaaattcggaatttctttttatttttatatttttaaattcatttaaatataaaaatagagcacaaacctcatcaaatg tgctcactagaaaattacacgtcctgcatttttcgtttttgatggtgacttctttttgtgacgtggcaccaattaatacagcaagcaggagcagtat ccggctcattttcaccctgaaaaatggaaaaaaattggatttttatgtagctttaagacacgacaaaccgttattttagagaaattacacgcagaa taagcgaatgagcgcggccgaatgcactgcaaattgtctacgttgtccagtttctcggccctgtgagcggagaaaagagagggagaaaa gaaaaatgaacaaatattggctttgaccgggattactagcaaaagaggtgactgatggaagagggaacaattaaatattagaaaaattcga aaaagttaattattttcgctggaaatcaccttaatttggggagtttcgaaagaaattttgataaaaatagaattatccacttttttatttcgtgaaaaa aacaacaatttcgactgaaaatccagctttaattcgagaaataacaaatatttatttatttaattaaattaaattaaattaaagaaaataattgaatta ctgtagtgatcgttgcgggacccgatgaaccgaaatcggtatgcgccttgtagttacggtaagaaaaacgggcggtgtcgagaatttaattt aaattgcatttccaaaacaattttcctcgtttgaaaataaattttacgagtttttggttagtttaaatgctaaaaacttgatttaatttaataaaacgta -continued cctaaaaattcagtttcgtagcagaaaacacgaaaatttcagtttttagtaaaattttcggaatttctattttcaagtcttgtttatagttactttttatg gtgttcaatcaacttttgaagtttaaaatgtttaaaacgtttaaaattactttacaagaaccgaaaaaaaccgaaaatatttcaatttttagtttttca gcaaccttttcttaaatcagaaataattttatgaaattttggttcaa tag-63

SEQ ID NO: 99 cgagaaacatcaaccatcgaagagcagcttccttggccagagtgtcgtctgataggtcgatgtagtcgagcaggcacacgactgctctgc acagttctccgttgtaaaagtagaaaaagcagagtttcgcgggaatactcgcgaaaatctctcgatctttgctccgacactccatcgcctcctt tcgtagagtttgccacgtgatgaacattttgcatgcggttcgttgatacttcgcaagtccttgaaagtattcggacgaggcgtagtatgaggtg attcgagccaatttgctcagcgagttcatgtcaatcggtccattgacgccgaattcggcgataaaaagctcggaaatctcctgttgcaactcg gcagtttgttcggcaaacccgatcaccgtgcagctcacatttttgcgtagctcatctagtttttcgatgtgctgcttgtcaactgacttgtttgtga tcttcatgaaagtttatctagaaaaattaaaattaaactgttttaatggaattaacattattacatacataaaaagcaagtttttttgattgattttcatta aaaatcgaggaaaaattgaaaatgaaagggtttcaacgcacgttatcttctaaaaaatttaaaaaattttcttctagatgatacgcttcacatac gcgacgcgtaacattggagcaacgttgtcactttttcttaaaaatctcttataagagttggcacggtgccagatccggaattccaccagatctt gaattaaaataagtttttttgcaagttttagcaagttgaagcaagtttttttattgattttcaccggaaatcgaggaaaattgaaaatgaaacgattt tcgaggcaaaaataaaaaatttccctccgattttgaagtccgtgaatgcgcgtgcggtgcaactgcgtacaaaacaccaaactttacgacag tgcggtaaattctacttttcaaagtttgagccccaaaattcgtttaatttttgtttaaaacttttcttgtttattgaattatttacatttttttcagtcgac polq-1

SEQ ID NO: 100 ttgaccaagatactttgaaatcatccgcggatcatacacaattagtacaacgtttgacatttctcctgaaaaatggaatttcagttctaaaaacac aaaaataaagttagaaattgttaaaaacaaaaaagtttatttgaattcgccgaagagcgcgccaaaacatgtgacatttctcggccgtgaaaa ctaggccaccgcggccacaaacaaattttagttttcttcgctgaaaaaaacatgtttttcagtctgaaatcagagtttttagtatgaaacaag him-6

SEQ ID NO: 101 ccctaaatatattcacaatatctcatatttctagatatgcagtttcttcttctggaactacacatcgttggccattatgcttcgcccatttggtaatga tttggatacttgcgttgcaccttgggtcttctatctaactcatccggtttttcggaagaaagttgttcagagaatatttatttttaggcctgactcatg ataataaagtttcgatttattttctataagtccgcagagattgaaaagtggcaaatttgattttgcttattccataaaagttatctctacttaattaattt tatcatgttttatgcaattttcaaagtaatgttggtgcgccaaaaaattctacttaagcttgaaaatttgagatgaaactctaaattgtatgcagttat tttggtaatacagctttcaaaacacagaacttgcatcttttgatcatttctaacaatgtagccttcacctaattttagttcccagaagttaactcaga cggataatgagcgttttaaatttttgaatttctggttttgccgccaatacttaacaagagcacacgctatcttgaggaaaacaactacctgaaaa ggggcgtagtcatttagttcacacttctctgtgcgtttttttaaataatgttagtttccaaaaatttttagagacccgaagaactcgggggatgtcc aattggggggattaccaactcgggggacacggttttaaaattatttttttcttgttaattctcgctctattgagaaaaatacagttttaaaaccgtgc ggcagttgcagaaatgggcgtattgcaagccacggttctgtgggcggggccaatcccccgagttggtaatcccccccaattgggcatcccc cgagttcttcgggtctcaatttttagaattgtttaaaaataataatgccaacccaaagcacaaaatccctgcctcttaagtgacagtcttcattctc cgagttttgaattccaggcgtgtgtgacgactcattcaaattattgtttttgtttttttttcagattctcactcaatttttgaaattttctgcgtttcaaaag gttttttcggaatatttttttaattctaaagcttcaaaaactgaattaaaagaattttctcctaaaaagtcgccgaagaaacgcagagaaaatcggc aaaaggcggcaaacattttattttcaaattttatccgctttcccttgtgtttatctttattttccctcaatttgcttaaccgaaacgtctgttttcagaat ataa xpa-1

SEQ ID NO: 102 ggacgtgcggcgaattgcaccaattggtgcatgttcaaaaaggaacggagaagagccaccctgtgaccactcgagcactaatttgaatga atcaacctccccaagtagtaacatactaaccgagaatagtttgaagttctgggggtataaacaagaatggagatagcaaaactaacgcccg agagtaagtaaatacttatatggtgagcctaagtctcgcgtcgatttattgttttctgttcagaacacaacgtgcatatctagaaattttcgatgat tcatgcaaaaatgttttcaaataatttttcaaaaactgaagaaagtttgagaaataatataaatttaggctttccttcagataaatttaaatataaaa aatcatatatattttcaagatgcgagaaaaatatggaagcggccagcagagatacgctatagcgctaaacaatgtgtgcgattcacaagagc -continued ttctgaaagataaaaattgtgactacgattcaataattgattcaaagtttgataagtcaatcgatttcaagtgaaaagaaagagcttgagaacat gatgagtagcaggtgtagaaaacgcatcgacgcgatttttttgttttgtttggcgccactaaacacacagacattcggtcatacactcttccaaa tatagtcaatatacagtgtgttcgagtgagagagaatggaacatgtcgaaatatagtgtctgaagacgagacactggattattttgacgggaa agcgtgttccttccggttgcaggatgctggtgcagcaaagtgtcaaaatcgatgggaacagggaaggaccccaaggataattgaaagatg agcgaggagaaagagagcgactgaatgagttattacgagcggcagatagccggaatagctggcctattttacattgcggtcgtcgctttttg cggaacgggtcgaacggttttcaatgcaattagacgattcgtcatctttttgacatttttttagatacaaaaaatacttatcaataaaaaagtttttta gaaaaacttaaaatatcgaatttatctttagaaaatgaattaaagaagatgaaaaataaaatgaaaatctaaaacagattccataccgtagtttc acacaaagggacatttatagttctcaaatttgtgtcccgccgcgaaatcaaaacaaaagaaagttagtccgtgtactccactcggacaacattgtt tcgcaacactttttttctgcgaacattaaaaaatataaatttgttcaacttccatttttttaatgttatcaaatgtttcaatttttcttaatttttatgatatt ttcagctgaaattttttgtttcgattagatcacaaactttttttgatgtttaattgaaatttagagatgtattagaaagtttttttaatcttcaaacaaaaa acatttttgtcaaatcgagacctcaaaataatttatcttttcaatacaatttagtttccttgcttttaacgttcaaatcttgatcatttctttttttttgtt tataaacgattgtttcagataa nth-1

SEQ ID NO: 103 actgggtcgacgagaagttttggaagtgagaatttactaaaaaaaagaattaaaattagaataattctgtagacatccacaaatcacctgttttt cagtcgatgaaaacttgaaagtttataatcgtctactttatcctccttcttttcaaagtcaattagaacaccatcagctcctgaacatcgatttttttat atatcgatcactgggaaagaatctgaaatcactgatataatagagacattgcattgttgacataccttgtcagtcgaactcgaatcaacgatct gatcttcatttttttgtgttagttggttagtcgttagtagattataaattcggtaataaatttatagtggtagaaattaatgagaattatatccacgaatc cgcgtgtactgcggaaatattcatttttatatttataaaaaatgttacaagtgagatcaaatttttttttaatgtatcatagaagagaagcgccaaat caatagaatgctgcacattttaccgcatccaatcgttccatttttctgaatttgaaataattattcatagctccataacggttgagtaacgtgaatga taattctgttttaaattattaagactaattcccctatttgaattccctccaaaataagaactgcaagactagcgatttgatttgagcaatttgcatcg cctactttccaaccaatcaaattaagtgtgcgaagttcgaagtcgcctacctaccatatacttcccatcgggtctcttaacaatcattggcttga acgaaacttctctacaaactctcgttggtggcgacagaaaccgtcttgtcattttgccacgtagcaatagatccgccaatgcttcaggaatctg atttgatttcagtgcttctgatggaatacttccaaagcatcgatgaaatgcctgtgggactccatcaatgtcttcgaattggaacttccatagaca acatggttgttctctgaattttaaaaaaaatgattatgattaatgattgagtataagttcctgagccagttgggcaacctacattccaagagaagg atcgcactcctttccaaatgtgatccttggaagtatggactttgtgtcaaggattgctcgagcatccagattccgtggtagaagatatcgattgt tccaaaaaatcatcgagaaccactagaatctctctgatcctagacctctcattatatgaatttacgatagaagttgtccgaaatctggcattttctc cccaatccatcggttttgtttcaattgggtgaatttttttagaaacgtctcacctgaatcaagaggatgtgatgaagatcttaaatctctgcagttca ccttcataacatacgtacatcagtggagacctacttccagggtctctgaaccatcgatcaggaatatgaattgttaaactgaacacgtgggtta ctgtagttatatttatatttctcacttaacaacaggaatcggtatctgtttgatagggttgaagtgtattccatctcgaaaatgaatcggaacatgg aagaattgtttcctggctagagatccacaaaagttcgagacgttgtcaccggtaatccgatctccgagaagaacaatctgtaagaggtctcat ctgggagaagcttatttcagtagttaccttctgttcagactctgcgattccttgactataatagtcgatcccttcaagattctgatgaattgcatcc gaaaatgcttctttaacaacttcgtgcaaatgaaaacgtaattcgttttgatcatcatactgaaacttcggaaagattttaagtattaccccgatcc aaatgtttcgaattaaagttataaatacggtacccggtttcgacacgatttttgtcaaactcgaggaaactacagtagtccttaaaggcgcatac taatagcgcaaaatctcaaccttcgcttaccaacttacccgcacaccttcctttctctgcgaatcaataataaaattcgaaatcggcgtcatcatt ctataaccagtacaatgaataatcaaactaaatagaaaggcagcttgaaacatttctttaatcttctcgcaacgaaatgtgctccggctctcca ggcttatcagtgttagaagagaagagaaggataaaacaacaataaaaacagttttcatttgtctcgtttcttgcttcttcccccacgatctgctg atctgaaaatgcattctttcagt sir-2.2

SEQ ID NO: 104 caagtggtatgccaactcatttgagagatctaaacatcgaagcccatcctctacttcgacagcccgtagaagttgtgtagcacattttgaacat gtgagcctgtacaaaagccataatacttctcaactactatcatcgtcatctctccgtcaccaatgatctctactcaaaacggttatggacggtttt tttgcataaggattcaactagccctacacgattgctttgatctctgtacatttttgcgtttaatatggatatttgcttttttaatggatttcgatcttcta -continued cttttattgttgatttttctggttttgtgggggttgtgtacaaattttgtttatttgttgtcggtaaccacgggtaccatattatgtgaatcgtttatcatc gtattaaatcatgtatacatgcattgtacagagtttttgaatataataaatgaacatgacgtcatttgcacctactttgtgcttttgaactttcactgtt tcagatatttttatttatgaaaaaaggtatctatgaacaagcttttcaatacattataactttgttgtatctggtctgatcctcaatatttttgagtcttc aaaagaaacaattataaattgcaatacatctcaacactgttttatggcgtctcaaattttgaaaaaaaaaaattattttataaaaattgatttgcagc agacatgttgaaaacggtgcttttcttttaaattatttttgttgtgataatgtaattaactacaactttacataaattgaactgaatatacgggtcattc atttttacaaaccttatctattctatcaataccatgactttttttcgcgaaaagtcagccgacatgacatgactcttatctctttttttttttgttaattcttt ttttgttgcgacaaattagtgtcaaaaaaacgtgaacccattcgatcacataacattttgaacttcaagaaaatcacacaatcgataaatgatgaag tatggtaagtcaaaattttctaatattccaactgattaatagttagtgtgtttgagttttactttttcaaattaatgtttacattaaaacaactataacaa tcctcaattgaaatattgtacacgaaataaaaatcaaaacatatgtatgaacatatttctcttatctttttgtattctgtcaaaggggtctaatttttttg accatttttttgtcagttagaaccaaataaaatcatgccgcatgtctgtgaaaaatcaccttattctttctctttgagattgataaaaacgttctgta ggttttccaaaatgttaactaaaaaatcaaatttaagccgtcggtatagtattacaggctaggtataggatgctcggataatattaattttaaaaat tcgaaaatgcatcatacataaaactttttaatacaaaatatagatgttttctttttatttatttattaatataacgtatctatataattttcaattaagcaat aaatatttttgaagatttgaggataaaactaagcaaattctaaaactgcaatgttcaatgaaattgcgttattcagtgttacctataaagatttttca aaacgttactctcttattcttctcccattcacgtgttgcactttctgccagccgccttctcggagaaactaggaaatatctgtgactttctctagcc actctctactctctcgtcagtgcaaatagagcgcgaatgctttaaaatgacgcatcaatcactctgtcggtcatttgattttacacttttcactgat agcttaaagctcggaagcggaactatagtgaaacattttataaattacgatttagattttttttgaattctgtatcatgctgcctaatttttaataatttg aatatttttaggc exo-3

SEQ ID NO: 105 tgcccagagagccgtcgaccaattcaacggagtcgatttcaacggaagagctctacgcgtcaacttggctcaaaacagaaacaactaattt tcatatcggtactttgttacttgtttgatctttaatgatctcaataataataaacccatgaaatcgttatcataaatatatatgctctatttttttatttcga atcttcatttggggtcaatctgatggcaagcgttgaggctagaagcttgaaggaacggcttcggttcgagcaagttttgaatcctgggctatg cgcagcccaatgtgagcttacaactgaaaattcaagtttcaacactcttcgcggtcttattttggactaattcctcatattttcagcttgaaatgga aaaaatctgtcgaaatcgatgctattcgaggggcggggccaaaacgcaaccctggcacggtttttacgcaactgccgcacgttttctccaa ggcagggtgagcggaaaaattaaaccgtcataaattttctgctacggcctaaaatcgtcatgtctggaatcttctctgtttacggttagtttttta ataatttattttaagtattaaacaatcggaaactggttaaaatagccaataaaactcgatattgtcctgaaattttgggatttttcggaaaaatcga attcgcgaagttttccctaatattttcatttgaaaaggcaattttaagtgtttagattcaaatttggttgcgaaatatttaaatcaattaaaatttttccttt tttttagttggaaacgctccattccagaccaccgaggaggagcttggaaacttcttcagcagcatcggacaaatcaacaacgtcaggtaact ctcccagccagcccgagcttcatgatttctaacgcaatatctctttcagaatcgtctgtgatcgcgaaaccggacgtccacgtggattcgcctt catcgagttcgcccgaggaaggatccgcacagagagccgtcgagcagatgaatggagccgagttcaatggaagaccactccgcgtcaac ctcgccaacaaataagttgatcttcatatcgggtttttgttactttttttgctcttcactgatctcattattaataacaatccaatgaaactatcgattta attatttaattcaatttcaactattctctaactaatctgttcaacattcggggaagtttctctatttgtcatccttccatccgccgacctgattcaacttt cttcttccccagctgctccgttcaagagcctactcgactactaacctgttgctgaaa ung-1

SEQ ID NO: 106 tccggcaaatcggcacatttccggaattgaaaatttccggcgaatcggcaaattgccggaattgaaaattttctgcgaatcggaaaatagtg ggaaattgaaaatttccggcgaatcggcaagtttgccggagtcgtaaatttctggcaactcagcaaattggaggaataaaacatttgcagac cggaaattgtcgcccacccctgttttgcactacgctttgacaagtgtgaatttattcgctttttttatttgcctgaattttgccgataaagaagatttc cggcaaagtggaaaaattgccggaatttaaaaatttccggcaaatcggcaaaatgcccaatttgccgcccacgcctgcttcacaaattgatta attgcagcctcttccgtagctgaacctctggaagaagccactacaacgagtgtgccagagccaacagagtttcaattgtcacgggacattta tagcactgtaaagccgactgatgaggctcatagcccgccgattcaagcccaaccgaagaaaaaagccacgccaagacggaagaaagc agatgacgtggaaactgtagtagctgacggaacagcgacgatcccgaagccgaagagaaaaaggccgccgaggaagaagcctgagc -continued cgaagccgaatatcgtttttgaaacaacgccgaatcctccgacagaaagcttcgcagccaacaacaatttccagcagttccagtttcaaaat cagcctggtagttggacctacaacaatggattcggcaatggatatgggtacggcggtggaaccactggatacatggataatcttgttggca gagggtttgacacggtttctcagcagcctggatttcagaatcaaggtacatttttttaaaaggaattgagaaaaatgtgccaaaaaattttaaag gtggactacgctttgtggggaaattgctttaaaatacgcctatggtaccacaatgaccgaatatcatgattaaaaaattcaaaaatttttttctaaa ttttatatgatttttttgaaaattggaaaaatcacagttttcccctaattcctatttgaattaccgccaattgaatttgttcgatggggcgcgcttgcac gtttttaaatttatttattttatttttttgttattttccaccgatttttaatgttttcggtgtatttttgctcgaattttagagaaaaagtcaaaataaatgc aaattttcgattaaaaagtgcgcttacaggcgtaaatcagtgaaattaattaattcaggttcgaaatcgtttaaaagcgttactttttcatttttacgcct gtaagcgtgctttttaatcgaaaatttgcatttatgttgatttttttctctaaaattcgagcaaaaatacaccgaaaacattaaaaatcggtggaaaa taacaaaaaaataaaataaataaatttaaaaacgtgcaagcgcgccccatcgaacaaattcaattggcggtaattcaaataggaattagggga aaactgtgatttttttcaattttcaaaaaatcatataaaatttataaatttttttttgaatttttttatcatgaaattcggtcattgtggtaccataggcatgtt ttaaagcaatttccccactagcgctaccccacctttaaaggaattgtgaaaattgtgaaaaaaaaaaatcaaaatttcgaaaaaaaaaagcgcta attttaactaaaatctctaatttttggccacttttccgtgctgcagcgtccgaaagtgcacttttttttgaattattattcttattattatacattaaaaacc cccgtactcctccaataacgccaatattatcgaccatctggacgtgaccgcgtgcaaccacggcctagctgccgccaccccattcaaacga gacatttcggcgggagagtccttttttttcgataattcggatttttttgtctgtttcaagtaattttcgccataaaaattaccattttcttcttcggtgcc atttctaatgattttccagtgcgttttgagtctgaaagtttgaaaataagagtttttgcacaaaaaatgtgtgagaaaagttcaagaaaatcgtcga aaaattcaataaattaattttaaaatttaaaaaaaaaattaattttttttaaaaatcaattctgtgcatacaccgccacgcaaaagtgcacacaattac ctaccgtagtcaatgcgaaattaaatgatttttatcgattttcttcattttcaggttacgaattcaccggtttgcctgcaaataactcgaataatttcc catttttgtgatttaattttttcaaatatccttatctatgccctcaggtttattttatctcatttccactcgtgtttttgaataaaaaattcttttttttttct tctagatttccgtttatttcaga mrt-2

SEQ ID NO: 107 atttttcgaatattttgtctgaaagtttcacgtgatgtcagagtgtctcatttcggcttgatctacgtagatctacgaaaatgcgggagttgagac gcagagttttcaactgatttcgcatggttaagaacgtgctgacgtcacattttgttgggcaaaaaatgcccgcgtttttgtagatcaaaccgtaa tgggacagcctggcaccacgtgaaattccagaaaaaatgtctgaacctactgtagttcacaatttaaaggcgcataccaaaaaattatagcg ggaattaaatttttatttaataatttttttcagttacagagcaattaaaaaaattcaatttcatcaaaattttatagaccaattttctcgctttatagctgag ctccgcgagccaaaataggaaggggagcacgaaaaaaaaaacagaaaaatgagctcgacagagcccatagcctcaagcgctaacgaac caaaaaatgcacacacacacaggaggcggagtcgtggaaatttcgaaaaaaaaaaacaagattttcttctctctcggctcaaatttgaatgcg gagcaagaatattacgggaacaaaaaaattctgagaatgcgtactgcacaacatatttgacgcgcaaaatatctcgttgcgaaaagcaaacta cagtgattctttaaatgacatttgtagtgtcgatttacgggatctcgattttcgaaatgaattcatttatcattgatcgagcccgtaaatcgacaca cgcactacagtagtaatttaaagggttactgtagttttgttttcgctacgagatattttgtgcgtcaaatatgttgcccaatacgcattctcaggatt ttttgttagcgtaataaaataacagaaaacacagaaaaaggcatgaaatttaatttgaaataccgcgctgagttttctaggccacgtgtcgtgt actccccgtggacaagcggtttttgccttatttttctgaagtacaaattctcaagtacaagtaaaaaagtacaaattttaccaaatttgaggaaaa gaactagcatgacaaaaatagaattagaaaaattctagagaaaaactacggatttctggcttccctcataaaatgaaatggaagagtttgccg aactaggccattttggctcagccatatctggagtagatttacggcgcgttccgtgtcgcggctcgattttagttgtaaaactaaatgaatttgtc cgtgtggagtacacgactttaccacgcgttgtccggcaggcgattgtcaatggagcgcgaaaaattcaatgcaccagatttgacgcgcaaa atttgaattttcaagttgtaaatcccttttttcttcccattgtcccatcaaatatccttcttcaaaaaaacccctgcgtctctcaggccatatctgcgg tagatttacggcgcgttgcgtgtcgcgtcgcggctcgattttagttgtctggcgggcgattatcaatgaagcgcgaataaatcaatgaggaa ggccagaaccccgtgaagatccaagaaaagttttctaggccacgttccgtgtactccacgtggaaaatgtcctttccggcaggagattgtca atggagcgcgaaaaattcaatgcaccagatttgaccacgcgtcgtgtactccacgtggaaaatgtggacactagggatctactaaatgcct ggaaaatcgtaaaaatctcgaaacttcctaaagaaaaaaaaagcaaatacacaaaaacgcattgatgtatgaacaaattgccctccccgtct cccaccaaaaactcccaaaaaattgctctttttttcatgtttatatggggggaccgcgggatttcataatagctccgtggtccgctcagctcatccg gagccaaaaagagcacacacacacacgcacacataaaagttgtaaactagtttcgagcaaaaatgatacgacggatgagtgtgtcacgca -continued atcagtgagcttctctcgctttcgaaagaaaaatctttttcgcaaaaagaaaaagtactttacactggccacagtgtaaaataagggtgaaaa
gatcgaaaatcggaggtttcaaatttgaatttccgcgcaaatgagagggacgaggtgcgatggcctacaaaactccgcaggtgtactcctc
tcggaaaacggtgcgagaattaatttttttaatttatatttaattttcagcgatttttctcagttttccggttaaaatttaaatttttcaggaaaa rae-1

SEQ ID NO: 108 aaactgcaatttcgtaaacgattgaaaattgagaaagatcaggtatctgaacaaaaacttgtacatttgaaatctcaacttcatttattccaggat
acctacaaatatgaatcctatgtgcttcaatgaattctacaggaaaatattcaataaatgaccaaatcgaaaaactttatttatgatcccaattatg
ttttctttgattatgctacaaattcaagaatcggcaaataatgggaaaatacgattttttttttcacaatcaatatatactgcttgatctctctgttagaa
tttcctccaaaatctgaactgtatgaccaaaaatcaatttttttgaaaatgcatttgtcccaatatttcctttctaccattctgctttgatctttttaacc
tttttattcgaataaaaatatattccgaattaaatacaattaatgtgtttccaccaactttacacataaaaattcattttctgatgtaaagatttttctaa
catacatgcattaacttatttctggagaaatatttctctggtttaaaaaaaaaaaacttctatttagttatgatttttccttttcacaacgtgaaaagttg
caaaacttctgcgaacgacgccacttctccacggtgttgtttctccggaacatttttccccagtgggacgccacgcgcaactgcgctctactg
ccaattttcaaaaacggaattctttcgctgaaatttctttaattttctttcgtttttcaacgtttttcattctctaaacttaaataatcgaaatatttcgaa
atgattaatgaagaaaggtaggcgttataatatttataatcaaaatttctcaatatcatgttagatattcattttggcgaatattcaacaattgaaa
atcaaaataccattatttatcgactggcgttatttttattgtttcagaaaagctgaaataaagcgaatgttggaaaaatgccgtaaaacggaaaa
ccgacagaaattttggcgatggttgcccaattttcagttgaacagctggcagactcctgttgtcattggtgttgcagctgtttctgctgcaattat
ctatcactatttttcctaattacccttattcctattgttcaatttttcttcatcctgattttgtgatctacctcatgtaataattttctcttcttctttatt
attttctgcgctctgtactttcttaaaactgtataaattaaaattgcaga rad-23

SEQ ID NO: 109 cccacacagccagaagatttttatgggcggcagacattttcttaaatccaataatgttttaatttgataaaatcgaagataaaagttcacgataa
acacaagtgaagttaaaaaataaaaataaaacattcaaaaaagaaataaacgcattctccgtaaatcgacacaatgacaattctggcaggtc
tcgccacgaagagtgttcaaatcatgtgcgcctttaagacgccaagccattttctcttctgtttttaccacttattttgttcttcaaaatggtttttt
gttttgttcttttattaataatcaaatgtttgtttattttatacatatatactgcttgttttgcattaatatcaatctgttatcgatatttatttctttttc
tttcaatacatgactctattcgtaacatttcacaatttttttgcagg brc-1

SEQ ID NO: 110 gaacgtccgacatgatgagatgcaataacctgaaaatgaggcactttatgataagaaaatgcggtaaaacatgcgaaatatggcaccataa
accgtgagcaggacaaagaacaaacacttggaaaagaaaagaaaatagaaagaaaaaaaggaaaactggagaaaacaaactcaataa
cacaacgcgagaaatacaatttcgtttcgtttttttcttctatttattagatttctcacaatttgttaccagtaaagtcacgttctatatttcaaactactc
ctaaaattcggtttgaacagttctctgataaacgaatttcgaagaacgatcagaaaacaaatctacggttgtgtgtgatcaatggggtcaaac
ggtggacgaaaggggacggcggagagaggaaaaagtgagagaaaataaataaaattgaccttcgagtgcagagttttgctggtattttgg
tcagaattgattatgaaaatctgaaaattaccgccgggaaagttgaaaatttgacgtggaaacgtttaaaaaaataagatgagaaagttagta
ctgtagatgtcgtcggatcaagtgcacagtacgcaagcaccgttacgaaaaattgcactaattgctcaattaaatttttttaaaaaattaattttta
tagtgtgttttgtgtttttttttctgctttttttaatgatttttaaaggcttgattatgtttttttctcaaaatttgaataatcaataacattaattaattact
ttattaaaaaaaccacatttggcattttaataaagcaagttatcgcgacaaacggcaaaaaatgtctctttttataaaaattgtttttttttgagttaagagaa
gatgtggagtttttttgaactacattagttttctaaaaatttttatcatctagattttgaggaaaaaagcagattatatatctttaatcttggttttaaaattt
ttttaaaaagcagaatattaaagtaaaatattataaaaagaaaaattcgtgtttgcaaaatttgtttgaacggaaccttgcaaaaatgatatttagc
agctaaactaactgaaaactactgcataaagctttcccaaaaagagctaccatccagaaaatgtttttttttttcaaagccgaaaaagaagaaa
aaaagatagaaaaccgaaaaagcagcatcgttttcgcgcactctttcttcttttttttcttcttttttctaaaaaaaaaatattctccgtagcttgaagtc
tcaggatttccaaagggaatttccttgatagaatatggaaaaacaagagagtcatcagagaagggagaggaaaagcggggatgctggcg
aagaccgggggcaccgactgaaatataggcaccggcggggaggcggggcgctctctcctctccgctttactccgccccgattgtcagtg -continued gagcaggtttgcaatgagtgttctctgatgccccctcagcgcgggagttttgaaatcaaatattttgtattttaacctactttattgatttttcaatta aaatgaaatgttatttgtttaaaatttaatttcag brc-2

SEQ ID NO: 111 tgtaggtctaaaaatatttgtttgagaataaatattcgaaatcaatctaacgtttttccaatctacaggtggcacgacacgctcacaaccaataa gtttcttgccacgctcgtcgatttttttgtagaattcccatttctgagagtgtttcttcgctttctgcttgctctggaacttctgaaataactttcccgcg attatttggatttctatatattttcaaactacttacctattttcgttttccaaagtctcgaattgtgtacttgtcgacgttggttccagatttgagcattat gaagaattccaattttaaaatcacaaactggctcaaaatctatacgctcgaatagagaattgtgtgatgtaagagcctgaaaattatatttgattt tctttccatcttttttttatttcgggaataataaaacattcaaaaagggctgagatctatctattttttcacatgcgacccatttctatttcacgtgaagc acatgattctgaagggcaatggaaatgaaaacccggaaaaacaaaatctttcagtttaaattgtatcaaaacaagtttttctagattacaaatgt acctgaatagtgatccatgaattgggacagaccacatcgaaataacatttcacacgtggcaatggagccattttgaagtttggctgaaattaa atttatgtcgagaaattaaaaaaaatcagagcgtcatcatgagaaaataggaaaggtttagactgtaaaatcaggttttcatggcgggaatga cattaaaatggtgataaggtgattatttttatcaaaagaatttttttgaatgattgcacctaaaatcgagtgctttttctttaatttgattatcaaaagaa aatacccaagaaatggaaaatgaaaatttaagagatgaaaggaaaaagcgacccggaaaaacatcaagctgggaagaaatctcaactag ttagaccaaagcttcgaactctgcgagcatgtatttttttttcctcactttctccttttcttctctatttctctagatctttattactgcgggggcaaaaa gagtaagagatagaaaagaatgacgcaaaaaatacacggatttaatatttgctttgctttttttattcagagaggaaaggtcaattgggggtttc ccctcgttttatgaatgaaaaccgcacataaatataattatttccacagttttaaacggcagaaacggttcgtgttataatttgtgagataattgat tttgcattacgaaattagaagaaaaggcggaaataaataaattagtgtcgcaatttttttttctcaaaaaggaaataatgcaattacgctccaccg gacagtaaaattctcagtttatttgaaaaacaaaaatttaatttttttcccttttttttcaattgaaatctcaaatttctgaactcaaaatgaaattttcaga ctttaccagaatattgtgacatcgaccg rad-50

SEQ ID NO: 112 atcgcagaaatgtgaaatcataaaatccatagtgagattgagttgtttattattttatgaaatgagataatcagttggataactactgct cacgccgtattcgatctatcattcgattctccgattctggaacatcaaattttaatcatagggagagaggttcgggtacttgagaaaa aaatgtcgtgtttcgagaggttttgaaaagtcagttgttaactggttcggtcaacatgtagagattgtagagaaatatgagaacttag agaattgacgtatgaagagaaaaaagtgggaaaggggagccgctgttgttttcgaaagaagaaaataagacagaaaaaaatcgg agaggaacataacaacaagttaagttgacttttgaactggaaatttgtcaatattgaaaaaaggaacagtgagaaatatcgatttcc acgtcgctcgattctatgaaaagaaattatgcacacacaagcttcacagtgagcatgctgaatgattgagcaaatacatgagaga ataagagaggaatgagatgaaaagaagcgttcaaatcaaaagaaaccagacaaaatggcgatttttttacgggaatatgaaccta ctgattggcagtggacagctggaagaataagaagatactgaaggaaggttgaagttgaagcttggaagacagatgatgagaga gaggaaaacctgtttctttttgattacgatcggacggaaatgagaaggaagtaagtgttttcacacgtaggtgggcattgagatcttt gaaggtgcattcgacaggttaataatcattctaaataccaggtgacaatggaggatacttttaaacagtaaatatattggaataaaa cataaaagttagtcttactcagaatttctaaaatttcagccttctggaacgaaaggtaaaatcataataataatacaagtggggctgtt agtagccctaaatacaagtaaaatgaccgaacacagccgttaaagaatgttgcagaaaattgcgaaatatttccttactcttaagaa caacattcgatgtgacgcaatatgatgcatttccttagacaaaaacgttcagttcaaaataaacaacaataaaaccgtttgtacgatt tctagaatacgagtttatcagttgttcggaaaatatcttatcaatcgtttgactgatgtttttttaaccatgtgagaatttgaaaaaaaattt catgattgccaaaaattaaaataaacaggaagcttttaccgagttttcgtgattttcagaatgaagaaattaatatgaagctcaaaatc aaaagcagagggaaaagaaaaaatcgaaatcttctttcggttaaacaacacgcgcttgcggaacttcggagcatcgtattttgtttt tgcgctctatttttgaatcggaaactgtttttttgtcagttttcgaaattgtttttttttctgtttttttacttcatgcaagagtttaactttacgca aaaattaattaaaaatacgcagaaggcccactttacacaggaattaattgaaaatactcaggaatttcactttacttagtcctttttcca gagtttccaacggaatcaatatattaatttaatttcgcaacatttttctttgaataaacctatttgcaaatgagaatgtttcagatatttgct tatcgaagcctgggaattgctt -continued

Y47D3A.29

SEQ ID NO: 113
Gcgtaaattggtttctataaattcttgacaaactcattccgaacggctgaaaatattgattgaactgaattcacattattcattaaaaaaaatagg ttagcctgttatgtagagaaatttagtgaataaaaaactgaatatgtatttatttaatagatttctcggcacacaggaattaggaataactcccaa aaaatagatatttggcaggagggccgaacagctgtgttttccgtgacgtcatacaggtcaatggacacaggatgtagtcatattacgggaac acacaattctgagaatgcgcactggggcatttgatttgacgcgcaatatctcttagcgaaaactatttacagtaagaatttaaattctaccgtagcgg gctcaattttcgaaaatatattttcttatcgaattttgagagcagtttttcagttttccatgcttgattttattattttatctttaaataaattttttcat tgaaaaaacgggaaaaacaccgggagaaattgatctggtgagaaaattataatatttctgctgttttcctgttgacaactttagaaatgtcaatt aaacaactatattttaaaataatcatttattttttaattacgtcaactagaaaacattaactttttgcgaaaattcacttctaccacactcatcatccc gaaaacagcgaggtctcatgaaattgcaagcgcgctctactgcaaggaaaggcagcgcgcgaagcaaattttcaaacaatttttgaacgt tttaccgcatttctcactttctcgcttaattttgctatgtttttgcgatttttttgtaattttcttcgtttttcag cku-80

SEQ ID NO: 114
tcactaaacaaaaaacatatatttgtaaaataccattttctttcatcaacagcttcaaaactatctgaagtgctggattttcgttcagctccgtcg atcagctcgaagtcttgctcctgttctggagtatcgctcattctggaaagatttaaatacaaccgaggaaccagaagagcgcatgaaaatata gagcgtgtaatttaacgtcagttattgacagagaaaatagaattacgaaagaccaaatcgggcaacgaggaaaacgtttaacacaaacaca acactgaaaataagcaagaaaaggaggaagttatcggaaaaccgaagaactttcaacttcggaaagaaccgtttaatttatgtttaaaatca aacaaaaaattcccgaaacatccctttaaactttgattttcacgaaaaacaacgaatgaccgaaaaatgtgatcaatctctgagagtgtgcac ttttgcgtgacggtgaactgtccgcgtgcaccagattcgacgcgcaaaataatcggcgcgaggttcgaacgaacgttcgtgaatttgtggg agcggtttttaatgtttaaaaatcagttttggtttattttatttgaaaaaaaaaacgataaaagctatattccagcagtatctaaaatgatcttcttta atattctaattttaatgttttaaaattcatttttcgctgcagcaaaaagttggtgtttgcgtacaaaacccgcgccagtcttgaaaaacgcacgcat tatttattcacatgtttcgcaatatttccatatgaacttctcaacatcaccaatttaaattaagttacagga him-10

SEQ ID NO: 115
cttgtttcatactaaaaactctgatttcagactgaaaaacatgtttttttcagcgaagaaaactaaaatttgtttgtggccgcggtggcctagttttc acggccgagaaatgtcacatgttttggcgcgctcttcggcgaattcaaataaactttttttgtttttaacaatttctaactttattttttgtgtttttagaa ctgaaattccatttttcaggagaa polq-1

SEQ ID NO: 116
ttctcctgaaaaatggaatttcagttctaaaaacacaaaaataaagttagaaattgttaaaaacaaaaaagtttatttgaattcgccgaagagcg cgccaaaacatgtgacatttctcggccgtgaaaactaggccaccgcggccacaaacaaattttagttttcttcgctgaaaaaaacatgtttttc agtctgaaatcagagtttttagtatgaaacaag lin-35

SEQ ID NO: 117
ctcttcttttactaatccatcaagcgacttttcacggagtaatctgaattaataatatttatcagtgcatatctctgaaaactaacttgacgacaaat gcttcgacatcaaaatccggctttgtgacgtccaaaacactagacattttacattcaatactgaaaaattaaagaaaattcaggaaaactcgag aatgaaaaaaaaacagatttgagacaccatcaatacaaagggaacgaaatttgggggaaatgctggttgccgaaaaaataagtagaaggta agatgtgttcaactggaacatacattttctgaattgcaaactcgatttctctcacattcacaatttttaatcacatttaatgcttcagttttagaaagtt ctgaagtatcctcttcttcctattcagtttctcaaaatcgatggtgtctccaggacgtgcacaaatgcgctctattgcgaattgtggaacatcatt gcgcgcgcgactagaaaaaaaatgagcgcgttcttgaaaattattttgctttctctaattttaaacgatttcgattacattttatctgaactttcttgg gtttaatcgaataaaaaacacaaaaatattcttcagactggtaaaaacttcttcaat Xenobiotic Toxicity Genes cyp-13A6

SEQ ID NO: 118
gtctagtttcaaaaaaaaattaaattaaattaaattgtgtaatatgtggcattatttatatactttttttgtcgatcatctgttaagttagtttttagtcttatc ttcttgtcgcacaaaacattatggtttgtgtttaatagaacaagaaagtgggtgacaagaatcgtatgatttggagaaacccagcaatcaaga -continued agattttgtttcaaaattcgtagtctggatactttagaatgtattctcaattttcgaataaagtttagaggatgtttttcaaacttttatcaatttttgaa aactatctgatggttttataattattacagtcacatatttgtagcttgtgaatctaaacctattatgtatattctcgttttaaaaaaattaattgccgaaa aaaagcaaaaaattttaatcttacgaaaaaaagtttttttttggatttatcagcttcagtgctcattttcatccctaactttctttcaagaaattttaga tatgaagaacaattttaaaattctagatcaaccaaatctctgaaacaaaactagttttctattgtttctacatattgatatttttttaaactccattatc atttttaatttttaaaaagttttctaactaccatctgctctccatcacctctttatgtttttgcatttgagcagtgaaaagtttgaagaatattggtaca acttttataccttccaaaaagtgcttgccccattctctatgttctcttatcagtacactatatctcaacagtcgacacatttgtgtggaaaagtgttg tttgtgtctgactgttgtttctaccaccgatactatttataaggtggtctaccgaaaaacatcaatacgtttctttttttattcctgaaaataaaaac cyp-13A7

SEQ ID NO: 119 gtttttattttcaggaataaaaaagaaacgtattgatgtttttcggtagaccaccttataaatagtatcggtggtagaaacaacagtcagacaca aacaacacttttccacacaaatgtgtcgactgttgagatatagtgtactgataagagaacatagagaatggggcaagcactttttggaaggta taaaagttgtaccaatattcttcaaacttttcactgctcaaatgcaaaaaacataaagaggtgatggagagcagatggtagttagaaaactttttt aaaaaattaaaaatgataatggagtttaaaaaaaaatatcaatatgtagaaacaatagaaaactagttttgtttcagagatttggttgatctagaat tttaaaattgttcttcatatctaaaatttcttgaaagaaagttagggatgaaaatgagcactgaagctgataaatccaaaaaaaaaactttttttcg taagattaaaatttttttgctttttttcggcaattaattttttaaaacgagaatatacataataggtttagattcacaagctacaaatatgtgactgtaa taattataaaaccatcagatagttttcaaaaattgataaaagtttgaaaaaacatcctctaaactttattcgaaaattgagaatacattctaaagtat ccagactacgaattttgaaacaaaatcttcttgattgctgggtttctccaaatcatacgattcttgtcacccactttcttgttctattaaacacaaac cataatgttttgtgcgacaagaagataagactaaaaactaacttaacagatgatcgacaaaaaagtatataaataatgccacatattacacaat ttaatttaatttaatttttttttgaaactagac cyp-13A11

SEQ ID NO: 120 gaatcttcgatgttcattgtgaattttgtatcactgccttgcctttattcacttcaggaattttatgttttacttgtaatctcaataaaaatgaactttcaa attaataataacaaactaattttctagttttacatcagatatctgctgagcttctgctcctcttccgtcaaaattaaatcaaattggctgagcagcg gcccagtcaactagcgaagttaggacataggttttctttttttttttttgttgaaatgggcaaattgccggaattgaaatttctggcaaattggcaaa ttgccggaattgaacatttgcccaaatctgcaaattgccggaattgaaatttctggcaaatgggcaaatcgccagaattgaaatttccgccaa attgtgattttgcactttttttctggaaatttcagaatttcaatttcaatcggcaaatttgtacgcatcctatttttgaaaagtaagcaaattctatgaaaa tatctaaagaaaacgggaaaaaaaactcaaaaagacactgtttttagtgtttccgttttataaaaaatgcctctaaacatttccgacaaatttgatg atccggcaaacgacacaccggcaatttgccgacgaaaaaagttgccaaacggcaattgttactggatcttatagtgatcaaattttggaaaa ctcaagtacagtcagaaaagcagtcagaacccagggtctattaaaacatcttttacacattgaaaagttacatatacttgaaaaaaggagaca tagagaaaaactcagatactgtctctgacaatttttctgctttgtgccactgaatggtaaacaagctgaaaggtataaaaactattgcaatttttg acagaatggtatttgaaatcaagg cyp-14A3

SEQ ID NO: 121 atgtaaccccaataatttttttttgttgcatttttactacttatatccgtttccatttttttaattttatgttgtcacgttttgtctaaatagtgtaatcttctt gtactaattattccaattattttaacccgtaagcgataaatgaaacaacactttttggtttttatttgctaattttaaataaattgtcatcaattctgaaaa ataataaattttaaaaaaataccgaagaggcaaacaagacattttggaaattctgatccggataaatattccgttagattttttattagactcgaaatt gcctgaaacccccgattttataacgaaacctcttgaaaacttctcaaaaaagagaagttaccaaactttaccaaatttggtctcccatcgacctt caatgtacctaactctagttgaatacgcaagataattaattgctacaaccaaaattaaacggcggtttcaaaaaaatattgttttcagccgctgc aacattgacaagtgggaaaaatttcaaattttaactaattttaggtcatttttttgagccgccataacttttttttgagaagttttcaagatattttattttg aagttcggagttttcagacaacttcgagtcaaataaaaaatatttttttaagtcgacgacaccacctcggagataatctttaaaaaaaatcttttcaga aatgcaaaaaattccaataagtgtcaaaactcccgagtagcgcttaagcagtggcacgtctgtatttatgtatttttgttttttttttttttactttattatttt gtgctttattactgttttttttttaaatttattttgtttcatgaaattttaggactaacgtgaaactcaacataaaaaaagctagaaaagtttcgcgtactg tattctatttttctttgattttattaatgtaatacatcacttttatatcttgagtgactaaactcttgttaagtgtgtttcaataatgttttgattttttga -continued ctttacttatacgtgctttgtagttttagtgacattagtgaccgaaagtgagacgataacaaattgggagcggtatataagtgaactacgaaacttct aaaaaaacaaaggctgtttcaca cyp14A5

SEQ ID NO: 122 tgtgggaaaagttggaggtttttgcacattttaggtgagcgaatatcccgttgaaattatagaaattaccgattgccggacagttttggaaattg tcaaatccatctattttcgaaaaattaatagaaaactacattggttttcagtatttgataagtctacgagacaaaaatgtctacgagacaaatgta cacaaattatcaaatttacacttccggcaattctgattttcggaaattgtccattccggcaattttgcaaaatttgaaattttataaaaataattctct acctgcctgcctacaggcatgccgcaactaaccttgaaaactttaaaagaaactccgaatttcttaaaattttaagtcggctggaaacttagaa atctcttgccaagataaaaaacatcgagaacatcgtaatcaattttatttgatttgatacgttcacaaagtgaaattccaatattgaaaatcaaatt caattaatcaattaagagttcagtgagtcgtccttgaaatgtaccaatttcacttgagcgctcagaatttcgttcaaaatcatcaatttctcgtcca aaaatcgatgaaattttgcgagtaggtacaagtttgtgctggaaattaatttattggttgtatggatatttttttttaatttaagaattaaaaatttacc atgaaaataaagtatgaaatattacaactatcagggtaaaccaagcaacgcgagatccagtcaaactgtacacgactaaactttaaatagca atactaatctaaaaagcaaatatttttctttaagtagaagcaaggcagaagtttgacatttttttccgaccagttgaattgtgattctatatacatctg gttcactcgaatttcagacaaacaactccacattcctcaatttctgtgatagaacaataacttattttcttcacatttctctttcaattatgcattttcat tctttaagtgtctttttttaaaatttgacaccatttgcccgcgactcgttgtccggaggtttcctcttacctcggagaaattccgctaaatctaccat gcatgagtctcaccacgtggacaacgagttactgtaacttgtgtcaatttacgggccgctatcctttttttaaatgatatgtaccaattgatacaa agaaatacttgttttgttatcaaaatagagtataaaatataaatgaaataattcaaaaattattctcaattgggccagatacaataggatagtggg gaagttcaaggatgatattgtgtcagacaaggagcaaaaatgcattaggccagtttttacagaattcattccaagtacagaatttttcaaacatt ccattaggaaatggtgaagaaaaccaatacatttcaacttccaaattttgaaatggatttaaagcttccctataaaatttgtttatgaaaataattt taacgatttcatttacaatcaccacatttttagaattctcagcacaggttgaattgttcagtacctttttttcaacatctagttcacctacatatgagtt cttaatttaattacgtttttttgaaaagtaaatatgttatttggcaagtccattcaaacaaaagacgtcgaccacttataatcaaaaagtacacttgc ggcagacatctcgatacttgttttctctgcctgttgtcactgatcttatcgatatgtaatattgtgaaatgttgcgcagtgttgaaaaataagatata aaattaggaaagaattgtataaaaatcagacaaaactattctgtccaacaaagatcatt cyp-25A4

SEQ ID NO: 123 gatgagatgcaataacctgaaaatgaggcactttatgataagaaaatgcggtaaaacatgcgaaatatggcaccataaaccgtgagcagg acaaagaacaaacacttggaaaagaaaagaaaatagaaagaaaaaaaggaaaactggagaaaacaaactcaataacacaacgcgaga aatacaatttcgtttcgtttttttcttctatttattagatttctcacaatttgttaccagtaaagtcacgttctatatttcaaactactcctaaaattcggttt gaacagttctctgataaacgaatttcgaagaacgatcagaaaacaaatctacggttgtgtgtgatcaatggggtcaaacggtggacgaaag gggacggcggagagaggaaaaagtgagagaaaataaataaaattgaccttcgagtgcagagttttgctggtattttggtcagaattgattat gaaaatctgaaaattaccgccgggaaagttgaaaatttgacgtggaaacgtttaaaaaaataagatgagaaagttagtactgtagatgtcgtc ggatcaagtgcacagtacgcaagcaccgttacgaaaaattgcactaattgctcaattaaatttttttaaaaaattaattttttatagtgtgttttgtgtt tttttctgctttttttaatgattttaaaggcttgattatgtttttttctcaaaatttgaataatcaataacattaattaattactttattaaaaaaccaca tttggcattttaataaagcaagttatcgcgacaaacggcaaaaatgtctctttttataaaaattgtttttttttgagttaagagaagatgtggagtttttt gaactacattagttttctaaaattttatcatctagattttgaggaaaaaagcagattatatatctttaatcttggttttaaaatttttttaaaaagcaga atattaaagtaaaatattataaaaagaaaaattcgtgtttgcaaaatttgtttgaacggaaccttgcaaaaatgatatttagcagctaaactaact gaaaactactgcataaagctttcccaaaaagagctaccatccagaaaatgtttttttttcaaagccgaaaaagaagaaaaaaagatagaaaa ccgaaaaagcagcatcgttttcgcgcactctttcttcttttttttctttctttttctaaaaaaaaatattctccgtagcttgaagtctcaggatttccaaa gggaatttccttgatagaatatggaaaaacaagagagtcatcagagaagggagaggaaaagcggggatgctggcgaagaccgggggc accgactgaaatataggcaccggcggggaggcggggcgctctctcctctccgctttactccgccccgattgtcagtggagcaggtttgca atgagtgttctctgatgccccctcagcgcgggagttttgaaatcaaatattttgtattttaacctactttattgatttttcaattaaaatgaaatgttat ttgtttaaaatttaatttcag -continued cyp-29A2

SEQ ID NO: 124 accatgtacccaatttctccagatgtctcaaaaagtccttcttcttgttaatatagctcgcctcctcaaattttgatcttccaattcctctccgccca atatattctagtccgtgtcttaccccttgacaaaaatgagcttttctcagattccgactaattccaaaaaaattccctacgttttgaataattgtcgcttt gtattttttttctcgttttcatacgggtgttcatcattcattttactttttaaaaattttcctctcgtttcttttgaacgtcccatttttattgcaatcg ttcattgtctagggtctatccttctaatcattcttcttctcagaaatatcacaaaccgtctgtgttgcattcaaatttttaagtaaaaataataaactaaa gaaccacaatgaaggtctaagttggcaaaattgaaaagccgaaagcttttcccggaataatagtaattactggagtgcatcccgaactgtct aaaagtagagaaaagattaagtggatatatatttttttatatttttttaatatagtaatctgtttgaactgttatacaaaccgaaatcgtgttagtttgga caaagttttgcatcaaatttttttttgagttttagatcgaactattgtgtttttaatgtaccagtcaatatttggcattcacaagcggtatagccaaatgt acccagagttgatcagatagcgtttttcttcactgtgttccgttgttatcaaataaattatgcaaaaactgcgaaaatttgagttcaaacattaaaa aaaatcatatttttctaggttattgcgagtttttagcaagaacaactaatgttttcatgtttaaacaaaaaaaactgagtgagtgagaaaaaaatctca tgtatgccatgggatcaagccatatattttccatagactaaaattatttagagatggaaaattgaaaacaggagacgggttactgtaggaagat ttttttaagactattgcaaatacataaatcttttgaatatattttacttcttcgaccgccgctttgaaacagtgcgttactgtgaacgttgaaaacca aacatttgaactcttcacctcacttgtccattttgttaattgtctagccaactgtagccacctttgatcaggtagacctttttccaatctgcgtctctca ttctctcaaattcacttagccatgttttgtacggacatcatttctgatacattaactacgataatagttgtgcacgctgtggtcatttgattaactttttt tcctgttgcagcagttcgcgagtatataacctgtctttaactgataaatcgtttgcattggtcgtttgaaggaaacaacaatacgctttccaaaaa cyp-31A1

SEQ ID NO: 125 tacagttacaattgaaataaatggaaatctctcttatttttacattgaaatttcttgctggtcacttcttccaatccaccgtagttaaccgactgggt ggtctactacccgtttctggttttctctgcactctcttcggagagagtgcagacaaaattctccgcgttcgcagtcctggttctgtttcgagacgt tgacgtcgcccgacaccactcctacaactgttcggacagcgtctgcaattttcgattagtaatatagttttggttgtgaatataatataaattgtg aaaaattgcattgagaattaggaaaagagcatgtgagaagaggaggggaatttttagaataactgagaatataatttagagaaacacgatta cttcgcatcaattcagaatatcttttaaaatctgagaaattttggttaaaaaataacacagggcgcttagtttgtggttttctcaattctgtttaatttt aaaacagtaattcttatttcgataaactaaaatgaatatgaaattttcttacgattaaaaaatgcatgaaaccagatataacaaattgaaggaaa actgaaaaacttcagaaagtgtttttttctgaaaataaaagcagaaaaattcgaagctcgcgcaaagaacgtaaacgcgctccattgctaact catttgaacattagttttttttcattgggctttcaatcttgtaagtgatgtttaggcatctaaaagttttataaattgacaaaatccagcttaaaagatg ctatcaaaaactaacttttcagaatatttatttggctaatgtttgacccatacgttttttgccgaaaagaatttcaaaaatgaaaagtatcttgaaat gcatcaaaatccgggaatattgccgatggtcagtttttcagcatttctaaattgagagactgaaatgggaatttatttatttttattcatctgcttttttt atttcatgaatatccgcatctgaaatcagcttttttttttcaggaaaattgattgaaagaagacaataacagctcgttgttcaacatctcgattcttcc atatgaatcgatgaatggaaaaaccgtggcatttggtaaagttttggctggaaccgaagttgtctcccgcatcgccttcaataaatcaaacac gaagggttccaaggcttgcgtcatcaccgactgtggagaagttatctgaaaggttttatcatagattttcaaatttttttggtttattattatttctttct ttttgttccgataagtccatatatgaaatttgtccagtttttatgaaaataaacatttattttatttaatattttttttattcatcatatgc cyp-31A3

SEQ ID NO: 126 tctgaaaaaacgttgatttaaaattttataaaaaatttgaagcaaaaatgaaagagaaaactaaaaaaaaagtaaatgtactgaagtgattggca gattaataataatttatcgataaaaccatttttttaaaaaacttcatcagtttttgtgagtgtcagcaaagaagaagaagattcacgatcaaaaattc gttgagcctatatgaaatagttgcgctggtttttcgacggggggatcaaatacgtcaaataggtcaaatagacgaagcattcataaaaagtac aatattcattgaaaaatagttttggatttgtttttttgtttcttcattttttttgttgaaaaaataatggtaattaaaagtttttaataattatttaaatca agattgaaatatcagaaaacgacaaaaattcgttcgagaactttctcaagactaccgtactctttaaagacgcatgacgattttcacatgggtctcac cacgacttgtctgaaatttgaatgttcgttcaaaaactttttttttttgcgattttcaaaaccaaagcttaacaaacaattttcctcaagttttcaacgct ttttgctcgtttttttcgctcaaataaattatttcagaaggttttgca -continued cyp-33B1

SEQ ID NO: 127 tatattcaaaaaaatatatttttttgtaaatgttcttgacaaggtgtcaggaaatcagaataaacattcaacaggtgtttatgtttttttttgtatcattcta aaaatcctaacccgtgcctgattttcataaaactaaaacactaaatgttgtcaatctgtgaccctggagcctagaataagttttccaaaatctgat tattaaaaacacaacaacagattttaaatagatttgagcacaagtcatgcattgagcataagccacaaatgaaataacgagagtgaatttttag agtctaattgaattgcattagcttttctaaaaactttttttcggctcaaaatcatttccacaaaaaaaacagttttaaaataataagagttggccttc agagcggttttgtgtttaacaaattataattcttattgtcagctcgattacgtttttttttcagtatctttcgttttgctttttgtttttagttactcgcca cgagagagggtttccctccaaatttcgcaaaaactagcacaaattatatgtatgtaccggaactaacctataatacttccgggttcatgccaaattc taatttctaaatccccagacagacacgctctcaacttcctccctctttttgtttatgaatgaatttagtttgtgacaatcagctaaaagtcgtgattt gaaaagttcaagaaatcgtcaagctcgtgaccacgaaaaagttctagtcacaatacatcatagactagaaagcatttctcgatcaactagttg acagctttttgtgaataaagattgagaattcgagttgttttcgaaccatgattacatggcttaacaataatacatgcagctcattgagtctatacaa acacaaaatacgggtctgcgtctaattatttcctacaatattttttgttattattcacaaaaaacgggagatagtcgacagctctcaaccggttgaa gagttgtgtcgtgaagaaacaatataaaaacattgaaaagtaataactgataacaacagttctcaaacaatattatagtgatcaa cyp-33E1

SEQ ID NO: 128 agcaaataaaataattttatggtttttcatttgaaaaaaaagttattaaccttccggcgcaaatgaataaaataataaaaatgattaagttattgca cggcccaattcatcgttgctatacttattgactacagaatatttttacttctatcaacaatgcaagtttgaaaatttccataaataagatttttcttatc actaccttttgcttattttcattttaatttcgtggtctctgctctcccttttctgacctgctgacagtttgaatcgtcttcaaactaaatactcggtatgt ttgcctaaatctcttgtaagagagtagtctctcattcagagaatttcactcttgttgttagaacaaacttcactggcgtgtattttgggaaaataga ttatatatatttaagagattaatacgatttctaattttagttgtccatcaaattgaatttttttgtgtcgtttttctgaataaacatctgaaattgattcacc atttttcaga cyp34A6

SEQ ID NO: 129 ttattaatattattgtatttctgaatgtaccgtattgtatttctacatattgaatcaataaattgttttgtacaataattctttggctgagactggtcgga caaattcaatgcaagcctgcaaacttattagactctaatagaaaatttttctcaaattggaacaattattctataattccttgccggttttgcagaaa aaatgttttttttaagaattaaaaatttaattatgttccaattaaacctacatcaatgctctagaattctccaaaacatcaaaaaaaatttgttgacaag attggaaaatctgaaatattttaatttttaatatcaaaccccccttcaaatgctacacaacttaaaaataaaaacaaaaagtgtggtcaacaactt tcaaagcgtagaacacgcattttgtgttgtgtgtcttatttcttttctacctcttatctatcgtctcattcgcgcgcttttcaattttgggggtaggctg agttagtataagaaaagttaataaaaaatattagtttctaattttcgagtttctaatctagcagtattttaaaata cyp-34A9

SEQ ID NO: 130 atctttaataattaaatgaataattaattgggagaaacatgtacataaataaaatttccattaaacaatgttcatttgtttaagctggcacagacca caaaagctgaaaccacaaagtttttttaaaccttgttcttttcttaaattttgtagtttcttatcttatcactcgtgtttcttgtcctccaaataattgtgaa aattgtagttaatgtgtcaaaaaagtcacatataagaagacgaacaacttgatttttttgttgacttcatttgaaaaaaaaatagaaaac cyp-34A10

SEQ ID NO: 131 tactgaattttgcaaaaatgaggagtataggaaaactcgctcagaaaatcgaaaaaaaaattagttccgttttgtaacactcagactttacaacta ccaattagaaaaaataataatacactaaaagagaagaatagaaatcagaagaagtcagtatcatgggagctcatgagttaattgcctgaaat gcgtattcccagaaataaaaatgcggtttcttagctctgagatctgaagtgtaagactgccaatagattccatgagattcgttgtgacaaggg gttctgaaaaaaggaatcgcgcaaatttatttattgcacagttgtagatgataaagtttctttcagatttgaataatttttaaaagcttctaaaaatta tcttgcagctaattgtccaaaaattattaaacatttgaatatttttctttgcttccaacaggttttatggaaattattaacaactgtaaaacgttaacgt agaataaagtaaatcgatcttgaaaacccaaaagaaccggccctatatttttggcaggtggaaattttgaatgaaatttaataatatagctcctg aacttttaaacgatgatattagatgttgaatgatcaatttccttgtagtcataaccatacggtttttgaaacatcataattttatcgaaatcacttgta aatcccccgggtacagctataaccaaccctattcgacaatttcaatttcggatattgtaaaaaaaaattttaaaggtggtgtagtcgaatttttttt attgctttattaggttcaaaattgtctgaaaaaaaccgaatttcataatgaaacttcttgaaaacttctcaaaaaaagttatgacggctcaaaaaa -continued tgacctaaaattagttaaaatttgaaatttgaccgacttgtcaatgacgcagctgctggaaacaatttttttttgaaattaccgtccaatttgggtat ttaagttaattatctcgcgttttcaacttcattataaagcttataaacagcgagaattttaaattttttttaccaaatctcgccgtccatcgaattcaaa atacataaatggtgttgaaaacgcaaaatacataattacatgctatactcacaatttgacggtgatttcaaaaaaaaaattgtttccagccgctgc gacattgacaagtcggtcaaatttcaaatttaaacgaattttagaccatttttttgagccgtcataacttttttttgttgagaagttttcaagaaatttc attatgaaattcggctttttcagacactttttagtctaataaagcaatcaaaaaattcgacttcaccacctttaacttagcaattgccaaaattttttta ttgcagtacatataaaattagaaacacacaatgtctcaaacctggaattactaggaatttttaagaaaatgactgaaaaaacaaactatgccaa ggacaaatttaatgtttttttcaaagtatagcatgtcgaaaatactgtttttgataattaaactgtttaatactactaatttttcacattctcatacgact atgaaaataagtgtaggaaatgtaacctgtgtgatgaacattctactttgccttatcaaattggaaaaacctcgtataaaatggtcaacaaaaa atgaaactgatttaacttctgatc cyp-35A1

SEQ ID NO: 132 aagttcacaatttattcattcatccatgtaaactgtatatttgaatttgtgttgtaaagaatttatcttcgaataaaatgtttttaaaggtttttaaattgt attctggtgagattgcttaaatagagtccttcggcgataaaaatgctaaaaattatatgaaaaaaactatacaaagaatatgtctcgaagtgttt cattccagatcaaagtcgaaaattagcttagaaaaaggatcttcgtcaaaacccctgatttaacaccaagacgaataggaaaaataaagtaa tttaaaataaaataaattacaagtgcgctccattgtaaaaacgctagaatttgcaaaaactgaacaatatttgattttcgactggaaaaaaaactt gttggtaaattgcatgaacagttttaaaatgtcattaagaaaactgatgccaatttttggttgttttctctcgtttaggaaattaaaattccctcttatt tttttagcatgaaccgtcaacgatttctggtcagataaattatggttattatagtgtgtagtttttttgagtttaaaccaatgtttcgaaatttttatcagt aaacagaaactacggtttgctgtatataagttaattccgatagcaaaagtagaaatccaaa cyp-35A2

SEQ ID NO: 133 cttctgtaataaaaaaaaattgaaatgtttagtgaggagagtgatagaaaataaaaaaagccgagactaaacattttccctgtgctgccctgttt ataaacgtttcaaaggaaaattctgaaccctgtaacaactgtcgtcgaccttcgaatagctcaaaaacatttggtctgcttgtggatcgcacgtt tgtttcacaaaattcattgtgatttgtcgtttgagatatatcccttctatcaatcaacatgttgatgccggaacttttaatcccaagaaatctgttaca caaagatcggaaaatacctttaattgcttacaacttttattaatagtcgatagatacacttgcttttgacttgccagaaatttaagtatgatgcttat caaataattacattgattacaattattaaataattgaataattgctaactacaactaaaaaattattcgaaactttttttgtaaaactaagaatcagtcc gcggatgaatggtaatattgttcaaattcgtctagaaaaaaaaccaaaaaaataattaaaaaatgagaaactgcgcaaaatatatatatttaaa atgaaacacaacgaggcggctctcgttaaccagcattgtgcaaataacccaaaaactctgttcacgccaaagtgctgaaaagagaaaaga ggctggcgtgaagccgacaggtataggtcctgaaaccgcgccccactggttactcgaatttgcgaatcattcttctttttttttttttcaaagcaa cttccctttattaatttcagattattgaacattcaattttttttttgttgtaaaaatcaattgtttttctccgaatagttaagaaaaatgtatgttttgaaa attatctgttcttgggaaataatagagttctgcaaacaaacttactatcagtcgattcgcctaattcgacccttctatcaaaaacgttgtgctgaatgt ataaattgtgaatttttgagtgaaaataactgataagagctttttttatcagtcaactgacagtgtgcatgttttgtataaaaacagtccactgatttc gaaaaatcaaatcagaat cyp-35A3

SEQ ID NO: 134 ctttgtaaattattttcaattaatttatttgcacatgtgaactattagaaaagaaaaagtttacttttatatttggtgctatattggtgataaatctatgc aattggtaataaatcggaaatacgtttattttctgcaattgaatataataaaaggtaaataaatgatgagtgcgagaaatttgagttccataattgt acaagccagggagttttgaaaaataacagaaccggtacctatttctctttttataacatataacatctgaaaccgacatgttaaataaaaaatttt gagaaagaaagttgttaattctcgttaatttgcgatatgtctataataaacctcgtagcatttctatcgactaaaaatttgttataatcagaaaaaa ccatcgaagttttcaagtcaaatttcaaaatactcttcacatcaaaacttgcaaaattaaactcacagactggaaaaggaaattcgaaaatgtct gaagaataacggttttggaaaccgagctgtactttttttccaggaagatcgttcacaaacaaaatcaaatagccataaattgaaatacttgcaca acttaaaaaaatacgagaacattgaagaaatatcgatgttcttcaatacacataaaatgttgttgtcatattgtttccatgagcaaatggctgaaat ctgggcaataataatatttgataaatgtccattactcacttggtatagcaactttatgaactaaagaaattataaaagaattgataattataaatgc aagacatcggggtcgaaacctaacgaatgatcgaaaatttggaaatttcaatgatatgactttttgtattgctagtagaaacatggaaacagc gaaaatattcgggaaaacggtattttgagaatgtgctattagagccataatggactgaacgatagcccaatttgtaattagaatcttacgattta -continued catttctgaaaatttatagatattaactttaaaacatatatgaatggatcttacaatccattaattacaatcaatacaataacattgttcatattaatta aaaataaagtaatgctcattaataaagacatcaaatgattaattttttaaaatgtgacatgatttatgtctcaaataatgtgtcttgttgtgattccatg aacggcagtaaaatataaaaacgatactatttgtagaagcaaaaaccatcaataaagttatttcaaagtcaatatgacttgttgctaagttctga aaagtctgaaatacttgcatagcttaaaagcgtaaaagtgaattactatgcataagtctgtgggcgaaatgcatgtgacaacatttgcacctgt ttggtttttaatagcctccaaatttaagactatgaaaattcattctgcggtccttcctgaacaatggcacgtccaaacgtctacaacatttgaatat ttatatttaatacaaaagtagaccataaaaatagaattaacatttttttgatcgacaatttccaaaaaaataacaaaaactgagattgttccaaattt tttttccaaaagttatataaaattttaaaaaaatttcaaaactttactatgatatatttacagcccccccccccacaaaaataacggatttcatcg ctttgaatttttaataaatttcaatgaaaatttatggaatagacacgggaccaggcggaagtcttgatactttttggtactgtgtaccaaccaaa aattgcagatacaaaaagaataaaaacattttttttaaatttttttattcaattttccgtatttttgaaccacacttaaataaactctatttgaagcaca gtcttatttccgtgttttcatcagagaccacagttccttatccttgcgttatcaattttcattacatctttacatcaaatcttttgtggcaaatgtacaaa atgtacattttgaagtaaatatacccgataagaattagttatcggtcaagagactgtttgattgctttatataaaatcagatatttcaattttaattctc aaatcgaa cyp-35A4

SEQ ID NO: 135 ttgtcttatattttattaaaatcggggcgaagccctgattttaaatccatattgttttttttgtcttccactatccctacaaataggaaagagaatgtgt tctttctgatgaagtaaaaacggcgcagccagccgacagccgaaattttcacgattttcggctggtagcgccagccgaaaaattaaaagaa gtcggctggcggcgccagccgacagccgaaccagctttttgtcggctggtagctttaaatttttttccagtttttttacagaaaattcgtccagtt cttacagaaaattcgcgtttctatgttttaaatttgataacatttgcagtaacggagactgctgacccggcgtttcccatgagaaaagagagag agagagagagggggagacagtgagatatacggcagagacatagacaggggagacaccattagagatcgtctcctatagagtgctgccg gcagggggcgttgtggacctgtgggaagaagggggggagacaaccgcacactgtgcggttgtaaatgcggaataatccatttaaaactaa ggaaaatagtggtctaatgcttaacagtgagccgcctagataaaacaaaaaaaagtcggctggctgcgccagccgacagccgaaattttc actattttcggctggtgccaccagccgacagccgaaaaattgaagtcaatcggctgtcggcgccagccgacagccgaaaaaatcagcca gccgctcagccctggtggggtggcgatgtgttggcagccaacccttcaacgaactgtatctcccgcctgtatctcccttcaaagtgagatcc tgtaacagtaattagagaccatatttacagccagcctacatgcatcactggagactctgtggagagggaggaggcaagagaaaggggag gcaagagggggcgggcgggcactgctgaaccttgaaagcgccgtagctccgctcacaattggaattgaaaaatgaaaagtatatatttga agtcaacgttaaaaggagaatatgatagcatttgaaattttggaaattggtgaagaatgaaaaaaaaagcctctggagcaaggcttgaagct cacaacttcaggaacggggctcgaggaactcatggccaaaaactttttatttgtctcgcttctcatagcaaaaataataagatttaaaacataa aattgattatccaacaaaaaactggtccaggaaaagagggaaactgaaaattcgaggtcaaaaattaaataaactaaaattgtgaaaaatgg tcgtagagagctgtgctttcagctggcattcggaatttatgcacttattacgaatttaacataaaatcccatttgatagtggaaaaattttcattttt ccagcaaaaacgtcatttttttgagaaaatgcagcaatttgcgatttctgaagttatttttaactttttgaaaaaaaaaaatatttttgaagagaaa atttcctgaaaaatacgtttttcaaaaaatttacctcaaaaagtgccaaactgaccgacttatggacgaaaaaccatcaaaaatcgctaatttgc acaccaaaaaaaaagggggggggggggaaatgcaattttcgatttcacactaaagagcccacttctatagcaatttttgagtttcactcaaaat atctcggctcaatgagctccaatctttctgaaaacaagaatacagaggtggggcaagctttttgaagagacagcaaaaaactgcatcaaaat ccatccacccaccgtcaagttacacgcgcgttttcatttaccacttttgtcggattttgaagcttaatatctcggctcctgtaaatcgaaatcggc tgaaaattcacaagaaaacttacttcactacgatcctcctgtcattaaattttcgtgagcttagaccgaaaactgacaaaacgccaaactttgct aacgctcgccactgacgccaagccttcagacacgctttcactaaatacagtctatttttccgtgttttcatcagagaccacagttttaaaataat gcgttttcaatttatttgatgtgatttatacattttcccatcagaaatgctgtgctaaatgtattcaatgtgtctttttgagtgaaaccactcttaatttat cagtcaacagataatgttgctttgtataaaaaggattcatcgaatttgaaattttcaatcaaa cyp-35A5

SEQ ID NO: 136 ggccaaaaaatagtaaaacttgatcgttttctgccattgaaaactgcgttactatcatgcttggtttttgggggcgctggtatagaatatgtgctca aggaagtgccggatatcagaaaactgatagttttgatcaaaaagttgtgtatgcctgtctttctgtctgtctgttgacactccctccgagaggca -continued gccagagcctcagagtgacaaatgcgaacggcagacggaatggaggaaaaggatgagcggtgctaataacagtacacagtttgacgaa aatccaagtttattgagcagggcagctttaagctgggaataaacaaggcaaaaacgtagagaatatttagggaattgggcacgaagatcag caacgagcagccatggcgttgggagaacgaagaaaagaagtgaagaatggctacattttaggccagaattaatatgagcaagggaataa acagcgcgcgctacgacactccgatgtgtacaatggcgcgcgcttgcatccttggcggcaaattcaaatgagaattatttaatttaattaattt aaatggtggaatgattattaaagaacgaacaaacggaattgtgtgagtaaattaccggcggatgattatcgctggattgtgggcaattcttgc cgataattataatccgcaaagttggggcggaggacctctactgaggccaagtcacaacactgtctaccgtctgtctattctatatctagaagat gtcaacattcagtggttatttttagtaataaaagtgtaaaacaaaacaattcagatctgcaaagctgaaaagtgatgaaaattgatatcttcaat tataatttatagtactttttaataattactctaattacaccccactgctttactttgaaatctcatatctcgctccattctgaagtagtcaactagaaa cggtaaaaaatccatagaaaattgtttttccaggtgacaatttttaaataaaaatggggtgcaatagtaatagagcaattatgctaattttgtgaa actgtagtttcaatactttaaactctatctgtacgttgttctctattgaaaaatacataccagatcagttatcaatttcatttctcatatgtcaatcgct attaattttactgataagaacacgctgtgtcagttgtgtcagttgtagttgcaacgagaaatacaatttctttttgggtttcttcttaagtttctcggc ttgaataatgggaaaactaattaacagttgactaaattatttaattttattatcccgcccttaaaaagttacccaaaaagatttagtgaagttatgtc gttctaatataatacttcgaacaacttgtgtcagttgtagtcagttgttaaaatctaaatttggtgataagatagtcgtatcactagttctgcaacgt tattatttaaatagccggagattgacaaaaatattcattcataatttttaaaaa cyp-35B3

SEQ ID NO: 137 tctttaatgataatttatgggatctgtatttctctttctgtcaataaaaattgaaaatgatttttacattctcaatattttctaaatcatgtttcgtgaagct gaagagtaaaattcgacatttagaaggtttcgttagaaaaatgaaaagtgtagtgccagaggggactttatctaaaacaggcctgaaggttc gacccgcgttacagttccagtctaaagtaataacactaattcaaaataatatatacgaaaaaaaacacttgaatattatttgatttttaaagattt tcaattttgaaattatcaaatttccttgaatttgggaatttttgaagaagtttcagatgcaggtttgaaatcctagaatgtgcaagtatgaaaactg aaacaaaatgtatttatacgactttttggtcactgccaaacttataatcggtcaaaactatgtttgcacaaatttctaacattaaaaataaacgatt ttaattttttttgaaaattatgcctgtatacatttcagcattataagagcgtttttaagcgattccctactgatgatactgtagcattctaaaattattg tagcttaatagctatctaatttgtaaaattaaatttaaaaaaataaatttgaagtggatctattagaaccttcatacaatatttcctactcttttaaattt gaaatttttcgagtcagtgctagtgatagatagaatacatccattccgtagttatctacgctttcctcttggaatcaacacatcaaaactcaaagt acgcctttattaaagaaccgtgctttgtagttttaaattacttgcttccattgtttgtagcctttccttataaaagatagcaggttctgtttaactatctc aatttcaaa cyp-35C1

SEQ ID NO: 138 atttttgaactaaataatatttcaaattgcacccgcaaatatcgtcacttttataccgataaacaaataaagtttagtgatgacttatgataagaac ctctttgagtctatatgtacgtgaaacaaacgttaaagaataacggctttacgtgttagtcattcataaaatttcataagttgatctggaaatttgtg ttatggacgttacgccattatttctcgtcactcaacgtctcgtcaatggtaattgtttttcagagacggtgaatcatgtttcagttgatgattttagg aaacgcatgccatgttgagacaccataataatttaaatttttgtgggtaccttttattgggattttctaacatttcagtcagaacttttagtagaattttttt atagatcttttttttttcagcttaaaattagtgttctaattactgtttaaaaaatgaaaactgaaacgtttgatgattttgttttaaaaaattttcaattttt ttcgatatgtttttattgattgtaagatcaactcttttaaagtttacttttcatttttttgttaataaataagaaaattttaccgactttttagaaatttaa tttattgaaaaactgataaacgtcttgttttgatcaattttccaataaagaatacttttagcgttagtcacaacatatactcaaaatgtgtcaaaaaaca atgtttcgaacagttttattgtttttttagcttcatcccgaacaactaaaaattgactttcccgataacttaagacgaataagtttaaaatttgaaat ctagttatttttcacgattttgacttttgttctgtccgcgccgaatctgaaacttgaacactaattcaatgtacacataagaatagacaagtagtga atatgcccattatcacacagactacatactttgactgttccaagcgtcgcaagcgtcgcaagtgtagcattttgagtcagtgataacaatgtaa gaaagtatataaagaacatgcatttgttcatttctattgcaaaaca cyp-35D1

SEQ ID NO: 139 tgattccaaatgataattggctagtcttaaaacattttatattttagggaattcgaaatcaaaactatgcacgtcatatcaaaatcaattttttgttcaa tattaatgttatttattcatttgacagctatcaataattatatttattaaaatagctgatagaactatttagggcattcacaaacatttcagaatgtttcc gaaagttcgcaacagcggattcgccacaatgcttcctcataacccatttgtaacaccatttttcaattgtaaacatgcttgtcaaaaatgcagta -continued tcattgggttgcaaaacataactcgggcatttgtatttaaatatattgaagttagaagaacggagctttgacaaacaggcaatgaatggagttt
gtttcaaataaatgaaatcacatccaacaaaaaccaactctgtgtatcaatcgcctcttggcaaacatttatcggagaaactctgaaacgggta
ctatttctagtttagttttggtatatttcacaactgaacaccttcacactgtttacttatttccactatatcagcattatttctcgagttccgataatcgt
ccaacattctatgagctttatctccaaactggctatatcgtaaatgcttgaaaaaataaaaaggatcatagcaatccgactcattagcaggtgtt
gtgggaatattatcaagaaatgcgttgtaattctccgtagtattttctgtttttagcttttcacaaatgtttcttatagtatccgaaaagcatgtctttc
catcttctaattgatcactgatatcatcaatctgaaaatattagattgatttttgctgagaagaacctcaaaaccaactatgaaaaaatcatttagt
ttgatgcagccgtcacggtagtttaacaaatgtgtacaagcaacttggacacaaggacgagggtcattgatgtagtaagattgcaaaaaag
gaactcagaacagtaagaaagccaaagttaaaagcattgttgtcctgaaaaatccttattagtgtgtgataaaaataaatttcacaagttggac
agttattatttcacaaaataaaatattattttgttgtgtgtactttacaattgacgaaaagatcaaaccgacgcaaaaatgatcaatataatccgttc
atatttgtttggtaaagcatttttctgctaatcaaaaactgttggtgcaaaataatcgcacgtttttttcgtttttttttaatttttggtctcaaaattaca
taaattttcggaaacatttctaacgctgaaaaaaacatttaattgtgtgaagtgtagccgtgaaaatgtgttaggtgttgctaccctcttatcttca
atcttatcatgtttttgtctcctttataaagaattgccggtgaacttgaagttcagatgtataactgtttctatc vem-1

SEQ ID NO: 140 tcccttgttatttgattttaagatttgcccttatgtcagtgtcttctgcatgagtacatgcatatttgcatattattagaatgttatgtataaaaagaaa
aagagagccacctcttaacgataatccaatttcttgttacgcagaaacgcctcgttttcctgtggactttcgatatcttcaacatgctgctattatc
actcccatgacccgtttcctatctgtttttatttcgattactacacatctgctagaaacacacgtcacgtgtgatttgtactcaccgttttctcctttc
atacttttagcctacaaaccacgaattgctttgtgacttgactcaattttctcccgaaactttttttcgtcctcaattcccactacccatttttcttgctt
ctccctgttgcaatattttcaatttcccatccaaaaacggcccgagcacgggttttcttttcctttttgtaggttcacttcttctttttcttcttcgtttct
attttttacacaatcattgttcacctttgggcaccccagtgaaacatttgtttgataaaaattgtgtgttccacggcactaaccacaaaatctttgc
tacaaatactactcgtattgtttgtgatgactgtggtgaaagtaagaagaatcgagagacattaggggacaaatataaaatagaaacgataag
gcgacgaaaacgcacattcttctcgatttccgaccgtcaatcgctgagtgaataattgttgacggcaactgggaaaatctgtgagaaaataat
gtaccatgttttcgaatttctaaaattagagataatttcttccgttttctcttttacatcttgtttcttcatttacaacaaatccttcttctttctctta
ccgctttgtgcacttgcactgtaaatgacggcaacttacggacctagcgttcgacgaacacagtcaaggacgctcacacatcgtcgacgggttc
acctgctctgttgcagtgatttttgatgtttttattggtgactagttttgactttttacaaa dhs-23

SEQ ID NO: 141 atttgaggactgggatgtcattaggactgaaattattctaaattagataatatattttaaggtaaaacgtctgtttaaattatttgtataagcaacaa
aaaataaacgaaaactaaaattctacctgaagttcaggtcctgaacaataacataaaaaaatttgggaaaacacgaaaaaaataaacttaaaaa
attaattaaaaaattaaagattaaaattaaagattaaataatctctagaacatagatctctaaaacacttcccgtagcggttcatttttgttcgagtc
tgactggcgttttctatgggaaacagaaaacaacacgctgtttgctcagtttcgagaattttggaattcacagacttattttgttttgccgtatatg
atcttaatcatagacatataatatttatgacaatgctttgctataattctgtgtggtgagcgttcgcagaaggttctgcacaattctttcaatgaaaa
aaaaaagaaaattataagaacttattagaaaattataagatgtagaaagttattcataaaagttagtattcccaagaaaaatcataaagaaagg
tttttttcaaggtttttttcagatttttggcgttgttcaacttgtattgcaatcattattattgcgatcattagtaatttaatataatttgctccagagca
tttgtaagcaatgaaatccaattttccctctgtggtgtttggtttagaaacttttgcaatttcgtcttgatgtgccgcggcatgccgcaaaaatcata
ggggatttgatttcccagtagttgaagttggcagagttaactataaggatgacctaaaacaagttttaggctacttgttatagacatggacttcg
atttctaatttggacagcatccgctacagtgaaagtctgcggattgatttcaaactctctaaaatcgaacgagttttcaattttttttcaattttgat
gcctaatttagtgaacacggtaattatagtttcttgtatataaaacccgtttaactccttaaattactgtttacgtttcgtgttgtaataaacgatctct
tgatcttcattcaactatgctggcacaaaaatagacacaattcgaagaggcgcagagggagtaacagacacaaaaaatgttaggacgtctg
cgatctcgccggtaagaaacactgaaaatactctctgcgtagtcacgaaagctacaaactttaatgtattcaaccaaataatgttaactgtata
aaaagaaacaaagaaaaaaaagtataaaaagaaactttaaaccaaaactaatcatcagattcaatatcttctatctgtttgacattctatttctgt
aagctcgaaaat -continued sodh-2

SEQ ID NO: 142 agtagagtcaatatcttgaaatgtttagaattctcgcgtatctcacatgttgaggtgagatatttgtaatgaatagtttcatagtctttggccaaaat atgattatacgttaaagcaaattttgatgttacgccgtttgaagaaatgtttttagcatgtttaacagagattcagactaaatttattctacacagttt ctgaagggatatttttttgccagagtcaattttcttgtaaaccagtgagccttaggtacatagaaaattttgaaaaatatccaagaataaaattttt ctgcatgccttattctgggcttatttttttgcggttttcaattcaattttatcgtatttcaaaaaattaaattagaacaaatgcatattcatttttacatcctt ttctaattggtaattataatttcaaaaatcttctttgcttatcatttgtaacaacaactacaaaaactgtactcgtagttttatctaaccgtattctttga ccgcatcctcccttttgaccattcaagtaaaaagatgacaatcgccgtctacatattgccacgtgacgcaaattacttataaaaccattcgtata aatatttcattgatttcttgaattcaaaaagc ugt-16

SEQ ID NO: 143 cccgaatttttttatcgcagaaaaccaagatggaataaataaatggataatctaattaaaaattgtaatttactatttggaatcaaaaataaataaa caaatcttataatatgtcagcaataaaaataataaaagaacaattgaaagttcaatgtgttgtcaagaaatccattaaagtatcgtcatcaacgg ggtcatcaatttccatgttgttgttattgtcttccataacatctatttccatgaagtcttagagtactgacaatagtttatttagtaaattaatttttgag aaagtttcttgacacattgctttgagactttgattaaatcacaaatgactcactattatcataattttctatccaaaatgttgatttcatttcaatttcca ttgaatcagctattccattacatccatcagttggtttacaaaatgggaccagtggcctcaatatctgtattttcttcctttttttgtgaaaatcgtacttt tgaaaatactaatggattctcgttctgatcgaaatgaggaaactgtgctgttttctaagaacacttgagacgtggatttttctttgttgttcttaaata cgaaaatcaaatttactgacaaaatatctaaaacttacaatcacttcgttgctgtagggataatcacaaaaatttgacatgattttctggttttcatt ctgaaaaactgggagcattttaatttgaaaaaaacgaaccgtagtctgccccaattgatttgttggtaaaggaagtgaattaaagcgacaagg aatacatttatctgttgaaagtgaatgcatttttctggaaagacggaataaattgaaattaaaacaatattcagttaaagggaaactgaattatcc caaacccgggttatttcaaaacggaatctacatcttactttaattctgattgtcagccctataacaactatttcatctattcaaaaagatacaaaaa taaaccaattaacattacttcgtagatacctcatcacatgaccaccctctcaagttgatataattaactttctaaattgaccaaaagtgtttgctaat gtgtatagggtatagtaaataggaaggagttcggaagttcgatgagagtaaatatcttttgtgaaatatctattggaaattagcggaaaaaaga taaattttctcctgaagtgcacaactaataacgaatatcttaatgtggaaataaatcaaatcaaatcaatatacatcccaatcatgacatccaag aaccccacaaaaatatgttcctaaaaactaactgataattaatttgaatgtttccaacagaaccttgctcgctttttgcacatttttccactttgtttc gctctacacgcttgtattttttttaattaattatatttttttcggcctcaataaaaattaaaattccagattgaacacatttaatgtcagaatataattaca gtacctttttatgacaaaacatatttcggtataatctcagatttccacttcttgtttcatggcccaagtttttctcaatgctcacttgtaacggaaaat ggagtcagtgaagctgttcaattctagataatatgatgctatcaaaggtcttaaaatttagataaaatgatgaaaatgacgacattaaagtgtag ccttactgaaaaaaccaattattgaactttaagaaaaaaaaacattttggaaaataaaggtaattcatttttcgtacacctaaaatttgaaaaaccg aaatttcagtgagaacgtcttcaactgcatcaaaaaaaattgtgaagaaaatcgaattgaaaagagaggctaaattggcttcatatctttaattta gccgattatacacgtcgggccagtctttttttaaatgactgtcatggaggacttgatttcaagattggaagtgatgaactacaaaaaaatatcaaa caatttttaactgcataaaaacggtttttctccgggatcaaagatgttttcggtatcaagtcacattcatggttcattaaaacatactatttttctagt cttaaaatgtaatctgtataattttatgttgttgattgaactcataatatgacaggatttttttttgtgatttctgtaatgaagtacagtcttacacgaaa actagagtaatacaagtcataaattttattcgtctttttttcccgtagtcctttcaataatgtatgaaaagcatttacaaactacaactctttcaaaaac tagagttcttatcatacaaaccacacatttttttgcagctctatataaaccaactgataatgaggttttgtctactctcattactcaatt ugt-63

SEQ ID NO: 144 gtgaataccacaactgaatgtctcgaatatggagccaatgattcggaaatctatgaggaaatggcatcgatttgcaagtatattgtacgggatt cgagagctcacggggactcggttccagagtgatttttgttgttcgccaattttatgattgtttcttgttgttaagttttctaaaaaataaattctttgat tttaataaatttcgaaaattcaaatattatggggacgccgagggaatcagggtgcaaaggcgctctaacgccaaatgacaaccgagcattg ggtctcgttaggaaatggcggcaaacgagacatttaaatttttttattacgggaacacaaaattctaataatgcgtattgcacaatatatcttacg cgctaagtatctcgtagcgaaaactacagtaatttttttaatgactacgcttgtgtcgatttacgagctcgattttagagatgaatttattttcgaata gtgtcagcgatatttcgctttaatttcgaatcgagcccgtaaatcgacacaaacgctacagtagtcatttaaagaaattactgtagttttcgctac gagatattttgtgcgtcaaatatgatgcgcaatacgcagtctcagaactttgtgttcccataataaaaagtgagagttttcatgcgcccttggag -continued cgctactgcacctcaatttcaaaaaacgcatttttctgcgtccccataatacaccgggattttcttttctcttcgtctgaaaaacaatcaatcatca ttaaaatcatcatctatcaccaatacagaatccatagatcaaacagatcaaaaaaccaacttgaacgcttgcaggcaactacgataaaaatat atttgtagtgtagtcatcatatcaatcatctagctataataatgcctgccgtataaatacaaaacacgatgatgatctttttgcgaaa gst-5

SEQ ID NO: 145 attagagaacttttcgagaagtctaccgttgtagttttcgaaatagtaatttatttagtgacgtttataaaggtttacatgatttggtttggaaattttttt aggagtttattcataaaaacaaagtaaccatggacattccagaagtctatagtacacgcgatcctaccgtacccttcagtatttctatcagattg atagctttcggtagtcaggtacagcctaaaaaattcctgcttgcctttttgcctacatgtctgcctaccttcagtcataatgcctacataatgatttt ttccaattgaaacttgcagacagaaattcaaatggcaaaaagaaacaaacaccgaaacattaatcacatttcttttcatatcagttttcctgtcaa agcacatttctggagtctgtgtgtatttttttgtgtctttatgtgatcggtgttgtgaaatttgtagttgatgttgataacatactttttttgaaacaaa aagtgattgattaggcttgaattcagagatatgttcgtgatactttgcgattctcgagccaaaaacacggtatccggtctcgacacgacaacttt ttcgcaaaatacaagctgatgtgcgccttgaaagagtactgtaatttcaacctttcgttgttgcggaattttcatagtttctcgttcaaaatatatgt atttattaaacaaaaaactaaaacaaaacaattgagaacacataaattgtgaaaaatcaatgagaccacagcaaaaaattttgtatctacagta ctctttaaaggcgcacatccgttcttattttcagcaaaaatgtcgcttcgagaccgggtaccgtattttttttgtgcaaaactttaggtctaggta atattaaaaaaaaattccacaaaactagaatctagagctttccattaaatttttgatgacatttgaaaattcatgatgatttttttccaacaatttcg aaatatccctcttttcacctggtccactgaattctctttccgaaagaccaccacaatttcagggctccgcccatttcgtggtttgtagccttcccg accctacgtttttgatgacaattgtgagagaagtgagaggttcagacacaaaaagcgacgtggtcgaatgagtataaatagagagtgaagtt tccaatttccctcacaattgtttgtttgcaatccactttccaaaaaaacacaacttcaatcaaaaatcatt

T16G1.6

SEQ ID NO: 146

Gctaaactttcgtattcgactgataatgagaacgtggaggagtatcgtgaggttctcactgaaaaagctgaacgtctcatggaagacttaaa gcgatggcacttgtacagtaaagatgtgacaaaggatttagaaacggcggaaaagttgactttatgataagaataccgataaaattatgaaat ttctcgaaacttttgaattgtgaagcaacttcttaataaagtaactcattgactttaatttttaaaccacggcttagagaaaattaaaaatcaaaca ctgcagctttttttgatgcgaaaattcattgatatggaacaaacctcaaatttgataaataatacaataatttgtcaagaaatcacaaaaacgttctt ttgaaatgcaagttataagacatacgcaagatgttatgtcggtggctggttttaactataaaatacgaaacaattgacctcctgacacaaaattt ccgagcttgatttgtctgatatcatttgtgctttggaattattgtttcatgtgcataaaatctacactgtgttcattcacgataagaagaatttcagac agaaaccacaggaggttcatcgatataaaatgctaatcatttgatttaaagaaccatactctttttactctcgtcgttaagaa Cell Division Toxicity Genes mei-1

SEQ ID NO: 147 cagctatcccgaattctcgagcgacatccgtcatctgaaagagatactaatgtcatgtgaagtggtattaaaaatatagtaagcacggtagaa acattaacttataaaattgagatttctgataaataaaatttttccgggagttctgtaaaacttcttacggttttaacttgataattccatagggtttaaa atttccttttgtttcttgagtttcttctcggaatttgaacaaaaataacgcgtttaatctcgaatcagtacaatgatggactacacggcagttttaaa aaaccaattaataataataatcctaaaaaatgagaagaatatttaagaaaatgtaaaagttttccgcggaattccgctaaaattcgaaaattgaa agtgttcaaattgcaagcgattgtgcattcagacgtgacagtgtctggggtgtattgcgtactcgacattttaactgacgacacttgtacttttgc gccatacttccggagctccagctccgcggagccctgagcaattatttttttactttttatgaaaagctttctatagatatcttttaagaagttacact ataattgtgcaaatcaaactggctccggacaacacaaatttcgtctatacctttatgatcttttttttgttaaacaagtgaaacaattatttcctttttca aactgctcttgtttcttctctttattaatcaattttttttttttttgctttgtgtaaattaattgtttgtcgcggatgagctaattctgaggtttgaccagcag aaatctgttttctgaaaaatcaataactcgccgcttaattttggttttattcaagtgatatgcaattagaaggttctaatcatttatatctcgctgaaa gatctcagatttcaagccttttgctaaggatttaattcctaaaactttttttgacctatcatttttttgtgtgatctaccgctgtaaatacttgttgttttgc ggctaaactctttcaatgtttccaacaagtgagccaatatcaagtaaaaaaagaaaaatcgttttctattcaaccattttattctgtaaataatatta -continued aattcatcttcacggtacaatcttcttctcccatctaataaagtccacgcacactccgttccgtcgtttccctattcgttatcattcatcatcttgcca ttttcttctccgccaaatcccattgtcttatactaaatttcatcctctcgtctgtagaagtgtatattattgaaaaattaaagtatattttcagg mei-2

SEQ ID NO: 148 cgcttcattttccaacaaaccaagtactggagccatttactataagaactaaattaaatattaaatatatcgtttcaagaattcattggaatgagg caaaagtaaatacttaggattaaaaaatccagctttatattaaaaactttaaaggcgcatatgagatgttattcgggtcccgcagcgctcatgc ggggtacgatagtacttcaaagaattacgcgggaatttcttttatgcgggaaaacggtttttttcttgtttactagttcctttctttcgtctaattttgat atcttgtgttttttccaattataaaatgtttgtctcttcttaaatttgaaattttgaaatttttcag mel-26

SEQ ID NO: 149 ctctccttctttcatattctgtgtccacttctcactcattgaatcatacatctctatgttttctcatagtcatcatatattgtcagctgcagaaatctcat catttttccaaacgaaaagctcttaagagaaatgcttgttttctgtggggtacagcgaatggcttctgtgggaatgcagtttgtgaatgtaaata gattgttatgcagtcttgcaaatgtgtcggaggccaaaagtagagtagacatatttgaaatttatagctttgagtgtccttagtctattttgatattt catttctgctttcctcagtctctcattccagctgcaaaaaataaaaataagaaaaaacacgaatcccgtccattcgccattcaacatagatcata ttcctcagatttttttgcagaatatgtaatttttgctgaatgctcgctctattgtccttcattggttatcaatctttttgcattaatagctttaatttttgat gttttcgaaagattagggaaaaatttttttaatgtgtcttttgtgacttgagattatatgctacactgaaaaaaattggtcgcataacatttcagagttcaa agtgtttttttctttcgattgtgtaagcggcaaaattctacttatcatgcatttttgtttcaatcaaaaaatttgatgtgatttgtacatggcgtcggtttg gtactagttgtccacttcctcagccatgaaaagtgtgagtaagtgataacgtttattatctttttttgaattcattctatgtttaagctacacgtatttaa ctagctgactcatttccaccaaatatgccaaaagacctccgagatttttttttgaagataatttcgatttcgcagaaaaaaaaaacatataagtgat gtgggggtgtgtcgccttcttcagctttccatagtgaaagtttcgtaaaaacaagcttgctatttcatttttccccgttctaataccttgtcgccca gaaaaaatatttatatgatctttttcaactctttttttgtaaaaatggccaaagattagctaatatttgtataccatcaaagttctgccaaaatctcgtt gaaacatccatcgtagaacactcattgggttccatcaatacatttttttgtgtaacatcagtcgattgttatcattcgtatatgcatggtcatctcaac cgccccttacgacgtcttcaaccattttctcttctaactctctttctctcaatttcacttctcactactctagtctattcaattctttgaaaaggcaaaaa aaaatgcataaaaagatgaagaagacattcaacagacgggtgtcttccttatttttattcaaatcaaaacaaatggcgaccttcttattcttctctt ttgcccgatgattcattttcttttttccattaattttgttatctattgctgaataacccgctttactgaatgtgtggactggcatttgccacgttgcatttt ggaaaagagccgatgtagttcttccgggtatatgtattcacagaacgattcataagatcagacatatagacataaaattcagcgcattctgcct tgtggtttgtcaactacttccgtctttttctgcatattcatttcccgcttctgctgtcttgttcatgaactcttgaactttgcactttgccctctttttaag tttctctcgattgatgcagcagcagcagactgtcattcatatttgtctagtgatttcgtaggttcaaacaacttattaagcggtttcacctaaaattt cgcatcccaaaataaaagttcaattgcgaactagaagtacccagaagcgaaattttttttgcttcaaaaatacggtacccggttttcaacaaaat cgttttcaagtgacatgagcgattttcctttttatggaaaatttctaattcaaaaataaatatttgaaataccttttttagattattatatttattcttggta ttttctctattcccactaaaatagactgatacgagaacagttcttgtttgcgcaaactcacatttctctctctatctctccgtctcttcttccgtatct ctctgacggtcccatactctctcactcatcgtcagacaccaccacttatcgatctattttcgacgagtgagcggctgttcgtcgcatgtttttttat aacttgattcgatcaatttcatcatatcttcttcacttatttgaatttccgttttgaacatcatttttccgtcggaaagttgaagcatttgtttgattttctc ggtggaagattagatttcaaaactttcgaaatttaacaatagaaaaagagaaaaaaagtgtagttattaggaaatattttagacaattttgttggca attaattgaaattaatttcttctttctacatattttaaaaatgtatctttttttctatttatatttcctttccggggatgagcgacaattattttcggcagc tctacaaaatgactgcttgagataaaatttctacttaaaatttattgtcgaaagatagaaaaatgttgcctcaaactgtaattttgtcgagttgcccaa aataattgtcgcacacctcagatttttttttctattatttttttaaataattaaaattacagtggaa cul-3

SEQ ID NO: 150 tattttgacttttgaattttggaggttttcaagaataggcaaacgttttggcatctttttgaaaaaaatctgatttttttggtagattctatccactttctaa aaattctacatgctctgaacaaagtggaaaatacactgaaaatttcagatcgaagtttcaggtgtttgaatttgtgtaatagtctgaaaaatctga atataagctttcaaatgagacatctcgaagaaaatgaatttgtgaaaaaatccaatttttttctaattcgagcacaaaatgatgtcggtctatcac acctccttgttgttaggtgaataattgttaaattcttaatctttatgatataacaaagataggcttctaactacgtcacgcctacatattcaatgaaat tttgtagtgctactactatttgtgcaagccggaatatgaatgtcctttcattttttttcgtcccaaaagtatataaaatatctcacgatatactcagag -continued attgggcaacaaagttcaggagaacttttgatgcacaccggaaataaaagggcttcactgctttttttgttgaattcatattggttttggcggga aatattgaatcattattgatacttttgaaacaggaatagacagtatttttcgtacggaaattcgataatttccgaaaatgttcggttgcctccctcg ccccctttgaaattacaggagactaaaattcgaagaatgcgtattacgaaacgtatacgcgcaaaatatctcatagcgaaaactacagtaatt ttttaaattactactgtagcgcttgtgtcgatttatgggctcgattaaaattgagcaaaaaatttagaaaatactatgcaggcgcggaggaaaat aaaatatcgatatcactattcggaaacaaattcatttcaaaaatcgagcacgtaaatcgacacaagcgctacagtagcaatttttaaaaaaatt actgtagttttcgctacgagatattttgcgcgtcaaatttgctgcgcaatacgcattctcagaattttgcgttaccgtaatatacacggtgaagaa cacgagccaccaggagtacggtagccctgactttaattgcaaaaaaagagaaaacagtgaaaaaaatctgtatataattgctattatttttaaa tttcgcaaaaaaaattagaaatgaccacattaattttgaattcctgcgcgaatgaattctatttttttgcgtattcctgcaatatttattggattttctctt agcctaaagcctaaaacgcagaaatttcgaaataataaattgaccattttttgaattattggtgcaaaattgagaaaaaattgtgaaaaattatacc attttttgaacaattacgctcagcttactaattgtaagattactcagatttatggcaaaacacgatttttacgccttcaaaaaatcctagcttttggc aaaacttacaggaaattaaaaaattcagaataaaaagtaataagatccaggaagccatgactcgaatcattgtagttgaactgtatgaatgatt tgatcccagcttcttccgccaccctaaacaccccataatttccgttttccgcttgaataggaaatgttgtatatttctgtactccttcctgaagtattaaaa ctcgttttcgtttattaaactgtttctttttttcagatcactcaacttcctcttctcaacgtcaacttcgactcggctaattataatttttatttattttttctga tttttttaaaattcttgtttttttctcaaatttccaatttcaacatcatcttattttcaaataaaaaatatttattttgcgactttctattaatttgaaacagc gaatattgttaatttattaagtaaatttaatcatttttagatcgttttcaaccgatttttcgagggctttcccacaaattttgtacttttaaataaatttaaagt ttattctaccgaaaacactatttatttttccacgtggacaccgccaattttctctgaaaattctaaaattctggttgaaaattaatttttaaagcttcct cacgagaaaagcgccaacgcacgaggagcgcgccagcaaacccgcattgacgcagtctcggtgcacttctgaactccaaaacacactg ttcccgttcgatttttctcgcattttttcatagtttttttcgaaattgaagcttttaaaggtgttttagacttgattcgaagtgaaatattgattgattgag ccggaaaataggcaaaaagttctggaaaaacgcgcgaaattaaaattccagtgactttcgagataatgatattgatttttccgagtaattaagt tgatatccagctatttatttttgcgtgacattctaattaccggattttcaaagtttttttcgaaaaaaaaacaaagcaaaatcgatttatttcgaattac tcgcgacttctcaactttgaagctgaaaatagttagttttgtttttttctgttatcagtgcgcgctttttctgcaataataacattccgcagtacgatttt ttcaaatttttttgcttttcgagaacggaaaatcaagtttatttcagtgtgcacgaaaaacgagcgagattctgacttgaccagttcgttcggaatc gactcatttttggag Cell Cycle Toxicity Genes cki-1

SEQ ID NO: 151 gatctgttctttccgaaaagaagtagttaacaggtgcggcttcactgggtggtctcatttttcattttaacctgttaatttattccggcttcacctcta atccttaatgacattaacatcttcctaatgtgtctaagcttttcccacggaaagctaatttcctctctcttatttttctcattaccgttctggttgagctt catcttataccgtgaatggtttcataattacgtgctacataatttgttatgctggtcgaggctcaacgtttcgaacatctggctcttttccttcagct aaccacaccactcttcgttacaatcccttctgcgcacacatatcctatctaccagccggacagatgctcgtttctcggtgcaaaacgttgaga gttgagatcgagcagccggttggtagttcttaatgacaaattgccaagactttttctgaattattttaggatttaaaacttttctaaagtattacgat agttcataatttctttctttttttaaaaattggctctttttttgtaatgtatggtatctaactaaaactaggcctcatttccataactattctttaaattgagtt gagctcaaagagttagacagaactggtgtgaatcatagaacccacctgtgtttttactttctttgaaaaatgtcggtcacttagtcgtctctctgt ctgttccttttcctaatcacaagtaacaacacacagtcttctttcacatatattatttgttgaccaatcgtagggtcaactatctagtactcgagacc gcctatttgaacagagctcctcactgtcaccaaatgtaccgtattgctttccggctgttattgttgttatcactgcttcttcttcctatcatgttaccc atccaactatacaccttagactagtcatcttattgatatacattcctcccatccaacacaacggtattctatttatttatccaattagtcatagtcgta ccaccatccagcacgaaggtgcctctttagtaaagagtagaaagaagaaccggatgggaaatgtttttgttacaaaaatgacacatattgta gtggacagaaggagtgagacagacatgagcaagccaatttgtttataatttctcttctagaaaaaaatacatttttccatacttcactagtcaaa acctttcacctttctaatacatctcgtaaaccataatcttgatagttctgagcatttcaatacgaaagcttctcactgtctagatctctgactgagtg -continued ccctcatcaaaagtgcaatctgtcatctgtttcctcataatcacggagcactaatttttctctctgcgtctctataatcagatatctctcgtcactaa gaactttccgaaatgtttatgcttctcatctgaccacttcggttccgcacaaaaaagtacggcattccaaaagaaatctgatccccctccgttca ttcgtggtccgagtcggtgccaccagtcgttgcgcattgaatatttgtttggtccgttccccttcttctccgactgctgacctcgggcactttgat gaccgggccaccacctcagtacccctctattacaccctctttgcctccgcgcatatgactccaccccttctcgtggaaggcgtgtatctcccc tctttttccgctattccctcgatggatatatattcaaatgtatgtgtgttcctgacgggagggcgtctcgcttgagagcatcgtcacatcttttacaa ttttacttatgatttacttcatcttcttcttcttactgcgattttgatatgcattcttatgtaaactattattattccaggtttcctcactcttttcaa cki-2

SEQ ID NO: 152 taggttaacactgataaatcttgcagaactgttttattttattaaatgagacattaccgatctaaataaatttacaatcccatcaaactttctcctttat cctccagaatcccatcattttcatcggcacttcttcaaaagtttaaatgtgagtgaccgcccgtctcgctctactaatcgtatatgcaaattttcttt gatatcatagaacctgtcatacttctccaagtatatgaaagacaattaaaactactgagagaaagaagtagttcgcgataaaaaagtacatat aatacaccttttcacctagaagagatgctttcaacttctacttttctggtcatatgtaaatagttgggtttttttgacagtttgacaggtttacggcagt caagacgacaaaaatggttatcaaaaggagctggcatacagccaataccaccagttctgatctttttacgattatcaaattgtacatgggggg ttaagttgaattttagtttcatttttttcaaaagtttaaactcgaaaaataactgaattgaaatatagtgaagttggcaatataccaagggtagaaaa tcagacgagtgattttatttctagacaatcttaaattgctcaaattgtggtcttttctatatttgaacttttaaatgcagcaatttgtgaaacatacaat tgaaacaaatttcctcaaaaactgccaccagctgaggtatcatgaagccttctgttcacacatgttgccacctaatcggtcacttatcctaatta acattcttccactaaattgtcccctagtcacccccacttgaacgatatacacaccaactgttctcgttcactaatacacttcttccggagggattc aactggttatattctgcagttgtcggcaggtgtgtggtagacggtgacgtaatattgcacagggtgtcggggaatgattatgaagtcgagatg cgcaacagctggtaattgaagccacgagagaaaatggaaaagactatgatgagggcacaaggatagaaaaattgactgggagtgacca aacaggcgaggtcacaatgaaattggtgaaaatggaaaccctaaaagtaactttagattttagaaaatagttggacgatttttcgttttcaaagt tcaaagcatgcattattatcatctgaagatgcacgatttgacttgtgtgactgatatctcgtcgcgatcttaccgtaacctacagtacttccatatt aactaaagttggttcgcttcgagacatcgggaacgtgagttatgtatttggcattattcgtcattttatattctagaaagatttacattctgtcaagt tggaatatttttttcttagccgtgcaatagaacttttgttgaatttctcagagtacaattttttatgaccgccgatttcctctcgataagcattacgttatt tacctatggttttcaactatttaatgagatttatcaggacctcccgtagttttatcttctatttttactcaaattttgagctcaaaaataacaggaaag atttaatcgaaaaaaacatatttctgaaatccaagagcaatcgcgcgctattgataatctggtttgccgcatttctcgcggcaacaacaaagag tttgaatcgaaacgccttttttatttgaaaaaaaaccttttttgttttaaaatttagtctatacgtgaatctaacacacacaaactgttcactaatttctct ttgttcgtctttttaccatttcatttcgaaactcgctgtcgtctcgtttctctcaccactcttcacacttttgccgcctaatcgatcgatcttgccgcg gcgcactcacatttttctcttatttcttaccggcaaaaaatgtacgttttaccgcacttttcgcttacattactatttcaaattctcttatcaaaattatt tcagaaacgaagtaacacaa pcn-1

SEQ ID NO: 153 catgaagaaacagtggccgtattgggaaaaatgaacgatttttcggcgggaataatttattttttttatgtttttctatgcgttttcgggtgttttcgg gttgctaagcgattggttgccttttttgaatcactagtcttggtttttgttgtttctgtgaatgaataattggtttttcgaggtttttttgtcaaacatgcct aaaaaataaattatgacgttttagttgatttgtttgttctttaaacgtctgaaaataaggtttaaatctaatttattaattataaaattcgtcaaaataag ttgcgcgtcaaattatatgtattgtacgcagtgtcaaactccaggcctcagttttcatgaatttaccagcgatttttgttataaatttttttattgaaat ttaaaatttttattttttcaaccaatttgcctcgaaaattcgttatttccccattaaaaaccgcttttctaaagtgttgcgcgtcaaataaaatgcctgg tacgcaatgcacggagaatgcgcaaaggacgactgctggcgcactttttgaatgcggtaaattgaggcgcgaagtttcattcgaaaacgc gcgcgaaacttcattcatcgcactttctccgttcatttcgtcctatttttttgtggtttttcgcgatttttttcgcttttctgagtgaaaaaataattttcctt cgtttttttcaatgaaaatccgcggaaaacccatttttttcccgtgaaaatccgcatttttcgctgtatttcataatttttattcagatctcccgtcaaa smo-1

SEQ ID NO: 154 ttgctgttcttaattgatttcataaatatgtataaagcattaaatttgaatatatttttaataaagaaaaatcgatattcacattagagcgcgcttgca atttcacgatgagacctgacgataccgcgcgaattaaatcgatcgctttttggcctaaaatgctcattaacaattgtttttgtagtttttagcttaaa attatattttaaaatccagtttgccttgttacatattggaaaacggtattttagagtttttcctcaaaaaccaagcgaaaaccttgaattttgttccg -continued aaaacttgttcaaaacatttttttcgttgaaaactcaaataattcaccaatttatctattttaggccgaaatctcttatttttttcagtccaaaaagcacc aaatttggtcaaaaacctgtccaaaatctaccgtaccctcgtgttgctcgtgaaatgcggtgcattgtgtgcaaacaccgcggcgtgaacatg cacactctgcaacgcgggaaatcatttcgaaaaggtttttaggcgcgtattgcccgatttttcggctcatttcgtgtgttttcatttatttttgccttc tttctccggtcgcgatgcgtttaattaagttttgcttctaaatttcgtcaatttcgctgaaaaaccacgtagaaaacttgataggaactggatatcc taaaaaaaaggatttccttgagaaaaatgggtttttttctgaatttcgcagtgatattcttgaaattctcagcgcagcgctccccagacaatcga tattcctaatttttcaagcatcttgtggctcagccagctgttctgtaattatcgatttatttgttacagcgtctatataaataccctagaaagtcatca ttctgcactcttaatacctttcactcgtgtgagttgcattctccatagcaactctacctctctccttctatctctttttctcttttcaaatctaatttcgttt cagagactcccgctataaacg rnf-1

SEQ ID NO: 155 ttcgctttaactcctccagaagttgacggtccgccagtgcctccactagtcgtcgggagtttatggttcagtttcgcctttttcatgtcctccggc ttcataatcgtatcatttaggcgtttgtgtttttacgttccattatttataagattctaaacgagaaactcttaagattttccggaaaataatgataaa aacggttgtgaaattgaatgagaataaaaaaacgaaacaagcacgagtgaggcaggtgcgctccaatgcgaatttctttgcgcggatgttt aaatggttatttttttatgggaatcgacaagtcacatgctacgctagagagagttttacattttacagtctttttggaatttaataatatatatattatc ataaaatcgaataaaaattgtttcgaataatgaatagctttgtttttcgtcttgacttctgaaataattttaaatttgagaaaaatttgtgtcgcaata tataattattaatattattaataatgtaatttttttataataaactgatttatattttaaaaacaaaaaaggaatgacaattcagtttagttttatgaaaaa ctttgaaaagacaaaaataattacagtaaacgcgctccgctagactccccaaatttgtttttgttttccaggcttgtgtccaggcaaattccagct ttctttttgtttcagaatttctaggtatttatctccgtgaaa Apoptosis Toxicity Genes egl-1

SEQ ID NO: 156 gaaaacttcgattcttatggttaaaacgagccttgttagtaaaaattattgagtgaataaataaattagatcaagtattttcacttctgccaaaattc aactaaatagaaatggttggaattaagttacaagctaccagtttacaaaacaataattgacaggtaatcggagtgaagacagtttttttgcctttg ataattttacattcacatttaattttacattcacataaaaaaagaatcacacatttttttcaattgacaagtttttgataaagtggaagacatcggag atatgacccgtcaaagttgctcagcagggtgcaaaactaaaagaggaaatactgtgaaacattttgacaatttagagaaatacacagcgaa agaatgaaatctaaaaaagcgtattaactttaactagataaacatactaacttattgaggtaaatctgagcagatcctcttcctattcccaatattt acccaattagtcttctgattgcgcacctgcatatcttaagtactcaaatacaacacacatcttgagaaatgatgactccacactcagaatgcaat tcacactattagaagccatgtgcaatatgaaaacaagcttatcctgaagctgcaaacccatttacctcatcaattatttgcgatgtgccgacctg ttgcatggcttccgacactgtaaggggataatctgtttgtcggcacgcttcaaccgattaattggcgtgtgaaacgatactaatccagtcgatt ctcgactaactgtaaacactttgatgctaaccgacgtgccggctaatatactctctgtgttacgtcagaatcctttaaatatgcaaatatggataa ggtggaatgatctcaagaggtgtgattgggtcaaattggattacgtaattcttaagtgggctaaaggtatactgtaactggggtgcaatttatgt gggaagtgcggcgaagttatattggggttttatagattctataacttgttacattgattttgaatagatttcaattttcagaaaagtgggaaaactg tatttacattttgaaagaaatttaatgcaacagaaaatagtgattggctggaaaagtgcccctatgttataaactttttgttgaagctttgaaattttt cacaaattattcaactgaagtctcacacgtcgaaaaatggccaaacaaatttttaaaaaatagaggcctgatcatagtttctgccatttcatggc cgtctgtgacgtcacatgaggtttttcgactatttggcttccagggttttacctgtttttaatttcaaaattatatattcttcagtaaatctctgaaagt cacagtcgtttcagcgaactttcaaggccgcgtgtgacgtcacactcttgcaaagaaagctgcacgtggtgtcaggttgtcccataacggttt gctctacgaaaaatgcgggaatttttttcatcaaaaaatgtgacgtcagcacgttcttaaccatgcgaaatcagttgagaagtctgcgtctaagt tcccgcgtttttttgtagatcacaacggaatgggacattctgacaccatgtgaagctggccttgagatagttttgtagattcaaaatatttttaatgt ccaatatttgttttcaaaacattcgttaaaatgtgcagaatatgttaaactgaaggttcctaggtttaaaacttcaagctaaagctttccggctcag ttctcaggttcaggtctgtaatctttctgtaagcttgtaatcttgttagttcctcagacagacttagctgctaaatttatttcatgtctaatattacactt -continued caagagctatgagtttgtcttcataaaagttttggctcccatataggaactttggaacatcatttgatccccgtttcgaaaacgttcgaaaattgtt ttgtttctttatttaaacccgacagttcaaattctttatcttgatcaaacccttttttttcatctgtccattcctcggccttaacctaatttatacagtttcg caataacctcccccgtgcttgctccagtaccagctgttgcgtcacgacttcttattttcaaaactcaaatcttgcatcacacctcatcaattaatc atcctcatcaagcctgcaaacttataccccttctctagacccctctcctgacatttgacactcctgtggtagaggggtgtggccttgcctggg cggggcgtgcaatgagaagctgtgcacgcacaccattcattcacacccaaaacattcacaccgattagtcgtattctaacttctcttttcaattc agttgatatgctggtaagtctagaaattatttattttgatctacatacctgtccaatattgttcgtctcccccctcccccctcctgagaaacaaattttt gtttttgtctgctcgcctcaccctcaacctctctctctctggatgtgttcgtggtgtagaaacaaaaacagattttgtttttttgtttttttgtttcttgttt tagaacttgtatcctagtaattgttagacatctccctactatctttcccctatataaaccccccttcaaaaccttactaatttccag cep-1

SEQ ID NO: 157 aacagaactcacccgtttctagaacaacgtttgctatcaactccaccccgaaagaatccaggtggttcgtctgacattatgctgcaattttatg agaatattcagacgcaacaacaacgtgacaaacgacgagataaaaatctatcaaggctgaaacaatgacaaaaaagaaatcccgacaaa tgaaaatggcgcctaaaacaaactttttttaaaggacgtcgggtttcattcacagatgggtctcggaacgaaatcatggagtacggtatcacac acttgaatttgaaagtgaacttctttatttgtttctcttgcaagtttaaacttaagtttttaattttttctgcttgtttctcaataaaataaaaatattact tgatttgtagcgcaga ced-3

SEQ ID NO: 158 ttctgcgtgaaatgtgatgtttctacagtaacccgtacaaccaaggcatcgaacttcacgacatttacgaattcaaatttgaattgcaaactttttt aattttatcgattttctttctttttgagctttatcaatagctctaagcgattattcaacagaatttcacttttttttacgcctaaatgattgaaaatttgataa aatatcaataatttacggttatcctcttcgtaatcttcgctttcttcccagagtagtgaaaatatcgactttttgatagaaactggattttttaacttcc ctgttcgaaaaactattttttccttaaatgagatctgaaataaggtgataaattaataaattaagtgtatttctgaggaaatttgactgttttagcaca attaatcttgtttcagaaaaaaaagtccagttttctagatttttccgtcttattgtcgaattaatatccctattatcactttttcatgctcatcctcgagcg gcagcgtctcaaagaattgtgagagcaaacgcgctccattgacctccacactcagccgccaaaaacaaacgttcgaacattcgtgtgttgt gcctccttttccgttatcttgcagtcatcttttgtcgtttttttctttgttctttttgttgaacgtgttgctaagcaattattacatcaattgaagaaaagg ctcgccgatttattgttgccagaaagattctgagattctcgaagtcgattttataatatttaaccttggtttttgcattgtttcgtttaaaaaaaaccact gtttatgtgaaaaacgattagtttactaataaaactacttttaaacctttacctttacctcaccgctccgtgttcatggctcatagattttcgatactc aaatccaaaaataaatttacgagggcaattaatgtgaaacaaaaacaatcctaagatttccacatgtttgacctctccggcaccttcttccttag ccccaccactccatcacctctttggcggtgttcttcgaaacccacttaggaaagcagtgtgtatctcatttggtatgctcttttcgattttatagct ctttgtcgcaatttcaatgctttaaacaatccaaatcgcattatatttgtgcatggaggcaaatgacggggttggaatcttagatgagatcagga gctttcagggtaaacgcccggttcattttgtaccacatttcatcattttcctgtcgtccttggtatcctcaacttgtcccggttttgttttcggtacac tcttccgtgatgccacctgctccgtctcaattatcgtttagaaatgtgaactgtccagatgggtgactcatattgctgctgctacaatccactttct tttctcatcggcatgcttacgagcccatcataaactttttttttccgcgaaatttgcaataaaccggccaaaaactttctccaaattgttacgcaata tatacaatccataagaatatcttctcaatgtttatgatttcttcgcagcactttctcttcgtgtgctaacatcttattttttataatatttccgctaaaattc cgatttttgagtattaatttatcgtaaaattatcataatagcaccgaaaactacaaaaaaatggtaaagtcttttaaatcggctcgacattatcgtatt aaggaatcacaaaattctgagaatgcgtactgcgcaacatatttgacgcgcaaaatatctcgtagcgaaaactacagtaattctttaaatgact actgtagcgcttgtgtcgatttacgggctcaatttttgaaaataattttttttttttcgaattttgacaacccgtaaatcgtcacaagcgctacggtagt catttaaaggattactgtagttctagctacgagatattttgcgcgccaaatatgatgcgtaatacgcattctctgaattttgtgtttccgtaataattt cacaagattttggcattcctctttaaaggcgcacggatttattccaatgggtctcggcacgcaaaaagtttgatagacttttaaattctccttgca tttttaattcaattactaaaattttcgtgaatttttctgttaaaattttaaaatcagttttctaatattttccaggctgacaaacagaaacaaaaacaca acaaacattttaaaaatcagttttcaaattaaaaataacgatttctcattgaaaattgtgttttatgtttgcgaaaataaaagagaactgattcaaaa caattttaacaaaaaaaaaccccaaaattcgccagaaatcaagataaaaaaattcaagagggtcaaaattttccgattttactgactttcacctttt ttttcgtagttcagtgcagttgttggagtttttgacgaaaactaggaaaaaaaatcgataaaaaattactcaaatcgagctgaattttgaggacaat -continued gtttaaaaaaaaacactatttttccaataatttcactcattttcagactaaatcgaaaatcaaatcgtactctgactacgggtcagtagagaggtc aaccatcagccgaag mev-1

SEQ ID NO: 159 aaattcgaggaattttagatttcatcttgaaatttgcaatggaaaaaataattattcaaagaaaatcacagaaaatgcaacaaaaaaaacaaaa aaagaacaaaaaacaagtcgaaaagtgcgcccgggtcgtttgctgacgcatctcttcaaacgagacgcgctgctggcgcacttctcgtgc cctgtgcgtgcatttccgcaacaaaattcaacacttgttttgaaacgcaccgccctgtttctttttttcaattttgataagaaaatcagcattgtttca gg ced-13

SEQ ID NO: 160 tagaaacatgtttcccgtaagtgacctatccagtgaaacaaaaacatgtttctgtccgccttccttccatcggtggaggtgcatgctagattgc ctcctaaactctaatacctaaaattttaataatttattgacaacatacagtttcaccgataaccgacactcttatttttttctgatcctgactattctgtt cattatttcagctcctatcatagaacgatctttccagatcttggacaagtcacagttacaggtaattttttcaacaggtgtttgtataatgtcttagtt tctgtaaaattgttttatcatgtaaaatatttcagattattcgagggcagaaaaacgtgatattactattggagaggaattgacaaagttgtgtgat aaatttaattttgag bmk-1

SEQ ID NO: 161 cgagtttcttgtgagaaccaaaaactattcctctgcaagaaaaaatttattaatccggcataaaatactttttattacaataggaacttcacagtc gcttcctccgacgctttgagcggtacatcgatgcttatcaccatgctgattgttacctttcttacccgtttgactttctgcaatttttaactgcaaag atgtttaatgcagatactcgaaagaaacgaaaaaatgataaaaaagtgaaaaaccccaaaaataaatttgaaaactccgcgtaagcttgctc gatcgctgcgagaccattgcataccgtactacttctttaaaggcgcacacatcaaatctagctgtttcgtgacaggacccagcaatgttcagc cgcgaagttttgaatcgccattttttttaatttctagaatgtttatagttttgctttcgatgagatttttaagcattatgaggaacaaatttttttaaaaa ctttagaagttttaaaatttaattttgcgattatgctttgctttcgcgtgtcctttccgttgttcctcgctccaaatatatcacagtaattaaccactact tatgtagttatcacgtttctaaaaatataaattcatttttatttctctattgattcggtttgttgctcttcttgtctcaatcttgtgctactgccgaatacc c tgctaatttttcgttttcagtcattcgattcacttgggttgttgtttaaaatggtaagatttttgcaggttactttctttcccatgaggtaaatgcatttat tgcgggtgcgctctatcgcacgacgccgcgaatcattgtatttcaaattgattttcctgttgcacttttattagttacaattttttattagttatttttagt tggattcgaca rad-51

SEQ ID NO: 162 gaaaacctaaaatgaacaaaatttttttgtcattaaataacaacgcttcggttaacgcttgaaattgatattcggaaaataaaaagcctgatttttgt tcgatttctgaaatatatttcatgctttacccgtttttaattgcgaacaattctaaatttgaaatataattttcaatcaacgaaaaacaattttcaagat aaaaaattattatataaatttaagctaagtattaataaattaataagtaatagtattcaaaaatcatagaatcttgcaagaaaaaatgttttaaagat ttaatagttcgagtgattgaaaaacgaatagtactttaaaaaataatgctttaaggcagaaaagtgatataaaaattaagctcaaaagggcaaa agataaggttaatgtccagttttggttttaaaatggttcggacacaatgtacatagtagacatttgggtgtcctcttccttctcttttccccattgcg tccactgaccctccttgctgtatgtctgcgcatcgtctttttctacacttttttcctttttccctggcccgttcctatcggtgcctttcacacacgcgag cggcagtggacgagacgggagggcgaggtgttgaacaagagtacagcaagtgcgcgccatcgaaaaagcggaaaaaaaaaatttcaaa tggcgctactttgaaaattgagaattctgtatttactgccagttttacttgcatttaaatttccatgttttctattctaaaacgaaaatctatctaagaa aaccccttaataaaaacctataaatcataaattgtgattcttaaattcgaaaatatgttcgttcaacttgacgcctagaaatatgtggacttaatcct gttataaatcagtagttgacgacaaaaaatagtagagcagcaaaagcagttctaacttgtgaaaaacatgaaagttcttgttttcgtcaagcgaa cgggggctcgaggaaggacttggcacgtgtctctaggccatgtttttctcaattttttgttgctctagagaaagcttttgctattgattatgggaca atcttggggatatgaaggtaacattttaaaaataagtttaggtaaatgtgtagcataatttttgaaaaaaaaagctccactgttaaaaatgccgat tttagggattgcgaaacgttcactatgtacacataaatggctatataatttgaatttgcattcaataaatcttttccttccaattgtatgttttaactta aaaataattaattaaaattatctcaggagtcaaaa The invention is a nucleic acid comprising a nucleic acid having a sequence as in one of SEQ ID NO: 1 through SEQ ID NO: 162 which is an inducible promoter and is operably linked, or fused, to a reporter gene. In one aspect, the reporter gene comprises a gene encoding a fluorescent protein.

The invention is a isolated nucleic acid comprising a nucleic acid having a sequence 95%, 96%, 97%, 98%, or 99% or more identical to the sequence as in one of SEQ ID NO: 1 through SEQ ID NO: 162 which is an inducible promoter and is operably linked or fused to a reporter gene. In one aspect, the reporter gene comprises a gene encoding a fluorescent protein.

The invention is a nucleic acid comprising a fragment of a nucleic acid having a sequence as in one of SEQ ID NO: 1 through SEQ ID NO: 162 wherein said fragment is 50, 100, 200, 300, 400, or 500 or more nucleotides in length which is an inducible promoter and is operably linked or fused to a reporter gene wherein the nucleic acid fragment is capable of promoting transcription of the reporter gene as described herein. In one aspect, the reporter gene comprises a gene encoding a fluorescent protein.

The invention is a nucleic acid comprising a fragment of a nucleic acid having a sequence at least 95%, 96%, 97%, 98%, or 99% identical to a sequence as in one of SEQ ID NO: 1 through SEQ ID NO: 162 wherein said fragment is 50, 100, 200, 300, 400, or 500 or more nucleotides in length which is an inducible promoter and is operably linked or fused to a reporter gene wherein the nucleic acid fragment is capable of promoting transcription of the reporter gene as described herein. In one aspect, the reporter gene comprises a gene encoding a fluorescent protein.

The invention is a transgene comprising a nucleic acid having a sequence as in one of SEQ ID NO: 1 through SEQ ID NO: 162 which is an inducible promoter and is operably linked or fused to a reporter gene. In one aspect, the reporter gene comprises a gene encoding a fluorescent protein.

The invention is a transgene comprising a nucleic acid having a sequence at least 95%, 96%, 97%, 98%, or 99% identical to a sequence as in one of SEQ ID NO: 1 through SEQ ID NO: 162 which is an inducible promoter and is operably linked or fused to a reporter gene. In one aspect, the reporter gene comprises a gene encoding a fluorescent protein.

The invention is a transgene comprising a fragment of a nucleic acid having a sequence as in one of SEQ ID NO: 1 through SEQ ID NO: 162 wherein said fragment is 50, 100, 200, 300, 400, or 500 or more nucleotides in length which is an inducible promoter is and operably linked or fused to a reporter gene wherein the nucleic acid fragment is capable of promoting transcription of the reporter gene as described herein. In one aspect, the reporter gene comprises a gene encoding a fluorescent protein.

The invention is a transgene comprising a fragment of a nucleic acid having a sequence at least 95%, 96%, 97%, 98%, or 99% identical to a sequence as in one of SEQ ID NO: 1 through SEQ ID NO: 162 wherein said fragment is 50, 100, 200, 300, 400, or 500 or more nucleotides in length which is an inducible promoter and is operably linked, or fused, to a reporter gene wherein the nucleic acid fragment is capable of promoting transcription of the reporter gene as described herein. In one aspect, the reporter gene comprises a gene encoding a fluorescent protein.

The invention is a construct comprising a nucleic acid having a sequence as in one of SEQ ID NO: 1 through SEQ ID NO: 162 which is an inducible promoter and is operably linked or fused to a reporter gene. In one aspect, the reporter gene comprises a gene encoding a fluorescent protein.

The invention is a construct comprising a nucleic acid having a sequence at least 95%, 96%, 97%, 98%, or 99% or more identical to a sequence as in one of SEQ ID NO: 1 through SEQ ID NO: 162 which is an inducible promoter and is operably linked, or fused, to a reporter gene. In one aspect, the reporter gene comprises a gene encoding a fluorescent protein.

The invention is a construct comprising a fragment of a nucleic acid having a sequence as in one of SEQ ID NO: 1 through SEQ ID NO: 162 wherein said fragment is 50, 100, 200, 300, 400, or 500 or more nucleotides in length which is an inducible promoter and is operably linked, or fused, to a reporter gene wherein the nucleic acid fragment is capable of promoting transcription of the reporter gene as described herein. In one aspect, the reporter gene comprises a gene encoding a fluorescent protein.

The invention is a construct comprising a fragment of a nucleic acid having a sequence at least 95%, 96%, 97%, 98%, or 99% identical to a sequence as in one of SEQ ID NO: 1 through SEQ ID NO: 162 wherein said fragment is 50, 100, 200, 300, 400, or 500 or more nucleotides in length which is an inducible promoter and is operably linked, or fused, to a reporter gene wherein the nucleic acid fragment is capable of promoting transcription of the reporter gene as described herein. In one aspect, the reporter gene comprises a gene encoding a fluorescent protein.

The invention is a transgenic organism comprising transgene which is a nucleic acid having a sequence as in one of SEQ ID NO: 1 through SEQ ID NO: 162 which is an inducible promoter and is operably linked, or fused, to a reporter gene wherein said nucleic acid is capable of promoting transcription of the reporter gene as described herein. In one aspect, the reporter gene comprises a gene encoding a fluorescent protein.

The invention is a transgenic organism comprising transgene which is a nucleic acid having a sequence at least 95%, 96%, 97%, 98%, or 99% identical to a sequence as in one of SEQ ID NO: 1 through SEQ ID NO: 162 which is an inducible promoter and is operably linked, or fused, to a reporter gene wherein said nucleic acid is capable of promoting transcription of the reporter gene as described herein. In one aspect, the reporter gene comprises a gene encoding a fluorescent protein.

The invention is a transgenic organism having a transgene which is a fragment of a nucleic acid having a sequence as in one of SEQ ID NO: 1 through SEQ ID NO: 162 wherein said fragment is 50, 100, 200, 300, 400, or 500 or more nucleotides in length which is an inducible promoter and is operably linked, or fused, to a reporter gene wherein the nucleic acid fragment is capable of promoting transcription of the reporter gene as described herein. In one aspect, the reporter gene comprises a gene encoding a fluorescent protein.

The invention is a transgenic organism having a transgene which is a fragment of a nucleic acid having a sequence at least 95%, 96%, 97%, 98%, or 99% identical to a sequence as in one of SEQ ID NO: 1 through SEQ ID NO: 162 wherein said fragment is 50, 100, 200, 300, 400, or 500 or more nucleotides in length which is an inducible promoter and is operably linked, or fused, to a reporter gene wherein the nucleic acid fragment is capable of promoting transcription of the reporter gene as described herein. In one aspect, the reporter gene comprises a gene encoding a fluorescent protein.

Inducible promoters for use in the nucleic acids, transgenes, constructs and transgenic organisms of the invention are typically chosen from those present in the host organism and are involved in promoting expression of its cognate gene in response to stimuli or an agent. Examples of stimuli or agents include, but are not limited to, stimuli or agents that cause oxidative stress, stimuli or agents that are genotoxic, stimuli or agents that cause xenobiotic stress.

Exemplary inducible promoters, constructs comprising the inducible promoters, transgenes comprising the inducible promoters, and transgenic organisms comprising the inducible promoters of the invention are described in more detail below.

The invention is a nucleic acid, transgenic organisms, transgene, or construct comprising a promoter of a gene involved in oxidative stress response fused, or operably, linked to a reporter gene where the oxidative stress response gene is from a pathway of cytoplasmic oxidative stress, mitochondrial oxidative stress, peroxisomal oxidative stress, endoplasmic reticulum oxidative stress, or nuclear oxidative stress (Zhong, M. et al. PLoS Genet 6, e1000848 (2010)). In a related aspect, the invention is a nucleic acid, transgenic organisms, transgene, or construct comprising a promoter of a gene involved in oxidative stress response fused, or operably, linked to a reporter gene where the oxidative stress response gene is from a pathway of cytoplasmic oxidative stress induced by juglone or other quinones or phenazine; mitochondrial oxidative stress induced by paraquat, mitomycin C, antimycin A, or maesanin; peroxisomal oxidative stress induced by aminotriazole or antimycin A; endoplasmic reticulum oxidative stress induced by tunicamycin, menadione or plumbagin; or nuclear oxidative stress induced by belomycin.

The invention is a nucleic acid from a gene involved in oxidative stress whose promoter is used in the transgenic organism, transgene, construct, or nucleic acid of the invention and is chosen from those involved in cytoplasmic oxidative stress that can involve pathways such as heat shock, phase I and phase II xenobiotic response, or proteasome. In one aspect, the gene is hsp-16.41, hsp-16.2, hsp-16.1, hsp-16.11, hsp-16.48, hsp-16.49, sod-1, gcs-1, hpo-15, dhs-18, gst-14, gst-32, W06H8.2, cyp-34A9, or ugt-41, where the promoter for the gene is fused, or operably linked, to a reporter gene.

The invention is a nucleic acid from a gene involved in oxidative stress response whose promoter is used in the transgenic organism, transgene, construct, or nucleic acid of the invention and is chosen from those involved in mitochondrial oxidative stress that can involve pathways such as heat shock or electron transport. In one aspect, the gene is hsp-6, hps-60, mtl-2, mtl-1, cdr-1, sod-3, eat-3, cyp-14A4, cyp-33C8, glrx-10, F56D5.3, B0222.9, F17A9.4, C35B1.5, or gst-4, where the promoter for the gene is fused, or operably linked, to a reporter gene.

The invention is a nucleic acid from a gene involved in oxidative stress whose promoter is used in the transgenic organism, transgene, construct, or isolated nucleic acid of the invention and is chosen from those involved in peroxisomal oxidative stress that can involve pathways such as heat shock or oxidative metabolism. In one aspect, the gene is hps-1, ctl-1, ctl-2, ctl-3, W01B11.6, F10D7.3, prx-1, prx-5, duox-2, prdx-2, pxn-2, mlt-7, ZK550.6, C28H8.11, or C35B1.5, where the promoter for the gene is fused, or operably linked, to a reporter gene.

The invention is a nucleic acid from a gene involved in oxidative stress whose promoter is used in the transgenic organism, transgene, construct, or nucleic acid of the invention and is chosen from those involved in the specification of apoptosis as in endoplasmic reticulum oxidative stress that can involve pathways such as heat shock, ERAD, or disulfide exchange. In one aspect, the gene is hsp-4, dnj-27, dnj-7, Y41C4A.11, arf-1.1, lips-11, srp-7, gale-1, ckb-2, fipr-24, arl-7, F07A11.2, C04F12.1, hke-4.1, or F22E5.6, where the promoter for the gene is fused, or operably linked, to a reporter gene.

The invention is a nucleic acid from a gene involved in oxidative stress whose promoter is used in the transgenic organism, transgene, construct, or nucleic acid of the invention and is chosen from those involved in nuclear oxidative stress that can involve pathways such as heat shock or oxidative base damage. In one aspect, the gene is ugt-1, hsp-17, cdr-5, dnj-15, dnj-25, pme-1, pme-2, pme-5, air-2, mlh-1, mlh-2, polq-1, him-6, xpa-1, nth-1, or cep-1, where the promoter for the gene is fused, or operably linked, to a reporter gene.

A promoter region for an oxidative stress response gene (hsp-16.41) has the following DNA sequence (SEQ ID NO:1) and activates transcription of its cognate gene (or a reporter gene fused or operably linked thereto) in response to or by e.g., heat shock. In one embodiment, the invention is an isolated promoter reporter construct nucleic acid comprising SEQ ID NO:1 operably linked or fused to a reporter gene. Preferably the reporter gene is one that encodes a fluorescent protein or a luminescent protein. Preferably, the reporter gene encodes a fluorescent protein comprising a GFP or RFP. In a related embodiment, the invention is a *C. elegans* line or strain having the promoter reporter construct stably integrated into the *C. elegans* genome at a single site or using a single copy insertion technology. In one aspect, this *C. elegans* line or strain has a constitutive reporter gene stably integrated into its genome in addition to the above construct wherein said constitutive reporter is detectably different than the reporter of promoter reporter construct (e.g., different fluorescent protein). Preferably, the constitutive reporter comprises a GFP.

A promoter region for an oxidative stress response gene (hsp-16.2) has the following DNA sequence (SEQ ID NO:2) and activates transcription of its cognate gene (or a reporter gene fused, or operably linked thereto) in response to or by e.g., heat shock. In one embodiment, the invention is an isolated promoter reporter construct nucleic acid comprising SEQ ID NO:2 operably linked or fused to a reporter gene. Preferably the reporter gene is one that encodes a fluorescent protein or a luminescent protein. Preferably, the reporter gene encodes a fluorescent protein comprising a GFP or RFP. In a related embodiment, the invention is a *C. elegans* line or strain having the promoter reporter construct stably integrated into the *C. elegans* genome at a single site or using a single copy insertion technology. In one aspect, this *C. elegans* line or strain has a constitutive reporter gene stably integrated into its genome in addition to the above construct wherein said constitutive reporter is detectably different than the reporter of promoter reporter construct (e.g., different fluorescent protein). Preferably, the constitutive reporter comprises a GFP.

A promoter region for an oxidative stress response gene (mtl-2) has the following DNA sequence (SEQ ID NO:27) and activates transcription of its cognate gene (or a reporter gene fused or operably linked thereto) in response to or by e.g., heavy metal ion toxicity like cadmium. In one embodiment, the invention is an isolated promoter reporter construct nucleic acid comprising SEQ ID NO:27 operably linked, or fused, to a reporter gene. Preferably the reporter gene is one that encodes a fluorescent protein or a luminescent protein. Preferably, the reporter gene encodes a fluorescent protein comprising a GFP or RFP. In a related embodiment, the invention is a *C. elegans* line or strain having the promoter reporter construct stably integrated into the *C. elegans* genome at a single site or using a single copy insertion technology. In one aspect, this *C. elegans* line or strain has a constitutive reporter gene stably integrated into its genome in addition to the above construct wherein said constitutive reporter is detectably different than the reporter of promoter reporter construct (e.g., different fluorescent protein). Preferably, the constitutive reporter comprises a GFP.

A promoter region for an oxidative stress response gene (ugt-1) has the following DNA sequence (SEQ ID NO:83) and activates transcription of its cognate gene (or a reporter gene fused or operably linked thereto) in response to or by e.g., heavy metal ion toxicity like cadmium. In one embodiment, the invention is an isolated promoter reporter construct nucleic acid comprising SEQ ID NO:83 operably linked, or fused, to a reporter gene. Preferably the reporter gene is one that encodes a fluorescent protein or a luminescent protein. Preferably, the reporter gene encodes a fluorescent protein comprising a GFP or RFP. In a related embodiment, the invention is a *C. elegans* line or strain having the promoter reporter construct stably integrated into the *C. elegans* genome at a single site or using a single copy insertion technology. In one aspect, this *C. elegans* line or strain has a constitutive reporter gene stably integrated into its genome in addition to the above construct wherein said constitutive reporter is detectably different than the reporter of promoter reporter construct (e.g., different fluorescent protein). Preferably, the constitutive reporter comprises a GFP A promoter region for an oxidative stress response gene (hsp-60) has the following DNA sequence (SEQ ID NO:26) and activates transcription of its cognate gene (or a reporter gene fused, or operably linked, thereto) in response to mitochondrial stress by e.g., paraquat. In one embodiment, the invention is an isolated promoter reporter construct nucleic acid comprising SEQ ID NO:26 operably linked, or fused, to a reporter gene. Preferably the reporter gene is one that encodes a fluorescent protein or a luminescent protein. Preferably, the reporter gene is encodes a fluorescent protein comprising a GFP or RFP. In a related embodiment, the invention is a *C. elegans* line or strain having the promoter reporter construct stably integrated into the *C. elegans* genome at a single site or using a single copy insertion technology. In one aspect, this *C. elegans* line or strain has a constitutive reporter gene stably integrated into its genome in addition to the above construct wherein said constitutive reporter is detectably different than the reporter of promoter reporter construct (e.g., different fluorescent protein). Preferably, the constitutive reporter comprises a GFP.

A promoter region for an oxidative stress response gene (hsp-6) has the following DNA sequence (SEQ ID NO:25) and activates transcription of its cognate gene (or a reporter gene fused, or operably linked, thereto) in response to mitochondrial stress by e.g., paraquat exposure. In one embodiment, the invention is an isolated promoter reporter construct nucleic acid comprising SEQ ID NO:25 operably linked, or fused, to a reporter gene. Preferably the reporter gene is one that encodes a fluorescent protein or a luminescent protein. Preferably, the reporter gene encodes a fluorescent protein comprising a GFP or RFP. In a related embodiment, the invention is a *C. elegans* line or strain having the promoter reporter construct stably integrated into the *C. elegans* genome at a single site or using a single copy insertion technology. In one aspect, this *C. elegans* line or strain has a constitutive reporter gene stably integrated into its genome in addition to the above construct wherein said constitutive reporter is detectably different than the reporter of promoter reporter construct (e.g., different fluorescent protein). Preferably, the constitutive reporter comprises a GFP.

A promoter region for an oxidative stress response gene (hsp-4) has the following DNA sequence (SEQ ID NO:55) and activates transcription of its cognate gene (or a reporter gene fused, or operably linked, thereto) in response to endoplasmic reticulum stress by e.g., exposure to tunicamycin. In one embodiment, the invention is an isolated promoter reporter construct nucleic acid comprising SEQ ID NO:55 operably linked, or fused, to a reporter gene. Preferably the reporter gene is one that encodes a fluorescent protein or a luminescent protein. Preferably, the reporter gene encodes a fluorescent protein comprising a GFP or RFP. In a related embodiment, the invention is a *C. elegans* line or strain having the promoter reporter construct stably integrated into the *C. elegans* genome at a single site or using a single copy insertion technology. In one aspect, this *C. elegans* line or strain has a constitutive reporter gene stably integrated into its genome in addition to the above construct wherein said constitutive reporter is detectably different than the reporter of promoter reporter construct (e.g., different fluorescent protein). Preferably, the constitutive reporter comprises a GFP.

In another aspect, the invention is an isolated nucleic acid or fragment thereof having 50, 100, 200, 300, 400, or 500 or more nucleotides, which is a promoter for a gene induced by heat shock, heavy metal ion toxicity, mitochondrial oxidative stress, or endoplasmic reticulum oxidative stress which is fused, or operably linked, to a reporter gene. In a specific aspect, the heavy metal ion stress is induced by cadmium or arsenic. In another specific aspect, the mitochondrial stress is induced by paraquat. In yet another specific the endoplasmic reticulum stress is induced by tunicamycin.

In another aspect, the invention is an isolated nucleic acid or fragment thereof having 50, 100, 200, 300, 400, or 500 or more nucleotides, which is a promoter for a gene chosen from hsp-16.41, hsp-16.2, mtl-2, ugt-1, hsp-60, hsp-6, and hsp-4 which is fused, or operably linked, to a reporter gene.

Apoptosis pathway genes: Apoptosis activation is important for understanding toxicology and in the creation of drugs to battle cancer. A compound that activates apoptosis leads to cell death is advantageous for combating cancer. However, activation of cell death would be a detrimental property for apoptosis occurs by either the intrinsic (DNA damage and unfolded protein response) or extrinsic (Ras/MAPK signaling) pathways. Cell death is initiated by activation of the caspase pathway. Caspases activate pathways leading cell corpse engulfment and DNA fragmentation. Thus, the invention relates to transgenic organisms and in particular, nematode strains for monitoring apoptotic gene activation. An apoptotic gene's promoter is used to drive expression of a reporter gene. In one specific aspect the reporter gene is one that expresses a fluorescent protein. Preferred fluorescent proteins are a protein comprising RFP or GFP.

Examples of genes involved in apoptosis whose promoter regions can be used in the transgenic animals, transgenes, constructs, or nucleic acids of the invention are chosen from those involved in the specification of apoptosis as in cep-1, lin-35, jnk-1, pmk-1, mpk-1, ces-2, ces-1, atl-1, atm-1, brc-1, dnj-11, chk-1, cki-1, rad-52, cki-2, dpl-1, ceh-20, efl-1, hlh-2, or daf-16; those involved in the execution of apoptosis as in cps-6, crn-1, crn-2, crn-3, crn-4, crn-5, crn-6, cyn-13, nuc-1, bec-1, ced-1, ced-10, ced-12, ced-2, ced-5, ced-6, ced-7fnta-1, gdi-1, or ggtb-1; or those involved in the core of apoptosis as in drp-1, egl-1, ced-9, ced-4, or ced-3 wherein said promoter is operably linked, or fused, to a reporter gene.

In another aspect, the invention is a nucleic acid or fragment thereof having 50, 100, 200, 300, 400, or 500 or more nucleotides, which is a promoter for a gene induced in apoptosis which is fused, or operably linked, to a reporter gene. In a specific aspect, the gene induced in apoptosis is in the extrinsic pathway. In a specific aspect, the gene induced in apoptosis is in the intrinsic pathway. In another specific aspect, the gene induced in intrinsic apoptosis pathway is a DNA damage gene or unfolded protein response gene). In yet another specific the gene induced in extrinsic apoptosis pathway is a RAS/MAPK pathway gene.

In another aspect, the invention is an isolated nucleic acid or fragment thereof having 50, 100, 200, 300, 400, or 500 or more nucleotides, which is a promoter for a gene chosen from cep-1, lin-35, jnk-1, pmk-1, mpk-1, ces-2, ces-1, atl-1, atm-1, brc-1, dnj-11, chk-1, cki-1, rad-52, cki-2, dpl-1, ceh-20, efl-1, hlh-2, daf-16, cps-6, crn-1, crn-2, crn-3, crn-4, crn-5, crn-6, cyn-13, nuc-1, bec-1, ced-1, ced-10, ced-12, ced-2, ced-5, ced-6, ced-7, fnta-1, gdi-1, ggtb-1, drp-1, egl-1, ced-9, ced-4, or ced-3 which is fused, or operably linked, to a reporter gene.

In another aspect, the invention is an isolated nucleic acid or fragment thereof having 50, 100, 200, 300, 400, or 500 or more nucleotides, or a nucleotide 95%, 96%, 97%, 98%, or 99% identical thereto, which is a promoter for a gene chosen from cep-1, lin-35, jnk-1, pmk-1, mpk-1, ces-2, ces-1, atl-1, atm-1, brc-1, dnj-11, chk-1, cki-1, rad-52, cki-2, dpl-1, ceh-20, efl-1, hlh-2, daf-16, cps-6, crn-1, crn-2, crn-3, crn-4, crn-5, crn-6, cyn-13, nuc-1, bec-1, ced-1, ced-10, ced-12, ced-2, ced-5, ced-6, ced-7, fnta-1, gdi-1, ggtb-1, drp-1, egl-1, ced-9, ced-4, or ced-3 which is fused, or operably linked, to a reporter gene.

Genotoxin or Carcinogen Pathway Genes

Genotoxins are compounds that cause DNA damage. Carcinogens are compounds that cause genotoxicity or other procancerous activity such as, stopping cell cycle arrest, stopping cell-cell inhibition signalling, stopping apoptosis induction, etc. The arrays or panels of the invention can include 1 or more representative transgenic organisms, or populations thereof, having a promoter from a genotoxin or carcinogen response pathway gene operably linked, or fused, to a reporter protein.

From the Gene Ontology database, there are 162 genes involved in the *C. elegans* response to DNA damage stimulus (GO:0006974) (Ashburner et al. Nat. Genet 25, 25-29 (2000)) This group was compared to a meta-study cataloging the genes highly expressed after carcinogen exposure (Waters et al. Mutat Res (2010)). 24 genes were identified pathway-specific genes (carcinogen and/or genotoxin responsive genes). In particular, the genes identified corresponded to enyzmes base excision repair, nucleotide excision repair, mismatch repair, recombination controlled repair. Additional genes for inclusion in panels related to carcinogenicity include, but are not limited to, those involved in cell cycle control and apoptosis. To reveal which sections of the promoter contain transcriptional control sequences, data from two sources, 1) the Model Organism ENCyclopedia Of DNA Elements (modENCODE) project, and 2) related species alignments are compared and optimal sequence regions are selected. Once identified, the promoters for these carcinogen and genotoxicity pathway genes can be used to generate the promoter reporter transgenes, constructs, isolated nucleic acids, or transgenic organisms of the invention using genetic engineering technology, such as those described herein.

In one aspect, the invention is an isolated nucleic acid or fragment thereof having 50, 100, 200, 300, 400, or 500 or more nucleotides of a promoter for a carcinogen pathway or genotoxin pathway gene which is fused, or operably linked to a reporter gene. A carcinogen pathway gene is a gene whose expression is altered (e.g., induced) in a cell, tissue or an organism upon exposure to a carcinogen or genotoxin. In another aspect, the invention is an isolated nucleic acid or fragment thereof which is a promoter for a gene induced in base excision repair, nucleotide excision repair, mismatch repair, recombination controlled repair, cell cycle control or apoptosis which is fused, or operably linked, to a reporter gene. In a specific aspect, the promoter for a gene induced in base excision repair is promoter for exo-3, nth-1, pme-1, or ung-1. In a specific aspect, the promoter for a gene induced in nucleotide excision repair is the promoter of xpa-1, mrt-2, ercc-1, or rad-23. In a specific aspect, the promoter for a gene induced in mismatch repair is the promoter for mlh-1, msh-4, msh-5, or msh-6. In a specific aspect, the promoter for a gene induced in recombination controlled repair is the promoter of brc-1, brc-2, rad-50, or cku-70. In a specific aspect, the promoter for a gene induced in cell-cycle control is the promoter for lin-35, mei-1, cki-1, or cki-2. In a specific aspect, the promoter for a gene induced in apoptosis is the promoter for cep-1, ced-3, ced-9, or ced-13.

In another aspect, the invention is an isolated nucleic acid or fragment thereof having 50, 100, 200, 300, 400, or 500 or more nucleotides, which is a promoter for a gene encoding a protein in a DNA damage response pathway that is induced by irradiation with UV or X-ray exposure which is fused, or operably linked, to a reporter gene.

In another aspect, the invention is an isolated nucleic acid or fragment thereof having 50, 100, 200, 300, 400, or 500 or more nucleotides, which is a promoter for a gene encoding a protein in a DNA damage response pathway that is induced N-ethyl-N-nitrosurea which is fused, or operably linked, to a reporter gene.

In another aspect, the invention is an isolated nucleic acid or fragment thereof having 50, 100, 200, 300, 400, or 500 or more nucleotides, which is a promoter for a gene encoding a protein in spindle formation that is induced by taxane which is fused, or operably linked, to a reporter gene.

In another aspect, the invention is an isolated nucleic acid or fragment thereof having 50, 100, 200, 300, 400, or 500 or more nucleotides, which is a promoter for a gene encoding a protein involved in regulating cell division or checkpoint control which is fused, or operably linked, to a reporter gene.

Endocrine Pathway and/or Xenobiotic Metabolism Genes

In one embodiment, the transgene, transgenic organism, or promoter reporter construct of the invention has a promoter or fragment thereof having 50, 100, 200, 300, 400, or 500 or more nucleotides, derived or obtained from a CYP P450 gene, ABC transporter gene, SDR/Redox gene, GST gene, or a Sol. Transporter gene, which is fused, or operably linked, to a reporter gene.

Examples of CYP P450 genes include, but are not limited to, the following *C. elegans* genes: cyp-13A1, cyp-13A2, cyp-13A3, cyp-13A4, cyp-13A5, cyp-13A6, cyp-13A7, cyp-13A8, cyp-13A10, cyp-13A11, cyp-13A12, cyp-13B2, cyp-14A1, cyp-14A2, cyp-14A3, cyp-14A4, cyp-14A5, cyp-23A1, cyp-25A1, cyp-25A2, cyp-25A3, cyp-25A4, cyp-25A5, cyp-25A6, cyp-29A2, cyp-29A3, cyp-29A4, cyp-31A2, cyp-31A3, cyp-32A1, cyp-32B1, cyp-33A1, cyp-33B1, cyp-33C1, cyp-33C2, cyp-33C3, cyp-33C4, cyp-33C5, cyp-33C6, cyp-33C7, cyp-33C8, cyp-33C9, cyp-33C11, cyp-33C12, cyp-33D1, cyp-33D3, cyp-33E1, cyp-33E2, cyp-33E3, cyp-34A1, cyp-34A2, cyp-34A3, cyp-34A4, cyp-34A5, cyp-34A6, cyp-34A7, cyp-34A8, cyp-34A10, cyp-35A1, cyp-35A2, cyp-35A3, cyp-35A4, cyp-35A5, cyp-35B1, cyp-35B2, cyp-35B3, cyp-35C1, cyp- 35D1, cyp-36A1, cyp-37A1, cyp-37B1, cyp-42A1, cyp-43A1, cyp-44A1, dpr-1, coq-6, fmo-1, fmo-2, fmo-3, fmo-4, fmo-5, pah-1, tbh-1, C01H6.4, C46H11.2, F30B5.4, R07B7.4, R07B7.5, T19B4.1, Y47D3A.22, and Y71G12B.4.

Examples of ABC transporter genes include, but are not limited to, the following *C. elegans* genes: abce-1, abcf-1, abcf-2, abcf-3, abch-1, pgp-1, pgp-2, pgp-3, pgp-4, pgp-5, pgp-7, pgp-8, pgp-9, abt-1, abt-2, abt-3, abt-4, abt-5, abt-6, abtm-1, cft-1, haf-1, haf-2, haf-3, haf-4, haf-6, haf-7, haf-8, hmt-1, mrp-2, mrp-3, mrp-4, mrp-6, mrp-7, mrp-8, pgp-10, pgp-11, pgp-12, pgp-13, pgp-14, pmp-1, pmp-2, pmp-3, pmp-4, wht-1, wht-2, wht-3, wht-4, wht-5, wht-6, wht-8, and wht-9.

Examples of SDR/Redox genes include, but are not limited to, the following *C. elegans* genes: dhs-1, dhs-2, dhs-3, dhs-4, dhs-6, dhs-7, dhs-8, dhs-9, dhs-11, dhs-12, dhs-13, dhs-14, dhs-15, dhs-16, dhs-17, dhs-17, dhs-18, dhs-19, dhs-20, dhs-22, dhs-23, dhs-24, dhs-25, dhs-26, dhs-28, dhs-29, dhs-30, dhs-31, ard-1, fasn-1, maoc-1, qdpr-1, sdz-8, C01G12.5, C06E4.3, C06E4.4, C06E4.6, C27D8.4, C30G12.2, C33E10.10, C41A3.1, C55A6.3, C55A6.4, C55A6.6, C55A6.7, D1054.8, DC2.5, E04F6.15, F02C12.2, F12E12.11, F20G2.1, F20G2.2, F25D1.5, F26D2.15, F28H7.2, F32A5.8, F54F3.4, F55E10.6, F59E11.2, H04M03.3, K10H10.6, R05D8.7, R05D8.9, R119.3, T01G6.1, T01G6.10, T25G12.2, W03F9.9, Y47G6A.21, Y47G6A.22, ZK697.14, ZK829.1, Y47G6A.21, Y47G6A.22, ZK697.14, ZK829.1, hsd-1, hsd-2, hsd-3, and C32D5.12.

Examples of GST genes include, but are not limited to, the following *C. elegans* genes: gst-1, gst-2, gst-3, gst-4, gst-5, gst-6, gst-8, gst-9, gst-10, gst-12, gst-13, gst-14, gst-15, gst-16, gst-18, gst-19, gst-20, gst-21, gst-23, gst-24, gst-25, gst-26, gst-27, gst-28, gst-29, gst-30, gst-31, gst-33, gst-34, gst-35, gst-37, gst-38, gst-39, gst-40, gst-41, gst-43, K10F12.4, K10F12.4, R11A8.5, W10C8.4, Y45G12C.3, Y53G8B.1, Y53G8B.1, F55A11.6, F55A11.6, F56A4.4, gstk-1, and gstk-2.

Examples of Sol. Transporter genes include, but are not limited to, the following *C. elegans* genes: vit-1, vit-2, vit-3, vit-4, vit-5, vit-6, egg-1, egg-2, irp-1, irp-2, lbp-1, lbp-2, lbp-3, lbp-4, lbp-5, lbp-6, lbp-7, lbp-8, lbp-9, nrf-5, cit-1.2, C06G1.1, C05C9.1, F10D11.6, T19C3.5, ZC513.1, ZC513.2, C31H1.1, T10B5.10, D1007.16, C55C3.1, F14D12.1b, F46H5.2a, and ZK616.8.

Specific Panels of Representative Transgenic Organisms or Populations of Representative Organisms In one embodiment, the invention is a panel or array of transgenic organisms as described herein. The panel or array in one aspect is provided in a multiwell plate wherein at least 2 or more (or 3 or more, 4 or more, etc. as described in more detail below) has a transgenic organism or population of transgenic representative organisms representative of one-type of response gene e.g., having a distinct transgene that is distinguishable by the identity of the gene from which the promoter of the transgene was obtained or derived.

Panels or arrays of the invention include 2 or more representative transgenic organisms or populations of representative transgenic organisms. Panels or arrays can include 3 or representative transgenic organisms or populations of representative transgenic organisms. Panels or arrays can include 4 or more representative transgenic organisms or populations of representative transgenic organisms. Panels or arrays can include 5 or more representative transgenic organisms or populations of representative transgenic organisms. Panels or arrays can include 6 or more representative transgenic organisms or populations of representative transgenic organisms. Preferably, the panel or array has a control organism or control population of organisms.

Panels or arrays can include from 2 to 384 representative transgenic organisms or populations of representative transgenic organisms. Panels or arrays can include from 2 to 96 representative transgenic organisms or populations of representative transgenic organisms. Panels or arrays can include from 2 to 48 representative transgenic organisms or populations of representative transgenic organisms. Panels or arrays can include from 2 to 24 representative transgenic organisms or populations of representative transgenic organisms. Panels or arrays can include from 2 to 12 representative transgenic organisms or populations of representative transgenic organisms. Panels or arrays can include from 2 to 6 representative transgenic organisms or populations of representative transgenic organisms. Preferably, the panel or array has a control organism or control population of organisms.

Panels or arrays can include from 3 to 384 representative transgenic organisms or populations of representative transgenic organisms. Panels or arrays can include from 3 to 96 representative transgenic organisms or populations of representative transgenic organisms. Panels or arrays can include from 3 to 48 representative transgenic organisms or populations of representative transgenic organisms. Panels or arrays can include from 3 to 24 representative transgenic organisms or populations of representative transgenic organisms. Panels or arrays can include from 3 to 12 representative transgenic organisms or populations of representative transgenic organisms. Panels or arrays can include from 3 to 6 representative transgenic organisms or populations of representative transgenic organisms. Preferably, the panel or array has a control organism or control population of organisms.

Panels or arrays can include from 4 to 384 representative transgenic organisms or populations of representative transgenic organisms. Panels or arrays can include from 4 to 96 representative transgenic organisms or populations of representative transgenic organisms. Panels or arrays can include from 4 to 48 representative transgenic organisms or populations of representative transgenic organisms. Panels or arrays can include from 4 to 24 representative transgenic organisms or populations of representative transgenic organisms. Panels or arrays can include from 4 to 12 representative transgenic organisms or populations of representative transgenic organisms. Panels or arrays can include from 4 to 6 representative transgenic organisms or populations of representative transgenic organisms. Preferably, the panel or array has a control organism or control population of organisms.

Panels or arrays can include from 5 to 384 representative transgenic organisms or populations of representative transgenic organisms. Panels or arrays can include from 5 to 96 representative transgenic organisms or populations of representative transgenic organisms. Panels or arrays can include from 5 to 48 representative transgenic organisms or populations of representative transgenic organisms. Panels or arrays can include from 5 to 24 representative transgenic organisms or populations of representative transgenic organisms. Panels or arrays can include from 5 to 12 representative transgenic organisms or populations of representative transgenic organisms. Panels or arrays can include from 4 to 6 representative transgenic organisms or populations of representative transgenic organisms. Preferably, the panel or array has a control organism or control population of organisms.

Selected Agents

A "selected agent" refers to a chemical, object, or external stimuli that is contacted with or exposed to the transgenic biosensor organism. The selected agent can be given or exposed to the transgenic organism. In one aspect, the selected agent is dosed in a range at concentrations below a lethal dose and at or above levels where a therapeutic effect is expected to be observed. Such ranges can be determined in dose finding studies. Acute assays can be conducted using the compositions and methods of the invention and can range from about 2 hours to about 24 hours, more preferably from about 2 hours to about 18 hours and more preferably from about 2 hours to about 10 hours.

Typically, chemicals are given to the animal or organism in the range of 1 picomolar to 10 millimolar. In other aspects, the organism are exposed to an agent like a physical object e.g., in their growth medium, lining the vesicle or microwell plate or as a gas.

In one aspect, the selected agent is a chemical. In one aspect, the selected agent is a drug candidate or an agent which is a component of a formulation for a drug product. In one aspect, the selected agent is water. In one aspect, the water is a drinking water. In one aspect, the water is wastewater. In one aspect, the selected agent is a food product or liquid or an additive of either. In a specific aspect, the food product, liquid, or additive of either is intended for human or animal consumption.

Methods for Creating Transgenic Organisms

The transgenic organisms of the invention and for use in the methods of the invention can be produced by any technique. Preferably, the transgenic organisms of the invention have single copy inserts of the desired transgene at defined genomic loci and are stable. The transgenic organisms of the invention have a response element (e.g., promoter) reporter gene construct stably inserted into the host organism's genome.

In one specific aspect, the transgene is an inducible promoter reporter gene construct. The optimal promoter and gene-intron sequences of target genes are identified from publicly or privately available databases. For example, one such public database is found at www.wormbase.org. Gateway-compatible PCR primer sets are created for both the promoter and gene intron regions. PCR reactions are gel purified and cloned into a targeting vector (e.g., a MosSCI targeting vector) containing the desired reporter gene (e.g., tag-RFP, RFP, his-RFP, mCherry, or his-mCherry). Desired construction is verified by PCR and/or restriction enzyme digestion.

MosSCI integration (Frokjaer-Jensen, C. et al., 2008 Nat Genet, 40 (11), 1375-83). Plasmid DNA mixtures are injected into MosSCI targeting strains. These strains have a Mos1 element at a specific genomic site on chromosome II and contain the unc-119(ed3) mutation, which is used for positive selection of the transgene. The injection mixes for MosSCI transgenesis contain three types of vectors: 1) the gateway reporter construct containing the unc 119(+) positive selection marker gene and sequences for homologous recombination into the *C. elegans* chromosome, 2) a transposase-producing plasmid, and 3) three plasmids acting as markers for tracking the presence of extrachromosomal arrays. Three injected animals are placed on each plate and transferred to 25° C. for 8 days.

After the 8 days at 25° C., the worms are screened for MosSCI events. Candidate insertion strains are homozygosed by clonally picking 8 Unc-119(+) animals that do not carry mCherry (RFP) arrays to individual plates. MosSCI typically produces one integrated transgene from ten injected animals. Thus, the 25 injections/construct are expected to yield 3-4 independent lines.

Desired insertions are verified by PCR with one primer annealing within the insertion and a second primer in reverse annealing outside the insertion. Outcrossing (2×) of the candidate lines confirms their chromosomal integration by observation of Mendelian segregation of the integration locus.

Validation of reporter construction. Candidate lines are imaged by confocal microscopy to record basal expression profiles. Animals are anesthetized on agarose pads on glass slides with glass coverslips. Laser confocal imaging is performed on a Pascal LMS system. Each worm is imaged with a fixed set of laser intensity settings and the level of RFP expression is quantified with NIH ImageJ.

Kits

The invention relates to a kit having one or more biosensor nematodes and materials for use thereof.

Thus, the kit of the invention has:

One or more transgenic biosensor nematode cultures and reagents necessary to reconstitute healthy populations;

Incubation buffer for delivering agent;

A control nematode culture that is similar to the transgenic biosensor nematode culture but does not have the inducible promoter reporter transgene; and A vesicle or reaction plate for containing and culturing one or more transgenic biosensor nematode cultures and the control nematode culture.

The reagents necessary to reconstitute healthy populations include a medium. In one aspect, the medium is M9, S-media, or CeMM.

The incubation buffer allows for delivery of the selected agent to the transgenic biosensor nematode culture substantially affecting the nematodes in a negative manner (the incubation buffer minus selected agent desirably does not kill the nematodes). In one aspect, the incubation buffer contains DMSO. In a more specific aspect, the incubation buffer has about 2% DMSO. In another aspect, the incubation buffer has acetone. In a specific aspect, the incubation buffer has about 5% acetone. In another aspect, the incubation buffer has methanol. In a more specific aspect, the incubation buffer has 2% methanol. In some aspect, the incubation buffer comprises 2 components which are a solvent for the selected agent and a buffer. The solvent for the selected agent in is chosen from a solvent comprising DMSO, DMFO, acetone, or methanol. In one aspect, the buffer contains detergent. One detergent for use in the incubation buffer is 0.01% triton x-100. The incubation buffers for use in the kits have capacity to increase uptake of the selected agent compounds.

The vesicle or reaction plate for containing one or more biosensor nematode cultures is of sufficient height, size and depth to contain each transgenic biosenor nematode population separate while allowing for the additional of appropriate reagents for growth and exposure to selected agent. Additionally, the vesicle or plate desirably does not interfere with reporter assay.

Typically, the vesicle or each well in a plate has a number of organisms sufficient to yield an adequate signal of the reporter gene. In one aspect, each vesicle or well has 10 or more organisms. In another aspect each vesicle or well has 50 or more organisms. In another aspect, each vesicle or well has 100 or more organisms. In another aspect, each vesicle or well has from 10 to 1000 organisms. In another aspect, each vesicle or well has from 50 to 1000 organisms. In another aspect, each vesicle or well has from 100 to 1000 organisms.

In another aspect, each vesicle or well has from 300 to 1000 organisms. In another aspect, each vesicle or well has from 300 to 800 organisms.

Generally, the nomenclature and the laboratory procedures utilized in the invention include molecular, biochemical, microbiological and recombinant DNA techniques. These techniques are explained in the literature. See, for example, Molecular Cloning: A laboratory Manual Sambrook et al., (1989); Current Protocols in Molecular Biology Volumes I-III Ausubel, R. M., ed. (1994); Ausubel et al., Current Protocols in Molecular Biology, John Wiley and Sons, Baltimore, Md. (1989); Perbal, A Practical Guide to Molecular Cloning, John Wiley & Sons, New York (1988); Watson et al., Recombinant DNA, Scientific American Books, New York; Birren et al. (eds) Genome Analysis: A Laboratory Manual Series, Vols. 1-4, Cold Spring Harbor Laboratory Press, New York (1998); Cell Biology: A Laboratory Handbook, Volumes I-III Cellis, J. E., ed. (1994); Oligonucleotide Synthesis Gait, M. J., ed. (1984); Nucleic Acid Hybridization Hames, B. D., and Higgins S. J., eds. (1985); Transcription and Translation Hames, B. D., and Higgins S. J., Eds. (1984); Animal Cell Culture Freshney, R. I., ed. (1986); Immobilized Cells and Enzymes IRL Press, (1986); A Practical Guide to Molecular Cloning Perbal, B., (1984) and "Methods in Enzymology Vol. 1-317, Academic Press; "PCR Protocols: A Guide To Methods And Applications", Academic Press, San Diego, Calif. (1990); Marshak et al., Strategies for Protein Purification and Characterization—A Laboratory Course Manual" CSHL Press (1996); all of which are incorporated by reference as if fully set forth herein.

Reagents useful in applying such techniques, such as restriction enzymes, coding sequences, fluorescent proteins and the like, are widely known in the art and commercially available from such vendors as New England BioLabs, Boehringer Mannheim, Amersham, Promega Biotec, U.S. Biochemicals, New England Nuclear, Life Technologies, Roche and a number of other sources.

References are provided throughout this document. The procedures therein are believed to be well known in the art. All the information contained in these references is incorporated herein by reference.

EXAMPLES

The examples below describe the construction and use of representative compositions for detecting and screening for response to exposure of whole organisms to selected agents e.g., a chemical or toxin. In these examples, the use of panels of transgenic nematodes as biosensors of toxicity pathway activation is described. The panels are composed of promoters of toxin-responsive genes fused to genes encoding reporter proteins. The promoter-reporter fusion construct is inserted into the nematode genome as a single copy gene insertion (e.g., using single copy or site specific insertion transgenesis techniques) at a defined genomic locus. The result is a set of transgenic nematodes strains or lines where each type of transgenic animal functions as a biosensor for a specific toxin (e.g., a representative transgenic organism). Toxins can be typed e.g., for their class of toxicity by observing which subset of strains show reporter activation.

The unique use of single copy insertion allows direct comparison between strains, where intensity of toxin response is de novo normalized between strains. This allows easier determination of the primary mode of toxicity (or other gene expression effects) when analyzing novel compounds. The transgenic strains or lines can be configured into panel sets (or arrays). It is contemplated that the arrays can be configured to be specific to various types of responses (e.g., toxicity), such as heavy metal, oxidative stress, endocrine disruption, xenobiotic, carcinogenic, genotoxic, neurotoxic, hepatatoxic, nephratoxic, immunotoxic, and others.

Example 1

Studies in *C. elegans* Having a hsp-16 Promoter-Red Fluorescent Protein Transgene The results described herein demonstrate remarkable responses of the whole organism biosensor to toxic insults (such as: heat shock, cadmium, arsenic, etc). For instance, a protein homeostasis reporter was created by fusing heat shock protein to a nuclear localized red fluorescent protein (hsp-16.42::hRFP) (the materials and methods for the construction of the transgenic organism are described in more detail in the examples below). Exposure to heat toxicity generates induction of nuclear localization. This heat shock gene reporter was screened for gene induction capacity using a heat-shock protocol. The hsp-16::hRFP construct is exposed to a 1 hr incubation at 30 C. Gene induction was screened 4 to 24 hrs after heat shock. Significant red fluorescence is observed in the nuclei of heat-shocked worm relative to control (FIG. 5).

Toxin sensitivity of hsp-16 was confirmed with exposure to heavy metals and metalloids. To develop a rapid screen for the hsp-16::hRFP expression, a fluorescent plate reader assay was developed. To test the sensitivity of this assay, a titrating concentration of nematodes were exposed to heat shock. The worms were transferred to a 96 well plate and red fluorescence was quantified. Good sensitivity for a red fluorescence signal occurs at concentrations of 50 or more worms (FIG. 3A). Next, the toxin dosage sensitivity was measured. The Phsp-16::hRFP reporter shows higher sensitivity to cadmium chloride relative to sodium bis-arsenite (FIG. 3B vs. FIG. 3C). The $EC_{50}$ for cadmium occurs near 0.2 mM while arsenic sensitivity is near 1.5 mM. Thus, the Phsp-16::hRFP reporter shows greater sensitivity to cadmium.

Example 2

Control Reporter

Advantageously, the transgenic animals described in these examples can have a control reporter (e.g., constitutively expressed). Exposure to some selected agents or toxins can lead to shortened life-span, lower brood sizes or other effects that need to be controlled. The problem becomes most pronounced in chronic assays. For instance, exposure to cadmium for 72 hrs leads to significant population effects (FIGS. 4A, B, and C). Thus, it was determined a control for population mass differences between assay wells is desirable. Introduction of a second constitutively expressed reporter gene can be used to control for various population differences.

To create a population control in the fluorescence reader assays, the hsp-16::hRFP was crossed into a line containing a constitutively-expressed neuronal marker (unc-47::GFP). Expression of the control reporter remains constant, while the inducible reporter responds to heat shock (FIGS. 5A and B). The use of a constitutive-expressed reporter allows normalization of induction reporter responses—a toxin's effect on population dynamics is controlled.

Example 3

COPAS Cytometry

The fluorescent expression patterns of individual nematodes was rapidly quantifiable using flow cytometry. The hsp-16::hRFP construct in unc-47::GFP background was sent subjected to COPAS biosorting analysis. Induction of the red fluorescence was observed (FIG. 6A) and COPAS biosorting generated size-dependent profiles for red and green fluorescence expression (FIG. 6B). As expected, the levels of fluorescence increase proportionally with nematode age.

Example 4

Gene Selection and Transgene Construct Construction

The genes chosen for an oxidative stress response panel were the following oxidative response genes (hsp-16.41, hsp16.2, hsp-6 and hsp-60, hsp-4, mlt-2, and ugt-1). To choose the oxidative-response gene promoters, a combination of modENCODE's TF-GFP ChIP-seq data and multi-z 6-species alignment was used to find the extent of conserved genomic regions containing TF sites in front of the oxidative-response gene's start codon. Promoter-reporter fusion constructs were designed for Gibson reaction cloning using APE plasmid editor (biologylabs.utah.edu/jorgensen/wayned/ape). In general, regions ranging from 300 to 4,000 bp upstream of start codon were chosen for promoter selection.

Example 5

Nematode Transgenesis

To make transgenic nematodes, the MosSCI transgenesis procedure was used. Briefly, using the custom transgenesis platform provided by Knudra Transgenics (www.knudra-.com/product/custom-transgenics), promoters are positioned in front of a red fluorescent protein fused to histone H2B. The gene is cloned into a vector pNU142, which contains left and right homologous recombination arms of the Mos1 locus (2094 bp and 1825 bp, respectively). The pNU142 plasmid ($Amp^r$) contains CBunc-119 gene obtained from the *C. Briggsae* genome for use as a positive-selection marker. The resulting construct is inserted as a single copy into the Mos1 ttTi5605 site in *C. elegans* strain COP66, which is homozygous for ttTi5605 and oxIs12 (unc-47::GFP) alleles. Strains obtained with the MosSCI transgenesis procedure are verified by PCR for single copy insertion at Mos1 locus. Verification oligos for insertion at Mos1 site are forward SEQ ID NO:163 (GATTCCATGATGGTAGCAAACTC) and reverse SEQ ID NO:164 (CAGATGATGAGCCAAGAAGAGTT), which gives a 325 bp product specific to strains homozygous for insertion at Mos1 loci. The resulting nematode is a two-color worm acting as in vivo transcriptional reporter of gene activation. For the results herein, the 7 types of two-color worms used are hsp-4, hsp-6, hsp-60, hsp-16.2, hsp-16.41, mtl-2, and ugt-1.

Example 7

Nematode Preparation

Two-color worms are grown to high density (0.5 ml worm pellet/plate) using Perfect-GROW HB101 plates (www.knudra.com/product/perfect-grow). Worms are recovered from the plate and cleaned by sucrose sedimentation. Animals are distributed on 5 cm NGM plates (seeded with HB101, (www.knudra.com/product/perfect-seed) at densities of 200 adult animals per plate. For heat shock, plates are exposed to 34° C. for 1.5 hr, and then allowed to recover at for 4 hrs at room temperature. For cadmium exposure, fresh seeded NGM plates are pre-incubated for 24 hrs with 700 ul of 10 mM $CdCl_2$. Cleaned nematodes were added at 200 adult animals per plate and incubated for 15 hrs at room temperature.

Example 8

Plate Reader Assay

Each strain is transferred with 1 ml of M9 into a 2 ml deep 96 well plate. Plate is allowed to stand for 5 minutes to settle worms. Excess M9 is siphoned off and a repeat wash/siphon step is performed. Settled worms are transferred (about 200 ul) to a black 96-well read plate (Corning, Inc. #3651). The plate is read in a fluorescence plate reader (Biotek, Inc., Synergy 4, with optical cubes for GFP detection at ex. 485/20, em. 528/20 and RFP detection at ex. 575/15, em. 620/15 with reading set as endpoint from bottom well at sensitivity of 50). Reads are normalized as RFP/GFP ratio, which adjust for population differences between wells. Fluorescence intensity readings of the reporters in the panel are calculated as ratio of induced RFP/GFP ratio divided by control RFP/GFP ratio.

In conclusion, the oxidative response panel demonstrates the inventive system is feasible for use in testing the effects of external stimuli on gene expression at the whole organism level. As shown herein, the exemplary toxicogenomics studies is remarkably sensitive and selective for detection of oxidative stress toxicity. Furthermore, a simple 7 gene panel can differentiate between different types of oxidative stress e.g., heat shock and metal exposure. The inventive system has advantages over cell culture methods because it is easier to use, less costly to implement, and is believed results more translatable to more complex animal studies like mammalian studies. Importantly, the inventive system is a whole organism approach, which detects cellular response in a native context. The ease of assay implementation makes the system ideal for high-throughput applications. With respect to a specific implementation, toxicogenomics is very valuable in drug discovery. With this invention, pharmaceutical companies will decrease their financial exposure because better toxicology capture at the front end of drug development translates to lower frequency of drugs failing in clinical trials due to unwanted side-effect toxicity.

Those skilled in the art will appreciate that the concepts, specific embodiments, and Examples disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A population of *C. elegans* comprising: a first population of transgenic *C. elegans* organisms each comprising:

a first inducible reporter gene comprising a first inducible promoter from a response pathway gene operably coupled to a reporter gene encoding a first fluorescent or luminescent protein; and a first constitutively expressed reporter gene comprising a first constitutive promoter operably coupled to a reporter gene encoding a second fluorescent or luminescent protein, wherein said first fluorescent or luminescent protein is detectably different from said second fluorescent or luminescent protein, wherein said first inducible reporter gene and said first constitutively expressed reporter gene are stably integrated into the genome, wherein said first constitutively expressed reporter gene is present in an amount of 1 to 50 copies, wherein expression of said first constitutively expressed reporter gene normalizes the expression of said first inducible reporter gene, thereby the expression of the first inducible reporter gene can be detected at expression levels of at least four fold above background levels of expression, and wherein the first population of transgenic *C. elegans* organisms comprises 2 to 384 transgenic *C. elegans* organisms.

2. The population of *C. elegans* of claim 1, further comprising a second population of transgenic *C. elegans* organisms each transgenic organism of the second population comprising;

a second inducible reporter gene comprising a second inducible promoter from a response pathway gene operably coupled to a reporter gene encoding a third fluorescent or luminescent protein; and a second constitutively expressed reporter gene comprising the first constitutive promoter operably coupled to a reporter gene encoding the second fluorescent or luminescent protein, wherein the first and third fluorescent or luminescent proteins are detectably different from the second fluorescent or luminescent protein, wherein the first inducible promoter and the second inducible promoter are promoters obtained from different response pathway genes, wherein said second inducible reporter gene and said second constitutively expressed reporter gene are stably integrated into the genome, wherein expression of said first constitutively expressed reporter gene normalizes the expression of said first inducible reporter gene and expression of said second constitutively expressed reporter normalizes the expression of said second inducible reporter gene, thereby the expression of the first and second inducible reporter genes can be detected at expression levels of at least four fold above background levels of expression.

3. The population of *C. elegans* of claim 2, further comprising a third population of transgenic *C. elegans* organisms each transgenic organism of the third population comprising;

a third inducible reporter gene comprising a third inducible promoter from a response pathway gene operably coupled to a reporter gene encoding a fourth fluorescent or luminescent protein; and a third constitutively expressed reporter gene comprising the first constitutive promoter operably coupled to a reporter gene encoding the second fluorescent or luminescent protein, wherein the first, third, and fourth fluorescent or luminescent proteins are detectably different from the second luminescent protein, wherein the first inducible promoter, the second inducible promoter, and the third inducible promoters are promoters obtained from different response pathway genes, wherein said third inducible reporter gene and said third constitutively expressed reporter gene are stably integrated into the genome, wherein expression of said first constitutively expressed reporter gene normalizes the expression of said first inducible reporter gene, expression of said second constitutively expressed reporter normalizes the expression of said second inducible reporter gene, and expression of said third constitutively expressed reporter normalizes the expression of said third inducible reporter gene, thereby the expression of the first, second, and third inducible reporter genes can be detected at expression levels of at least four fold above background levels of expression.

4. The population of *C. elegans* of claim 3, further comprising a fourth population of transgenic *C. elegans* organisms each transgenic organism of the fourth population comprising;

a fourth inducible reporter gene comprising a fourth inducible promoter from a response pathway gene operably coupled to a reporter gene encoding a fifth fluorescent or luminescent protein; and a fourth constitutively expressed reporter gene comprising the first constitutive promoter operably coupled to a reporter gene encoding the second fluorescent or luminescent protein, wherein the first, third, fourth, and fifth fluorescent or luminescent proteins are detectably different from the second fluorescent or luminescent protein, wherein the first inducible promoter, the second inducible promoter, the third inducible promoters, and fourth inducible promoters are promoters obtained from different response pathway genes, wherein expression of said first constitutively expressed reporter gene normalizes the expression of said first inducible reporter gene, expression of said second constitutively expressed reporter normalizes the expression of said second inducible reporter gene, expression of said third constitutively expressed reporter normalizes the expression of said third inducible reporter gene, and expression of said fourth constitutively expressed reporter normalizes the expression of said fourth inducible reporter gene, thereby the expression of the first, second, third, and fourth inducible reporter genes can be detected at expression levels of at least four fold above background levels of expression.

5. The population of *C. elegans* of claim 1, wherein the first inducible reporter gene comprises the first inducible promoter from a response pathway gene operably coupled to a reporter gene encoding a first fluorescent protein.

6. The population of *C. elegans* of claim 5, wherein the first fluorescent protein is selected from the group consisting of: GFP, RFP, and CFP.

7. The population of *C. elegans* of claim 1, further comprising a control population *C. elegans* wherein said control population does not express an inducible promoter reporter transgene.

8. The population of *C. elegans* of claim 3, wherein the fourth fluorescent or luminescent protein is detectably different from the first fluorescent or luminescent protein.

9. The population of *C. elegans* of claim 8, wherein the second fluorescent or luminescent protein is selected from the group consisting of: GFP, RFP, and CFP.

10. The population of *C. elegans* of claim 1, wherein the first inducible gene is present as a single copy in the genome of each *C. elegans* organism.

11. The population of *C. elegans* of claim 1, wherein the response pathway gene is selected from the group consisting of: an oxidative stress pathway gene, a genotoxin response pathway gene, a carcinogen pathway gene, and xenobiotic pathway gene.

12. The population of *C. elegans* of claim 11, wherein the oxidative stress response pathway gene is selected from the group consisting of: hsp-16.41, hsp-16.2, mt1-2, ugt-1, hsp-60, hsp-6, and hsp-4; wherein the genotoxin response pathway gene and the carcinogen pathway gene are selected from the group consisting of: a base excision repair gene selected from the group consisting of: exo-3, nth-1, pme-1, and ung-1, a nucleotide excision repair gene selected from the group consisting of: xpa-1, mrt-2, ercc-1, rad-23, a mismatch repair gene selected from the group consisting of: mlh-1, msh-4, msh-5, and msh-6, a recombination controlled repair gene selected from the group consisting of: brc-1, brc-2, rad-50, and cku-70; a cell cycle control gene selected from the group consisting of: lin-35, mei-1, cki-1, and cki-2, and an apoptosis gene selected from the group consisting of: cep-1, ced-3, ced-9, and ced-13, and wherein the xenobiotic metabolism pathway gene is selected from the group consisting of: cyp-13A1, cyp-13A2, cyp-13A3, cyp-13A4, cyp-13A5, cyp-13A6, cyp-13A7, cyp-13A8, cyp-13A10, cyp-13A11, cyp-13A12, cyp-13B2, cyp-14A1, cyp-14A2, cyp-14A3, cyp-14A4, cyp-14A5, cyp-23A1, cyp-25A1, cyp-25A2, cyp-25A3, cyp-25A4, cyp-25A5, cyp-25A6, cyp-29A2, cyp-29A3, cyp-29A4, cyp-31A2, cyp-31A3, cyp-32A1, cyp-32B1, cyp-33A1, cyp-33B1, cyp-33C1, cyp-33C2, cyp-33C3, cyp-33C4, cyp-33C5, cyp-33C6, cyp-33C7, cyp-33C8, cyp-33C9, cyp-33C11, cyp-33C12, cyp-33D1, cyp-33D3, cyp-33E1, cyp-33E2, cyp-33E3, cyp-34A1, cyp-34A2, cyp-34A3, cyp-34A4, cyp-34A5, cyp-34A6, cyp-34A7, cyp-34A8, cyp-34A10, cyp-35A1, cyp-35A2, cyp-35A3, cyp-35A4, cyp-35A5, cyp-35B1, cyp-35B2, cyp-35B3, cyp-35C1, cyp-35D1, cyp-36A1, cyp-37A1, cyp-37B1, cyp-42A1, cyp-43A1, cyp-44A1, dpr-1, coq-6, fmo-1, fmo-2, fmo-3, fmo-4, fmo-5, pah-1, tbh-1, CO1H6.4, C46H11.2, F30B5.4, R07B7.4, R07B7.5, T19B4.1, Y47D3A22, Y71G12B0.4, abce-1, abcf-1, abcf-2, abcf-3, abch-1, pgp-1, pgp-2, pgp-3, pgp-4, pgp-5, pgp-7, pgp-8, pgp-9, abt-1, abt-2, abt-3, abt-4, abt-5, abt-6, abtm-1, cft-1, haf-1, haf-2, haf-3, haf-4, haf-6, haf-7, haf-8, hint-I, mrp-2, mrp-3, mrp-4, mrp-6, mrp-7, mrp-8, pgp-10, pgp-11, pgp-12, pgp-13, pgp-14, prop-I, prop-2, prop-3, prop-4, wht-1, wht-2, wht-3, wht-4, wht-5, wht-6, wht-8, and wht-9, dhs-1, dhs-2, dhs-3, dhs-4, dhs-6, dhs-7, dhs-8, dhs-9, dhs-11, dhs-12, dhs-13, dhs-14, dhs-15, dhs-16, dhs-17, dhs-17, dhs-18, dhs-19, dhs-20, dhs-22, dhs-23, dhs-24, dhs-25, dhs-26, dhs-28, dhs-29, dhs-30, dhs-31, ard-1, fasn-1, maoc-1, qdpr-1, sdz-8, C01G12.5, C06E4.3, C06E4.4, C06E4.6, C27D8.4, C30G12.2, C33E10.10, C41A3.1, C55A6.3, C55A6.4, C55A6.6, C55A6.7, D1054.8, DC2.5, E04F6.15, F02C12.2, F12E12.11, F20G2.1, F20G2.2, F25D1.5, F26D2.15, F28H7.2, F32A5.8, F54F3.4, F55E10.6, F59E11.2, H04M03.3, K10H10.6, R05D8.7, R05D8.9, R119.3, T01G6.1, T01G6.10, T25G12.2, W03F9.9, Y47G6A.21, Y47G6A.22, ZK697.14, ZK829.1, Y47G6A.21, Y47G6A.22, ZK697.14, ZK829.1, hsd-1, hsd-2, hsd-3, C32D5.12, gst-1, gst-2, gst-3, gst-4, gst-5, gst-6, gst-8, gst-9, gst-10, gst-12, gst-13, gst-14, gst-15, gst-16, gst-18, gst-19, gst-20, gst-21, gst-23, gst-24, gst-25, gst-26, gst-27, gst-28, gst-29, gst-30, gst-31, gst-33, gst-34, gst-35, gst-37, gst-38, gst-39, gst-40, gst-41, gst-43, K10F12.4, K10F12.4, R11A8.5, W1008.4, Y45G12C.3, Y53G8B.1, Y53G8B.1, F55A11.6, F55A11.6, F56A4.4, gstk-1, gstk-2, vit-1, vit-2, vit-3, vit-4, vit-5, vit-6, egg-I, egg-2, irp-1, irp-2, Ibp-1, Ibp-2, Ibp-3, Ibp-4, Ibp-5, Ibp-6, Ibp-7, Ibp-8, Ibp-9, nrf-5, cit-1.2, C06G1.1, C05C9.1, F10D11.6, T19C3.5, ZC513.1, ZC513.2, C31HI.1, T10B5.10, D1007.16, C55C3.1, F14D12.1b, F46H5.2a, and ZK616.8.

13. The population of *C. elegans* of claim 1, wherein the first population further comprises a selected agent.

* * * * *